US011292801B2

(12) United States Patent
Buckman et al.

(10) Patent No.: US 11,292,801 B2
(45) Date of Patent: Apr. 5, 2022

(54) CALPAIN MODULATORS AND THERAPEUTIC USES THEREOF

(71) Applicant: Blade Therapeutics, Inc., South San Francisco, CA (US)

(72) Inventors: Brad Owen Buckman, Oakland, CA (US); Shendong Yuan, San Ramon, CA (US); John Beamond Nicholas, Redwood City, CA (US); Jingyuan Ma, Palo Alto, CA (US); Kumaraswamy Emayan, Albany, CA (US); Marc Adler, Orinda, CA (US)

(73) Assignee: Blade Therapeutics, Inc., South San Francisco, CA (US)

( * ) Notice: Subject to any disclaimer, the term of this patent is extended or adjusted under 35 U.S.C. 154(b) by 27 days.

(21) Appl. No.: 16/312,916

(22) PCT Filed: Jun. 29, 2017

(86) PCT No.: PCT/US2017/040109
§ 371 (c)(1),
(2) Date: Dec. 21, 2018

(87) PCT Pub. No.: WO2018/009417
PCT Pub. Date: Jan. 11, 2018

(65) Prior Publication Data
US 2020/0392157 A1 Dec. 17, 2020

Related U.S. Application Data

(60) Provisional application No. 62/358,504, filed on Jul. 5, 2016.

(51) Int. Cl.
C07D 498/18 (2006.01)
A61P 1/16 (2006.01)
A61P 13/12 (2006.01)
A61P 11/00 (2006.01)
C07D 245/06 (2006.01)
C07D 267/00 (2006.01)
C07D 405/12 (2006.01)
C07D 407/12 (2006.01)
C07D 413/12 (2006.01)
C07D 471/18 (2006.01)
C07D 498/04 (2006.01)

(52) U.S. Cl.
CPC .............. *C07D 498/18* (2013.01); *A61P 1/16* (2018.01); *A61P 11/00* (2018.01); *A61P 13/12* (2018.01); *C07D 245/06* (2013.01); *C07D 267/00* (2013.01); *C07D 405/12* (2013.01); *C07D 407/12* (2013.01); *C07D 413/12* (2013.01); *C07D 471/18* (2013.01); *C07D 498/04* (2013.01)

(58) Field of Classification Search
CPC .. C07D 498/18; C07D 245/06; C07D 267/00; C07D 405/12; C07D 407/12; C07D 413/12; C07D 471/18; C07D 498/04
See application file for complete search history.

(56) References Cited

U.S. PATENT DOCUMENTS

| | | | |
|---|---|---|---|
| 4,708,871 A | 11/1987 | Geysen |
| 4,833,092 A | 5/1989 | Geysen |
| 4,863,940 A | 9/1989 | Sharma |
| 5,145,684 A | 9/1992 | Liversidge et al. |
| 5,223,409 A | 6/1993 | Ladner et al. |
| 5,331,573 A | 7/1994 | Balaji et al. |
| 5,403,484 A | 4/1995 | Ladner et al. |
| 5,463,124 A | 10/1995 | Jacobi et al. |
| 5,500,807 A | 3/1996 | Lavin et al. |
| 5,556,762 A | 9/1996 | Pinilla et al. |
| 5,571,689 A | 11/1996 | Heuckeroth et al. |
| 5,644,048 A | 7/1997 | Yau |
| 5,663,143 A | 9/1997 | Ley et al. |
| 5,750,373 A | 3/1998 | Gerrard et al. |
| 5,852,007 A | 12/1998 | Chatterjee |
| 5,952,322 A | 9/1999 | Hoover et al. |
| 6,083,944 A | 7/2000 | Chatterjee et al. |
| 6,103,720 A | 8/2000 | Lubisch et al. |
| 6,172,072 B1 | 1/2001 | Lubisch et al. |
| 6,251,917 B1 | 6/2001 | Lubisch et al. |
| 6,358,978 B1 | 3/2002 | Ritzeler et al. |
| 6,380,220 B1 | 4/2002 | Lubisch et al. |
| 6,436,925 B1 | 8/2002 | Lubisch et al. |
| 6,448,254 B1 | 9/2002 | Lubisch et al. |
| 6,482,832 B1 | 11/2002 | Lubisch et al. |
| 6,506,559 B1 | 1/2003 | Fire et al. |
| 6,582,827 B1 | 5/2003 | Lubisch et al. |

(Continued)

FOREIGN PATENT DOCUMENTS

| | | |
|---|---|---|
| CA | 2328440 | 10/1999 |
| CA | 2328720 | 10/1999 |
| CA | 2943005 | 9/2015 |
| CN | 105669520 | 6/2016 |
| EP | 0530167 | 3/1993 |
| EP | 1493739 | 1/2005 |
| GB | 2467561 | 8/2010 |
| WO | WO 1984/03506 | 9/1984 |
| WO | WO 1984/03564 | 9/1984 |
| WO | WO 1987/05297 | 9/1987 |
| WO | WO 1991/13889 | 9/1991 |
| WO | WO 1992/13549 | 8/1992 |
| WO | WO 1994/000095 | 1/1994 |
| WO | WO 1995/09859 | 4/1995 |
| WO | WO 1996/12499 | 5/1996 |

(Continued)

OTHER PUBLICATIONS

CAS Registry No. 2094533-75-0; STN entry date: May 2, 2017; Benzamide, N-(2-amino-1,1-dimethyl-2-oxoethyl)-2-bromo-5-chloro-3-fluoro-, in 1 page.

(Continued)

*Primary Examiner* — Daniel R Carcanague
(74) *Attorney, Agent, or Firm* — Knobbe Martens Olson & Bear LLP

(57) ABSTRACT

Disclosed herein are small molecule calpain modulator compositions, pharmaceutical compositions, the use and preparation thereof. Some embodiments relate to macrocyclic α-keto amide derivatives and their use as therapeutic agents.

22 Claims, No Drawings

(56) References Cited

U.S. PATENT DOCUMENTS

| | | | |
|---|---|---|---|
| 6,573,099 B2 | 6/2003 | Graham | |
| 6,630,493 B1 | 10/2003 | Lubisch et al. | |
| 6,656,687 B1 | 12/2003 | Hyldig-Nielsen | |
| 7,329,746 B2 * | 2/2008 | Coburn | C07D 267/00 540/453 |
| 7,956,093 B2 | 6/2011 | Lubisch et al. | |
| 7,964,624 B1 | 6/2011 | Cottrell et al. | |
| 8,283,363 B2 | 10/2012 | Mack et al. | |
| 9,434,762 B2 | 9/2016 | Abell et al. | |
| 10,590,084 B2 | 3/2020 | Buckman et al. | |
| 10,934,261 B2 | 3/2021 | Buckman et al. | |
| 2003/0153508 A1 | 8/2003 | Ohmoto et al. | |
| 2003/0153519 A1 | 8/2003 | Kay et al. | |
| 2003/0167490 A1 | 9/2003 | Hunter et al. | |
| 2004/0097508 A1 | 5/2004 | Lubisch et al. | |
| 2004/0242542 A1 | 12/2004 | Shea et al. | |
| 2008/0311036 A1 | 12/2008 | Wang et al. | |
| 2010/0144805 A1 | 6/2010 | Wagner et al. | |
| 2010/0216844 A1 | 8/2010 | Kling et al. | |
| 2010/0298326 A1 | 11/2010 | Kling et al. | |
| 2011/0021434 A1 | 1/2011 | Abell et al. | |
| 2011/0059968 A1 | 3/2011 | Hornberger et al. | |
| 2011/0086879 A1 | 4/2011 | Mack et al. | |
| 2011/0152265 A1 | 6/2011 | Kling et al. | |
| 2011/0152325 A1 | 6/2011 | Kling et al. | |
| 2012/0010235 A1 | 1/2012 | Chu et al. | |
| 2014/0005227 A1 | 1/2014 | Kling et al. | |
| 2015/0065477 A1 | 3/2015 | Kling et al. | |
| 2015/0133368 A1 | 5/2015 | Chang et al. | |
| 2015/0368213 A1 | 12/2015 | Natale et al. | |
| 2019/0194139 A1 | 6/2019 | Buckman et al. | |
| 2020/0123114 A1 | 4/2020 | Buckman et al. | |
| 2021/0009564 A1 | 1/2021 | Buckman et al. | |
| 2021/0113560 A1 | 4/2021 | Buckman et al. | |
| 2021/0253642 A1 * | 8/2021 | Buckman | A61P 19/04 |

FOREIGN PATENT DOCUMENTS

| | | |
|---|---|---|
| WO | WO 1998/016512 | 4/1998 |
| WO | WO 1998/21186 | 5/1998 |
| WO | WO 1998/41092 | 9/1998 |
| WO | WO 1998/41506 | 9/1998 |
| WO | WO 1999/17790 | 4/1999 |
| WO | WO 1999/50264 | 10/1999 |
| WO | WO 1999/54304 | 10/1999 |
| WO | WO 2000/000823 | 1/2000 |
| WO | WO 2000/039585 | 7/2000 |
| WO | WO 2000/055114 | 9/2000 |
| WO | WO 2000/055125 | 9/2000 |
| WO | WO 2001/089584 | 11/2001 |
| WO | WO 2003/024955 | 3/2003 |
| WO | WO 2003/059269 | 7/2003 |
| WO | WO 2003/064440 | 8/2003 |
| WO | WO 2003/080182 | 10/2003 |
| WO | WO 2004/014844 | 2/2004 |
| WO | WO 2004/062601 | 7/2004 |
| WO | WO 2005/000793 | 1/2005 |
| WO | WO 2005/014006 | 2/2005 |
| WO | WO 2005/014534 | 2/2005 |
| WO | WO 2003/091202 | 9/2005 |
| WO | WO 2006/052722 | 5/2006 |
| WO | WO 2007/016476 | 2/2007 |
| WO | WO 2007/025307 | 3/2007 |
| WO | WO 2007/076423 | 7/2007 |
| WO | WO 2007/081530 | 7/2007 |
| WO | WO 2007/089618 | 8/2007 |
| WO | WO 2007/097980 | 8/2007 |
| WO | WO 2007/109080 | 9/2007 |
| WO | WO 2007/141473 | 12/2007 |
| WO | WO 2005/102381 | 3/2008 |
| WO | WO 2008/048121 | 4/2008 |
| WO | WO 2008/080969 | 7/2008 |
| WO | WO 2008/106058 | 9/2008 |
| WO | WO 2008/152093 | 12/2008 |
| WO | WO 2008/154642 | 12/2008 |
| WO | WO 2010/023609 | 3/2010 |
| WO | WO 2010/077836 | 7/2010 |
| WO | WO 2010/094755 | 8/2010 |
| WO | WO 2011/082285 | 7/2011 |
| WO | WO 2011/133346 | 10/2011 |
| WO | WO 2011/133871 | 10/2011 |
| WO | WO 2011/159781 | 12/2011 |
| WO | WO 2012/021788 | 2/2012 |
| WO | WO 2012/024620 | 2/2012 |
| WO | WO 2012/040242 | 3/2012 |
| WO | WO 2012/076639 | 6/2012 |
| WO | WO 2012/122420 | 9/2012 |
| WO | WO 2012/122422 | 9/2012 |
| WO | WO 2012/140500 A9 | 10/2012 |
| WO | WO 2013/033396 | 3/2013 |
| WO | WO 2013/076063 | 5/2013 |
| WO | WO 2013/104613 | 7/2013 |
| WO | WO 2013/149800 | 10/2013 |
| WO | WO 2013/166319 | 11/2013 |
| WO | WO 2014/075146 | 5/2014 |
| WO | WO 2015/002915 | 1/2015 |
| WO | WO 2015/073763 | 5/2015 |
| WO | WO 2015/124443 | 8/2015 |
| WO | WO 2015/179441 | 11/2015 |
| WO | WO 2016/027284 | 2/2016 |
| WO | WO 2016/036893 | 3/2016 |
| WO | WO 2016/037157 | 3/2016 |
| WO | WO 2016/089648 | 6/2016 |
| WO | WO-2017004342 A1 * | 1/2017 ............. A61P 37/00 |
| WO | WO 2017/100201 | 6/2017 |
| WO | WO 2017/156071 | 9/2017 |
| WO | WO 2017/156074 | 9/2017 |
| WO | WO 2018/064119 | 4/2018 |
| WO | WO 2018/236913 | 12/2018 |
| WO | WO 2019/190885 | 10/2019 |
| WO | WO 2019/190999 | 10/2019 |
| WO | WO 2019/217465 | 11/2019 |
| WO | WO 2020/006177 | 1/2020 |
| WO | WO 2020/006294 | 1/2020 |

OTHER PUBLICATIONS

CAS Registry No. 1629446-68-9; STN entry date: Oct. 21, 2014; Benzamide, 3-cyano-N-[(1S)-1-formyl-2-phenylethyl], in 1 page.
CAS Registry No. 2094410-58-7; STN entry date: May 2, 2017; Benzamide, 2-bromo-5-chloro-N-(1-cyano-2-methoxy-1-methylethyl)-3-fluoro-, in 1 page.
CAS Registry No. 2037707-18-7; STN entry date: Nov. 25, 2016; Alanine, 3-fluoro-N-(2-fluoro-6-methoxybenzoyl)-, in 1 page.
CAS Registry No. 1938924-09-4; STN entry date: Jun. 24, 2016; D-Leucine, N-(2-bromo-6-fluoro-3-methylbenzoyl)-, in 1 page.
CAS Registry No. 2048401-56-3; STN entry date: Dec. 14, 2016; 4-Hexenoic acid, 2-[(4,5-dichloro-2-methoxybenzoyl)amino]-, in 1 page.
CAS Registry No. 2026949-92-6; STN entry date: Nov. 8, 2016; D-Leucine, N-[(6-bromo-3,4-dihydro-3-oxo-2H-1,4-benzoxazin-7-yl)carbonyl]-, in 1 page.
CAS Registry No. 1031704-04-7; STN entry date: Jun. 30, 2008; L-Valine, N-[(5,7,8,10-tetrahydro-7,8-dioxo-6-undecyl-2-phenazinyl)carbonyl]-, in 1 page.
CAS Registry No. 566157-42-4; STN entry date: Aug. 14, 2003; Alanine, N-[(9,10-dihydro-9-oxo-3-acridinyl)carbonyl]-2-methyl-, in 1 page.
CAS Registry No. 289062-66-4; STN entry date: Sep. 14, 2000; Acetic acid, [(2,4-dichlorobenzoyl)amino](phenylthio)-, in 1 page.
CAS Registry No. 15643-65-9; STN entry date: Nov. 16, 1984; Acetic acid, [(3,4-dichlorobenzoyl)amino]phenoxy-, in 1 page.
CAS Reg. No. 1187056-39-8, Entered STN: Oct. 1, 2009; Acetic acid, 2-cyano-2-[(2,6-difluorobenzoyl)amino]-, ethyl ester in 1 page.
CAS Reg. No. 885026-68-6, Entered STN: May 19, 2006; Benzamide, N-(2-butoxy-1-cyano-1-methylethyl)-2,6-dichloro- in 1 page.
CAS Reg. No. 1825463-80-6; STN Entry Date Dec. 9, 2015; Benzamide, N-(cyanocyclopropylmethyl)-6-fluoro-2,3- in 1 page.
CAS Reg No. 1551381-70-4, STN Entry Date: Feb. 20, 2014; Benzamide, N-(1-cyanopropyl)-2,6-difluoro-3-methyl- in 1 page.

(56) References Cited

OTHER PUBLICATIONS

CAS Reg No. 1555291-73-0, STN Entry Date: Feb. 25, 2014; Benzamide, 4-chloro-N-(1-cyanobutyl)-2,5-difluoro- in 1 page.
CAS Reg No. 1551443-75-4, STN Entry Date: Feb. 20, 2014; Benzamide, 4-chloro-N-(1-cyano-1-methylpropyl)-2,5-difluoro- in 1 page.
CAS Registry No. 1347051-33-5, Entered STN: Dec. 1, 2011; 1H-Imidazole-5-hexanoic acid, β-[[[(6S,8aS)-octahydro-4-oxo-2-(phenylmethyl)sulfonyl]pyrrolo[1,2-a]pyrazin-6-yl]carbonyl]amino]-a-oxo-, methyl ester, 1 page.
CAS Registry No. 1026166-23-3, Entered STN: Jun. 8, 2008 ; Hexanoic acid, 3-[[[(1R,2S,5S)-3-[(2S)-2-cyclohexyl-2-[(3,3-dimethyl-1-oxobutyl)amino]acetyl]-6,6-dimethyl-3-azabicyclo[3.1.0]hex-2-yl]carbonyl]amino]-6,6,6-trifluoro-2-oxo-, 1 page.
CAS Registry No. 2026817-08-1, Entered STN: Nov. 8, 2016; D-Leucine, N-[[3-(3-thienyl)-1H-pyrazol-4-yl]carbonyl]-, 1 page.
CAS Registry No. 2049278-49-9, Entered STN: Dec. 15, 2016; 4-Hexenoic acid, 2-[[[1-methyl-3-(2-thienyl)-1H-pyrazol-4-yl]carbonyl]amino]-, 1 page.
CAS Registry No. 2039960-52-4, Entered STN: Nov. 28, 2016; 5-Hexenoic acid, 2-[[[1-methyl-3-(2-thienyl)-1H-pyrazol-4-yl]carbonyl]amino]-, 1 page.
CAS Registry No. 2026895-95-2, Entered STN:Nov. 8, 2016; L-Norleucine, N-[[3-(5-chloro-2-thienyl)-1H-pyrazol-4-yl]carbonyl]-, 1 page.
CAS Registry No. 2026863-64-7, Entered STN: Nov. 8, 2016; L-Norleucine, N-[[4-(5-chloro-2-thienyl)-1H-pyrrol-3-yl]carbonyl]-, 1 page.
CAS Registry No. 1796920-43-8, Entered STN: Jul. 8, 2015; 1H-Pyrrole-3-carboxamide, N-(2-amino-1-methyl-2-oxoethyl)-4-(5-chloro-2-thienyl)-, 1 page.
Gopalsamy et al., 2004, Identification of [(naphthalene-1-carbonyl)-amino]-acetic acid derivatives as nonnucleoside inhibitors of HCV NS5B RNA dependent RNA polymerase. Bioorg Med Chem Lett. 14(16):4221-4224.
Kling et al., 2018, Mitigating the Metabolic Liability of Carbonyl Reduction: Novel Calpain Inhibitors with P1' Extension, ACS Med Chem Lett. 9(3):221-226.
Li et al., 1996, Novel peptidyl alpha-keto amide inhibitors of calpains and other cysteine proteases, J Med Chem. 39(20):4089-4098.
Lubisch et al., 2003, Benzoylalanine-derived ketoamides carrying vinylbenzyl amino residues: discovery of potent water-soluble calpain inhibitors with oral bioavailability, J Med Chem. 46(12):2404-2412.
Muniappan et al., 2017, Calpain Inhibition Attenuates Adipose Tissue Inflammation and Fibrosis in Diet-induced Obese Mice, Sci Rep. 7:14398.
Nimmrich et al., 2008, Inhibition of Calpain Prevents N-Methyl-D-aspartate-Induced Degeneration of the Nucleus Basalis and Associated Behavioral Dysfunction, J Pharmacol Exp Ther. 327(2):343-352.
Ross et al., 2013, Biosynthetic Multitasking Facilitates Thalassospiramide Structural Diversity in Marine Bacteria, J Am Chem Soc. 135(3):1155-1162.
Singh et al., 2015, Identification of amino acid appended acridines as potential leads to anti-cancer drugs. Bioorg Med Chem Lett. 25(18):3854-3858.
Vengeliene et al., 2016, The Calpain Inhibitor A-705253 Attenuates Alcohol-Seeking and Relapse with Low Side-Effect Profile, Neuropsychopharmacology. 41(4):979-988 [online published Jul. 28, 2015].
Zhang et al., 2016, Family-wide Structural Characterization and Genomic Comparisons Decode the Diversity-oriented Biosynthesis of Thalassospiramides by Marine Proteobacteria, J Biol Chem. 291(53):27228-27238.
European Extended Search Report dated Jan. 23, 2020 for Application No. EP 17824731.8, filed Feb. 4, 2019.
Beaucage S.L., Oligodeoxyribonucleotides synthesis. Phosphoramidite approach., (1993) Methods Mol. Biol., 20, 33-61.
Boyer et al., Induction and regulation of epithelial-mesenchymal transitions., (2000) Biochem. Pharmacol, 60, 1091-1099.
Branton et al., TGF-beta and fibrosis., (1999) Microbes Infect, 1(15), 1349-1365.
Brooks et al., CHARMM: A program for macromolecular energy, minimization, and dynamics calculations, (1983) J. Comp. Chem., 4, 187-217.
Burkert et al., Pitfalls in the use of the torsion angle driving method for the calculation of conformational interconversions., (1982) J Comp. Chem, 3, 40-46.
Capaldi et al., Signal amplification through nucleotide extension and excision on a dendritic DNA platform., (2000) Nucleic Acids Res., 28(7), e21.
Chubanov et al., Natural and synthetic modulators of SK (K(ca)2) potassium channels inhibit magnesium-dependent activity of the kinase-coupled cation channel TRPM7., (2012) Br J Pharmacol, 166(4), 1357-1376.
Clackson et al., Making antibody fragments using phage display libraries. (1991) Nature, 352:624-628.
Coburn et al., Potent and specific inhibition of human immunodeficiency virus type 1 replication by RNA interference., (2002) J. Virol., 76, 9225-9231.
Cohen et al., Molecular Modeling Software and Methods for Medicinal Chemistry, (1990) Journal of Medicinal Chemistry, 33(3), 883-894.
Connolly M.L., Solvent-Accessible Surfaces of Proteins and Nucleic Acids., (1983) Science, 221(4612), 709-713.
Cwirla et al., Peptides on phage: a vast library of peptides for identifying ligands., (1990) Proc. Natl. Acad. Sci. USA, 87, 6378.
Davis et al., The Crystal Structures of Human Calpains 1 and 9 Imply Diverse Mechanisms of Action and Auto inhibition., (2007) J. Mol. Biol., 366, 216-229.
De Maria et al., Calpain Expression and Activity during Lens Fiber Cell Differentiation., (2009) J. Biol. Chem., 284 (20), 13542-50.
Dunbrack et al., Meeting review: the Second Meeting on the Critical Assessment of Techniques for Protein Structure Prediction (CASP2), Asilomar, California, Dec. 13-16, 1996., (1997) Folding and Design, 2, R27; 16 pages.
Egholm et al., PNA hybridizes to complementary oligonucleotides obeying the Watson-Crick hydrogen-bonding rules., (1993) Nature, 365(6446), 566-568.
Friedman et al., Therapy for fibrotic diseases: nearing the starting line., (2013) Sci. Transl. Med., 5(167), 167-17 pages.
Geysen et al., Small peptides induce antibodies with a sequence and structural requirement for binding antigen comparable to antibodies raised against the native protein., (1985) Proc. Natl. Acad. Sci. USA, 82(1), 178-182.
Geysen et al., Strategies for epitope analysis using peptide synthesis., (1987) Journal of Immunological Methods., 102(2), 259-274.
Geysen et al., Use of peptide synthesis to probe viral antigens for epitopes to a resolution of a single amino acid., (1984) Proc. Natl. Acad. Sci. USA, 81, 3998-4002.
Gooch et al., Invovlement of calcineurin in transforming growth factor-beta-mediated regulation of extracellular maxtrix accumulation., (2004) J. Biol Chem., 279(15), 15561-70.
Goodford P.J., A computational procedure for determining energetically favorable binding sites on biologically important macromolecules., (1985) J. Med. Chem, 28, 849-857.
Goodsell et al., Automated docking of substrates to proteins by simulated annealing., (1990) Protein., 8(3): 195-202.
Hata et al., Calpain 8/nCL-2 and Calpain 9/nCL-4 Constitute an Active Protease Complex, G-Calpain, Involved in Gastric Mucosal Defense., (2010) PloS Genet., 6(7), e1001040 in 14 pages.
Hyrup et al., Peptide nucleic acids (PNA): synthesis, properties and potential applications., (1996) Bioorg Med Chem., 4(1), 5-23.
Iwano et al., Evidence that fibroblasts derive from epithelium during tissue fibrosis., (2002) J Chit Invest., 110(3): 341-350.
Janda et al., Ras and TGF-beta cooperatively regulate epithelial cell plasticity and metastasis: dissection of Ras signaling pathways., (2002) J. Cell Biol, 156, 299-313.
Jones et al. Improved methods for building protein models in electron density maps and the location of errors in these models., (1991) Acta Cryst., A47, 110-119.

(56) References Cited

OTHER PUBLICATIONS

Kalluri et al., Epithelial-mesenchymal transition and its implications for fibrosis., (2003) J Clin Invest, 112(12), 1776-1784.
Kang, et al., Antibody redesign by chain shuffling from random combinatorial immunoglobulin libraries., (1991) Proc. Natl. Acad. Sci. USA, 88, 11120-11123.
Kiemer, et al., Identification of genes involved in epithelial-mesenchymal transition and tumor progression., (2001) Oncogene, 20, 6679-6688.
Kim et al., Targeting Calpains: a Therapeutic Strategy for the Treatment of TGFbeta Mediated Mesenchymal Transition and Associated Pathologies., (2014) 64th Annual Meeting of the American Society of Human Genetics.
Kraulis, MOLSCRIPT: a program to produce both detailed and schematic plots of protein structures., (1991) J Appl Cryst., 24, 946-950.
Kuntz et al., A geometric approach to macromolecule-ligand interactions., (1982) J. Mol. Biol., 161, 269-288.
Kuntz I.D., Structure-Based Strategies for Drug Design and Discovery, (1992) Science 257:1078-1082.
Leask et al., TGF-beta signaling and the fibrotic response., (2004) FASEB J., 18(7), 816-827.
LeBleu et al., Origin and function of myofibroblasts in kidney fibrosis., (2013) Nat Med, 19(8), 1047-1053.
Lee et al., Bleomycin delivery by osmotic minipump: similarity to human scleroderma interstitial lung disease., (2014) Am J Physiol Lung Cell Mol Physiol, 306(8), L736-748.
Lee et al., Molecular Cloning and Characterization of a Novel Tissue-Specific Calpain Predominantly Expressed in the Digestive Tract., (1998) Biol Chem., 379(2), 175-183.
Li et al., Suppression of atherogenesis by delivery of TGFbeta1ACT using adeno-associated virus type 2 in LDLR knockout mice., (2006) Biochem Biophys Res Commun., 344(3): 701-707.
Lowman et al., Selecting high-affinity binding proteins by monovalent phage display., (1991) Biochemistry, 30(45): 10832-10838.
Ma et al., Expression of calpain small subunit 2 in mammalian tissues., (2004) Curr Eye Res., 29(4-5), 337-347.
Mag et al., Synthesis and selective cleavage of an oligodeoxynucleotide containing a bridged internucleotide 5'-phosphorothioate linkage., (1991) Nucleic Acids Res., 19(7): 1437-1441.
Mani et al., The epithelia-mesenchymal transition generates cells with properties of stem cells., (2008) Cell, 122(4), 704-715.
Marks et al., By-passing immunization. Human antibodies from V-gene libraries displayed on phage., (1991), J Mol Biol., 222, 581-597.
McKay et al., Characterization of a Potent and Specific Class of Antisense Oligonucleotide Inhibitor of Human Protein Kinase C-α Expression., (1999) Biol. Chem., 274(3): 1715-1722.
Miranker et al., Functionality maps of binding sites: a multiple copy simultaneous search method., (1991) Proteins. 11(1): 29-34.
Miyazono K., Transforming growth factor-beta signaling in epithelial-mesenchymal transition and progression of cancer., (2009) Proc Jpn Acad Ser. B. Phys. Bio. Sci., 85(8), 314-323.
Navia et al., Use of structural information in drug design., (1992) Current Opinion in Structural Biology, 2(2): 202-210.
Nielsen, P.E., Peptide nucleic acid (PNA): A model structure for the primordial genetic material?, (1993) Origins of life and evolution of biospheres, 23(5), 323-327.
Nieto M.A., The snail superfamily of zinc-finger transcription factors., (2002) Nat Rev Mol Cell Biol., 3, 155-166.
Nishibata et al., Automatic creation of drug candidate structures based on receptor structure. Starting point for artificial lead generation., (1991) Tetrahedron, 47(43), 8985-8990.
Peng et al., Bleomycin induces molecular changes directly relevant to idiopathic pulmonary fibrosis: A model for "active" disease., (2013) PLOS One, 8(4), e59348; 15 pages.
Piccirillo et al., TGF-β1 Somatic Gene Therapy Prevents Autoimmune Disease in Nonobese Diabetic Mice., (1998) J Immunol., 161 (8): 3950-3956.

Piera-Velazquez et al., Role of endothelial-mesenchymal transition (EndoMT) in the pathogenesis of fibrotic disorders. (2011), Am J Pathol., 179(3), 1074-1080.
Savary et al., Role of TGF-β signaling in EMT, cancer progression and metastasis., (2011) Drug Discovery Today: Disease Models, 8(2-3), 121-126.
Schoofs et al., Epitopes of an influenza viral peptide recognized by antibody at single amino acid resolution., (1988) J Immunol., 140(2): 611-616.
Singh et al., EMT, cancer stem cells and drug resistance: an emerging axis of evil in the war on cancer., (2010) Oncogene, 29(34), 4741-4751.
Smith G.P., Surface presentation of protein epitopes using bacteriophage expression systems., (1991) Current Opin Blotechnol., 2, 668-673.
Stewart et al., Lentivirus-delivered stable gene silencing by RNAi in primary cells., (2003) RNA, 9, 493-501.
Strutz et al., Identification and characterization of a fibroblast marker: FSP1., (1995) J Cell Biol, 130(2): 393-405.
Summerton J., Morpholino antisense oligomers: the case for an RNase H-independent structural type., (1999) Biochim Biophys Acta., 1489, 141-158.
Suzuki et al., Structure, activity, and biology of calpain., (2004) Diabetes, 53(Suppl 1): S12-S18.
Tojo et al., The ALK-5 Inhibitor A-83-01 inhibits Smad signaling and epithelial-to-mesenchymal transition by transforming growth factor-beta. (2005) Cancer Sci, 96(11), 791-800.
Verlinde et al., Structure-based drug design: progress, results and challenges., (1994) Structure, 2, 577-587.
Wahlestedt et al., Potent and nontoxic antisense oligonucleotides containing locked nucleic acids., (2000) PNAS USA, 97(10): 5633-5638.
Weiner et al., A new force field for molecular mechanical simulation of nucleic acids and proteins., (1984) J Am Chem Soc. 106, 765-784.
Willis et al., TGF-beta-induced EMT: mechanisms and implications for fibrotic lung disease., (2007) Amer J Physiol Lung Cell Mol Physiol, 293(3): L525-L534.
Wu et al. Critical role of calpain-mediated cleavage of calcineurin in excitotoxic neurodegeneration. (2004), J Biol Chem. 279(6), 4929-4940.
Wu et al., Detection of epithelial to mesenchymal transition in airways of a bleomycin induced pulmonary fibrosis model derived from an a-smooth muscle actin-Cre transgenic mouse., (2007) Respir Res., 8(1), 1; 11 pages.
Wynn T., Cellular and molecular mechanisms of fibrosis., (2008) J Pathol., 214(2): 199-210.
Xue et al., The Gatekeeper Effect of Epithelial-Mesenchymal Transition Regulates the Frequency of Breast Cancer Metastasis., (2003) Cancer Res., 63, 3386-3394.
Yang et al., Dissection of key events in tubular epithelial to myofibroblast transition and its implications in renal interstitial fibrosis., (2001) Am J Pathol., 159(4): 1465-1475.
Yoshikawa et al., Isolation of Two Novel Genes, Down-regulated in Gastric Cancer., (2000) Jpn J Cancer Res., 91(5), 459-463.
Zeisberg et al., Renal Fibrosis: Collagen Composition and Assembly Regulates Epithelial-Mesenchymal Transdifferentiation., (2001) Am J Pathol., 159(4): 1313-1321.
Zimmerman et al., The calpain small subunit gene is essential: its inactivation results in embryonic lethality. (2000) IUBMB Life, 50(1), 63-68.
Bihovsky et al., 2004, 1,2-Benzothiazine 1,1-dioxide α-ketoamide analogues as potent calpain I inhibitors, Bioorg Med Chem Lett. 14(4):1035-1038.
Blum et al., 2003, Complementary use of ion trap / time-of-flight mass spectrometry in combination with capillary high-pressure liquid chromatography: Early characterization of in vivo metabolites of the cathepsin K inhibitor NVP-AAV490 in rat. J Chromatography B. 787:255-270.
Brodney et al., 2015, Utilizing Structures of CYP2D6 and BACE1 Complexes To Reduce Risk of Drug—Drug Interactions with a Novel Series of Centrally Efficacious BACE1 Inhibitors, J Med Chem. 58:3223-3252.

(56) References Cited

OTHER PUBLICATIONS

CAS Registry No. 1309010-71-6; STN entry date: Jun. 13, 2011; D-Alanine, N-[(1-phenyl-1H-imidazol-5-yl)carbonyl] in 1 page.
Chatterjee et al., 1999, P2-achiral, P'-extended alpha-ketoamide inhibitors of calpain I. Bioorg Med Chem Lett. 9(16):2371-2374.
Chen et al., 2012, New Tripeptide-Based Macrocyclic Calpain Inhibitors Formed by N-Alkylation of Histidine, Chern Biodiver. 9(11):2473-2484.
Damalanka et al., 2016, Oxadiazole-Based Cell Permeable Macrocyclic Transition State Inhibitors of Norovirus 3CL Protease, J Med Chem. 59(5):1899-1913.
Donald et al., 1991, C10 N-Acyl Modified FK-506: A Possible Hybrid Analogue of the Transition State of Peptidyl-Prolyl Cis-Trans Isomerization, Tetrahedron Lett., 32(10):1375-1378.
Dourdin et al., 2001, Reduced Cell Migration and Disruption of the Actin Cytoskeleton in Calpain-deficient embryonic Fibroblasts, J Biol Chem. 276(51):48382-48388.
Gardiner et al., 2006, Ring closing metathesis of a- and b-amino acid derived dienes, J Organomet Chem. 691:5487-5496.
Goll et al., 2003, The Calpain System, Physiol Rev. 83(3):731-801.
Jánossy et al., 2004, Calpain as a multi-site regulator of cell cycle, Biochem Pharmacol. 67(8):1513-1521.
Jones et al., 2009, Efficient Large-Scale Synthesis of CAT811, a Potent Calpain Inhibitor of Interest in the Treatment of Cataracts, Aust J Chem. 62:671-675.
Jones et al., 2013, A Template-Based Approach to Inhibitors of Calpain 2, 20S Proteasome, and HIV-1 Protease, Chem Med Chem. 8(12):1918-1921.
Jones et al., 2014, The Preparation of Macrocyclic Calpain Inhibitors by Ring Closing Metathesis and Cross Metathesis, Aust J. Chem. 67:1257-1263.
Kim et al., 2011, Synthesis of chromone carboxamide derivatives with antioxidative and calpain inhibitory properties, Eur J Med Chem. 46(5):1721-1728.
Kim et al., 2015, Discovery and structure-activity relationships of pyrazolodiazepine derivatives as the first small molecule agonists of the Drosophila sex peptide receptor, Bioorg Med Chem. 23:1808-1816.
Kling et al., 2017, Discovery of Novel and Highly Selective Inhibitors of Calpain for the Treatment of Alzheimer's Disease: 2☐(3-Phenyl☐1H☐pyrazol-1-yl)-nicotinamides, J Med Chem. 60:7123-7138.
Lamouille et al., 2014, Molecular mechanisms of epithelial-mesenchymal transition, Nat Rev Mol Cell Biol. 15(3):178-196 in 46 pages.
Lee et al., 2005, Synthesis and biological evaluation of chromone carboxamides as calpain inhibitors, Bioorg Med Chem Lett., 15(11):2857-2860.
Leloup et al., 2006, Involvement of calpains in growth factor-mediated migration, Int J Biochem Cell Biol. 38(12):2049-2063.
Li et al., 2015, Synthesis and Cytotoxic Activities of Novel Amino Acid-Conjugates of Pyrrole Derivatives. Youji Huaxue. 35:167-174.
Lu et al., 2015, Mechanism of Action of Thalassospiramides, A New Class of Calpain Inhibitors, Sci Rep. 5:8783 in 8 pages.
Lubisch et al., 2002, Discovery of phenyl alanine derived ketoamides carrying benzoyl residues as novel calpain inhibitors, Bioorg Med Chem Lett., 12(10):1335-1338.
Mandadapu et al., 2013, Macrocyclic Inhibitors of 3C and 3C-like Proteases of Picornavirus, Norovirus, and Coronavirus, Bioorg Med Chem Lett. 23(13):3709-3712.
Miettinen et al., 1994, TGF-β Induced Transdifferentiation of Mammary Epithelial Cells to Mesenchymal Cells: Involvement of Type I Receptors, j Cell Biol. 127(6 Pt 2):2021-2036.
Morton et al., 2013, A Macrocyclic Calpain Inhibitor Slows the Development of Inherited Cortical Cataracts in a Sheep Model, Invest Ophthal Visual Science. 54(1):389-395.
Nam et al., 2008, Design and synthesis of 4-quinolinone 2-carboxamides as calpain inhibitors, Bioorg Med Chem Lett., 18(1):205-209.

Nema et al., 2011, Excipients and Their Role in Approved Injectable Products: Current Usage and Future Directions, Pda J Pharm Sci Technol. 65(3):287-332.
Oh et al., 2007, Thalassospiramides A and B, Immunosuppressive Peptides from the Marine Bacterium *Thalassospira* sp., Org Ltts. 9(8):1525-1528.
Pegorier et al., 2010, Bone Morphogenetic Protein (BMP)-4 and BMP-7 regulate differentially Transforming Growth Factor (TGF)-β1 in normal human lung fibroblasts (NHLF), Respir Res. 11:85 in 11 pages.
Pehere et al., 2012, New β-Strand Templates Constrained by Huisgen Cycloaddition, Org Lett. 14(5):1330-1333.
Pehere et al., 2013, New cylindrical peptide assemblies defined by extended parallel β-sheets, Org Biomol Chem. 11(3):425-429.
Pehere et al., 2013, Synthesis and Extended Activity of Triazole-Containing Macrocyclic Protease Inhibitors, Chem Eur J. 19:7975-7981.
Powell et al., 1998, Compendium of Excipients for Parenteral Formulations, pDA; J Pharm Sci Technol. 52(5):238-311.
Ravulapalli et al., 2009, Distinguishing between calpain heterodimerization and homodimerization, FEBS J. 276(4):973-982.
Rotstein et al., 2014, Spirocyclic hypervalent iodine(III)-mediated radiofluorination of non-activated and hindered aromatics, Nature Comm. 5:4365-4371.
Rotstein et al., 2016, Mechanistic Studies and Radiofluorination of Structurally Diverse Pharmaceuticals with Spirocyclic Iodonium(III) Ylides, Chem Sci. 7(7):4407-4417.
Santos et al., 2012, Distinct Regulatory Functions of Calpain 1 and 2 during Neural Stem Cell Self-Renewal and Differentiation, PLoS One 7(3):e33468 in 12 pages.
Sasmal et al., 2011, Structure-activity relationship studies of novel pyrazole and imidazole carboxamides as cannabinoid-1 (CB1) antagonists. Bioorg Med Chem Lett. 21(16):4913-4918.
Schád et al., 2002, A novel human small subunit of calpains, Biochem J 342(Pt 2):383-388.
Skogh et al., 2013, Aminocarbonylation of 4☐Iodo☐1H☐imidazoles with an Amino Acid Amide Nucleophile: Synthesis of Constrained H☐Phe-Phe-NH2 Analogues. J Org Chem. 78:12251-12256.
Stoermer et al., 2009, Base-Sensitivity of Arginine Alpha-Ketoamide Inhibitors of Serine Proteases, Aust J Chem. 62(9):988-992.
Von Dobeneck et al., 1976, Diaminopyrrolinone, Liebigs Ann Chem., 3:476-486.
Walker et al., 2001, General method for the synthesis of cyclic peptidomimetic compounds, Tetrahed Letts. 42(34):5801-5804.
Woon et al., 2011, Structure guided development of potent reversibly binding penicillin binding protein inhibitors, ACS Med Chem Lett., 2(3):219-223 and Supporting Information, S1-S46.
Young et al., 2010, Beyond the Canonical 20 Amino Acids: Expanding the Genetic Lexicon, J Biol Chem. 285(15):11039-11044.
Zhong et al., 2005, 3-(2-Chlorophenyl)-N-(2-cyano-4-methyl-2-pentyl)-5-methylisoxazole-4-carboxamide. Acta Cryst. Section E. E61:o2621-o2622 in 7 pages.
Bogen et al., Toward the Back-Up of Boceprevir (SCH 503034): Discovery of New Extended P4-Capped Ketoamide Inhibitors of Hepatitis C virus NS3 Serine Protease with Improved Potency and Pharmacokinetic Profiles. J Med Chem. (2009) 52(12): 3679-3688.
Brouillette et al., Supporting Information for Valuable Versatile Reactivity of Thiaaisatoic Anhydrides: Expedient Solid-Phase Synthesis of Thieno [1,4]diazepine-2,5-diones, Synlett (2008) 15:2360-2364; Aug. 22, 2008 pp. 1-58.
CAS Registry No. 1422551-25-4, N-[(1S)-2-amino-1-(1H-imidazol-5-ylmethyl)-2-oxoethyl]-3-(3-fluorophenyl)-1H-Pyrazole-4-carboxamide, Entered STN Mar. 7, 2013.
Celatka et al., 2002, Asymmetric synthesis of a C1-C19 fragment of Ulapualide A. Tetrahed Lttrs. 43(39): 7043-7046.
Gafni et al., "Calpain Activation in Huntington's Desearse". J Neuroscience (2002) 22(12): 4842-4849.
Jansen et al., 1961. Some 4-Substituted Oxazoles. J Chem Society pp. 405-411. (see Reaxys-Abs).
REAXYS Database, 2002, Database Accession No. 9305036, Elsevier Life Sciences IP Limited, 1 page.

(56) References Cited

OTHER PUBLICATIONS

REAXYS Database, 1961, Database Accession No. 849427, Elsevier Life Sciences IP Limited, 2 page.

Wang et al., Synthesis and Biological Activity of 6-Substituted Pyrrolo [2,3-d]pyrimidine Thienoyl Regioisomers as Inhibitors of de Novo Purine Biosynthesis with Selectivity for Cellular Uptake by High Affinity Folate Receptors and the Proton-Coupled Folate Transporter over the Reduced Folate Carrier. J Med Chem. (2012) 55(4):1758-1770.

Yildiz-Unal et al., "Neuroprotective Strategies Against Calpain-Mediated Neurodegernation". Neuropsychiatr Dis Treat. (2015) 11:297-310.

Abell et al., 2009, Molecular Modeling, Synthesis, and Biological Evaluation of Macrocyclic Calpain Inhibitors, Angew Chem Int Ed Engl. 48(8):1455-1458.

Cohrt A. Emil. 2014, Solid-phase synthesis of peptide thioureas and thiazole-containing macrocycles through Ru-catalyzed ring-closing metathesis, ACS Comb Sci. 16(2):71-77 and Supporting Information in 55 pages.

Halland et al., 2014, Small Macrocycles As Highly Active Integrin α2β1 Antagonists, ACS Med Chem Lett. 5(2):193-198.

Low et al., 2016, Rational Design of Calpain inhibitors Based on Calpastatin Peptidomimetics, J Med Chem. 59(11):5403-5415.

Stuart et al., 2011, Molecular Modeling: A Search for a Calpain Inhibitor as a New Treatment for Cataractogenesis, J Med Chem. 54(21):7503-7522.

Wells et al., 2001, 1,2-Benzothiazine 1,1-Dioxide P2-P3 Peptide Mimetic Aldehyde Calpain I Inhibitors, J Med Chem. 44:3488-3503.

International Search Report and Written Opinion dated Aug. 31, 2017 for Application No. PCT/US2017/040109, filed Jun. 29, 2017.

International Preliminary Report on Patentability [Corrected] dated Aug. 2, 2018 for Application No. PCT/US2017/040109, filed Jun. 29, 2017.

Cao et al., Novel Biologically Active Series of N-acetylglucosamine Derivatives for the suppressive activities on GAG Release. Carbohydrate Res. (2016) 443: 73-79.

CAS Registry No. 1980787-62-9/-71-0/-72-1; "D-Glucose", Entered STN Aug. 26, 2016 in 3 pages.

Australian Examination Report dated Mar. 25, 2021 for Application No. 2017292646, filed Jan. 21, 2019.

* cited by examiner

CALPAIN MODULATORS AND THERAPEUTIC USES THEREOF

BACKGROUND

Field of the Invention

The present invention relates to the fields of chemistry and medicine. More particularly, the present invention relates to macrocyclic α-keto amide compounds as small molecule calpain modulators, compositions, their preparation, and their use as therapeutic agents.

Description of the Related Art

Fibrotic disease accounts for an estimated 45% of deaths in the developed world but the development of therapies for such diseases is still in its infancy. The current treatments for fibrotic diseases, such as for idiopathic lung fibrosis, renal fibrosis, systemic sclerosis, and liver cirrhosis, are few in number and only alleviate some of the symptoms of fibrosis while failing to treat the underlying cause.

Despite the current limited understanding of the diverse etiologies responsible for these conditions, similarities in the phenotype of the affected organs, across fibrotic diseases, strongly support the existence of common pathogenic pathways. At present, it is recognized that a primary driver of fibrotic disease is a high transforming growth factor-beta (TGFβ) signaling pathway which can promote the transformation of normally functioning cells into fibrosis-promoting cells. Termed "myofibroblasts," these transformed cells can secrete large amounts of extracellular matrix proteins and matrix degrading enzymes, resulting in the formation of scar tissue and eventual organ failure. This cellular process is transformative and termed "myofibroblast differentiation" (which includes Epithelial-to-Mesenchymal Transition (EpMT) and its variations like Endothelial-to-Mesenchymal Transition (EnMT) and Fibroblast-to-Myofibroblast Transition (FMT)). This process is a major target for the treatment of fibrotic diseases. Myofibroblast differentiation has also been shown to occur within cancer cells that have been chronically exposed to high TGFβ, causing stationary epithelial cells to become motile, invasive, and metastasize. Thus, within the context of cancer, the signaling has been documented to associate with the acquisition of drug resistance, immune system evasion, and development of stem cell properties.

Despite the tremendous potential of myofibroblast differentiation-inhibiting drugs, and the numerous attempts to develop a working treatment, the data gathered thus far has yet to translate into practical therapy. This is partly due to the lack of an ideal target protein. Initial strategies to target the myofibroblast differentiation process focused on proximal inhibition of the TGFβ signaling pathway by various methods, including targeting ligand activators (e.g. alpha-v integrins), ligand-receptor interactions (e.g., using neutralizing antibodies) or TGFβ receptor kinase activity (e.g., small molecule chemical compound drugs to block signal transduction). Unfortunately, TGFβ is a pleiotropic cytokine with many physiological functions such that global suppression of TGFβ signaling was also associated with severe side effects. Additionally, current data suggests that such proximal inhibition may be vulnerable to pathologic workaround strategies (i.e., due to redundancy or compensation), that would limit the utility of such drugs. Further complicating matters is that, in cancer, TGFβ signaling early on functions as an anti-tumorigenic growth inhibitor but later becomes tumor promoting and is another reason why selective inhibition of pathogenic elements of signaling is so strongly desired. In light of these inherent limitations, current treatment strategies have refocused on identification and inhibition of critical distal events in TGFβ signaling, which in theory would preferentially target the pathologic, but not physiological functions of TGFβ signaling.

SUMMARY

A compound having the structure of the formula I:

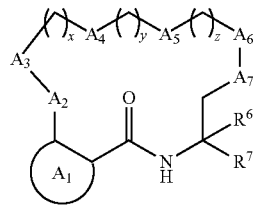

or a pharmaceutically acceptable salt thereof, wherein:

$A_1$ is selected from the group consisting of optionally substituted 3-10 membered heterocycloalkyl, optionally substituted $C_{6-10}$ aryl, optionally substituted 5-10 membered heteroaryl, and optionally substituted $C_{3-10}$ carbocyclyl;

$A_2$ is selected from the group consisting of optionally substituted 3-10 membered heterocycloalkyl, optionally substituted $C_{6-10}$ aryl, optionally substituted 5-10 membered heteroaryl, and optionally substituted $C_{3-10}$ carbocyclyl, —CH$_2$—, —C(R)(R)—, —S—, —O—, —NR—, —CH=CH—, —OC(O)NH—, —NHC(O)NH—, —NHC(O)O—, —NHC(O)—, —NHC(S)NH—, —NHC(S)O—, —NHC(S)—, and single bond;

$A_3$ is selected from the group consisting of optionally substituted $C_{6-10}$ aryl, optionally substituted 5-10 membered heteroaryl, optionally substituted 3-10 membered heterocycloalkyl, optionally substituted $C_{3-10}$ carbocyclyl, —CH$_2$—, —C(R)(R)—, —S—, —O—, —NR—, —CH=CH—, and single bond;

$A_4$ is selected from the group consisting of optionally substituted $C_{6-10}$ aryl, optionally substituted 5-10 membered heteroaryl, optionally substituted 3-10 membered heterocycloalkyl, optionally substituted $C_{3-10}$ carbocyclyl, —CH$_2$—, —C(R)(R)—, —S—, —O—, —NR—, optionally substituted $C_2$-$C_6$ alkenyl, and single bond;

$A_5$ is selected from the group consisting of optionally substituted $C_{6-10}$ aryl, optionally substituted 5-10 membered heteroaryl, optionally substituted 3-10 membered heterocycloalkyl, optionally substituted $C_{3-10}$ carbocyclyl, —CH$_2$—, —C(R)(R)—, —S—, —O—, —NR—, optionally substituted $C_2$-$C_6$ alkenyl, and single bond;

$A_6$ is selected from the group consisting of optionally substituted $C_{6-10}$ aryl, optionally substituted 5-10 membered heteroaryl, optionally substituted 3-10 membered heterocycloalkyl, optionally substituted $C_{3-10}$ carbocyclyl, —CH$_2$—, —C(R)(R)—, —S—, —O—, —NR—, optionally substituted $C_2$-$C_6$ alkenyl, and single bond;

$A_7$ is selected from the group consisting of optionally substituted $C_{6-10}$ aryl, optionally substituted 5-10 membered heteroaryl, optionally substituted 3-10 membered heterocycloalkyl, optionally substituted $C_{3-10}$ carbocyclyl, —CH$_2$—, —C(R)(R)—, —S—, —O—, —NR—, optionally substituted $C_2$-$C_6$ alkenyl, and single bond;

x is an integer from 0 to 2;
y is an integer from 1 to 4;
z is an integer from 0 to 4;

R⁷ is independently selected from —CH(OH)—R¹ and —COR¹;

R¹ is selected from the group consisting of H, OH, —CH$_2$F, —CH$_2$Cl, —COOH, —C(=O)N(R)(OR), —NR$^2$R$^3$, —CONR$^2$R$^3$, —CH(CH$_3$)=CH$_2$, —CH(CF$_3$)NR$^2$R$^3$, —C(F)=CHCH$_2$CH$_3$,

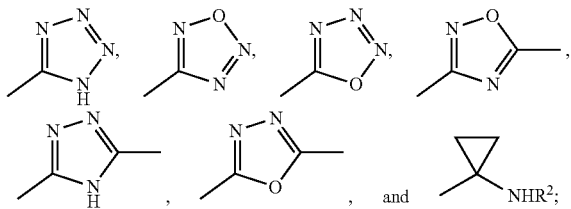

and each R, R$^2$, and R$^3$ are independently selected from —H, optionally substituted C$_{1-4}$ alkyl, optionally substituted C$_2$-C$_6$ alkynyl, optionally substituted C$_{1-8}$ alkoxyalkyl, optionally substituted 2- to 5-membered polyethylene glycol, optionally substituted C$_{3-7}$ carbocyclyl, optionally substituted 5-10 membered heterocyclyl, optionally substituted C$_{6-10}$aryl, and optionally substituted 5-10 membered heteroaryl; and R$^6$ is independently selected from —H, optionally substituted C$_{1-4}$ alkyl.

Other embodiments disclosed herein include a pharmaceutical composition comprising a therapeutically effective amount of a compound disclosed herein and a pharmaceutically acceptable excipient.

Other embodiments disclosed herein include a method of treating diseases and conditions mediated at least in part by the physiologic effects of CAPN1, CAPN2, or CAP9, or combinations thereof, comprising administering to a subject in need thereof a compound disclosed herein.

In some embodiments, compounds disclosed herein are specific inhibitors of one of: CAPN1, CAPN2 or CAPN9.

In some embodiments, compounds disclosed herein are selective inhibitors of one of: CAPN1, CAPN2 or CAPN9.

In some embodiments, compounds disclosed herein are selective inhibitors of: CAPN1 and CAPN2, or CAPN1 and CAPN9, or CAPN2 and CAPN9.

In some embodiments, compounds disclosed herein are effective inhibitors of CAPN1, CAPN2 and/or CAPN9.

In some embodiments, the macrocyclic α-keto amide compounds disclosed herein are broadly effective in treating a host of conditions arising from fibrosis or inflammation, and specifically including those associated with myofibroblast differentiation. Accordingly, compounds disclosed herein are active therapeutics for a diverse set of diseases or disorders that include or that produces a symptom which include, but are not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases or disorders.

In some embodiments, the compounds disclosed herein are used to treat diseases or conditions or that produces a symptom in a subject which include, but not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases.

In certain embodiments methods are provided for alleviating or ameliorating a condition or disorder, affected at least in part by the enzymatic activity of calpain 1 (CAPN1), calpain 2 (CAPN2), and/or calpain 9 (CAPN9), or mediated at least in part by the enzymatic activity of CAPN1, CAPN2, and/or CAPN9 wherein the condition includes or produces a symptom which includes: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and/or rheumatoid arthritis.

In some embodiments, the methods, compounds, and/or compositions of the present invention are used for prophylactic therapy.

In some embodiments, the CAPN1, CAPN2, and/or CAPN9 inhibiting compounds demonstrate efficacy in animal models of human disease. Specifically, in-vivo treatment of mice, rabbits, and other mammalian subjects with compounds disclosed herein establish the utility of these compounds as therapeutic agents to modulate CAPN1, CAPN2, and/or CAPN9 activities in humans and thereby ameliorate corresponding medical conditions.

Some embodiments provide compounds, pharmaceutical compositions, and methods of use to inhibit myofibroblast differentiation. Some embodiments provide compounds, pharmaceutical compositions, and methods of use for inhibiting CAPN1, CAPN2, and/or CAPN9 or combinations of these enzyme activities such as CAPN1 and CAPN2, or CAPN1 and CAPN9, or CAPN2 and CAPN9. Some embodiments provide methods for treatment of diseases and disorders by inhibiting CAPN1, CAPN2, and/or CAPN9 or combinations of these enzymatic activities.

DETAILED DESCRIPTION

In some embodiments, compounds that are macrocyclic α-keto amides are provided that act as calpain modulators. Various embodiments of these compounds include compounds having the structures of Formula I as described above or pharmaceutically acceptable salts thereof.

In some embodiments of compounds of Formula I:

A$_4$ is selected from the group consisting of optionally substituted C$_{6-10}$ aryl, optionally substituted 5-10 membered heteroaryl, optionally substituted 3-10 membered heterocyclyl, optionally substituted C$_{3-10}$ carbocyclyl, —CR$_2$—, —S—, —O—, —NR—, —CH=CH—, and single bond;

$A_5$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH═CH—, and single bond;

$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH═CH—, and single bond;

$A_7$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH═CH—, and single bond;

$R^7$ is —$COR^1$;

$R^1$ is selected from the group consisting of H, —OH, —$CH_2F$, —$CH_2Cl$, —COOH, —C(═O)N(R)OR, —$NH_2$, —$CONR^2R^3$, —CH($CH_3$)═$CH_2$, —CH($CF_3$)$NR^2R^3$, —C(F)═$CHCH_2CH_3$,

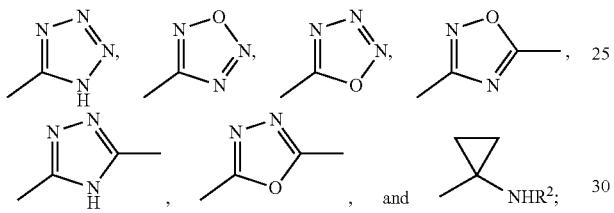

and each R, $R^2$, and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, and optionally substituted 5-10 membered heteroaryl.

Some embodiments of compounds of Formula (I) include compounds having the structure of Formula (I-a):

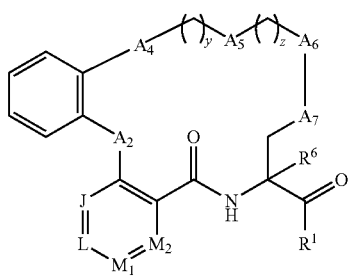

I-a or a pharmaceutically acceptable salt thereof, wherein:

J, L, $M_1$ and $M_2$ are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-a) or their pharmaceutically acceptable salts; J, L, $M_1$, and $M_2$ are selected from the group consisting of CH and N.

Some embodiments of compounds of Formula (I) include compounds having the structure of Formula (I-b):

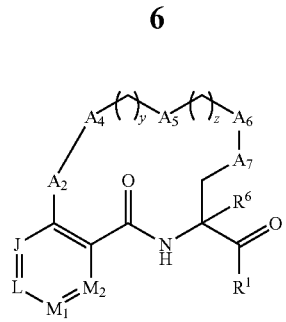

I-b or a pharmaceutically acceptable salt thereof, wherein:

J, L, $M_1$ and $M_2$ are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-b) or their pharmaceutically acceptable salts; J, L, $M_1$, and $M_2$ are selected from the group consisting of CH and N.

Some embodiments of compounds of Formula (I) include compounds having the structure of Formula (I-d):

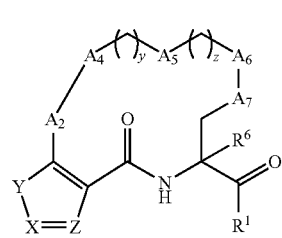

I-d or a pharmaceutically acceptable salt thereof, wherein:

Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (Id-1):

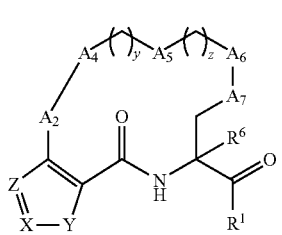

Id-1 or a pharmaceutically acceptable salt thereof, wherein:

Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (Id-2):

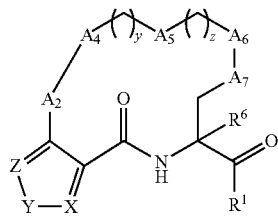

Id-2 or a pharmaceutically acceptable salt thereof, wherein:

Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (I-g):

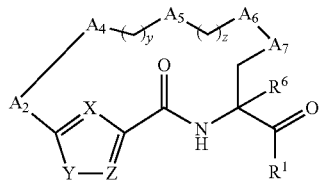

I-g or a pharmaceutically acceptable salt thereof, wherein:

Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of formula I-g1

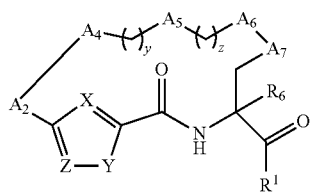

I-g1 or a pharmaceutically acceptable salt thereof, wherein:

Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl Some embodiments of compounds of Formula (I) include compounds having the structure of Formula (I-z):

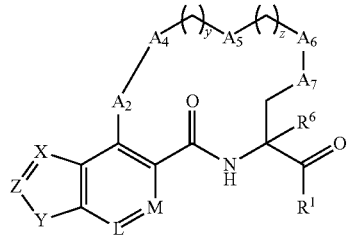

I-z or a pharmaceutically acceptable salt thereof, wherein:

Y is selected from the group consisting of $NR^5$, O, and S; X and Z are each independently selected from the group consisting of $C(R^4)$ and N; L and $M_1$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-z) or their pharmaceutically acceptable salts; L and $M_1$ are selected from the group consisting of CH and N.

Some embodiments of compounds of Formula (I) include compounds having the structure of formula I-z1:

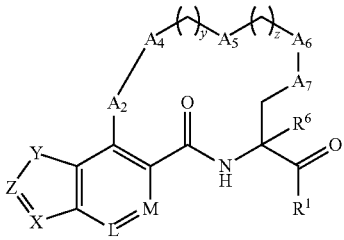

I-z1 or a pharmaceutically acceptable salt thereof, wherein:

Y is selected from the group consisting of $NR^5$, O, and S; X and Z are each independently selected from the group consisting of $C(R^4)$ and N; L and $M_1$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-z1) or their pharmaceutically acceptable salts, L and $M_1$ are independently selected from the group consisting of CH and N.

Some embodiments of compounds of Formula (I) include compounds having the structure of Formula (II-a):

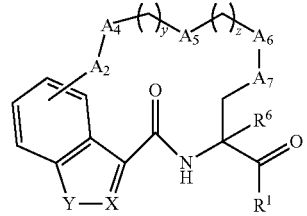

II-a or a pharmaceutically acceptable salt thereof, wherein:

Y is selected from the group consisting of $NR^5$, O, and S; and X is selected from the group consisting of $C(R^4)$ and N; $R^4$ is selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (II-b):

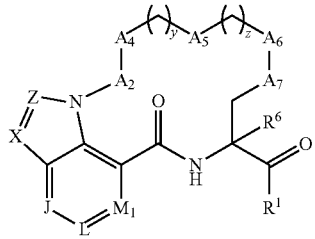

II-b or a pharmaceutically acceptable salt thereof, wherein:

X and Z are each independently selected from the group consisting of $C(R^4)$ and N;

J, L, and $M_1$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (II-b) or their pharmaceutically acceptable salts; J, L and $M_1$ are selected from the group consisting of CH and N.

Some embodiments of compounds of Formula (I) include compounds having the structure of Formula (II-c):

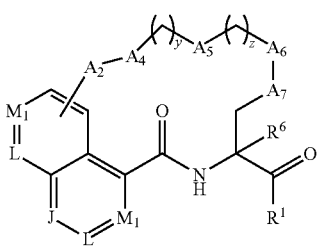

II-c or a pharmaceutically acceptable salt thereof, wherein:

X and Z are each independently selected from the group consisting of $C(R^4)$ and N;

J is selected from the group consisting of $C(R^4)$ and N; each L and each $M_1$ are independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (II-c) or their pharmaceutically acceptable salts; J, L and $M_1$ are selected from the group consisting of CH and N.

Some embodiments of compounds of Formula (I) include compounds having the structure of Formula (II-d):

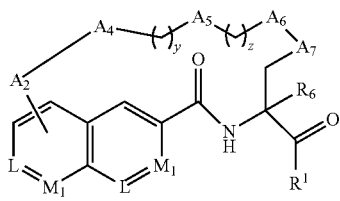

II-d or a pharmaceutically acceptable salt thereof, wherein:

each L and each $M_1$ are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (II-d) or their pharmaceutically acceptable salts; L and $M_1$ are selected from the group consisting of CH and N.

In some embodiments of Formula (I), (I-a), (I-b), (I-d), (Id-1), (Id-2), (I-g), (I-g1), (I-z), (I-z1), (II-a), (II-b), (II-c), or (II-d), $A_2$ is —$CH_2$—.

In some embodiments of Formula (I), (I-a), (I-b), (I-d), (Id-1), (Id-2), (I-g), (I-g1), (I-z), (I-z1), (II-a), (II-b), (II-c), or (II-d), $A_2$ is —O—.

Some embodiments of compounds of Formula (I) include compounds having the structure of Formula (I-c):

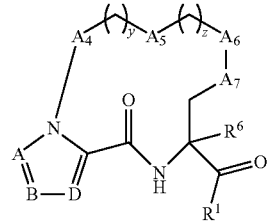

I-c or a pharmaceutically acceptable salt thereof, wherein:

A, B, and D are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

Some embodiments of compounds of Formula (I) include compounds having the structure of Formula (I-h):

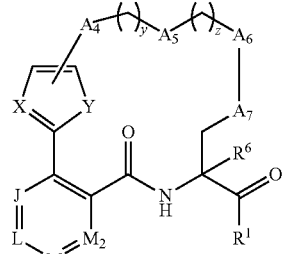

I-h or a pharmaceutically acceptable salt thereof, wherein:

Y is selected from the group consisting of $NR^5$, O, and S;

X is selected from the group consisting of $C(R^4)$ and N;

J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-h) or their pharmaceutically acceptable salts; J, L, $M_1$, and $M_2$ are selected from the group consisting of CH and N.

Some embodiments of compounds of Formula (I) include compounds having the structure of Formula (I-j):

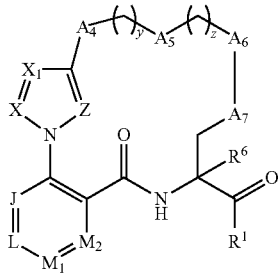

I-j or a pharmaceutically acceptable salt thereof, wherein:
Y is selected from the group consisting of $NR^5$, O, and S; X is selected from the group consisting of $C(R^4)$ and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-j) or their pharmaceutically acceptable salts; J, L, $M_1$, and $M_2$ are selected from the group consisting of CH and N.

Some embodiments of compounds of Formula (I) include compounds having the structure of Formula (I-k):

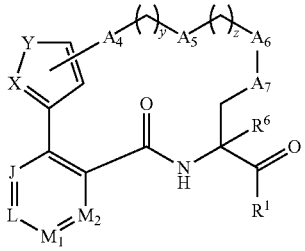

I-k or a pharmaceutically acceptable salt thereof, wherein:
Y is selected from the group consisting of $NR^5$, O, and S; X is selected from the group consisting of $C(R^4)$ and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-k) or their pharmaceutically acceptable salts; J, L, $M_1$, and $M_2$ are selected from the group consisting of CH and N.

Some embodiments of compounds of Formula (I) include compounds having the structure of Formula (I-l):

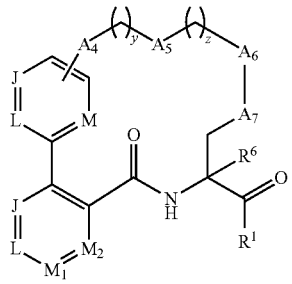

I-l or a pharmaceutically acceptable salt thereof, wherein:
each J, L, M, $M_1$ and $M_2$ are independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-1) or their pharmaceutically acceptable salts; J, L, $M_1$, and $M_2$ are selected from the group consisting of CH and N.

Some embodiments of compounds of Formula (I) include compounds having the structure of Formula (I-m):

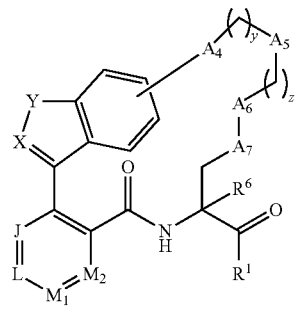

I-m or a pharmaceutically acceptable salt thereof, wherein:
Y is selected from the group consisting of $NR^5$, O, and S; X is selected from the group consisting of $C(R^4)$, and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-m) or their pharmaceutically acceptable salts; J, L, $M_1$, and $M_2$ are selected from the group consisting of CH and N.

Some embodiments of compounds of Formula (I) include compounds having the structure of Formula (I-n):

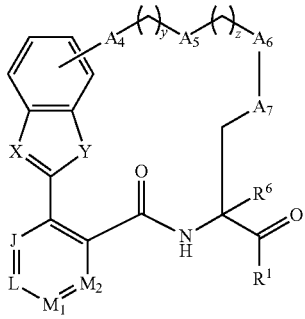

I-n or a pharmaceutically acceptable salt thereof, wherein:
Y is selected from the group consisting of $NR^5$, O, and S; X is selected from the group consisting of $C(R^4)$ and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-n) or their pharmaceutically acceptable salts; J, L, $M_1$, and $M_2$ are selected from the group consisting of CH and N.

Some embodiments of compounds of Formula (I) include compounds having the structure of Formula (I-o):

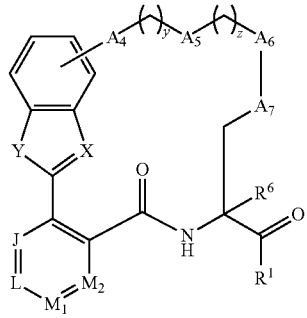

I-o or a pharmaceutically acceptable salt thereof, wherein:

Y is selected from the group consisting of $NR^5$, O, and S; X is selected from the group consisting of $C(R^4)$ and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-o) or their pharmaceutically acceptable salts; J, L, $M_1$, and $M_2$ are selected from the group consisting of CH and N.

Some embodiments of compounds of Formula (I) include compounds having the structure of Formula (I-p):

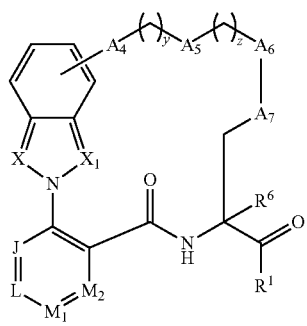

I-p or a pharmaceutically acceptable salt thereof, wherein:

X and $X_1$ are each independently selected from the group consisting of $C(R^4)$ and N; J, L, $M_1$ and $M_2$ are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-p) or their pharmaceutically acceptable salts; J, L, $M_1$, and $M_2$ are selected from the group consisting of CH and N.

Some embodiments of compounds of Formula (I) include compounds having the structure of Formula (I-q):

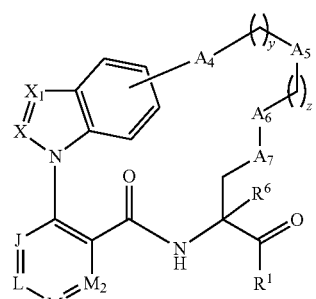

I-q or a pharmaceutically acceptable salt thereof, wherein:

X and $X_1$ are each independently selected from the group consisting of $C(R^4)$ and N; J, L, and M are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-q) or their pharmaceutically acceptable salts; J, L, $M_1$, and $M_2$ are selected from the group consisting of CH and N.

Some embodiments of compounds of Formula (I) include compounds having the structure of Formula (I-r):

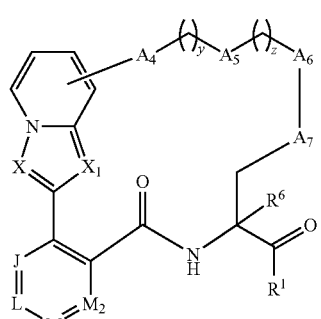

I-r or a pharmaceutically acceptable salt thereof, wherein:

X and $X_1$ are each independently selected from the group consisting of $C(R^4)$ and N;

J, L, and M are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-r) or their pharmaceutically acceptable salts; J, L, $M_1$, and $M_2$ are selected from the group consisting of CH and N.

Some embodiments of compounds of Formula (I) include compounds having the structure of Formula (I-s):

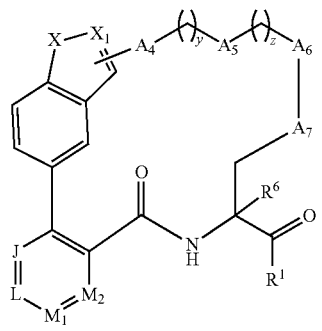

I-s or a pharmaceutically acceptable salt thereof, wherein:

X is selected from the group consisting of $C(R^4)$ and N;

$X_1$ is selected from the group consisting of $C(R^4)$ and N, or $X_1$ is a carbon atom bonded to the $A_4$ group;

J, L, $M_1$ and $M_2$ are each independently selected from the group consisting of $C(R^4)$ and N; and each $R^4$ is independently selected from the group consisting of —H, $C_{1-4}$ alkyl, $C_{3-7}$ carbocyclyl, halo, hydroxy, and $C_1$-$C_6$ alkoxy.

In some embodiments of compounds of Formula (I-s) or their pharmaceutically acceptable salts; J, L, $M_1$, and $M_2$ are selected from the group consisting of CH and N.

Some embodiments of compounds of Formula (I) include compounds having the structure of Formula (I-t):

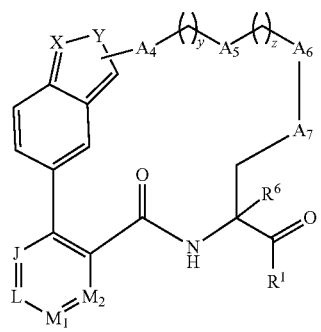

I-t or a pharmaceutically acceptable salt thereof, wherein:

Y is selected from the group consisting of $NR^5$, O, and S, or

Y is a nitrogen atom bonded to the $A_4$ group, wherein the $A_4$ group is —CH$_2$—; and X is selected from the group consisting of $C(R^4)$ and N; J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-t) or their pharmaceutically acceptable salts; J, L, $M_1$, and $M_2$ are selected from the group consisting of CH and N.

Some embodiments of compounds of Formula (I) include compounds having the structure of Formula (I-u):

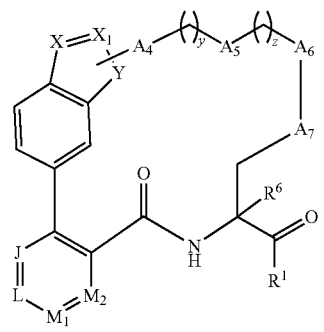

I-u or a pharmaceutically acceptable salt thereof, wherein:

X is selected from the group consisting of $C(R^4)$ and N;

$X_1$ is selected from the group consisting of $C(R^4)$ and N, or $X_1$ is a carbon atom bonded to the $A_4$ group; Y is selected from the group consisting of $NR^5$, O, and S, or Y is a nitrogen atom bonded to the $A_4$ group, wherein the $A_4$ group is —CH$_2$—;

J, L, $M_1$ and $M_2$ are each independently selected from the group consisting of $C(R^4)$ and N;

each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-u) or their pharmaceutically acceptable salts; J, L, $M_1$, and $M_2$ are selected from the group consisting of CH and N.

Some embodiments of compounds of Formula (I) include compounds having the structure of Formula (I-v):

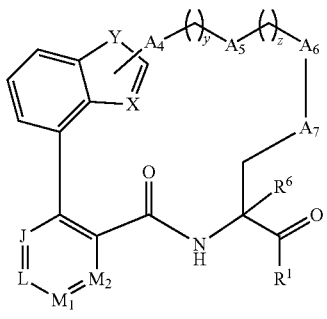

I-v or a pharmaceutically acceptable salt thereof, wherein:

X is selected from the group consisting of $C(R^4)$ and N;

Y is selected from the group consisting of $NR^5$, O, and S, or

Y is a nitrogen atom bonded to the $A_4$ group, wherein the $A_4$ group is —CH$_2$—;

J, L, $M_1$ and $M_2$ are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of compounds of Formula (I-v) or their pharmaceutically acceptable salts; J, L, $M_1$, and $M_2$ are selected from the group consisting of CH and N Some embodiments of compounds of Formula (I) include compounds having the structure of Formula (I-w):

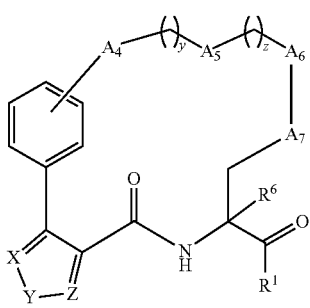

I-w or a pharmaceutically acceptable salt thereof, wherein:
Y is selected from the group consisting of $NR^5$, O, and S; X and Z are each independently selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (I-x):

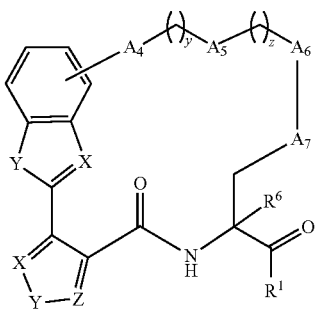

I-x or a pharmaceutically acceptable salt thereof, wherein:
each Y is independently selected from the group consisting of $NR^5$, O, and S; each X is independently selected from the group consisting of $C(R^4)$ and N; Z is selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and each $R^5$ is independently selected from the group consisting of —H, $C_{1-4}$ alkyl, and $C_{3-7}$ carbocyclyl.

Some embodiments of compounds of Formula (I) include compounds having the structure of Formula (I-y):

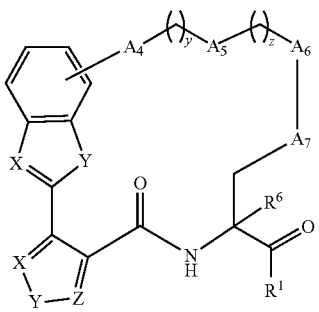

I-y or a pharmaceutically acceptable salt thereof, wherein:
each Y is independently selected from the group consisting of $NR^5$, O, and S; each X is independently selected from the group consisting of $C(R^4)$ and N; Z is selected from the group consisting of $C(R^4)$ and N; each $R^4$ is independently selected from the group consisting of —H, $C_{1-4}$ alkyl, $C_{3-7}$ carbocyclyl, halo, hydroxy, and $C_1$-$C_6$ alkoxy; and each $R^5$ is independently selected from the group consisting of —H, $C_{1-4}$ alkyl, and $C_{3-7}$ carbocyclyl.

In some embodiments of Formula (I), (I-a) to (I-d), (Id-1), (Id-2), (I-g), (I-g1), (I-z), (I-z1), (I-h), (I-j) to (I-z), or (II-a) to (II-d), $A_4$ is —O—.

In some embodiments of Formula (I), (I-a) to (I-d), (Id-1), (Id-2), (I-g), (I-g1), (I-z), (I-z1), (I-h), (I-j) to (I-z), or (II-a) to (II-d), $A_4$ is —$CH_2$—.

Some embodiments of compounds of Formula (I) include compounds having the structure of Formula (I-e):

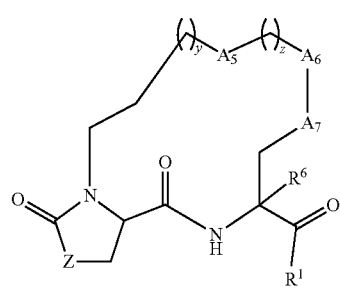

I-e or a pharmaceutically acceptable salt thereof, wherein:
Z is selected from the group consisting of $NR^5$ and $CH(R^4)$; $R^4$ is selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

Some embodiments of compounds of Formula (I) include compounds having the structure of Formula (I-f):

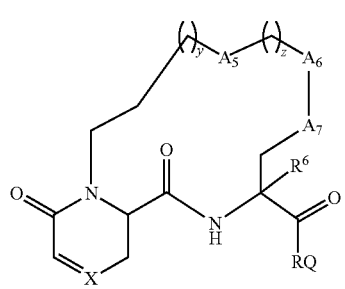

I-f or a pharmaceutically acceptable salt thereof, wherein:
X is selected from the group consisting of $C(OR^5)$, —$C(R^4)$, and N; $R^4$ is selected from the group consisting of —H, $C_{1-4}$ alkyl, $C_{3-7}$ carbocyclyl, halo, hydroxy, and $C_1$-$C_6$ alkoxy; and $R^5$ is selected from the group consisting of —H, $C_{1-4}$ alkyl, and $C_{3-7}$ carbocyclyl.

In some embodiments of Formula (I), (I-a) to (I-h), (Id-1), (Id-2), (I-g1), (I-z1), (I-j) to (I-z), or (II-a) to (II-d), y is 1.
In some embodiments of Formula (I), (I-a) to (I-h), (Id-1), (Id-2), (I-g1), (I-z1), (I-j) to (I-z), or (II-a) to (II-d), y is 2.
In some embodiments of Formula (I), (I-a) to (I-h), (Id-1), (Id-2), (I-g1), (I-z1), (I-j) to (I-z), or (II-a) to (II-d), y is 3.
In some embodiments of Formula (I), (I-a) to (I-h), (Id-1), (Id-2), (I-g1), (I-z1), (I-j) to (I-z), or (II-a) to (II-d), y is 4.
In some embodiments of Formula (I), (I-a) to (I-h), (Id-1), (Id-2), (I-g1), (I-z1), (I-j) to (I-z), or (II-a) to (II-d), $A_5$ is O.

In some embodiments of Formula (I), (I-a) to (I-h), (Id-1), (Id-2), (I-g1), (I-z1), (I-j) to (I-z), or (II-a) to (II-d), $A_5$ is O or single bond.

In some embodiments of Formula (I), (I-a) to (I-h), (Id-1), (Id-2), (I-g1), (I-z1), (I-j) to (I-z), or (II-a) to (II-d), z is 0 or 2.

In some embodiments of Formula (I), (I-a) to (I-h), (Id-1), (Id-2), (I-g1), (I-z1), (I-j) to (I-z), or (II-a) to (II-d), $A_6$ is —$CH_2$— or —CH=CH—.

In some embodiments of Formula (I), (I-a) to (I-h), (Id-1), (Id-2), (I-g1), (I-z1), (I-j) to (I-z), or (II-a) to (II-d), $A_7$ is —CH=CH—, single bond, or phenyl.

In some embodiments of Formula (I), (I-a) to (I-h), (Id-1), (Id-2), (I-g1), (I-z1), (I-j) to (I-z), or (II-a) to (II-d), $A_7$ is

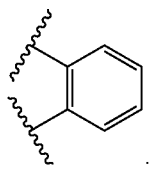 [SMILES: *c1ccccc1*]

In some embodiments of Formula (I), (I-a) to (I-h), (Id-1), (Id-2), (I-g1), (I-z1), (I-j) to (I-z), or (II-a) to (II-d), $R^1$ is —$CONR^2R^3$.

In some embodiments of Formula (I), (I-a) to (I-h), (Id-1), (Id-2), (I-g1), (I-z1), (I-j) to (I-z), or (II-a) to (II-d), $R^2$ is —H and $R^3$ is optionally substituted $C_{1-4}$ alkyl.

In some embodiments of Formula (I), (I-a) to (I-h), (Id-1), (Id-2), (I-g1), (I-z1), (I-j) to (I-z), or (II-a) to (II-d), $R^3$ is $C_{1-4}$ alkyl or benzyl.

Some embodiments include a compound selected from the group consisting of:

1

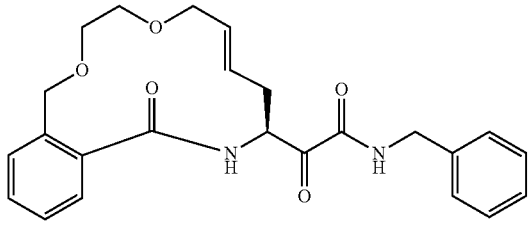

2

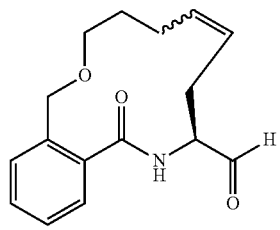

3

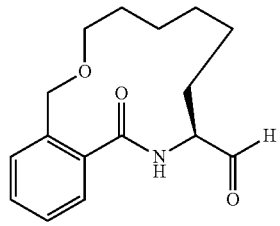

4

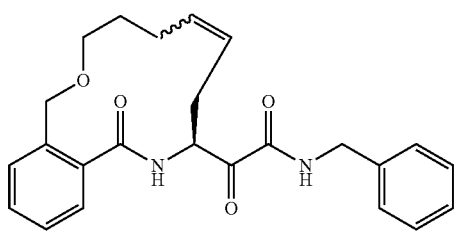

5

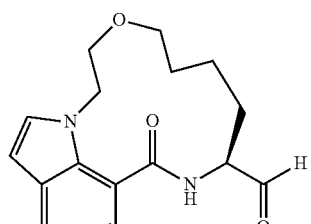

6

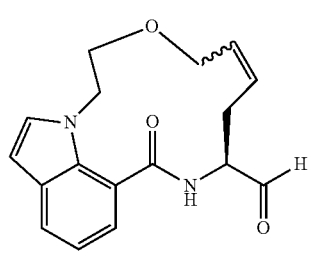

7

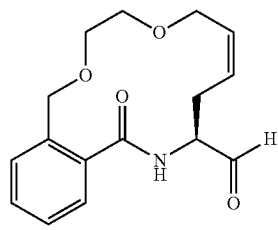 [SMILES: O=C[C@@H]1C/C=C\COCCOCc2ccccc2C(=O)N1]

8

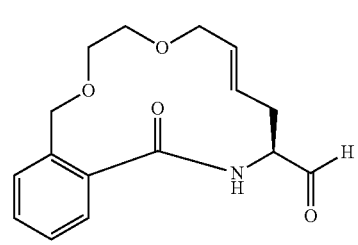

9

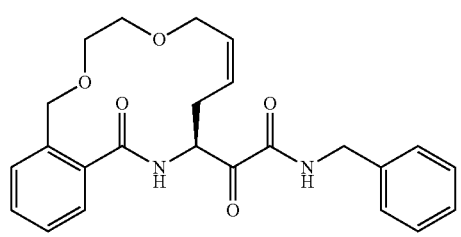 [SMILES: O=C(NCc1ccccc1)C(=O)[C@@H]1C/C=C\COCCOCc2ccccc2C(=O)N1]

21
10 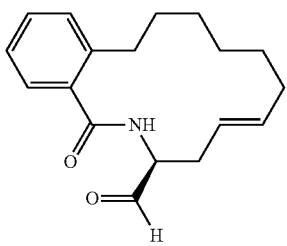 [SMILES: O=C[C@@H]1C/C=C/CCCCCCc2ccccc2C(=O)N1]
11 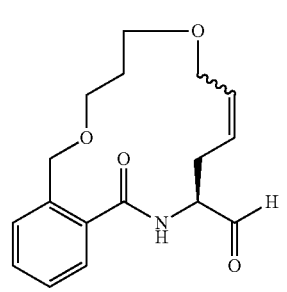 [SMILES: O=C[C@@H]1CC=CCOCCCOCc2ccccc2C(=O)N1]
12 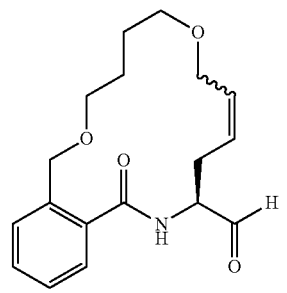
13 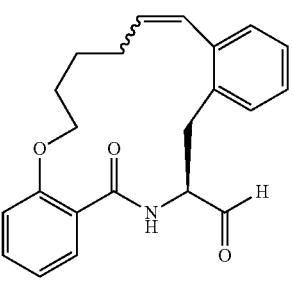
14 
15 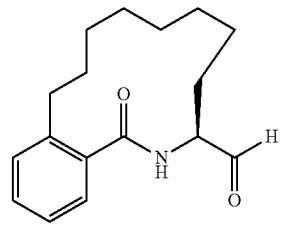
22
16 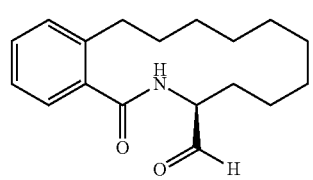 [SMILES: O=C[C@@H]1CCCCCCCCCc2ccccc2C(=O)N1]
17 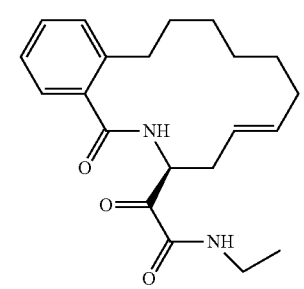 [SMILES: CCNC(=O)C(=O)[C@@H]1C/C=C/CCCCCCc2ccccc2C(=O)N1]
18 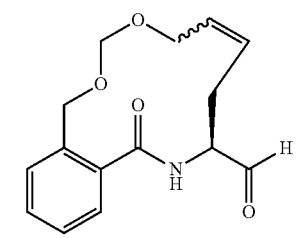
19 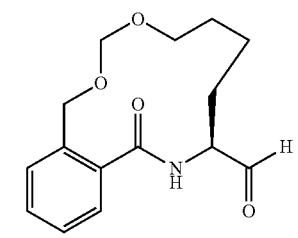
20 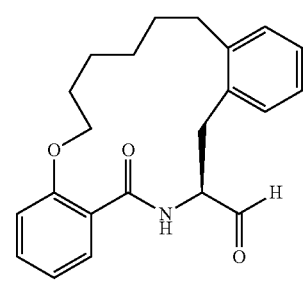
21 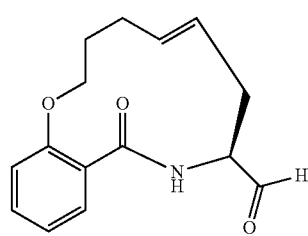

-continued
22
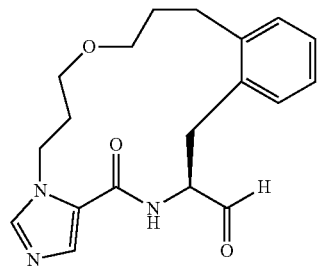
23
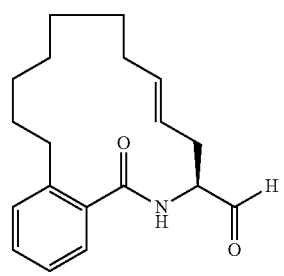 [SMILES: O=C[C@@H]1C/C=C/CCCCCCCc2ccccc2C(=O)N1]
24
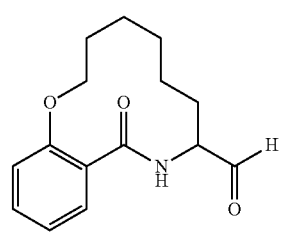 [SMILES: O=CC1CCCCCCOc2ccccc2C(=O)N1]
25
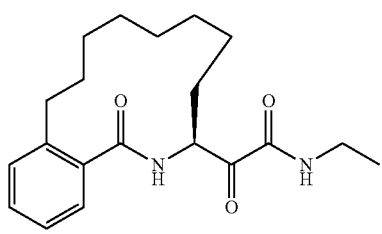
26
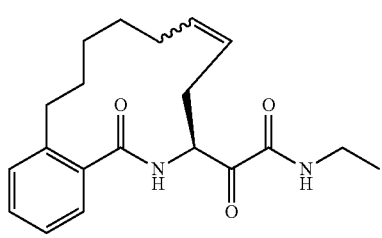 [SMILES: CCNC(=O)C(=O)[C@@H]1CC=CCCCCCc2ccccc2C(=O)N1]
27
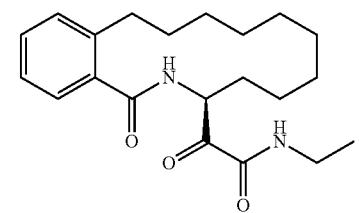 [SMILES: CCNC(=O)C(=O)[C@@H]1CCCCCCCCCc2ccccc2C(=O)N1]
-continued
28
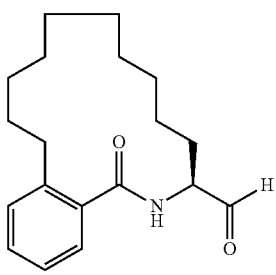
29
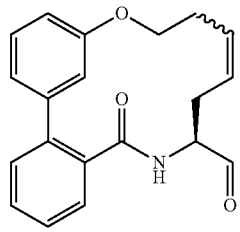
30
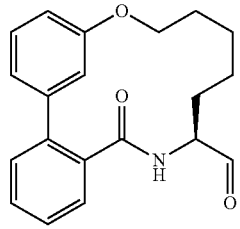 [SMILES: O=C[C@@H]1CCCCCOc2cccc(c2)-c2ccccc2C(=O)N1]
31
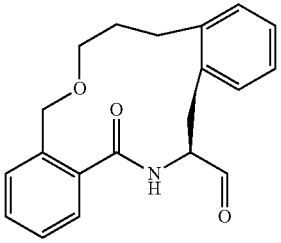
32
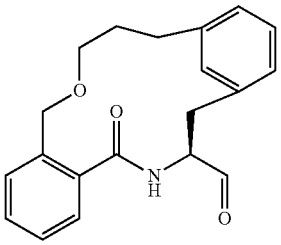
33
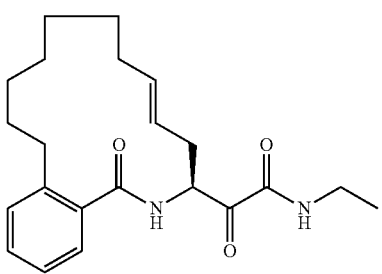 [SMILES: CCNC(=O)C(=O)[C@@H]1C/C=C/CCCCCCCc2ccccc2C(=O)N1]

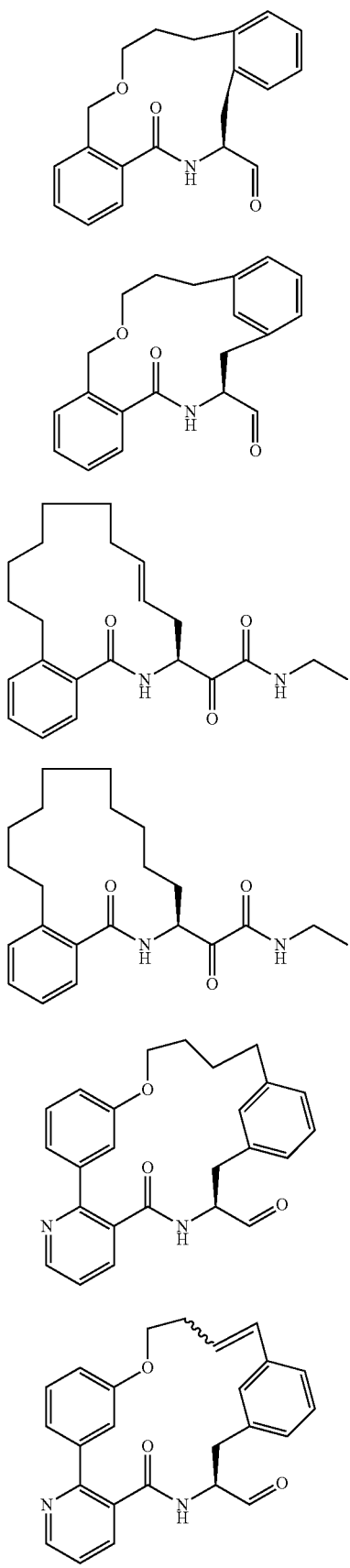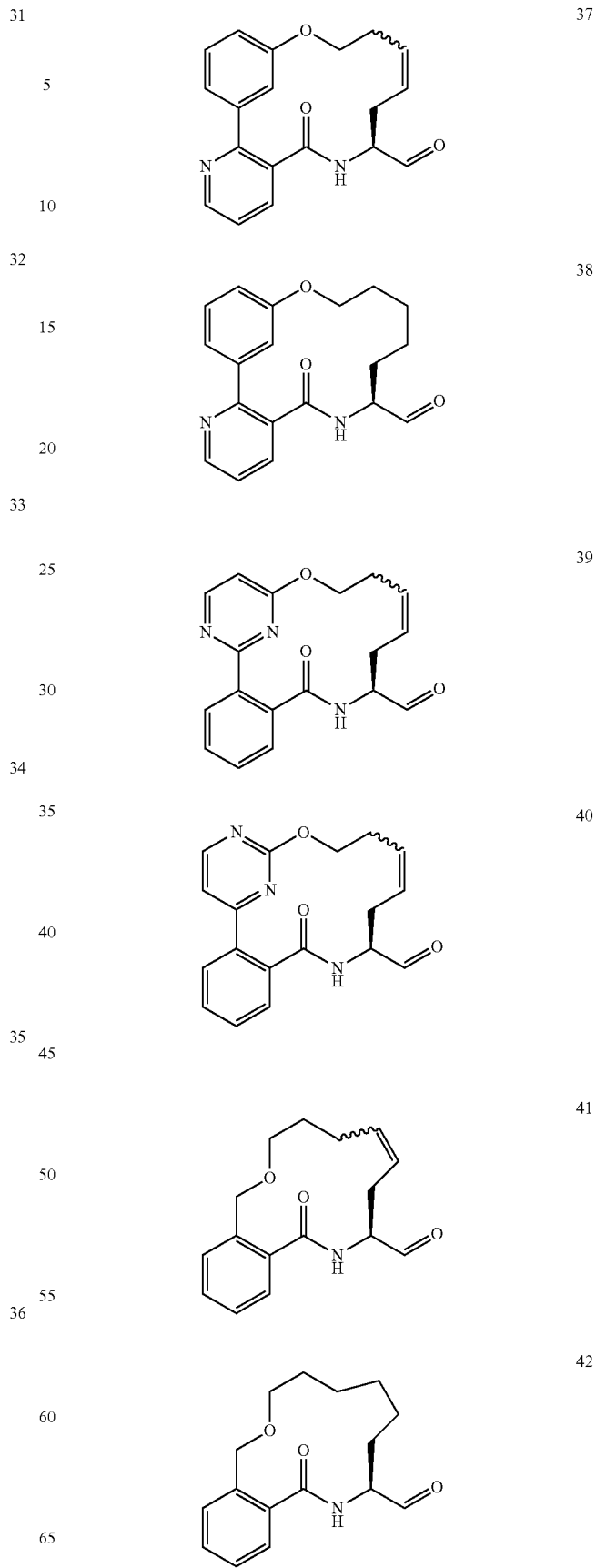

43
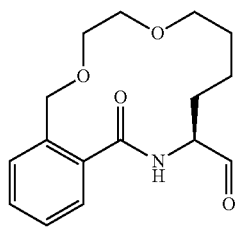 [SMILES: O=C[C@@H]1CCCCOCCOCc2ccccc2C(=O)N1]
44
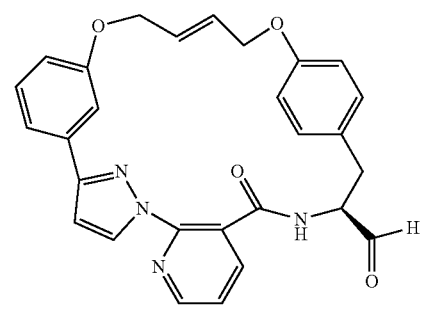
45
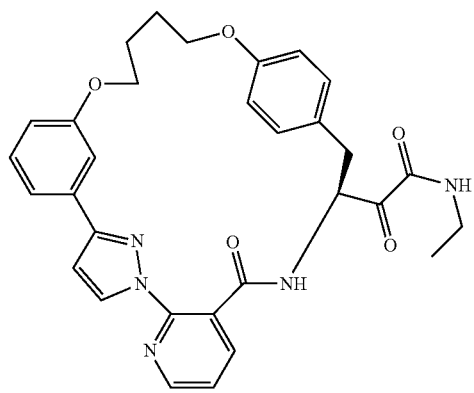
46
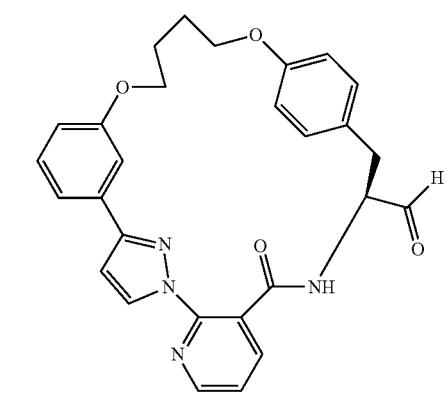
47
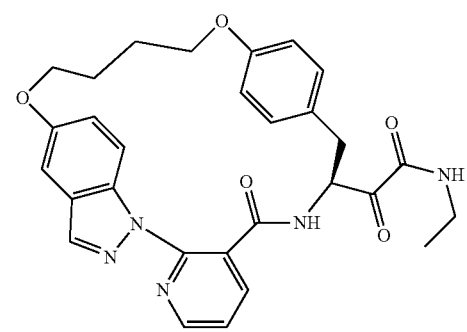
48
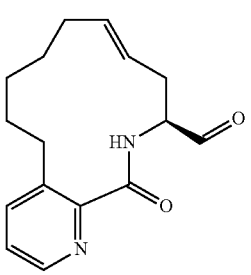
49
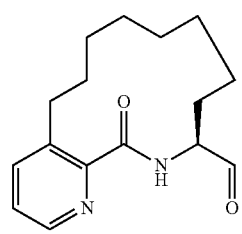 [SMILES: O=C[C@@H]1CCCCCCCCc2cccnc2C(=O)N1]
50
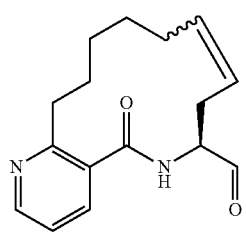 [SMILES: O=C[C@@H]1CC=CCCCCCc2ncccc2C(=O)N1]
51
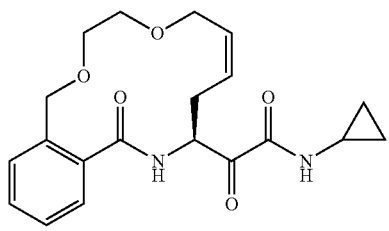 [SMILES: O=C(NC1CC1)C(=O)[C@@H]1CCCCOCCOCc2ccccc2C(=O)N1]
52
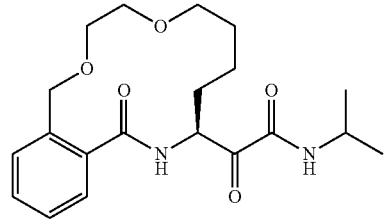 [SMILES: CC(C)NC(=O)C(=O)[C@@H]1CCCCOCCOCc2ccccc2C(=O)N1]
53
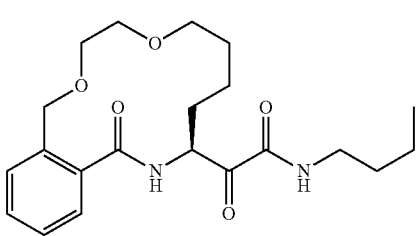 [SMILES: CCCCNC(=O)C(=O)[C@@H]1CCCCOCCOCc2ccccc2C(=O)N1]

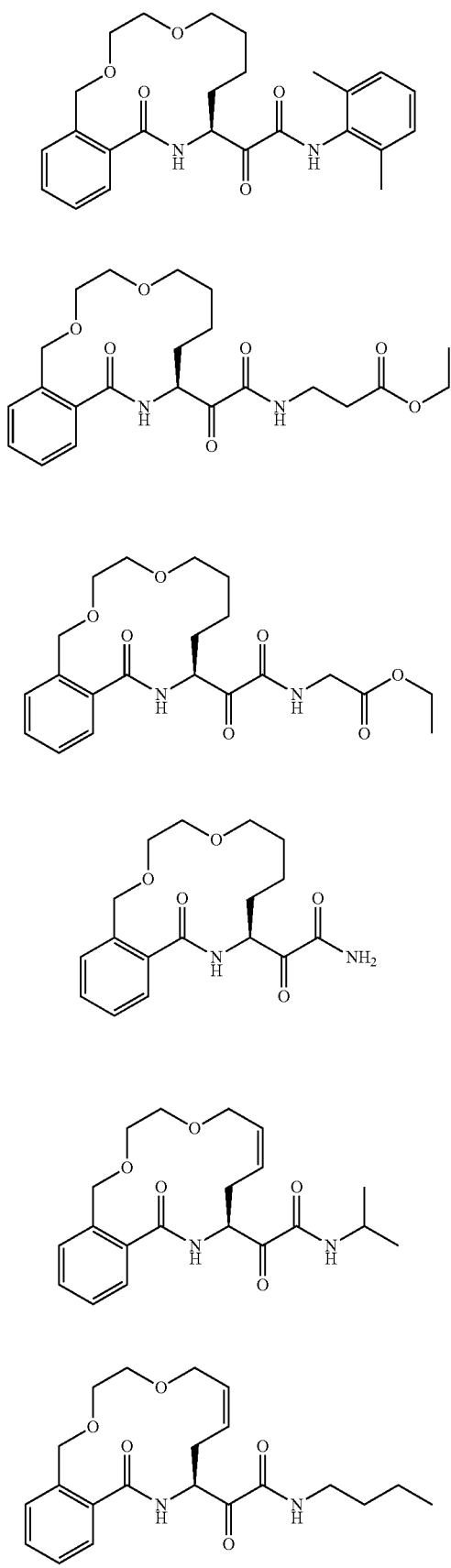
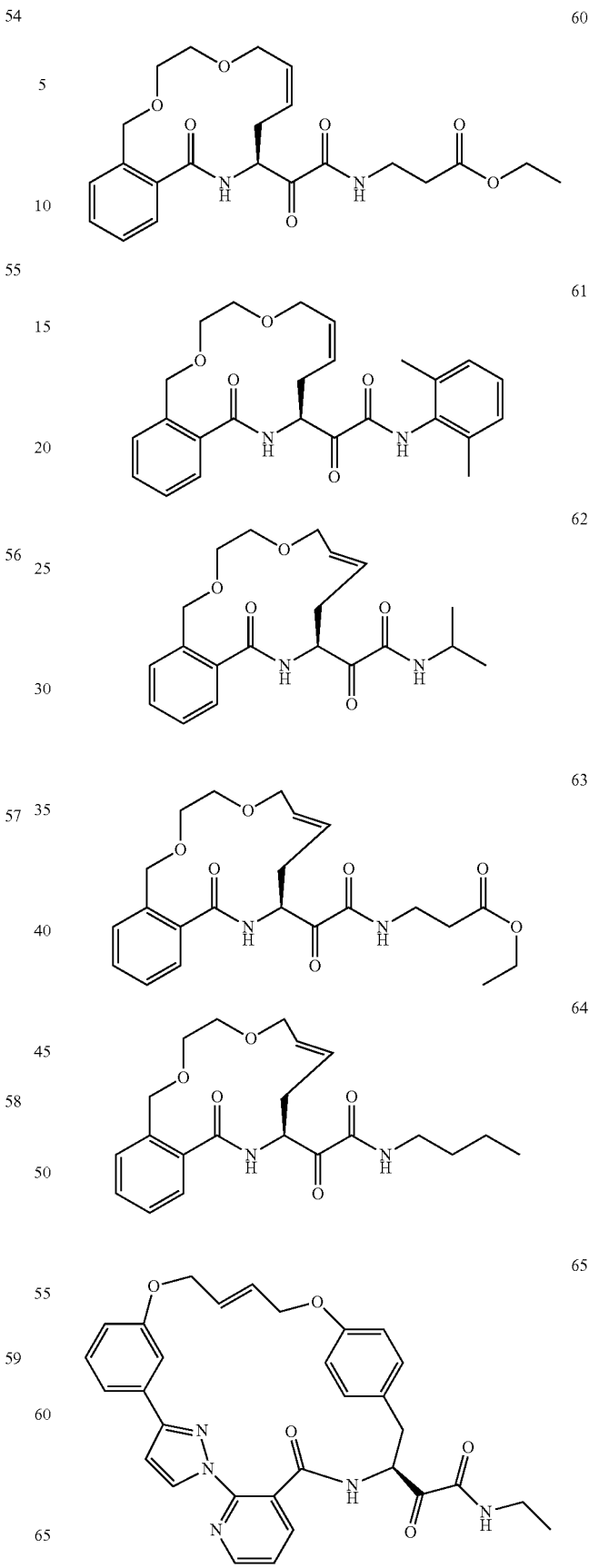

US 11,292,801 B2
31
-continued
66
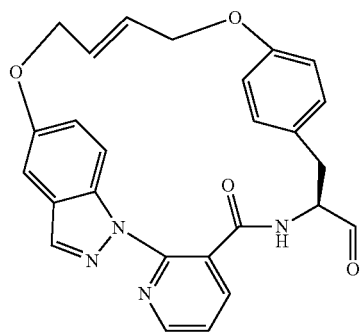
67
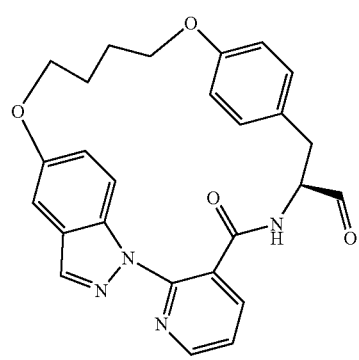
68
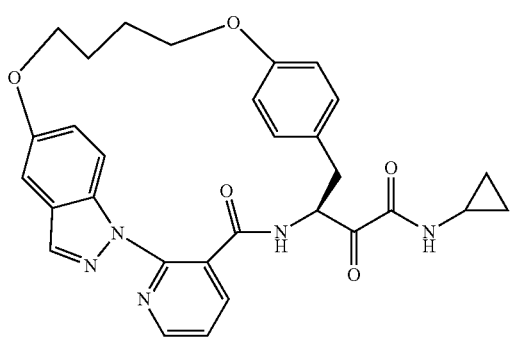
69
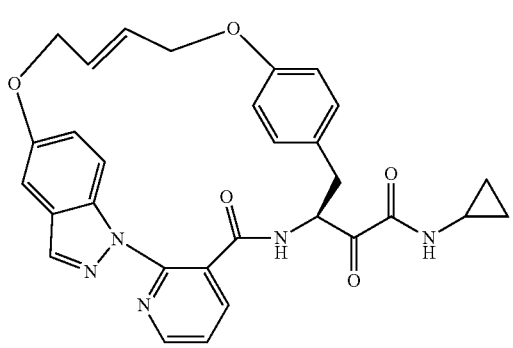
32
-continued
70
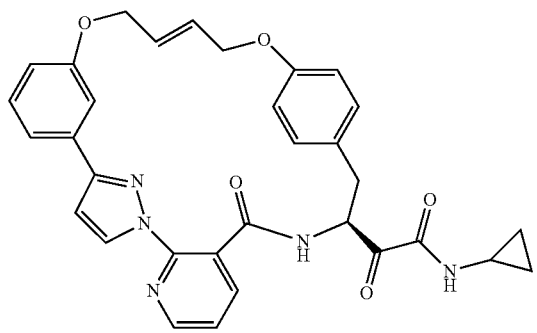
71
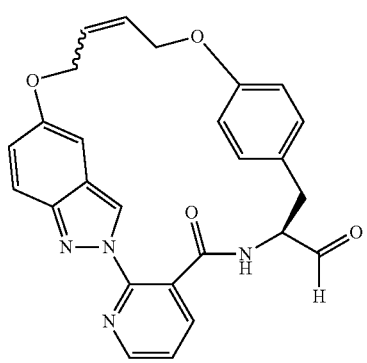
72
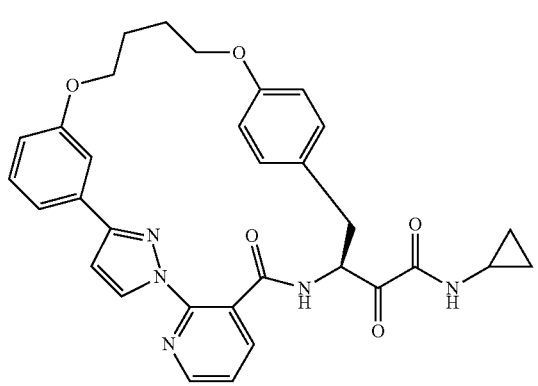
73
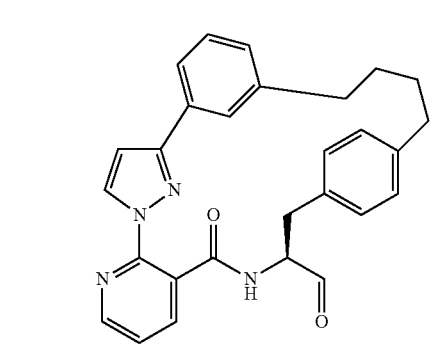

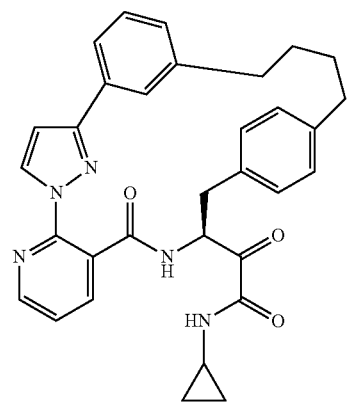
74
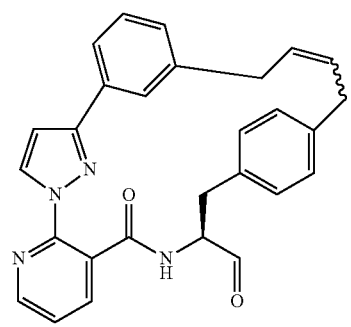
75
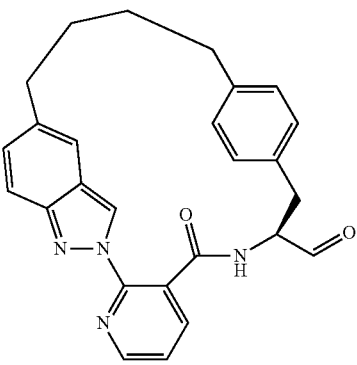
76
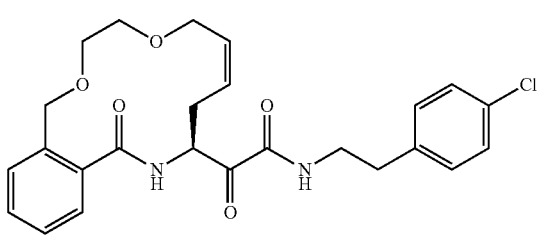 [SMILES: O=C(NCCc1ccc(Cl)cc1)C(=O)[C@@H]1C/C=C\COCCOCc2ccccc2C(=O)N1]
77
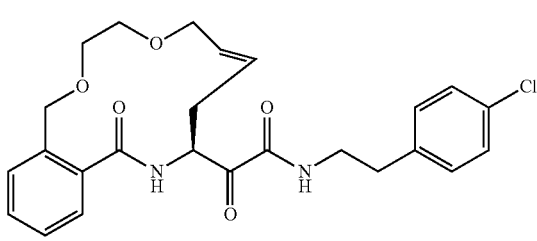
78
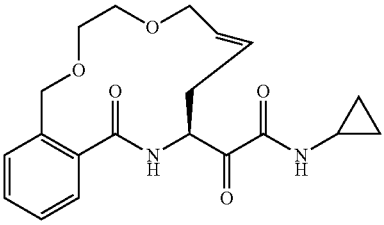
79
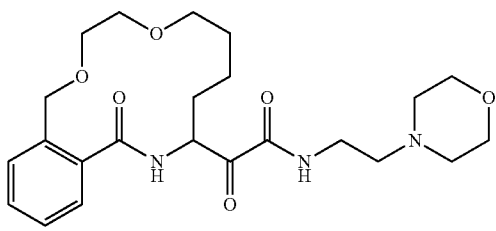 [SMILES: O=C(NCCN1CCOCC1)C(=O)C1CCCCOCCOCc2ccccc2C(=O)N1]
80
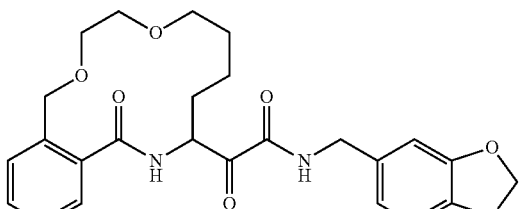
81
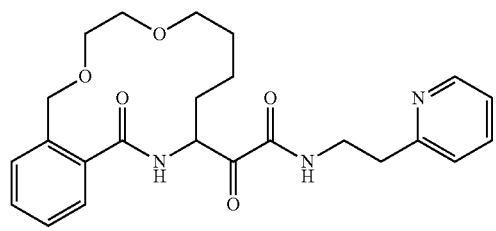 [SMILES: O=C(NCCc1ccccn1)C(=O)C1CCCCOCCOCc2ccccc2C(=O)N1]
82
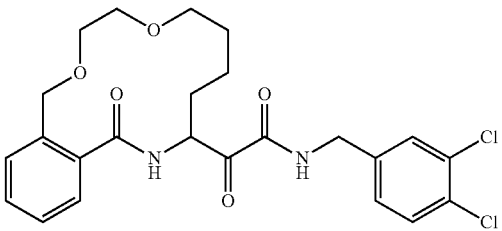 [SMILES: O=C(NCc1ccc(Cl)c(Cl)c1)C(=O)C1CCCCOCCOCc2ccccc2C(=O)N1]
83
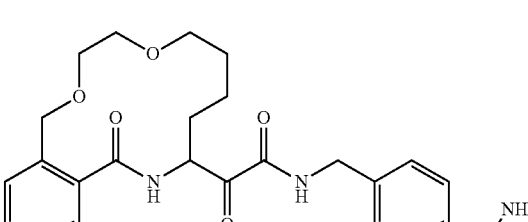
84

85
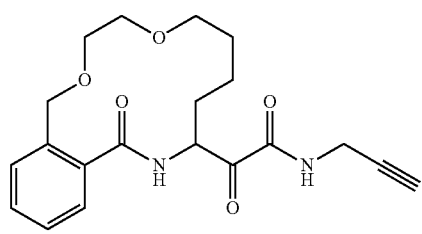 [SMILES: C#CCNC(=O)C(=O)C1CCCCOCCOCc2ccccc2C(=O)N1]
86
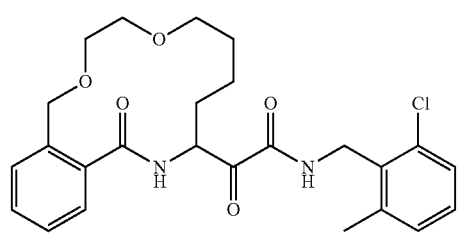 [SMILES: Cc1cccc(Cl)c1CNC(=O)C(=O)C1CCCCOCCOCc2ccccc2C(=O)N1]
87
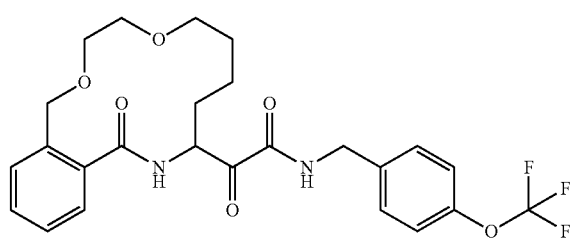 [SMILES: O=C(NCc1ccc(OC(F)(F)F)cc1)C(=O)C1CCCCOCCOCc2ccccc2C(=O)N1]
88
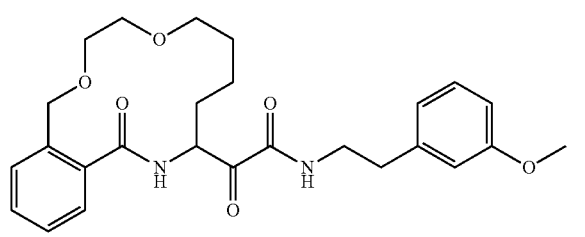 [SMILES: COc1cccc(CCNC(=O)C(=O)C2CCCCOCCOCc3ccccc3C(=O)N2)c1]
89
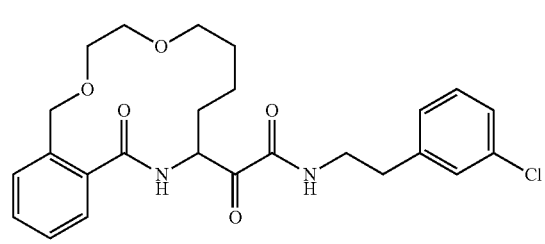 [SMILES: O=C(NCCc1cccc(Cl)c1)C(=O)C1CCCCOCCOCc2ccccc2C(=O)N1]
90
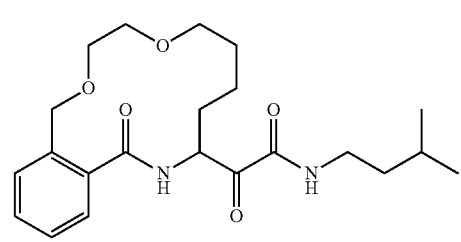 [SMILES: CC(C)CCNC(=O)C(=O)C1CCCCOCCOCc2ccccc2C(=O)N1]
91
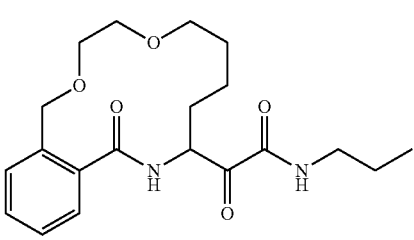 [SMILES: CCCNC(=O)C(=O)C1CCCCOCCOCc2ccccc2C(=O)N1]
92
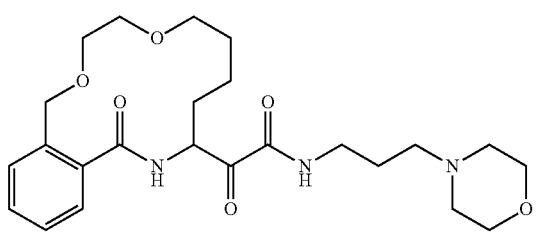 [SMILES: O=C(NCCCN1CCOCC1)C(=O)C1CCCCOCCOCc2ccccc2C(=O)N1]
93
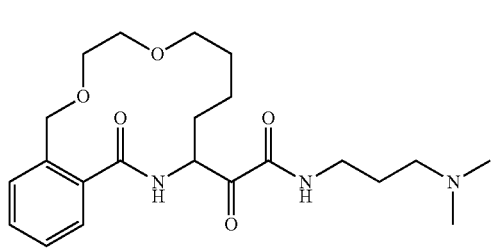 [SMILES: CN(C)CCCNC(=O)C(=O)C1CCCCOCCOCc2ccccc2C(=O)N1]
94
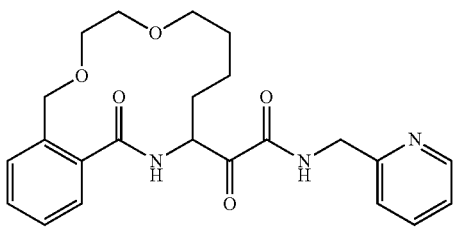 [SMILES: O=C(NCc1ccccn1)C(=O)C1CCCCOCCOCc2ccccc2C(=O)N1]
95
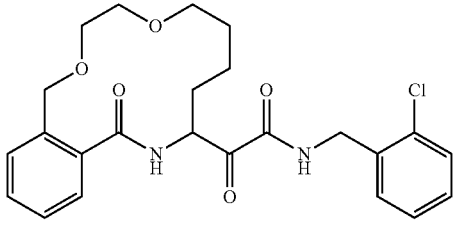 [SMILES: O=C(NCc1ccccc1Cl)C(=O)C1CCCCOCCOCc2ccccc2C(=O)N1]
96
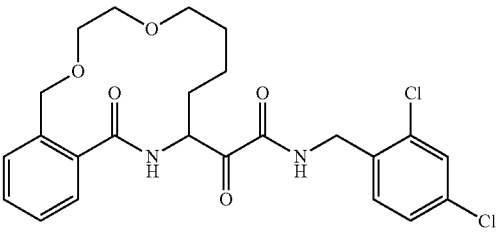 [SMILES: O=C(NCc1ccc(Cl)cc1Cl)C(=O)C1CCCCOCCOCc2ccccc2C(=O)N1]

97
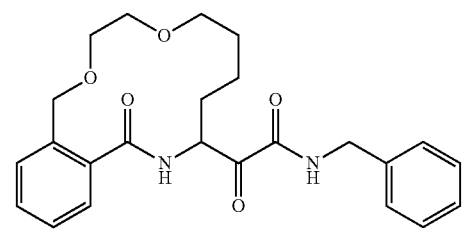 [SMILES: O=C(NCc1ccccc1)C(=O)C1CCCCOCCOCc2ccccc2C(=O)N1]
98
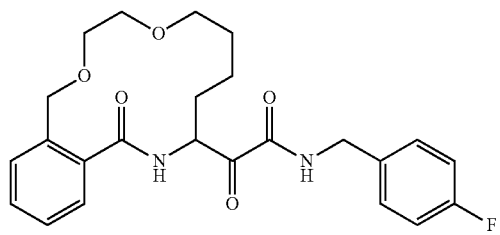 [SMILES: O=C(NCc1ccc(F)cc1)C(=O)C1CCCCOCCOCc2ccccc2C(=O)N1]
99
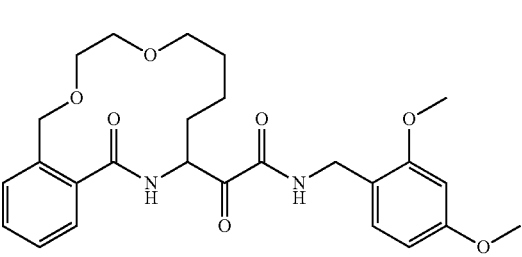 [SMILES: COc1ccc(CNC(=O)C(=O)C2CCCCOCCOCc3ccccc3C(=O)N2)c(OC)c1]
100
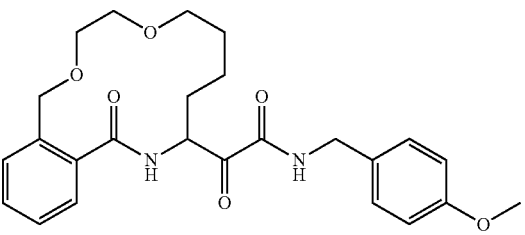 [SMILES: COc1ccc(CNC(=O)C(=O)C2CCCCOCCOCc3ccccc3C(=O)N2)cc1]
101
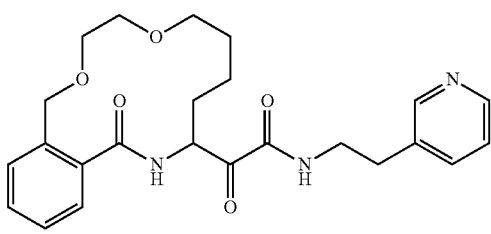 [SMILES: O=C(NCCc1cccnc1)C(=O)C1CCCCOCCOCc2ccccc2C(=O)N1]
102
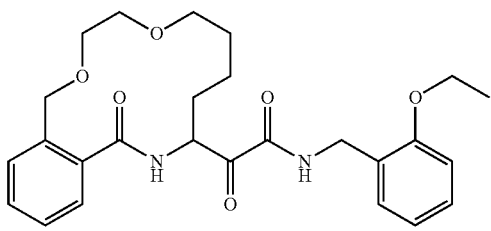 [SMILES: CCOc1ccccc1CNC(=O)C(=O)C1CCCCOCCOCc2ccccc2C(=O)N1]
103
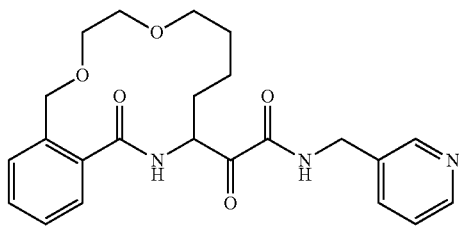
104
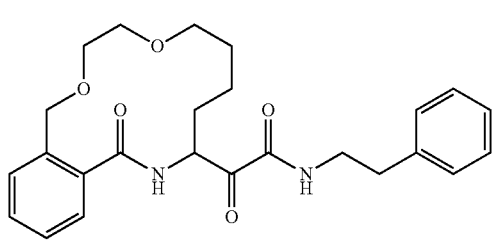 [SMILES: O=C(NCCc1ccccc1)C(=O)C1CCCCOCCOCc2ccccc2C(=O)N1]
105
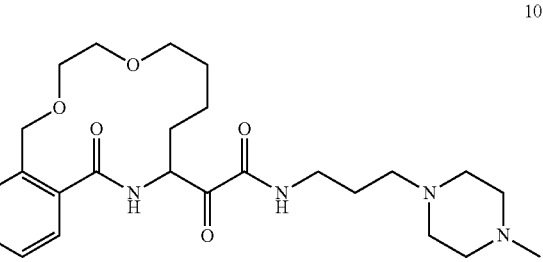
106
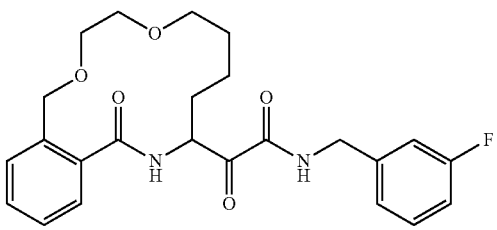 [SMILES: O=C(NCc1cccc(F)c1)C(=O)C1CCCCOCCOCc2ccccc2C(=O)N1]
107
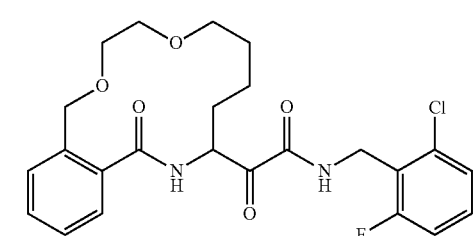
108
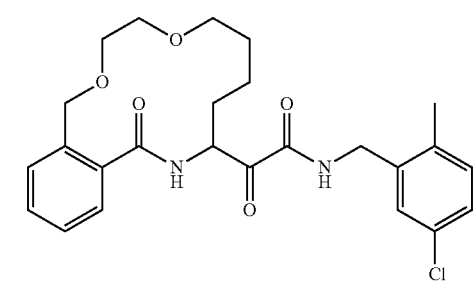 [SMILES: Cc1ccc(Cl)cc1CNC(=O)C(=O)C1CCCCOCCOCc2ccccc2C(=O)N1]

109
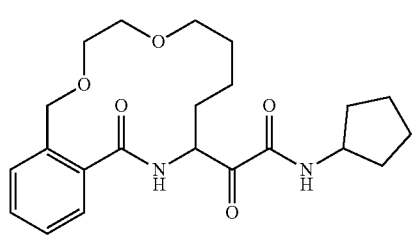 [SMILES: O=C(NC1CCCC1)C(=O)C1CCCCOCCOCc2ccccc2C(=O)N1]
110
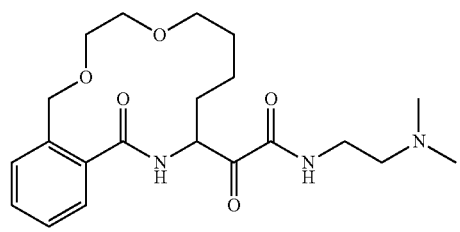 [SMILES: CN(C)CCNC(=O)C(=O)C1CCCCOCCOCc2ccccc2C(=O)N1]
111
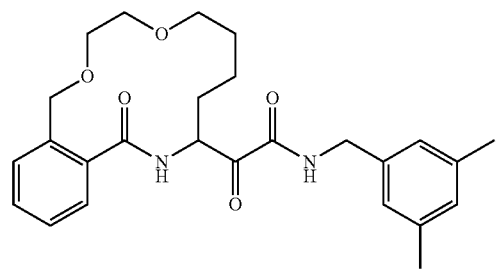 [SMILES: Cc1cc(C)cc(CNC(=O)C(=O)C2CCCCOCCOCc3ccccc3C(=O)N2)c1]
112
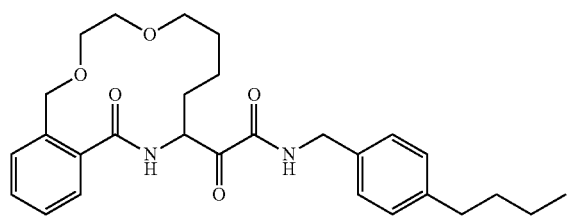 [SMILES: CCCCc1ccc(CNC(=O)C(=O)C2CCCCOCCOCc3ccccc3C(=O)N2)cc1]
113
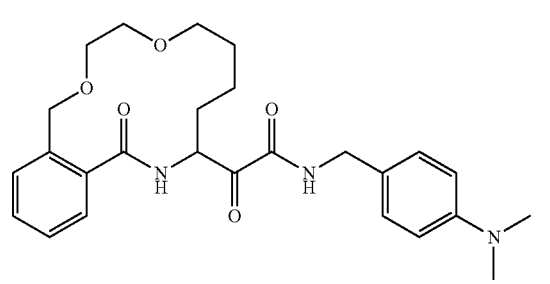 [SMILES: CN(C)c1ccc(CNC(=O)C(=O)C2CCCCOCCOCc3ccccc3C(=O)N2)cc1]
114
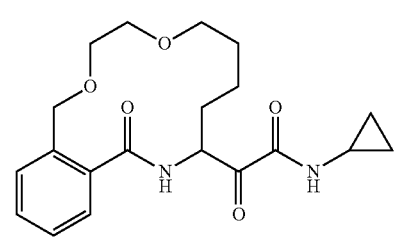 [SMILES: O=C(NC1CC1)C(=O)C1CCCCOCCOCc2ccccc2C(=O)N1]
115
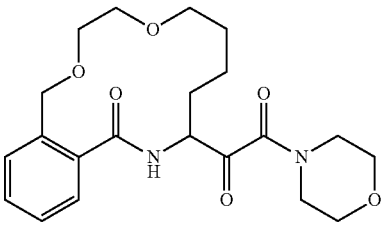 [SMILES: O=C1NC(C(=O)C(=O)N2CCOCC2)CCCCOCCOCc2ccccc21]
116
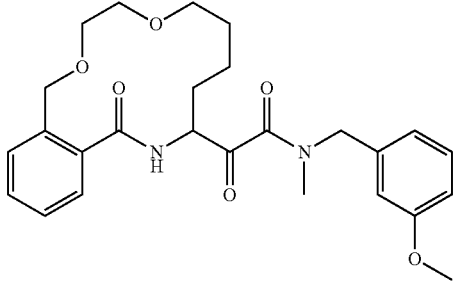 [SMILES: COc1cccc(CN(C)C(=O)C(=O)C2CCCCOCCOCc3ccccc3C(=O)N2)c1]
117
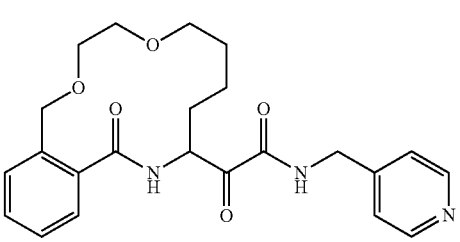 [SMILES: O=C(NCc1ccncc1)C(=O)C1CCCCOCCOCc2ccccc2C(=O)N1]
118
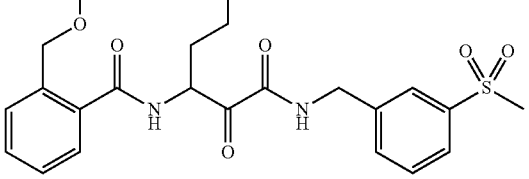
119
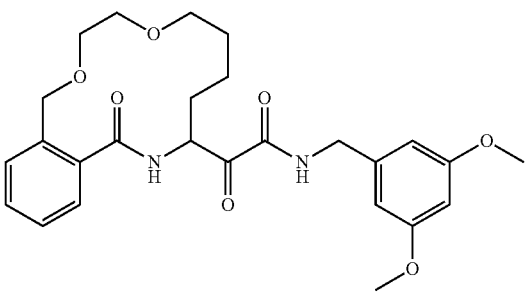 [SMILES: COc1cc(CNC(=O)C(=O)C2CCCCOCCOCc3ccccc3C(=O)N2)cc(OC)c1]
120
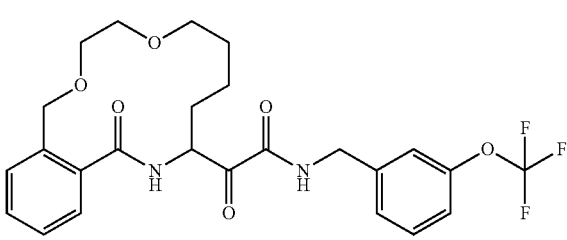

121
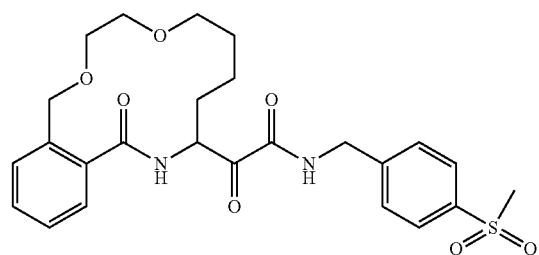
122
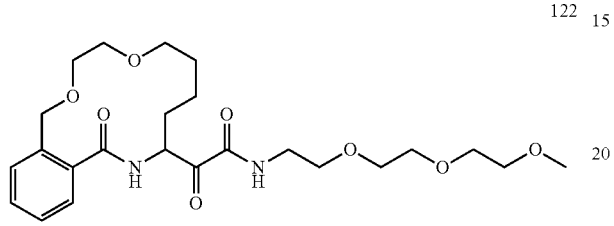
123
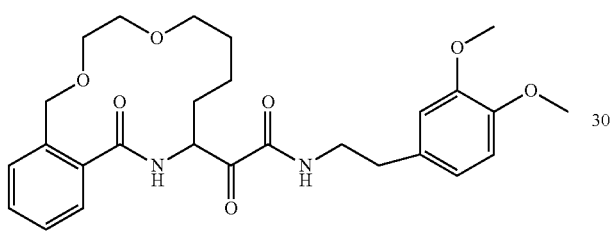
124
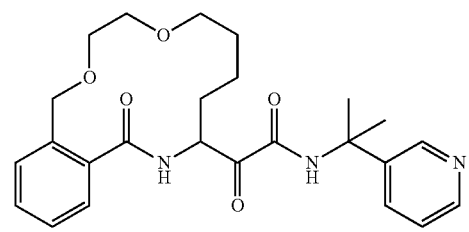
125
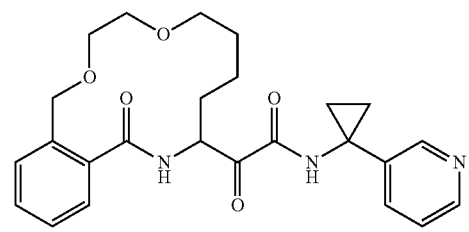
126
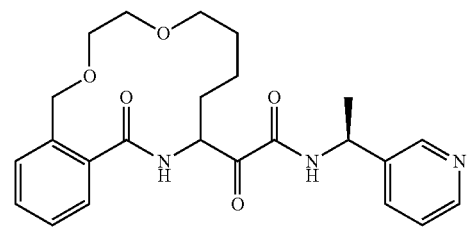
127
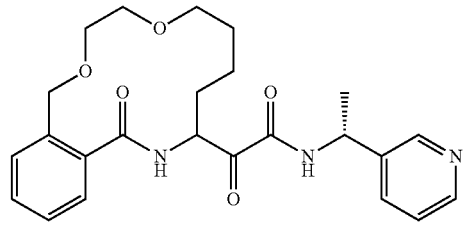 [SMILES: C[C@@H](NC(=O)C(=O)C1CCCCOCCOCc2ccccc2C(=O)N1)c1cccnc1]
128
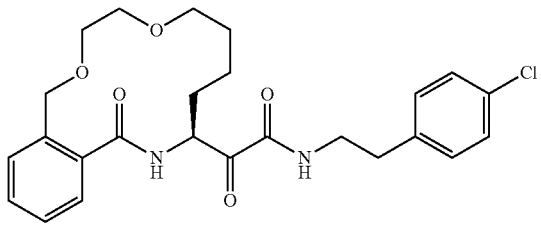 [SMILES: O=C(NCCc1ccc(Cl)cc1)C(=O)[C@@H]1CCCCOCCOCc2ccccc2C(=O)N1]
129
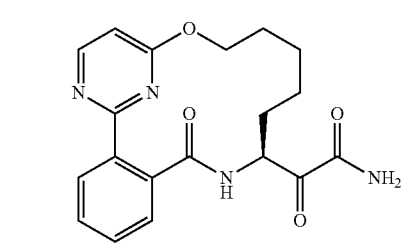
130
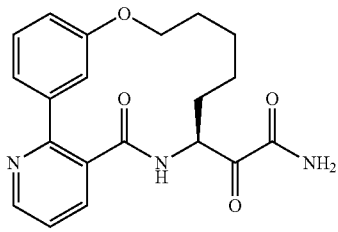 [SMILES: NC(=O)C(=O)[C@@H]1CCCCCOc2cccc(c2)-c2ncccc2C(=O)N1]
131
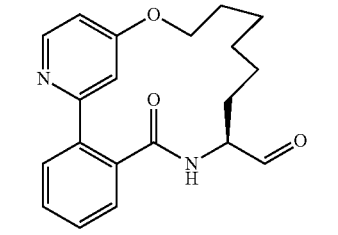
132
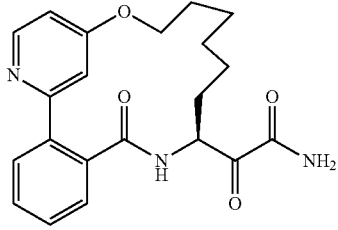

133 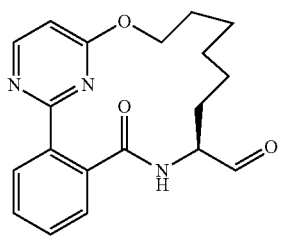
134 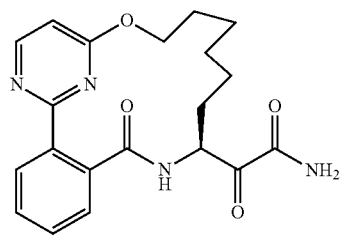
135 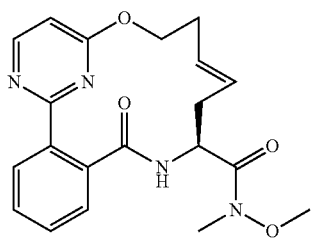 [SMILES: CON(C)C(=O)[C@@H]1C/C=C/CCOc2ccnc(n2)-c2ccccc2C(=O)N1]
136 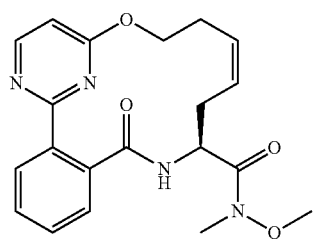 [SMILES: CON(C)C(=O)[C@@H]1C/C=C\CCOc2ccnc(n2)-c2ccccc2C(=O)N1]
137 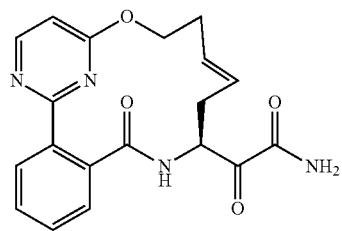 [SMILES: NC(=O)C(=O)[C@@H]1C/C=C/CCOc2ccnc(n2)-c2ccccc2C(=O)N1]
138 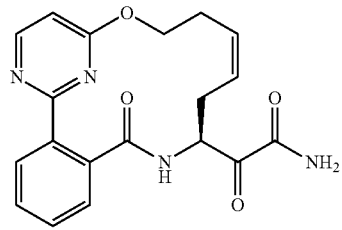 [SMILES: NC(=O)C(=O)[C@@H]1C/C=C\CCOc2ccnc(n2)-c2ccccc2C(=O)N1]
139 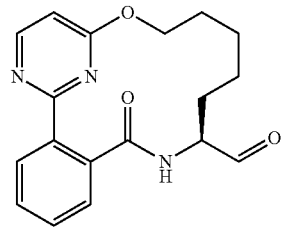 [SMILES: O=C[C@@H]1CCCCCOc2ccnc(n2)-c2ccccc2C(=O)N1]
140 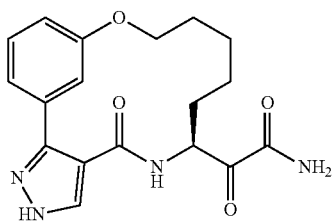
141 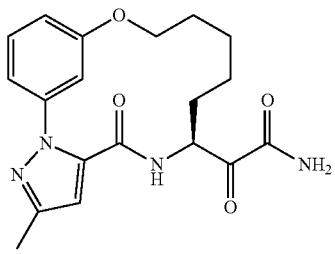
142 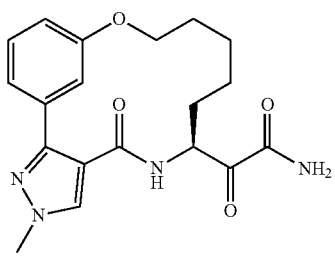
143 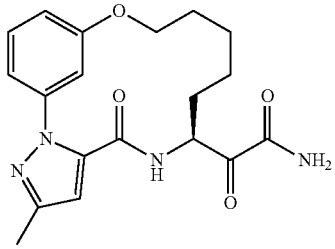
144 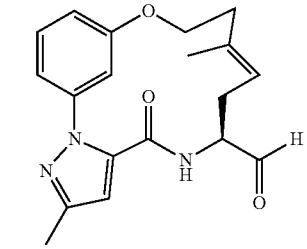

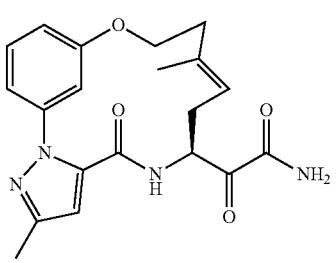

145

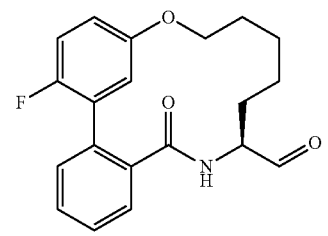 [SMILES: O=C[C@@H]1CCCCCOc2ccc(F)c(c2)-c2ccccc2C(=O)N1]

146

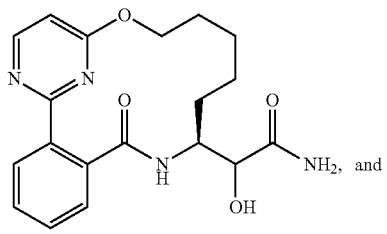

147

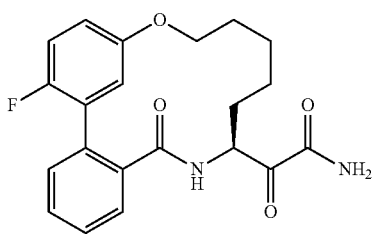 [SMILES: NC(=O)C(=O)[C@@H]1CCCCCOc2ccc(F)c(c2)-c2ccccc2C(=O)N1]

148

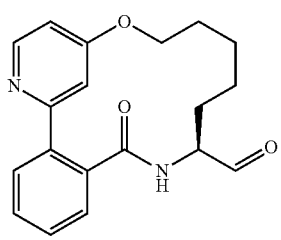 [SMILES: O=C[C@@H]1CCCCCOc2ccnc(c2)-c2ccccc2C(=O)N1]

149 or a pharmaceutically acceptable salt thereof.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Prodrugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "polyethylene glycol" refers to the formula

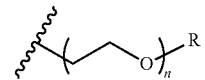

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{10}$ aryloxy" or "$C_{10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

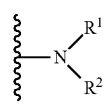

and R$^1$ and R$^2$ are defined as selected from the group consisting of hydrogen and alkyl, or R$^1$ and R$^2$ together with the nitrogen to which they are attached form a heteroaryl, it is meant that R$^1$ and R$^2$ can be selected from hydrogen or alkyl, or alternatively, the substructure has structure:

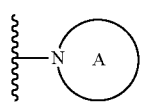

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

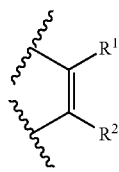

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

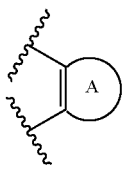

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

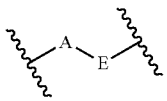

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR$, —$PO_2(R)_2$, —$PO_3(R)_2$, —$CONHNHSO_2R$, —$COHNS_2R$, and —CONRCN, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

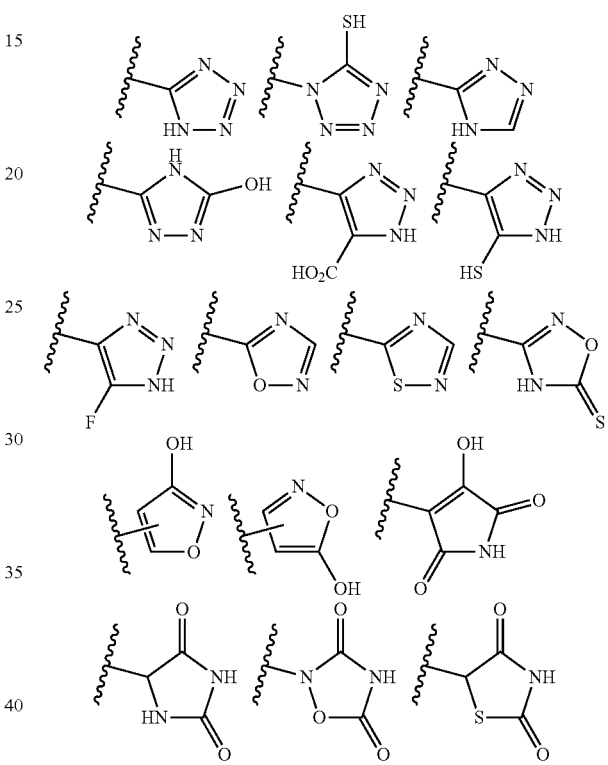

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a Methods of Preparation The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)).

If the compounds of the present technology contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis of Compounds of Formula I

In one embodiment, the method involves reacting an appropriately substituted hydroxy benzoate derivative (II) with an alcohol containing a terminal vinylic group (III) under Mitsunobu reaction conditions to yield an aryl ether derivative (IV) with a terminal vinylic group. The resulting product was then subjected to hydrolysis under basic conditions to yield the carboxylic acid derivative (V) which was then subjected to amide-coupling conditions with an amino acid derivative (V-1) wherein the carboxylic acid is protected as the Weinreb amide and the amino acid derivative contains a terminal vinyl group as shown in the scheme below (Scheme 1). The resulting amide derivative (VI) is then subjected to ring-closing metathesis reaction conditions to yield the macrocyclic α-keto amide derivative (VII). The macrocyclic α-keto amide derivative is subjected to reduction of the Weinreb amide upon treatment with DIBAL or even LAH to the corresponding aldehyde (VIII). Alternatively, the internal double-bond is reduced by hydrogenolysis to yield the product (IX) which is then subjected to reduction of the Weinreb amide upon treatment with DIBAL or even LAH to the corresponding aldehyde (X). The resulting aldehyde derivative is then subjected to various reaction conditions as shown in the scheme to yield the final products with the structures as described in the general Formula I. See Scheme 2. The aldehyde then undergoes a cyanohydrin reaction upon treatment with alkyl nitriles to yield the α-hydroxy amide derivative which is then subjected to oxidation conditions with Dess-Martin Periodinane (DMP) oxidation (with hypervalent iodine) or by an oxidizing agent such as PCC (pyridinium chlorochromate) to yield the macrocyclic α-ketoamide products (XI and XII). The skilled artisan will once again appreciate that there are many other oxidizing conditions and agents which are within the scope of this disclosure to oxidize the hydroxyl group. This synthesis route is generally shown in Scheme 1.

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

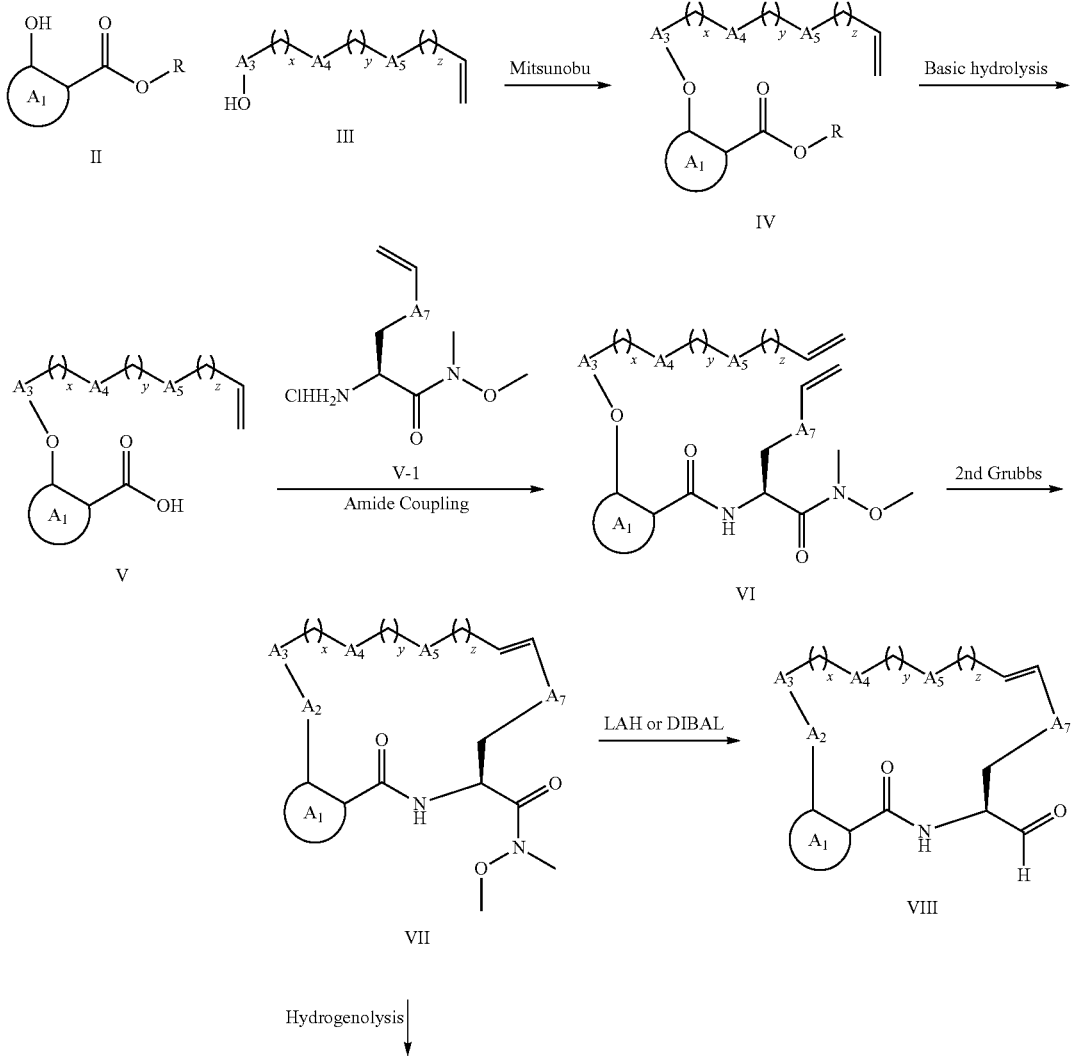

Scheme 1

-continued

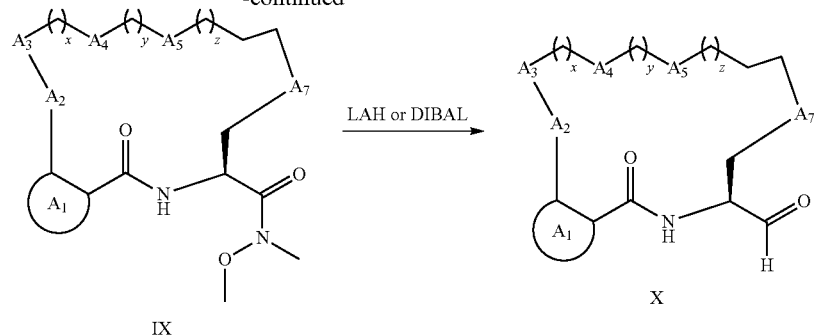

IX → X (LAH or DIBAL)

Scheme 2

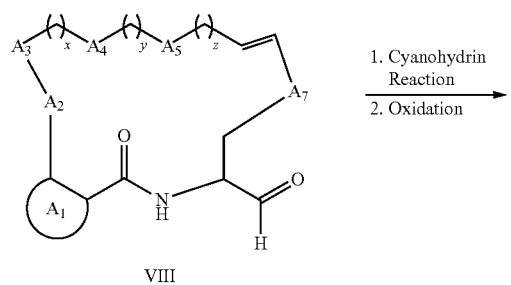

VIII

1. Cyanohydrin Reaction
2. Oxidation

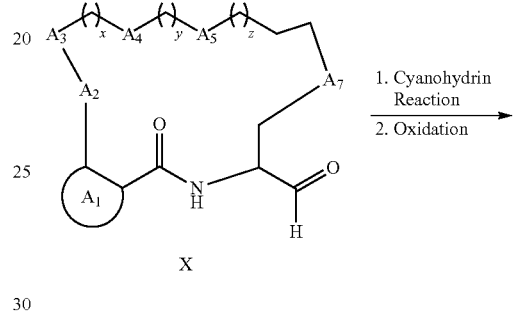

X

1. Cyanohydrin Reaction
2. Oxidation

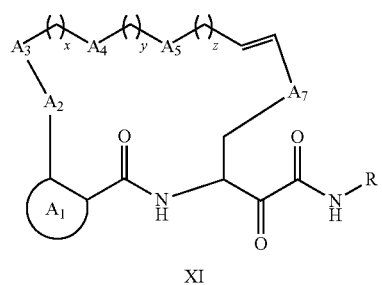

XI

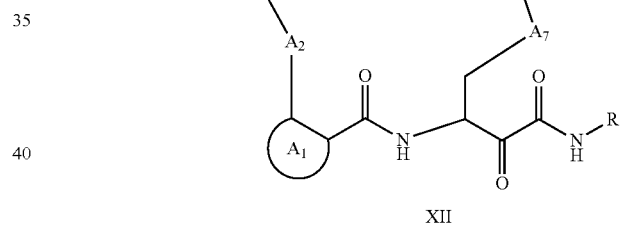

XII

In one embodiment, the method involves reacting an appropriately substituted tolyl derivative (XIII) with an alkyl halide (XIV) in presence of a base such as LDA to yield the alkylated derivative (XV) which is then subjected to the same conditions as in Scheme 1 and is further transformed to yield the final products (XVII and XIX) as described in general formula I. See Scheme 3 shown below.

Scheme 3

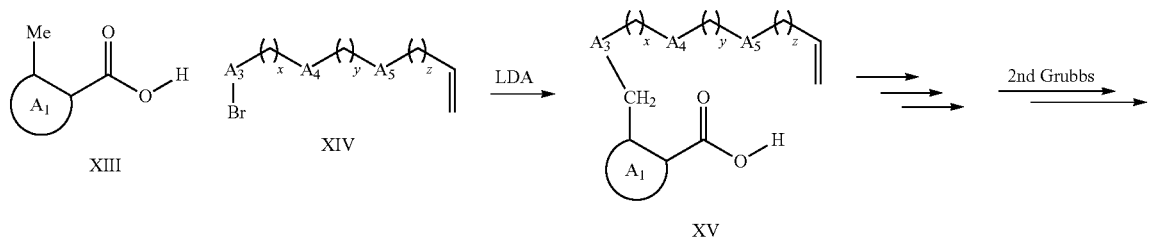

XIII + XIV → (LDA) → XV → → → 2nd Grubbs →

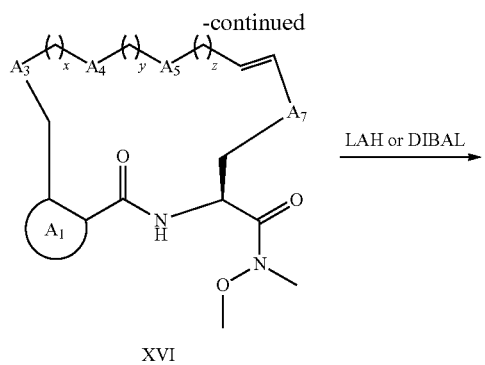 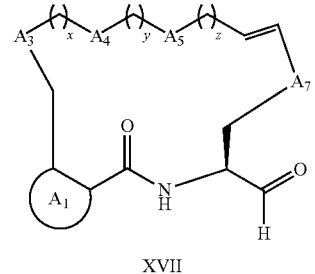

In another embodiment, a benzylic halide (XX) is subjected to treatment with an alcohol containing a terminal vinylic group (XXI) in presence of a base such as a metal hydride to yield the alkylated product (XXII) which is then subjected to the same conditions as in Scheme 1 and is further transformed to yield the final products (XXIV and XXVI) as described in general formula I. See Scheme 4 shown below Scheme 4

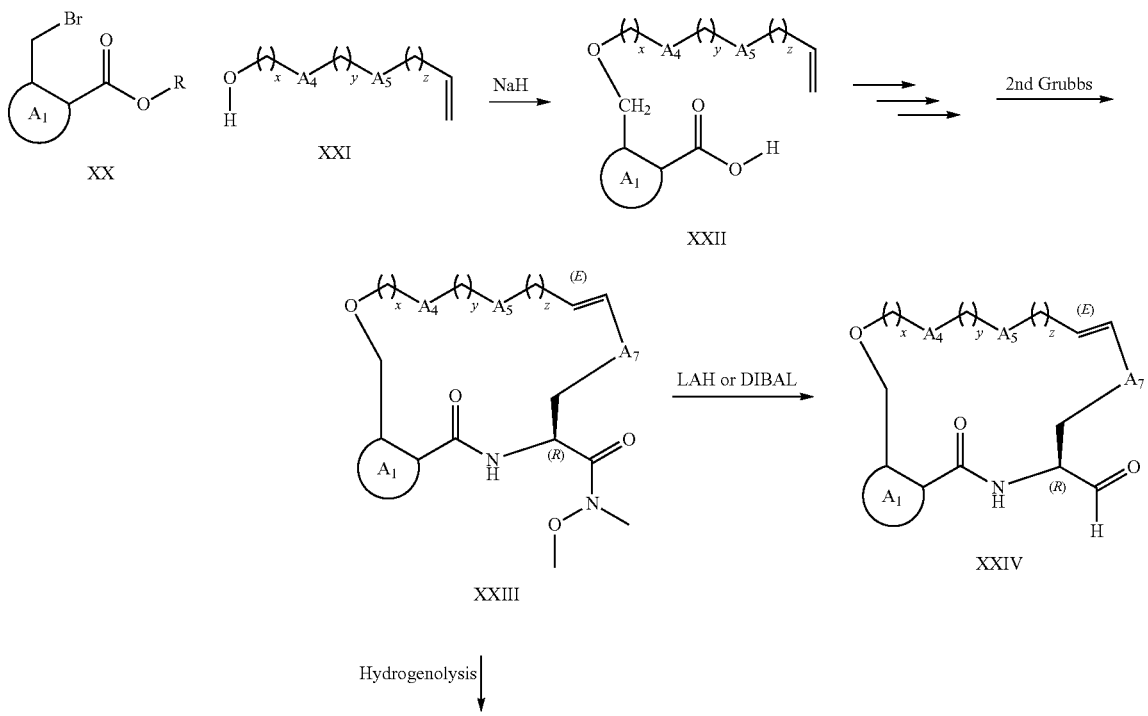

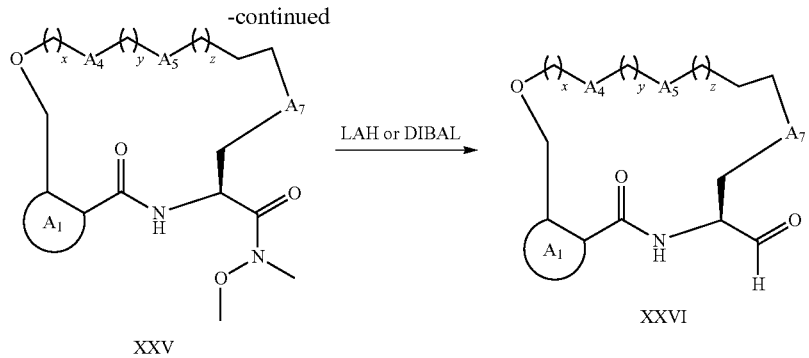

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modem Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

The compounds and compositions described herein, if desired, may be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compounds and compositions described herein are formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 99.99 wt % of a compound of the present technology based on the total formulation, with the balance being one or more suitable pharmaceutical excipients. Preferably, the compound is present at a level of about 1 80 wt %. Representative pharmaceutical formulations are described below.

FORMULATION EXAMPLES

The following are representative pharmaceutical formulations containing a compound of Formula I.

Formulation Example 1—Tablet Formulation

The following ingredients are mixed intimately and pressed into single scored tablets.

| Ingredient | Quantity per tablet, mg |
|---|---|
| Compounds disclosed herein | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
|---|---|
| Compounds disclosed herein | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| Compounds disclosed herein | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
|---|---|
| Compounds disclosed herein | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
| --- | --- |
| Compounds disclosed herein | 500 mg |
| Witepsol ® H-15 | balance |

Methods of Treatment

The compounds disclosed herein or their tautomers and/or pharmaceutically acceptable salts thereof can effectively act as CAPN1, CAPN2, and/or CAPN9 inhibitors and treat conditions affected at least in part by CAPN1, CAPN2, and/or CAPN9. Some embodiments provide pharmaceutical compositions comprising one or more compounds disclosed herein and a pharmaceutically acceptable excipient. Some embodiments provide a method for treating a fibrotic disease with an effective amount of one or more compounds as disclosed herein.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Some embodiments include combinations of a compound, composition or pharmaceutical composition described herein with any other pharmaceutical compound approved for treating fibrotic or myofibroblast differentiation associated diseases or disorders.

Some embodiments provide a method for inhibiting CAPN1, CAPN2, and/or CAPN9 and/or a method for treating a disease affected at least in part by CAPN1, CAPN2, and/or CAPN9 with an effective amount of one or more compounds as disclosed herein.

The compounds disclosed herein are useful in inhibiting CAPN1, CAPN2, and/or CAPN9 enzymes and/or treating disorders relating to fibrosis or myofibroblast differentiation.

Some embodiments provide a method for inhibiting CAPN1, CAPN2, and/or CAPN9 which method comprises contacting cells (including neurons/microglia/invading macrophages) with an effective amount of one or more compounds as disclosed herein.

Some embodiments provide a method for treating a fibrotic disease, which method comprises administering to a subject an effective amount of one or more compounds or a pharmaceutical composition disclosed herein comprising a pharmaceutically acceptable excipient.

Some embodiments provide a method for treating a disease affected at least in part by CAPN1, CAPN2, and/or CAPN9, which method comprises administering to a subject an effective amount of one or more compounds or a pharmaceutical composition disclosed herein comprising a pharmaceutically acceptable excipient.

Some embodiments provide a method for inhibiting CAPN1, CAPN2, and/or CAPN9 is provided wherein the method comprises contacting cells with an effective amount of one or more compounds disclosed herein. In some embodiments a method for inhibiting CAPN1, CAPN2, and/or CAPN9 is performed in-vitro or in-vivo.

Calpains are also expressed in cells other than neurons, microglia and invading macrophages. In particular, they are important in skeletal muscle and herein inhibition of calpains also refers to inhibition in these cells as well.

Selective Inhibition

Some embodiments provide a method for competitive binding with calpastatin (CAST), the method comprising contacting a compound disclosed herein with CAPN1, CAPN2, and/or CAPN9 enzymes residing inside a subject. In such a method, the compound specifically inhibits one or more of the enzymes selected from the group consisting of: CAPN1, CAPN2, and CAPN9 by at least 2-fold, by at least 3-fold, by at least 4-fold, by at least 5-fold, by at least 10-fold, by at least 15-fold, by at least 20-fold, by at least 50-fold, by at least 100-fold, by at least 150-fold, by at least 200-fold, by at least 400-fold, or by at least 500-fold.

Some embodiments provide a method for selectively inhibiting CAPN1 in the presence of CAPN2 and CAPN9, which includes contacting cells (including neurons/microglia/invading macrophages) with an effective amount of one or more compounds disclosed herein.

Some embodiments provide a method for selectively inhibiting CAPN2 in the presence of CAPN1 and CAPN9, which includes contacting cells (including neurons/microglia/invading macrophages) with an effective amount of one or more compounds disclosed herein.

Some embodiments provide a method for selectively inhibiting CAPN9 in the presence of CAPN2 and CAPN1, which includes contacting cells (including neurons/microglia/invading macrophages) with an effective amount of one or more compounds disclosed herein.

Some embodiments provide a method for selectively inhibiting CAPN1 and CAPN2 in the presence of CAPN9, which includes contacting cells (including neurons/microglia/invading macrophages) with an effective amount of one or more compounds disclosed herein.

Some embodiments provide a method for selectively inhibiting CAPN1 and CAPN9 in the presence of CAPN2, which includes contacting cells (including neurons/microglia/invading macrophages) with an effective amount of one or more compounds disclosed herein.

Some embodiments provide a method for selectively inhibiting CAPN2 and CAPN9 in the presence of CAPN1, which includes contacting cells (including neurons/microglia/invading macrophages) with an effective amount of one or more compounds disclosed herein.

Some embodiments provide a method for treating a fibrotic disease, which method comprises administering to a subject an effective amount of one or more compounds which specifically inhibits CAPN1, CAPN2, and/or CAPN9, said compounds or a pharmaceutical composition comprising one or more compounds disclosed herein and a pharmaceutically acceptable excipient.

Some embodiments provide a method for treating a disease affected at least in part by CAPN1, CAPN2, and/or CAPN9, which method comprises administering to a subject an effective amount of one or more compounds which specifically inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a fibrotic disease, which method comprises administering to a subject an effective amount of one or more compounds which selectively inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a disease affected at least in part by CAPN1, CAPN2, and/or CAPN9, which method comprises administering to a subject an effective amount of one or more compounds which selectively inhibits CAPN1, CAPN2, and/or CAPN9, said compounds being selected from compounds disclosed herein or a pharmaceutical composition comprising one or more compounds disclosed herein and a pharmaceutically acceptable excipient.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:5.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:10.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:20.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:50.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:100.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:200.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:250.

Some embodiments provide a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:500.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:5.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:10.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:20.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:50.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:100.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:200.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:250.

Some embodiments provide a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:500.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:5.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:10.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:20.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:50.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:100.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:200.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:250.

Some embodiments provide a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:500.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:5.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:10.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:20.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:50.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:100.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:200.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:250.

Some embodiments provide a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:500.

Some embodiments provide a method for prophylactic therapy or treatment of a subject having a fibrotic disorder wherein said method comprising administering an effective amount of one or more compounds disclosed herein to the subject in need thereof.

Some embodiments provide a method for prophylactic therapy or treatment of a subject having a disorder affected by CAPN1, CAPN2, and/or CAPN9 wherein said method comprising administering an effective amount of one or more compounds disclosed herein to the subject in need thereof.

Some embodiments provide a method for inhibiting myofibroblast differentiation (e.g., Epithelial/Endothelial-to-Mesenchymal Transition (EpMT/EnMT)) is provided wherein the method comprises contacting cells with an effective amount of one or more compounds disclosed herein. In one aspect, the method for inhibiting myofibroblast differentiation (e.g., Epithelial/Endothelial-to-Mesenchymal Transition (EpMT/EnMT)) is performed in-vitro or in-vivo.

Some embodiments provide a method for treating a disease or condition selected from the group consisting of or that produces a symptom selected from the group consisting of: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases, wherein which method comprises administering to a subject an effective amount of one or more compounds disclosed herein to a subject in need thereof.

Some embodiments provide a method for treating liver fibrosis.

Some embodiments provide a method for treating cardiac fibrosis.

Some embodiments provide a method for treating fibrosis in rheumatoid arthritis diseases.

Some embodiments provide a method for treating a condition affected by CAPN1, CAPN2, and/or CAPN9, which is in both a therapeutic and prophylactic setting for subjects. Both methods comprise administering of one or more compounds disclosed herein to a subject in need thereof.

Some embodiments provide a method for treating stiff skin syndrome.

Preferred embodiments include combinations of a compound, composition or pharmaceutical composition described herein with other CAPN1, CAPN2, and/or CAPN9 inhibitor agents, such as anti-CAPN1, CAPN2, AND/OR CAPN9 antibodies or antibody fragments, CAPN1, CAPN2, and/or CAPN9 antisense, iRNA, or other small molecule CAPN1, CAPN2, and/or CAPN9 inhibitors.

Some embodiments include combinations of a compound, composition or pharmaceutical composition described herein to inhibit myofibroblast differentiation (e.g., Epithelial/Endothelial-to-Mesenchymal Transition (EpMT/EnMT)). Some embodiments include combinations of one or more of these compounds which are inhibitors of one or more (or all three) CAPN1, CAPN2, and/or CAPN9, alone or in combination with other TGFβ signaling inhibitors, could be used to treat or protect against or reduce a symptom of a fibrotic, sclerotic or post inflammatory disease or condition including: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, postvasectomy pain syndrome, and rheumatoid arthritis.

Some embodiments include a combination of the compounds, compositions and/or pharmaceutical compositions described herein with an additional agent, such as anti-inflammatories including glucocorticoids, analgesics (e.g. ibuprofen), aspirin, and agents that modulate a Th2-immune response, immunosuppressants including methotrexate, mycophenolate, cyclophosphamide, cyclosporine, thalidomide, pomalidomide, leflunomide, hydroxychloroquine, azathioprine, soluble bovine cartilage, vasodilators including endothelin receptor antagonists, prostacyclin analogues, nifedipine, and sildenafil, IL-6 receptor antagonists, selective and non-selective tyrosine kinase inhibitors, Wnt-pathway modulators, PPAR activators, caspase-3 inhibitors, LPA receptor antagonists, B cell depleting agents, CCR2 antagonists, pirfenidone, cannabinoid receptor agonists, ROCK inhibitors, miRNA-targeting agents, toll-like receptor antagonists, CTGF-targeting agents, NADPH oxidase inhibitors, tryptase inhibitors, TGFD inhibitors, relaxin receptor agonists, and autologous adipose derived regenerative cells.

Indications

In some embodiments, the compounds and compositions comprising the compounds described herein can be used to treat a host of conditions arising from fibrosis or inflammation, and specifically including those associated with myofibroblast differentiation. Example conditions include liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders), cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic reperfusion injury associated fibrosis, injection fibrosis, cirrhosis, diffuse parenchymal lung disease, post-vasectomy pain syndrome, and rheumatoid arthritis diseases or disorders.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

It will be apparent to the skilled artisan that methods for preparing precursors and functionality related to the compounds claimed herein are generally described in the literature. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:
DCM=dichloromethane
DIEA=N,N-Diisopropylethylamine
DIPEA=N,N-Diisopropylethylamine
DMF=N,N-dimethylformamide
DMP=Dess Martin Periodinane
ESBL=extended-spectrum β-lactamase
EA=ethyl acetate
EtOAc=ethyl acetate
FCC=flash column chromatography
HATU=2-(7-aza-1H-benzotriazole-1-yl)-1,1,3,3-tetramethyluronium hexafluorophosphate
MeCN=acetonitrile
MsCl=methanesulfonyl chloride
NMR=nuclear magnetic resonance
PE=petroleum ether
prep=preparatory
Py=pyridine
sat.=saturated
TBDMSCl=tert-butyldimethylsilyl chloride
TBS=tert-butyldimethylsilyl
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Examples 1 and 2

(S,Z)-12-Oxo-1,3,4,6,9,10,11,12-octahydrobenzo[f][1,4]dioxa[9]azacyclo-tetradecine-10-carbaldehyde (1) and (S,E)-12-Oxo-1,3,4,6,9,10,11,12-octahydrobenzo[f][1,4]dioxa[9]azacyclotetradecine-10-carbaldehyde (2)

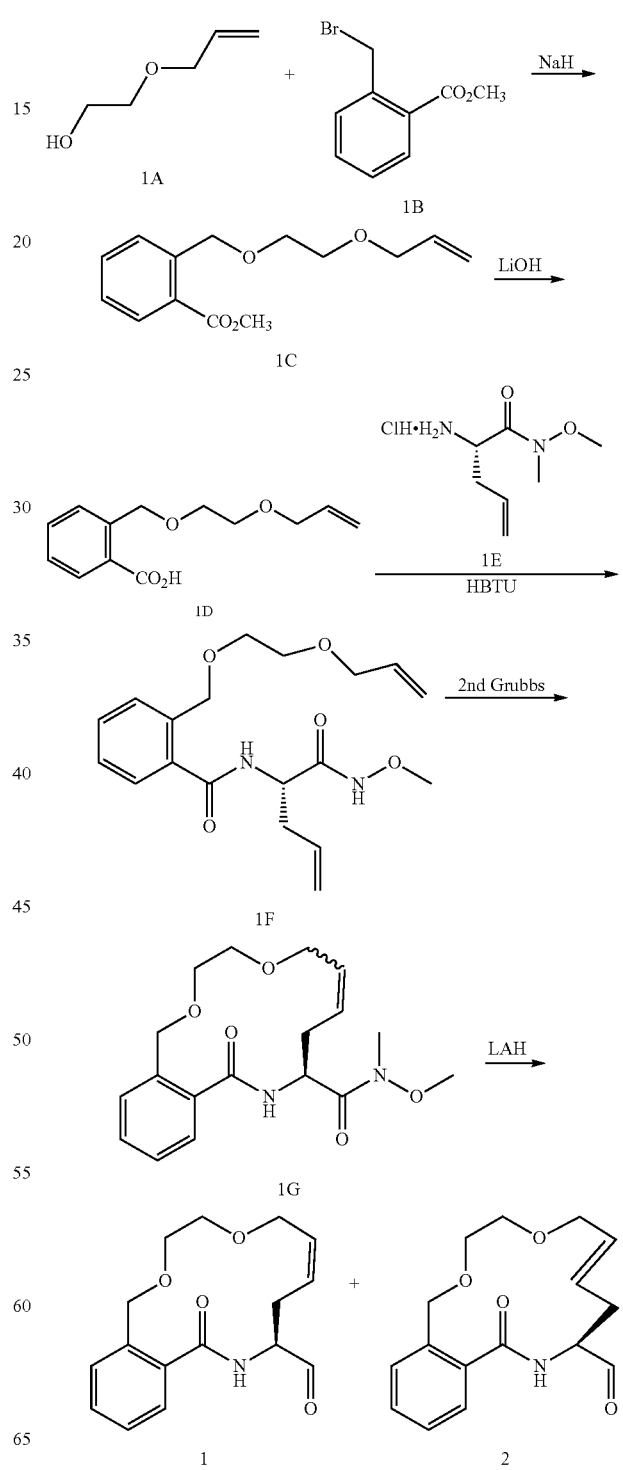

Step 1: Synthesis of Compound 1C

To a suspended solution of NaH (193 mg, 60% in mineral oil, 1.2 eq) in 35 mL dry THF under $N_2$ was slowly added a solution of 1A (490 mg, 1.1 eq) in 5 mL dry THF. The mixture was stirred at room temperature for 1 hr. A solution of 1B (1.0 g, 1.0 eq) in 5 mL THF was added. The resulting mixture was stirred at room temperature for 3 hrs. THF was removed in vacuo; the residue was suspended in 50 mL acetate and 10 mL hexane, and then washed with saturated aqueous $NaHCO_3$ and brine. The crude mixture was purified on ISCO (24 g, silica gel column chromatography) to provide compound 1C oil (720 mg, yield 66%).

Step 2: Synthesis of Compound 1D

Compound 1C (720 mg) was treated with LiOH in MeOH and water to provide acid 4 (675 mg, yield 99%).

Step 3: Synthesis of Compound 1F

Compound 1D (670 mg, 1.0 eq), 1E (605 mg, 1.1 eq.) and HBTU (1.3 g, 1.2 eq.) were combined in 15 mL DMF, the mixture was stirred at room temperature for 5 min., and then DIEA (1.2 mL, 2.5 eq) was added. The resulting mixture was stirred at room temperature for 30 min. The mixture was diluted with 50 mL ethyl acetate and 20 mL hexane, washed with 1N HCl, water and saturated $NaHCO_3$. The crude mixture was purified on ISCO (24 g column) to afford compound 1F (1.0 g, yield 99%).

Step 4: Synthesis of Compound 1G

Compound 1F (950 mg, 1.0 eq) was dissolved in 600 mL 1,2-dichloroethane, then added $2^{nd}$ Grubbs catalyst (110 mg, 5%). The mixture was heated at 85° C. for 1 hr. The solvent was removed in vacuo, the crude mixture was directly purified on ISCO (40 g column) to afford compound 1G (850 mg, yield 93%) a mixture of E/Z that contained a small amount ligand.

Step 5: Synthesis of Compound 1 and 2

Compound 1G (300 mg, 1.0 eq) was dissolved in 15 mL dry THF, cooled to −50° C. under $N_2$. A solution of 1N LAH in THF (0.91 mL, 1.05 eq) was added dropwise at −50° C. The resulting mixture was stirred at −30° C. to −10° C. for 2 hr. The reaction was quenched with 1N HCl at −20° C., then extracted with 2×30 mL acetate to afford a mixture E/Z (222 mg, yield 89%).

E/Z mixture was separated with preparatory-HPLC separation to provide purified compound 1 and compound 2.

Compound 1: MS (ESI) m/z $(M+H)^+$: 290.1; $^1$H-NMR: (400 MHz, DMSO-d6) δ 9.61 (s, 1H), 8.58 (d, 1H), 7.34-7.48 (m, 4H), 5.62 (m, 2H), 4.73 (d, 1H), 4.57 (m, 1H), 4.41 (d, 1H), 3.92 (m, 1H), 3.76 (m, 2H), 3.38-3.57 (m, 4H), 2.65 (m, 1H), 2.27 (m, 1H) ppm.

Compound 2: MS (ESI) m/z $(M+H)^+$: 290.1; $^1$H-NMR: (400 MHz, DMSO-d6) δ 9.56 (s, 1H), 8.74 (d, 1H), 7.34-7.48 (m, 4H), 5.51-5.62 (m, 2H), 4.84 (d, 1H), 4.05 (m, 1H), 3.71-3.92 (m, 2H), 3.33-3.47 (m, 4H), 2.59 (m, 1H), 2.52 (m, 1H) ppm.

Examples 3 and 4

(S,Z)—N-benzyl-2-oxo-2-(12-oxo-1,3,4,6,9,10,11,12-octahydrobenzo[f][1,4]dioxa[9]azacyclotetradecin-10-yl)acetamide (3) and (S,E)-N-benzyl-2-oxo-2-(12-oxo-1,3,4,6,9,10,11,12-octahydrobenzo[f][1,4]dioxa[9]azacyclotetradecin-10-yl)acetamide (4)

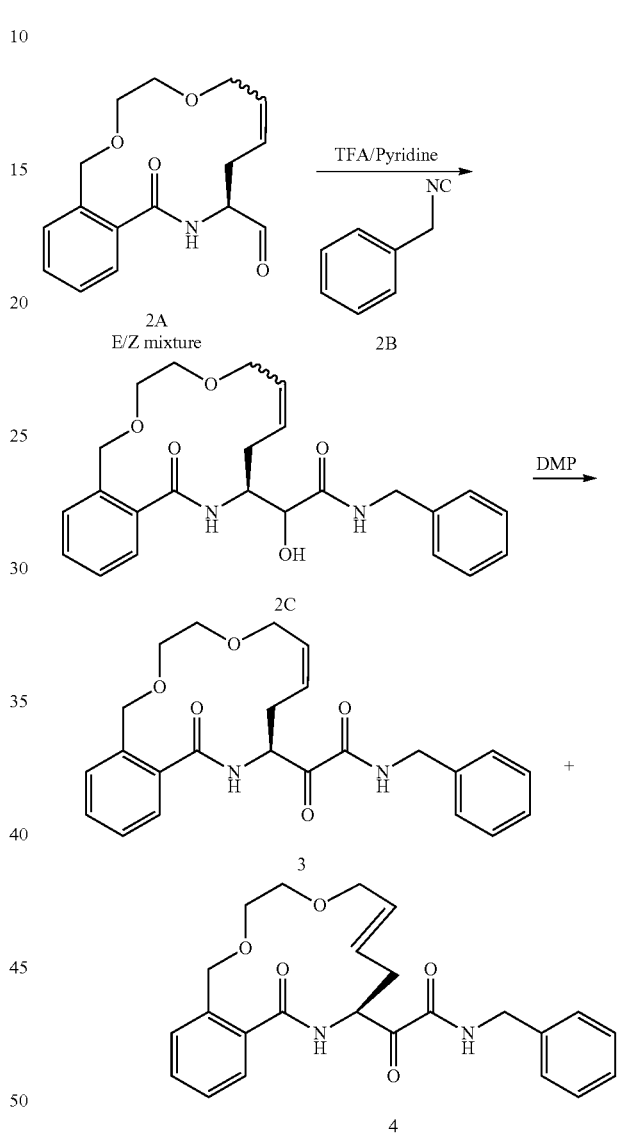

Step 1: Synthesis of Compound 2C

To a solution of compound 2A (mixture of E/Z) (150 mg, 1.0 eq.) in DCM (20 mL) cooled to 0° C. was added a solution of 2B (isocyanomethyl)benzene (121 mg, 2.00 eq) in DCM (2 mL) and solution of pyridine (190 mg, 4.0 eq.) in DCM (1 mL), then TFA (176 mg, 3.0 eq) in DCM (1 mL) was added slowly to the above reaction mixture over 10 min, then the reaction was stirred at 0° C. for 50 min and at 20° C. for 13 hrs. The reaction mixture was quenched with 1 M HCl (25 mL). To the solution was added ethyl acetate (100 mL) and separated. The organic layer was washed with NaHCO$_3$ (10 mL) and brine. The crude mixture was purified on silica-gel column to afford compound 2C (105 mg, yield 47.7%).

Step 2: Synthesis of Compounds 3 and 4

To a solution of compound 2C (E/Z mixture) (100 mg, 1.0 eq) in 20 mL dry DCM was added DMP (535 mg, 4.0 eq). The resulting mixture was stirred at room temperature for 15 hrs then the mixture was diluted with DCM (50 mL), quenched by adding 10% Na$_2$S$_2$O$_3$/saturated NaHCO$_3$ (v/v=1/1, ~20 mL). The organic layer was separated. The aqueous layer was extracted with DCM (30 mL×2). The combined organic layer was washed with H$_2$O (10 mL), brine (10 mL), dried over anhydrous Na$_2$SO$_4$, filtered and concentrated. The mixture was separated on silica-gel column to afford purified compound 3 and compound 4.

Compound 3: MS (ESI) m/z (M+H)$^+$: 423.4; $^1$H-NMR: (400 MHz, CDCl$_3$) δ 8.46 (d, 1H), 7.70 (m, 1H), 7.19-7.42 (m, 9H), 5.74 (m, 2H), 5.40 (m, 1H), 5.04 (d, 1H), 4.51 (m, 2H), 4.39 (d, 1H), 4.12 (m, 1H), 3.92 (m, 1H), 3.62 (m, 4H), 2.72-2.84 (m, 2H) ppm.

Compound 4: MS (ESI) m/z (M+H)$^+$: 423.4; $^1$H-NMR: (400 MHz, CDCl$_3$) δ 8.35 (d, 1H), 7.86 (m, 1H), 7.18-7.45 (m, 9H), 5.80 (m, 1H), 5.47-5.61 (m, 2H), 4.86 (d, 1H), 4.49-4.59 (m, 3H), 3.98 (m, 2H), 3.62 (m, 3H), 3.51 (m, 1H), 2.78 (m, 2H) ppm.

Examples 5 and 6

(S)-11-Oxo-2,3,4,5,8,9,10,11-octahydrobenzo[b][1]oxa[5]azacyclotridecine-9-carbaldehyde (5) and (S)-11-Oxo-2,3,4,5,6,7,8,9,10,11-decahydrobenzo[b][1]oxa[5]azacyclotridecine-9-carbaldehyde (6)

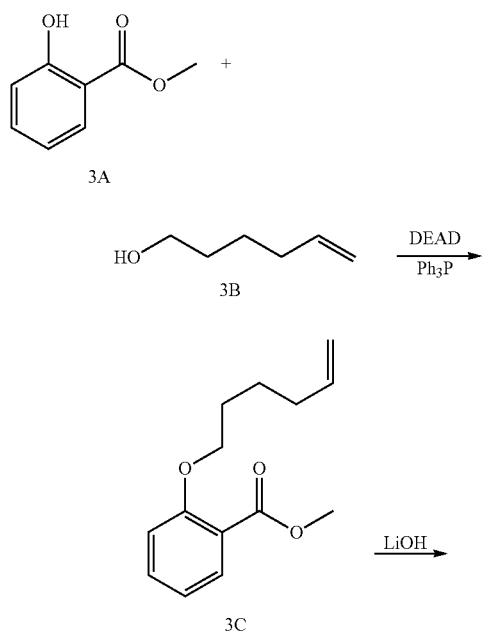

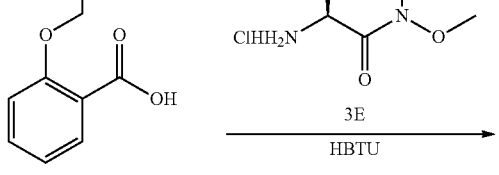

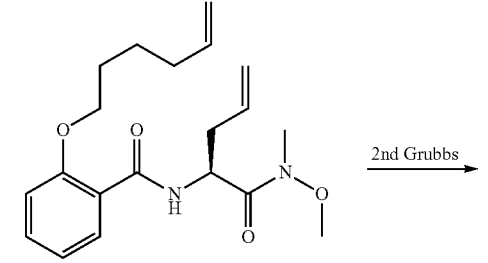

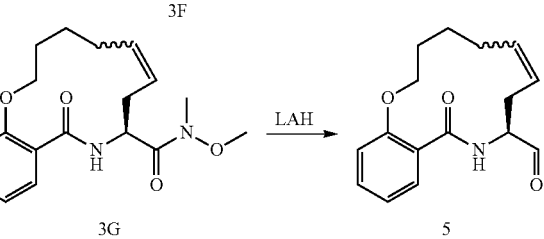

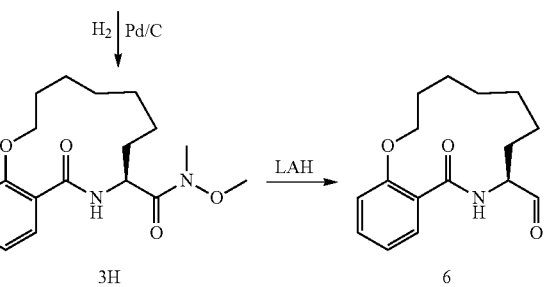

Step 1: Synthesis of Compound 3C

To a solution of 3A (2.0 g, 1.0 eq), 3B (1.5 g, 1.1 eq) and PPh$_3$ (1.14 g, 1.2 eq) in 10 mL dry THF at 0° C. under N$_2$ was slowly added a solution of DEAD (3.2 g, 1.2 eq) in 5 mL dry THF. The mixture was stirred at room temperature for overnight. The reaction mixture was diluted with 150 mL hexane, the precipitated white solid Ph$_3$PO was removed by filtration. The crude mixture was purified on ISCO to provide compound 3C clear oil (1.97 g, yield 64%).

Step 2: Synthesis of Compound 3D

Compound 3C (1.9 g) was treated with LiOH in MeOH and water to provide acid 3D (1.8 g, yield 95%).

Step 3: Synthesis of Compound 3F

Compound 3D (250 mg, 1.0 eq), 5 (288 mg, 1.3 eq) and HBTU (560 mg, 1.3 eq) were combined in 15 mL DMF, the mixture was stirred at room temperature for 5 mins, and then DIEA (600 mg, 4.0 eq) was added. The resulting mixture was stirred at room temperature for 1 hr. The mixture was diluted with 50 mL ethyl acetate and 20 mL Hexane, washed with 1N HCl, water and saturated NaHCO$_3$. The crude mixture was purified on ISCO to afford compound 3F (350 mg, yield 85.5%).

Step 4: Synthesis of Compound 3G

Compound 3F (150 mg, 1.0 eq) was dissolved in 250 mL 1,2-dichloroethane, then added 2$^{nd}$ Grubbs catalyst (18 mg, 5%). The mixture was heated at 85° C. for 1 hr. The solvent was removed in vacuo, the crude mixture was directly purified on ISCO to afford compound 3G (105 mg, yield 76%) a mixture of E/Z that contained a small amount of ligand.

Step 5: Synthesis of Compound 3H

A solution of compound 3G (130 mg) and Pd/C (20 mg, 10%) in 40 mL MeOH was hydrogenated at 50 psi for 15 hr. The catalyst was removed, and crude product was purified on silica gel column to afford compound 3H (110 mg, yield 90%).

Step 6: Synthesis of Compound 5

Compound 3G (100 mg, 1.0 eq) was dissolved in 8 mL dry THF, cooled to −50° C. under N$_2$. A solution of 1N LAH in THF (0.33 mL, 1.1 eq) was added dropwise at −50° C. The resulting mixture was stirred at −30° C. to −10° C. for 2 hrs. The reaction was quenched with 1N HCl at −20° C., then extracted with 2×30 mL acetate to afford a mixture E/Z of compound 5 (64 mg, yield 78%). MS (ESI) m/z (M+H)$^+$: 274.4; $^1$H-NMR: (400 MHz, CDCl$_3$) δ 9.63 (s, 1H), 8.48 (m, 1H), 8.23 (d, 1H), 7.45 (m, 1H), 7.09 (t, 1H), 6.94 (d, 1H), 5.76 (m, 1H), 5.36 (m, 1H), 4.68 (m, 1H), 4.26 (m, 2H), 2.71 (m, 1H), 2.49 (m, 1H), 2.27 (m, 1H), 1.77-2.12 (m, 5H) ppm.

Step 7: Synthesis of Compound 6

Compound 3H (110 mg, 1.0 eq) was dissolved in dry THF (10 mL) and cooled to −78° C. under N$_2$. LAH (1M, 0.32 mL, 1.1 eq) was added dropwise. The mixture was stirred at −30° C. for 2 hr. Then the reaction was quenched by adding 1N HCl at −10° C. The mixture was extracted by 3×20 mL acetate. The organic phase was washed with water and brine. The crude mixture was purified on silica-gel column to afford compound 6 (65 mg, yield 68%). MS (ESI) m/z (M+H)$^+$: 276.1; $^1$H-NMR: (400 MHz, CDCl$_3$) δ 9.68, (s, 1H), 8.25 (m, 1H), 8.14 (dd, 1H), 7.45 (m, 1H), 7.07 (m, 1H), 6.97 (d, 1H), 4.67 (m, 1H), 4.24 (m, 1H), 4.1 (m, 1H), 2.12-1.82 (m, 4H), 1.7-1.38 (m, 8H) ppm.

Example 7

(S)—N-benzyl-2-oxo-2-(11-oxo-2,3,4,5,8,9,10,11-octahydrobenzo[b][1]oxa[5]azacyclotridecin-9-yl) acetamide (7)

Synthesis of Compound 7

Compound 7 was prepared following the procedure of Example 3 using Example 5 and compound 2B. MS (ESI) m/z (M+H)$^+$: 274.4; $^1$H-NMR: (400 MHz, CDCl$_3$) δ 8.45 (d, 1H), 8.13 (d, 1H), 7.21-7.44 (m, 7H), 7.03 (t, 1H), 6.94 (d, 1H), 5.86 (m, 1H), 5.52 (m, 1H), 5.40 (m, 1H), 4.45-4.60 (m, 2H), 3.99-4.19 (m, 2H), 2.60-2.81 (m, 2H), 2.12-2.36 (m, 2H), 1.83-2.01 (m, 4H) ppm.

Examples 8 and 9

(S)-11-Oxo-2,3,4,5,8,9,10,11-octahydrobenzo[b][1]oxa[5]azacyclotridecine-9-carbaldehyde (8) and (S)-11-Oxo-2,3,4,5,6,7,8,9,10,11-decahydrobenzo[b][1]oxa[5]azacyclotridecine-9-carbaldehyde (9)

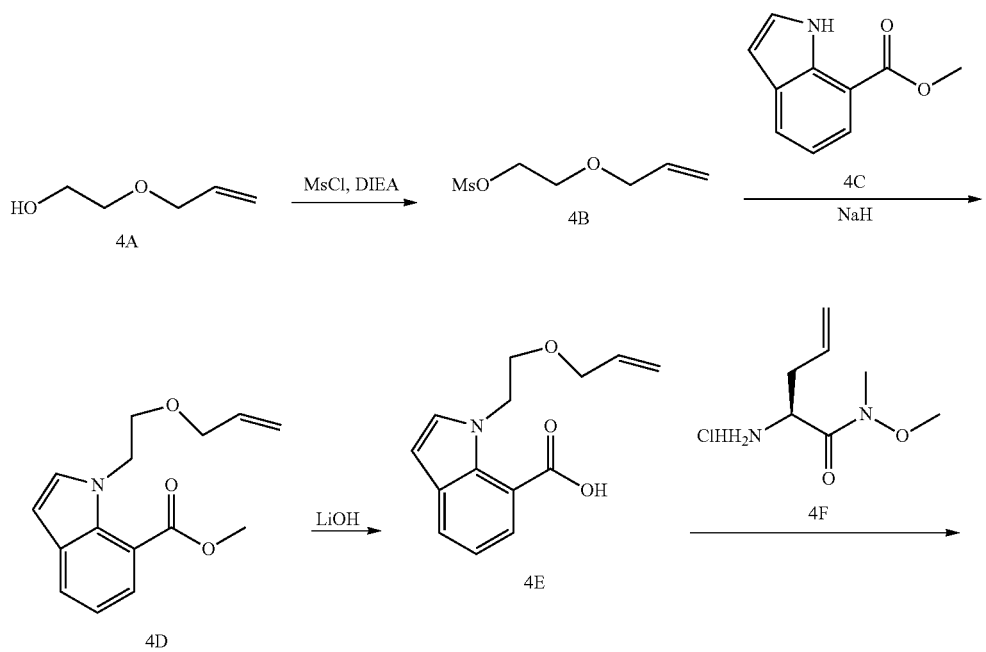

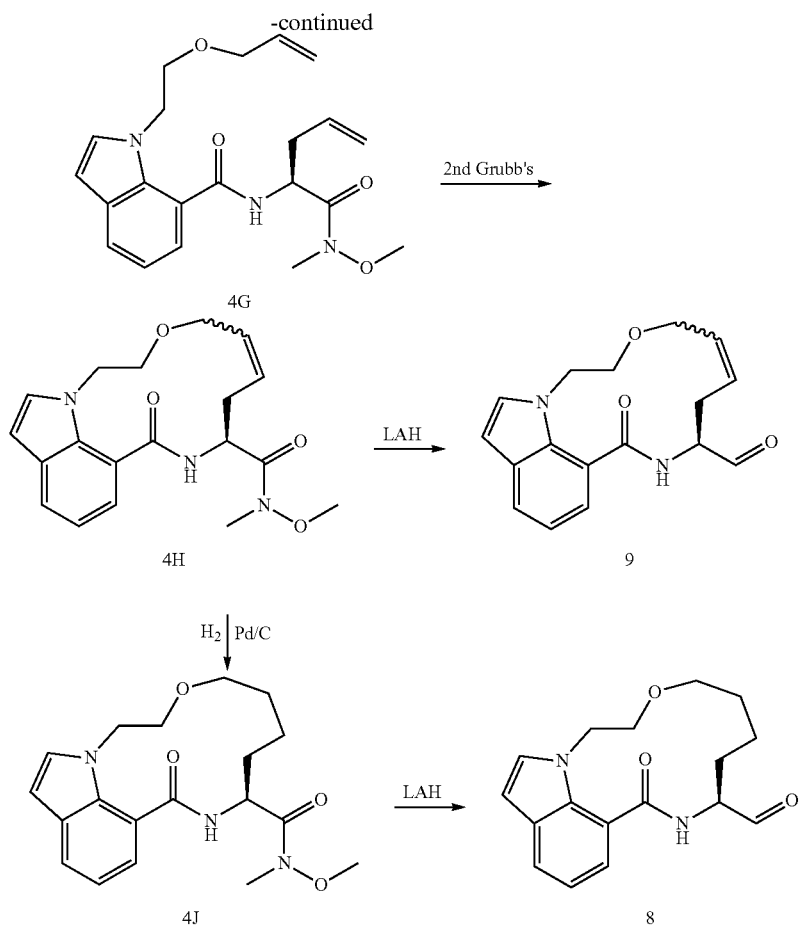

Step 1: Synthesis of Compound 4B

To a solution of alcohol 4A (5.1 g, 1.0 eq) in DCM (50 mL) cooled to 0° C. was added a solution of Et$_3$N (7 g, 1.4 eq) followed by dropwise addition of MsCl (6.9 g, 1.2 eq). The reaction was stirred at 0° C. for 2 hrs. The reaction mixture was quenched with water and the organic layer was washed with NaHCO$_3$ (10 mL) and brine, dried over Na$_2$SO$_4$. The crude mixture was filtered and evaporated under reduced pressure to afford the compound 4B, which was used for next step reaction without further purification.

Step 2: Synthesis of Compound 4D

To a suspension of NaH (0.9 g, 60% in mineral oil, 1.5 eq) in 20 mL dry DMF under N$_2$ was slowly added a solution of 4C (2.6 g, 1 eq) in 10 mL dry DMF. The mixture was stirred at room temperature for 1 hr. A solution of 4B (3 g, 1.0 eq) in 5 mL DMF was added. The resulting mixture was stirred at room temperature. overnight. The residue was suspended in 100 mL acetate and 20 mL hexane, then washed with water (3 times) and brine. The crude mixture was purified on ISCO (40 g, silica gel column) to provide compound 4D.

Synthesis of Compound 8

Compound 8 was prepared following the procedure of Example 30 using intermediate 4D. MS (ESI) m/z (M+H)$^+$: 301.5; $^1$H-NMR: (400 MHz, CDCl$_3$) δ 9.68 (s, 1H), 7.72 (d, 1H), 7.38 (d, 1H), 7.1 (d, 1H), 7.07 (m, 1H), 6.72 (d, 1H), 6.58 (d, 1H), 5.2 (m, 1H), 4.25 (m, 1H), 3.61 (m, 1H), 3.52 (m, 1H), 3.45-3.38 (m, 2H), 2.7-2.58 (m, 1H), 2.05-1.95 (m, 1H), 1.7-1.45 (m, 5H) ppm.

Synthesis of Compound 9

Compound 9 was prepared following the procedure of Example 29 using intermediate 4D. MS (ESI) m/z (M+H)$^+$: 298.9; $^1$H-NMR: (400 MHz, CDCl$_3$) δ 9.81 (s, 0.3H), 9.79 (s, 0.7H), 7.72 (m, 1H), 7.38 (m, 1H), 7.1-7.05 (m, 2H), 6.74 (m, 1H), 6.57 (m, 1H), 6.0 (m, 1H), 5.63 (m, 1H), 5.4-5.1 (m, 1H), 4.9 (m, 1H), 4.2-4.0 (m, 2H), 3.98-3.8 (m, 1H), 3.7-3.58 (m, 2H), 3.4-3.1 (m, 1H), 2.3-2.18 (m, 1H) ppm.

Example 10

(S,E)-1-Oxo-1,2,3,4,7,8,9,10,11,12-decahydrobenzo[c][1]aza-cyclotetradecine-3-carbaldehyde (10)

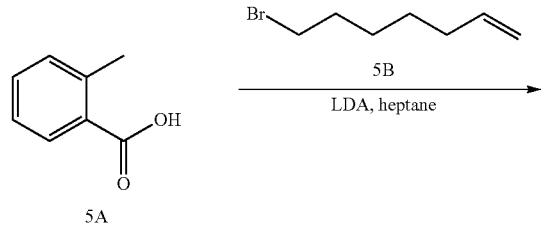

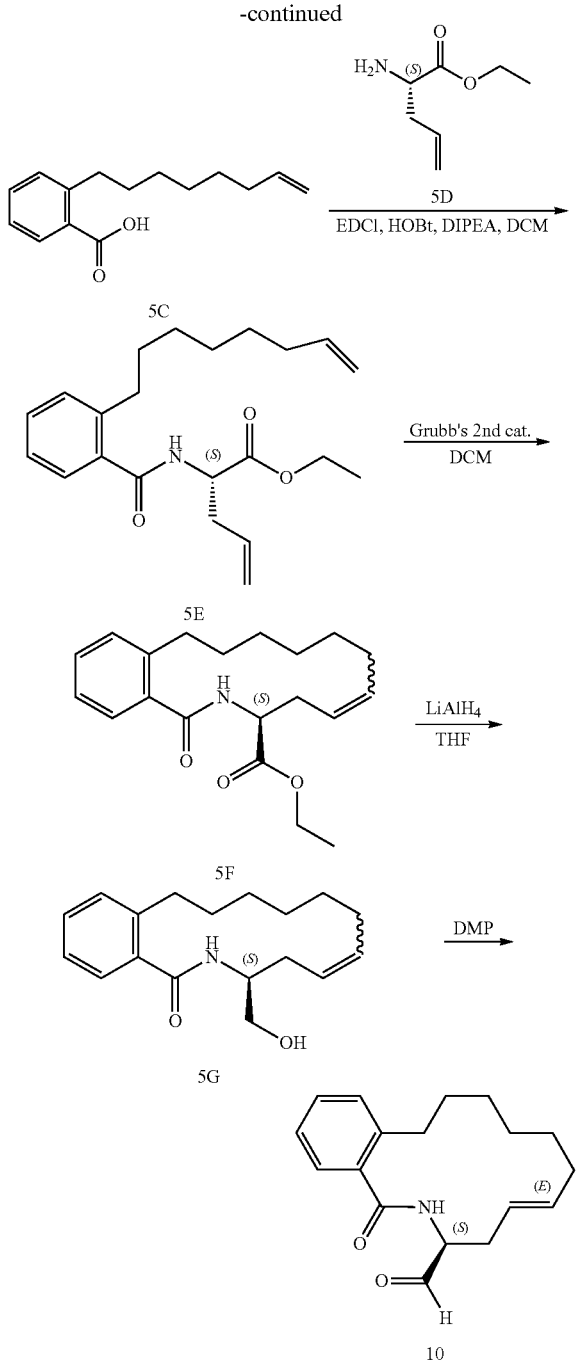

Step 1: Synthesis of Compound 5C

To a solution of LDA (2M, 18.66 mL) in THF (30 mL) was compound 5A (2 g, 14.69 mmol) in THF (14 mL) and heptan (14 mL) at −30° C. dropwise in 30 min. The mixture was stirred at −30° C. for 1.5 hrs. To the deep red reaction was added compound 5B (3.67 g, 20.71 mmol) in THF (10 mL) at −30° C. The mixture was stirred at −30° C. for 2 hr. The mixture was quenched with water (80 mL) and separated. The organic layer was extracted with water (50 mL×2). The combined aqueous layers were acidified with 1M HCl to pH~2 and extracted with ethyl acetate (50 mL×3). The combined organic layers were dried over $Na_2SO_4$ and concentrated. The residue was purified by column chromatography ($SiO_2$, Petroleum ether/Ethyl acetate=1/0 to 10/1) to afford compound 5C as colorless oil. H NMR (400 MHz, $CDCl_3$): δ 8.09-7.96 (m, 1H), 7.52-7.36 (m, 1H), 7.36-7.20 (m, 2H), 5.90-5.71 (m, 1H), 5.03-4.87 (m, 2H), 3.10-2.95 (m, 2H), 2.10-1.98 (m, 2H), 1.71-1.54 (m, 2H), 1.47-1.30 (m, 6H).

Step 2: Synthesis of Compound 5E

A mixture of compound 5C (1 g, 4.30 mmol), 5D (773.24 mg, 4.30 mmol, HCl), HOBt (581.61 mg, 4.30 mmol), EDCI (1.24 g, 6.46 mmol), DIPEA (3.76 mL, 21.52 mmol) in DCM (50 mL) was stirred at 15° C. for 3 hrs. The mixture was concentrated. The residue was dissolved in DCM (100 mL) and washed with 1N HCl (20 mL), sat. $NaHCO_3$ (2×20 mL) and separated. The organic layer was dried and concentrated. The residue was purified by column chromatography ($SiO_2$, Petroleum ether/Ethyl acetate=5:1 to 3:1) to afford compound 5E (1.11 g, yield 72.21%) as colorless oil. MS (ESI) m/z (M+H)$^+$ 358; $^1$H NMR (400 MHz, $CDCl_3$): δ 7.40-7.33 (m, 2H), 7.26-7.19 (m, 2H), 6.37-6.24 (m, 1H), 5.88-5.68 (m, 2H), 5.21-5.14 (m, 2H), 5.02-4.85 (m, 3H), 4.30-4.20 (m, 2H), 2.79-2.71 (m, 2H), 2.66-2.58 (m, 1H), 2.07-2.00 (m, 2H), 1.65-1.58 (m, 3H), 1.42-1.29 (m, 9H).

Step 3: Synthesis of Compound 5F

To a solution of compound 5E (1.11 g, 3.1 mmol eq) in DCM (310 mL) was added Grubb's 2nd (162.12 mg, 270 mmol). The mixture was stirred at 50° C. under $N_2$ for 15 hrs. The mixture was concentrated. The residue was purified by column chromatography ($SiO_2$, Petroleum ether/Ethyl acetate=5:1 to 2:1) to afford compound 5F (200 mg, 16.71% yield) as white solid. MS (ESI) m/z (M+H)$^+$ 329.9; $^1$H NMR (400 MHz, DMSO-$d_6$): δ 8.52-8.46 (m, 1H), 7.40-7.23 (m, 4H), 5.50-5.40 (m, 1H), 5.37-5.28 (m, 1H), 4.56-4.49 (m, 1H), 4.19-4.10 (m, 2H), 2.92-2.83 (m, 1H), 2.43-2.27 (m, 1H), 2.13-2.05 (m, 1H), 1.85-1.76 (m, 1H), 1.70-1.54 (m, 2H), 1.46-1.30 (m, 2H), 1.30-1.14 (m, 5H), 1.10-0.97 (m, 3H).

Step 4: Synthesis of Compound 5G

To a solution of compound 5F (200 mg, 607.11 μmol) in THF (15 mL) was added LAH (46.08 mg, 1.21 mmol) at 0° C. in portions. The mixture was stirred at 0° C. for 2 hrs. The mixture was quenched with water (0.1 mL) and 15% NaOH (0.3 mL) at 0° C. and stirred at 15° C. for 10 min, then added $Na_2SO_4$ (1 g). The mixture was filtered and filtrate was concentrated. The residue was triturated in ethyl acetate (5 mL) and filtered to afford compound 5G (85.0 mg, yield 45.89%) as white solid. MS (ESI) m/z (M+H)$^+$ 287.9; H NMR (400 MHz, DMSO-$d_6$): δ 7.88-7.82 (m, 1H), 7.36-7.25 (m, 3H), 7.25-7.17 (m, 1H), 5.41-5.28 (m, 2H), 4.80-4.76 (m, 1H), 4.04-3.92 (m, 1H), 3.50-3.41 (m, 1H), 3.30-3.23 (m, 1H), 3.01-2.92 (m, 1H), 2.46-2.33 (m, 1H), 2.11-1.96 (m, 2H), 1.86-1.75 (m, 1H), 1.68-1.53 (m, 2H), 1.47-1.31 (m, 2H), 1.29-1.13 (m, 1H), 1.10-0.98 (m, 3H).

Step 5: Synthesis of Compound 10

To a solution of compound 5G (85 mg, 295.76 µmol) in DCM (15 mL) was added DMP (501.77 mg, 1.18 mmol). The mixture was stirred at 20° C. for 3 hrs. The reaction mixture was quenched by addition saturated aqueous. Na$_2$S$_2$O$_3$ (12 mL), saturated aqueous NaHCO$_3$ (5 mL) and stirred for 30 min. The mixture was separated, washed with water (10 mL×2), brine (10 mL), dried over Na$_2$SO$_4$, filtered and concentrated under reduced pressure to give a residue. The residue was triturated in (i-Pr)$_2$O (3 mL) to afford compound 10 (12.2 mg, yield 13.88%) as white solid. MS (ESI) m/z (M+H)$^+$ 286.1; $^1$H NMR (400 MHz, DMSO-d$_6$): δ 9.60 (s, 1H), 8.51-8.45 (m, 1H), 7.43-7.22 (m, 4H), 5.48-5.29 (m, 2H), 4.54-4.47 (m, 1H), 2.93-2.84 (m, 1H), 2.69-2.54 (m, 2H), 2.21-1.99 (m, 2H), 1.90-1.75 (m, 1H), 1.68-1.55 (m, 2H), 1.46-1.28 (m, 2H), 1.27-1.15 (m, 1H), 1.13-0.98 (m, 3H).

Example 11

(S)-13-Oxo-1,4,5,7,10,11,12,13-octahydro-3h-benzo[g][1,5]dioxa[10]aza-cyclopentadecine-11-carbaldehyde (11)

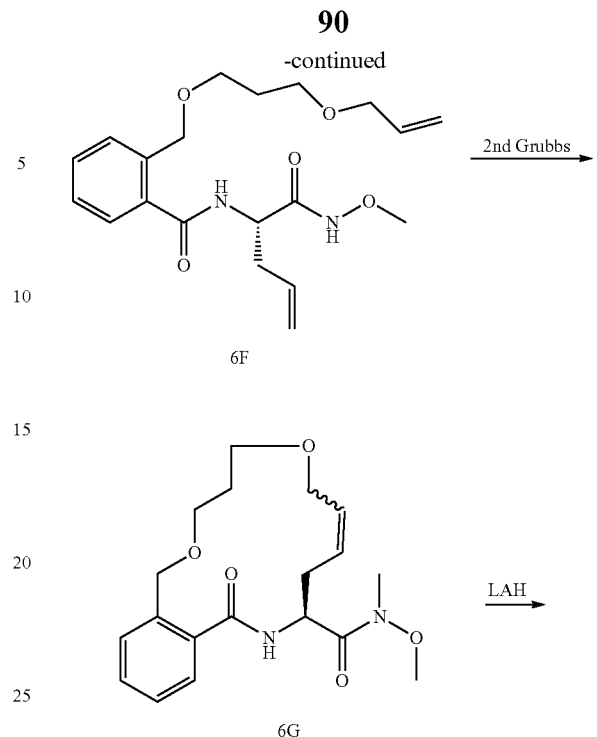

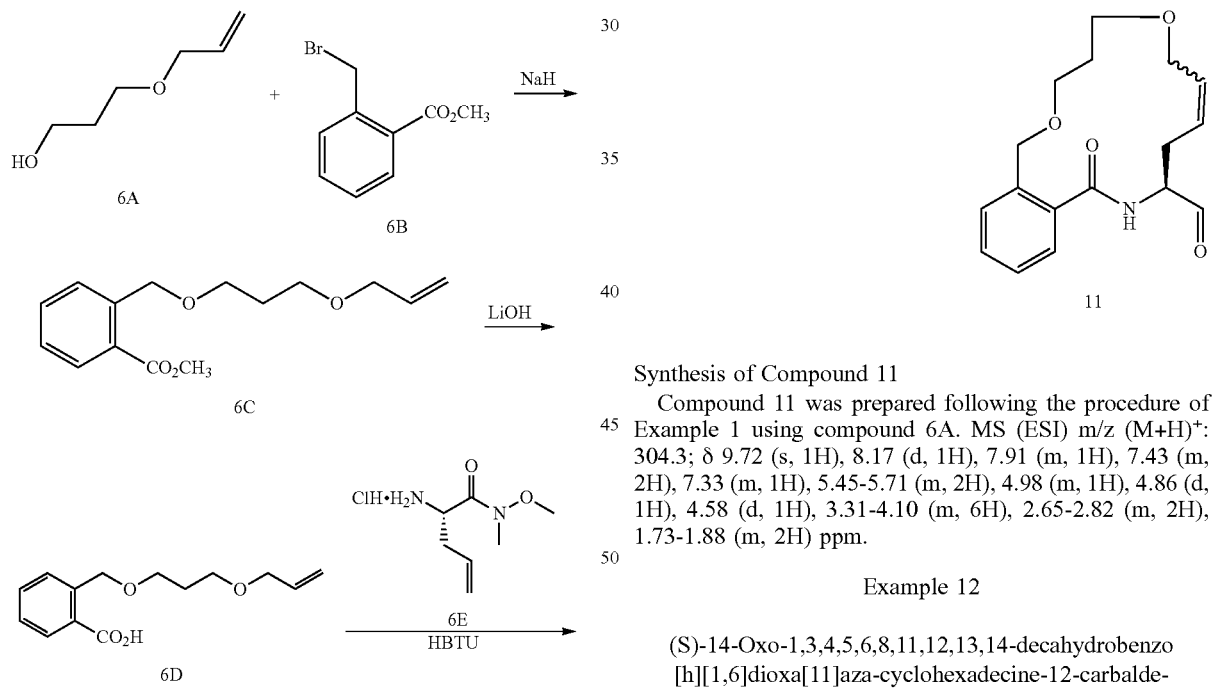

Synthesis of Compound 11

Compound 11 was prepared following the procedure of Example 1 using compound 6A. MS (ESI) m/z (M+H)$^+$: 304.3; δ 9.72 (s, 1H), 8.17 (d, 1H), 7.91 (m, 1H), 7.43 (m, 2H), 7.33 (m, 1H), 5.45-5.71 (m, 2H), 4.98 (m, 1H), 4.86 (d, 1H), 4.58 (d, 1H), 3.31-4.10 (m, 6H), 2.65-2.82 (m, 2H), 1.73-1.88 (m, 2H) ppm.

Example 12

(S)-14-Oxo-1,3,4,5,6,8,11,12,13,14-decahydrobenzo[h][1,6]dioxa[11]aza-cyclohexadecine-12-carbaldehyde (12)

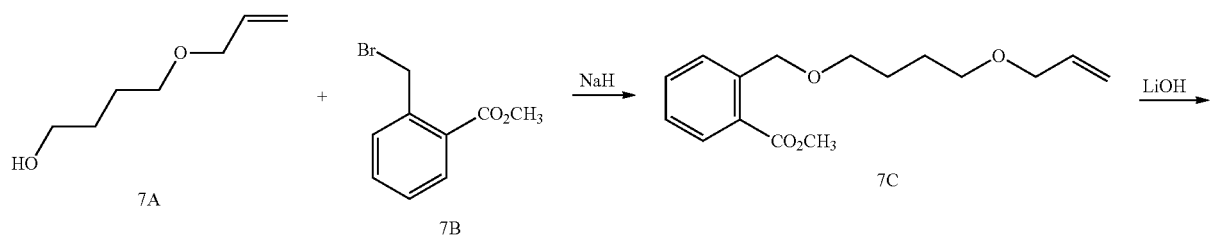

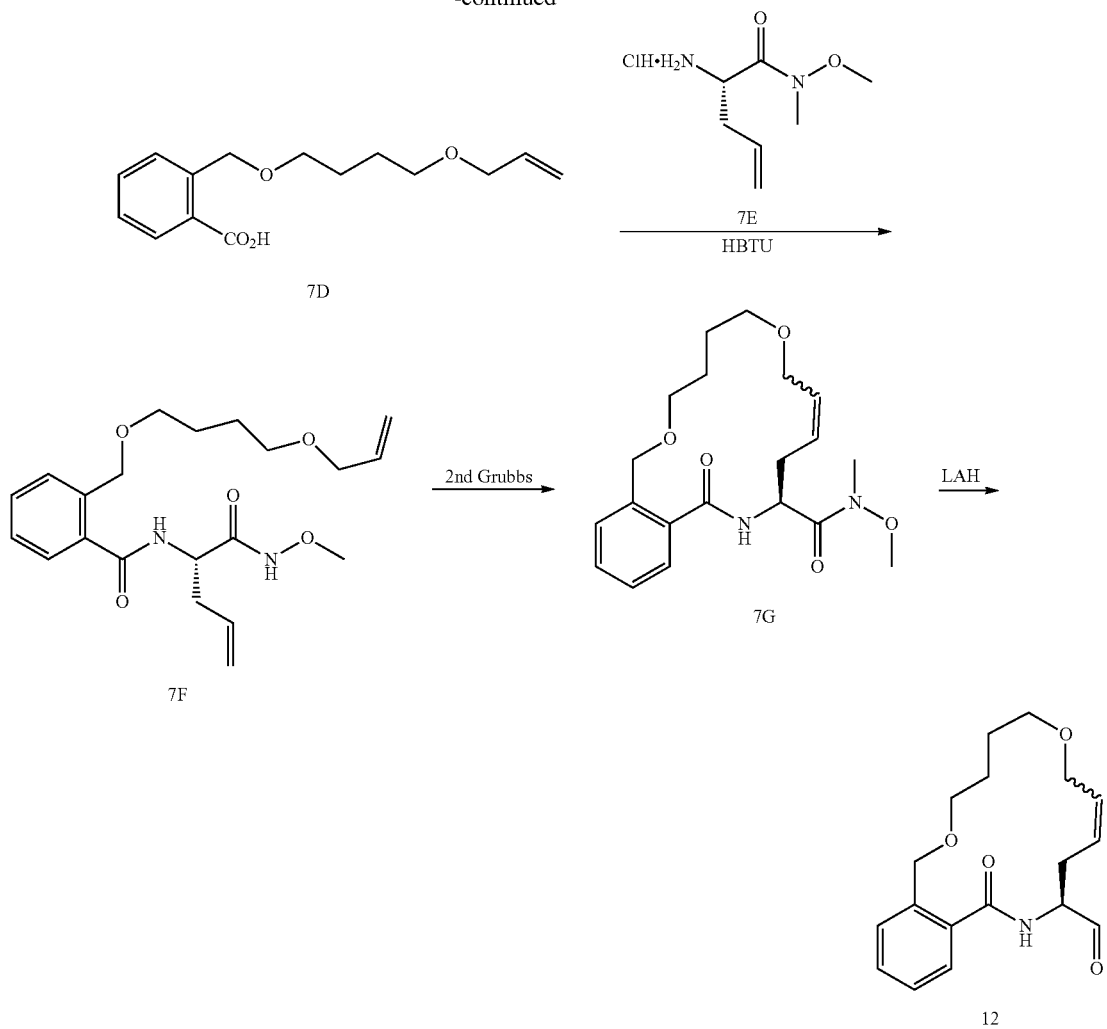
Synthesis of Compound 12
Compound 12 was prepared following the procedure of Example 1 using compound 7A. MS (ESI) m/z (M+H)$^+$: 318.0; δ 9.70 (s, 1H), 8.08 (d, 1H), 7.88 (m, 1H), 7.45 (m, 2H), 7.34 (m, 1H), 5.63 (m, 2H), 5.05 (m, 1H), 4.91 (d, 1H), 4.46 (d, 1H), 3.93 (m, 2H), 3.66 (m, 1H), 3.54 (m, 1H), 3.42 (m, 2H), 2.69-2.85 (m, 2H), 1.51-1.73 (m, 2H) ppm.
Example 13
(S)-19-Oxo-6,7,8,9,16,17,18,19-octahydrodibenzo[b,h][1]oxa[5]aza-cyclopentadecine-17-carbaldehyde (13)
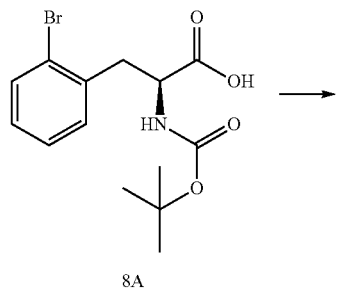
8A
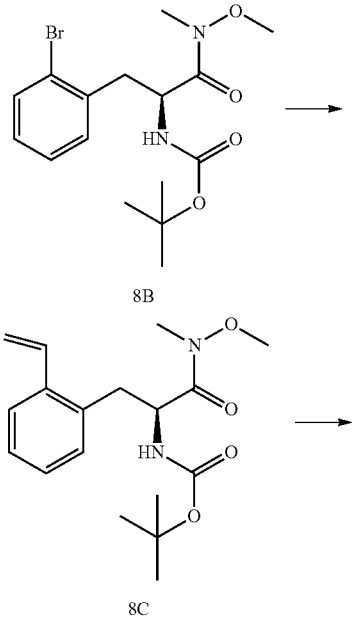

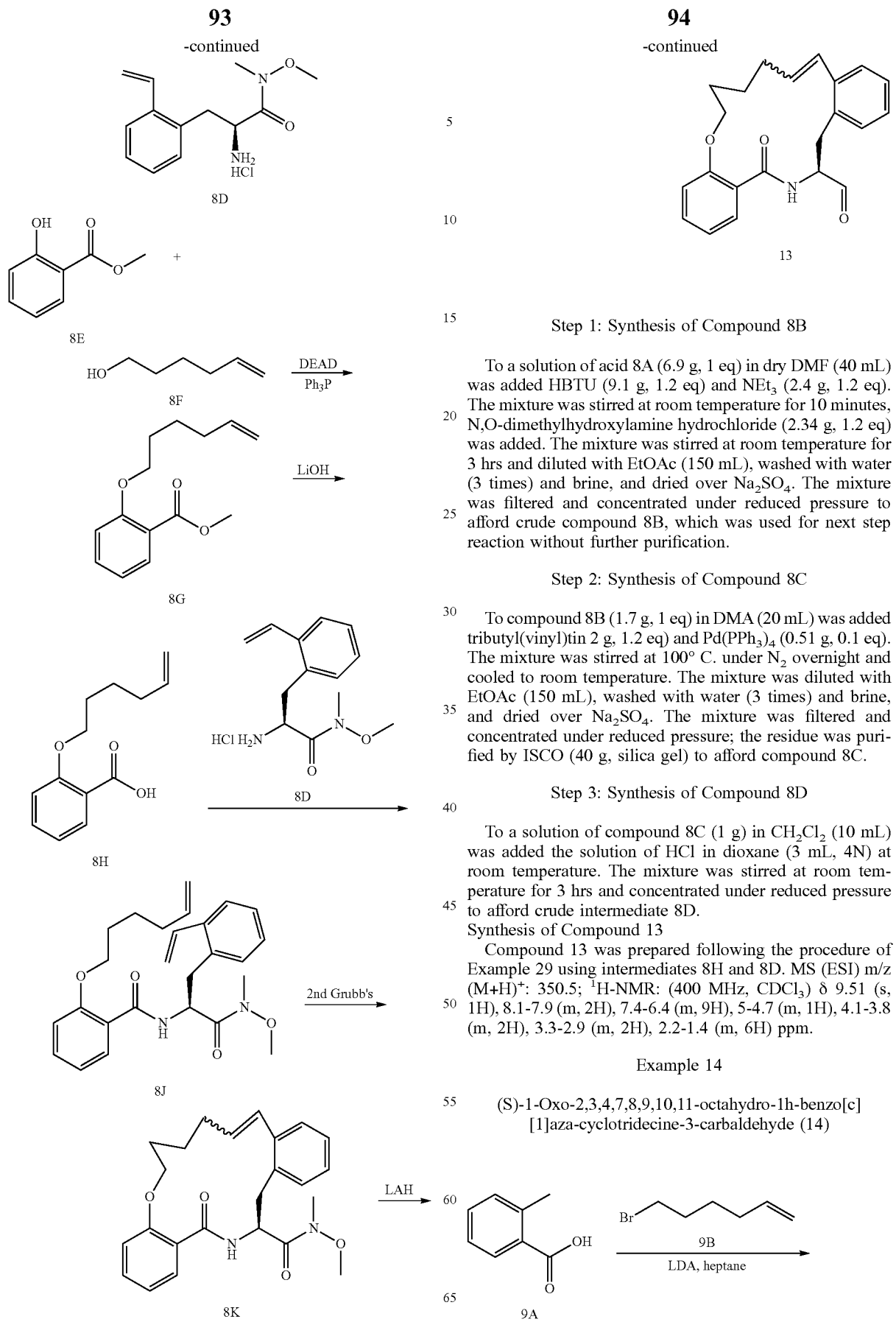

Step 1: Synthesis of Compound 8B

To a solution of acid 8A (6.9 g, 1 eq) in dry DMF (40 mL) was added HBTU (9.1 g, 1.2 eq) and NEt₃ (2.4 g, 1.2 eq). The mixture was stirred at room temperature for 10 minutes, N,O-dimethylhydroxylamine hydrochloride (2.34 g, 1.2 eq) was added. The mixture was stirred at room temperature for 3 hrs and diluted with EtOAc (150 mL), washed with water (3 times) and brine, and dried over Na₂SO₄. The mixture was filtered and concentrated under reduced pressure to afford crude compound 8B, which was used for next step reaction without further purification.

Step 2: Synthesis of Compound 8C

To compound 8B (1.7 g, 1 eq) in DMA (20 mL) was added tributyl(vinyl)tin 2 g, 1.2 eq) and Pd(PPh₃)₄ (0.51 g, 0.1 eq). The mixture was stirred at 100° C. under N₂ overnight and cooled to room temperature. The mixture was diluted with EtOAc (150 mL), washed with water (3 times) and brine, and dried over Na₂SO₄. The mixture was filtered and concentrated under reduced pressure; the residue was purified by ISCO (40 g, silica gel) to afford compound 8C.

Step 3: Synthesis of Compound 8D

To a solution of compound 8C (1 g) in CH₂Cl₂ (10 mL) was added the solution of HCl in dioxane (3 mL, 4N) at room temperature. The mixture was stirred at room temperature for 3 hrs and concentrated under reduced pressure to afford crude intermediate 8D.

Synthesis of Compound 13

Compound 13 was prepared following the procedure of Example 29 using intermediates 8H and 8D. MS (ESI) m/z (M+H)⁺: 350.5; ¹H-NMR: (400 MHz, CDCl₃) δ 9.51 (s, 1H), 8.1-7.9 (m, 2H), 7.4-6.4 (m, 9H), 5-4.7 (m, 1H), 4.1-3.8 (m, 2H), 3.3-2.9 (m, 2H), 2.2-1.4 (m, 6H) ppm.

Example 14

(S)-1-Oxo-2,3,4,7,8,9,10,11-octahydro-1h-benzo[c][1]aza-cyclotridecine-3-carbaldehyde (14)

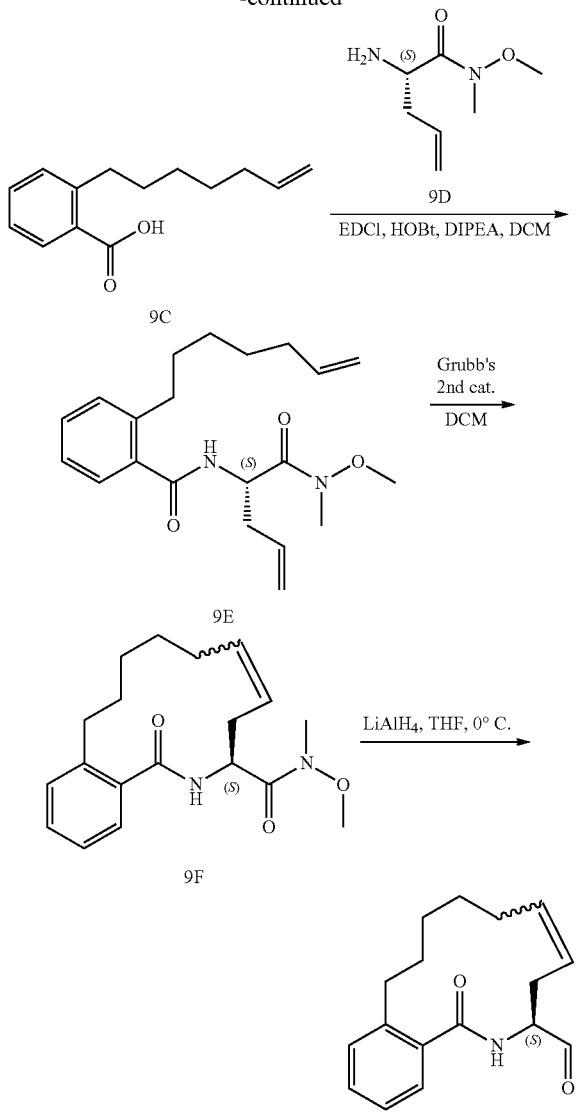

Step 1: Synthesis of Compound 9C

To a solution of LDA (2M, 18.36 mL, THF/heptane) was added dropwise a solution of compound 9A (2.00 g, 14.69 mmol) in THF (20.00 mL) and heptane (20.00 mL) at −30° C., Then the reaction was stirred at −30° C. for 0.5 hr, then compound 9B (3.35 g, 20.57 mmol) was added dropwise to the above mixture. The reaction was stirred at −30° C. for 2 hrs. The reaction mixture was quenched with water (100 mL) at −30° C., and the organic phase was extracted twice with water (50 mL). The combined aqueous phase was acidified (pH~2) with 1N HCl and then extracted with EtOAc (3×80 mL). The combined organic phases were dried over $Na_2SO_4$, filtered and the filtrate was concentrated in vacuo. The residue was purified by column chromatography ($SiO_2$, Petroleum ether/Ethyl acetate=1/0 to 10:1) to give Compound 9C (2.10 g, yield: 65.49%) as colorless oil. $^1$H NMR (400 MHz, $CDCl_3$) δ 8.04 (dd, J=1.5, 8.1 Hz, 1H), 7.50-7.43 (m, 1H), 7.31-7.24 (m, 2H), 5.88-5.74 (m, 1H), 5.03-4.90 (m, 2H), 3.07-2.97 (m, 2H), 2.12-2.02 (m, 2H), 1.69-1.59 (m, 2H), 1.51-1.36 (m, 4H).

Step 2: Synthesis of Compound 9E

To a solution of Compound 9C (2.00 g, 9.16 mmol), Compound 9D (1.78 g, 9.16 mmol, HCl), EDCI (2.63 g, 13.74 mmol) and HOBt (1.24 g, 9.16 mmol) in DCM (60.00 mL) was added DIPEA (2.96 g, 22.90 mmol, 4.00 mL). Then the reaction was stirred at 20° C. for 16 hrs. The reaction mixture was directly concentrated in vacuo, the residue was added 1N HCl (30 mL) and extracted with EtOAc (120 mL), the organic phase was washed with sat. $NaHCO_3$ (25 mL×3) and brine (40 mL), dried over $Na_2SO_4$, filtered and the filtrate was concentrated in vacuo. The residue was purified by column chromatography ($SiO_2$, Petroleum ether/Ethyl acetate=1/0 to 5:1) to give Compound 9E (1.60 g, yield: 39.74%) as brown oil. The residue was directly used in the next step without further purification. $^1$H NMR (400 MHz, $CDCl_3$) δ 7.37 (d, J=7.7 Hz, 1H), 7.35-7.29 (m, 1H), 7.25-7.14 (m, 2H), 6.50 (br d, J=8.2 Hz, 1H), 5.87-5.72 (m, 2H), 5.33-5.22 (m, 1H), 5.19-5.08 (m, 2H), 5.02-4.88 (m, 2H), 3.83 (s, 3H), 3.24 (s, 3H), 2.84-2.72 (m, 2H), 2.71-2.62 (m, 1H), 2.55-2.44 (m, 1H), 2.06-2.00 (m, 2H), 1.64-1.56 (m, 2H), 1.44-1.30 (m, 4H). MS (ESI) m/z (M+H)$^+$ 359.1.

Step 3: Synthesis of Compound 9F

A solution of compound E (1.60 g, 4.46 mmol) and Grubbs's 2$^{nd}$ catalyst (190.00 mg, 223.80 μmol) in DCM (700.00 mL) was stirred at 48° C. for 16 hrs. The reaction mixture was directly concentrated in vacuo. The residue was purified by column chromatography ($SiO_2$, Petroleum ether/ Ethyl acetate=1/0 to 10:1) to give compound 9F (750.00 mg, yield: 49.37%) as white solid. $^1$H NMR (400 MHz, DMSO-$d_6$) δ 7.40-7.34 (m, 1H), 7.32-7.27 (m, 1H), 7.21-7.14 (m, 2H), 6.40 (br d, J=9.8 Hz, 1H), 5.58-5.43 (m, 2H), 5.38-5.26 (m, 1H), 3.87-3.81 (m, 3H), 3.30-3.20 (m, 4H), 2.64-2.50 (m, 1H), 2.49-2.39 (m, 1H), 2.21-2.02 (m, 3H), 1.80-1.67 (m, 1H), 1.59-1.48 (m, 2H), 1.47-1.21 (m, 3H). MS (ESI) m/z (M+H)$^+$ 331.2.

Step 4: Synthesis of Compound 14

To a solution of compound 9F (136.00 mg, 411.60 μmol) in THF (10.00 mL) cooled to 0° C. was added a solution of $LiAlH_4$ (1M, 600.00 μl) in THF. Then the reaction was stirred at 0° C. for 1 hrs. The reaction mixture was quenched with 1N HCl (10 mL) and extracted with EtOAc (40 mL), the organic layer was washed with 1N HCl (15 mL), water (15 mL) and brine (15 mL), dried over $Na_2SO_4$, the solid was removed by filtration, the filtrate was concentrated to give the desired compound 14 (98.00 mg, yield: 85.73%) as white solid. $^1$H NMR (400 MHz, DMSO-$d_6$) δ 9.74 (s, 0.17H), 9.72 (s, 0.79H), 7.48-7.39 (m, 1H), 7.37-7.29 (m, 1H), 7.25-7.15 (m, 2H), 6.15 (br d, J=7.5 Hz, 1H), 5.60-5.38 (m, 2H), 4.99-4.85 (m, 1H), 3.24-3.04 (m, 1H), 2.94-2.83 (m, 1H), 2.66-2.42 (m, 1H), 2.19-1.98 (m, 3H), 1.79-1.64 (m, 1H), 1.57-1.40 (m, 3H), 1.39-1.28 (m, 2H). MS (ESI) m/z (M+H)$^+$ 272.1.

Example 15

(S)-1-Oxo-2,3,4,5,6,7,8,9,10,11-decahydro-1h-benzo[c][1]aza-cyclotridecine-3-carbaldehyde (15)

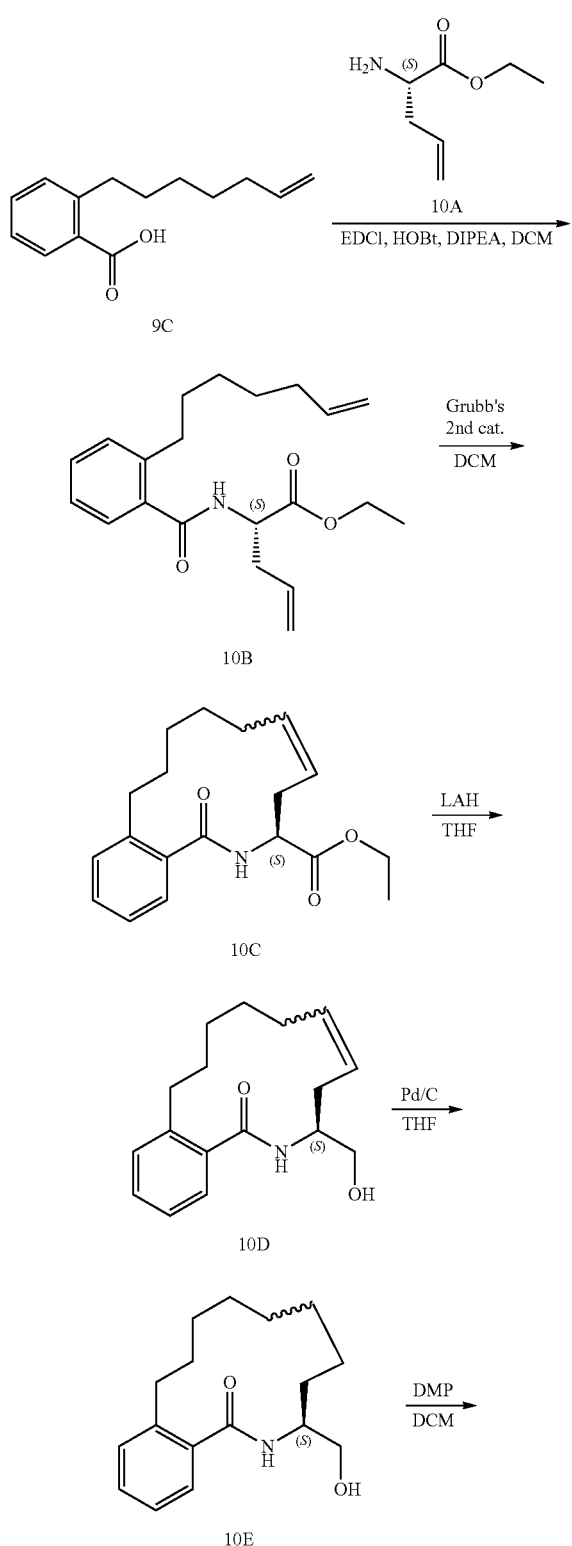

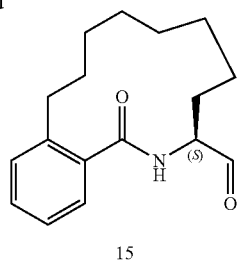

Step 1: Synthesis of Compound 10B

To a solution of compound 9C (1.5 g, 6.87 mmol), compound 10A (1.3 g, 7.22 mmol, HCl), EDCI (1.7 g, 8.93 mmol) and HOBt (928 mg, 6.87 mmol) in DCM (70 mL) was added DIEA (3.6 mL, 20.61 mmol) at 0° C. After addition, the reaction mixture was stirred at 20° C. for 14 hrs. The reaction mixture was concentrated and the residue was dissolved into 70 mL of EtOAc, the mixture was washed with 1N HCl (20 mL×2), NaHCO$_3$ (20 mL×3) and brine (20 mL). The mixture was dried over Na$_2$SO$_4$ and concentrated in vacuum to afford compound 10B (2.0 g, yield 82.22%) as white solid. $^1$H NMR (400 MHz, CDCl$_3$): δ. 7.41-7.30 (m, 2H), 7.28-7.16 (m, 2H), 6.29 (br d, J=7.8 Hz, 1H), 5.87-5.68 (m, 2H), 5.22-5.11 (m, 2H), 5.02-4.82 (m, 3H), 4.31-4.19 (m, 2H), 2.84-2.69 (m, 3H), 2.66-2.56 (m, 1H), 2.09-1.99 (m, 2H), 1.66-1.59 (m, 2H), 1.46-1.27 (m, 7H). MS (ESI) m/z (M+H)$^+$ 343.9.

Step 2: Synthesis of Compound 10C

To a solution of compound 10B (2.0 g, 5.82 mmol) in DCM (700 mL) was added Grubbs's 2$^{nd}$ catalyst (350 mg, 582.00 μmol) under N$_2$ atmosphere. After addition, the reaction mixture was stirred at 50° C. for 14 hrs. The reaction mixture was concentrated in vacuum. The residue was purified by column chromatography (SiO$_2$, Petroleum ether/Ethyl acetate=5:1) to afford compound 10C (350 mg, yield: 18.11%) as white solid. $^1$H NMR (400 MHz, CDCl$_3$): δ 7.41 (d, J=7.5 Hz, 1H), 7.34-7.28 (m, 1H), 7.23-7.14 (m, 2H), 6.17 (br d, J=9.0 Hz, 1H), 5.55-5.42 (m, 2H), 4.97-4.86 (m, 1H), 4.26 (q, J=7.1 Hz, 2H), 3.21-3.10 (m, 1H), 2.84-2.73 (m, 1H), 2.53-2.42 (m, 1H), 2.24-2.04 (m, 3H), 1.80-1.67 (m, 1H), 1.57-1.24 (m, 8H). MS (ESI) m/z (M+H)$^+$ 315.9.

Step 3: Synthesis of Compound 10D

To a solution of LiAlH$_4$ (168 mg, 4.44 mmol) in THF (25 mL) was added a solution of compound 10C (350 mg, 1.11 mmol) in THF (5 mL) at 0° C. under N$_2$ atmosphere. After addition, the reaction mixture was stirred at 0° C. for 1 hr. Then 0.16 mL of water was added into the reaction mixture at 0° C. slowly and 0.16 mL of NaOH (15%) was added, after that, 0.5 mL of water was added and 5 g of Na$_2$SO$_4$ was added. The mixture was stirred for 10 min and filtered. The filtrate was concentrated in vacuum to afford compound 10D (300 mg, yield 88.98%) as light yellow solid. MS (ESI) m/z (M+H)$^+$ 273.8.

Step 4: Synthesis of Compound 10E

To a solution of compound 10D (160 mg, 526.76 µmol) in THF (20 mL) was added Pd/C (30 mg, 526.76 µmol, 5% purity) under $N_2$ atmosphere. Then the suspension was degassed under vacuum and purged with $H_2$, 3 times. The mixture was stirred under $H_2$ (15 psi) at 20° C. for 18 hrs. The reaction mixture was filtered and the filtrate was concentrated in vacuum. The residue was purified by column chromatography ($SiO_2$, Petroleum ether/Ethyl acetate=5:1) to afford desired compound 10E (110 mg, yield: 72.04%) as white solid. $^1$H NMR (400 MHz, DMSO-$d_6$): δ 7.94 (br d, J=9.0 Hz, 1H), 7.31-7.14 (m, 4H), 4.65 (t, J=5.7 Hz, 1H), 3.96-3.85 (m, 1H), 3.41-3.34 (m, 1H), 3.28-3.23 (m, 1H), 2.94-2.85 (m, 1H), 2.46-2.38 (m, 1H), 1.74-1.21 (m, 14H). MS (ESI) m/z (M+H)$^+$ 275.9.

Step 5: Synthesis of Compound 15

To a solution of compound 10E (100 mg, 363.13 µmol) in DCM (30 mL) was added DMP (308 mg, 726.26 µmol). After addition, the reaction mixture was stirred at 20° C. for 5 hrs. 10 mL of 10% $Na_2S_2O_3$ and 5 mL of saturated aqueous $NaHCO_3$ was added into the reaction mixture and the mixture was stirred for 15 min. Then the mixture was separated and the organic layer was washed with water (10 mL) and brine (10 mL). The mixture was dried over $Na_2SO_4$ and concentrated in vacuum to afford compound 15 (60 mg, yield: 59.23%) as white solid. $^1$H NMR (400 MHz, DMSO-$d_6$) δ 9.58 (s, 1H), 8.75 (br d, J=8.5 Hz, 1H), 7.38-7.21 (m, 4H), 4.44-4.31 (m, 1H), 2.96-2.84 (m, 1H), 2.03-1.89 (m, 1H), 1.60-1.22 (m, 14H). MS (ESI) m/z (M+H)$^+$ 274.1.

Example 16

(S)-1-Oxo-1,2,3,4,5,6,7,8,9,10,11,12-dodecahydrobenzo[c][1]aza-cyclotetradecine-3-carbaldehyde (16)

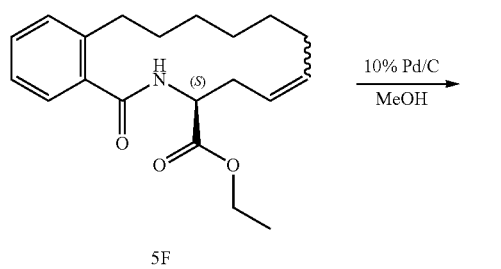

5F

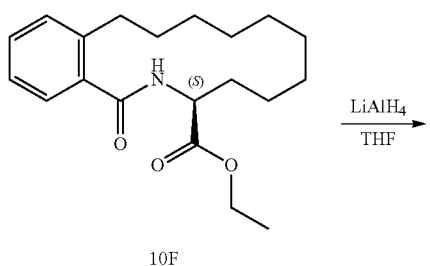

10F

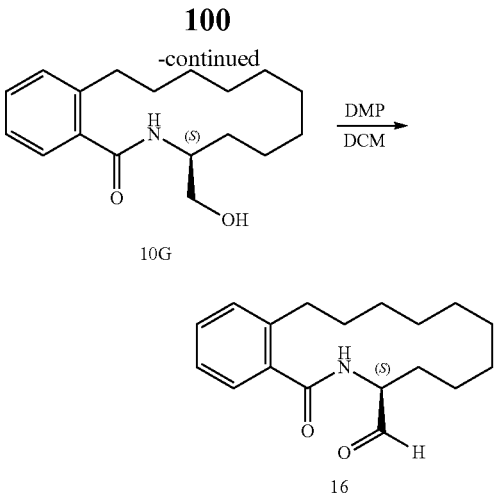

10G

16

Step 1: Synthesis of Compound 10F

To a solution of compound 5F (200 mg, 607.11 µmol) in MeOH (10 mL) was added Pd/C (20 mg, 10% purity) under $N_2$. The suspension was degassed under vacuum and purged with $H_2$ several times. The mixture was stirred under $H_2$ (15 psi) at 22° C. for 1 hr. The mixture was filtered. The filtrate was concentrated to afford compound 10F (180 mg, crude) as white solid used for next step without further purification. MS (ESI) m/z (M+H)$^+$ 331.9.

Step 2: Synthesis of Compound 10G

To a solution of 10F (180 mg, 543.07 µmol) in THF (15 mL) was added $LiAlH_4$ (41.22 mg, 1.09 mmol) at 0° C. in portions. The mixture was stirred at 0° C. for 2 hrs. The mixture was quenched with water (0.05 mL) and 15% NaOH (0.15 mL) at 0° C. The mixture was stirred at 15° C. for 10 min, then added $Na_2SO_4$ (1 g). The mixture was filtered and filtrate was concentrated. The residue was triturated in ethyl acetate (5 mL) and filtered to afford compound 10G (115 mg, 68.49% yield) as white solid. MS (ESI) m/z (M+H)$^+$ 289.9. $^1$H NMR (400 MHz, DMSO-$d_6$): δ 8.01-7.93 (m, 1H), 7.34-7.17 (m, 4H), 4.70-4.63 (m, 1H), 4.02-3.91 (m, 1H), 3.47-3.41 (m, 1H), 3.10-2.91 (m, 1H), 2.46-2.38 (m, 1H), 1.54-1.09 (m, 16H).

Step 3: Synthesis of Compound 16

To a solution of compound 10G (115 mg, 397.36 µmol) in DCM (50 mL) was added DMP (674.15 mg, 1.59 mmol) at 0° C. in portions. The mixture was stirred at 22° C. for 2 hrs. The reaction mixture was quenched by addition sat. $Na_2S_2O_3$ (12 mL), sat. $NaHCO_3$ (5 mL) and stirred for 30 min, then separated. The organic layers were washed with water (10 mL×2), brine (10 mL), dried over $Na_2SO_4$, filtered and concentrated under reduced pressure to give a residue. The residue was triturated in (i-Pr)$_2$O (3 mL) to afford compound 16 (27.2 mg, 22.44% yield) as white solid. MS (ESI) m/z (M+H)$^+$ 288.1. $^1$H NMR (400 MHz, DMSO-$d_6$): δ 9.59 (s, 1H), 8.81-8.75 (m, 1H), 7.43-7.23 (m, 4H), 4.28-4.21 (m, 1H), 2.87-2.78 (m, 1H), 2.68-2.58 (m, 1H), 1.87-1.78 (m, 1H), 1.73-1.63 (m, 1H), 1.59-1.44 (m, 2H), 1.41-1.13 (m, 12H).

Example 17

(S,E)-N-ethyl-2-oxo-2-(1-oxo-1,2,3,4,7,8,9,10,11,12-decahydrobenzo[c][1]azacyclotetradecin-3-yl)acetamide (17)

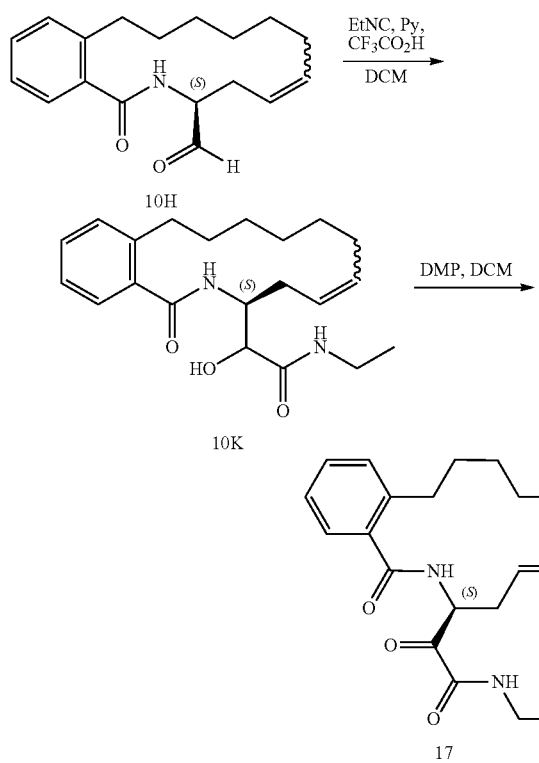

Step 1: Synthesis of Compound 10K

To a solution of compound 10H (165 mg, 578.18 μmol) in DCM (10 mL) cooled to 0° C. was added a solution of isocyanoethane (63.69 mg, 1.16 mmol, 2.00 eq) in DCM (2 mL) and solution of Py (187 μl, 2.31 mmol) in DCM (1 mL), then TFA (0.13 mL, 1.73 mmol) in DCM (1 mL) was added slowly to the above reaction mixture for 10 min, then the reaction was stirred at 0° C. for 50 min and at 20° C. for 13 hrs. The reaction mixture was quenched with 1M HCl (5 mL). To the solution was added ethyl acetate (60 mL) and separated. The organic layer was washed with NaHCO$_3$ (10 mL) and separated. The organic layer was concentrated. The residue was purified by column chromatography (SiO$_2$, Petroleum ether/Ethyl acetate=3/1 to 1/1) to afford compound 10K (32 mg, 14.78% yield) as brown solid. MS (ESI) m/z (M+H)$^+$ 359.1. $^1$H NMR (400 MHz, DMSO-d$_6$): δ 7.86-7.75 (m, 1H), 7.53-7.35 (m, 1H), 7.34-7.13 (m, 3H), 5.80-5.45 (m, 1H), 5.39-5.21 (m, 2H), 4.36-4.22 (m, 1H), 4.01-3.86 (m, 1H), 3.19-2.88 (m, 3H), 2.23-1.91 (m, 3H), 1.84-1.72 (m, 1H), 1.68-1.46 (m, 3H), 1.45-1.29 (m, 2H), 1.25-1.09 (m, 2H), 1.08-0.93 (m, 6H).

Step 2: Synthesis of Compound 17

To a solution of compound 10K (32 mg, 89.27 μmol) in DCM (10 mL) and DMSO (1 mL) was added DMP (151.45 mg, 357.07 μmol). The mixture was stirred at 19° C. for 1.5 hrs. The reaction mixture was quenched by addition sat. Na$_2$S$_2$O$_3$ (10 mL), sat. NaHCO$_3$ (12 mL) and stirred for 30 min. The mixture was separated. The organic layers were washed with water (2×10 mL), brine (10 mL), dried over Na$_2$SO$_4$, filtered and concentrated under reduced pressure to give a residue. The residue was triturated in (i-Pr)$_2$O to afford compound 17 (7.90 mg, 24.62% yield) as white solid. MS (ESI) m/z (M+H)$^+$ 357.1. $^1$H NMR (400 MHz, DMSO-d$_6$) δ 8.82-8.74 (m, 1H), 8.52-8.44 (m, 1H), 7.38-7.18 (m, 4H), 5.52-5.40 (m, 1H), 5.39-5.28 (m, 1H), 5.28-5.18 (m, 1H), 3.27-3.02 (m, 2H), 2.87-2.72 (m, 1H), 2.61-2.57 (m, 1H), 2.24-1.99 (m, 2H), 1.90-1.73 (m, 1H), 1.70-1.50 (m, 2H), 1.49-1.26 (m, 3H), 1.25-1.14 (m, 1H), 1.14-0.98 (m, 6H).

Examples 18 and 19

(S)-11-Oxo-2,3,8,9,10,11-hexahydro-5h-benzo[e][1,4]dioxa[8]azacyclotridecine-9-carbaldehyde (18) and (S)-11-Oxo-2,3,6,7,8,9,10,11-octahydro-5h-benzo[e][1,4]dioxa[8]azacyclotridecine-9-carbaldehyde (19)

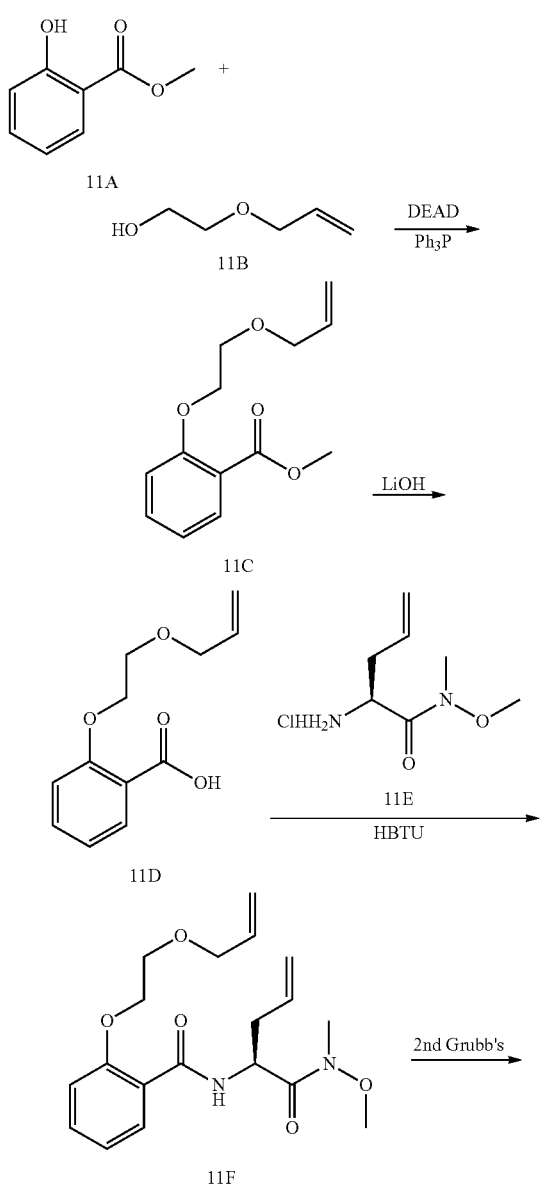

103

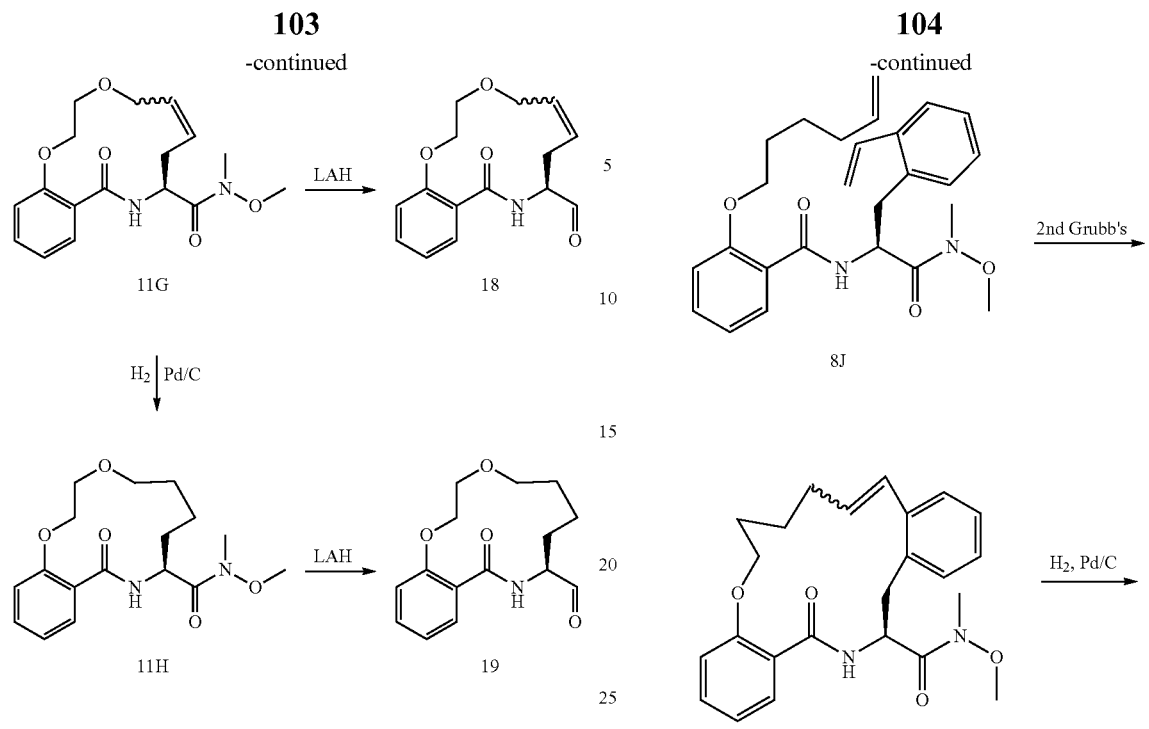

Synthesis of Compound 18

Compound 18 was prepared following the procedure of Example 5 using compound 11B. MS (ESI) m/z (M+H)$^+$: 276.2; $^1$H NMR (400 MHz, DMSO-d6) δ 9.67 (s, 0.5H), 9.62 (s, 0.5H), 8.90 (d, 0.5H), 8.52 (d, 0.5H), 8.21 (d, 0.5H), 8.15 (d, 0.5H), 7.45 (m, 1H), 7.11 (m, 1H), 6.93 (d, 1H), 6.09 (m, 0.5H), 5.82 (m, 1H), 5.61 (m, 0.5H), 4.85 (m, 0.5H), 4.38 (m, 0.5H), 3.76-4.29 (m, 6H), 2.46-2.83 (m, 2H) ppm.

Synthesis of Compound 19

Compound 19 was prepared following the procedure of Example 6 using compound 11B. MS (ESI) m/z (M+H)$^+$: 278.4; $^1$H NMR (400 MHz, DMSO-d6) δ 9.65 (s, 1H), 8.79 (d, 1H), 8.20 (d, 1H), 7.47 (t, 1H), 7.11 (t, 1H), 4.33 (m, 2H), 4.23 (m, 1H), 3.87 (m, 2H), 3.66 (m, 2H), 1.59-1.88 (m, 6H) ppm.

Example 20

(S)-19-Oxo-6,7,8,9,10,11,16,17,18,19-decahydrodibenzo[b,h][1]oxa[5]aza-cyclopentadecine-17-carbaldehyde (20)

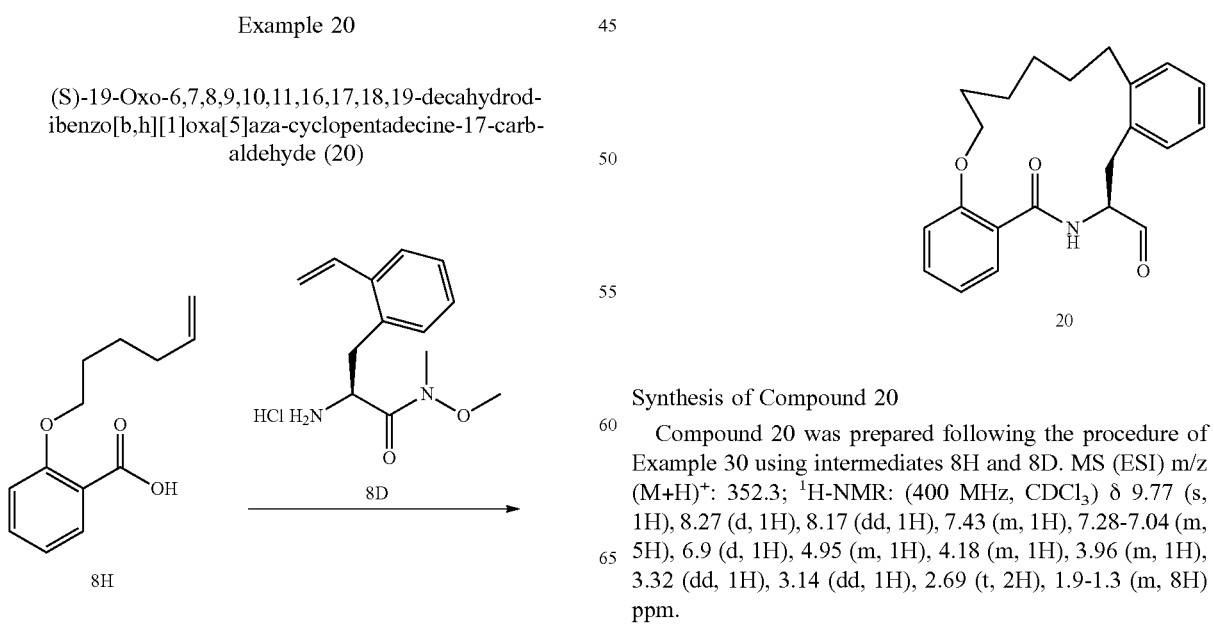

Synthesis of Compound 20

Compound 20 was prepared following the procedure of Example 30 using intermediates 8H and 8D. MS (ESI) m/z (M+H)$^+$: 352.3; $^1$H-NMR: (400 MHz, CDCl$_3$) δ 9.77 (s, 1H), 8.27 (d, 1H), 8.17 (dd, 1H), 7.43 (m, 1H), 7.28-7.04 (m, 5H), 6.9 (d, 1H), 4.95 (m, 1H), 4.18 (m, 1H), 3.96 (m, 1H), 3.32 (dd, 1H), 3.14 (dd, 1H), 2.69 (t, 2H), 1.9-1.3 (m, 8H) ppm.

Example 21
(S)-10-Oxo-3,4,7,8,9,10-hexahydro-2h-benzo[b][1]oxa[5]aza-cyclododecine-8-carbaldehyde (21)
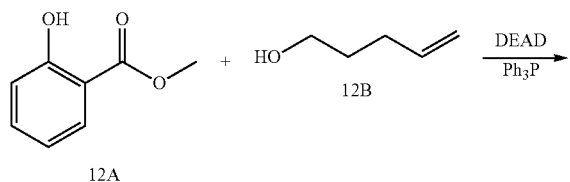
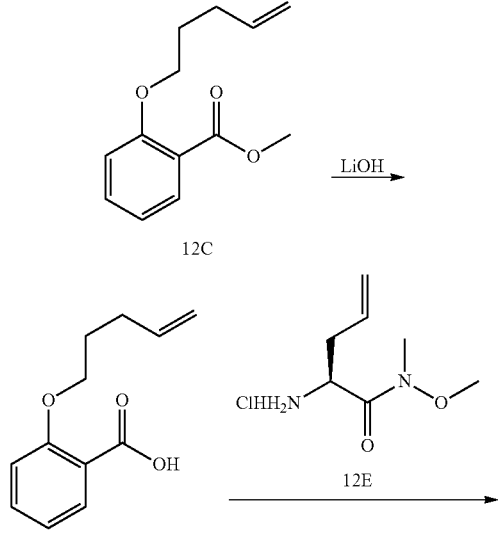
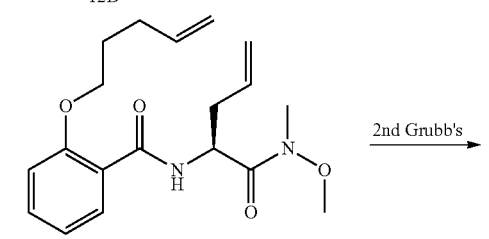
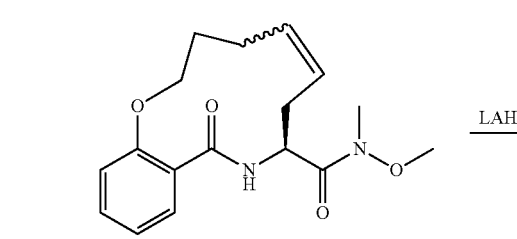
Synthesis of Compound 21
Compound 21 was prepared following the procedure of Example 29 using intermediates 12D and 12E. MS (ESI) m/z (M+H)$^+$: 260; $^1$H NMR (400 MHz, CDCl$_3$) δ 9.67 (s, 1H), 8.27 (d, 1H), 8.16 (m, 1H), 7.45 (m, 1H), 7.1-6.98 (m, 2H), 5.84 (m, 0.7H), 5.59 (m, 0.3H), 5.55 (m, 0.3H), 5.43 (m, 0.7H), 4.65 (m, 0.7H), 4.47 (m, 0.3H), 4.37 (m, 1H), 4.17 (m, 1H), 2.7-2.0 (m, 6H) ppm.
Example 22
(S)-19-Oxo-6,7,8,9,10,11,16,17,18,19-decahydro-5h-benzo[g]imidazo[1,5-a][1,4]diazacyclopentadecine-17-carbaldehyde (22)
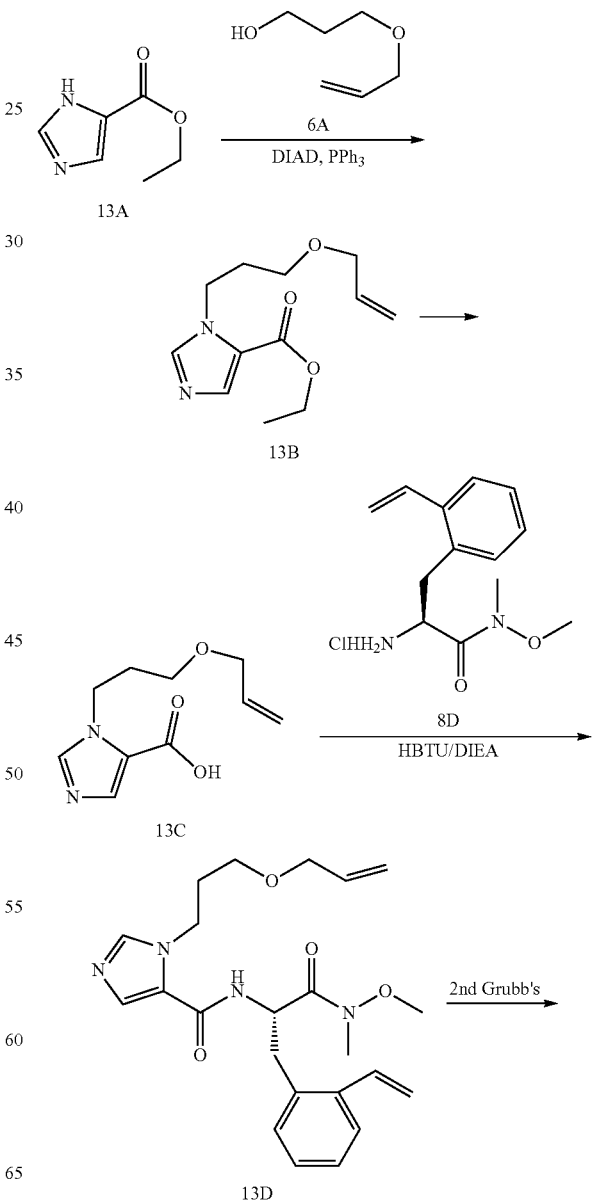

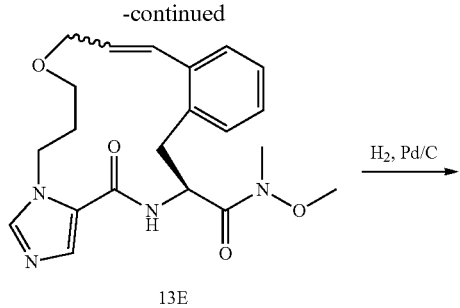

13E

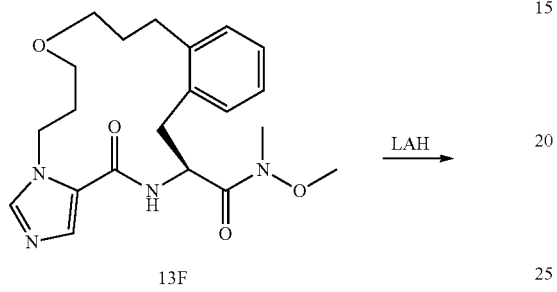

13F

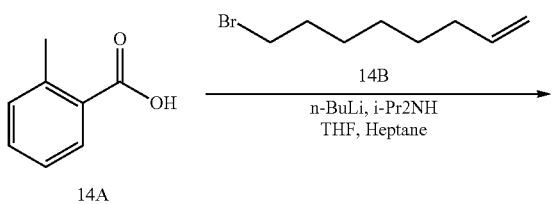

22

Step 1: Synthesis of Compound 13B

To a solution of 13A (1.8 g, 1.0 eq), 6A (1.5 g, 1 eq) and PPh$_3$ (3.9 g, 1.2 eq) in 10 mL dry THF at 0° C. under N$_2$ was slowly added a solution of DIAD (3 g, 1.15 eq) in 5 mL dry THF. The mixture was stirred at room temperature for overnight. The reaction mixture was diluted with 150 mL EtOAc, washed with 1 N HCl. The aqueous phase was treated with 1N NaOH to adjust pH to 9, and extracted with EtOAc (3 times). The combined organic phase was concentrated and the residue was purified on ISCO to provide compound 13B.

Step 2: Synthesis of Compound 13C

Compound 13B (1.9 g) was treated with LiOH in MeOH and water to provide acid 13C.

Synthesis of Compound 22

Compound 22 was prepared following the procedure of Example 30 starting from step 3 using intermediates 13C and 8D. MS (ESI) m/z (M+H)$^+$: 374.4; $^1$H NMR (400 MHz, CDCl$_3$) δ 9.77 (s, 1H), 7.52 (s, 1H), 7.3 (s, 1H), 7.15-7.05 (m, 3H), 6.97 (m, 1H), 6.41 (d, 1H), 4.8 (m, 1H), 4.66 (m, 1H), 4.31 (m, 1H), 3.5-3.4 (m, 3H), 3.35-3.25 (m, 3H), 3.13 (m, 1H), 2.74 (m, 1H), 2.55 (m, 1H), 2.09 (m, 1H), 1.96 (m, 1H), 1.71 (m, 1H) ppm.

Example 23

(S,E)-1-Oxo-2,3,4,7,8,9,10,11,12,13-decahydro-1h-benzo[c][1]aza-cyclopentadecine-3-carbaldehyde (23)

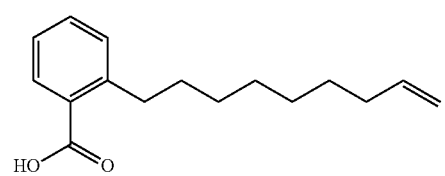

14A

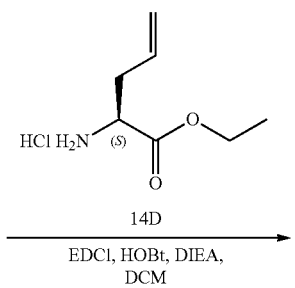

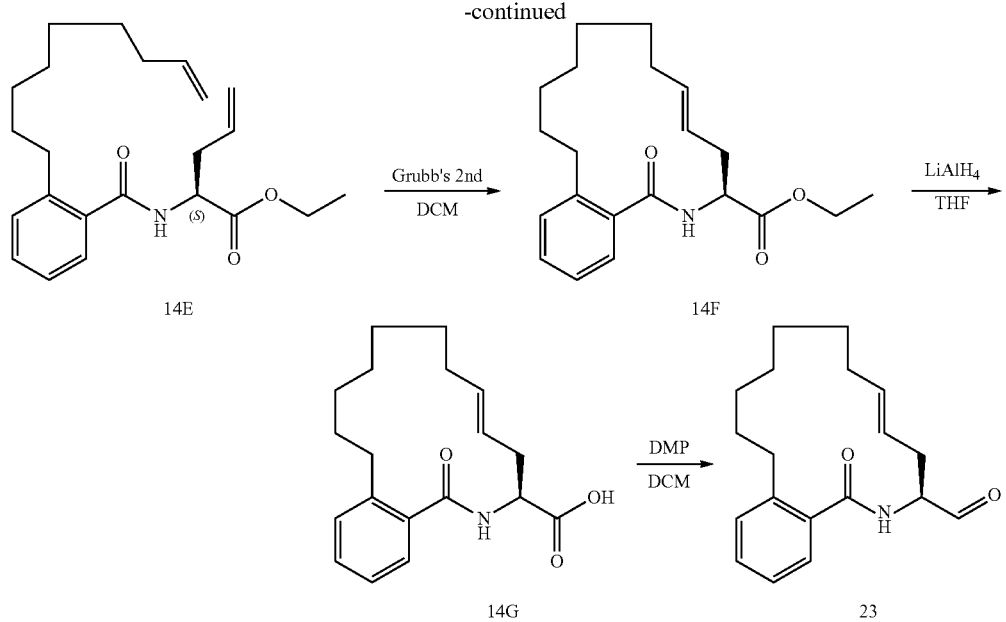

Step 1: Synthesis of Compound 14C

THF (21 mL) was cooled to −50° C., n-BuLi (2.5 M, 10.3 mL) was added dropwise. After addition, i-Pr$_2$NH (2.6 g, 25.7 mmol, 3.6 mL) was added to the solution dropwise. After addition, the solution was stirred at −50° C. for 0.5 hr. Then the solution was warmed up to −30° C., and a solution of compound 14A (1.4 g, 10.3 mmol, 1.4 mL) in THF (10 mL) and Heptane (10 mL) was added. Then a solution of compound 14B (2.4 g, 12.4 mmol, 2.1 mL) in THF (8 mL) was added. The reaction was stirred at −30° C. for 1 hr. The mixture was quenched with H$_2$O (100 mL). The organics were separated and extracted with H$_2$O (50 mL×2). The aqueous phase was acidified with 1N HCl to pH~2 and then extracted with EtOAc (100 mL×2). The organics were collected, dried with Na$_2$SO$_4$, filtered and concentrated to afford compound 14C (4.4 g, crude) as light yellow oil, which was used directly for the next step without further purification. $^1$H NMR (CDCl$_3$, 400 MHz): δ 7.90-7.88 (m, 1H), 7.34-7.31 (m, 1H), 7.15-7.09 (m, 2H), 5.72-5.63 (m, 1H), 4.87-4.76 (m, 2H), 2.90-2.86 (m, 2H), 1.92-1.87 (m, 2H), 1.50-1.47 (m, 2H), 1.26-1.14 (m, 8H).

Step 2: Synthesis of Compound 14E

To a solution of compound 14C (1.00 g, 4.06 mmol) and compound 14D (880 mg, 4.87 mmol) in DCM (20 mL) was added EDCI (1.17 g, 6.09 mmol), HOBt (550 mg, 4.06 mmol), and DIEA (1.8 mL, 10.2 mmol). The mixture was stirred at 25° C. for 12 hrs. The solvent was removed in vacuo. The residue was dissolved in EtOAc (30 mL), washed with 1N HCl (30 mL). The organics were collected and concentrated. The residue was purified by column (Petroleum Ether:Ethyl Acetate=5:1) to give compound 14E (2 g, yield: 62.4%) as white solid. MS (ESI) m/z (M+H)$^+$ 372.2. $^1$H NMR (CDCl$_3$, 400 MHz): δ 7.38-7.33 (m, 2H), 7.25-7.21 (m, 2H), 6.30-6.28 (m, 1H), 5.86-5.79 (m, 2H), 5.19-5.15 (m, 2H), 5.00-4.88 (m, 3H), 4.27-4.23 (m, 2H), 2.80-2.71 (m, 3H), 2.63-2.55 (m, 1H), 2.04-2.00 (m, 2H), 1.61-1.58 (m, 2H), 1.38-1.29 (m, 12H).

Step 3: Synthesis of Compound 14F

To a solution of compound 14E (500 mg, 1.35 mmol) in DCM (180 mL) was added Grubb's 2nd (115 mg, 0.14 mmol). The mixture was stirred at 40° C. for 48 hrs under N$_2$. The solvent was removed in vacuo. The residue was purified by column (Petroleum Ether:Ethyl Acetate=5:1) to afford compound 14F (540 mg, yield: 56.4%) as white solid. MS (ESI) m/z (M+H)$^+$ 344.1. $^1$H NMR (CDCl$_3$, 400 MHz): δ 7.46-7.44 (m, 1H), 7.33-7.31 (m, 1H), 7.24-7.21 (m, 2H), 6.18-6.15 (m, 1H), 5.54-5.43 (m, 2H), 4.88-4.82 (m, 1H), 4.29-4.23 (m, 2H), 3.14-3.09 (m, 1H), 2.87-2.73 (m, 1H), 2.51-2.49 (m, 1H), 2.35-2.20 (m, 1H), 2.10-1.98 (m, 2H), 1.60-1.57 (m, 1H), 1.38-1.24 (m, 12H).

Step 4: Synthesis of Compound 14G

To a solution of compound 14F (130 mg, 0.38 mmol) in THF (10 mL) was added LiAlH$_4$ (44 mg, 1.14 mmol) at 0° C. The mixture was stirred at 0° C. for 1 hr. The mixture was diluted with EtOAc (20 mL), quenched with H$_2$O (0.09 mL), 15% aqueous NaOH (0.09 mL), H$_2$O (0.27 mL). The mixture was warmed up to 25° C. and stirred for 15 min. Then MgSO4 was added and stirred for 15 min. The solid was filtered. The filtrate was collected and concentrated. The residue was purified by column (Petroleum Ether:Ethyl Acetate=1:1) to afford compound 14G (122 mg, yield: 52.94%) as white solid. MS (ESI) m/z (M+H)$^+$ 302.1. $^1$H NMR (CDCl$_3$, 400 MHz): δ 7.35-7.30 (m, 2H), 7.22-7.20 (m, 2H), 5.83-5.82 (m, 1H), 5.47-5.44 (m, 2H), 4.31-4.25 (m, 1H), 3.83-3.79 (m, 1H), 3.73-3.69 (m, 1H), 3.15-3.14 (m, 1H), 2.49-2.39 (m, 2H), 2.23-2.10 (m, 1H), 2.04-1.95 (m, 2H), 1.58-1.14 (m, 10H).

Step 5: Synthesis of Compound 23

To a solution of compound 14G (200 mg, 0.67 mmol) in DCM (10 mL) was added DESS-MARTIN PERIODINANE (422 mg, 0.99 mmol). The mixture was stirred at 25° C. for 12 hrs. The reaction was diluted with DCM (20 mL), quenched with a solution of 10% aqueous Na$_2$S$_2$O$_3$ and 10% aqueous NaHCO₃ (v/v=1/1) (30 mL). The organics were collected, washed with brine (30 mL). The organics were collected, dried with Na₂SO₄, filtered and concentrated to afford compound 23 (180 mg, yield: 86.71%) as white solid. MS (ESI) m/z (M+H)⁺ 300.1. ¹H NMR (DMSO-d₆, 400 MHz): δ 9.59 (s, 1H), 8.59 (d, J=8.0 Hz, 1H), 7.46-7.41 (m, 1H), 7.39-7.33 (m, 1H), 7.30-7.20 (m, 2H), 5.56-5.38 (m, 2H), 4.56-4.47 (m, 1H), 2.98-2.88 (m, 1H), 2.70-2.58 (m, 1H), 2.47-2.39 (m, 1H), 2.20-2.08 (m, 1H), 2.05-1.96 (m, 2H), 1.54-1.41 (m, 2H), 1.38-1.07 (m, 8H).

Example 24

(S)-10-Oxo-3,4,5,6,7,8,9,10-octahydro-2h-benzo[b][1]oxa[5]aza-cyclododecine-8-carbaldehyde (24)

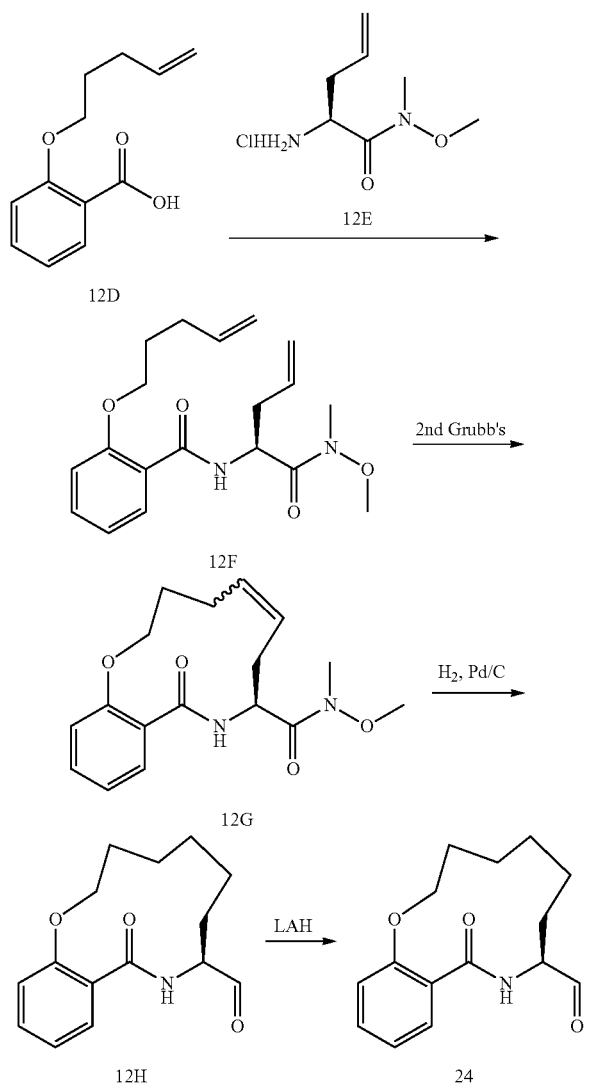

Synthesis of Compound 24

Compound 24 was prepared following the procedure of Example 30 using intermediates 12D and 12E. MS (ESI) m/z (M+H)⁺: 262.4; ¹H NMR (400 MHz, CDCl₃) δ 9.63 (s, 1H), 8.5 (s, 1H), 8.08 (m, 1H), 7.45 (m, 1H), 7.1 (t, 1H), 7.01 (d, 1H), 4.57 (m, 1H), 4.3 (m, 1H), 4.04 (m, 1H), 2.05-1.5 (m, 10H) ppm.

Example 25

(S)—N-ethyl-2-oxo-2-(1-oxo-2,3,4,5,6,7,8,9,10,11-decahydro-1h-benzo[c][1]aza-cyclotridecin-3-yl)acetamide (25)

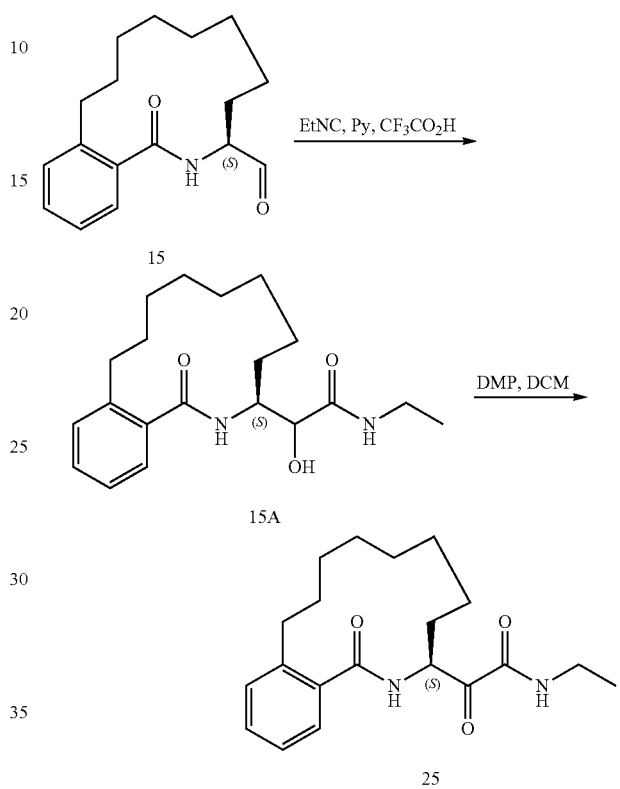

Step 1: Synthesis of Compound 15A

To a solution of compound 15 (130 mg, 475.55 µmol) in DCM (15 mL) was added isocyanoethane (52 mg, 951.09 µmol) in DCM (1 mL) at 0° C., then TFA (106 µl, 1.43 mmol) in DCM (2 mL) was added drop wise into the reaction mixture followed by Py (154 µL, 1.90 mmol) in DCM (2 mL) at 0° C. After addition, the reaction mixture was stirred at 0° C. for 1 h, then at 20° C. for 14 hrs. Then, 20 mL of 1N HCl was added into the reaction mixture and stirred for 10 min. Then the mixture was poured into 50 mL of water and extracted with EtOAc (50 mL×3), the combined extracts were washed with 1N HCl (30 mL) and brine (30 mL). The mixture was dried over Na₂SO₄ and concentrated in vacuum. The residue was triturated with 5 mL of EtOAc to afford compound 15A (50 mg, yield 29.74%) as white solid. ¹H NMR (400 MHz, DMSO-d₆) δ 7.96-7.84 (m, 1H), 7.76-7.60 (m, 1H), 7.34-7.14 (m, 4H), 4.29-4.15 (m, 1H), 3.92-3.84 (m, 1H), 3.17-2.85 (m, 4H), 2.44-2.33 (m, 1H), 1.67-1.10 (m, 14H), 1.04-0.94 (m, 3H). MS (ESI) m/z (M+H)⁺ 346.9.

Step 2: Synthesis of Compound 25

To a solution of compound 15A (50 mg, 144.32 µmol) in DCM (20 mL) was added DMP (92 mg, 216.48 µmol) at 0° C. After addition, the reaction mixture was stirred at 25° C.

for 18 hrs. 10 mL of 10% $Na_2S_2O_3$ and 10 mL of 5% aqueous $NaHCO_3$ was added into the reaction mixture, and the mixture was stirred for 15 min. Then the mixture was separated and the organic layer was washed with water (15 mL×2), the mixture was dried over $Na_2SO_4$ and concentrated in vacuum to afford compound 25 (13 mg, yield 29.87%) as white solid. $^1H$ NMR (400 MHz, DMSO-$d_6$) δ 8.77-8.67 (m, 2H), 7.34-7.27 (m, 1H), 7.26-7.15 (m, 3H), 5.26-5.15 (m, 1H), 3.23-3.08 (m, 2H), 2.82-2.71 (m, 1H), 2.60-2.53 (m, 1H), 1.92-1.80 (m, 1H), 1.58-1.24 (m, 13H), 1.05 (t, J=7.3 Hz, 3H) MS (ESI) m/z $(M+H)^+$ 345.2.

Example 26

(S)—N-ethyl-2-oxo-2-(1-oxo-2,3,4,7,8,9,10,11-octahydro-1h-benzo[c][1]aza cyclotridecin-3-yl)acetamide (26)

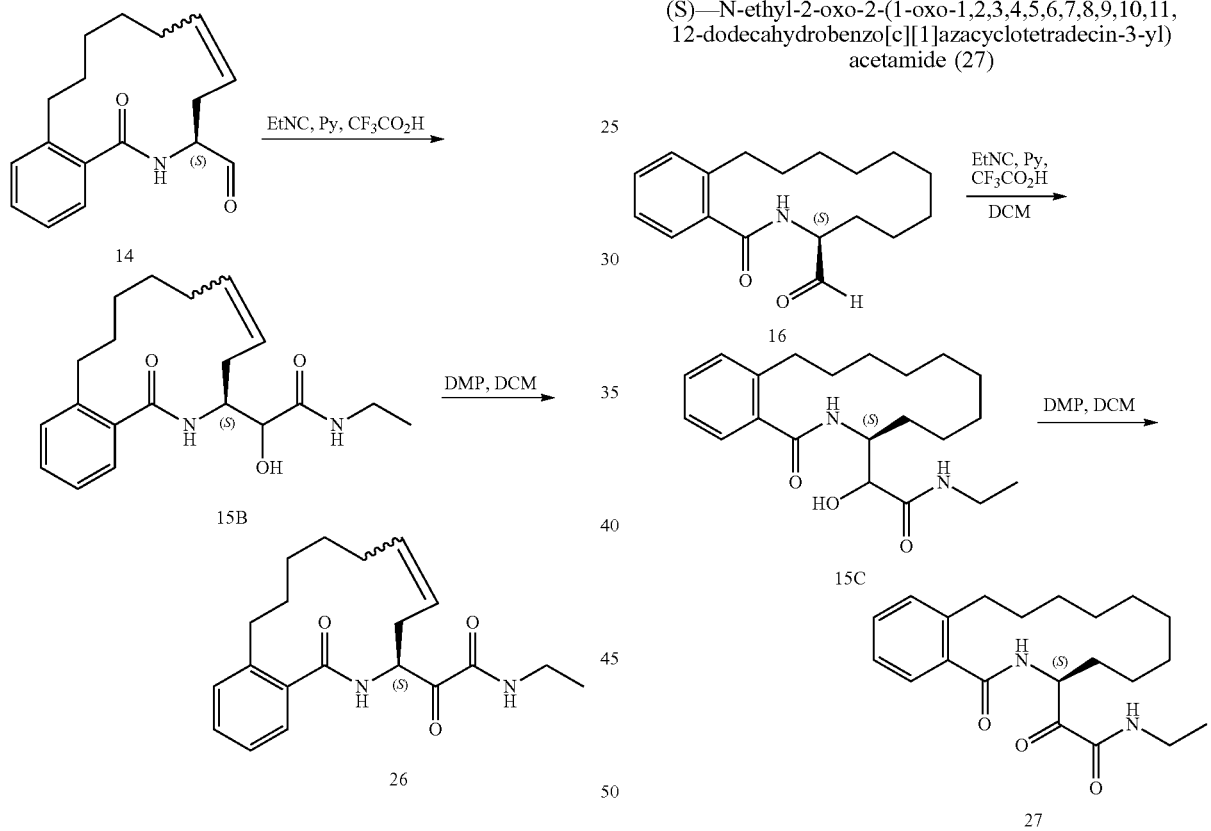

Step 1: Synthesis of Compound 15B

To a solution of compound 14 (290 mg, 1.07 mmol) in DCM (15 mL) cooled to 0° C. was added isocyanoethane (121 mg, 2.19 mmol) and solution of pyridine (363 μL, 4.49 mmol), then TFA (242 μL, 3.26 mmol) in DCM (1 mL) was added slowly to the above reaction mixture for 15 mins. Then the reaction was stirred at 0° C. for 45 mins and at 20° C. for 15 hrs. The mixture was diluted with ethyl acetate (70 mL), washed with 1N HCl (2×20 mL), saturated aqueous $NaHCO_3$ (20 mL), brine (20 mL), dried over anhydrous $Na_2SO_4$, filtered and concentrated. The residue was triturated with EtOAc (16 mL), the solid was collected to afford compound 2 (140 mg, yield, 36.1%) as white solid. MS (ESI) m/z $(M+H)^+$ 346.1.

Step 2: Synthesis of Compound 26

To a solution of compound 15B (50 mg, 145.16 μmol) in DCM (20 mL) was added DMP (92 mg, 217.74 μmol) at 0° C. After addition, the reaction mixture was stirred at 25° C. for 16 hrs. 10 mL of 10% $Na_2S_2O_3$ and 10 mL of 5% aqueous $NaHCO_3$ was added into the reaction mixture, the mixture was stirred for 15 min. Then the mixture was separated and the organic layer was washed with water (15 mL×2), then brine (15 mL). The mixture was dried over $Na_2SO_4$ and concentrated in vacuum to afford compound 26 (35 mg, yield: 66.9%) as white solid. $^1H$ NMR (400 MHz, DMSO-$d_6$) δ 8.81-8.73 (m, 1H), 8.47 (br d, J=8.6 Hz, 1H), 7.34-7.14 (m, 4H), 5.55-5.28 (m, 3H), 3.24-3.10 (m, 2H), 2.88-2.77 (m, 1H), 2.43-2.35 (m, 1H), 2.16-1.90 (m, 3H), 1.70-1.57 (m, 1H), 1.53-1.10 (m, 6H), 1.09-1.01 (m, 3H) MS (ESI) m/z $(M+H)^+$ 343.2.

Example 27

(S)—N-ethyl-2-oxo-2-(1-oxo-1,2,3,4,5,6,7,8,9,10,11,12-dodecahydrobenzo[c][1]azacyclotetradecin-3-yl)acetamide (27)

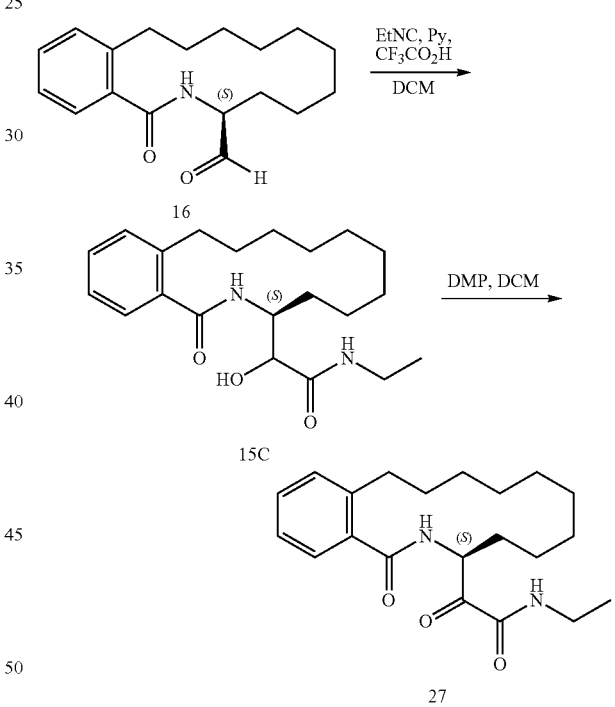

Step 1: Synthesis of Compound 15C

To a solution of compound 16 (210 mg, 730.69 μmol) in DCM (8 mL) cooled to 0° C. was added a solution of isocyanoethane (80.5 mg, 1.46 mmol) in DCM (1 mL) and a solution of Py (0.24 mL, 2.92 mmol) in DCM (1 mL), then TFA (162 μL, 2.19 mmol) in DCM (1 mL) was added slowly to the above reaction mixture for 10 min, then the reaction was stirred at 0° C. for 50 min and at 20° C. for 13 hrs. The reaction mixture was quenched with 1M HCl (5 mL). To the solution was added ethyl acetate (60 mL) and separated. The organic layer was washed with $NaHCO_3$ (10 mL) and separated. The organic layer was concentrated. The residue was triturated in ethyl acetate (5 mL) to afford compound 15C (115 mg, 40.91% yield) as brown solid. MS (ESI) m/z (M+H)$^+$ 361. $^1$H NMR (400 MHz, DMSO-d$_6$): δ 8.52-8.23 (m, 1H), 8.00-7.58 (m, 1H), 7.38-7.15 (m, 4H), 5.75-5.45 (m, 1H), 4.66-4.15 (m, 1H), 4.06-3.82 (m, 1H), 3.21-2.95 (m, 4H), 1.68-1.01 (m, 19H).

Step 2: Synthesis of Compound 27

To a solution of compound 15C (115 mg, 319.01 μmol) in DCM (10 mL) was added DMP (541 mg, 1.28 mmol) at 0° C. in portions. The mixture was stirred at 22° C. for 3 hrs. The reaction mixture was quenched by addition saturated aqueous Na$_2$S$_2$O$_3$ (12 mL), saturated aqueous NaHCO$_3$ (5 mL) and stirred for 30 min. The mixture was separated. The organic layers were washed with water (2×10 mL), brine (10 mL), dried over Na$_2$SO$_4$, filtered and concentrated under reduced pressure to give a residue. The residue was purified by preparatory-HPLC (HCl condition) to afford compound 27 (10.9 mg, 9% yield) as white solid. MS (ESI) m/z (M+H)$^+$ 359.2. $^1$H NMR (400 MHz, DMSO-d$_6$): δ 8.78-8.65 (m, 2H), 7.37-7.20 (m, 4H), 5.21-5.14 (m, 1H), 3.22-3.08 (m, 2H), 2.91-2.82 (m, 1H), 2.59-2.53 (m, 1H), 1.90-1.78 (m, 1H), 1.67-1.41 (m, 5H), 1.39-1.17 (m, 1H), 1.11-1.01 (m, 3H).

Example 28

(S)-1-Oxo-2,3,4,5,6,7,8,9,10,11,12,13-dodecahydro-1h-benzo[c][1]aza-cyclopentadecine-3-carbaldehyde (28)

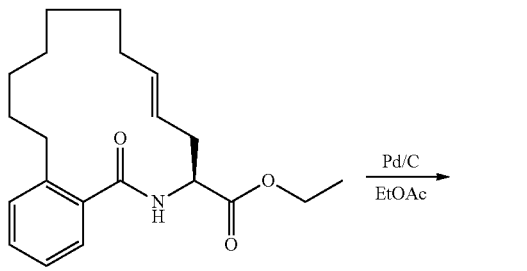

14F

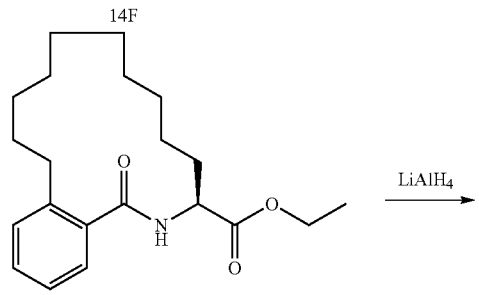

14J

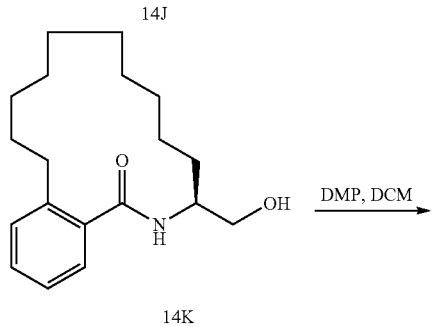

14K

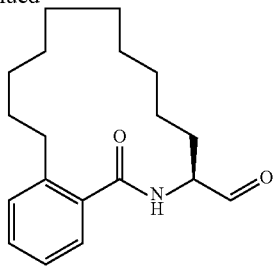

28

Step 1: Synthesis of Compound 14J

To a solution of compound 14F (300 mg, 0.87 mmol) in EtOAc (20 mL) was added wet Pd/C (130 mg, 10% purity). The mixture was stirred at 25° C. under H$_2$ at 15 psi for 1 hr. The Pd/C was filtered. The filtrate was collected and concentrated to afford compound 14J (280 mg, yield: 91.86%) as white solid. MS (ESI) m/z (M+H)$^+$ 371.3. $^1$H NMR (CDCl$_3$, 400 MHz): δ 7.44-7.43 (m, 1H), 7.34-7.32 (m, 1H), 7.24-7.20 (m, 2H), 6.29-6.27 (m, 1H), 4.90-4.85 (m, 1H), 4.28-4.23 (m, 2H), 3.35-3.30 (m, 1H), 2.46-2.39 (m, 1H), 2.06-2.05 (m, 1H), 1.53-1.26 (m, 21H).

Step 2: Synthesis of Compound 14K

To a solution of compound 14J (280 mg, 0.81 mmol) in THF (10 mL) at 0° C. was added LiAlH$_4$ (93 mg, 2.43 mmol). The mixture was stirred at 0° C. for 1 hr. The reaction was diluted with EtOAc (10 mL), quenched with H$_2$O (0.1 mL), 15% aqueous NaOH (0.1 mL), H$_2$O (0.3 mL). The reaction was warmed up to 25° C. and stirred for 15 min. Then MgSO$_4$ was added and stirred for 15 min. The solid was filtered. The filtrate was collected and concentrated. The residue was purified by preparatory-HPLC to afford compound 14K (170 mg, yield: 68.43%) as white solid. MS (ESI) m/z (M+H)$^+$ 303.9.

Step 3: Synthesis of Compound 28

To a solution of compound 14K (170 mg, 0.56 mmol) in DCM (20 mL) was added DESS-MARTIN PERIODINANE (356 mg, 0.84 mmol). The mixture was stirred at 25° C. for 12 hrs. The reaction was quenched with a solution of 10% aqueous Na$_2$S$_2$O$_3$ and 10% aqueous NaHCO$_3$ (v/v=1/1) (20 mL). The organics were collected, washed with brine (20 mL). The organics were collected, dried with Na$_2$SO$_4$, filtered and concentrated to afford compound 28 (130 mg, yield: 73.83%) as white solid. MS (ESI) m/z (M+H)$^+$ 301.9. $^1$H NMR (DMSO-d$_6$, 400 MHz): δ 9.60 (s, 1H), 8.57 (d, J=8.8 Hz, 1H), 7.49-7.43 (m, 1H), 7.40-7.33 (m, 1H), 7.31-7.23 (m, 2H), 4.59-4.41 (m, 1H), 3.09-2.94 (m, 1H), 2.47-2.40 (m, 1H), 1.92-1.81 (m, 1H), 1.54-1.15 (m, 17H).

Examples 29 and 30
(S)-11-Oxo-3-oxa-10-aza-1(1,2),2(1,3)-dibenzenacycloundecaphan-6-ene-9-carbaldehyde (29) and (S)-11-Oxo-3-oxa-10-aza-1(1,2),2(1,3)-dibenzenacycloundecaphane-9-carbaldehyde (30)
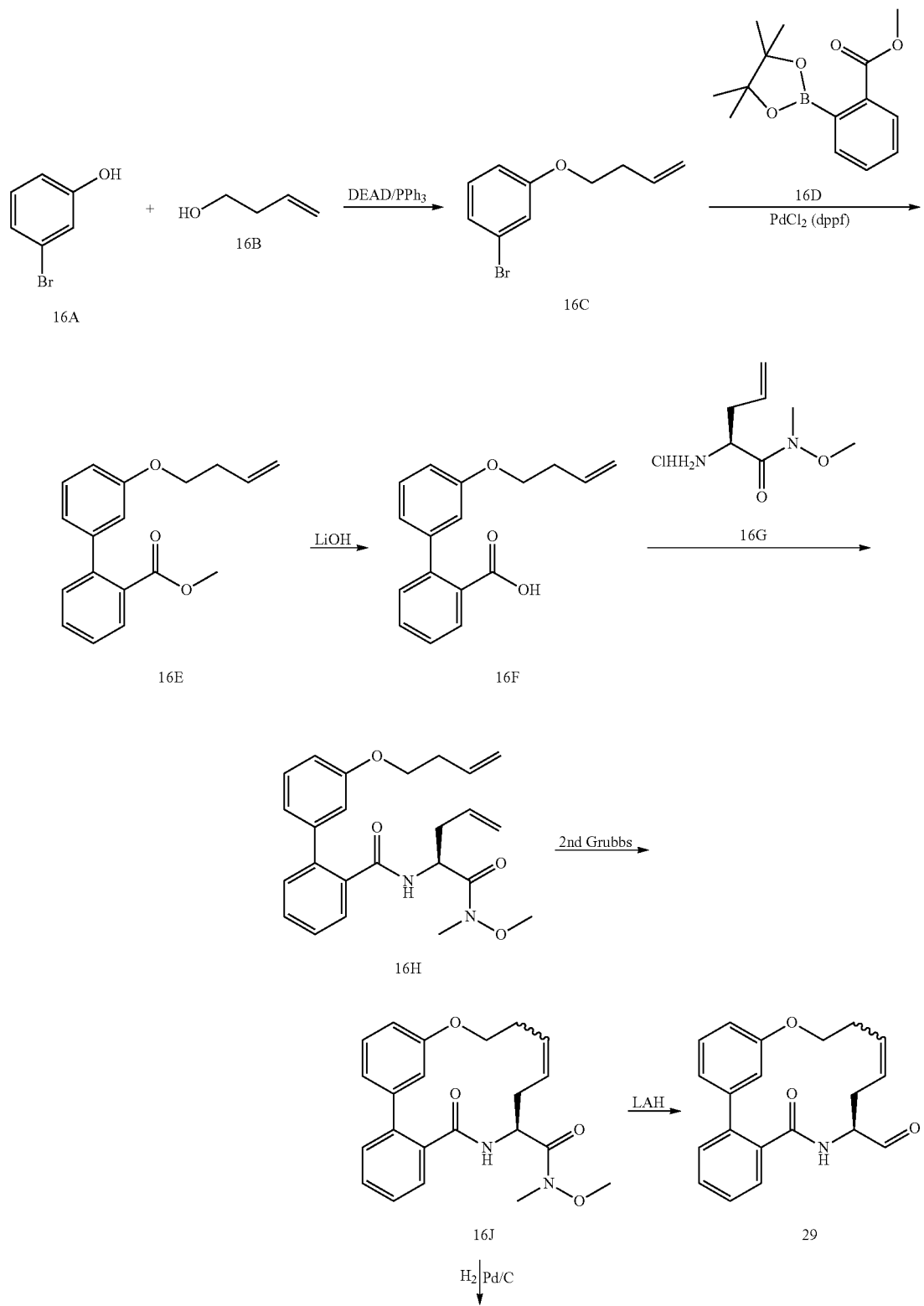

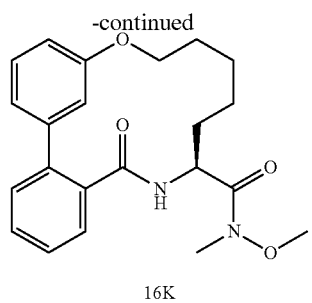

16K

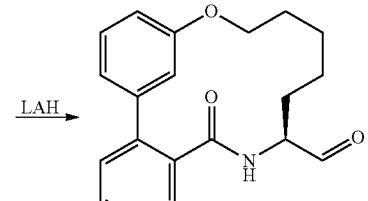

30

Step 1: Synthesis of Compound 16C

To a solution of 16A (1.0 g, 1.0 eq), 16B (0.46 g, 1.1 eq) and PPh₃ (1.8 g, 1.2 eq) in 10 mL dry THF at 0° C. under N₂ was slowly added a solution of DEAD (1.2 g, 1.2 eq) in 5 mL dry THF. The mixture was stirred at room temperature for overnight. The reaction mixture was diluted with 150 mL hexane, the precipitated white solid Ph₃PO was removed by filtration. The crude mixture was purified on ISCO to provide compound 16C clear oil (1.1 g, yield 77%).

Step 2: Synthesis of Compound 16E

Compound 16C (1 g, 1.0 eq), 16D (1.27 g, 1.1 eq) were dissolved in 20 mL 1,4-dioxane, then added 2M K₂CO₃ in water (3 mL). The mixture was flushed with N₂, then added PdCl₂(dppf)CH₂Cl₂ (0.33 g, 0.1 eq). The resulting mixture was heated at 90° C. for 2 hrs in a sealed-tube. The reaction mixture was diluted with 100 mL ethyl acetate, washed with water and brine. The crude mixture was directly purified on ISCO silica gel column to provide 16E (1.06 g, yield 85%).

Step 3: Synthesis of Compound 16F

Compound 16E (1 g) was treated with LiOH in MeOH and water to provide acid 16F (0.91 g, yield 96%).

Step 4: Synthesis of Compound 16H

Acid 16F coupled with amine 16G to afford compound 16H.

Step 5: Synthesis of Compound 16K

Compound 16H was subjected to the ring-closing metathesis reaction with $2^{nd}$ Grubbs catalyst to provide compound 16J.

Step 6: Synthesis of Compound 16K

Compound 16J was hydrogenated at 50 psi in present of Pd/C (10%) to yield compound 16K.

Step 7: Synthesis of Compound 29

Compound 16J was treated with LAH at −50° C. to give compound 29. MS (ESI) m/z (M+H)⁺ 322.2. ¹H NMR (400 MHz, DMSO-d₆): δ 9.56 (s, 0.24H), 9.44 (s, 0.76H), 7.94 (d, 0.76H), 7.75 (d, 0.24H), 7.26-7.51 (m, 3H), 6.78-7.03 (m, 3H), 6.17 (d, 0.24H), 5.94 (d, 0.76H), 5.52 (m, 1H), 5.18 (m, 1H), 4.58-4.67 (m, 1H), 4.21-4.40 (m, 2H), 2.07 (m, 1H), 2.42 (m, 2H), 2.21 (m, 1H) ppm).

Step 8: Synthesis of Compound 30

Compound 16K was treated with LAH at −50° C. to provide 30. MS (ESI) m/z (M+H)⁺ 324.5. ¹H NMR (400 MHz, DMSO-d₆): δ 9.50 (s, 1H), 7.71 (d, 1H), 7.26-7.52 (m, 4H), 7.05 (d, 1H), 6.95 (m, 2H), 5.96 (d, 1H), 4.68 (m, 1H), 4.29 (m, 2H), 1.12-2.05 (m, 8H) ppm).

Example 31

(S)-17-Oxo-5,7,8,9,14,15,16,17-octahydrodibenzo[c,i][1]oxa[6]aza-cyclotridecine-15-carbaldehyde (31)

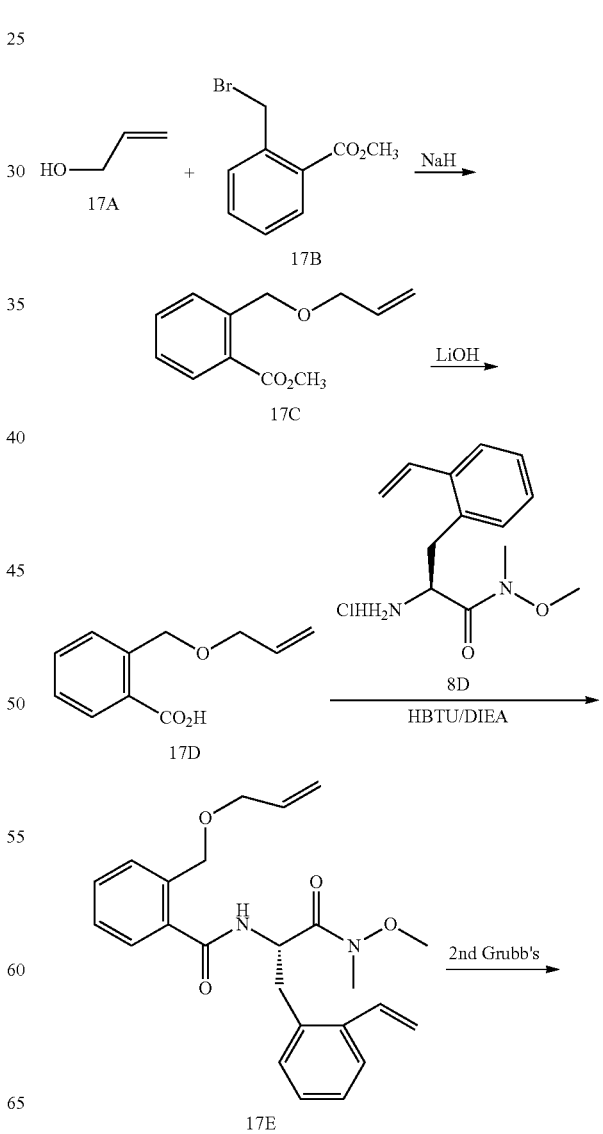

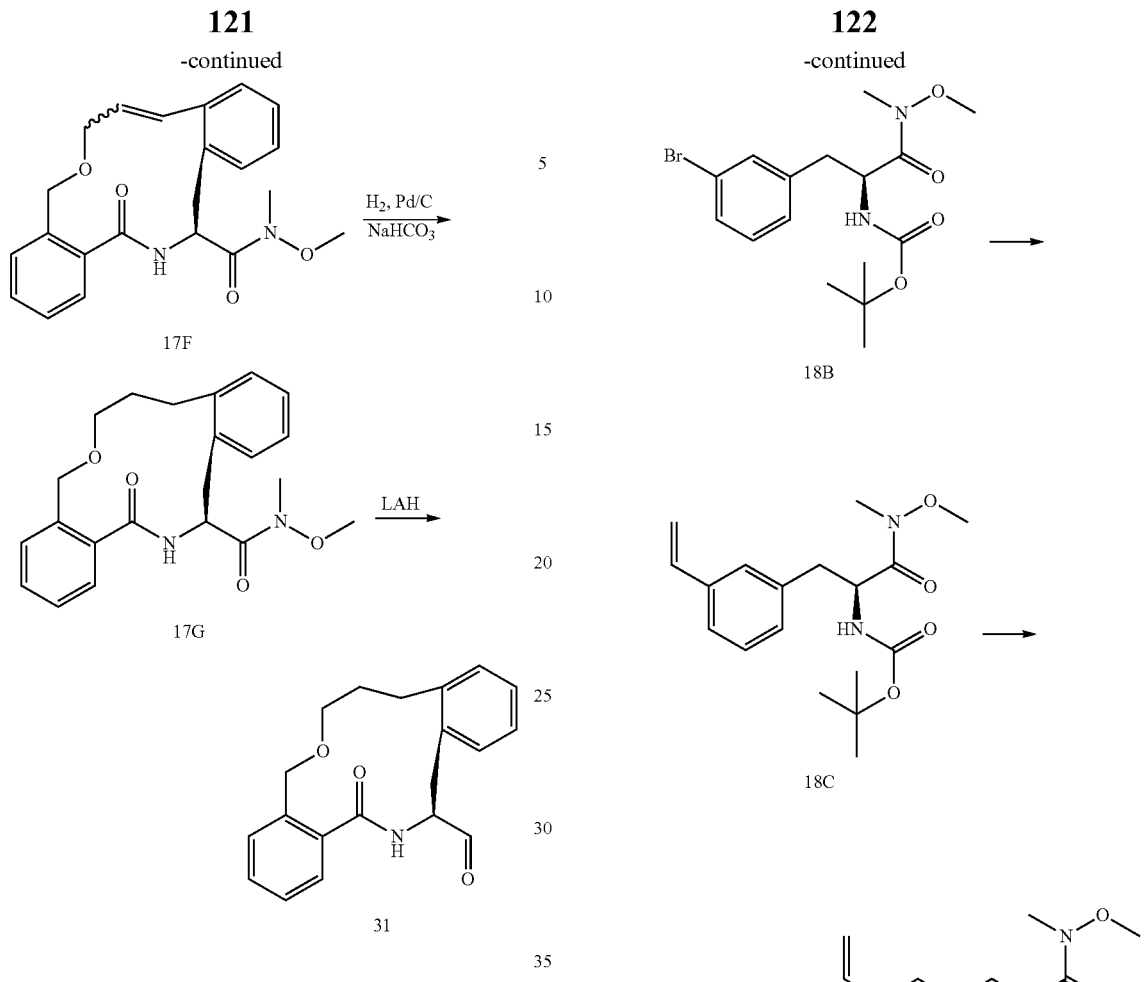
Synthesis of Compound 31
Compound 31 was prepared following the procedure of Example 30 using intermediates 17D and 8D. MS (ESI) m/z (M+H)⁺: 324.5; $^1$H NMR (400 MHz, CDCl$_3$) δ 9.72 (s, 1H), 8.32 (m, 1H), 7.92 (d, 1H), 7.4-7 (m, 7H), 4.75 (m, 1H), 4.62 (d, 1H), 4.37 (d, 1H), 3.4-3.2 (m, 4H), 3-2.7 (m, 2H), 2.2-1.8 (m, 2H) ppm.
Example 32
(S)-2-Oxo-10-oxa-3-aza-1(1,2),6(1,3)-dibenzena-cycloundecaphane-4-carbaldehyde (32)
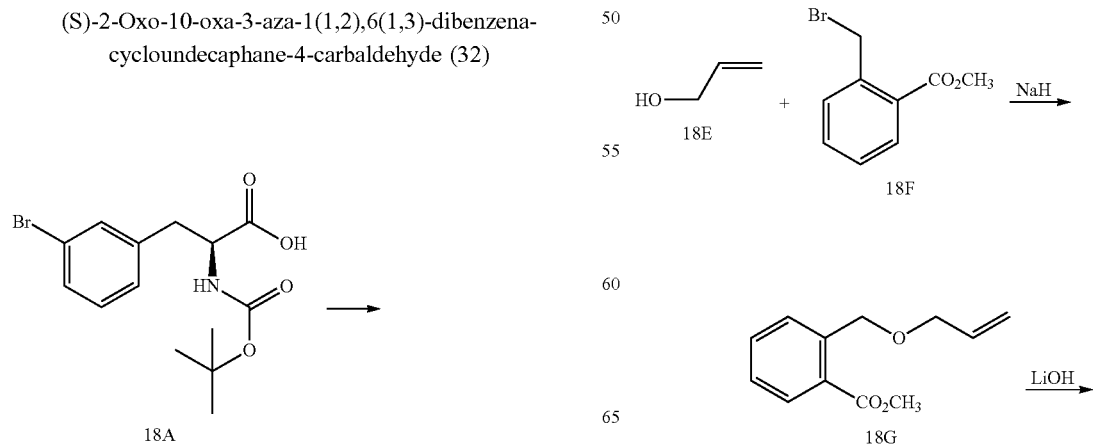

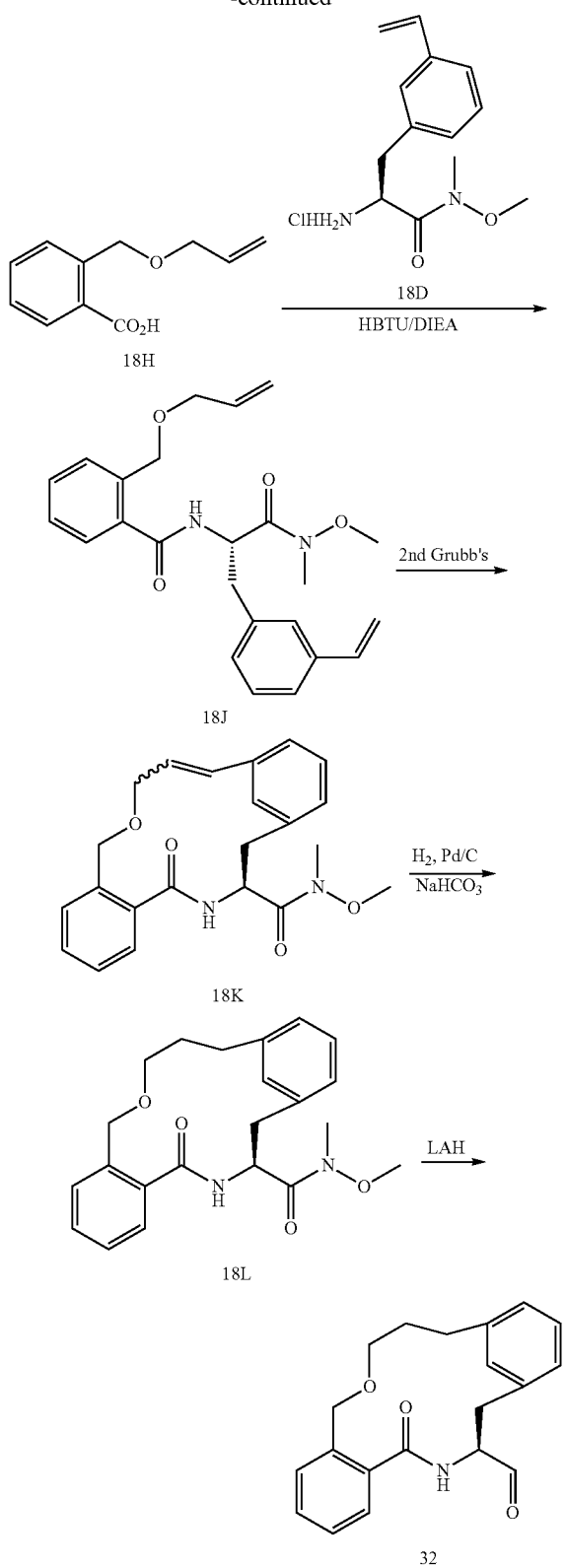

Synthesis of Compound 18D

Intermediate 18D was prepared following the procedure of intermediate 8D and then further used in the synthesis of compound 32.

Synthesis of Compound 32

Compound 32 was prepared following the procedure of Example 30 using intermediates 18H and 18D. MS (ESI) m/z (M+H)$^+$: 324.5; $^1$H NMR (400 MHz, CDCl$_3$) δ 9.69 (s, 1H), 7.72 (m, 1H), 7.5-6.9 (m, 8H), 5.08 (m, 1H), 4.62 (d, 1H), 4.38 (d, 1H), 3.4-3.2 (m, 4H), 2.7-2.6 (m, 2H), 2.1-1.9 (m, 2H) ppm.

Example 33

(S,E)-N-ethyl-2-oxo-2-(1-oxo-2,3,4,7,8,9,10,11,12,13-decahydro-1h-benzo[c][1]azacyclopentadecin-3-yl)acetamide (33)

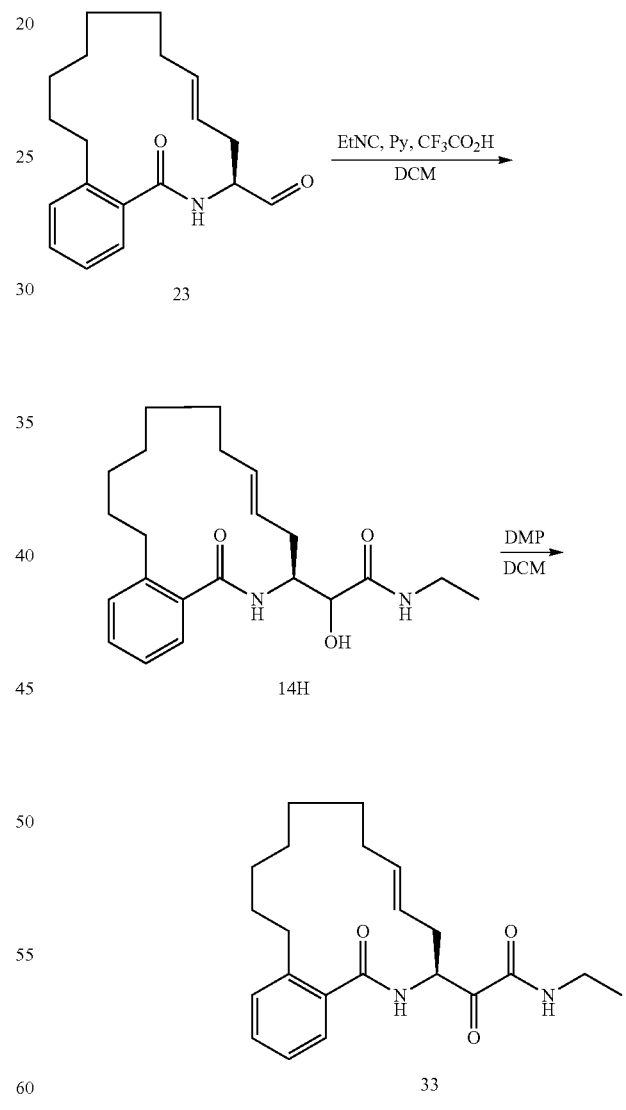

Step 1: Synthesis of Compound 14H

To a solution of compound 23 (387 mg, 1.29 mmol) and isocyanoethane (80 mg, 1.42 mmol) in DCM (10 mL) was added Py (0.42 mL, 5.16 mmol). The mixture was cooled to 0° C. Then TFA (0.2 mL, 2.58 mmol) was added dropwise. The mixture was warmed up to 25° C. and stirred for 12 hrs. The mixture was diluted with DCM (20 mL), quenched with 1N HCl (10 mL). The organics were collected and concentrated. The residue was purified by preparatory-HPLC (HCl) to afford compound 14H (140 mg, yield: 28.84%) as white solid. MS (ESI) m/z (M+H)$^+$ 373.2. $^1$H NMR (DMSO-d$_6$, 400 MHz): δ 8.02 (d, J=8.8 Hz, 0.4H), 7.95-7.89 (m, 0.6H), 7.86-7.78 (m, 0.4H), 7.67-7.57 (m, 0.6H), 7.42-7.40 (m, 1H), 7.31-7.29 (m, 1H), 7.22-7.20 (m, 2H), 5.83-5.82 (m, 0.3H), 5.62-5.51 (m, 0.6H), 5.42-5.30 (m, 2H), 4.32-4.27 (m, 1H), 3.97-3.95 (m, 1H), 3.19-3.03 (m, 3H), 2.42-2.08 (m, 2H), 2.05-1.87 (m, 2H), 1.55-1.06 (m, 11H), 1.01-0.97 (m, 3H).

Step 2: Synthesis of Compound 33

To a solution of compound 14H (140 mg, 0.38 mmol) in DCM (20 mL) was added DESS-MARTIN PERIODINANE (240 mg, 0.56 mmol). The mixture was stirred at 25° C. for 12 hrs. The reaction was diluted with DCM (30 mL), quenched with a solution of 10% aqueous Na$_2$S$_2$O$_3$ and 10% aqueous NaHCO$_3$ (v/v=1/1) (50 mL). The organics were collected, washed with brine (50 mL). The organics were collected, dried with Na$_2$SO$_4$, filtered and concentrated to afford compound 33 (80 mg, yield: 57.05%) as white solid. MS (ESI) m/z (M+H)$^+$ 371.3. $^1$H NMR (DMSO-d$_6$, 400 MHz): δ 8.81 (t, J=5.6 Hz, 1H), 8.68 (d, J=8.0 Hz, 1H), 7.38-7.21 (m, 4H), 5.57-5.43 (m, 2H), 5.26-5.18 (m, 1H), 3.25-3.12 (m, 2H), 2.90-2.79 (m, 1H), 2.58-2.53 (m, 1H), 2.20-2.09 (m, 1H), 2.05-1.94 (m, 2H), 1.55-1.14 (m, 11H), 1.08 (t, J=7.6 Hz, 3H).

Example 34

(S)—N-ethyl-2-oxo-2-(1-oxo-2,3,4,5,6,7,8,9,10,11,12,13-dodecahydro-1h-benzo[c][1]azacyclopentadecin-3-yl)acetamide (34)

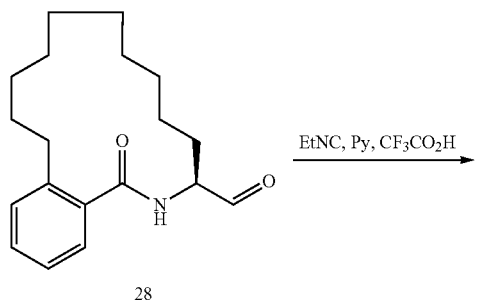

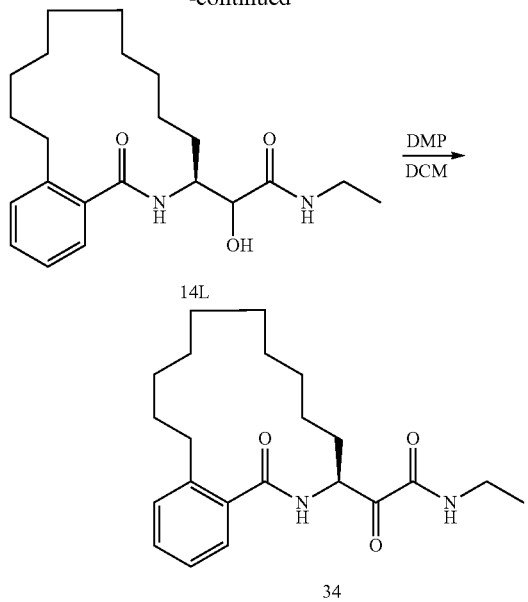

Step 1: Synthesis of Compound 14L

To a solution of compound 28 (200 mg, 0.67 mmol) and isocyanoethane (41 mg, 0.73 mmol) in DCM (20 mL) at 0° C. was added pyridine (0.22 mL, 2.65 mmol). Then TFA (0.1 mL, 1.33 mmol) was added dropwise. The mixture was then warmed up to 25° C. and stirred for 12 hrs. The reaction was washed with 1N HCl (20 mL). The organics were collected and concentrated. The residue was purified by preparatory-HPLC (acid) to afford compound 14L (140 mg, yield: 56.28%) as white solid. MS (ESI) m/z (M+H)$^+$ 375.1. $^1$H NMR (DMSO-d$_6$, 400 MHz): δ 7.97-7.94 (m, 0.6H), 7.78-7.75 (m, 0.6H), 7.57-7.47 (m, 0.6H), 7.46-7.42 (m, 0.3H), 7.40-7.35 (m, 0.7H), 7.34-7.26 (m, 1H), 7.25-7.15 (m, 2H), 5.74-5.72 (m, 0.3H), 5.56-5.54 (m, 0.7H), 4.29-4.24 (m, 1H), 3.93-3.91 (m, 1H), 3.16-3.07 (m, 3H), 2.33-2.27 (m, 1H), 1.51-1.18 (m, 20H), 1.03-0.97 (m, 3H).

Step 2: Synthesis of Compound 34

To a solution of compound 14L (140 mg, 0.37 mmol) in DCM (10 mL) was added DMP (238 mg, 0.56 mmol). The mixture was stirred at 25° C. for 12 hrs. The reaction was diluted with DCM (20 mL), quenched with a solution of 10% aqueous Na$_2$S$_2$O$_3$ and 10% aqueous NaHCO$_3$ (v/v=1/1) (30 mL). The organics were collected, washed with brine (30 mL). The organics were collected, dried with Na$_2$SO$_4$, filtered and concentrated to afford compound 34 (23.10 mg, yield: 16.08%) as white solid. MS (ESI) m/z (M+H)$^+$ 373.3. $^1$H NMR (DMSO-d$_6$, 400 MHz): δ 8.77 (t, J=5.6 Hz, 1H), 8.60 (d, J=8.0 Hz, 1H), 7.39-7.22 (m, 4H), 5.37-5.26 (m, 1H), 3.24-3.10 (m, 2H), 3.03-2.91 (m, 1H), 2.44-2.38 (m, 1H), 1.84-1.71 (m, 1H), 1.58-1.48 (m, 3H), 1.47-1.22 (m, 14H), 1.07 (t, J=7.6 Hz, 3H).

Examples 35 and 36

(S)-3-Oxo-12-oxa-4-aza-2(2,3)-pyridina-1,7(1,3)-dibenzenacyclododecaphane-5-carbaldehyde (35) and (S)-3-Oxo-12-oxa-4-aza-2(2,3)-pyridina-1,7(1,3)-dibenzenacyclododecaphan-8-ene-5-carbaldehyde (36)

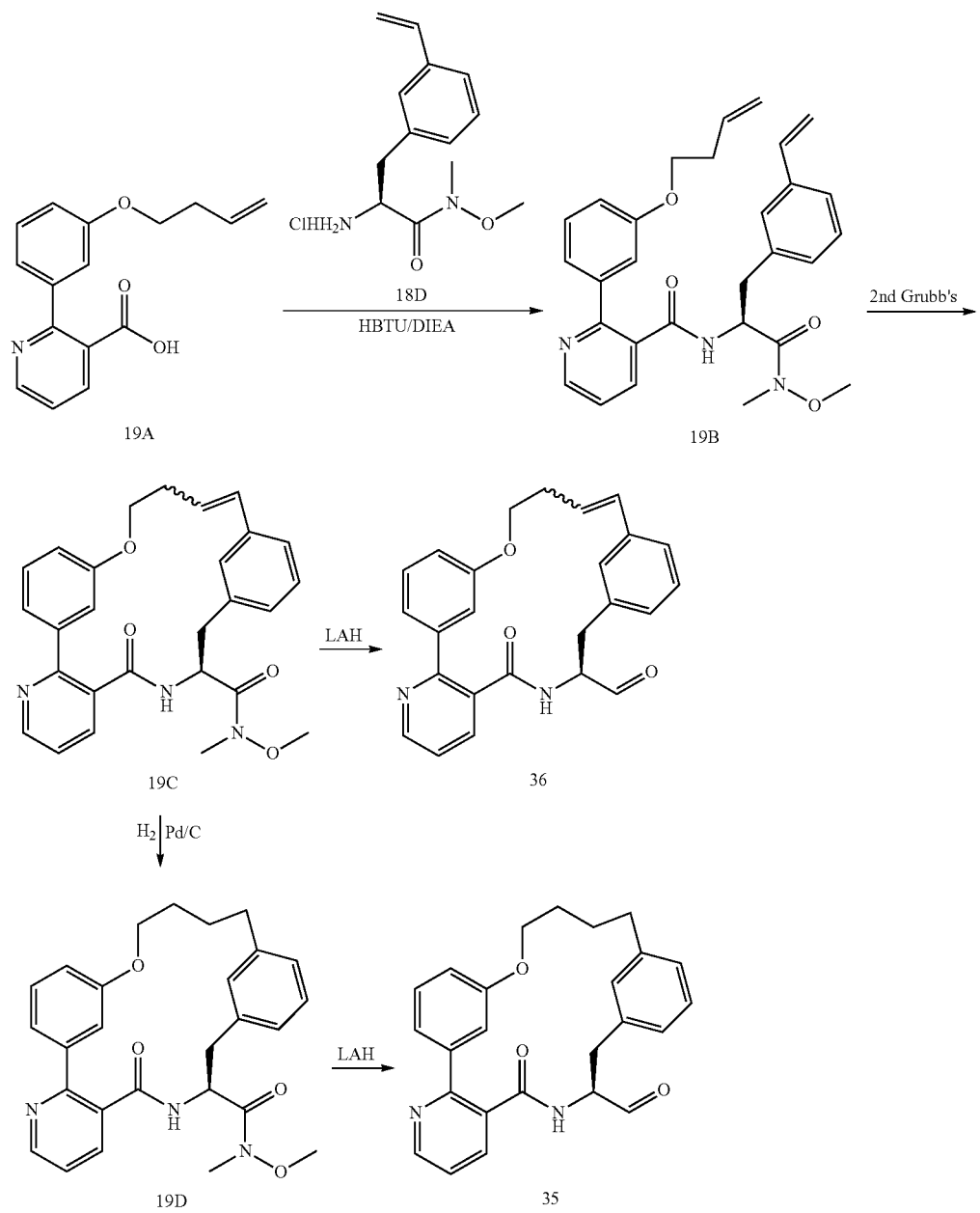

Synthesis of Compound 35

Compound 35 was prepared following the procedure of Example 30 using intermediates 19A and 18D. MS (ESI) m/z (M+H)+: 401.3; $^1$H NMR (400 MHz, CDCl$_3$) δ 9.55 (s, 1H), 8.72 (m, 1H), 8.11 (m, 1H), 7.5-7.4 (m, 2H), 7.15 (d, 1H), 7.1-6.95 (m, 4H), 6.76 (d, 1H), 6.27 (s, 1H), 5.62 (d, 1H), 4.75 (m, 1H), 4.22 (m, 1H), 4.2-4.08 (m, 1H), 2.9-2.55 (m, 4H), 2.0-1.5 (m, 4H) ppm.

Synthesis of Compound 36

Compound 36 was prepared following the procedure of Example 29 using intermediates 19A and 18D. MS (ESI) m/z (M+H)+: 399.4; $^1$H NMR (400 MHz, CDCl$_3$) δ 9.62 (s, 1H), 8.71 (m, 1H), 7.91 (m, 1H), 7.53 (m, 1H), 7.38 (t, 1H), 7.35-7.25 (m, 2H), 7.15-7.05 (m, 2H), 6.92 (d, 1H), 6.8 (d, 1H), 6.32 (d, 1H), 6.05 (s, 1H), 5.89 (m, 1H), 5.79 (d, 1H), 4.89 (m, 1H), 4.6-4.45 (m, 2H), 3.25 (dd, 1H), 2.8-2.65 (m, 2H), 2.58 (m, 1H) ppm.

Examples 37 and 38

(S)-11-Oxo-3-oxa-10-aza-1(2,3)-pyridina-2(1,3)-benzenacycloundecaphan-6-ene-9-carbaldehyde (37) and (S)-11-Oxo-3-oxa-10-aza-1(2,3)-pyridina-2(1,3)-benzenacycloundecaphane-9-carbaldehyde (38)

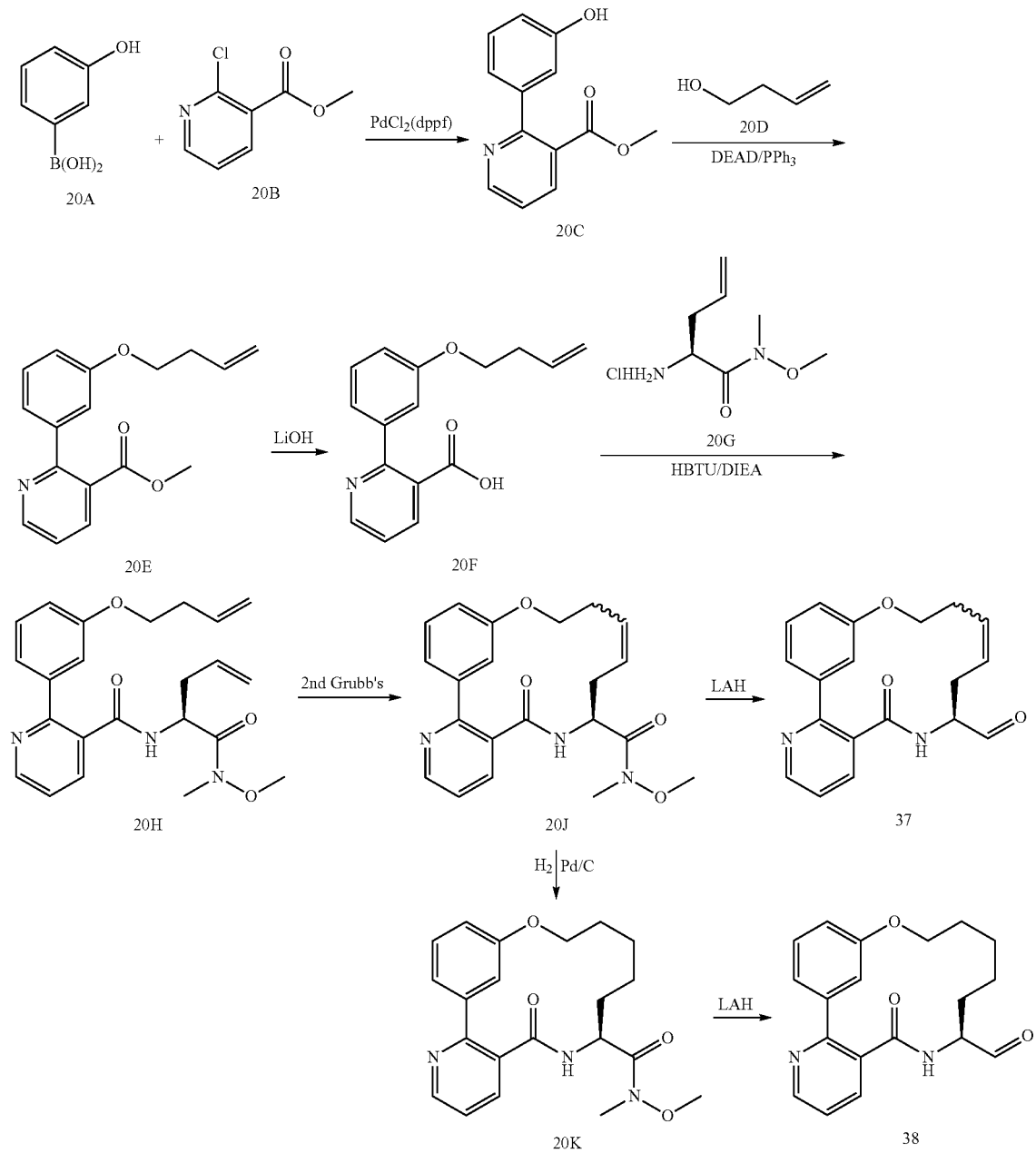

Synthesis of Compound 37

Compound 37 was prepared following the procedure of Example 29 using intermediates 20F and 20G. MS (ESI) m/z (M+H)+: 355.5; 1H NMR (400 MHz, CDCl3) δ 9.57 (s, 0.24H), 9.47 (s, 0.76H), 8.73 (m, 1H), 8.23 (m, 0.76H), 8.04 (m, 0.24H), 7.5-7.2 (m, 3H), 7.1-6.89 (m, 2H), 6.25 (d, 0.24H), 6.1 (d, 0.76H), 5.55 (m, 1H), 5.2 (m, 1H), 4.76-4.62 (m, 1H), 4.4-4.2 (m, 2H), 2.9-2.76 (m, 1H), 2.5-2.4 (m, 2H), 2.34-2.18 (m, 1H) ppm.

Synthesis of Compound 38

Compound 38 was prepared following the procedure of Example 30 using intermediates 20F and 20G. MS (ESI) m/z (M+H)+: 357.4; 1H NMR (400 MHz, CDCl3) δ 9.3 (s, 1H), 8.7 (m, 1H), 8.01 (m, 1H), 7.5-7.3 (m, 3H), 7.1-7.0 (m, 3H), 4.62 (m, 1H), 4.4-4.2 (m, 2H), 2.02 (m, 1H), 1.9-1.3 (m, 7H) ppm.

Example 39

(S)-3-Oxo-11-oxa-4-aza-1(2,4)-pyrimidina-2(1,2)-benzenacyclo undecaphan-7-ene-5-carbaldehyde (39)

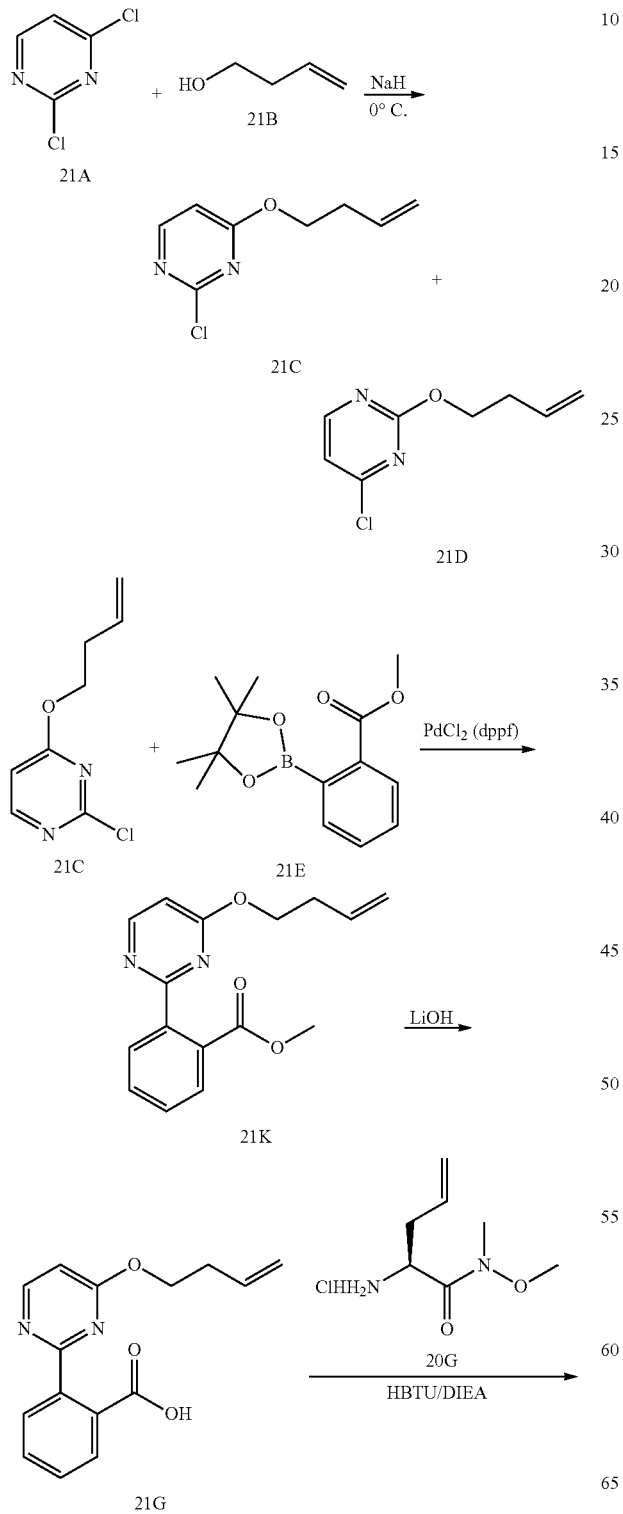

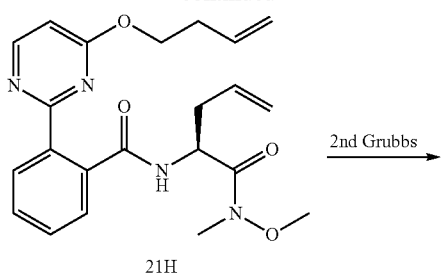

Step 1: Synthesis of Compounds 21C and 21D

To a solution of compound 21B (0.73 g, 1.0 eq) in 20 mL dry THF was added NaH (442 mg, 60% in mineral oil, 1.1 eq). The mixture was stirred at room temperature for 1 hr under $N_2$ and then cooled to 0° C. Compound 21A (1.5 g, 1.0 eq) was added at 0° C. The resulting mixture was stirred at 0° C. for 1 hr. The reaction was quenched with saturated $NH_4Cl$, and then extracted with 2×50 mL ethyl acetate. The crude mixture was purified on silica-gel to afford compound 21C (0.74 g, yield 40%), compound 21D (0.65 g, yield 35%).

Synthesis of Compound 39

Compound 39 was prepared following the procedure of compound 29 using intermediates 21C and 21E. MS (ESI) m/z (M+H)$^+$: 324.4; $^1$H NMR (400 MHz, DMSO-d6) δ 9.68 (s, 0.3H), 9.41 (s, 0.7H), 8.47 (m, 1H), 7.81 (d, 0.3H), 7.72 (d, 0.7H), 7.54 (m, 3H), 6.82 (d, 0.3H), 6.58 (m, 1H), 6.17 (d, 0.7H), 5.41-5.65 (m, 1H), 5.12-5.32 (m, 1H), 4.61-4.98 (m, 2H), 4.17-4.32 (m, 1H), 2.56-2.71 (m, 1H), 2.35 (m, 2H), 2.07 (m, 1H) ppm.

Example 40

(S)-11-Oxo-3-oxa-10-aza-1(2,3)-pyridina-2(1,3)-benzena-cycloundecaphane-9-carbaldehyde (40)

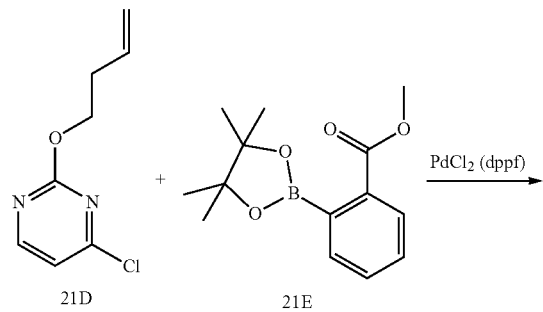

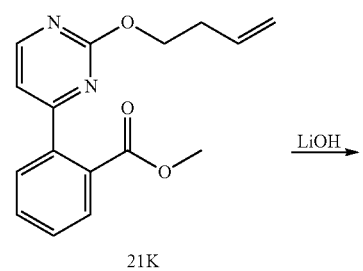

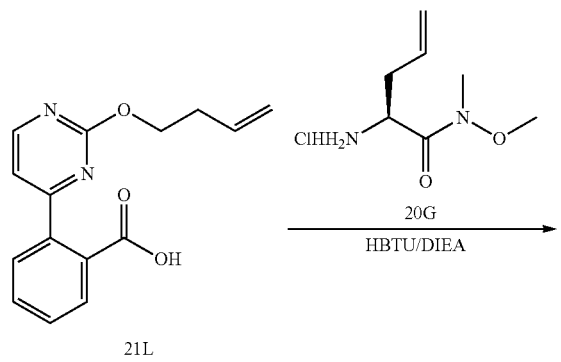

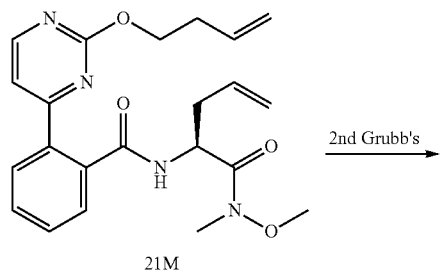

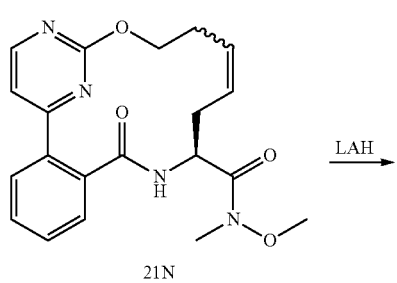

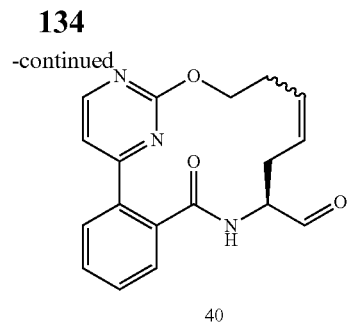

Synthesis of Compound 40

Compound 40 was prepared following the procedure of compound 29 using intermediates 21D and 21E. MS (ESI) m/z (M+H)$^+$: 322.2; $^1$H NMR (400 MHz, DMSO-d6) δ 9.72 (s, 0.4H), 9.44 (s, 0.6H), 8.61 (m, 1H), 7.84 (d, 0.6H), 7.71 (d, 0.4H), 7.26-7.58 (m, 3H), 7.18 (d, 0.4H), 7.11 (d, 0.4H), 7.04 (d, 0.6H), 6.54 (d, 0.6H), 5.44-5.65 (m, 1H), 5.12-5.30 (m, 1H), 4.42-4.85 (m, 3H), 2.66 (m, 2H), 2.43 (m, 2H) ppm.

Examples 41 and 42

(S)-11-Oxo-1,3,4,5,8,9,10,11-octahydrobenzo[c][1]oxa[6]azacyclotridecine-9-carbaldehyde (41) and (S)-11-Oxo-1,3,4,5,6,7,8,9,10,11-decahydrobenzo[c][1]oxa[6]azacyclotridecine-9-carbaldehyde (42)

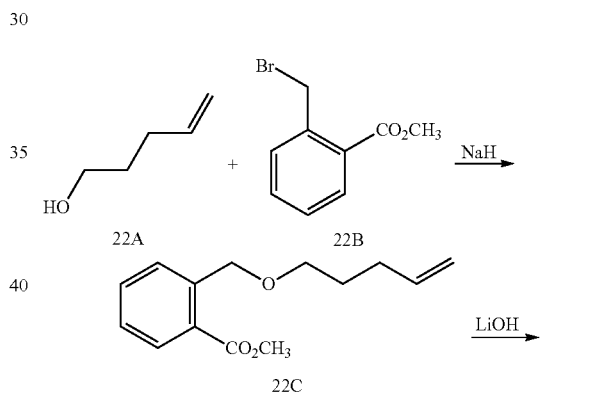

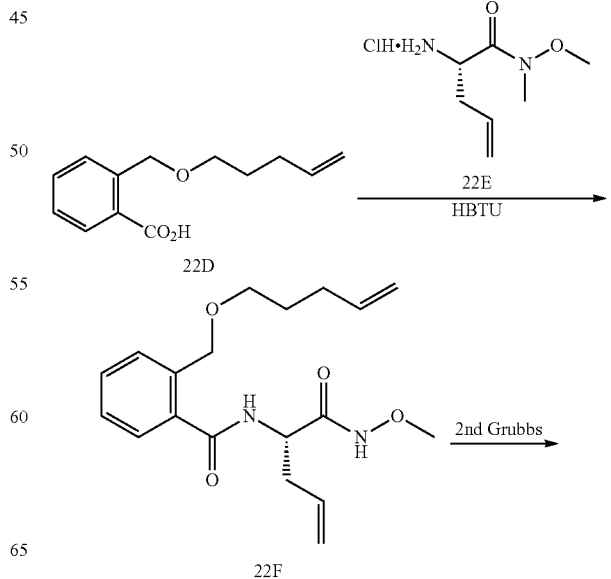

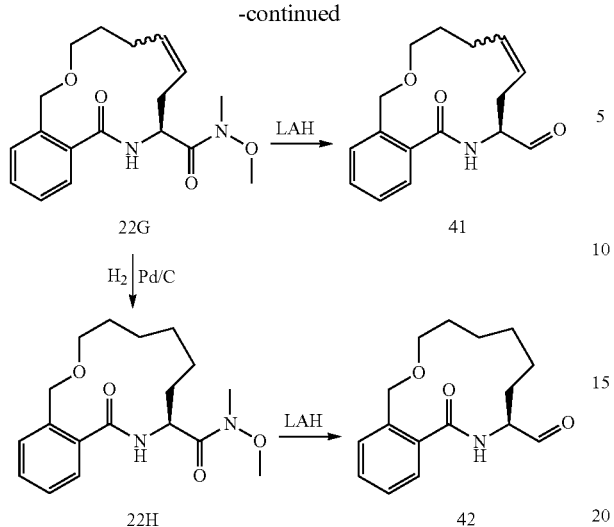

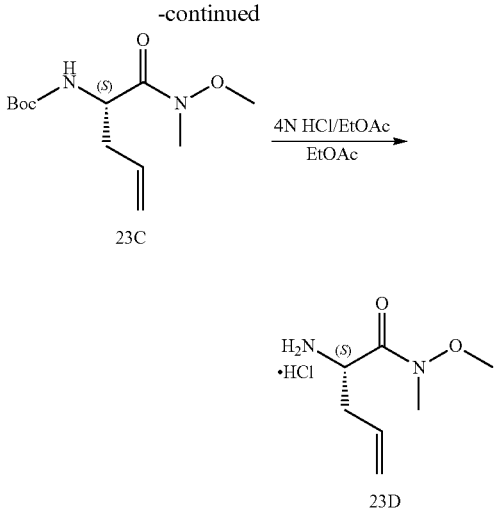

Synthesis of Compound 41

Compound 41 was prepared following the procedure of Example 29 using intermediates 22D and 22E. MS (ESI) m/z (M+H)$^+$: 274.3; $^1$H NMR (400 MHz, CDCl$_3$) δ 9.66 (s, 1H), 8.0 (d, 1H), 7.81 (d, 1H), 7.42 (m, 2H), 7.35 (d, 1H), 5.6 (m, 1H), 5.3 (m, 1H), 4.8 (m, 2H), 4.2 (d, 1H), 3.6 (m, 2H), 2.8 (m, 1H), 2.35 (m, 3H), 2.1 (m, 1H), 1.8 (m, 3H) ppm.

Synthesis of Compound 42

Compound 42 was prepared following the procedure of Example 30 using intermediates 22D and 22E. MS (ESI) m/z (M+H)$^+$: 276.3; $^1$H NMR (400 MHz, CDCl$_3$) δ 9.65 (s, 1H), 7.64 (d, 1H), 7.4 (m, 2H), 7.35 (d, 1H), 7.0 (d, 1H), 4.8 (m, 2H), 4.4 (d, 1H), 3.6 (m, 2H), 2.08 (m, 1H), 1.2-1.8 (m, 8H) ppm.

Example 43

(S)-12-Oxo-1,3,4,6,7,8,9,10,11,12-decahydrobenzo[f][1,4]dioxa[9]aza-cyclotetradecine-10-carbaldehyde (43)

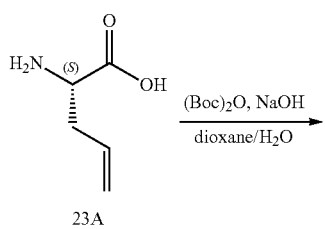

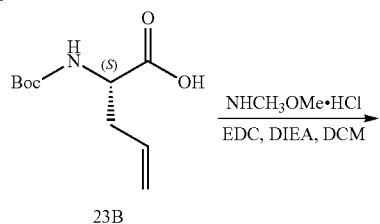

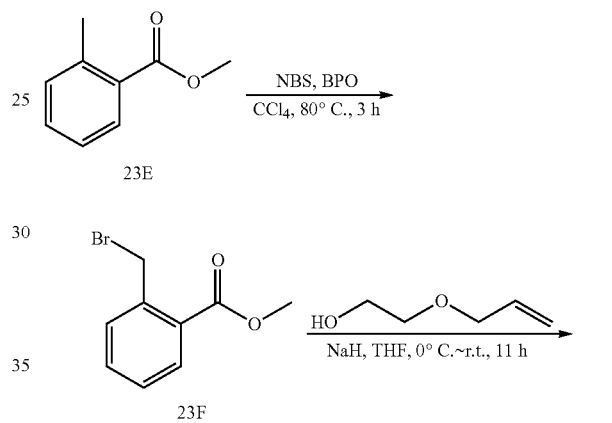

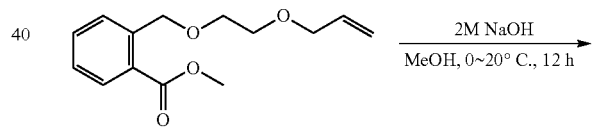

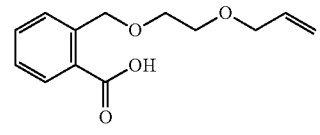

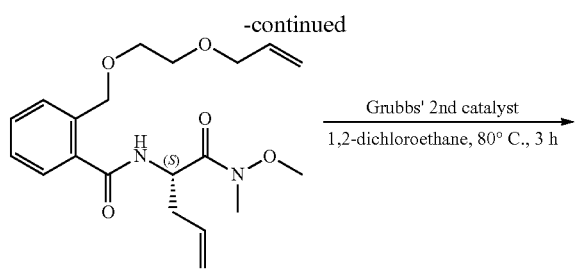

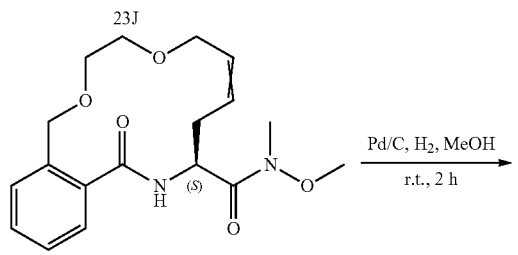

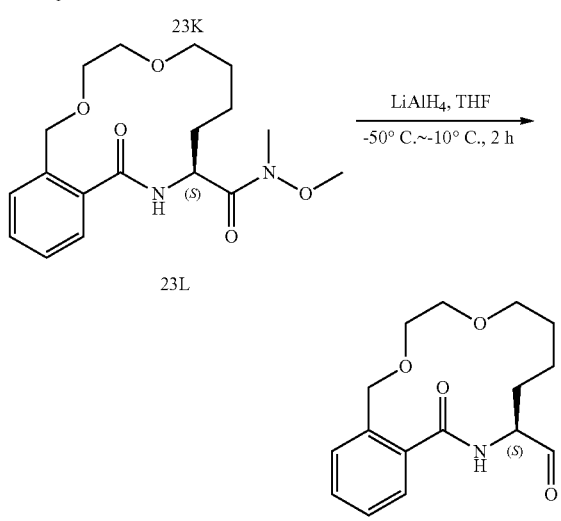

Step 1: Synthesis of Compound 23B

To a mixture of compound 23A (30.0 g, 261 mmol) in dioxane (300 mL) and H₂O (300 mL) was added NaOH (20.85 g, 521 mmol) in portions at 0° C. After NaOH was dissolved, Boc₂O (68.2 g, 313 mmol) was added to the mixture in portions at 15° C. The mixture was stirred at 20° C. for 16 hrs. The volatile dioxane was removed by evaporation. The crude mixture was diluted with H₂O (100 mL) and acidified to pH~3-4 with 1N KHSO₄ aqueous solution. This aqueous solution was extracted with MTBE (500 mL×3). The combined organic layers were washed with brine (300 mL), dried over anhydrous MgSO₄, filtered and concentrated to afford compound 23B (59.0 g, crude) as yellow oil, which was used into the next step without further purification. ¹H NMR (400 MHz, DMSO-d₆) δ 12.52 (s, 1H), 7.05 (d, J=8.4 Hz, 1H), 5.83-5.70 (m, 1H), 5.15-4.99 (m, 2H), 3.96-3.87 (m, 1H), 2.45-2.37 (m, 1H), 2.36-2.24 (m, 1H), 1.41-1.29 (m, 9H).

Step 2: Synthesis of Compound 23C

To a solution of compound 23B (35.0 g, 162.6 mmol) in DCM (800 mL) was added EDCI (34.3 g, 179 mmol) at 0° C. The mixture was stirred at 0° C. for 5 min. Then DIEA (85.2 mL, 488 mmol) was added into reaction mixture, followed by N-methoxymethanamine (23.8 g, 244 mmol, HCl salt). The reaction mixture was stirred at 25° C. for 15 hrs. The mixture was washed with HCl (1N, 100 mL) and sat. NaHCO₃ (100 mL), then brine (100 mL). The mixture was dried over Na₂SO₄, filtered and concentrated. The residue was purified by column chromatography (SiO₂, Petroleum ether/Ethyl acetate=5/1 to 1:1) to give compound 23C (20.5 g, yield 48.8%) as yellow oil

Step 3: Synthesis of Compound 23D

To a solution of compound 23C (27.0 g, 104 mmol) in ethyl acetate (50 mL) was added HCl/EtOAc (4M, 60 mL) at 0° C. Then, the mixture was stirred at 10° C. for 2 hrs. The mixture was concentrated in vacuum to afford compound 23D (20.0 g, crude, HCl salt), which was used for the next step without further purification. ¹H NMR (400 MHz, DMSO-d₆) δ 8.41 (br.s., 3H), 5.83-5.70 (m, 1H), 5.21-5.09 (m, 2H), 4.31-4.20 (m, 1H), 3.75 (s, 3H), 3.16 (s, 3H), 2.58-2.52 (m, 2H)

Step 4: Synthesis of Compound 23F

A solution of compound 23E (30 g, 200 mmol) in CCl₄ (40 mL) was added drop-wise to a stirring mixture of benzoyl peroxide (1.45 g, 5.99 mmol) and NBS (35.6 g, 200 mmol) in CCl₄ (300 mL) at 0° C. The mixture was heated to reflux (80° C.) and stirred for 3 hrs under nitrogen. The precipitated succinimide was removed by filtration and the filter cake was washed with carbon tetrachloride (30 mL×2). The combined filtrates were washed successively with 2N NaOH (150 mL), and water (100 mL×2), and the solution was dried over anhydrous MgSO₄, filtered (Celite), and evaporated under vacuum to afford compound 23F (45 g, crude) as yellow oil, which was used for next step without further purification. ¹H NMR (400 MHz, DMSO-d₆) δ 7.88 (d, J=7.6 Hz, 1H), 7.63-7.57 (m, 2H), 7.51-7.44 (m, 1H), 5.02 (s, 2H), 3.87 (s, 3H).

Step 5: Synthesis of Compound 23G

To a suspension of NaH (4.92 g, 123.11 mmol, 60% in mineral oil) in anhydrous THF (300 mL) was added a solution of 2-allyloxyethanol (12.0 mL, 112.8 mmol) in anhydrous THF (50 mL) slowly at 0° C. under N₂ atmosphere. The mixture was stirred at 15° C. for 1 hr. Then a solution of compound 23F (23.5 g, 102.6 mmol) in anhydrous THF (50 mL) was added. The mixture was stirred at 15° C. for 10 hrs. The mixture was quenched by addition of H₂O (~175 mL) slowly at 0° C. Then the mixture was extracted with ethyl acetate (150 mL). The organic layer was separated and the aqueous layer was extracted with ethyl acetate (75 mL×3). The combined organic layer was washed with saturated NaHCO₃ (75 mL), brine (75 mL), dried over anhydrous MgSO₄, filtered and concentrated. The residue was purified by flash column chromatography (eluent: Petroleum Ether/Ethyl Acetate=12/1 to 10/1) to afford compound 23G (13.1 g, yield 51.0%) as colorless oil. ¹H NMR (400 MHz, DMSO-d₆) δ 7.83 (d, J=7.2 Hz, 1H), 7.64-7.58 (m, 2H), 7.43-7.41 (m, 1H), 5.92-5.86 (m, 1H), 5.28-5.24 (m, 1H), 5.16-5.13 (m, 1H), 4.81 (s, 2H), 3.98-3.96 (m, 2H), 3.82 (s, 3H), 3.62-3.57 (m, 4H).

Step 6: Synthesis of Compound 23H

NaOH aqueous solution (2 M, 269.7 mL) was added to a solution of compound 23G (45 g, 179.8 mmol) in MeOH (250 mL) at 0° C. The mixture was stirred at 20° C. for 12 hrs. The volatile solvent was evaporated in vacuum. The residue was diluted with H₂O (100 mL), acidified to pH~2 with 2 N HCl, and then extracted with ethyl acetate (150 mL×3). The combined organic layer was washed with brine (100 mL), dried over MgSO₄, filtered and concentrated to afford compound 23H (40 g, yield 94.2%) as pale yellow oil, which was used for next step directly. ¹H NMR (DMSO-d₆, 400 MHz) δ 12.93 (br.s., 1H), 7.86 (dd, J=1.2 Hz, 8.0 Hz, 1H), 7.65-7.63 (m, 1H), 7.59-7.55 (m, 1H), 7.40-7.38 (m, 1H), 5.94-5.85 (m, 1H), 5.30-5.24 (m, 1H), 5.16-5.13 (m, 1H), 4.85 (s, 2H), 3.65-3.62 (m, 2H), 3.59-3.57 (m, 2H).

Step 7: Synthesis of Compound 23J

To a mixture of compound 23D (30.0 g, 154.1 mmol, HCl salt) and DIEA (64.7 mL, 370.4 mmol) in DMF (500 mL) was added compound 23H (35.00 g, 148.1 mmol). Then HOBt (22 g, 163.0 mmol) was added, followed by EDCI (31.24 g, 163.0 mmol). The mixture was stirred at 20° C. for 10 hrs. The mixture was diluted with H₂O (1500 mL), extracted with ethyl acetate (500 mL×3). The combined organic layer was washed with saturated NaHCO₃ (500 mL), 1N HCl (500 mL), brine (500 mL), dried over anhydrous MgSO₄, filtered and concentrated. The residue was purified by flash column chromatography (Petroleum Ether/Ethyl Acetate=1/1 to DCM/Ethyl Acetate=8/1) to afford compound 23J (42.8 g, yield 76.7%) as pale yellow oil. ¹H NMR (DMSO-d₆, 400 MHz) δ 8.53 (d, J=8.0 Hz, 1H), 7.51-7.44 (m, 3H), 7.38-7.36 (m, 1H), 5.90-5.84 (m, 2H), 5.27-5.23 (m, 1H), 5.17-5.15 (m, 1H), 5.12 (br.s., 1H), 5.09-5.07 (m, 1H), 4.95 (br.s., 1H), 4.62 (s, 2H), 3.97-3.95 (m, 2H), 3.81 (s, 3H), 3.62-3.53 (m, 4H), 3.15 (s, 3H), 2.44-2.35 (m, 2H). MS (ESI) m/z (M+Na⁺) 399.2.

Step 8: Synthesis of Compound 23K

Grubbs' 2nd catalyst (451 mg, 531.50 μmol) was added to a solution of compound 23J (4.00 g, 10.63 mmol) in 1,2-dichloroethane (1.60 L). The mixture was heated to 80° C. and stirred for 10 hrs. The mixture was concentrated. The residue was purified by preparatory-HPLC (HCl) to afford Z-isomer (1.16 g, yield 52.5%), E-isomer (2.0 g, yield 30.4%) and compound 23K (mixture of Z/E isomers, 0.32 g, yield 8.4%).

Step 9: Synthesis of Compound 23L

Pd/C (150 mg, Wt %~5%) was added to a solution of compound 23K (0.5 g, 1.44 mmol) in MeOH (50 mL). The mixture was stirred at 20° C. for 2 h under H₂ atmosphere (balloon). The mixture was filtered through a pad of Celite. The filtrate was concentrated in vacuum. The residue was purified by preparatory-HPLC (HCl) to afford compound 23L (350 mg, yield 69.4%) was obtained as colorless sticky oil. ¹H NMR (400 MHz, DMSO-d₆) δ 8.35 (d, J=7.6 Hz, 1H), 7.48-7.36 (m, 4H), 4.90 (br s, 1H), 4.81 (d, J=10.4 Hz, 1H), 4.53 (d, J=10.0 Hz, 1H), 3.80 (s, 3H), 3.65-3.53 (m, 3H), 3.51-3.44 (m, 1H), 3.44-3.39 (m, 2H), 3.14 (s, 3H), 1.72-1.64 (m, 2H), 1.63-1.35 (m, 4H). MS (ESI) m/z (M+Na⁺) 373.0.

Step 10: Synthesis of Compound 43

A solution of compound 23L (150 mg, 0.43 mmol) in THF (10 mL) was cooled to −50° C. Then LiAlH₄ (1M solution in THF, 0.45 mL, 0.45 mmol) was added slowly. The mixture was stirred at −30° C.~−10° C. for 2 hrs. The mixture was quenched by the addition of 1N HCl (~2 mL). Then the mixture was diluted with H₂O (10 mL), extracted with ethyl acetate (15 mL×3). The combined organic layer was washed with H₂O (10 mL), brine (10 mL), dried over MgSO₄ and concentrated to afford compound 43 (100 mg, yield 79.9%) as white solid. ¹H NMR (400 MHz, DMSO-d₆) δ 9.66 (s, 1H), 8.87 (d, J=6.8 Hz, 1H), 7.59-7.57 (m, 1H), 7.54-7.48 (m, 3H), 4.75-4.64 (m, 2H), 4.21-4.20 (m, 1H), 3.66-3.43 (m, 6H), 1.95-1.82 (m, 1H), 1.81-1.57 (m, 3H), 1.50-1.46 (m, 2H). MS (ESI) m/z (M+H⁺) 292.1.

Example 44

(2²E,6S,11E)-4-oxo-2¹H-9,14-dioxa-5-aza-3(2,3)-pyridina-2(3,1)-pyrazola-1(1,3),8(1,4)-dibenzenacyclotetradecaphan-11-ene-6-carbaldehyde (44)

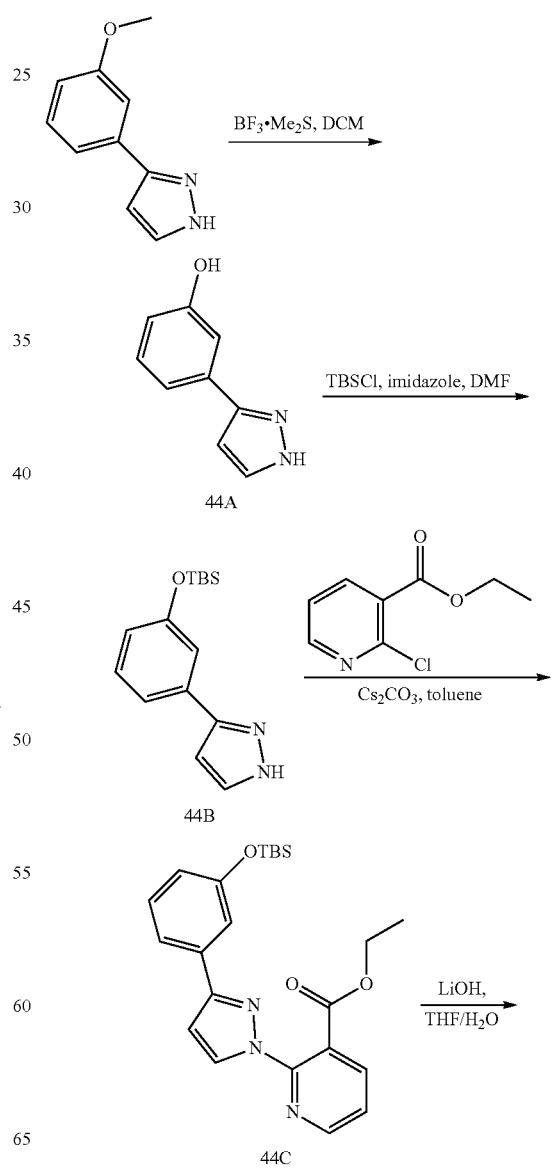

-continued

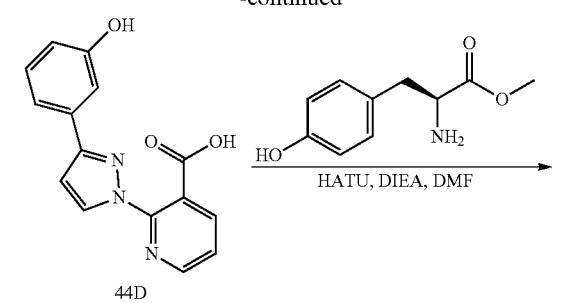

44D

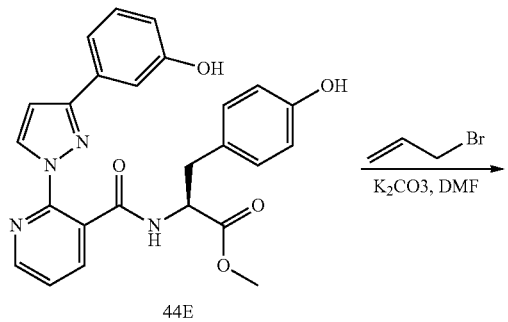

44E

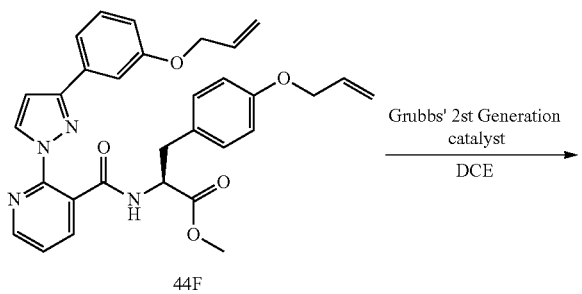

44F

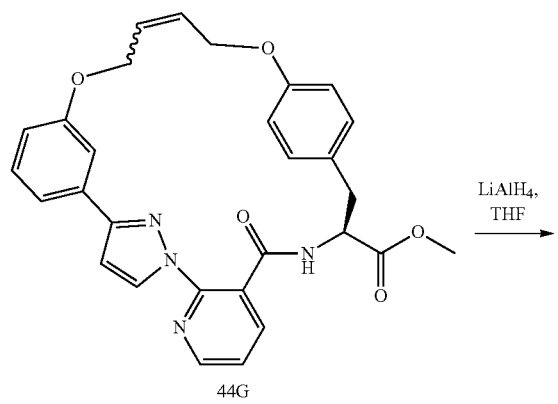

44G

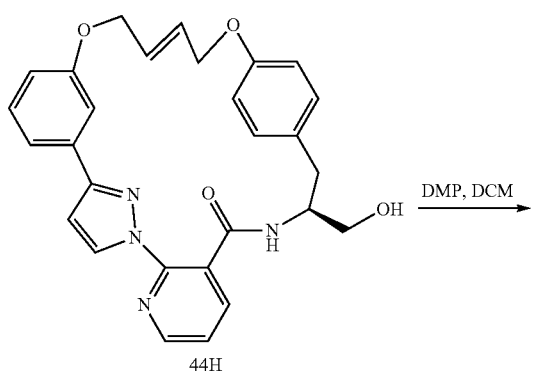

44H

-continued

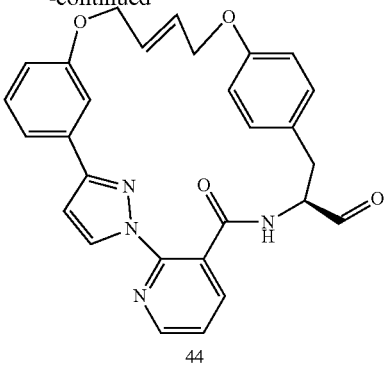

44

Step 1: Synthesis of Compound 44A

To a solution of 3-(3-methoxyphenyl)-1H-pyrazole (2 g, 11.48 mmol) in DCM (50 mL) was added BF$_3$.Me$_2$S (8.15 g, 57.40 mmol, 7.1 mL) at 0° C. The mixture was stirred at 15° C. for 48 h. The mixture was quenched with H$_2$O (10 mL), then neutralized with NaHCO$_3$ (50 mL), extracted with EtOAc (30 mL×3). The organic phase was concentrated to give a residue. The crude product compound 44A (1.5 g, yield: 81.5%) was used for the next step without further purification as white solid. $^1$H NMR (400 MHz, DMSO-d$_6$) δ 9.39 (br. s, 1H), 7.66 (d, J=2.2 Hz, 1H), 7.22-7.14 (m, 3H), 6.71-6.65 (m, 1H), 6.59 (d, J=2.3 Hz, 1H).

Step 2: Synthesis of Compound 44B

To a solution of compound 44A (1.5 g, 9.37 mmol) in DMF (5 mL) and DCM (20 mL) was added imidazole (1.28 g, 18.74 mmol) and TBSCl (1.84 g, 12.18 mmol). The mixture was stirred at 20° C. for 16 h. The reaction mixture was concentrated under reduced pressure to remove DCM. The residue was diluted with sat. NaHCO$_3$ (60 mL) and then extracted with EtOAc (20 mL×3). The combined organic layers were washed with brine (50 mL), dried over Na$_2$SO$_4$, filtered and concentrated under reduced pressure to give a residue. The residue was purified by column chromatography (SiO$_2$, Petroleum ether/Ethyl acetate=10/1 to 5:1). Compound 44B (2.2 g, yield: 85.6%) was obtained as white solid. $^1$H NMR (400 MHz, CDCl$_3$) δ 7.51 (d, J=2.2 Hz, 1H), 7.28-7.11 (m, 4H), 6.74-6.69 (m, 1H), 6.49 (d, J=2.2 Hz, 1H), 0.90 (s, 9H), 0.13 (s, 6H). MS (ESI) m/z (M+H)$^+$ 274.8.

Step 3: Synthesis of Compound 44C

To a mixture of compound 44B (2 g, 7.29 mmol), Cs$_2$CO$_3$ (7.13 g, 21.87 mmol) in toluene (50 mL) was added ethyl 2-chloronicotinate (1.38 g, 8.02 mmol). The resultant mixture was degassed and purged with nitrogen for three times, and then the mixture was heated to 110° C. and stirred for 48 h. The reaction mixture was diluted with H$_2$O (100 mL) and extracted with EtOAc (10 mL×2). The combined organic layers were dried over Na$_2$SO$_4$, filtered and concentrated under reduced pressure to give a residue. The residue was purified by column chromatography (SiO$_2$, Petroleum ether/Ethyl acetate=10/1). Compound 44C (2 g, yield: 64.7%) was obtained as a white solid. $^1$H NMR (400 MHz, CDCl$_3$) δ 8.50 (dd, J=1.8, 4.9 Hz, 1H), 8.42 (d, J=2.6 Hz, 1H), 7.94 (dd, J=1.7, 7.6 Hz, 1H), 7.43 (d, J=7.7 Hz, 1H), 7.37-7.33 (m, 1H), 7.30-7.23 (m, 2H), 6.82 (dd, J=1.5, 7.9 Hz, 1H), 6.75 (d, J=2.6 Hz, 1H), 4.33 (q, J=7.1 Hz, 2H), 1.16 (t, J=7.2 Hz, 3H), 1.01 (s, 9H), 0.24 (s, 6H). MS (ESI) m/z (M+H)$^+$ 424.0.

Step 4: Synthesis of Compound 44D

To a solution of 44C (2 g, 4.72 mmol) in THF (15 mL) and H$_2$O (5 mL) was added LiOH.H$_2$O (990 mg, 23.60 mmol). The mixture was stirred at 20° C. for 16 h. 20 mL of water was added into the reaction mixture, and the mixture was extracted with MTBE (15 mL×2). The aqueous layer was acidified by 1N HCl to pH~4 at 0° C., and filtered. The cake was dried to give a residue. Compound 44D (1.1 g, yield: 82.9%) was obtained as a white solid. $^1$H NMR (400 MHz, DMSO-d$_6$) δ 13.54-12.88 (m, 1H), 9.50 (s, 1H), 8.62-8.53 (m, 1H), 8.49 (d, J=2.6 Hz, 1H), 8.07 (dd, J=1.0, 7.4 Hz, 1H), 7.46 (dd, J=4.9, 7.5 Hz, 1H), 7.38-7.26 (m, 2H), 7.26-7.15 (m, 1H), 6.95 (d, J=2.6 Hz, 1H), 6.81-6.74 (m, 1H). MS (ESI) m/z (M+H)$^+$ 281.9.

Step 5: Synthesis of Compound 44E

To a solution of compound 44D (900 mg, 3.20 mmol) and methyl L-tyrosinate (1.04 g, 4.48 mmol, HCl) in DMF (20 mL) was added HATU (1.83 g, 4.80 mmol) and DIEA (1.24 g, 9.60 mmol, 1.68 mL). The mixture was stirred at 20° C. for 16 h. The solution was poured into H$_2$O (100 mL). The solid was filtered, collected and dissolved in EtOAc. The filtrate was extracted with EtOAc (20 mL×2), subsequently washed with 1N HCl (30 mL), sat. NaHCO$_3$ (30 mL) and brine (30 mL). The organic phases were combined and dried over Na$_2$SO$_4$, filtered and the solvent was removed in vacuo. The residue was used directly for next step without further purification. Compound 44E (1.2 g, yield: 81.8%) was obtained as a yellow oil. $^1$H NMR (400 MHz, DMSO-d$_6$) δ 9.53 (s, 1H), 9.21 (s, 1H), 8.80 (d, J=7.3 Hz, 1H), 8.53 (dd, J=1.5, 4.9 Hz, 1H), 8.41 (d, J=2.6 Hz, 1H), 7.73 (dd, J=1.5, 7.5 Hz, 1H), 7.43 (dd, J=4.9, 7.5 Hz, 1H), 7.26-7.14 (m, 3H), 6.91 (d, J=2.6 Hz, 1H), 6.87 (s, 1H), 6.86 (s, 1H), 6.78-6.72 (m, 1H), 6.62-6.54 (m, 2H), 4.61 (q, J=7.5 Hz, 1H), 3.45 (s, 3H), 2.83-2.74 (m, 2H). MS (ESI) m/z (M+H)$^+$ 459.0.

Step 6: Synthesis of Compound 44F

To a solution of compound 44E (2.5 g, 5.45 mmol) in DMF (40 mL) was added K$_2$CO$_3$ (2.26 g, 16.35 mmol) and 3-bromoprop-1-ene (1.98 g, 16.35 mmol, 1.42 mL). The mixture was stirred at 20° C. for 16 h. The reaction was diluted with 300 mL H$_2$O, filtered. The cake was dissolved in DCM (100 mL) and MeOH (10 mL), dried over Na$_2$SO$_4$, filtered, collected and concentrated to give a residue. The crude product compound 44F (2.2 g, yield: 75%) was used into the next step without further purification as a gray solid. $^1$H NMR (400 MHz, CDCl$_3$) δ 8.56-8.46 (m, 1H), 8.38 (d, J=2.4 Hz, 1H), 7.95 (dd, J=1.7, 7.6 Hz, 1H), 7.39 (br s, 2H), 7.33-7.28 (m, 1H), 6.93-6.81 (m, 3H), 6.79-6.65 (m, 5H), 6.14-5.94 (m, 2H), 5.51-5.24 (m, 4H), 5.14-4.98 (m, 1H), 4.59 (br d, J=5.1 Hz, 2H), 4.44 (br d, J=5.3 Hz, 2H), 3.53 (s, 3H), 3.07-2.99 (m, 2H). MS (ESI) m/z (M+H)$^+$ 539.0.

Step 7: Synthesis of Compound 44G

To a solution of compound 44F (2.7 g, 5.01 mmol) in DCE (600 mL) was added Grubbs catalyst 2$^{nd}$ generation (425 mg, 501.00 umol). The mixture was stirred at 90° C. for 48 h. The mixture was concentrated to give a residue. The residue was purified by column chromatography (SiO$_2$, Petroleum ether/Ethyl acetate=3/1~1/2). Compound 44G (1.2 g, yield: 47%) was obtained as a gray solid. $^1$H NMR (400 MHz, CDCl$_3$) δ 8.55 (dd, J=1.8, 4.6 Hz, 1H), 8.18-8.12 (m, 2H), 7.70-7.63 (m, 1H), 7.53-7.46 (m, 1H), 7.36 (dd, J=4.7, 7.6 Hz, 1H), 7.28-7.23 (m, 1H), 7.05 (s, 1H), 6.90-6.84 (m, 1H), 6.57-6.50 (m, 3H), 6.43 (d, J=8.6 Hz, 2H), 5.95-5.87 (m, 1H), 5.85-5.77 (m, 1H), 4.84-4.71 (m, 3H), 4.66-4.60 (m, 1H), 4.57-4.50 (m, 1H), 3.71 (s, 3H), 3.08 (dd, J=3.7, 14.8 Hz, 1H), 2.81 (dd, J=8.3, 14.7 Hz, 1H). MS (ESI) m/z (M+H)$^+$ 511.2.

Step 8: Synthesis of Compound 44H

To a solution of compound 44G (430 mg, 842.25 umol) in THF (15 mL) under N$_2$ was added LiAlH$_4$ (96 mg, 2.53 mmol) at 0° C. in portions. The mixture was stirred at 0° C. for 2 h. The mixture was quenched with water (0.1 mL), 15% NaOH (0.1 mL) and water (0.3 mL) at 0° C. The mixture was stirred at 0° C. for 15 min, then added Na$_2$SO$_4$ (1 g). The mixture was filtered and filtrate was concentrated. The residue was purified by column chromatography (SiO$_2$, Petroleum ether:Ethyl acetate=1:1 to 1:3) to afford compound 11 (150 mg, yield: 35.9%) as off-white solid. $^1$H NMR (400 MHz, CDCl$_3$) δ 8.57-8.44 (m, 1H), 8.34-8.13 (m, 2H), 7.45 (br d, J=7.5 Hz, 1H), 7.38-7.32 (m, 1H), 7.30-7.25 (m, 1H), 7.03 (s, 1H), 6.95 (br d, J=5.5 Hz, 1H), 6.86 (br d, J=8.2 Hz, 1H), 6.61 (br d, J=8.4 Hz, 2H), 6.55-6.42 (m, 3H), 6.08-5.90 (m, 1H), 5.90-5.78 (m, 1H), 4.81-4.54 (m, 4H), 4.27-4.08 (m, 1H), 3.74-3.55 (m, 2H), 3.47 (s, 1H), 2.78-2.69 (m, 1H), 2.64 (br dd, J=7.3, 14.6 Hz, 1H). MS (ESI) m/z (M+H)$^+$ 483.1.

Step 9: Synthesis of Compound 44

To a solution of compound 44H (50 mg, 103.62 umol) in DCM (5 mL) was added DMP (131 mg, 310.86 umol). The mixture was stirred at 25° C. for 2 h. The reaction mixture was quenched by addition of sat. NaHCO$_3$ (10 mL) and Na$_2$S$_2$O$_3$ (10 mL) at 25° C., and then the mixture was stirred until the solution was clear, and extracted with DCM (10 mL×2). The combined organic layers were washed with H$_2$O (30 mL) and brine (30 mL), dried over Na$_2$SO$_4$, filtered and concentrated under reduced pressure to give a residue. The residue in DCM:PE=10:1 (10 mL) was stirred and filtered the cake. Compound 44 (20 mg, yield: 40.17%) was obtained as a white solid. $^1$H NMR (400 MHz, CDCl$_3$) δ 9.63 (d, J=0.9 Hz, 1H), 8.55 (dd, J=1.8, 4.6 Hz, 1H), 8.23 (dd, J=1.8, 7.7 Hz, 1H), 8.18 (d, J=2.6 Hz, 1H), 7.47-7.36 (m, 2H), 7.31-7.26 (m, 2H), 7.00 (d, J=1.8 Hz, 1H), 6.90-6.84 (m, 1H), 6.61 (d, J=8.6 Hz, 2H), 6.52-6.46 (m, 3H), 6.00-5.92 (m, 1H), 5.88-5.78 (m, 1H), 4.80-4.70 (m, 2H), 4.68-4.62 (m, 1H), 4.59-4.52 (m, 1H), 4.49-4.42 (m, 1H), 3.01-2.94 (m, 1H), 2.90-2.82 (m, 1H). MS (ESI) m/z (M+H)+ 481.2.

Example 45

N-ethyl-2-oxo-2-((6S,E)-4-oxo-2¹H-9,14-dioxa-5-aza-3(2,3)-pyridina-2(3,1)-pyrazola-1(1,3),8(1,4)-dibenzenacyclotetradecaphane-6-yl)acetamide (45)

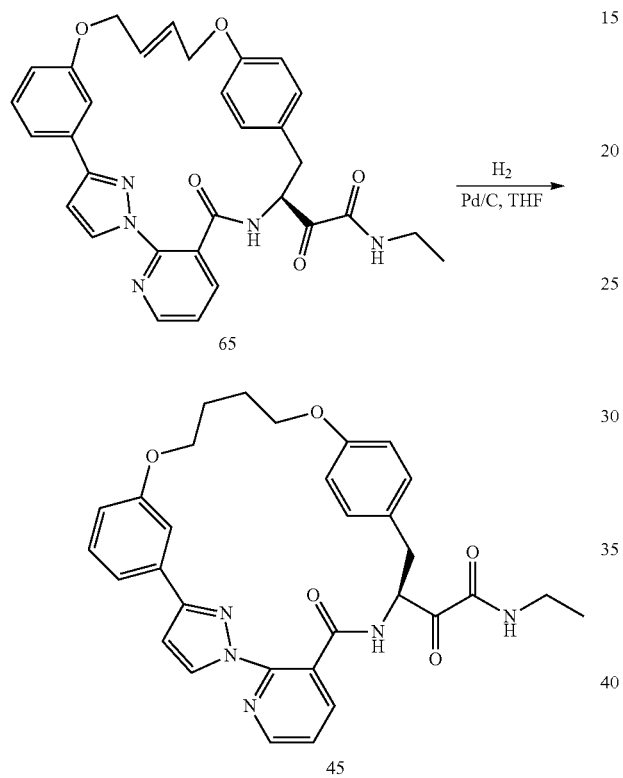

Step 1: Synthesis of Compound 45

To a solution of compound 65 (25 mg, 45.32 umol) in THF (5 mL) was added Pd/C (5 mg) under N₂. The mixture was stirred at 15° C. for 2 h under H₂ balloon. The reaction mixture was filtered and concentrated under reduced pressure to give a residue. The residue was purified by preparatory-TLC (SiO₂, DCM:EtOAc=1:1). Compound 45 (5 mg, yield: 20%) was obtained as a grey solid. ¹H NMR (400 MHz, ACETONITRILE-d₃) δ 8.57 (dd, J=1.8, 4.6 Hz, 1H), 8.28 (d, J=2.6 Hz, 1H), 8.02 (dd, J=1.8, 7.5 Hz, 1H), 7.48 (dd, J=4.9, 7.7 Hz, 2H), 7.31-7.22 (m, 3H), 7.16 (d, J=2.9 Hz, 1H), 6.94-6.86 (m, 3H), 6.82 (d, J=2.6 Hz, 1H), 6.57-6.49 (m, 2H), 5.32 (ddd, J=2.1, 6.2, 9.8 Hz, 1H), 4.33-4.22 (m, 2H), 4.09-3.96 (m, 2H), 3.37-3.27 (m, 2H), 3.05 (dd, J=2.0, 15.0 Hz, 1H), 2.55 (dd, J=9.7, 15.0 Hz, 1H), 1.98 (d, J=2.4 Hz, 1H), 1.95-1.93 (m, 1H), 1.92-1.84 (m, 2H), 1.16 (t, J=7.3 Hz, 3H). MS (ESI) m/z (M+H)+ 554.2.

Example 46

(6S,E)-4-oxo-2¹H-9,14-dioxa-5-aza-3(2,3)-pyridina-2(3,1)-pyrazola-1(1,3),8(1,4)-dibenzenacyclotetradecaphane-6-carbaldehyde (46)

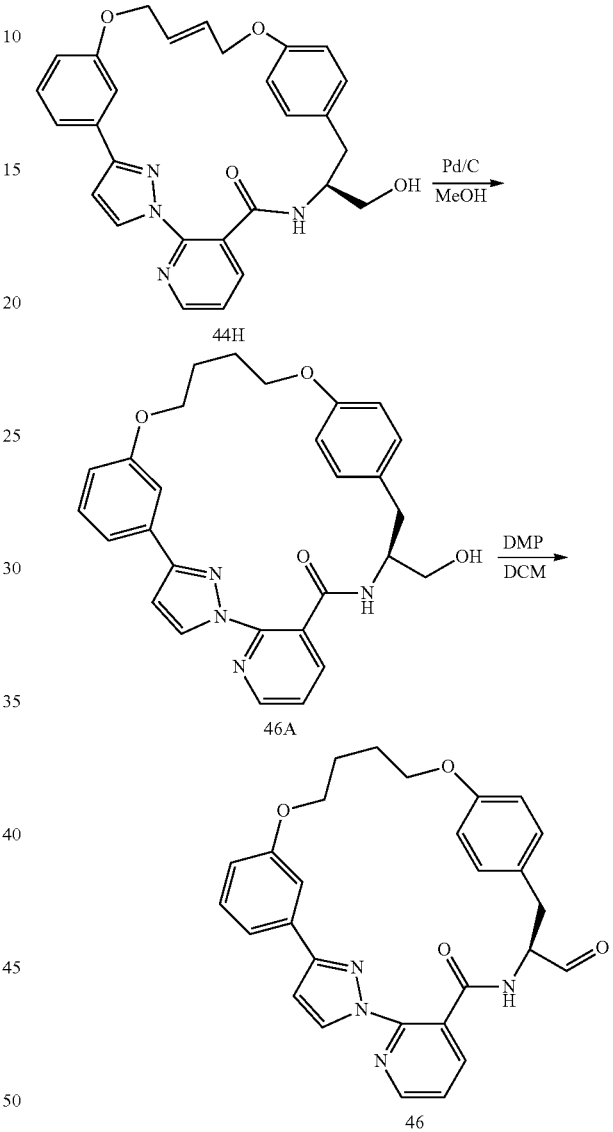

Step 1: Synthesis of Compound 46A

To a solution of compound 44H (100 mg, 207.24 umol) in MeOH (30 mL) was added Pd/C (20 mg, 10% purity) under N₂. The suspension was degassed under vacuum and purged with H₂ several times. The mixture was stirred under H₂ (15 psi) at 15° C. for 2 h. The mixture was filtered. The filtrate was concentrated. The residue was purified by preparatory-TLC (SiO₂, Dichloromethane:Methanol=10:1) to afford compound 46A (62 mg, yield: 61.7%) as off-white solid. ¹H NMR (400 MHz, CDCl₃) δ 8.57 (br d, J=4.6 Hz, 1H), 8.27 (d, J=7.5 Hz, 1H), 7.98 (d, J=1.5 Hz, 1H), 7.49-7.33 (m, 2H), 7.33-7.21 (m, 2H), 7.05 (s, 1H), 6.82 (br d, J=8.2 Hz, 3H), 6.74-6.54 (m, 3H), 4.24-4.02 (m, 5H), 3.73-3.56 (m, 1H), 3.49-3.36 (m, 2H), 3.25 (dd, J=6.9, 11.1 Hz, 1H), 2.87-2.65 (m, 2H), 1.98-1.93 (m, 2H). MS (ESI) m/z (M+H)+ 485.2.

Step 2: Synthesis of Compound 46

Compound 46 was prepared following the procedure of Example 52 using intermediate 27B. Compound 46 was obtained as white solid (10.0 mg, yield: 16.2%). ¹H NMR (400 MHz, CDCN-d₃) δ 9.51 (d, J=0.7 Hz, 1H), 8.58 (dd, J=1.9, 4.7 Hz, 1H), 8.25 (d, J=2.6 Hz, 1H), 8.13 (dd, J=1.8, 7.7 Hz, 1H), 7.51-7.37 (m, 2H), 7.24 (d, J=4.6 Hz, 2H), 7.12 (s, 1H), 6.89-6.80 (m, 4H), 6.54 (d, J=7.7 Hz, 2H), 4.42-4.37 (m, 1H), 4.23-4.18 (m, 2H), 4.03 (dt, J=3.0, 6.0 Hz, 2H), 3.04 (d, J=2.9 Hz, 1H), 2.68 (dd, J=9.6, 15.1 Hz, 1H), 1.92-1.76 (m, 4H). MS (ESI) m/z (M+H)+ 483.2.

Example 47

N-ethyl-2-oxo-2-((5S)-3-oxo-1H-8,13-dioxa-4-aza-1(1,5)-indazola-2(2,3)-pyridina-7(1,4)-benzenacyclotridecaphane-5-yl)acetamide (47)

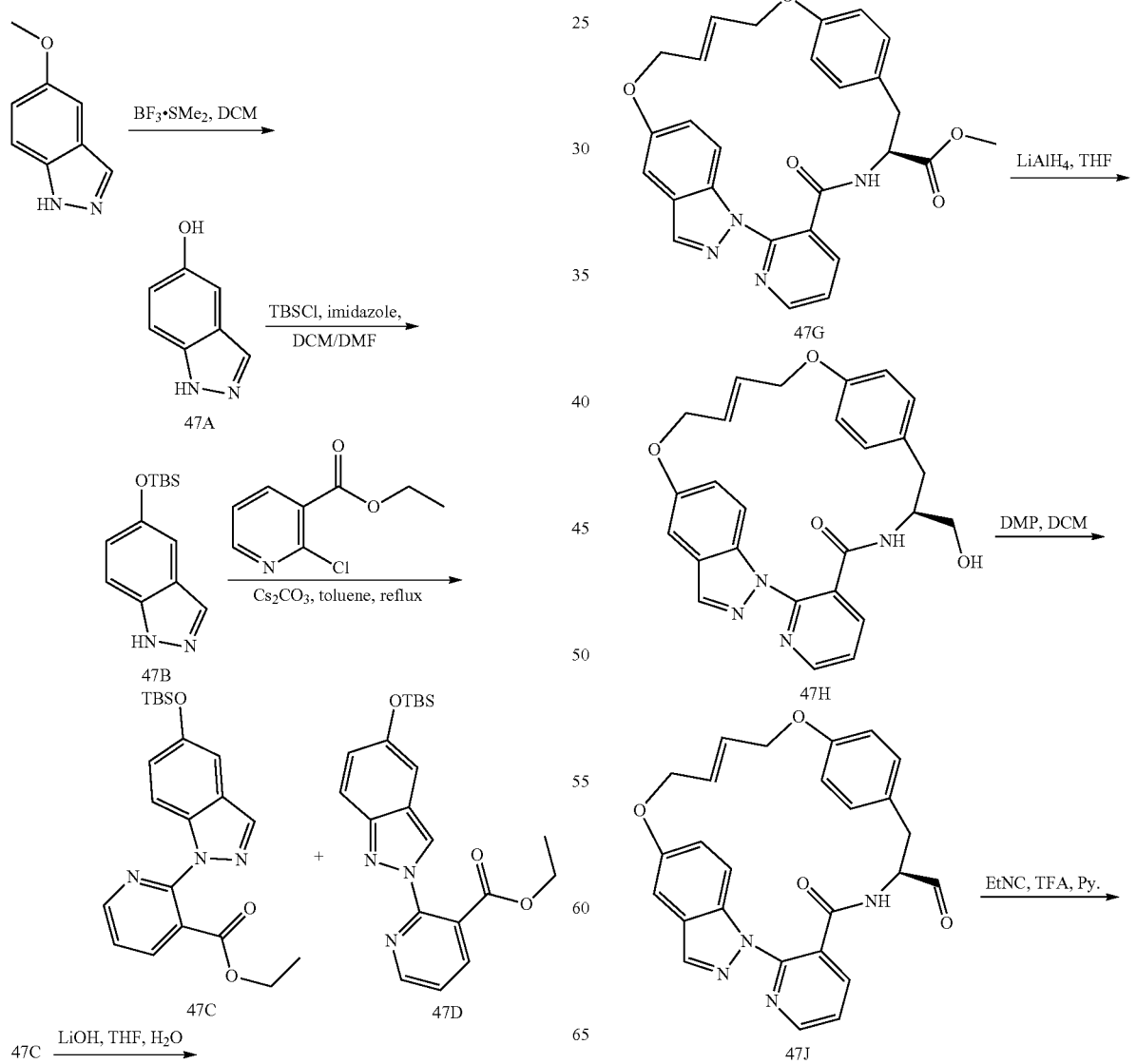

-continued

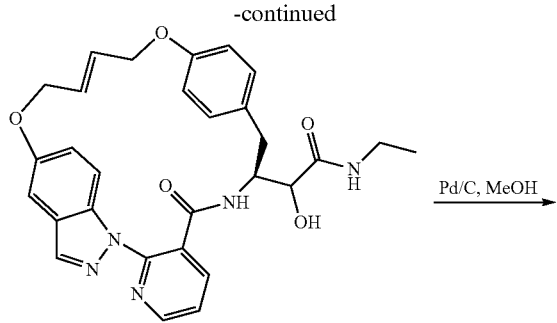

47K

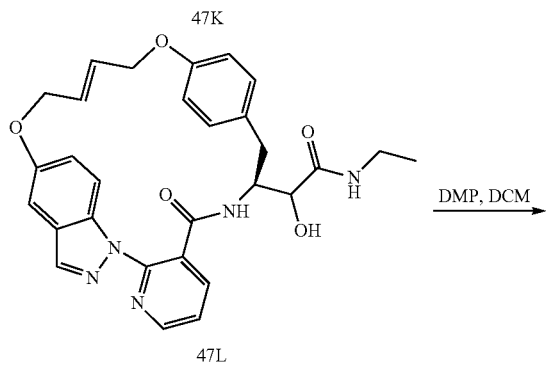

47L

47

Step 1: Synthesis of Compound 47A

Compound 47A was prepared following the procedure of Example 44 using 5-methoxy-1H-indazole. Compound 47A was obtained as off-white solid (8.8 g, yield: 92%). $^1$H NMR (400 MHz, DMSO-$d_6$) δ 12.79-12.59 (m, 1H), 9.00 (br s, 1H), 7.81 (s, 1H), 7.32 (d, J=8.8 Hz, 1H), 6.95 (d, J=1.8 Hz, 1H), 6.87 (dd, J=2.2, 8.8 Hz, 1H).

Step 2: Synthesis of Compound 47B

Compound 47B was prepared following the procedure of Example 44 using intermediate 47A. Compound 47B was obtained as white solid (15 g, yield: 88.37%). H NMR (400 MHz, CDCl$_3$) δ 7.97 (s, 1H), 7.35 (d, J=8.8 Hz, 1H), 7.13 (d, J=1.8 Hz, 1H), 6.99 (dd, J=2.2, 8.8 Hz, 1H), 1.01 (s, 9H), 0.21 (s, 6H).

Step 3: Synthesis of Compounds 47C and 47D

Compounds 47C and 47D were prepared following the procedure of Example 44 using intermediate 47B. Compounds 47C (2.3 g, yield: 16.70%) and 47D (3.1 g, yield: 22.52%) were obtained as off-white solid.

Step 4: Synthesis of Compound 47E

Compound 47E was prepared following the procedure of Example 44 using intermediate 47C. Compound 47E was obtained as red solid (2.7 g, yield: 87.64%). H NMR (400 MHz, DMSO-$d_6$) δ 13.07 (br s, 1H), 9.46 (s, 1H), 8.66-8.57 (m, 1H), 8.20-8.03 (m, 3H), 7.46-7.37 (m, 1H), 7.12-7.01 (m, 2H).

Step 5: Synthesis of Compound 47F

Compound 47F was prepared following the procedure of Example 44 using intermediate 47E. Compound 47F was obtained as light yellow solid (4.5 g, yield: 97.37%). $^1$H NMR (400 MHz, DMSO-$d_6$) δ 9.42 (s, 1H), 9.24 (s, 1H), 8.82 (d, J=8.0 Hz, 1H), 8.61-8.56 (m, 1H), 8.18 (d, J=9.0 Hz, 1H), 8.00 (s, 1H), 7.77-7.72 (m, 1H), 7.42-7.35 (m, 1H), 7.10-6.97 (m, 4H), 6.67 (d, J=8.3 Hz, 2H), 4.62-4.50 (m, 1H), 3.61 (s, 3H), 2.92-2.84 (m, 2H). MS (ESI) m/z (M+H)$^+$ 433.0.

Step 6: Synthesis of Compound 47G

Compound 47G was prepared following the procedure of Example 44 using intermediate 47F. Compound 47G was obtained as white solid (300 mg, yield: 26.27%). $^1$H NMR (400 MHz, DMSO-$d_6$) δ 8.65-8.59 (m, 1H), 8.42 (br s, 1H), 7.99 (br s, 1H), 7.94-7.87 (m, 1H), 7.68 (s, 1H), 7.51-7.44 (m, 1H), 7.15-7.04 (m, 2H), 6.61-6.52 (m, 2H), 6.47-6.40 (m, 2H), 6.14-6.02 (m, 1H), 5.84-5.73 (m, 1H), 4.94-4.84 (m, 1H), 4.82-4.74 (m, 1H), 4.68-4.59 (m, 1H), 4.55-4.44 (m, 1H), 4.29-4.17 (m, 1H), 3.66 (s, 3H), 2.83-2.73 (m, 1H), 2.64-2.54 (m, 1H). MS (ESI) m/z (M+H)$^+$ 485.0.

Step 7: Synthesis of Compound 47H

Compound 47H was prepared following the procedure of Example 44 using intermediate 47G. Compound 47H was obtained as off-white solid (100 mg, yield: 70.76%). $^1$H NMR (400 MHz, DMSO-$d_6$) δ 8.59-8.52 (m, 1H), 7.99-7.84 (m, 2H), 7.83-7.77 (m, 1H), 7.73 (br s, 1H), 7.47-7.38 (m, 1H), 7.18-7.13 (m, 1H), 7.12-7.05 (m, 1H), 6.40 (s, 2H), 6.35-6.27 (m, 2H), 6.04-5.92 (m, 1H), 5.82-5.71 (m, 1H), 4.88-4.71 (m, 2H), 4.61-4.52 (m, 1H), 4.50-4.40 (m, 1H), 3.89-3.77 (m, 1H), 3.46-3.41 (m, 2H), 3.17-3.09 (m, 1H), 2.74-2.61 (m, 1H). MS (ESI) m/z (M+H)$^+$ 457.0.

Step 8: Synthesis of Compound 47J

Compound 47J was prepared following the procedure of Example 44 using intermediate 47H. Compound 47J was obtained as white solid (80 mg, yield: 70.71%). MS (ESI) m/z (M+H)$^+$ 456.1.

Step 9: Synthesis of Compound 47K

Compound 47K was prepared following the procedure of Example 52 using intermediate 47J and isocyanoethane. Compound 47K was obtained as light yellow solid (80 mg, yield: 60.3%). MS (ESI) m/z (M+H)$^+$ 528.1.

Step 10: Synthesis of Compound 47L

Compound 47L was prepared following the procedure of Example 46 using intermediate 47K. Compound 47L was obtained as white solid (35 mg, yield: 62.26%). MS (ESI) m/z (M+H)+ 530.1.

Step 11: Synthesis of Compound 47

Compound 47 was prepared following the procedure of Example 52 using intermediate 47L. Compound 47 was obtained as off-white solid (5 mg, yield: 16.4%). $^1$H NMR (400 MHz, DMSO-$d_6$) δ 8.84-8.75 (m, 1H), 8.64-8.55 (m, 1H), 8.20 (br s, 1H), 7.97 (s, 1H), 7.89-7.79 (m, 2H), 7.52-7.44 (m, 1H), 7.28 (s, 1H), 7.04-6.96 (m, 1H), 6.77-6.65 (m, 2H), 6.37-6.27 (m, 2H), 5.15-5.03 (m, 1H), 4.46-4.35 (m, 1H), 4.32-4.21 (m, 1H), 4.00-3.89 (m, 1H), 3.82-3.71 (m, 1H), 3.28-3.15 (m, 2H), 2.93-2.83 (m, 1H), 2.38-2.31 (m, 1H), 1.79-1.74 (m, 2H), 1.27-1.20 (m, 2H), 1.11 (t, J=7.2 Hz, 3H). MS (ESI) m/z (M+H)+ 528.2.

Example 48

(S,E)-15-Oxo-6,7,8,9,12,13,14,15-octahydro-5h-pyrido[2,3-c][1]aza-cyclotridecine-13-carbaldehyde (48)

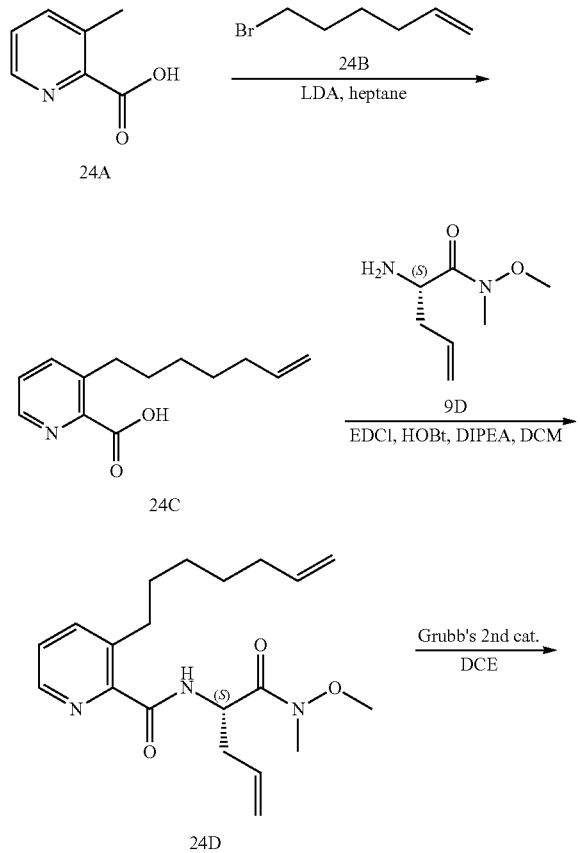

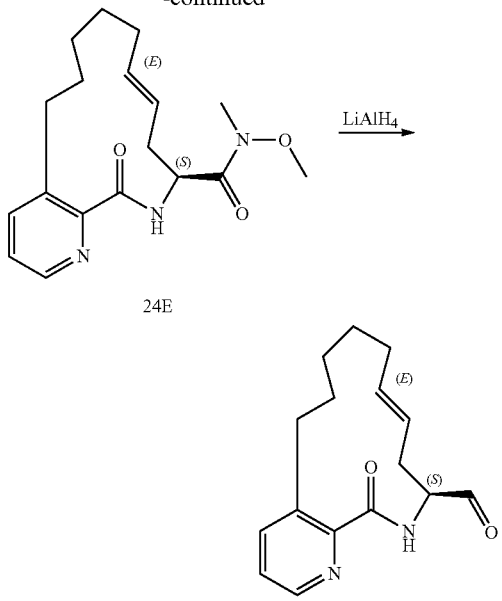

Step 1: Synthesis of Compound 24C

To a solution of LDA (2M, 8.02 mL) in THF (15 mL) was added dropwise a solution of compound 24A (1 g, 7.29 mmol) in THF (10 mL) at −78° C. over 0.5 hr. Then the reaction mixture was stirred at −30° C. for 0.5 hr. After that, the reaction mixture was cooled to −78° C. Then compound 24B (1.19 g, 7.29 mmol, 974 μL) in THF (10 mL) was added dropwise, and the reaction mixture was stirred at −30° C. for 1 hr. The reaction mixture was quenched by addition H$_2$O (30 mL). Then the mixture was concentrated under reduced pressure to remove solvent, and then extracted with MTBE (2×20 mL). The water layers were neutralized by 1N HCl to pH~2, and then extracted with EtOAc (20 mL×3). The combined organic layers were washed with brine (20 mL), dried over Na$_2$SO$_4$, filtered and concentrated under reduced pressure to give the compound 24C (500 mg, yield: 26.89%) as a yellow oil. $^1$H NMR (400 MHz, CDCl$_3$) δ 8.46-8.42 (m, 1H), 7.74-7.70 (m, 1H), 7.51-7.46 (m, 1H), 5.85-5.74 (m, 1H), 5.05-4.88 (m, 2H), 3.22-3.17 (m, 2H), 2.11-1.93 (m, 2H), 1.72-1.52 (m, 2H), 1.49-1.35 (m, 4H). MS (ESI) m/z (M+H)+ 219.9.

Step 2: Synthesis of Compound 24D

To a solution of compound 24C (500 mg, 2.28 mmol), 9D (577 mg, 2.96 mmol, HCl), EDCI (655 mg, 3.42 mmol) and HOBt (308 mg, 2.28 mmol) in DCM (30 mL) was added dropwise DIEA (1.19 mL, 6.84 mmol) at 0° C., and then the mixture was stirred at 20° C. for 21 hrs. The reaction mixture was concentrated under reduced pressure to remove DCM. The residue was diluted with EtOAc (20 mL) and HCl (1N, 10 mL). The combined organic layers were washed with HCl (1N, 20 mL) and aqueous NaHCO$_3$ (20 mL×2), dried over Na$_2$SO$_4$, filtered and concentrated under reduced pressure to give a residue. The residue was purified by column chromatography (SiO$_2$, Petroleum ether/Ethyl acetate=10:1 to 5:1) to give the compound 24D (500 mg, yield: 61.01%) as an orange oil. $^1$H NMR (400 MHz, CDCl$_3$) δ 8.66 (br d, J=8.4 Hz, 1H), 8.41 (d, J=4.6 Hz, 1H), 7.56 (d, J=7.7 Hz, 1H), 7.34-7.27 (m, 1H), 5.94-5.68 (m, 2H), 5.33-4.87 (m, 5H), 3.81 (s, 3H), 3.23 (s, 3H), 3.20-3.06 (m, 2H), 2.70-2.47 (m, 2H), 2.17-1.99 (m, 2H), 1.71-1.52 (m, 2H), 1.48-1.33 (m, 4H). MS (ESI) m/z (M+23)+ 382.1

Step 3: Synthesis of Compound 24E

A solution of compound 24D (500 mg, 1.39 mmol) in DCE (140 mL) was degassed and purged with N$_2$ for 3 times, then Grubbs catalyst 2nd generation (118 mg, 139 µmol) was added. The mixture was stirred at 95° C. for 48 hrs under N$_2$ atmosphere. The reaction mixture was concentrated under reduced pressure to give a residue. The residue was purified by column chromatography (SiO$_2$, Petroleum ether/Ethyl acetate=5/1 to 2:1) to give the compound 24E (300 mg, yield: 65.12%) as a white solid. $^1$H NMR (400 MHz, CD$_3$OD) δ 8.44-8.33 (m, 1H), 7.70-7.65 (m, 1H), 7.65-7.52 (m, 1H), 7.39 (dd, J=4.7, 7.8 Hz, 1H), 5.56-5.43 (m, 2H), 5.29 (br d, J=10.1 Hz, 1H), 3.85 (s, 3H), 3.50-3.40 (m, 1H), 3.34 (s, 3H), 2.55-2.44 (m, 2H), 2.26-2.15 (m, 1H), 2.13-2.04 (m, 1H), 1.72-1.49 (m, 3H), 1.37-1.09 (m, 4H). MS (ESI) m/z (M+H)+ 332.4.

Step 4: Synthesis of Compound 48

To a solution of compound 24E (100 mg, 301.74 µmol) in THF (5 mL) was added LiAlH$_4$ (1 M, 452 µL). The mixture was stirred at −40° C. for 2 hrs. The reaction mixture was quenched by addition THF:H$_2$O~5:1 (1.2 mL), dried over Na$_2$SO$_4$, and stirred for 30 min, then filtered to give the organic layers. The organic layers were concentrated under reduced pressure to give a residue. The residue was purified by prep-TLC (SiO$_2$, Petroleum ether/Ethyl acetate=1/1) to give compound 48 (25 mg, yield: 30.42%) as a white solid. $^1$H NMR (400 MHz, CDCl$_3$) δ 9.80 (s, 1H), 8.55-8.33 (m, 1H), 7.91 (br d, J=8.4 Hz, 1H), 7.57 (d, J=7.7 Hz, 1H), 7.38-7.29 (m, 1H), 5.63-5.49 (m, 1H), 5.47-5.38 (m, 1H), 5.03-4.90 (m, 1H), 3.91-3.75 (m, 1H), 2.87 (br d, J=13.2 Hz, 1H), 2.60-2.49 (m, 1H), 2.17-2.07 (m, 1H), 2.01 (br s, 1H), 1.96-1.87 (m, 1H), 1.80-1.69 (m, 1H), 1.57-1.42 (m, 2H), 1.34-1.28 (m, 1H), 1.11-0.99 (m, 2H). MS (ESI) m/z (M+H)+ 273.1

Example 49

(S)-15-Oxo-6,7,8,9,10,11,12,13,14,15-decahydro-5h-pyrido[2,3-c][1]aza-cyclotridecine-13-carbaldehyde (49)

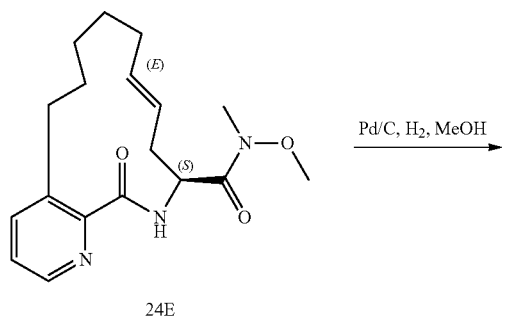

24E

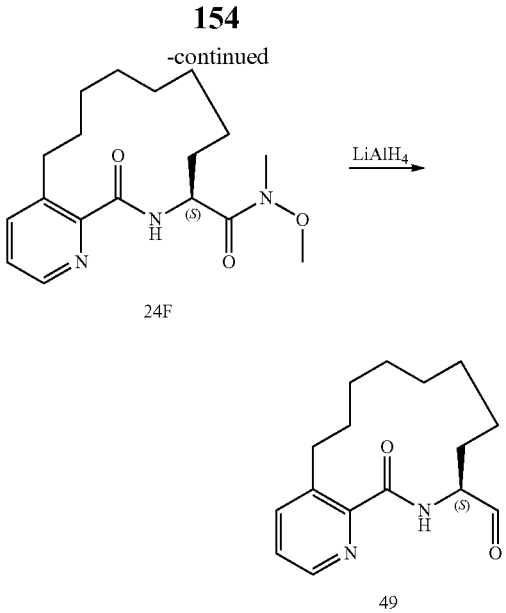

24F

49

Step 1: Synthesis of Compound 24F

To a solution of compound 24E (110 mg, 331.92 µmol) in MeOH (8 mL) was degassed and purged with N$_2$ for 3 times, and a mixture of Pd/C (30 mg, purity: 10%) in MeOH (2 mL) was added dropwise. Then the mixture was degassed and purged with H$_2$ for 3 times, and stirred at 20° C. for 0.5 hr under H$_2$. The catalyst was filtered off using Celite, and then concentrated under reduced pressure to give a residue. The residue was purified by preparatory-TLC (SiO$_2$, Petroleum ether/Ethyl acetate=1:1) to give compound 24F (101 mg, yield: 91.26%) as a white solid. $^1$H NMR (400 MHz, CDCl$_3$) δ 8.43-8.38 (m, 1H), 7.81 (br d, J=8.8 Hz, 1H), 7.62-7.55 (m, 1H), 7.33-7.25 (m, 1H), 5.36-5.24 (m, 1H), 3.85-3.78 (m, 4H), 3.23 (s, 3H), 2.64-2.50 (m, 1H), 2.13-1.93 (m, 1H), 1.93-1.81 (m, 2H), 1.73-1.61 (m, 2H), 1.54-1.46 (m, 3H), 1.39-1.31 (m, 2H), 1.25-1.12 (m, 3H), 1.10-1.01 (m, 1H).

Step 2: Synthesis of Compound 49

To a solution of compound 24F (100 mg, 299.91 µmol) in THF (8 mL) was added LAH (1M, 449 µL). The mixture was stirred at −40° C. for 1 hr. The reaction mixture was quenched by addition THF:H$_2$O=5:1 (1.2 mL), dried over Na$_2$SO$_4$, and stirred for 30 min, then filtered to give the organic layers. The organic layers were concentrated under reduced pressure to give a residue. The residue was purified by preparatory-TLC (SiO$_2$, DCM/Ethyl acetate=1/1) to give compound 49 (40 mg, yield: 48.61%) as a white solid. $^1$H NMR (400 MHz, CDCl$_3$) δ 9.71 (s, 1H), 8.42 (d, J=3.7 Hz, 1H), 7.82 (d, J=7.3 Hz, 1H), 7.60 (d, J=7.7 Hz, 1H), 7.32 (dd, J=4.7, 7.8 Hz, 1H), 4.98-4.82 (m, 1H), 3.87-3.75 (m, 1H), 2.72-2.58 (m, 1H), 2.35-2.22 (m, 1H), 1.75-1.60 (m, 3H), 1.51-1.44 (m, 3H), 1.38-1.29 (m, 3H), 1.21-1.12 (m, 3H), 1.08-0.99 (m, 1H). MS (ESI) m/z (M+H)+ 275.0

Example 50

(S)-5-Oxo-6,7,8,11,12,13,14,15-octahydro-5h-pyrido[3,2-c][1]aza-cyclotridecine-7-carbaldehyde (50)

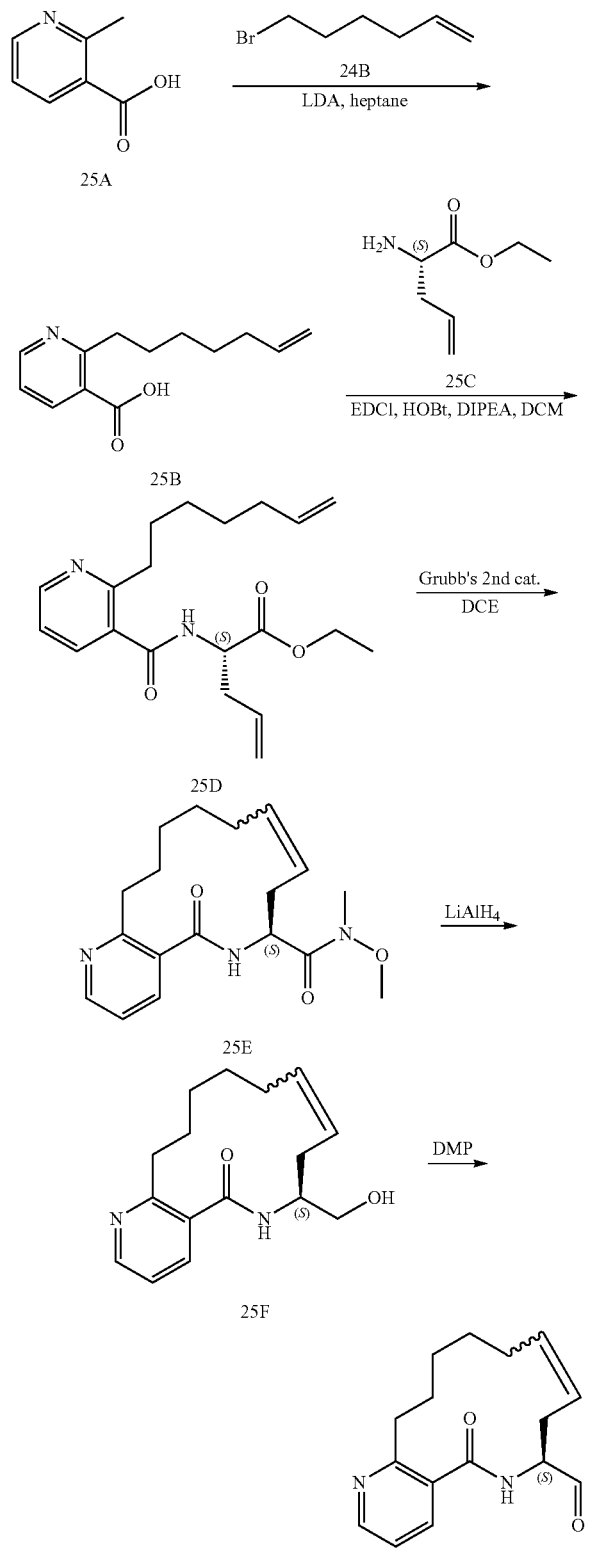

Step 1: Synthesis of Compound 25B

To a solution of compound 25A (2 g, 14.58 mmol) in THF (50 mL) was added LDA (2M, 17.50 mL) at −60° C. dropwise over 30 min. The mixture was stirred at −40° C. for 1.5 hrs. To the deep red reaction was added compound 24B (2.75 mL, 20.56 mmol) in THF (8 mL) at −40° C. The mixture was stirred at −40° C. for 2 hrs. Then water (20 mL) and conc. HCl (5 mL) was added, and the mixture was extracted with ethyl acetate (2×30 mL). The combined organic layers were dried over $Na_2SO_4$, filtered and concentrated to afford compound 25B (2.20 g, crude) as yellow oil. $^1$H NMR (400 MHz, DMSO-$d_6$) δ 8.67-8.63 (m, 1H), 8.20-8.16 (m, 1H), 7.41-7.36 (m, 1H), 5.84-5.67 (m, 1H), 5.02-4.86 (m, 2H), 3.13-2.99 (m, 2H), 2.04-1.98 (m, 2H), 1.95-1.88 (m, 1H), 1.70-1.58 (m, 2H), 1.42-1.23 (m, 4H).

Step 2: Synthesis of Compound 25D

To a solution of compound 25B (250 mg, 1.14 mmol) in DCM (10 mL) was added 25C (204.8 mg, 1.14 mmol, HCl), DIEA (1 mL, 5.70 mmol), HOBt (154 mg, 1.14 mmol) and EDCI (437 mg, 2.28 mmol). The mixture was stirred at 23° C. for 12 hrs. The mixture was concentrated and diluted with ethyl acetate (30 mL), then washed with 1N HCl (10 mL) and saturated $NaHCO_3$ (2×10 mL) and the brine (10 mL), the organic layer dried over $Na_2SO_4$ and filtered and concentrated in vaccuo. The residue was purified by column chromatography ($SiO_2$, Petroleum Ether:Ethyl Acetate=1:0 to 4:1) to afford compound 25D (200 mg, 272.90 μmol, 23.94% yield) as colorless oil. MS (ESI) m/z (M+H)$^+$ 345.1.

Step 3: Synthesis of Compound 25E

To a solution of compound 25D (200 mg, 580.64 μmol) in DCE (100 mL) was added Grubb's catalyst (59.15 mg, 69.68 μmol). The mixture was stirred at 90° C. for 38 hrs. The mixture was concentrated. The residue was purified by column chromatography ($SiO_2$, Petroleum ether/Ethyl acetate=5/1 to 2/1) to afford compound 25E (83 mg, yield 40.62%) as dark yellow solid. MS (ESI) m/z (M+H)$^+$ 317.3. $^1$H NMR (400 MHz, DMSO-$d_6$) δ 8.72-8.60 (m, 1H), 8.52-8.47 (m, 1H), 7.64-7.53 (m, 7.7 Hz, 1H), 7.33-7.26 (m, 1H), 5.53-5.36 (m, 2H), 4.67-4.60 (m, 1H), 4.15 (m, 2H), 3.12-2.97 (m, 1H), 2.60-2.53 (m, 2H), 2.31-2.16 (m, 1H), 2.12-1.89 (m, 2H), 1.77-1.62 (m, 1H), 1.58-1.42 (m, 2H), 1.41-1.31 (m, 1H), 1.31-1.20 (m, 6H), 1.19-1.08 (m, 1H).

Step 4: Synthesis of Compound 25F

To a solution of compound 25E (80 mg, 252.84 μmol) in THF (10 mL) was added LAH (1M, 505.68 μL) at 0° C. dropwise. The mixture was stirred at 0° C. for 2 hrs. The mixture was quenched with water (0.02 mL) and 15% NaOH (0.06 mL) at 0° C. The mixture was stirred at 15° C. for 10 min, then added $Na_2SO_4$ (0.5 g). The mixture was filtered and filtrate was concentrated. The residue was purified by column chromatography ($SiO_2$, Petroleum ether/Ethyl acetate=1/1 to 1/2) to afford compound 25F (40 mg, yield 53.57%) as white solid. MS (ESI) m/z (M+1)$^+$ 274.9. $^1$H NMR (400 MHz, DMSO-$d_6$) δ 8.47-8.44 (m, 1H), 8.07-8.01 (m, 1H), 7.66-7.63 (m, 1H), 7.26-7.22 (m, 1H), 5.43-5.34 (m, 2H), 4.83-4.79 (m, 1H), 4.07-3.98 (m, 1H), 3.46-3.37 (m, 1H), 3.32-3.25 (m, 2H), 3.19-3.11 (m, 1H), 2.38-2.31 (m, 1H), 2.10-2.01 (m, 1H), 2.01-1.86 (m, 2H), 1.81-1.71 (m, 1H), 1.54-1.42 (m, 2H), 1.38-1.23 (m, 2H), 1.21-1.09 (m, 1H).

Step 5: Synthesis of Compound 50

To a solution of compound 25F (24 mg, 87.48 μmol) in DCM (10 mL) and DMSO (1 mL) was added DMP (74.21 mg, 174.96 μmol) at 0° C. in portions. The mixture was stirred at 30° C. for 18 hrs. The mixture was quenched with saturated aqueous NaHCO₃ (6 mL) and sat. Na₂S₂O₃ (6 mL). The mixture was stirred for 20 min and extracted with DCM (3×20 mL). The combined organic layers were dried over Na₂SO₄ and concentrated. The mixture was filtered and filtrate was concentrated. The solid was stirred in (i-Pr)₂O (2 mL) and filtered to afford compound 50 (2.7 mg, yield 10.32%) as white solid. MS (ESI) m/z (M+H)$^+$ 291.1. $^1$H NMR (400 MHz, CDCl₃) δ 9.64 (s, 1H), 8.53-8.48 (m, 1H), 7.72-7.68 (m, 1H), 7.16-7.07 (m, 1H), 6.14-6.08 (m, 1H), 5.57-5.45 (m, 1H), 5.45-5.33 (m, 1H), 4.88-4.81 (m, 1H), 3.20-3.09 (m, 1H), 2.91-2.81 (m, 1H), 2.77-2.66 (m, 1H), 2.16-2.02 (m, 4H), 1.82-1.66 (m, 1H), 1.42-1.30 (m, 4H).

Example 51

(S,Z)—N-cyclopropyl-2-oxo-2-(12-oxo-1,3,4,6,9,10,11,12-octahydrobenzo[f][1,4]dioxa[9]azacyclotetradecin-10-yl)acetamide (51)

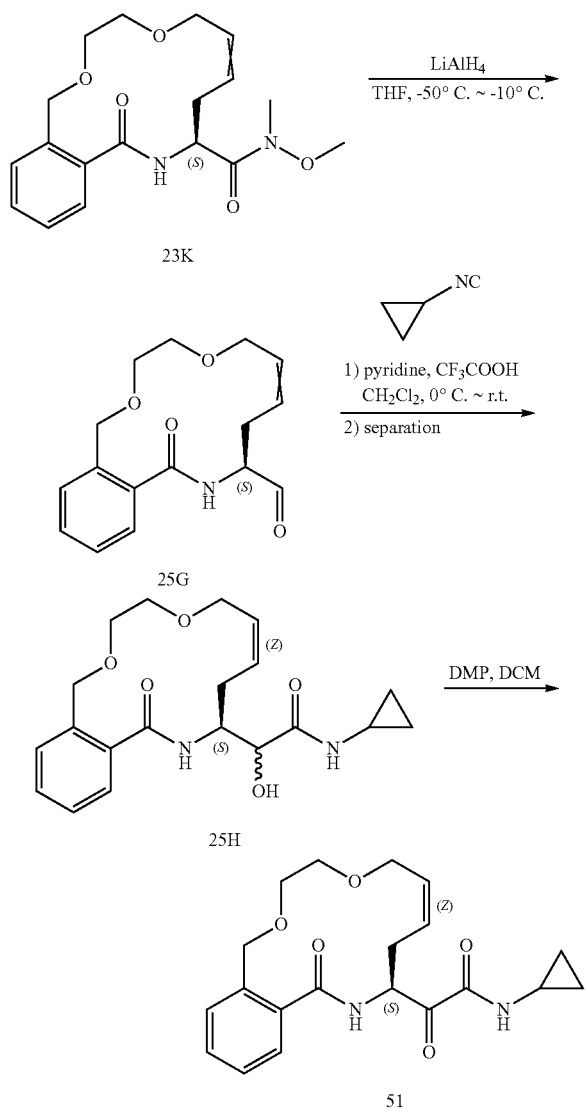

Step 1: Synthesis of Compound 25G

A solution of LiAlH₄ in THF (1M, 3.6 mL, 3.6 mmol) was added to a solution of compound 23K (1.2 g, 3.44 mmol) in THF (5.00 mL) at −50° C. The mixture was stirred for 1 hr at −10° C. The mixture was quenched by the addition of 1N HCl (~15 mL) at −10° C. Then the mixture was diluted with H₂O (10 mL), extracted with ethyl acetate (15 mL×3). The combined organic layer was washed with H₂O (15 mL), brine (15 mL), dried over anhydrous MgSO₄, filtered and concentrated to afford compound 25G (650.00 mg, crude) as pale green solid, which was used for next step directly.

Step 2: Synthesis of Compound 25H

To a solution of compound 25G (400 mg, 1.38 mmol) in DCM (10 mL) at 0° C. was added isocyanocyclopropane (111 mg, 1.66 mmol) and pyridine (0.45 mL, 5.52 mmol), followed by dropwise addition of CF₃COOH (0.2 mL, 2.76 mmol). The reaction mixture was stirred at 0° C. for 10 minutes and then allowed to warm to room temperature (15° C.). The mixture was stirred at 15° C. for 16 h. The mixture was diluted with DCM (30 mL), washed with saturated NaHCO₃ (10 mL×2) and brine (10 mL). The organic layer was dried over anhydrous MgSO₄, filtered and concentrated. The residue was purified by preparatory-HPLC (HCl) to afford pure compound 25H (60 mg, yield 11.6%) as white solid. The configuration of double bond was confirmed in next step. $^1$H NMR (400 MHz, DMSO-d₆) δ 8.00 (d, J=8.0 Hz, 1H), 7.91 (d, J=4.0 Hz, 1H), 7.56-7.54 (m, 1H), 7.44-7.38 (m, 3H), 5.60-5.55 (m, 3H), 4.78 (d, J=11.2 Hz, 1H), 4.60 (d, J=11.2 Hz, 1H), 4.19-4.15 (m, 1H), 4.12-4.10 (m, 1H), 4.01-3.98 (m, 1H), 3.86-3.82 (m, 1H), 3.54-3.42 (m, 4H), 2.65-2.61 (m, 1H), 2.29-2.26 (m, 1H), 0.61-0.57 (m, 2H), 0.48-0.46 (m, 2H). MS (ESI) m/z (M+Na)$^+$ 375.1.

Step 3: Synthesis of Compound 51

Dess-Martin periodinane (204 mg, 0.48 mmol) was added to a solution of compound 25H (60 mg, 0.16 mmol) in DCM (10 mL). The mixture was stirred at 20° C. for 12 hrs. Additional Dess-Martin periodinane (150 mg) was added and the mixture was stirred for additional 20 hrs at 20° C. The mixture was diluted with DCM (20 mL), and then quenched by the addition of 10% Na₂S₂O₃/saturated NaHCO₃ (v/v=1/1, 20 mL). The organic layer was separated, and the aqueous layer was extracted with DCM (20 mL×2). The combined organic layer was washed with H₂O (20 mL), brine (10 mL), dried over MgSO₄, filtered and concentrated to afford compound 51 (38 mg, yield 63.68%) was obtained as white solid. $^1$H NMR (400 MHz, DMSO-d₆) δ 8.81 (d, J=5.2 Hz, 1H), 8.52 (d, J=6.0 Hz, 1H), 8.01-7.40 (m, 4H), 5.75-5.69 (m, 1H), 5.64-5.57 (m, 1H), 5.09-5.04 (m, 1H) 4.87 (d, J=10.8 Hz, 1H), 4.46 (d, J=10.8 Hz, 1H), 4.10-4.06 (m, 1H), 3.86-3.82 (m, 1H), 3.57-3.45 (m, 4H), 2.81-2.76 (m, 1H), 2.69-2.63 (m, 1H), 2.56-2.55 (m, 1H), 0.70-0.65 (m, 2H), 0.60-0.56 (m, 2H). MS (ESI) m/z (M+Na)$^+$ 373.1.

Example 52

(S)—N-isopropyl-2-oxo-2-(12-oxo-1,3,4,6,7,8,9,10,11,12-decahydrobenzo[f][1,4]dioxa[9]azacyclotetradecin-10-yl)acetamide (52)

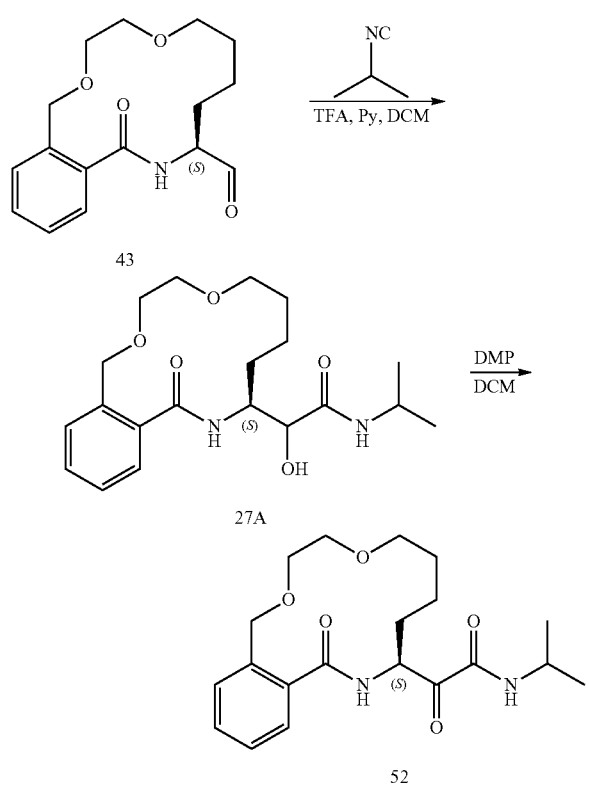

Step 1: Synthesis of Compound 27A

To a solution of compound 43 (400 mg, 1.37 mmol) and 2-isocyanopropane (113.6 mg, 1.64 mmol, 156 µL) in DCM (10 mL) was added pyridine (433 mg, 5.48 mmol, 442.31 µL) at 0° C. Then TFA (312 mg, 2.74 mmol, 203 µL) was added dropwise. After addition, the mixture was warmed up to 25° C. and stirred for 12 hrs. The mixture was treated with HCl (30 mL), extracted with ethyl acetate (30 mL). The organic layer was washed with saturated aqueous NaHCO$_3$ (30 mL), dried over Na$_2$SO$_4$ and concentrated. The residue was purified by preparatory-HPLC (basic) to afford compound 27A (130.0 mg, yield 25.1%) as a white solid. $^1$H-NMR (400 MHz, DMSO-d$_6$) δ 7.97-7.57 (m, 2H), 7.53-7.31 (m, 4H), 5.71-5.46 (m, 1H), 4.97-4.85 (m, 1H), 4.45-4.34 (m, 1H), 4.27-4.14 (m, 1H), 4.03-3.83 (m, 2H), 3.62-3.36 (m, 6H), 1.67-1.20 (m, 6H), 1.12-1.00 (m, 6H).

Step 2: Synthesis of Compound 52

To a solution of compound 27A (60.0 mg, 159 µmol) in DCM (20.0 mL) was added DMP (336 mg, 793 µmol). The mixture was stirred at 25° C. for 48 hrs. The mixture quenched with 10% Na$_2$S$_2$O$_3$/saturated NaHCO$_3$ (v/v=1/1, 50 mL), extracted with DCM (20 mL) and washed with brine (20 mL×3). The combined organic layers were dried over Na$_2$SO$_4$ and concentrated to yield compound 52. (50 mg, yield 83.8%) was obtained as a white solid. $^1$H-NMR (400 MHz, DMSO-d$_6$) δ 8.61 (d, J=7.2 Hz, 1H), 8.52 (d, J=8.0 Hz, 1H), 7.51-7.33 (m, 4H), 5.14-5.03 (m, 1H), 4.73 (d, J=10.4 Hz, 1H), 4.54 (d, J=10.0 Hz, 1H), 3.99-3.84 (m, 1H), 3.67-3.39 (m, 6H), 1.88-1.76 (m, 1H), 1.73-1.37 (m, 5H), 1.17-1.02 (m, 6H). MS (ESI) m/z (M+H)$^+$ 377.2.

Example 53

(S)—N-butyl-2-oxo-2-(12-oxo-1,3,4,6,7,8,9,10,11,12-decahydrobenzo[f][1,4]dioxa[9]azacyclotetradecin-10-yl)acetamide (53)

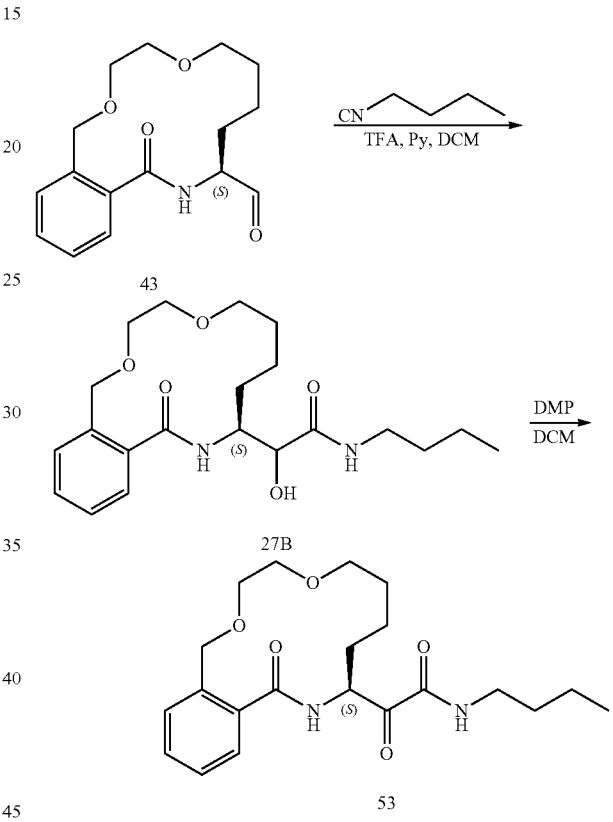

Step 1: Synthesis of Compound 27B

Compound 27B was prepared following the procedure of Example 52 using compound 43 and 1-isocyanobutane. Compound 27B was obtained as white solid (120 mg, yield: 22.2%). $^1$H-NMR (400 MHz, DMSO-d$_6$) δ 7.96-7.82 (m, 1H), 7.78-7.68 (m, 1H), 7.51-7.33 (m, 4H), 5.74-5.60 (m, 1H), 4.96-4.85 (m, 1H), 4.46-4.37 (m, 1H), 4.26-4.13 (m, 1H), 4.07-3.93 (m, 1H), 3.60-3.37 (m, 6H), 3.20-2.99 (m, 2H), 1.67-1.19 (m, 10H), 0.94-0.80 (m, 3H).

Step 2: Synthesis of Compound 53

Compound 53 was prepared following the procedure of Example 52 using intermediate 27B. Compound 53 was obtained as white solid (45.0 mg, yield: 75.4%). $^1$H-NMR (400 MHz, DMSO-d$_6$) δ 8.70-8.59 (m, 2H), 7.50-7.36 (m, 4H), 5.10-5.01 (m, 1H), 4.72 (d, J=10.0 Hz, 1H), 4.54 (d, J=10.4 Hz, 1H), 3.67-3.38 (m, 6H), 3.22-3.05 (m, 2H), 1.87-1.37 (m, 7H), 1.34-1.16 (m, 3H), 0.90-0.79 (m, 3H). MS (ESI) m/z (M+H)+ 391.2.

Example 54

(S)—N-(2,6-dimethylphenyl)-2-oxo-2-(12-oxo-1,3,4,6,7,8,9,10,11,12-decahydrobenzo[f][1,4]dioxa[9]azacyclotetradecin-10-yl)acetamide (54)

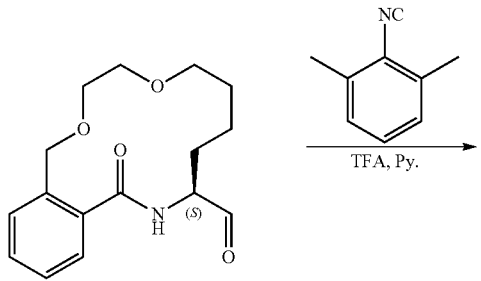

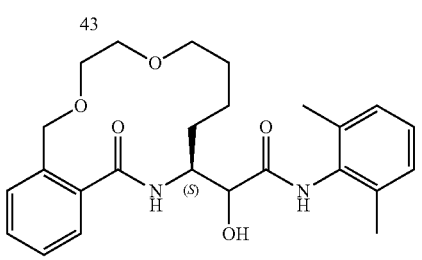

Step 1: Synthesis of Compound 27C

Compound 27C was prepared following the procedure of Example 52 using compound 43 and 2-isocyano-1,3-dimethylbenzene. Compound 27C was obtained as white solid (200 mg, yield: 33.1%). MS (ESI) m/z (M+H)+ 441.2.

Step 2: Synthesis of Compound 54

Compound 54 was prepared following the procedure of Example 52 using intermediate 27C. Compound 54 was obtained as white solid (80.0 mg, yield: 80.4%). 1H NMR (400 MHz, DMSO-d6) δ 10.09 (s, 1H), 8.83 (d, J=6.8 Hz, 1H), 7.50-7.39 (m, 4H), 7.14-7.06 (m, 3H), 5.04-4.98 (m, 1H), 4.72-4.66 (m, 1H), 4.62-4.57 (m, 1H), 3.68-3.38 (m, 6H), 2.10 (s, 6H), 1.93-1.75 (m, 2H), 1.67-1.43 (m, 4H). MS (ESI) m/z (M+H)+ 439.3.

Example 55

Ethyl (S)-3-(2-oxo-2-(12-oxo-1,3,4,6,7,8,9,10,11,12-decahydrobenzo[f][1,4]dioxa[9]azacyclotetradecin-10-yl)acetamido)propanoate (55)

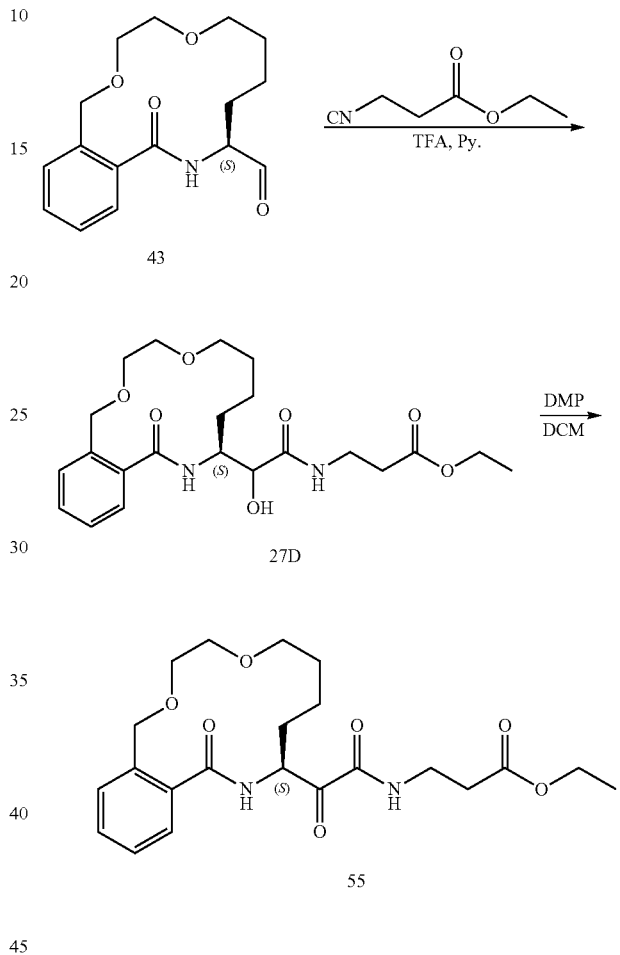

Step 1: Synthesis of Compound 27D

Compound 27D was prepared following the procedure of Example 52 using compound 43 and ethyl 3-isocyanopropanoate. Compound 27D was obtained as white solid (200 mg, yield: 33.4%). MS (ESI) m/z (M+H)+ 437.2.

Step 2: Synthesis of Compound 55

Compound 55 was prepared following the procedure of Example 52 using intermediate 27D. Compound 55 was obtained as white solid (130.0 mg, yield: 72.6%). 1H-NMR (400 MHz, CDCl3) δ 8.51-8.38 (m, 1H), 7.74-7.64 (m, 1H), 7.42-7.21 (m, 4H), 5.07-4.98 (m, 1H), 4.76-4.66 (m, 1H), 4.62-4.53 (m, 1H), 4.12-4.01 (m, 2H), 3.77-3.65 (m, 2H), 3.63-3.32 (m, 6H), 2.53-2.44 (m, 2H), 1.97-1.76 (m, 2H), 1.55-1.49 (m, 4H), 1.24-1.10 (m, 3H). MS (ESI) m/z (M+H)+ 435.2.

Example 56

Ethyl (S)-(2-oxo-2-(12-oxo-1,3,4,6,7,8,9,10,11,12-decahydrobenzo[f][1,4]dioxa[9]azacyclotetradecin-10-yl)acetyl)glycinate (56)

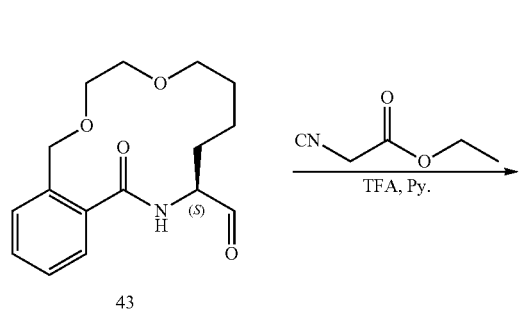

Step 1: Synthesis of Compound 27E

Compound 27E was prepared following the procedure of Example 52 using compound 43 and ethyl 2-isocyanoacetate. Compound 27E was obtained as white solid (200 mg, yield: 34.6%). MS (ESI) m/z (M+Na)+ 445.3.

Step 2: Synthesis of Compound 56

Compound 56 was prepared following the procedure of Example 52 using intermediate 27E. Compound 56 was obtained as white solid (160.0 mg, yield: 73.1%). $^1$H-NMR (400 MHz, CDCl$_3$) δ 8.59-8.50 (m, 1H), 7.75-7.67 (m, 1H), 7.40-7.21 (m, 4H), 5.03-4.95 (m, 1H), 4.72-4.64 (m, 1H), 4.62-4.54 (m, 1H), 4.19-4.02 (m, 3H), 3.94-3.84 (m, 1H), 3.77-3.65 (m, 2H), 3.64-3.49 (m, 2H), 3.49-3.33 (m, 2H), 1.96-1.80 (m, 2H), 1.57-1.45 (m, 4H), 1.25-1.14 (m, 3H). MS (ESI) m/z (M+H)+ 435.2.

Example 57

(S)-2-Oxo-2-(12-oxo-1,3,4,6,7,8,9,10,11,12-decahydrobenzo[f][1,4]dioxa[9]azacyclotetradecin-10-yl)acetamide (57)

Step 1: Synthesis of Compound 28A

To a solution of compound 43 (300 mg, 1.03 mmol) and 2-hydroxy-2-methyl-propanenitrile (100 mg, 1.18 mmol) in DCM (10 mL) was added TEA (0.18 mL, 1.24 mmol). The mixture was stirred at 25° C. for 12 hrs. The reaction was diluted with DCM (20 mL), washed with 1N HCl (20 mL). The organics were collected, washed with brine (20 mL). The organics were collected, dried with $Na_2SO_4$, filtered and concentrated to afford compound 28A (320 mg, yield: 97.58%) as colorless oil. $^1$H-NMR (400 MHz, DMSO-$d_6$) δ 8.36 (d, J=8.4 Hz, 1H), 7.45-7.36 (m, 1H), 6.75-6.66 (m, 1H), 4.92-4.86 (m, 1H), 4.43-4.36 (m, 2H), 4.10-4.08 (m, 1H), 3.56-3.45 (m, 6H), 1.76-1.36 (m, 6H). MS (ESI) m/z $(M+H)^+$ 319.1.

Step 2: Synthesis of Compound 28C

To a solution of compound 28A (320 mg, 1.01 mmol) in MeOH (6 mL) was added HCl/MeOH (4M, 6.00 mL). The mixture was stirred at 25° C. for 12 hrs. The solvent was removed in vacuo. Then the residue was dissolved in THF (4 mL) and $H_2O$ (4 mL). The solution was stirred at 25° C. for 1 hr. The reaction was diluted with $H_2O$ (10 mL), extracted with EtOAc (20 mL×2). The organics were collected and concentrated. The residue was purified by preparatory-HPLC (TFA) to afford compound 28C (40 mg) as white solid. $^1$H-NMR (400 MHz, DMSO-$d_6$) δ 7.93 (d, J=8.8 Hz, 0.6H), 7.49 (d, J=6.8 Hz, 0.3H), 7.51-7.50 (m, 0.6H), 7.45-7.27 (m, 4H), 7.25-7.15 (m, 1.5H), 4.95-4.85 (m, 1H), 4.45-4.35 (m, 1H), 4.32-4.15 (m, 1H), 3.99-3.85 (m, 1H), 3.63-3.40 (m, 6H), 1.70-1.20 (m, 6H).

Step 3: Synthesis of Compound 57

To a solution of compound 28C (40.0 mg, 119 μmol) in DCM (10 mL) was added DMP (252 mg, 595 μmol). The mixture was stirred at 25° C. for 48 hrs. The mixture quenched with 10% aqueous $Na_2S_2O_3$ and saturated aqueous $NaHCO_3$ (v/v=1/1, 50 mL), extracted with DCM (20 mL) and washed with brine (20 mL×3). The combined organic layers were dried over $Na_2SO_4$ and concentrated to afford compound 57 (16.0 mg, 40.2% yield) was obtained as a white solid. $^1$H-NMR (400 MHz, DMSO-$d_6$) δ 8.61 (d, J=6.8 Hz, 1H), 8.02 (s, 1H), 7.76 (s, 1H), 7.48-7.39 (m, 4H), 5.11-5.03 (m, 1H), 4.73 (d, J=10.0 Hz, 1H), 4.54 (d, J=10.0 Hz, 1H), 3.66-3.36 (m, 6H), 1.89-1.39 (m, 6H). MS (ESI) m/z $(M+H)^+$ 335.1.

Example 58

(S,Z)—N-isopropyl-2-oxo-2-(12-oxo-1,3,4,6,9,10,11,12-octahydrobenzo[f][1,4]dioxa[9]azacyclotetradecin-10-yl)acetamide (58)

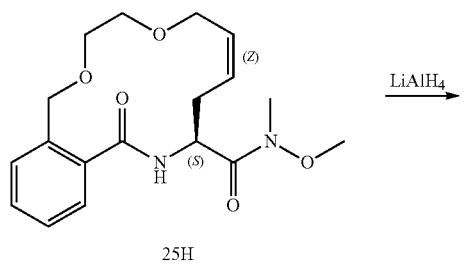

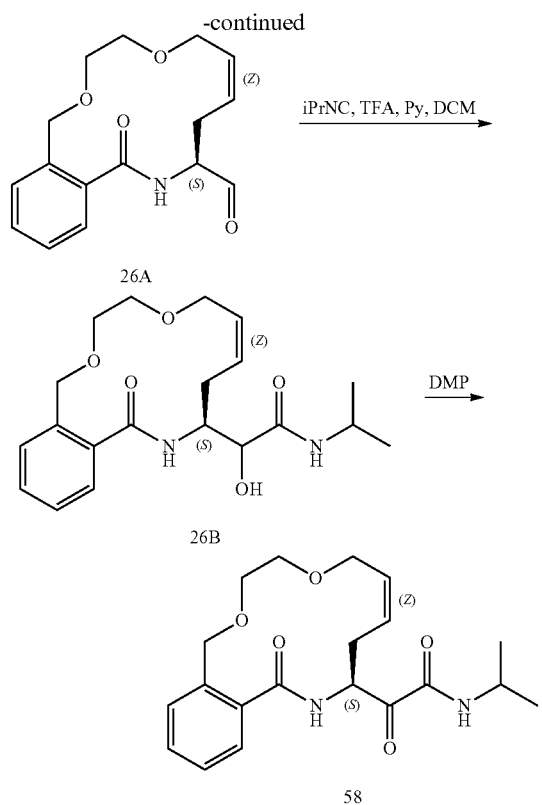

Step 1: Synthesis of Compound 26A

To a solution of compound 1 (1.0 g, 2.87 mmol) in THF (30 mL) cooled to 0° C. was added a solution of LiAlH$_4$ (1M, 3.44 mL) in THF. Then the reaction was stirred at 0° C. for 2 hrs. The reaction mixture was quenched with 1N HCl (15 mL) and extracted with EtOAc (30 mL×3). The organic layer was washed with 1N HCl (20 mL) and brine (20 mL), dried over $Na_2SO_4$, the solid was removed by filtration, the filtrate was concentrated to give compound 26A (660 mg, 78.69% yield) as light yellow solid. The residue was used directly without further purification. $^1$H NMR (400 MHz, CD$_3$OD) δ 9.58 (s, 1H), 8.77 (br d, J=6.2 Hz, 1H), 7.58 (dd, J=1.5, 7.1 Hz, 1H), 7.49-7.37 (m, 3H), 5.72-5.62 (m, 1H), 5.61-5.51 (m, 1H), 4.89 (d, J=11.2 Hz, 1H), 4.43 (d, J=11.2 Hz, 1H), 4.19-4.05 (m, 2H), 3.87-3.77 (m, 1H), 3.53-3.46 (m, 3H), 3.44-3.38 (m, 1H), 2.70-2.61 (m, 1H), 2.57-2.53 (m, 1H). MS (ESI) m/z $(M+H)^+$ 289.9.

Step 2: Synthesis of Compound 26B

To a solution of compound 26A (241 mg, 832.96 μmol) in DCM (15.00 mL) cooled to 0° C. was added 2-isocyanopropane (143.9 mg, 2.08 mmol) and pyridine (329.44 mg, 4.16 mmol), then TFA (379.9 mg, 3.33 mmol) in DCM (1 mL) was added slowly to the above reaction mixture for 0.2 hr. Then the reaction was stirred at 0° C. for 2 hrs and at 20° C. for 15 hrs. The mixture was quenched with 1N HCl (15 mL) and stirred at 20° C. for 0.5 hr, extracted with ethyl acetate (30 mL×3), the combined organic was washed with brine (20 mL), dried over anhydrous $Na_2SO_4$, filtered and concentrated. The residue was purified by preparatory-HPLC (HCl) to give compound 26B (150 mg, 47.79% yield) as white solid. MS (ESI) m/z $(M+H)^+$ 377.1.

Step 3: Synthesis of Compound 58

To a solution of compound 26B (140 mg, 371.90 μmol) in DCM (20 mL) was added DMP (631 mg, 1.49 mmol). Then the reaction was stirred at 20° C. for 20 hrs. The reaction mixture was added aqueous NaHCO$_3$ (10 mL), saturated aqueous Na$_2$S$_2$O$_3$ (26 mL) and DCM (30 mL), the mixture was stirred for 30 mins for change to clear solution, extracted with DCM (10 mL), the combined organic was washed with H$_2$O (20 mL×2) and brine (30 mL), dried over Na$_2$SO$_4$, filtered and the filtrate was concentrated in vacuo to give compound 58 (103 mg, 72.82% yield) as off-white solid. $^1$H NMR (400 MHz, CDCl$_3$) δ 8.42 (br s, 1H), 7.74-7.64 (m, 1H), 7.45-7.33 (m, 2H), 7.26-7.22 (m, 1H), 6.75 (br d, J=6.8 Hz, 1H), 5.84-5.64 (m, 2H), 5.40 (td, J=4.7, 9.2 Hz, 1H), 5.11-5.01 (m, 1H), 4.42 (br d, J=10.8 Hz, 1H), 4.16-4.02 (m, 2H), 3.96-3.86 (m, 1H), 3.70-3.55 (m, 4H), 2.85-2.67 (m, 2H), 1.24-1.18 (m, 6H). MS (ESI) m/z (M+Na)$^+$ 375.1.

Example 59

(S,Z)—N-butyl-2-oxo-2-(12-oxo-1,3,4,6,9,10,11,12-octahydrobenzo[f][1,4]dioxa[9]azacyclotetradecin-10-yl)acetamide (59)

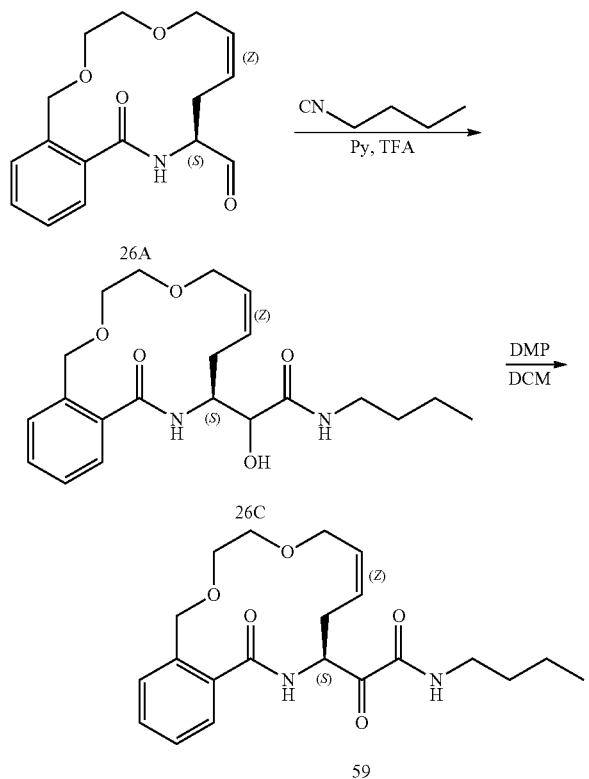

Step 1: Synthesis of Compound 26C

To a solution of compound 26A (200 mg, 691.25 μmol) in DCM (10 mL) was added a solution of 1-isocyanobutane (230 mg, 2.77 mmol) in DCM (1 mL). Then pyridine (219 mg, 2.77 mmol) in DCM (1 mL) was added into the reaction mixture followed by TFA (236 mg, 2.07 mmol) in DCM (1 mL) at 0° C. After addition, the reaction mixture was stirred at 25° C. for 14 hrs. 20 mL of 1N HCl was added into the reaction mixture and the mixture was stirred for 20 min. 50 mL of EtOAc was added into the reaction mixture and the mixture was washed with water (30 mL) and brine (30 mL). The mixture was dried over Na$_2$SO$_4$ and concentrated in vacuum to afford compound 26C (120 mg, yield 44.41%) as white solid. MS (ESI) m/z (M+H)$^+$ 391.1.

Step 2: Synthesis of Compound 59

To a solution of compound 26C (120 mg, 307.32 μmol) in DCM (30 mL) was added DMP (326 mg, 768.30 μmol). After addition, the reaction mixture was stirred at 25° C. for 14 hrs. 20 mL of sat. Na$_2$S$_2$O$_3$ and 10 mL of saturated aqueous. NaHCO$_3$ was added into the reaction mixture, the mixture was stirred for 30 min. The mixture was separated and the organic layer was washed with water (20 mL) and brine (20 mL). The mixture was dried over Na$_2$SO$_4$ and concentrated in vacuum to afford compound 59 (70 mg, 56.52% yield) as light yellow solid. $^1$H NMR (400 MHz, DMSO-d$_6$) δ 8.77-8.68 (m, 1H), 8.58-8.49 (m, 1H), 7.57-7.36 (m, 4H), 5.78-5.66 (m, 1H), 5.65-5.54 (m, 1H), 5.10-5.01 (m, 1H), 4.89 (br d, J=10.8 Hz, 1H), 4.47 (br d, J=10.8 Hz, 1H), 4.14-4.03 (m, 1H), 3.90-3.79 (m, 1H), 3.62-3.44 (m, 4H), 3.21-3.08 (m, 2H), 1.50-1.37 (m, 2H), 1.28-1.21 (m, 2H), 0.84 (t, J=7.4 Hz, 3H). MS (ESI) m/z (M+H)$^+$ 389.2.

Example 60

Ethyl (S,Z)-3-(2-oxo-2-(12-oxo-1,3,4,6,9,10,11,12-octahydrobenzo[f][1,4]dioxa[9]azacyclotetradecin-10-yl)acetamido)propanoate (60)

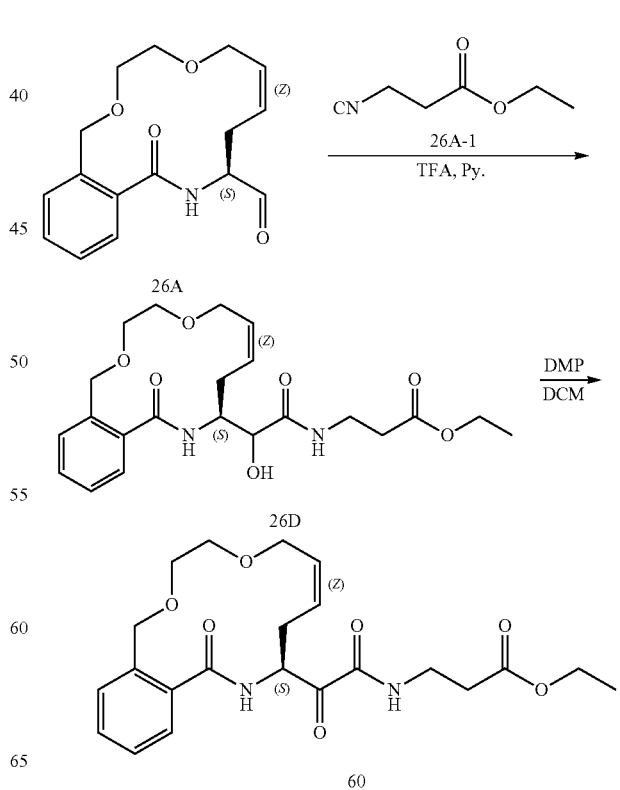

Step 1: Synthesis of Compound 26D

A mixture of compound 26A (200 mg, 691.25 μmol), compound 26A-1 (88 μL, 691.25 μmol) in DCM (15 mL) was degassed and purged with N$_2$ for 3 times, and the mixture was added dropwise pyridine (230 μL, 2.77 mmol) and TFA (155 μL, 2.07 mmol) at 0° C. The mixture was stirred at 25° C. for 16 hrs. The reaction mixture was quenched by addition HCl (1N, 30 mL) for 0.2 hr, and then diluted with EtOAc (40 mL). The combined organic layers were washed with H$_2$O (20 mL×3), dried over Na$_2$SO$_4$, filtered and concentrated under reduced pressure to give a residue. The residue was purified by preparatory-HPLC (HCl) to give the compound 26D (110 mg, yield: 36.63%) as a white solid. $^1$H-NMR (400 MHz, DMSO-d$_6$) δ 8.04-7.85 (m, 2H), 7.54 (br d, J=7.3 Hz, 1H), 7.44-7.30 (m, 4H), 5.57 (s, 3H), 4.81 (d, J=11.5 Hz, 1H), 4.55 (d, J=11.2 Hz, 2H), 4.04-3.92 (m, 3H), 3.89-3.68 (m, 2H), 3.55-3.43 (m, 4H), 3.36-3.18 (m, 2H), 2.45-2.34 (m, 3H), 2.31-2.20 (m, 1H), 1.22-1.09 (m, 3H).

Step 2: Synthesis of Compound 60

To a solution of compound 26D (100 mg, 230.16 μmol) in DMSO (5 mL) was added DCM (20 mL) and DMP (295 mg, 690.48 μmol), then the mixture was degassed and purged with N$_2$ for 3 times. The mixture was stirred at 25° C. for 18 hrs. The reaction mixture was quenched by addition of saturated aqueous Na$_2$S$_2$O$_3$ (15 mL) and saturated aqueous NaHCO$_3$ (15 mL), and then diluted with DCM (10 mL) and washed with H$_2$O (20 mL×3). The combined organic layers were washed with brine (20 mL), dried over Na$_2$SO$_4$, filtered and concentrated under reduced pressure to give a residue. The residue was stirred in i-Pr$_2$O (5 mL) and CH$_3$CN (0.1 mL) for 30 min and filtered to give the compound 60 (28 mg, yield: 27.85%) as a white solid. $^1$H NMR (400 MHz, CDCl$_3$) δ 8.43 (d, J=4.4 Hz, 1H), 7.71-7.66 (m, 1H), 7.45-7.34 (m, 3H), 7.24 (br d, J=4.2 Hz, 1H), 5.81-5.66 (m, 2H), 5.43-5.37 (m, 1H), 5.06 (d, J=11.0 Hz, 1H), 4.42 (d, J=10.8 Hz, 1H), 4.19-4.08 (m, 3H), 3.91 (dd, J=5.8, 11.4 Hz, 1H), 3.66-3.58 (m, 6H), 2.81-2.66 (m, 2H), 2.58 (t, J=6.2 Hz, 2H), 1.26 (t, J=7.2 Hz, 3H). MS (ESI) m/z (M+H)$^+$ 433.2.

Example 61

(S,Z)—N-(2,6-dimethylphenyl)-2-oxo-2-(12-oxo-1,3,4,6,9,10,11,12-octahydrobenzo[f][1,4]dioxa[9]azacyclotetradecin-10-yl)acetamide (61)

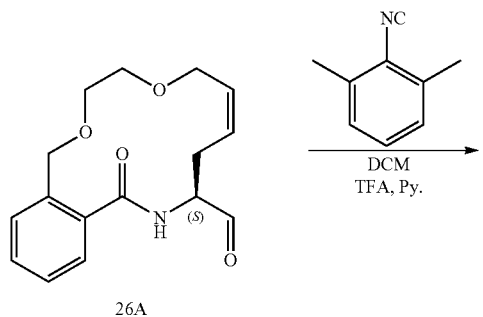

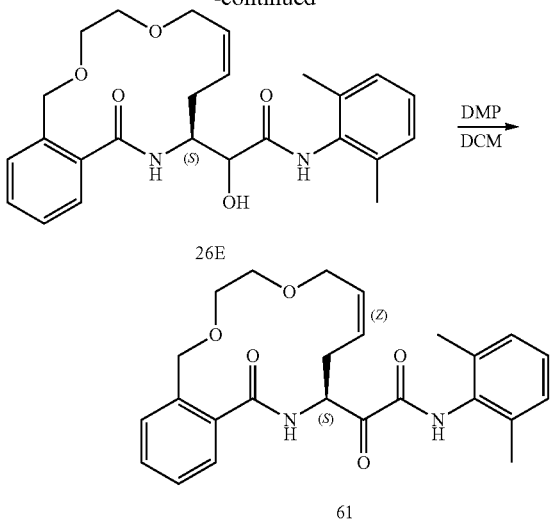

Step 1: Synthesis of Compound 26E

To a stirred solution of compound 26A (200 mg, 691.25 μmol) in DCM (15 mL) was added 2-isocyano-1,3-dimethylbenzene (363 mg, 2.77 mmol) and pyridine (219 mg, 2.77 mmol, 223 μL) at 0° C. Then TFA (236 mg, 2.07 mmol, 154 μL) was added dropwise. The reaction mixture was stirred for 30 min at 0° C. Then the reaction temperature was allowed to 25° C. and stirred for 16 hrs. The mixture was diluted with DCM (10 mL), washed with 1N HCl (2×20 mL), saturated aqueous NaHCO$_3$ (2×20 mL), the organic phase was dried over anhydrous Na$_2$SO$_4$, filtered and concentrated. The residue was purified by preparatory-HPLC (HCl condition) to afford compound 26E (150 mg, yield: 48% yield) as a white solid. $^1$H NMR (CDCl$_3$, 400 MHz): δ 8.77 (br d, J=6.0 Hz, 1H), 8.46 (br s, 1H), 7.78 (d, J=6.2 Hz, 1H), 7.43-7.39 (m, 2H), 7.17-6.99 (m, 4H), 5.79-5.74 (m, 2H), 5.15 (d, J=11.7 Hz, 1H), 4.64 (br d, J=3.7 Hz, 1H), 4.47-4.38 (m, 1H), 4.32 (d, J=11.7 Hz, 1H), 4.12 (br dd, J=5.1, 10.8 Hz, 1H), 3.86 (br dd, J=4.5, 10.7 Hz, 1H), 3.65-3.52 (m, 4H), 2.99-2.90 (m, 1H), 2.61 (br d, J=13.2 Hz, 2H), 2.21 (s, 6H). MS (ESI) m/z (M+H)$^+$ 439.1.

Step 2: Synthesis of Compound 61

To a mixture of compound 26E (150 mg, 342.06 μmol) in DCM (20 mL) and DMSO (500 μL) was added DMP (435 mg, 1.03 mmol) in one portion at 25° C. under N$_2$. The mixture was stirred at 25° C. for 36 hrs. The reaction mixture was diluted with DCM (10 mL), saturated aqueous NaHCO$_3$ (10 mL) and saturated aqueous Na$_2$S$_2$O$_3$ (10 mL), then stirred for 30 min. The organic layers were washed with water (50 mL×2), dried over Na$_2$SO$_4$, filtered and concentrated under reduced pressure to give a residue. The residue was diluted with dichloromethane (2 mL) and petroleum ether (10 mL), the solid was collected and was dried in vacuo to afford compound 61 (50 mg, yield: 31%) as a white solid. $^1$H NMR (CDCl$_3$, 400 MHz): δ 8.57-8.48 (m, 1H), 8.25 (br s, 1H), 7.77-7.68 (m, 1H), 7.44-7.38 (m, 2H), 7.29 (br s, 1H), 7.18-7.08 (m, 3H), 5.84-5.71 (m, 2H), 5.52-5.44 (m, 1H), 5.12 (d, J=10.8 Hz, 1H), 4.45 (d, J=11.0 Hz, 1H), 4.15 (br dd, J=5.6, 11.1 Hz, 1H), 3.94 (dd, J=5.6, 11.4 Hz, 1H), 3.69-3.55 (m, 4H), 2.93-2.83 (m, 1H), 2.83-2.71 (m, 1H), 2.26 (s, 6H). MS (ESI) m/z (M+H)$^+$ 437.2.

Example 62

(S,E)-N-isopropyl-2-oxo-2-(12-oxo-1,3,4,6,9,10,11,12-octahydrobenzo[f][1,4]dioxa[9]azacyclotetradecin-10-yl)acetamide (62)

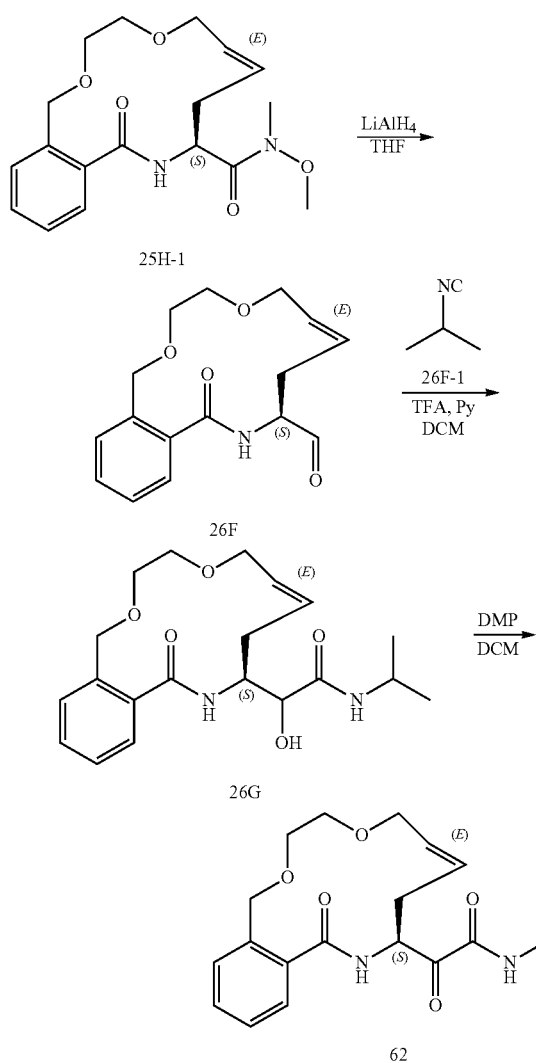

Step 1: Synthesis of Compound 26F

To a solution of compound 25H-1 (1.75 g, 5.02 mmol) in THF (10 mL) at −50° C. was added LiAlH₄ (1M, 5.3 mL) dropwise. After addition, the mixture was warmed up to −10° C. and stirred for 2 hrs. The mixture was quenched with 1N HCl (30 mL), extracted with EtOAc (25 mL×2). The organics were collected, washed with brine (50 mL). The organics were collected, dried with Na$_2$SO$_4$, filtered and concentrated to afford compound 26F (1.12 g, yield: 77.11%) as white solid, which was used directly without further purification. $^1$H NMR (400 MHz, DMSO-d$_6$) δ 9.63 (s, 1H), 8.61 (d, J=8.4 Hz, 1H), 7.52-7.36 (m, 4H), 5.72-5.59 (m, 2H), 4.77 (d, J=11.6 Hz, 1H), 4.62-4.59 (m, 1H), 4.44 (d, J=11.2 Hz, 1H), 3.90-3.82 (m, 1H), 3.81-3.70 (m, 1H), 3.55-3.44 (m, 5H), 2.67-2.62 (m, 1H), 2.31-2.28 (m, 1H).

Step 2: Synthesis of Compound 26G

To a solution of compound 26F (280 mg, 0.97 mmol) and 26F-1 (0.11 mL, 1.16 mmol) in DCM (20 mL) was added pyridine (0.32 mL, 3.87 mmol) at 0° C. Then TFA (0.14 mL, 1.94 mmol) was added dropwise. The mixture was warmed up to 25° C. and stirred for 12 hrs. The mixture was washed with 1N HCl (20 mL). The organics were collected, washed with saturated NaHCO$_3$ (20 mL). The organics were collected, dried with Na$_2$SO$_4$, filtered and concentrated. The residue was purified by preparatory-HPLC (Neutral) to afford compound 26G (120 mg, yield: 31.42%) as white solid. MS (ESI) m/z (M+H)$^+$ 377.2.

Step 3: Synthesis of Compound 62

To a solution of compound 26G (120 mg, 0.32 mmol) in DCM (20 mL) was added DMP (680 mg, 1.59 mmol). The mixture was stirred at 25° C. for 36 h. The reaction was diluted with DCM (20 mL), quenched with a solution of 10% aqueous Na$_2$S$_2$O$_3$ and 10% aqueous NaHCO$_3$ (v/v=1/1) (40 mL). The organics were collected, washed with brine (40 mL). The organics were collected, dried with Na$_2$SO$_4$, filtered and concentrated to afford compound 62 (92.50 mg, yield: 77.42%) as gray solid. MS (ESI) m/z (M+H)$^+$ 375.2. H NMR (400 MHz, CDCl$_3$) δ 8.27 (d, J=5.2 Hz, 1H), 7.91-7.81 (m, 1H), 7.64-7.57 (m, 0.1H), 7.48-7.36 (m, 2H), 7.34-7.29 (m, 1H), 7.00-6.65 (m, 1H), 5.87-5.75 (m, 1H), 5.65-5.58 (m, 1H), 5.57-5.47 (m, 1H), 4.89-4.79 (m, 1H), 4.65-4.58 (m, 1H), 4.17-4.06 (m, 1H), 4.04-3.90 (m, 2H), 3.77-3.63 (m, 3H), 3.62-3.50 (m, 1H), 2.79 (t, J=6.8 Hz, 2H), 1.29-1.18 (m, 6H).

Example 63

Ethyl (S,E)-3-(2-oxo-2-(12-oxo-1,3,4,6,9,10,11,12-octahydrobenzo[f][1,4]dioxa[9]azacyclotetradecin-10-yl)acetamido)propanoate (63)

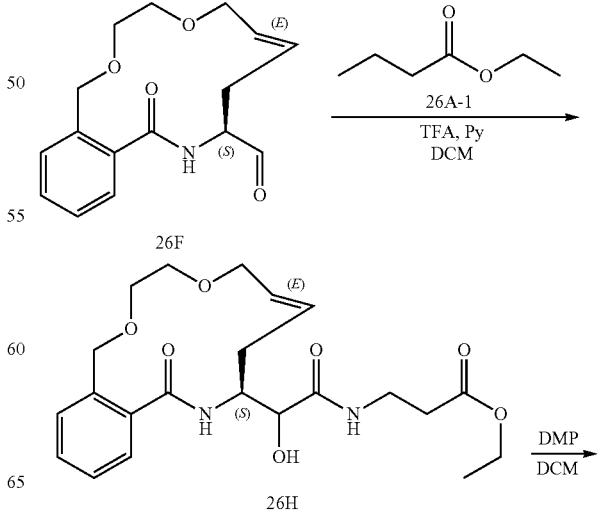

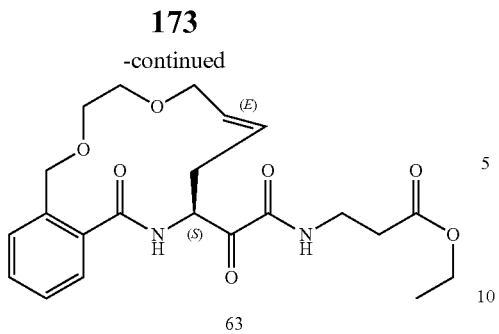

63

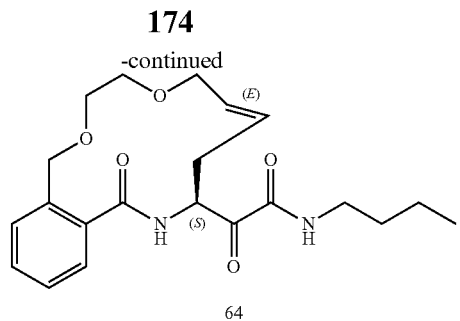

64

Step 1: Synthesis of Compound 26H

Compound 26H was prepared following the procedure of Example 62 using intermediates 26F and 26A-1. Compound 26H was obtained as white solid (120 mg, yield: 28.5%). MS (ESI) m/z (M+H)$^+$ 435.2.

Step 2: Synthesis of Compound 63

Compound 63 was prepared following the procedure of Example 62 using intermediate 26H. Compound 63 was obtained as white solid (83.5 mg, yield: 69.8%). $^1$H NMR (400 MHz, CDCl$_3$) δ 8.22 (d, J=6.0 Hz, 1H), 7.80-7.74 (m, 1H), 7.43-7.32 (m, 3H), 7.25-7.20 (m, 1H), 5.78-5.69 (m, 1H), 5.52 (q, J=6.0 Hz, 1H), 5.45-5.37 (m, 1H), 4.78 (d, J=11.6 Hz, 1H), 4.52 (d, J=11.6 Hz, 1H), 4.11 (q, J=7.2 Hz, 2H), 3.96-3.76 (m, 2H), 3.68-3.33 (m, 6H), 2.68 (t, J=6.8 Hz, 2H), 2.54 (t, J=6.0 Hz, 2H), 1.21 (t, J=7.6 Hz, 3H). MS (ESI) m/z (M+H)$^+$ 433.2.

Example 64

(S,E)-N-butyl-2-oxo-2-(12-oxo-1,3,4,6,9,10,11,12-octahydrobenzo[f][1,4]dioxa[9]azacyclotetradecin-10-yl)acetamide (64)

Step 1: Synthesis of Compound 26J

Compound 26J was prepared following the procedure of Example 62 using intermediates 26F and 1-isocyanobutane. Compound 26J was obtained as white solid (120 mg, yield: 31.7%). MS (ESI) m/z (M+H)$^+$ 391.2.

Step 2: Synthesis of Compound 64

Compound 64 was prepared following the procedure of Example 62 using intermediate 26J. Compound 64 was obtained as white solid (65.2 mg, yield: 52.3%). $^1$H NMR (400 MHz, CDCl$_3$) δ 8.31 (d, J=5.2 Hz, 1H), 7.93-7.83 (m, 1H), 7.52-7.40 (m, 2H), 7.33-7.30 (m, 1H), 6.99-6.91 (m, 1H), 5.88-5.78 (m, 1H), 5.64-5.47 (m, 2H), 4.88 (d, J=11.2 Hz, 1H), 4.61 (d, J=11.6 Hz, 1H), 4.04-3.90 (m, 2H), 3.71-3.62 (m, 3H), 3.58-3.50 (m, 1H), 3.36 (q, J=7.2 Hz, 2H), 2.78 (t, J=6.8 Hz, 2H), 1.60-1.55 (m, 2H), 1.46-1.35 (m, 2H), 0.96 (t, J=7.6 Hz, 3H). MS (ESI) m/z (M+H)$^+$ 389.2.

Example 65

N-ethyl-2-oxo-2-((2$^2$E,6S,11E)-4-oxo-2$^1$H-9,14-dioxa-5-aza-3(2,3)-pyridina-2(3,1)-pyrazola-1(1,3),8(1,4)-dibenzenacyclotetradecaphan-11-en-6-yl)acetamide (65)

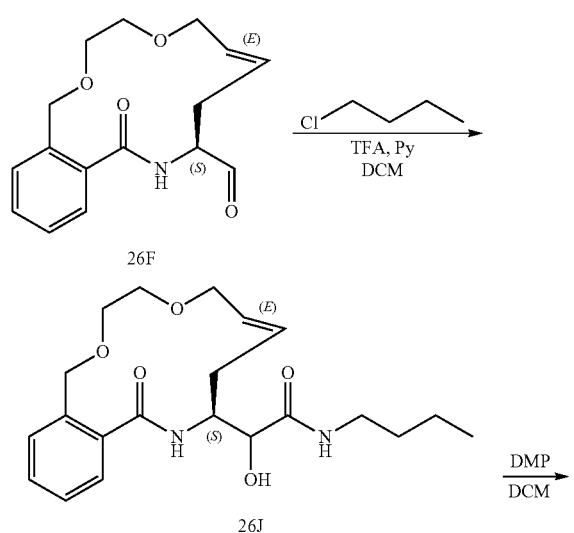

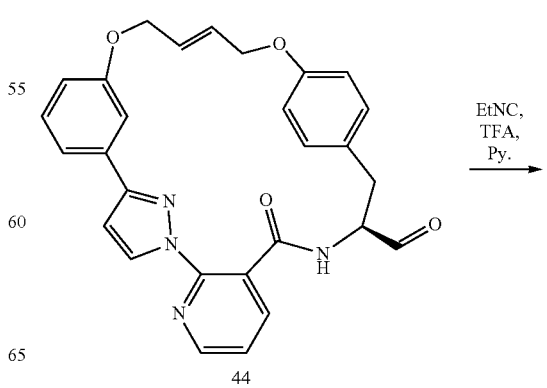

44

-continued

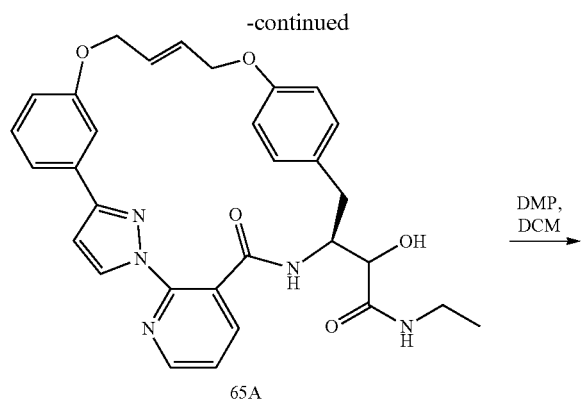

65A 5.87-5.76 (m, 1H), 5.46-5.38 (m, 1H), 4.85-4.74 (m, 2H), 4.69-4.60 (m, 1H), 4.56-4.46 (m, 1H), 3.46-3.34 (m, 2H), 3.18 (dd, J=3.1, 14.6 Hz, 1H), 2.69 (dd, J=9.9, 14.8 Hz, 1H), 1.22 (t, J=7.3 Hz, 3H). MS (ESI) m/z (M+H)+ 552.1.

Example 66

(5S,E)-3-oxo-1¹H-8,13-dioxa-4-aza-1(1,5)-indazola-2(2,3)-pyridina-7(1,4)-benzenacyclotridecaphan-10-ene-5-carbaldehyde (66)

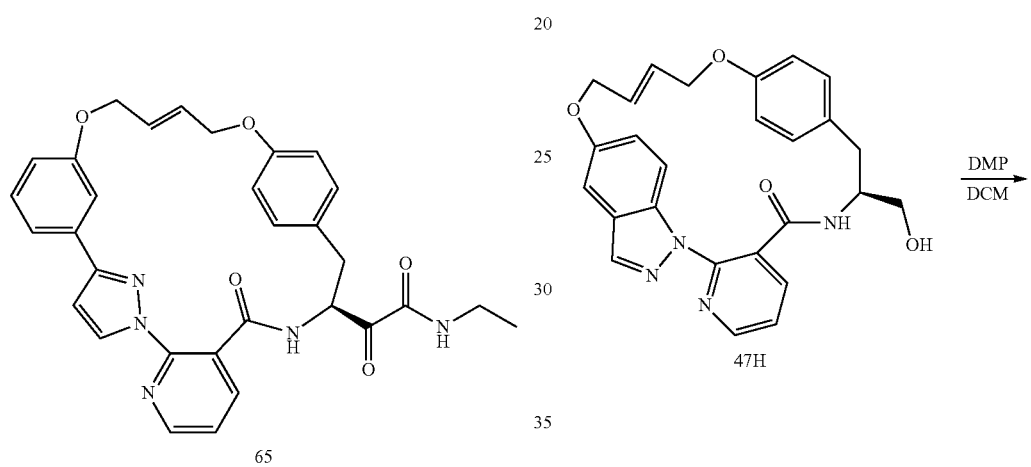

65

47H

Step 1: Synthesis of Compound 65A

Compound 65A was prepared following the procedure of Example 52 using compound 44 and isocyanoethane. Compound 65A was obtained as grey solid (70 mg, yield: 38%). MS (ESI) m/z (M+H)+ 554.1.

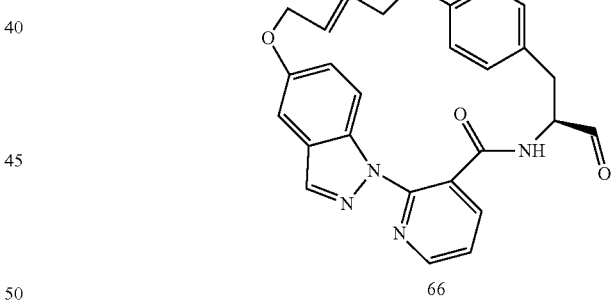

66

Step 1: Synthesis of Compound 66

Step 2: Synthesis of Compound 65

Compound 65 was prepared following the procedure of Example 52 using intermediate 27B. Compound 65 was obtained as white solid (35.0 mg, yield: 50%). ¹H NMR (400 MHz, CDCl₃) δ 8.53 (dd, J=1.8, 4.9 Hz, 1H), 8.17 (d, J=2.6 Hz, 1H), 8.07 (dd, J=1.8, 7.7 Hz, 1H), 7.59-7.52 (m, 1H), 7.37-7.30 (m, 2H), 7.05-6.99 (m, 1H), 6.89 (ddd, J=0.9, 2.6, 8.2 Hz, 1H), 6.84 (t, J=5.5 Hz, 1H), 6.60-6.53 (m, 3H), 6.48 (d, J=2.6 Hz, 1H), 6.43-6.36 (m, 2H), 5.98-5.89 (m, 1H), Compound 66 was prepared following the procedure of Example 52 using intermediate 47H. Compound 66 was obtained as off-white solid (100 mg, yield: 75.72%). ¹H NMR (400 MHz, DMSO-d₆) δ 9.49 (s, 1H), 8.72-8.55 (m, 1H), 8.10-7.92 (m, 2H), 7.69 (br. s, 1H), 7.57-7.40 (m, 1H), 7.22-6.97 (m, 2H), 6.66-6.49 (m, 2H), 6.47-6.39 (m, 2H), 6.09-5.96 (m, 1H), 5.86-5.69 (m, 1H), 4.84 (br. s, 2H), 4.58 (br. s, 2H), 4.42-4.15 (m, 0.5H), 3.90-3.57 (m, 0.5H), 3.12-2.67 (m, 2H). MS (ESI) m/z (M+H)+ 455.1.

Example 67

(5S)-3-oxo-1¹H-8,13-dioxa-4-aza-1(1,5)-indazola-2(2,3)-pyridina-7(1,4)-benzenacyclotridecaphane-5-carbaldehyde (67)

and

N-cyclopropyl-2-oxo-2-((5S)-3-oxo-1¹H-8,13-dioxa-4-aza-1(1,5)-indazola-2(2,3)-pyridina-7(1,4)-benzenacyclotridecaphane-5-yl)acetamide (68)

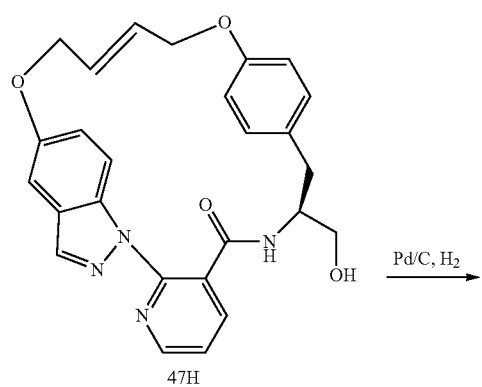

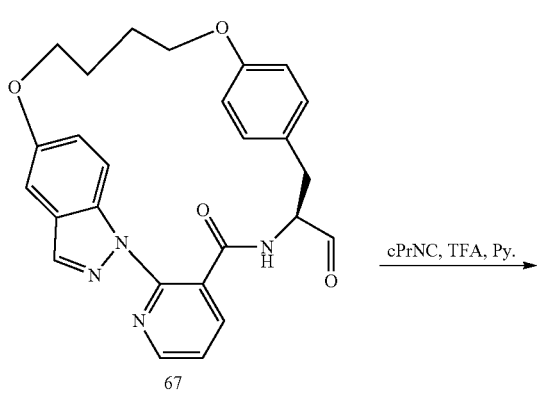

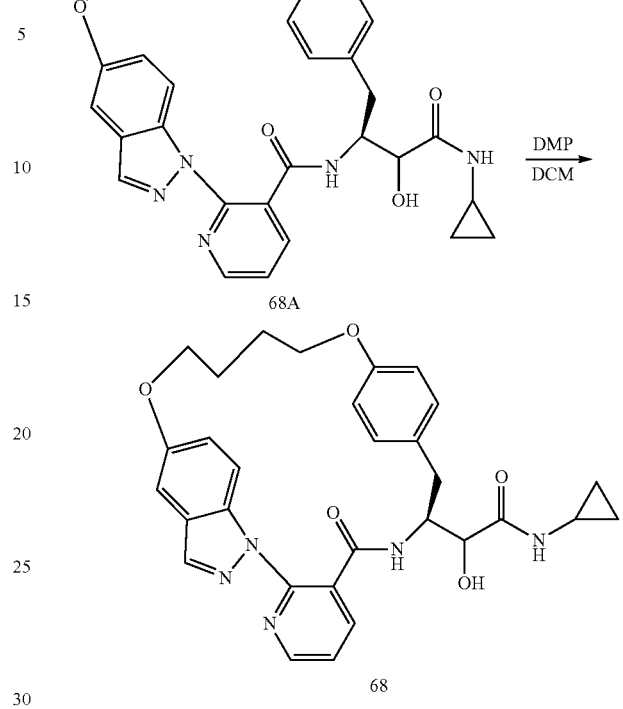

Step 1: Synthesis of Compound 67A

Compound 67A was prepared following the procedure of Example 46 using intermediate 47H. Compound 67A was obtained as white solid (190 mg, yield: 88.91%). MS (ESI) m/z (M+H)$^+$ 459.1.

Step 2: Synthesis of Compound 67

Compound 67 was prepared following the procedure of Example 52 using intermediate 67A. Compound 67 was obtained as light yellow solid (160 mg, yield: 83.74%). $^1$H NMR (400 MHz, DMSO-d$_6$) δ 9.56 (d, J=1.3 Hz, 1H), 8.66-8.58 (m, 1H), 8.19 (br s, 1H), 8.09-8.03 (m, 1H), 7.96 (s, 1H), 7.85 (d, J=8.8 Hz, 1H), 7.53-7.46 (m, 1H), 7.26 (d, J=2.0 Hz, 1H), 7.06-6.97 (m, 1H), 6.71-6.63 (m, 2H), 6.32-6.24 (m, 2H), 4.39-4.26 (m, 2H), 4.22-4.11 (m, 1H), 3.96-3.74 (m, 2H), 2.88-2.78 (m, 1H), 2.63-2.54 (m, 1H), 2.03-1.74 (m, 4H). MS (ESI) m/z (M+H)$^+$ 457.2.

Step 3: Synthesis of Compound 68A

Compound 68A was prepared following the procedure of Example 52 using compound 67 and isocyanocyclopropane. Compound 68A was obtained as light yellow solid (30 mg, yield: 27.53%). MS (ESI) m/z (M+H)$^+$ 564.1.

Step 4: Synthesis of Compound 68

Compound 68 was prepared following the procedure of Example 52 using intermediate 68A. Compound 68 was obtained as off-white solid (15 mg, yield: 49.18%). $^1$H NMR (400 MHz, DMSO-d$_6$) δ 8.83 (br d, J=5.3 Hz, 1H), 8.62-8.54 (m, 1H), 8.18 (br s, 1H), 7.95 (s, 1H), 7.86-7.76 (m, 2H), 7.50-7.40 (m, 1H), 7.26 (br d, J=1.5 Hz, 1H), 7.01-6.93 (m, 1H), 6.69 (br d, J=8.4 Hz, 2H), 6.31 (br d, J=8.4 Hz, 2H), 5.14-5.00 (m, 1H), 4.43-4.33 (m, 1H), 4.29-4.19 (m, 1H), 3.98-3.85 (m, 1H), 3.81-3.67 (m, 1H), 2.84-2.76 (m, 1H), 2.22-2.10 (m, 1H), 1.80-1.67 (m, 3H), 1.21 (br s, 2H), 0.74-0.59 (m, 4H). MS (ESI) m/z (M+H)+ 540.2.

Example 68

N-cyclopropyl-2-oxo-2-((5S,E)-3-oxo-1$^1$H-8,13-dioxa-4-aza-1(1,5)-indazola-2(2,3)-pyridina-7(1,4)-benzenacyclotridecaphan-10-en-5-yl)acetamide (69)

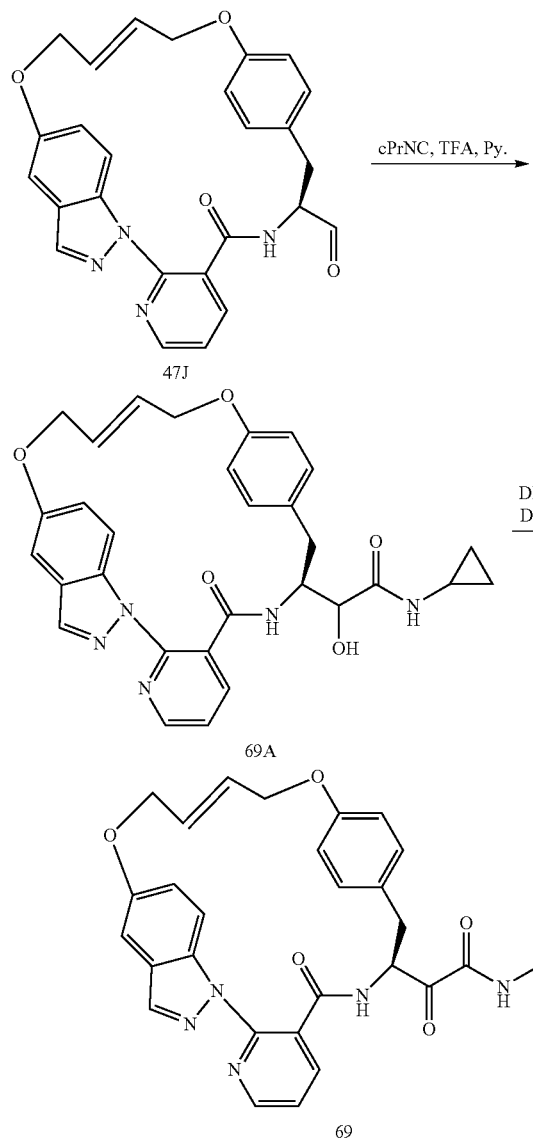

Step 1: Synthesis of Compound 69A

Compound 69A was prepared following the procedure of Example 52 using intermediate 47J and isocyanocyclopropane. Compound 69A was obtained as light yellow solid (53 mg, yield: 49.6%). MS (ESI) m/z (M+H)+ 540.1.

Step 2: Synthesis of Compound 69

Compound 69 was prepared following the procedure of Example 52 using intermediate 69A. Compound 69 was obtained as light yellow solid (20 mg, yield: 35.99%). $^1$H NMR (400 MHz, DMSO-d$_6$) δ 8.87-8.75 (m, 1H), 8.68-8.58 (m, 1H), 8.46 (brs, 1H), 8.02 (br s, 1H), 7.82 (s, 1H), 7.69 (s, 1H), 7.52-7.41 (m, 1H), 7.17-7.03 (m, 2H), 6.67-6.56 (m, 2H), 6.54-6.42 (m, 2H), 6.20-6.05 (m, 1H), 5.85-5.73 (m, 1H), 5.08 (br s, 1H), 4.95-4.85 (m, 1H), 4.84-4.76 (m, 1H), 4.71-4.62 (m, 1H), 4.56-4.47 (m, 1H), 2.88-2.72 (m, 2H), 1.24 (s, 1H), 0.75-0.60 (m, 4H). MS (ESI) m/z (M+H)+ 538.2.

Example 69

N-cyclopropyl-2-oxo-2-((2$^2$E,6S,11E)-4-oxo-2$^1$H-9,14-dioxa-5-aza-3(2,3)-pyridina-2(3,1)-pyrazola-1(1,3),8(1,4)-dibenzenacyclotetradecaphan-11-en-6-yl)acetamide (70)

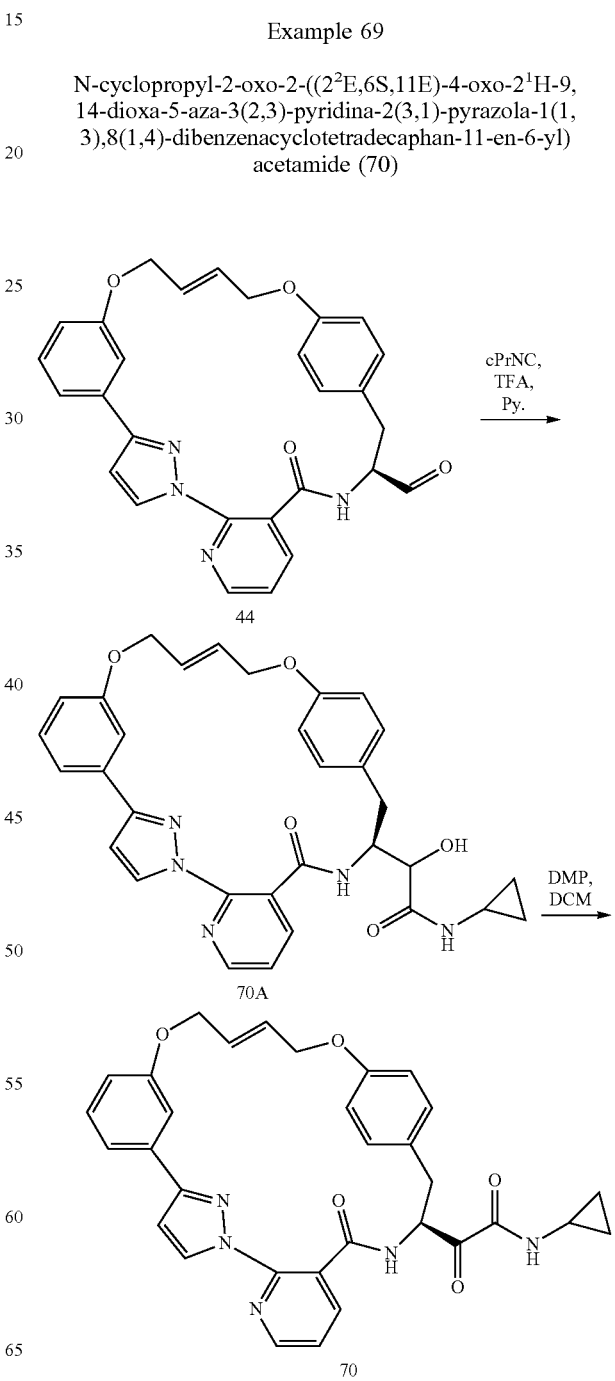

Step 1: Synthesis of Compound 70A

Compound 70A was prepared following the procedure of Example 52 using compound 44 and isocyanocyclopropane. Compound 70A was obtained as white solid (140 mg, yield: 61.97%). MS (ESI) m/z (M+H)⁺ 566.2.

Step 2: Synthesis of Compound 70

Compound 70 was prepared following the procedure of Example 52 using intermediate 70A. Compound 70 was obtained as white solid (35 mg, yield: 58.54%). $^1$H NMR (400 MHz, ACETONITRILE-d$_3$) δ 8.51 (dd, J=1.7, 4.7 Hz, 1H), 8.28 (d, J=2.6 Hz, 1H), 7.83 (dd, J=1.7, 7.6 Hz, 1H), 7.51-7.36 (m, 3H), 7.30 (t, J=7.9 Hz, 1H), 7.13 (s, 1H), 6.88 (dd, J=1.8, 8.2 Hz, 1H), 6.79 (d, J=3.5 Hz, 1H), 6.67-6.59 (m, 3H), 6.40 (d, J=8.8 Hz, 2H), 6.07-5.97 (m, 1H), 5.87-5.77 (m, 1H), 5.27-5.19 (m, 1H), 4.95-4.86 (m, 1H), 4.80-4.72 (m, 1H), 4.68-4.60 (m, 1H), 4.56-4.47 (m, 1H), 2.93 (dd, J=2.0, 15.0 Hz, 1H), 2.82-2.79 (m, 1H), 2.38 (dd, J=10.6, 15.0 Hz, 1H), 0.82-0.74 (m, 2H), 0.69-0.59 (m, 2H). MS (ESI) m/z (M+H)⁺ 564.2.

Example 70

(1³Z,1⁴E,5S)-3-oxo-1²H-8,13-dioxa-4-aza-1(2,5)-indazola-2(2,3)-pyridina-7(1,4)-benzenacyclotride-caphan-10-ene-5-carbaldehyde (71)

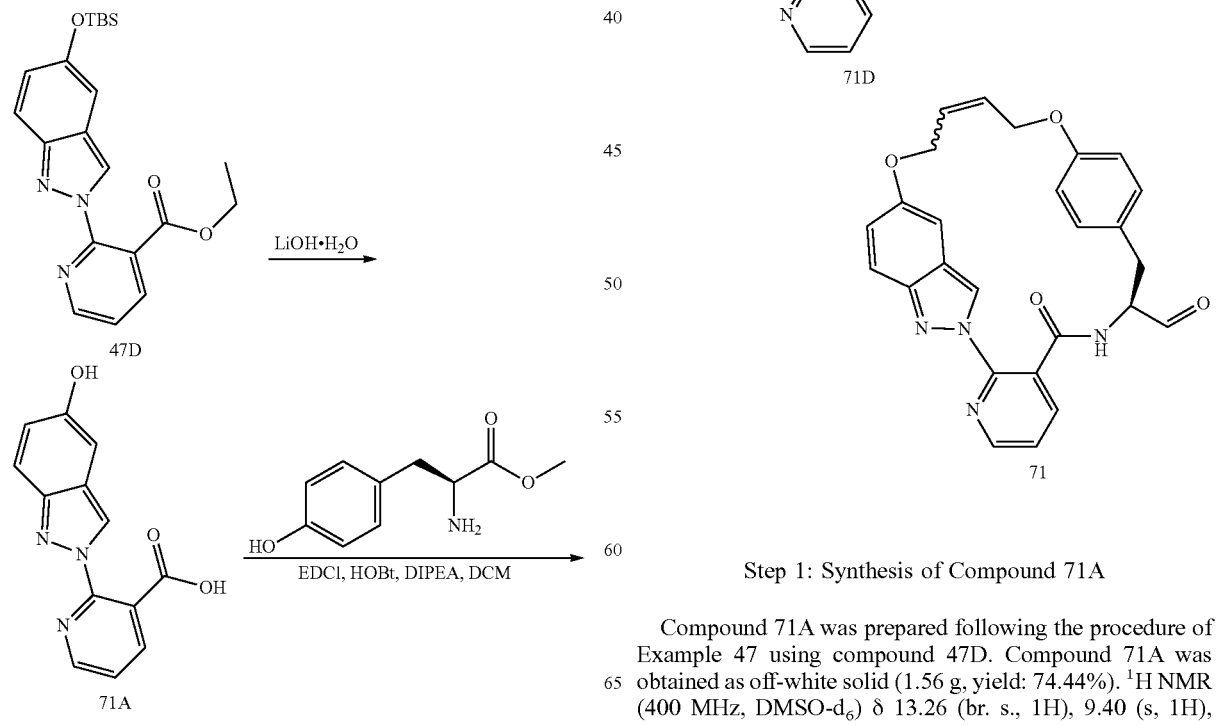

Step 1: Synthesis of Compound 71A

Compound 71A was prepared following the procedure of Example 47 using compound 47D. Compound 71A was obtained as off-white solid (1.56 g, yield: 74.44%). $^1$H NMR (400 MHz, DMSO-d$_6$) δ 13.26 (br. s., 1H), 9.40 (s, 1H), 8.75-8.73 (m, 1H), 8.64 (dd, J=1.7, 4.7 Hz, 1H), 8.14 (dd, J=1.7, 7.6 Hz, 1H), 7.56 (dd, J=4.9, 7.5 Hz, 1H), 7.48 (d, J=9.3 Hz, 1H), 6.93 (dd, J=2.2, 9.3 Hz, 1H), 6.91-6.87 (m, 1H).

Step 2: Synthesis of Compound 71B

Compound 71B was prepared following the procedure of Example 47 using intermediate 71A and methyl L-tyrosinate. Compound 71B was obtained as brown solid (410 mg, yield: 34.22%). $^1$H NMR (400 MHz, DMSO-d$_6$) δ 9.38 (s, 1H), 9.25 (s, 1H), 8.93 (d, J=7.8 Hz, 1H), 8.70 (s, 1H), 8.61 (dd, J=1.8, 4.8 Hz, 1H), 7.82-7.75 (m, 1H), 7.54 (dd, J=4.9, 7.7 Hz, 1H), 7.39 (d, J=9.3 Hz, 1H), 7.03 (d, J=8.5 Hz, 2H), 6.95-6.87 (m, 2H), 6.66 (d, J=8.5 Hz, 2H), 4.64-4.53 (m, 1H), 3.56 (s, 3H), 2.88 (d, J=7.5 Hz, 2H). MS (ESI) m/z (M+H)$^+$ 433.1.

Step 3: Synthesis of Compound 71C

Compound 71C was prepared following the procedure of Example 47 using compound 71B. Compound 71C was obtained as brown solid (65 mg, yield: 13.52%). $^1$H NMR (400 MHz, DMSO-d$_6$) δ 8.87 (d, J=6.8 Hz, 1H), 8.67 (dd, J=1.8, 4.9 Hz, 1H), 8.44 (d, J=0.7 Hz, 1H), 8.00 (dd, J=1.8, 7.5 Hz, 1H), 7.64 (dd, J=4.7, 7.6 Hz, 1H), 7.44 (d, J=9.3 Hz, 1H), 7.05 (d, J=1.8 Hz, 1H), 6.93 (dd, J=2.3, 9.4 Hz, 1H), 6.57 (d, J=8.6 Hz, 2H), 6.41 (d, J=8.8 Hz, 2H), 5.84 (s, 2H), 4.76 (br. s., 2H), 4.63-4.49 (m, 2H), 4.49-4.41 (m, 1H), 3.64 (s, 3H), 2.93 (s, 1H), 2.79-2.73 (m, 1H). MS (ESI) m/z (M+H)$^+$ 485.1.

Step 4: Synthesis of Compound 71D

To a solution of compound 71C (60.0 mg, 123.8 umol) in THF (10 mL) was added LiBH$_4$ (14.0 mg, 642.7 umol) at 0° C. Then the reaction was stirred at 20° C. for 24 h. Additional LiBH$_4$ (17.0 mg, 780.5 umol) was added to the above mixture and the reaction was stirred at 20° C. for 6 h. The reaction mixture was quenched with MeOH (2 mL), sat. NH$_4$Cl (10 mL) and extracted with EtOAc (30 mL×3), the combined organic was washed with brine (20 mL), dried over Na$_2$SO$_4$. The solid was removed by filtration and the filtrate was concentrated to give the residue. The residue was purified by flash silica gel chromatography (ISCO®; 4 g SepaFlash® Silica Flash Column, Eluent of 3080% Ethylacetate/Petroleum ether gradient @ 20 mL/min) to give compound 71D (31.0 mg, yield 54.63%) as white solid. MS (ESI) m/z (M+H)$^+$ 457.2.

Step 5: Synthesis of Compound 71

Compound 71 was prepared following the procedure of Example 52 using compound 71D. Compound 71 was obtained as white solid (15 mg, yield: 40.29%). $^1$H NMR (400 MHz, DMSO-d$_6$) δ 9.47 (s, 1H), 8.87 (d, J=5.7 Hz, 1H), 8.68 (dd, J=1.7, 4.7 Hz, 1H), 8.56 (s, 1H), 8.13 (dd, J=1.7, 7.6 Hz, 1H), 7.69-7.61 (m, 1H), 7.39 (d, J=9.3 Hz, 1H), 7.08 (d, J=2.0 Hz, 1H), 6.93-6.88 (m, 1H), 6.51 (d, J=8.6 Hz, 2H), 6.37 (d, J=8.6 Hz, 2H), 5.81 (d, J=2.4 Hz, 2H), 4.76 (br. s., 2H), 4.56 (br. s., 2H), 4.25-4.12 (m, 1H), 2.95 (d, J=13.2 Hz, 1H), 2.79-2.70 (m, 1H). MS (ESI) m/z (M+H)$^+$ 455.2

Example 71

N-cyclopropyl-2-oxo-2-((6S,E)-4-oxo-2$^1$H-9,14-dioxa-5-aza-3(2,3)-pyridina-2(3,1)-pyrazola-1(1,3),8 (1,4)-dibenzenacyclotetradecaphane-6-yl)acetamide (72)

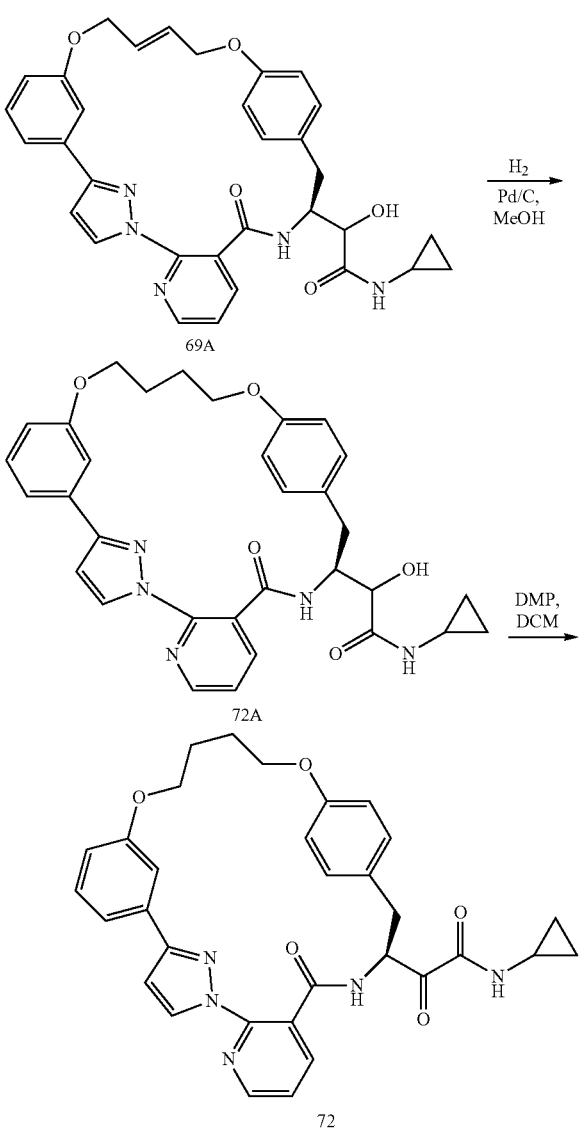

Step 1: Synthesis of Compound 72A

To a solution of compound 69A (80 mg, 141.44 umol) in MeOH (8 mL) was added Pd/C (10 mg) under N$_2$. The suspension was degassed under vacuum and purged with H$_2$ for 3 times. The mixture was stirred at 25° C. for 1 h under H$_2$ balloon. The reaction mixture was filtered and concentrated under reduced pressure to give a residue. The residue was purified by preparatory-TLC (SiO$_2$, DCM:EtOAc=1: 1.5) and preparatory-HPLC (HCl). Compound 72A (40 mg, yield: 49.32%) was obtained as a white solid. MS (ESI) m/z (M+H)$^+$ 568.1.

Step 2: Synthesis of Compound 72

Compound 72 was prepared following the procedure of Example 52 using intermediate 72A and methyl L-tyrosinate. Compound 72 was obtained as brown solid (20 mg, yield: 55.91%). $^1$H NMR (400 MHz, DMSO-$d_6$) δ 8.89 (d, J=6.0 Hz, 1H), 8.81 (d, J=5.1 Hz, 1H), 8.58 (dd, J=1.8, 4.6 Hz, 1H), 8.29 (d, J=2.6 Hz, 1H), 7.96 (dd, J=1.7, 7.6 Hz, 1H), 7.55 (dd, J=4.7, 7.6 Hz, 1H), 7.26-7.19 (m, 2H), 7.16 (s, 1H), 6.97 (d, J=8.4 Hz, 2H), 6.93 (d, J=2.4 Hz, 1H), 6.90-6.86 (m, 1H), 6.56 (d, J=8.4 Hz, 2H), 5.12 (dd, J=6.1, 9.2 Hz, 1H), 4.18 (br s, 2H), 4.08-4.01 (m, 1H), 3.99-3.92 (m, 1H), 2.93-2.89 (m, 1H), 2.82-2.74 (m, 1H), 2.59-2.53 (m, 1H), 1.90-1.74 (m, 4H), 0.69-0.63 (m, 2H), 0.61-0.55 (m, 2H). MS (ESI) m/z (M+H)$^+$ 566.2.

Example 72

(10S,E)-12-oxo-2$^1$H-11-aza-1(2,3)-pyridina-2(1,3)-pyrazola-3(1,3),8(1,4)-dibenzenacyclododecaphane-10-carbaldehyde (73)

and

N-cyclopropyl-2-oxo-2-((10S,E)-12-oxo-2'H-11-aza-1(2,3)-pyridina-2(1,3)-pyrazola-3(1,3),8(1,4)-dibenzenacyclododecaphane-10-yl)acetamide (74)

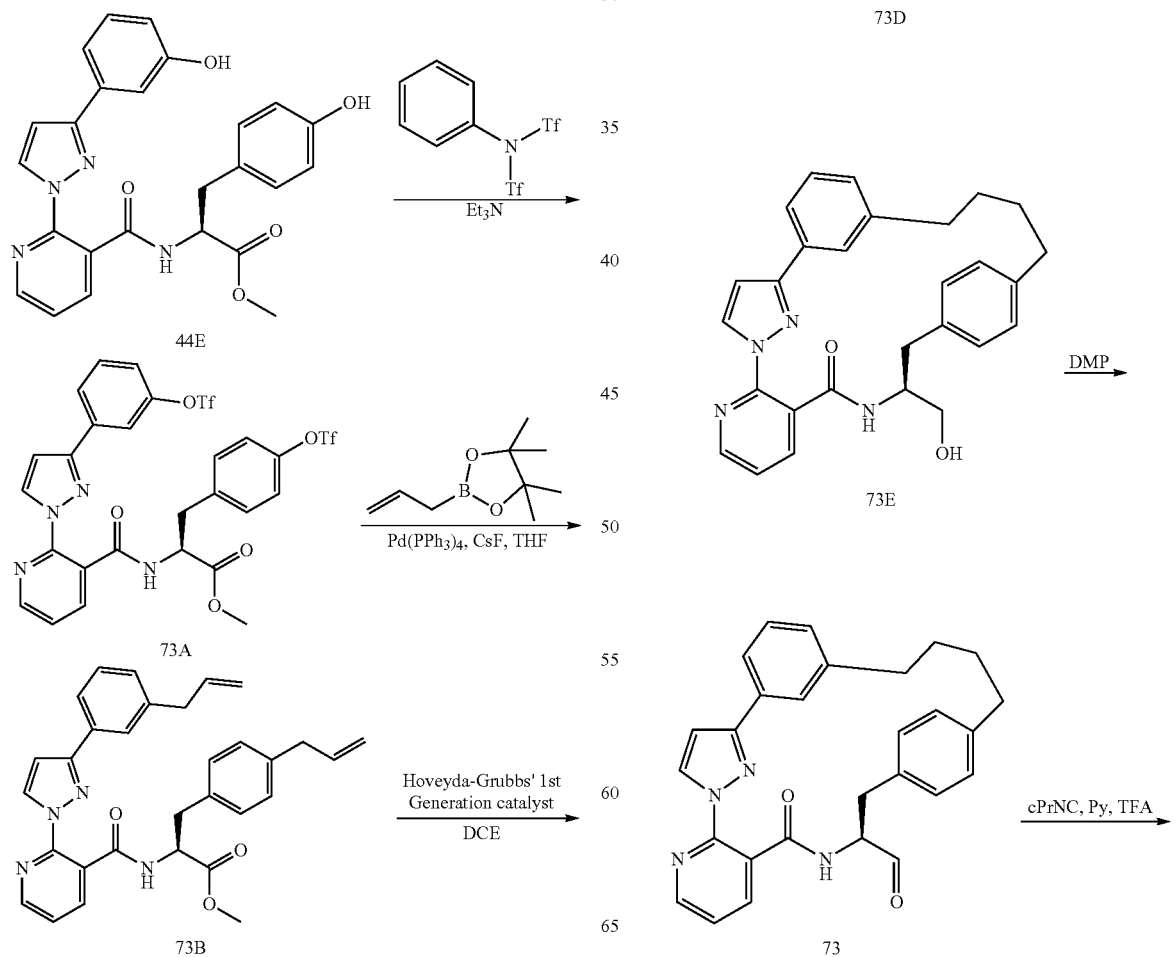

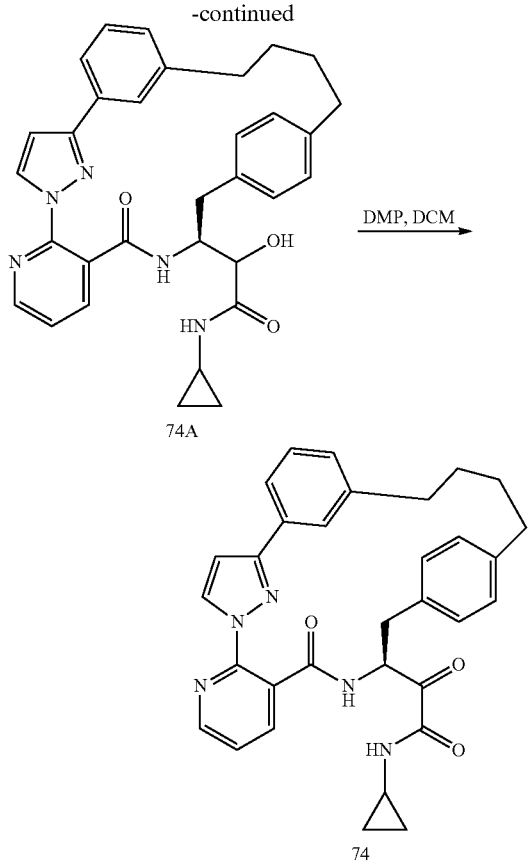

Step 1: Synthesis of Compound 73A

To a solution of compound 44E (4.5 g, 9.82 mmol) in THF (100 mL) was added 1,1,1-trifluoro-N-phenyl-N-(trifluoromethylsulfonyl)methanesulfonamide (13.5 g, 37.81 mmol) and Et$_3$N (5.96 g, 58.92 mmol, 8.20 mL) at 0° C. The mixture was stirred at 20° C. for 2 h. The reaction mixture was concentrated under reduced pressure to remove solvent. The residue was diluted with H$_2$O (20 mL) and extracted with EtOAc (30 mL×2). The combined organic layers were washed with 1N. HCl (30 mL×2), sat. NaHCO$_3$ (20 mL×2) and brine (40 mL), dried over Na$_2$SO$_4$, filtered and concentrated under reduced pressure to give a residue. The residue was purified by column chromatography (SiO$_2$, Petroleum ether/Ethyl acetate=4/1 to 2:1) to give the compound 73A (3.7 g, yield: 52.14%) as a brown solid. $^1$H NMR (400 MHz, DMSO-d$_6$) δ 8.97 (d, J=7.7 Hz, 1H), 8.55 (d, J=4.9 Hz, 1H), 8.54-8.48 (m, 1H), 7.91-7.83 (m, 2H), 7.65-7.56 (m, 2H), 7.44 (dd, J=4.5, 7.6 Hz, 2H), 7.31-7.20 (m, 4H), 7.14 (d, J=2.6 Hz, 1H), 4.71-4.64 (m, 1H), 3.47 (s, 3H), 3.07 (dd, J=5.5, 13.9 Hz, 1H), 2.87 (dd, J=9.5, 13.9 Hz, 1H). MS (ESI) m/z (M+H)$^+$ 723.1.

Step 2: Synthesis of Compound 73B

A mixture of compound 73A (3.7 g, 5.12 mmol), 2-allyl-4,4,5,5-tetramethyl-1,3,2-dioxaborolane (4.3 g, 25.60 mmol) and CsF (3.89 g, 25.60 mmol) in THF (100 mL) was degassed and purged with N$_2$ for 3 times. Then to the mixture was added Pd(PPh$_3$)$_4$ (888 mg, 768.00 umol), and stirred at 80° C. for 16 h under N$_2$ atmosphere. The reaction mixture was concentrated under reduced pressure to remove solvent. The residue was diluted with H$_2$O (40 mL) and extracted with EtOAc (25 mL×3). The combined organic layers were washed with 1N HCl (20 mL), sat. NaHCO$_3$ (20 mL×2) and brine (40 mL), dried over Na$_2$SO$_4$, filtered and concentrated under reduced pressure to give a residue. The residue was purified by column chromatography (SiO$_2$, Petroleum ether/Ethyl acetate=2/1 to 1:1) to give the compound 73B (2 g, yield: 77.11%) as a yellow solid. $^1$H NMR (400 MHz, DMSO-d$_6$) δ 8.88 (d, J=7.3 Hz, 1H), 8.53 (dd, J=1.4, 4.7 Hz, 1H), 8.44 (d, J=2.4 Hz, 1H), 7.71-7.61 (m, 3H), 7.42 (dd, J=4.9, 7.5 Hz, 1H), 7.32 (t, J=7.6 Hz, 1H), 7.15 (br d, J=7.5 Hz, 1H), 7.05-6.90 (m, 5H), 6.00-5.82 (m, 2H), 5.10-4.97 (m, 4H), 4.68-4.60 (m, 1H), 3.46 (s, 3H), 3.25 (br d, J=6.6 Hz, 2H), 2.97-2.87 (m, 1H), 2.87-2.78 (m, 1H). MS (ESI) m/z (M+H)$^+$ 507.2.

Step 3: Synthesis of Compound 73C

To a solution of compound 73B (2.00 g, 3.95 mmol) in DCE (800 mL) was added Hoveyda-grubbs catalyst 1$^{st}$ generation (237 mg, 395.00 umol). The mixture was stirred at 90° C. for 64 h. The reaction mixture was concentrated under reduced pressure to give a residue. The residue was purified by column chromatography (SiO$_2$, Petroleum ether/ Ethyl acetate=3/1 to 1:1) to give compound 12 (1.1 g, yield: 43.65%) as a white solid. Compound 73C (50 mg) was separated via preparatory-TLC to give compound 73C-E (30 mg) and compound 73C-Z (16 mg).

73C-E: $^1$H NMR (400 MHz, CDCl$_3$) δ 8.62 (dd, J=1.7, 4.5 Hz, 1H), 8.56 (dd, J=1.4, 7.8 Hz, 1H), 8.39 (br d, J=6.8 Hz, 1H), 8.00 (d, J=2.4 Hz, 1H), 7.55-7.48 (m, 2H), 7.30-7.21 (m, 3H), 7.18-7.11 (m, 1H), 7.11-7.08 (m, 1H), 6.96 (d, J=7.9 Hz, 2H), 6.82 (d, J=7.9 Hz, 2H), 6.70 (d, J=2.4 Hz, 1H), 6.03-5.92 (m, 1H), 5.85-5.74 (m, 1H), 5.05-4.95 (m, 1H), 3.58-3.47 (m, 2H), 3.39 (br d, J=8.2 Hz, 2H), 3.33 (br d, J=7.1 Hz, 1H), 3.29 (s, 3H), 3.18-3.02 (m, 2H). 73C-Z: $^1$H NMR (400 MHz, CDCl$_3$) δ 8.67 (dd, J=1.7, 4.7 Hz, 1H), 8.40 (dd, J=1.7, 7.8 Hz, 1H), 7.89 (d, J=2.4 Hz, 1H), 7.57-7.47 (m, 3H), 7.34-7.22 (m, 3H), 7.11 (br d, J=7.5 Hz, 1H), 6.97 (d, J=7.9 Hz, 2H), 6.81-6.69 (m, 4H), 5.80-5.71 (m, 1H), 5.47-5.37 (m, 1H), 4.98 (td, J=4.7, 7.3 Hz, 1H), 3.53-3.44 (m, 2H), 3.41-3.32 (m, 2H), 3.29 (br s, 1H), 3.26 (s, 3H), 3.18-3.09 (m, 2H). MS (ESI) m/z (M+H)$^+$ 479.1.

Step 4: Synthesis of Compound 73D

A solution of compound 73C (400 mg, 835.88 umol) in MeOH (8 mL) was degassed and purged with N$_2$ for 3 times, and a mixture of Pd/C (50 mg, 10% purity) in MeOH (7 mL) was added dropwise. Then the mixture was degassed and purged with H$_2$ for 3 times, and stirred at 20° C. for 3 h under H₂ balloon. The catalyst was filtered off using Celite, and concentrated under reduced pressure to give a residue. The residue was purified by preparatory-TLC (SiO₂, Petroleum ether/Ethyl acetate=1:1) to give the compound 73D (380 mg, yield: 94.60%) as a white solid. ¹H NMR (400 MHz, CDCl₃) δ 8.96 (br d, J=6.6 Hz, 1H), 8.69-8.52 (m, 2H), 8.25-7.79 (m, 1H), 7.67-7.35 (m, 2H), 7.35-7.13 (m, 2H), 7.13-6.97 (m, 4H), 6.91-6.67 (m, 1H), 5.13-4.95 (m, 1H), 3.17-3.05 (m, 3H), 2.91-2.69 (m, 1H), 2.68-2.51 (m, 1H), 2.49-2.29 (m, 1H), 2.29-2.08 (m, 1H), 1.79-1.65 (m, 2H), 1.58-1.37 (m, 1H), 1.37-1.17 (m, 1H).

Step 5: Synthesis of Compound 73E

A solution of LiBH₄ (91 mg, 4.16 mmol) in THF (10 mL) was cooled to 0 °C. And then compound 73D (400 mg, 832.36 umol) in THF (10 mL) was added dropwise at 0° C. The resulting mixture was stirred at 0° C. for 5 h. The reaction mixture was quenched by addition NH₄Cl (10 mL), and then diluted with H₂O (20 mL) and extracted with EtOAc (30 mL×2). The combined organic layers were washed with brine (40 mL×3), dried over Na₂SO₄, filtered and concentrated under reduced pressure to give a residue. The residue was purified by preparatory-TLC (SiO₂, Petroleum ether/Ethyl acetate=1/1) to give a compound 73E (300 mg, yield: 79.64%) as a white solid. ¹H NMR (400 MHz, CDCl₃) δ 8.66-8.57 (m, 2H), 8.27-8.19 (m, 2H), 7.56-7.50 (m, 2H), 7.32-7.23 (m, 2H), 7.15-7.05 (m, 3H), 6.96 (d, J=8.2 Hz, 2H), 6.82 (d, J=2.6 Hz, 1H), 4.11 (br s, 1H), 3.72-3.48 (m, 2H), 3.03-2.79 (m, 2H), 2.70-2.57 (m, 2H), 2.52-2.40 (m, 1H), 2.31-2.17 (m, 1H), 1.75-1.64 (m, 2H), 1.62-1.41 (m, 2H). MS (ESI) m/z (M+Na)⁺ 475.0.

Step 6: Synthesis of Compound 73

Compound 73 was prepared following the procedure of Example 52 using intermediate 73E. Compound 73 was obtained as brown solid (220 mg, yield: 84.86%). ¹H NMR (400 MHz, CDCl₃) δ 9.42 (s, 1H), 9.26 (br d, J=6.4 Hz, 1H), 8.65-8.60 (m, 2H), 8.11 (d, J=2.6 Hz, 1H), 7.55-7.50 (m, 1H), 7.48 (d, J=7.3 Hz, 1H), 7.29-7.23 (m, 3H), 7.03 (s, 5H), 6.80 (d, J=2.4 Hz, 1H), 4.48-4.43 (m, 1H), 3.40-3.33 (m, 1H), 3.21-3.13 (m, 1H), 2.73-2.59 (m, 2H), 2.33-2.19 (m, 2H), 1.79-1.62 (m, 3H), 1.52-1.25 (m, 3H). MS (ESI) m/z (M+H)⁺ 451.1.

Step 7: Synthesis of Compound 74A

Compound 74A was prepared following the procedure of Example 52 using compound 44 and isocyanocyclopropane. Compound 74A was obtained as white solid (70 mg, yield: 58.88%). MS (ESI) m/z (M+H)⁺ 536.2.

Step 8: Synthesis of Compound 74

Compound 74 was prepared following the procedure of Example 52 using intermediate 74A. Compound 74 was obtained as white solid (40 mg, yield: 57.36%). ¹H NMR (400 MHz, DMSO-d₆) δ 9.11 (d, J=6.6 Hz, 1H), 8.83 (d, J=5.3 Hz, 1H), 8.59 (dd, J=1.8, 4.9 Hz, 1H), 8.29 (d, J=2.6 Hz, 1H), 8.23 (dd, J=1.8, 7.7 Hz, 1H), 7.62 (dd, J=4.9, 7.5 Hz, 1H), 7.50 (d, J=7.7 Hz, 1H), 7.34 (d, J=8.2 Hz, 2H), 7.25 (t, J=7.6 Hz, 1H), 7.17-7.11 (m, 3H), 7.08 (d, J=7.7 Hz, 1H), 6.90 (d, J=2.6 Hz, 1H), 5.08 (dd, J=6.9, 9.8 Hz, 1H), 3.05 (d, J=13.9 Hz, 1H), 2.81-2.73 (m, 2H), 2.69-2.62 (m, 2H), 2.38-2.29 (m, 1H), 2.14-2.05 (m, 1H), 1.77-1.66 (m, 2H), 1.38-1.26 (m, 2H), 0.65 (br d, J=7.3 Hz, 2H), 0.60-0.53 (m, 2H). MS (ESI) m/z (M+H)⁺ 534.2.

Example 73

(2²E,10S)-12-oxo-2¹H-11-aza-1(2,3)-pyridina-2(1,3)-pyrazola-3(1,3),8(1,4)-dibenzenacyclododecaphan-5-ene-10-carbaldehyde (75)

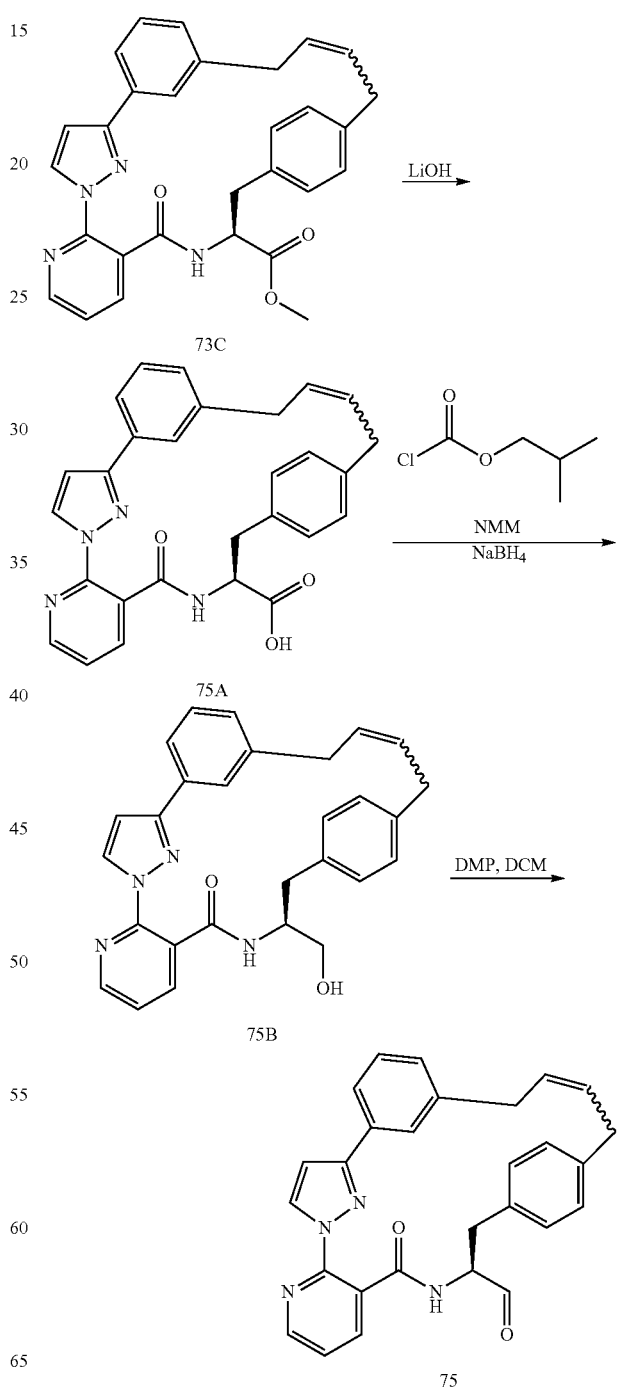

Step 1: Synthesis of Compound 75A

To a solution of compound 73C (100 mg, 208.97 umol) in THF (5 mL) and H$_2$O (5 mL) was added LiOH.H$_2$O (44 mg, 1.04 mmol). The mixture was stirred at 20° C. for 16 h. 10 mL of water was added into the reaction mixture, and the mixture was extracted with MTBE (10 mL×2). The aqueous layer was acidified by 1N HCl to pH~2-3 at 0° C., and extracted with EtOAc (10 mL×2), the organic phase was collected, dried over Na$_2$SO$_4$, filtered and concentrated to give a residue. Compound 75A (80 mg, yield: 82.4%) was obtained as a white solid. $^1$H NMR (400 MHz, CDCl$_3$) δ 8.68-8.55 (m, 1H), 8.42-8.19 (m, 1H), 7.94-7.86 (m, 1H), 7.56-7.42 (m, 3H), 7.31-7.22 (m, 2H), 7.18-7.08 (m, 1H), 6.94-6.72 (m, 4H), 6.67-6.53 (m, 1H), 5.97-5.60 (m, 1H), 5.73-5.60 (m, 0.5H), 5.54-5.42 (m, 0.5H), 4.87-4.73 (m, 1H), 3.52-2.90 (m, 6H).

Step 2: Synthesis of Compound 75B

To a cooled (−40° C.) solution of compound 75A (80 mg, 172.22 umol) in DME (6 mL) was successively added NMM (70 mg, 688.88 umol) and isobutyl carbonochloridate (47 mg, 344.44 umol). After 30 min, a solution of NaBH$_4$ (26 mg, 688.88 umol) in H$_2$O (2 mL) was added at 0° C., and the mixture was stirred at 25° C. for 3 h. The excess lithium borohydride was quenched by addition of aqueous saturated ammonium chloride solution (0.5 mL) at 0° C. The mixture was partitioned between ethyl acetate (10 mL) and aqueous saturated NaHCO$_3$ (20 mL). The aqueous layer was extracted with EtOAc (2×10 mL). The combined organic layers were dried over Na$_2$SO$_4$, filtered and concentrated under reduced pressure to give a residue. The residue was purified by preparatory-TLC (SiO$_2$, PE:EtOAc=1:1). Compound 75B (40 mg, yield: 46.9%) was obtained as a white solid. MS (ESI) m/z (M+H)$^+$ 451.2.

Step 3: Synthesis of Compound 75

Compound 75 was prepared following the procedure of Example 52 using intermediate 75B. Compound 75 was obtained as white solid (20 mg, yield: 46.21%). $^1$H NMR (400 MHz, ACETONITRILE-d$_3$) δ 9.52 (s, 0.6H), 9.48 (s, 0.4H), 8.65 (dd, J=1.6, 4.9 Hz, 0.6H), 8.62 (dd, J=1.8, 4.8 Hz, 0.4H), 8.32 (dd, J=1.8, 7.8 Hz, 0.6H), 8.25 (dd, J=1.8, 7.8 Hz, 0.4H), 8.17 (d, J=2.8 Hz, 0.4H), 8.05 (d, J=2.5 Hz, 0.6H), 7.61 (dd, J=4.8, 7.8 Hz, 0.6H), 7.57-7.53 (m, 1H), 7.48 (br d, J=7.8 Hz, 0.4H), 7.45 (s, 0.6H), 7.41-7.26 (m, 2H), 7.24-7.16 (m, 1.6H), 7.03 (s, 2H), 6.89 (s, 1H), 6.77 (dd, J=1.3, 2.5 Hz, 1H), 6.01-5.89 (m, 0.8H), 5.78-5.69 (m, 0.6H), 5.61-5.52 (m, 0.6H), 4.49 (ddd, J=2.8, 7.1, 10.2 Hz, 0.6H), 4.42 (ddd, J=2.8, 6.5, 9.8 Hz, 0.4H), 3.59-3.38 (m, 1.6H), 3.35 (br t, J=6.5 Hz, 1H), 3.29-3.22 (m, 2H), 3.12 (dd, J=2.9, 14.9 Hz, 0.5H), 2.82 (dd, J=10.5, 14.8 Hz, 0.7H), 2.72 (dd, J=10.0, 14.8 Hz, 0.7H). MS (ESI) m/z (M+H)$^+$ 449.1.

Example 74

(1$^3$Z,1$^4$Z,5S)-3-oxo-1$^2$H-4-aza-1(2,5)-indazola-2(2,3)-pyridina-7(1,4)-benzenacycloundecaphane-5-carbaldehyde (76)

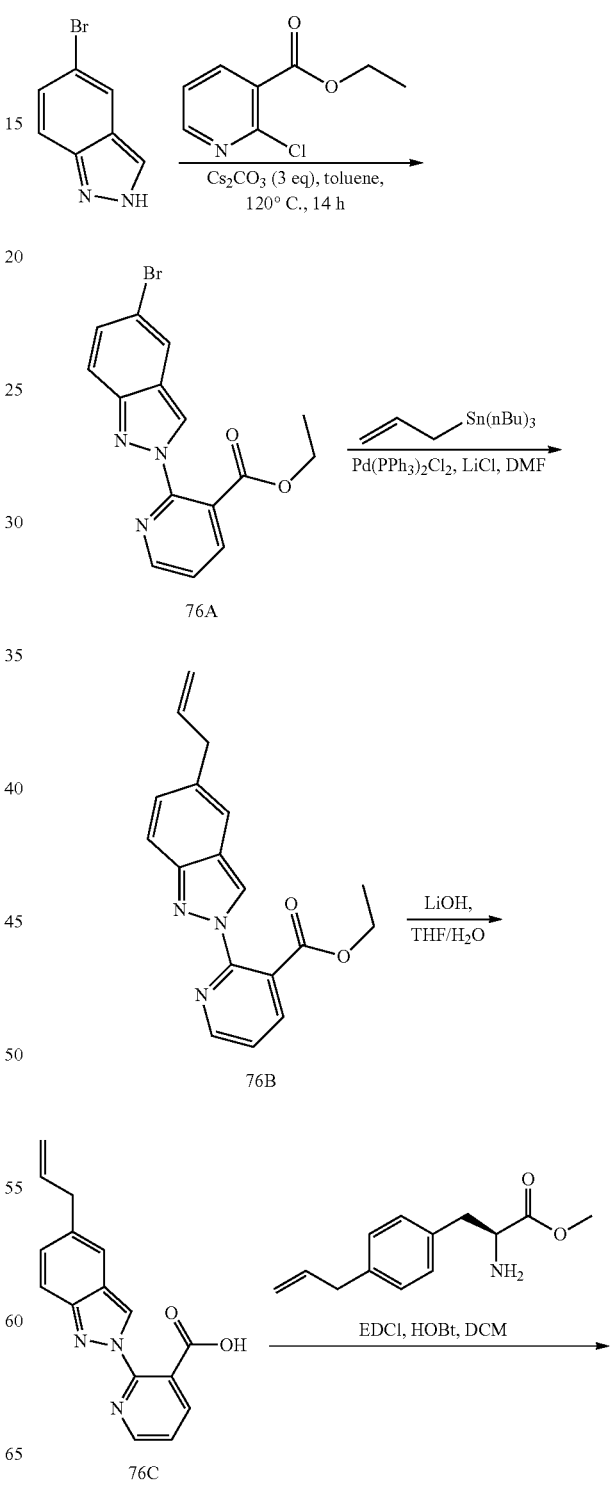

76A

76B

76C

193
-continued

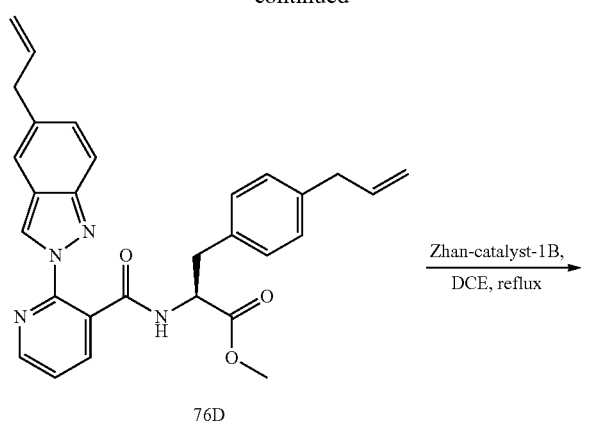

76D

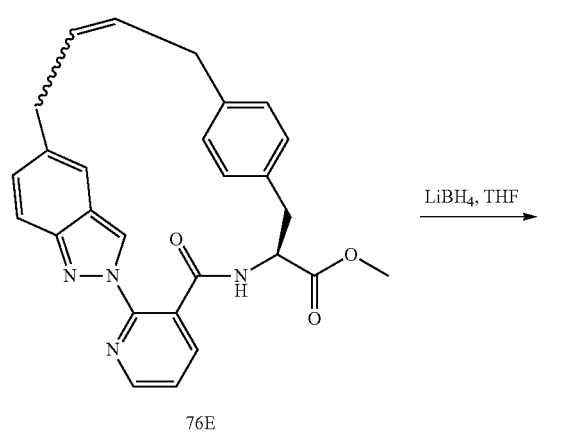

76E

Zhan-catalyst-1B, DCE, reflux →

LiBH₄, THF →

Pd/C, H₂, MeOH →

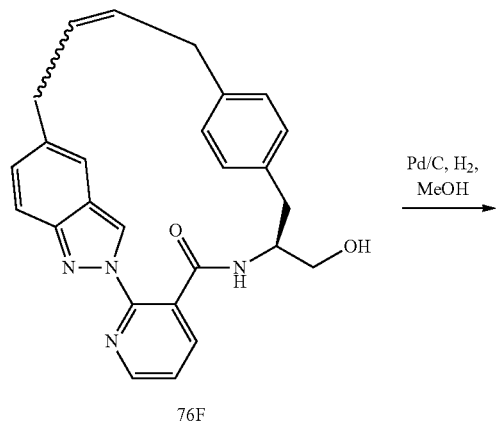

76F

DMP, DCM →

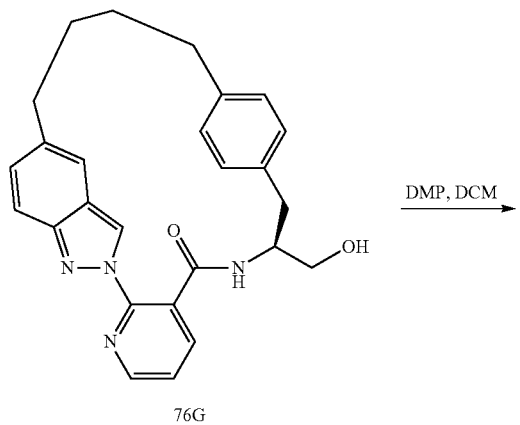

76G

194
-continued

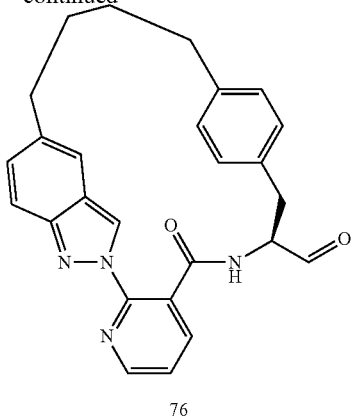

76

Step 1: Synthesis of Compound 76A

To a solution of 5-bromo-2H-indazole (5 g, 25.38 mmol) and ethyl 2-chloronicotinate (4.71 g, 25.38 mmol) in toluene (200 mL) was added $Cs_2CO_3$ (24.8 g, 76.13 mmol). The mixture was stirred at 120° C. for 14 h. The mixture was filtered and the filtrate was concentrated. The residue was purified by column chromatography ($SiO_2$, petroleum ether: ethyl acetate=10:1) to afford compound 76A (3.15 g, yield: 34.49%) as a white solid. $^1$H NMR (400 MHz, DMSO-$d_6$) δ 9.18-9.14 (m, 1H), 8.83-8.68 (m, 1H), 8.33-8.23 (m, 1H), 8.14-8.04 (m, 1H), 7.78-7.63 (m, 2H), 7.48-7.34 (m, 1H), 4.28-4.06 (m, 2H), 1.13-0.93 (m, 3H). MS (ESI) m/z $(M+H)^+$ 345.9.

Step 2: Synthesis of Compound 76B

A mixture of compound 76A (1.5 g, 4.33 mmol), allyl-tributylstannane (1.39 mL, 4.55 mmol), LiCl (46 mg, 1.08 mmol), dichloropalladium; triphenylphosphane (152 mg, 216.5 umol), DMF (60 mL) was stirred at 90° C. for 40 min. The mixture was quenched with 10% KF (30 mL) and stirred for 15 mins, extracted with EA (3×20 mL). The combined organic layers were dried over $Na_2SO_4$, filtered and concentrated to give a residue. The residue was purified by column chromatography ($SiO_2$, Petroleum ether/Ethyl acetate=5/1 to 3/1) to afford compound 76B (1.1 g, yield: 82.7%) as a white solid.

Step 3: Synthesis of Compound 76C

To a solution of compound 76B (1.3 g, 4.23 mmol) in THF (40 mL) was added a solution of LiOH.H₂O (888 mg, 21.15 mmol) in H₂O (40 mL) at 0° C. After addition the reaction mixture was stirred for 14 hr at 25° C. The reaction mixture was diluted with H₂O (20 mL) and extracted with MTBE (50 mL). The aqueous phase was neutralized by 1N HCl to the pH~4 and then filtered to afford desired compound. The filtrate was extracted with EtOAc (30 mL×3). The combined organic layers were washed with brine (30 mL), dried over $Na_2SO_4$, filtered and concentrated under reduced pressure to give compound 76C (930 mg, yield 78.72%) as a white solid. MS (ESI) m/z $(M+H)^+$ 279.8.

Step 4: Synthesis of Compound 76D

To a solution of compound 76C (930 mg, 3.33 mmol), methyl (S)-3-(4-allylphenyl)-2-aminopropanoate (851.58 mg, 3.33 mmol, HCl) HOBt (472 mg, 3.50 mmol) and DIEA (3 mL, 16.65 mmol) in DMF (40 mL) was added EDCI (894 mg, 4.66 mmol) at 0° C. under $N_2$ atmosphere. After addition, the reaction mixture was stirred at 25° C. for 14 hr. The reaction mixture was diluted with $H_2O$ 10 mL and extracted with EtOAc (30 mL×2). The combined organic layers were washed with 1N HCl (30 mL), sat. $NaHCO_3$ (30 mL×3), and brine (30 mL), dried over $Na_2SO_4$, filtered and concentrated under reduced pressure to give a residue. The residue was purified by flash silica gel chromatography to afford compound 76D (1.15 g, yield 71.86%) as a brown liquid. $^1$H NMR (400 MHz, DMSO-$d_6$) δ 8.98 (d, J=7.8 Hz, 1H), 8.89 (s, 1H), 8.65-8.64 (m, 1H), 7.82-7.81 (m, 1H), 7.59-7.57 (m, 1H), 7.54 (s, 1H), 7.45 (d, J=8.8 Hz, 1H), 7.15 (d, J=8.3 Hz, 3H), 7.06 (d, J=8.0 Hz, 2H), 6.08-5.87 (m, 2H), 5.21-4.99 (m, 4H), 4.69-4.57 (m, 1H), 3.56 (s, 3H), 3.43 (d, J=6.5 Hz, 2H), 3.31 (s, 2H), 3.03-2.90 (m, 2H). MS (ESI) m/z (M+H)$^+$ 481.2.

Step 5: Synthesis of Compound 76E

A mixture of compound 76D (520 mg, 1.08 mmol) and Zhan-catalyst-1B (79 mg, 108.21 umol) in DCE (350 mL) was degassed and purged with $N_2$ for 3 times, and then the mixture was stirred at 90° C. for 14 hr under $N_2$ atmosphere. The reaction mixture was concentrated under reduced pressure to remove solvent and then diluted with EtOAc 30 mL. The mixture was filtered and concentrated under reduced pressure to give a residue. The residue was purified by flash silica gel chromatography to afford compound 76E (100 mg, yield 19.44%) as a white solid. $^1$H NMR (400 MHz, DMSO-$d_6$) δ 8.68-6.67 (m, 1H), 8.49 (d, J=6.5 Hz, 1H), 8.29 (s, 1H), 8.00-7.97 (m, 1H), 7.67-7.64 (m, 1H), 7.30-7.17 (m, 2H), 7.04 (d, J=8.8 Hz, 1H), 6.64 (d, J=7.8 Hz, 2H), 6.49 (d, J=7.8 Hz, 2H), 6.32-6.16 (m, 1H), 6.00-5.86 (m, 1H), 4.21-4.18 (m, 1H), 3.72 (s, 3H), 3.55-3.36 (m, 3H), 3.31-3.27 (m, 1H), 2.81 (d, J=13.8 Hz, 1H), 2.44 (s, 1H). MS (ESI) m/z (M+H)$^+$ 453.1.

Step 6: Synthesis of Compound 76F

To a solution of compound 76E (130 mg, 287.29 umol) was added a solution of $LiBH_4$ (31 mg, 1.44 mmol) in THF (10 mL) at 0° C. After addition, the reaction mixture was stirred for 2 hr at 25° C. The reaction mixture was quenched by addition sat. $NH_4Cl$ (30 mL), extracted with EtOAc (15 mL×2). The combined organic layers were washed with $H_2O$ (30 mL) and aqueous NaCl (30 mL), dried over $Na_2SO_4$, filtered and concentrated under reduced pressure to give compound 76F (125 mg, yield 82.0%) as a white solid. MS (ESI) m/z (M+H)$^+$ 389.2.

Step 7: Synthesis of Compound 76G

To a solution of compound 76F (100 mg, 235.58 umol) in MeOH (50 mL) was added Pd/C (100 mg, 706.74 umol) in MeOH (50 mL). After that, the mixture was degassed and purged with $H_2$ for 3 times, and then stirred at 25° C. for 2 hr under $H_2$ atmosphere. The reaction mixture was filtered and concentrated under reduced pressure to give a residue. The residue was purified by flash silica gel chromatography to afford compound 76G (50 mg, yield 49.76%) as a white solid. $^1$H NMR (400 MHz, DMSO-$d_6$) δ 8.68-8.69 (m, 1H), 8.63 (d, J=8.0 Hz, 1H), 8.30 (s, 1H), 8.07-8.09 (m, 1H), 7.63-7.66 (m, 1H), 7.40 (d, J=9.0 Hz, 1H), 6.95-6.98 (m, 1H), 6.79-6.86 (m, 3H), 6.73 (d, J=7.8 Hz, 2H), 4.93 (t, J=5.6 Hz, 1H), 4.00-4.06 (m, 2H), 3.53-3.58 (m, 1H), 2.92 (d, J=14.6 Hz, 1H), 2.63 (d, J=5.3 Hz, 1H), 2.58 (s, 2H), 2.45 (s, 2H), 1.63-1.71 (m, 4H). MS (ESI) m/z M$^+$ 426.1.

Step 8: Synthesis of Compound 76B

Compound 76 was prepared following the procedure of Example 52 using intermediate 76G. Compound 76 was obtained as yellow solid (39.21 mg, yield: 46.21%). $^1$H NMR (400 MHz, DMSO-$d_6$) δ 9.49 (s, 1H), 8.98 (d, J=6.0 Hz, 1H), 8.75-8.68 (m, 1H), 8.60 (s, 1H), 8.15-8.13 (m, 1H), 7.68-7.65 (m, 1H), 7.18-7.11 (m, 2H), 6.74 (d, J=8.8 Hz, 1H), 6.54 (s, 4H), 4.20-4.09 (m, 1H), 3.06 (d, J=14.6 Hz, 1H), 2.87-2.83 (m, 1H), 2.42-2.22 (m, 4H), 1.74-1.51 (m, 4H). MS (ESI) m/z (M+H)$^+$ 425.1.

Example 75

(S,Z)—N-(4-chlorophenethyl)-2-oxo-2-(12-oxo-1,3,4,6,9,10,11,12-octahydrobenzo[f][1,4]dioxa[9]aza-cyclotetradecin-10-yl)acetamide (77)

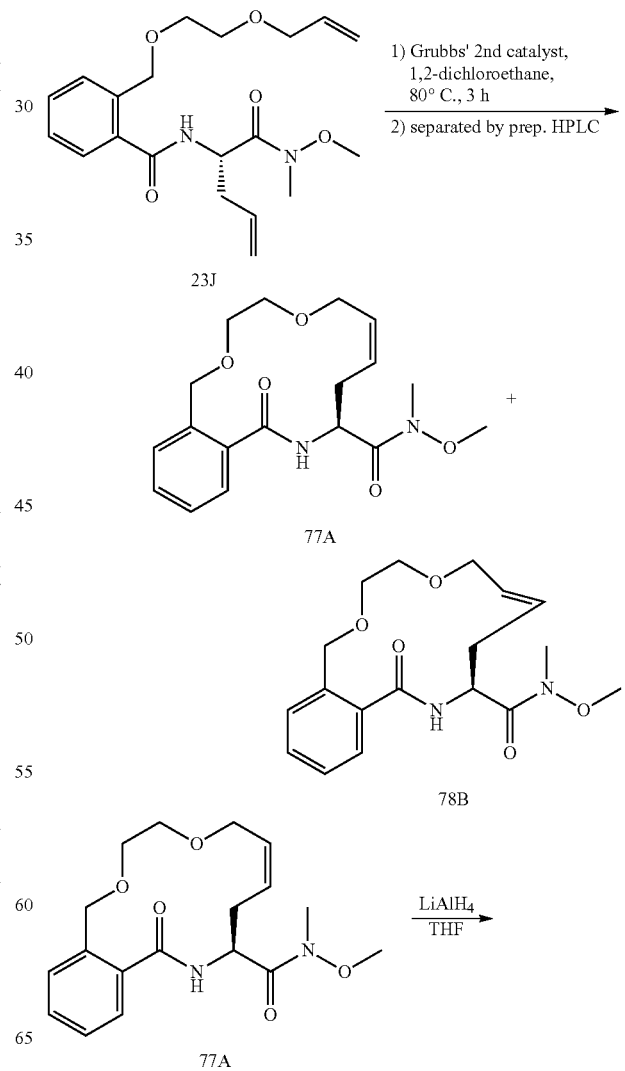

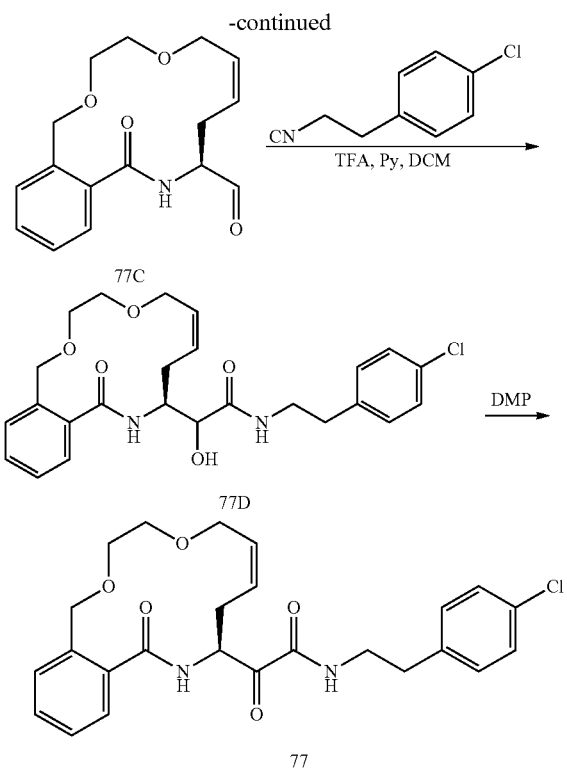

Step 1: Synthesis of Compounds 77A and 77B

Grubbs' 2nd catalyst (451 mg, 531.50 umol) was added to a solution of compound 23J (4.0 g, 10.63 mmol) in 1,2-dichloroethane (1.60 L). The mixture was heated to 80° C. and stirred for 10 h. The mixture was concentrated. The residue was purified by flash column chromatography (DCM/EA=10/1 to 3/1) to give two fractions, which was purified by prep-HPLC (TFA) to give compound 77A (1.18 g, yield 31.8%) as off-white solid and compound 77B (2.06 g, yield 54.9%) as pale yellow oil Compound 77B: $^1$H NMR (400 MHz, DMSO-d$_6$) δ 8.50 (br. d, J=8.8 Hz, 1H), 7.45-7.33 (m, 4H), 5.74-5.56 (m, 2H), 5.06 (br d, J=7.5 Hz, 1H), 4.75 (d, J=11.0 Hz, 1H), 4.42 (d, J=11.0 Hz, 1H), 3.95-3.87 (m, 1H), 3.83-3.73 (m, 4H), 3.62-3.53 (m, 2H), 3.51-3.41 (m, 2H), 3.15 (s, 3H), 2.36 (t, J=6.5 Hz, 2H). MS (ESI) m/z (M+Na)$^+$ 371.1.

Compound 77A: $^1$H NMR (400 MHz, DMSO-d$_6$) δ 8.35 (d, J=6.5 Hz, 1H), 7.54 (dd, J=1.8, 7.3 Hz, 1H), 7.48-7.33 (m, 3H), 5.73-5.53 (m, 2H), 4.94 (d, J=10.5 Hz, 1H), 4.85-4.74 (m, 1H), 4.46 (d, J=10.5 Hz, 1H), 4.05 (dd, J=6.0, 11.5 Hz, 1H), 3.91-3.77 (m, 4H), 3.64-3.56 (m, 1H), 3.55-3.45 (m, 3H), 3.15 (s, 3H), 2.73 (td, J=11.0, 13.6 Hz, 1H), 2.37-2.27 (m, 1H). MS (ESI) m/z (M+Na)$^+$ 371.1.

Step 2: Synthesis of Compound 77C

To a solution of compound 77A (5.50 g, 15.79 mmol) in THF (85.00 mL) cooled to 0° C. was added a solution of LiAlH$_4$ (1M, 18.00 mL) in THF. Then the reaction was stirred at 0° C. for 2 h. The reaction mixture was quenched with 1N HCl (40 mL) and extracted with EtOAc (50 mL×3). The organic layer was washed with 1N HCl (30 mL) and brine (40 mL), dried over Na$_2$SO$_4$. The solid was removed by filtration, the filtrate was concentrated to give the residue, which was just the compound 77C (3.80 g, yield 83.18%) was obtained as light yellow solid. The residue was used directly without further purification. $^1$H NMR (400 MHz, DMSO-d$_6$) δ 9.58 (s, 1H), 8.76-8.73 (m, 1H), 7.61-7.55 (m, 1H), 7.52-7.35 (m, 3H), 5.70-5.65 (m, 1H), 5.65-5.55 (m, 1H), 4.90-4.87 (m, 1H), 4.45-4.43 (m, 1H), 4.17-4.08 (m, 2H), 3.86-3.80 (m, 1H), 3.52-3.48 (m, 3H), 3.44-3.40 (m, 1H), 2.68-2.64 (m, 1H), 2.55-2.52 (m, 1H).

Step 3: Synthesis of Compound 77D

Compound 77A was prepared following the procedure of Example 52 using compound 77C and 1-chloro-4-(2-isocyanoethyl)benzene. Compound 77D was obtained as white solid (38 mg, yield: 9.2%). $^1$H NMR (400 MHz, DMSO-d$_6$) δ 8.01 (d, J=7.7 Hz, 1H), 7.94 (t, J=5.5 Hz, 1H), 7.52 (d, J=7.5 Hz, 1H), 7.43-7.33 (m, 3H), 7.32-7.26 (m, 2H), 7.23-7.17 (m, 2H), 5.82 (s, 1H), 5.62-5.49 (m, 2H), 4.83-4.72 (m, 1H), 4.56 (d, J=11.2 Hz, 1H), 4.12 (s, 2H), 3.98-3.79 (m, 2H), 3.54-3.35 (m, 5H), 3.27-3.21 (m, 1H), 2.81-2.66 (m, 2H), 2.31 (s, 1H), 2.23-2.15 (m, 1H). MS (ESI) m/z (M+H)$^+$ 473.1.

Step 4: Synthesis of Compound 77

Compound 77 was prepared following the procedure of Example 52 using intermediate 77D. Compound 77 was obtained as white solid (18 mg, yield: 18.6%). $^1$H NMR (400 MHz, DMSO-d$_6$) δ 8.82 (t, J=5.9 Hz, 1H), 8.51 (d, J=5.8 Hz, 1H), 7.53-7.39 (m, 4H), 7.34-7.27 (m, 2H), 7.27-7.19 (m, 2H), 5.75-5.68 (m, 1H), 5.56 (d, J=5.8 Hz, 1H), 5.08-5.02 (m, 1H), 4.88 (d, J=10.8 Hz, 1H), 4.47 (d, J=11.0 Hz, 1H), 4.08 (dd, J=6.5, 11.8 Hz, 1H), 3.85 (dd, J=5.8, 11.5 Hz, 1H), 3.58-3.38 (m, 6H), 2.78 (t, J=3.5, 7.0 Hz, 2H), 2.69-2.57 (m, 1H), 2.45-2.38 (m, 1H). MS (ESI) m/z (M+H)$^+$ 471.1.

Example 76

(S,E)-N-(4-chlorophenethyl)-2-oxo-2-(12-oxo-1,3,4,6,9,10,11,12-octahydrobenzo[f][1,4]dioxa[9]azacyclotetradecin-10-yl)acetamide (78)

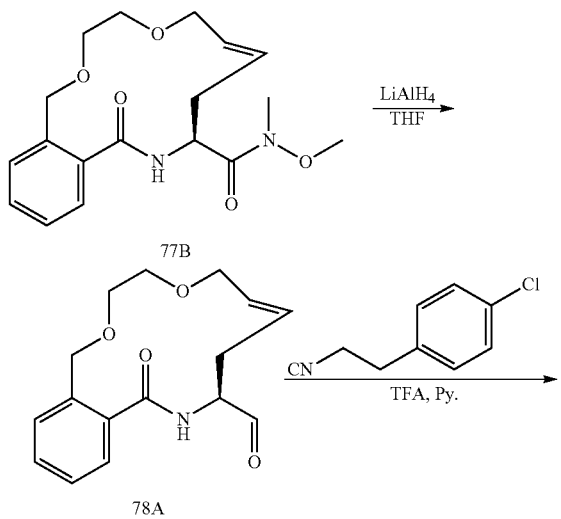

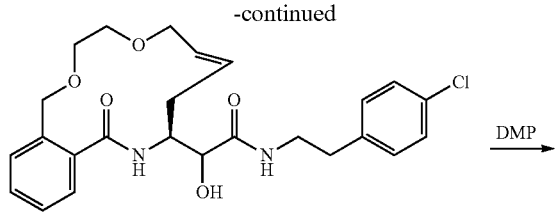

78B

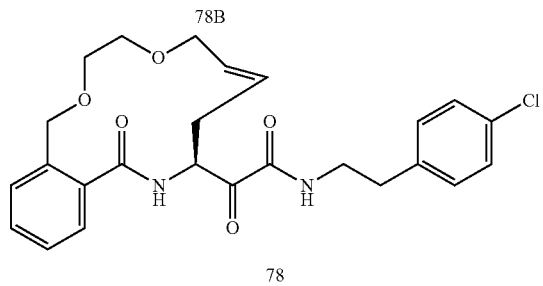

78

Step 1: Synthesis of Compound 78A

To a solution of compound 77B (1.75 g, 5.02 mmol) in THF (10 mL) at −50° C. was added LiAlH$_4$ (1M, 5.3 mL) dropwise. After addition, the mixture was warmed up to −10° C. and stirred for 2 h. The mixture was quenched with 1N HCl (30 mL), extracted with EtOAc (25 mL×2). The organics were collected, washed with brine (50 mL), dried with Na$_2$SO$_4$, filtered and concentrated to afford compound 78A (1.12 g, yield 77.1%) as white solid, which was used directly without further purification. $^1$H NMR (400 MHz, DMSO-d$_6$) δ: 9.63 (s, 1H), 8.61 (d, J=8.4 Hz, 1H), 7.52-7.36 (m, 4H), 5.72-5.59 (m, 2H), 4.77 (d, J=11.6 Hz, 1H), 4.63-4.59 (m, 1H), 4.45 (d, J=11.2 Hz, 1H), 3.91-3.70 (m, 2H), 3.65-3.39 (m, 4H), 2.68-2.61 (m, 1H), 2.32-2.27 (m, 1H).

Step 2: Synthesis of Compound 78B

Compound 78B was prepared following the procedure of Example 52 using compound 78A and 1-chloro-4-(2-isocyanoethyl)benzene. Compound 78B was obtained as white solid (50 mg, yield: 10.9%). MS (ESI) m/z (M+H)$^+$ 473.2.

Step 3: Synthesis of Compound 78

Compound 78 was prepared following the procedure of Example 75 using intermediate 78B. Compound 78 was obtained as white solid (40 mg, yield: 79.5%). $^1$H NMR (400 MHz, CDCl$_3$) δ 8.30-8.25 (m, 1H), 7.81-7.76 (m, 1H), 7.38-7.32 (m, 2H), 7.24-7.19 (m, 3H), 7.11-7.05 (m, 2H), 6.93-6.87 (m, 1H), 5.79-5.69 (m, 1H), 5.49-5.35 (m, 2H), 4.81-4.76 (m, 1H), 4.53-4.47 (m, 1H), 3.94-3.82 (m, 2H), 3.59-3.40 (m, 6H), 2.84-2.73 (m, 2H), 2.69-2.61 (m, 2H). MS (ESI) m/z (M+H)$^+$ 471.2.

Example 77

(S,E)-N-cyclopropyl-2-oxo-2-(12-oxo-1,3,4,6,9,10,11,12-octahydrobenzo[f][1,4]dioxa[9]azacyclotetradecin-10-yl)acetamide (79)

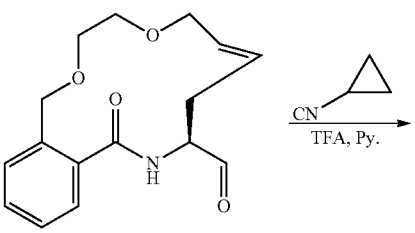

78A

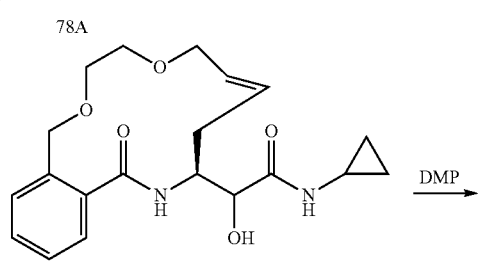

79A

79

Step 1: Synthesis of Compound 79A

Compound 79A was prepared following the procedure of Example 52 using compound 78A and isocyanocyclopropane. Compound 79A was obtained as white solid (50 mg, yield: 10.9%). $^1$H NMR (400 MHz, CDCl$_3$) δ 8.05-7.93 (m, 1H), 7.90-7.68 (m, 1H), 7.45-7.25 (m, 2H), 5.78-5.76 (m, 0.4H), 5.77-5.67 (m, 1H), 5.53-5.45 (m, 1H), 5.39-5.38 (m, 0.5H), 4.90-4.82 (m, 1H), 4.34-4.29 (m, 2H), 3.93-3.91 (m, 2H), 3.80-3.76 (m, 1H), 3.60-3.36 (m, 6H), 2.60-2.57 (m, 1.5H), 2.27-2.12 (m, 2H), 0.59-0.45 (m, 4H). MS (ESI) m/z (M+H)$^+$ 375.2.

Step 2: Synthesis of Compound 79

Compound 79 was prepared following the procedure of Example 75 using intermediate 79A. Compound 79 was obtained as white solid (50 mg, yield: 50.3%). $^1$H NMR (DMSO-d$_6$, 400 MHz) δ 8.84 (br.d., J=4.8 Hz, 1H), 8.60 (br.d., J 0.0 Hz, 1H), 7.53-7.33 (m, 4H), 5.78-5.60 (m, 2H), 5.40-5.30 (m, 1H), 4.72 (d, J=11.0 Hz, 1H), 4.47 (d, J=11.0 Hz, 1H), 3.96-3.88 (m, 1H), 3.86-3.77 (m, 1H), 3.62-3.56 (m, 2H), 3.50 (br.s., 2H), 2.85-2.75 (m, 1H), 2.65-2.58 (m, 1H), 2.37-2.25 (m, 1H), 0.75-0.65 (m, 2H), 0.64-0.52 (m, 2H). MS (ESI) m/z (M+H)$^+$ 373.1.

Example 78

Compounds 80-127

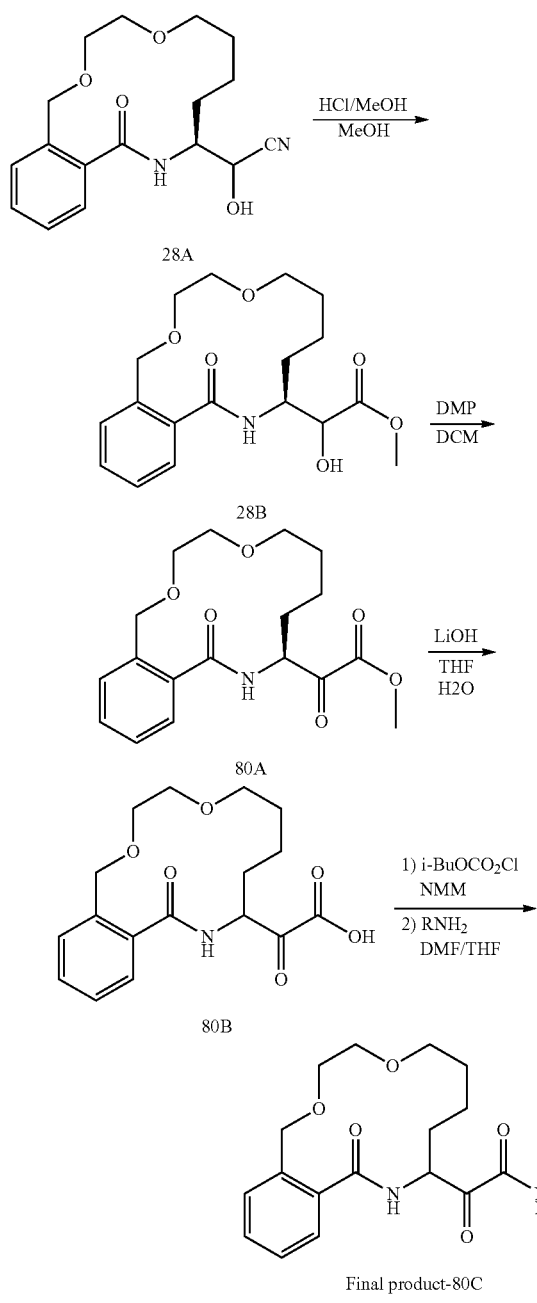

Step 1: Synthesis of Compound 28B

To a solution of compound 28A (6.8 g, 21.36 mmol) in MeOH (100 mL) was added HCl/MeOH (4M, 100 mL) dropwise. After addition, the mixture was stirred at 25° C. for 12 h. The solvent was removed in vacuo. The residue was dissolved in THF (50 mL), H₂O (50 mL) and stirred at 25° C. for 1 h. The reaction was extracted with EtOAc (100 mL×2). The organics were collected and concentrated. The residue was purified by column (PE/EA=1/1) to afford compound 28B (3.3 g, yield 41.7%) as white solid. MS (ESI) m/z (M+H)⁺ 352.1.

Step 2: Synthesis of Compound 80A

Compound 80A was prepared following the procedure of Example 52 using intermediate 28B. Compound 80A was obtained as light yellow solid (410 mg, yield: 70.26%). ¹H NMR (400 MHz, DMSO-d₆) δ 8.93 (d, J=6.8 Hz, 1H), 7.47-7.38 (m, 4H), 4.72-4.69 (m, 1H), 4.65-4.54 (m, 2H), 3.80 (s, 3H), 3.62-3.45 (m, 5H), 1.85-1.71 (m, 2H), 1.60-1.42 (m, 4H). MS (ESI) m/z (M+H)⁺ 350.1.

Step 3: Synthesis of Compound 80B

To a solution of compound 80A (10.1 g, 28.91 mmol) in THF (100 mL) and H₂O (100 mL) was added LiOH.H₂O (6.07 g, 144.55 mmol) at 0° C. portionwise. The mixture was stirred at 0° C. for 1 h. The reaction was acidified with 1N HCl to pH~4. The mixture was extracted with EtOAc (150 mL×2). The organics were collected, dried with Na₂SO₄, filtered and concentrated to afford compound 80B (8.5 g, yield: 87.67%) as light yellow solid. ¹H NMR (400 MHz, DMSO-d₆) δ 8.79 (d, J=7.2 Hz, 1H), 7.45-7.38 (m, 4H), 4.76-4.71 (m, 1H), 4.66 (d, J=10.4 Hz, 1H), 4.52 (d, J=10.0 Hz, 1H), 3.58-3.44 (m, 5H), 1.84-1.42 (m, 6H). MS (ESI) m/z (M+H)⁺ 336.0.

Step 4: Synthesis of Compound 80A

To a solution of compound 80B (1 eq) in THF (10 mL) at −40° C. was added i-BuOCO₂Cl (1.1 eq) and NMM (1.5 eq) dropwise. The mixture was stirred at −40° C. for 0.5 h. Then a solution of corresponding amine (RNH₂) (1.2 eq) in THF/DMF (2 mL/1 mL) was added. The mixture was stirred at −40° C. for 1 h. The reaction was washed with saturated NaHCO₃ (30 mL), extracted with EtOAc (20 mL×2). The organics were collected, dried with Na₂SO₄, filtered and concentrated. The residue was washed with isopropyl ether/CH₃CN (v/v=1/1) (5 mL). The solid was filtered, collected and dried in vacuo to afford the Final product-80C.

Synthesis of Compounds 80-127

N-(2-morpholinoethyl)-2-oxo-2-(12-oxo-1,3,4,6,7,8,9,10,11,12-decahydrobenzo[f][1,4]dioxa[9]azacyclotetradecin-10-yl)acetamide (80)

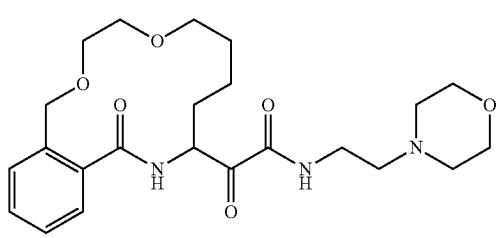

Compound 80 (87.4 mg, yield 24.5%) was obtained as white solid. ¹H NMR (400 MHz, CDCl₃) δ 8.49 (d, J=4.8 Hz, 1H), 7.76-7.68 (m, 1H), 7.39-7.23 (m, 4H), 5.07-4.99 (m, 1H), 4.73 (d, J=9.6 Hz, 1H), 4.57 (d, J=10.0 Hz, 1H), 3.76-3.67 (m, 2H), 3.65-3.59 (m, 4H), 3.59-3.50 (m, 2H), 3.49-3.36 (m, 2H), 3.32 (q, J=6.0 Hz, 2H), 2.43 (t, J=6.0 Hz, 2H), 2.39-2.30 (m, 4H), 1.98-1.80 (m, 2H), 1.57-1.49 (m, 4H). MS (ESI) m/z (M+Na)⁺ 470.2.

203

N-(benzo[d][1,3]dioxol-5-ylmethyl)-2-oxo-2-(12-oxo-1,3,4,6,7,8,9,10,11,12-decahydrobenzo[f][1,4]dioxa[9]azacyclotetradecin-10-yl)acetamide (81)

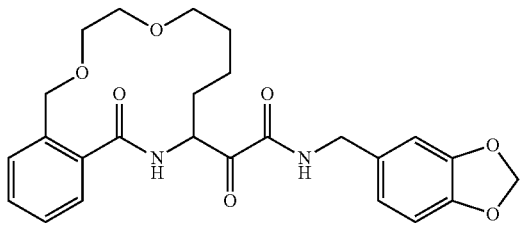

81

Compound 81 (45 mg, yield 16.1%) was obtained as white solid. ¹H NMR (400 MHz, CDCl₃) δ 8.64 (br d, J=4.8 Hz, 1H), 7.86-7.72 (m, 1H), 7.47-7.37 (m, 2H), 7.34-7.29 (m, 1H), 7.09 (br s, 1H), 6.78-6.59 (m, 3H), 5.91 (s, 2H), 5.13-5.00 (m, 1H), 4.77-4.57 (m, 2H), 4.47-4.26 (m, 2H), 3.87-3.74 (m, 2H), 3.69-3.43 (m, 4H), 2.03-1.90 (m, 2H), 1.76-1.58 (m, 4H). MS (ESI) m/z (M+H)⁺ 469.1.

2-Oxo-2-(12-oxo-1,3,4,6,7,8,9,10,11,12-decahydrobenzo[f][1,4]dioxa[9]aza-cyclotetradecin-10-yl)-N-(2-(pyridin-2-yl)ethyl)acetamide (82)

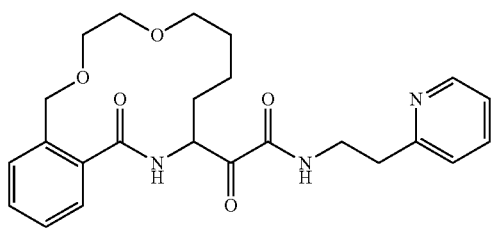

82

Compound 82 (60 mg, yield 22.9%) was obtained as white solid. ¹H NMR (400 MHz, DMSO-d₆) δ 8.88 (br s, 1H), 8.70 (br d, J=6.5 Hz, 1H), 8.58 (br d, J=3.5 Hz, 1H), 7.83-7.73 (m, J=6.8, 6.8 Hz, 1H), 7.53 (br d, J=3.5 Hz, 4H), 7.38-7.22 (m, 2H), 5.18 (br s, 1H), 4.82 (br d, J=10.0 Hz, 1H), 4.62 (br d, J=10.0 Hz, 1H), 3.78-3.58 (m, 6H), 3.51 (br s, 2H), 3.09-2.95 (m, 2H), 1.86 (br s, 1H), 1.78-1.47 (m, 5H). MS (ESI) m/z (M+H)⁺ 440.1.

N-(3,4-dichlorobenzyl)-2-oxo-2-(12-oxo-1,3,4,6,7,8,9,10,11,12-decahydrobenzo[f][1,4]dioxa[9]azacyclotetradecin-10-yl)acetamide (83)

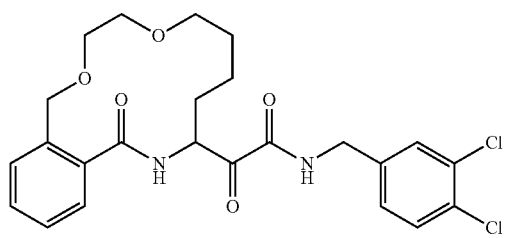

83

204

Compound 83 (20 mg, yield 6.8%) was obtained as white solid. ¹H NMR (400 MHz, DMSO-d₆) δ 9.26 (s, 1H), 8.76 (d, J=6.5 Hz, 1H), 7.53-7.19 (m, 7H), 4.96-4.85 (m, 1H), 4.68-4.51 (m, 2H), 4.42-4.22 (m, 2H), 3.56 (br.s., 3H), 3.50-3.39 (m, 3H), 1.86-1.39 (m, 6H). MS (ESI) m/z (M+H)⁺ 493.1.

2-Oxo-2-(12-oxo-1,3,4,6,7,8,9,10,11,12-decahydrobenzo[f][1,4]dioxa[9]aza-cyclotetradecin-10-yl)-N-(4-sulfamoylbenzyl)acetamide (84)

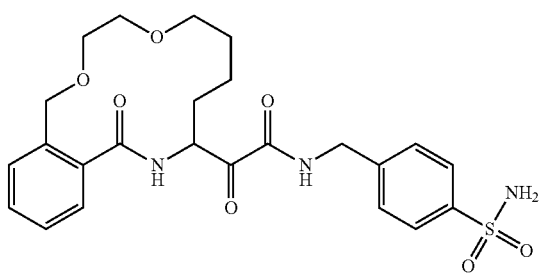

84

Compound 84 (120 mg, yield 40%) was obtained as white solid. ¹H NMR (400 MHz, DMSO-d₆) δ 9.36-9.25 (m, 1H), 8.73 (br d, J=6.8 Hz, 1H), 7.68 (br d, J=8.2 Hz, 2H), 7.48-7.22 (m, 8H), 5.04-4.91 (m, 1H), 4.66 (br d, J=9.9 Hz, 1H), 4.51 (br d, J=9.9 Hz, 1H), 4.45-4.29 (m, 2H), 3.64-3.50 (m, 4H), 3.48-3.43 (m, 2H), 1.86-1.39 (m, 6H). MS (ESI) m/z (M+H)⁺ 504.2.

2-Oxo-2-(12-oxo-1,3,4,6,7,8,9,10,11,12-decahydrobenzo[f][1,4]dioxa[9]aza-cyclotetradecin-10-yl)-N-(prop-2-yn-1-yl)acetamide (85)

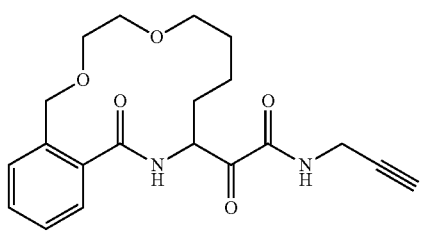

85

Compound 85 (58.1 mg, yield 36.0%) was obtained as white solid. ¹H NMR (DMSO-d₆, 400 MHz) δ 9.10 (br t, J=5.7 Hz, 1H), 8.66 (br d, J=6.8 Hz, 1H), 7.47-7.32 (m, 4H), 5.00 (br t, J=7.4 Hz, 1H), 4.69 (d, J=10.1 Hz, 1H), 4.51 (d, J=9.9 Hz, 1H), 3.89 (br d, J=4.0 Hz, 2H), 3.64-3.41 (m, 6H), 3.13-3.07 (m, 1H), 1.86-1.71 (m, 1H), 1.70-1.38 (m, 5H). MS (ESI) m/z (M+H)⁺ 373.1.

N-(2-chloro-6-methylbenzyl)-2-oxo-2-(12-oxo-1,3,4,6,7,8,9,10,11,12-decahydrobenzo[f][1,4]dioxa[9]azacyclotetradecin-10-yl)acetamide (86)

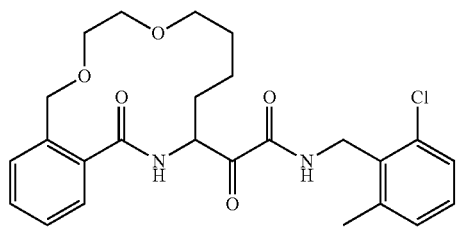

86

Compound 86 (110.8 mg, yield 42.5%) was obtained as white solid. ¹H NMR (DMSO-d$_6$, 400 MHz) δ 8.82 (br s, 1H), 8.62 (br d, J=5.7 Hz, 1H), 7.53-7.04 (m, 7H), 5.02 (br s, 1H), 4.74-4.60 (m, 1H), 4.47 (br s, 3H), 3.54 (br d, J=19.6 Hz, 1H), 2.33 (br s, 3H), 1.90-1.35 (m, 6H). MS (ESI) m/z (M+H)⁺ 473.2.

2-Oxo-2-(12-oxo-1,3,4,6,7,8,9,10,11,12-decahydrobenzo[f][1,4]dioxa[9]aza-cyclotetradecin-10-yl)-N-(4-(trifluoromethoxy)benzyl)acetamide (87)

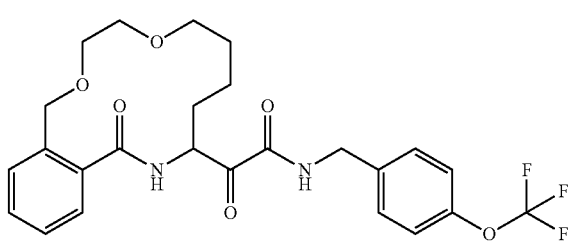

87

Compound 87 (172.1 mg, yield 75.6%) was obtained as white solid. ¹H NMR (400 MHz, CDCl$_3$) δ 8.71 (br d, J=5.2 Hz, 1H), 7.76-7.70 (m, 1H), 7.41-7.34 (m, 2H), 7.27-7.22 (m, 1H), 7.22-7.19 (m, 1H), 7.17-7.08 (m, 2H), 6.98-6.93 (m, 2H), 4.97-4.90 (m, 1H), 4.62-4.57 (m, 1H), 4.54-4.50 (m, 1H), 4.40 (d, J=6.4 Hz, 2H), 3.77-3.68 (m, 2H), 3.62-3.57 (m, 1H), 3.55-3.44 (m, 2H), 3.40-3.33 (m, 1H), 1.93-1.87 (m, 2H), 1.71-1.56 (m, 3H), 1.51-1.46 (m, 1H). MS (ESI) m/z (M+H)⁺ 509.1.

N-(3-methoxyphenethyl)-2-oxo-2-(12-oxo-1,3,4,6,7,8,9,10,11,12-decahydrobenzo[f][1,4]dioxa[9]azacyclotetradecin-10-yl)acetamide (88)

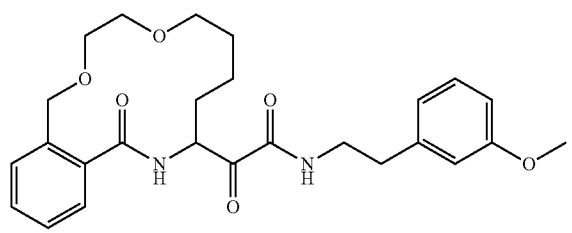

88

Compound 88 (99.9 mg, yield 47.2%) was obtained as white solid. ¹H NMR (400 MHz, CDCl$_3$) δ: 8.53 (br d, J=4.8 Hz, 1H), 7.79-7.73 (m, 1H), 7.45-7.38 (m, 2H), 7.34-7.29 (m, 1H), 7.23-7.15 (m, 1H), 6.99-6.92 (m, 1H), 6.80-6.71 (m, 3H), 5.12-5.03 (m, 1H), 4.76 (d, J=9.6 Hz, 1H), 4.63 (d, J=10.0 Hz, 1H), 3.82-3.73 (m, 5H), 3.69-3.41 (m, 6H), 2.85-2.75 (m, 2H), 2.03-1.85 (m, 2H), 1.63-1.54 (m, 4H). MS (ESI) m/z (M+H)⁺ 469.2.

N-(3-chlorophenethyl)-2-oxo-2-(12-oxo-1,3,4,6,7,8,9,10,11,12-decahydrobenzo[f][1,4]dioxa[9]azacyclotetradecin-10-yl)acetamide (89)

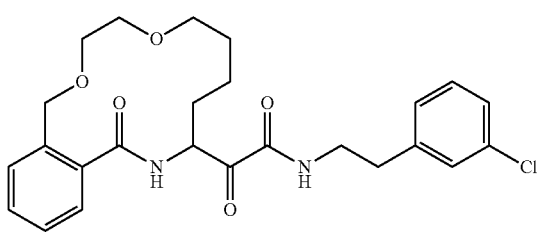

89

Compound 89 (114.9 mg, yield 54.3%) was obtained as white solid. ¹H NMR (400 MHz, CDCl$_3$) δ: 8.52 (br d, J=5.2 Hz, 1H), 7.74-7.68 (m, 1H), 7.39-7.31 (m, 2H), 7.28-7.22 (m, 1H), 7.16-7.07 (m, 3H), 7.02-6.96 (m, 1H), 6.91-6.84 (m, 1H), 5.02-4.95 (m, 1H), 4.68 (d, J=10.0 Hz, 1H), 4.57 (d, J=9.2 Hz, 1H), 3.76-3.67 (m, 2H), 3.63-3.56 (m, 1H), 3.56-3.41 (m, 4H), 3.40-3.35 (m, 1H), 2.81-2.68 (m, 2H), 1.94-1.78 (m, 2H), 1.69-1.55 (m, 4H). MS (ESI) m/z (M+H)⁺ 473.1.

N-isopentyl-2-oxo-2-(12-oxo-1,3,4,6,7,8,9,10,11,12-decahydrobenzo[f][1,4]dioxa[9]azacyclotetradecin-10-yl)acetamide (90)

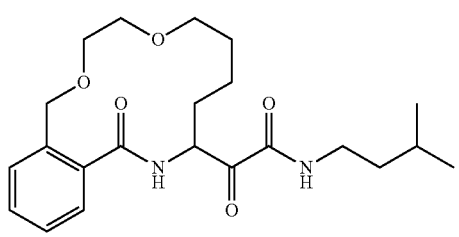

90

Compound 90 (159 mg, yield 87.9%) was obtained as white solid. ¹H NMR (400 MHz, CDCl$_3$) δ 8.54 (d, J=4.6 Hz, 1H), 7.82-7.72 (m, 1H), 7.47-7.36 (m, 2H), 7.35-7.28 (m, 1H), 6.82 (s, 1H), 5.11-5.03 (m, 1H), 4.76 (d, J=9.7 Hz, 1H), 4.65 (d, J=9.7 Hz, 1H), 3.84-3.73 (m, 2H), 3.69-3.63 (m, 1H), 3.63-3.56 (m, 1H), 3.55-3.49 (m, 1H), 3.46 (t, J=5.8 Hz, 1H), 3.36-3.22 (m, 2H), 2.02-1.87 (m, 2H), 1.64-1.50 (m, 5H), 1.41 (q, J=7.3 Hz, 2H), 0.87 (dd, J=1.0, 6.5 Hz, 6H). MS (ESI) m/z (M-1)⁺ 403.2.

2-Oxo-2-(12-oxo-1,3,4,6,7,8,9,10,11,12-decahydrobenzo[f][1,4]dioxa[9]azacyclotetradecin-10-yl)-N-propylacetamide (91)

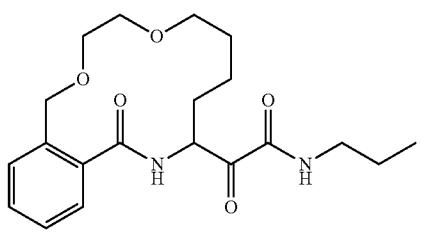

Compound 91 (18 mg, yield 7.87%) was obtained as white solid. $^1$H NMR (CDCl$_3$, 400 MHz) δ 8.47 (br d, J=5.1 Hz, 1H), 7.73-7.69 (m, 1H), 7.37-7.33 (m, 2H), 7.27-7.23 (m, 1H), 6.82 (br s, 1H), 5.02 (ddd, J=3.2, 5.3, 10.0 Hz, 1H), 4.70 (d, J=9.7 Hz, 1H), 4.58 (d, J=9.7 Hz, 1H), 3.76-3.67 (m, 2H), 3.63-3.50 (m, 2H), 3.48-3.35 (m, 2H), 3.19 (quint, J=6.8, 13.8 Hz, 2H), 1.97-1.81 (m, 2H), 1.65-1.52 (m, 4H), 1.50-1.44 (m, 2H), 40.85 (t, J=7.5 Hz, 3H). MS (ESI) m/z (M+H)$^+$ 377.2.

N-(3-morpholinopropyl)-2-oxo-2-(12-oxo-1,3,4,6,7,8,9,10,11,12-decahydrobenzo[f][1,4]dioxa[9]azacyclotetradecin-10-yl)acetamide (92)

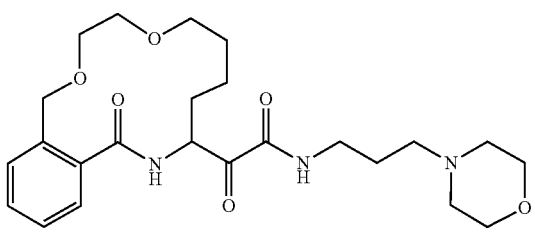

Compound 92 (170 mg, yield 61.5%) was obtained as white solid. $^1$H NMR (400 MHz, DMSO-d$_6$) δ 8.76 (t, J=5.5 Hz, 1H), 8.67 (d, J=6.8 Hz, 1H), 7.46-7.33 (m, 4H), 5.02 (t, J=7.4 Hz, 1H), 4.70 (d, J=9.9 Hz, 1H), 4.54 (d, J=10.1 Hz, 1H), 3.64-3.44 (m, 1H), 3.25-3.05 (m, 2H), 2.34-2.21 (m, 6H), 1.81-1.38 (m, 8H). MS (ESI) m/z (M+H)$^+$ 462.2.

N-(3-(dimethylamino)propyl)-2-oxo-2-(12-oxo-1,3,4,6,7,8,9,10,11,12-decahydrobenzo[f][1,4]dioxa[9]azacyclotetradecin-10-yl)acetamide (93)

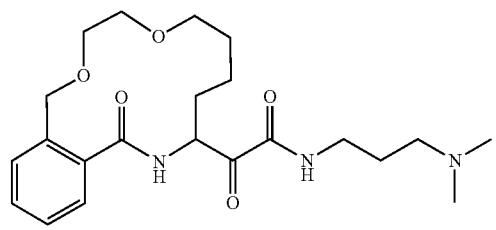

Compound 93 (35.0 mg, yield 12.8%) was obtained as white solid. $^1$H NMR (400 MHz, CDCl$_3$) δ 8.44 (br d, J=5.5 Hz, 1H), 7.96 (br s, 1H), 7.80-7.73 (m, 1H), 7.45-7.37 (m, 2H), 7.34-7.29 (m, 1H), 5.16-5.07 (m, 1H), 4.77 (d, J=9.7 Hz, 1H), 4.71-4.63 (m, 1H), 3.83-3.72 (m, 2H), 3.69-3.63 (m, 1H), 3.62-3.56 (m, 1H), 3.55-3.49 (m, 1H), 3.48-3.42 (m, 1H), 3.37 (q, J=6.2 Hz, 2H), 2.38-2.30 (m, 2H), 2.19 (s, 6H), 2.08-1.84 (m, 4H), 1.73-1.62 (m, 4H). MS (ESI) m/z (M+H)$^+$ 420.2.

2-Oxo-2-(12-oxo-1,3,4,6,7,8,9,10,11,12-decahydrobenzo[f][1,4]dioxa[9]aza-cyclotetradecin-10-yl)-N-(pyridin-2-ylmethyl)acetamide (94)

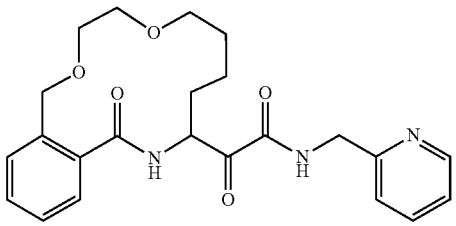

Compound 94 (65.0 mg, yield 25.1%) was obtained as white solid. $^1$H NMR (400 MHz, CDCl$_3$) δ: 8.53 (br d, J=4.8 Hz, 1H), 7.79-7.73 (m, 1H), 7.45-7.38 (m, 2H), 7.34-7.29 (m, 1H), 7.23-7.15 (m, 1H), 6.99-6.92 (m, 1H), 6.80-6.71 (m, 3H), 5.12-5.03 (m, 1H), 4.76 (d, J=9.6 Hz, 1H), 4.63 (d, J=10.0 Hz, 1H), 3.82-3.73 (m, 5H), 3.69-3.41 (m, 6H), 2.85-2.75 (m, 2H), 2.03-1.85 (m, 2H), 1.63-1.54 (m, 4H). MS (ESI) m/z (M+H)$^+$ 469.2.

N-(2-chlorobenzyl)-2-oxo-2-(12-oxo-1,3,4,6,7,8,9,10,11,12-decahydrobenzo[f][1,4]dioxa[9]azacyclotetradecin-10-yl)acetamide (95)

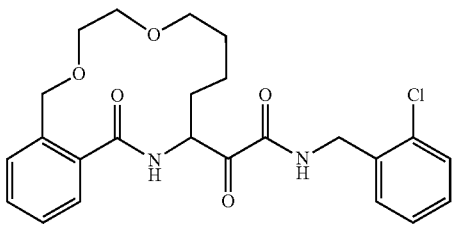

Compound 95 (10 mg, yield 3%) was obtained as white solid. $^1$H NMR (400 MHz, CDCl$_3$) δ 8.63 (br d, J=4.4 Hz, 1H), 7.83-7.63 (m, 1H), 7.42-7.31 (m, 2H), 7.25-7.15 (m, 4H), 7.13-6.94 (m, 2H), 5.06-4.88 (m, 1H), 4.67-4.46 (m, 4H), 3.78-3.66 (m, 2H), 3.63-3.51 (m, 2H), 3.47-3.32 (m, 2H), 1.93-1.81 (m, 2H), 1.75-1.58 (m, 4H). MS (ESI) m/z (M+H)$^+$ 459.2.

209

N-(2,4-dichlorobenzyl)-2-oxo-2-(12-oxo-1,3,4,6,7,8,9,10,11,12-decahydrobenzo[f][1,4]dioxa[9]azacyclotetradecin-10-yl)acetamide (96)

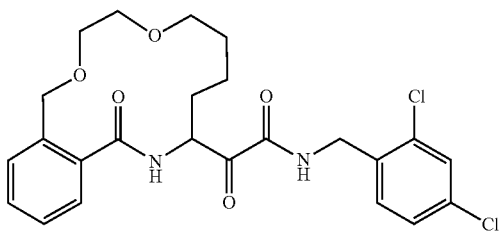

96

Compound 96 (40 mg, yield 12.69%) was obtained as white solid. $^1$H NMR (400 MHz, CDCl$_3$) δ 8.79 (br d, J=4.4 Hz, 1H), 7.87-7.73 (m, 1H), 7.51-7.37 (m, 2H), 7.35-7.29 (m, 2H), 7.27-7.22 (m, 2H), 7.01-6.96 (m, 1H), 5.03-4.94 (m, 1H), 4.69-4.55 (m, 2H), 4.52 (d, J=6.4 Hz, 2H), 3.85-3.76 (m, 2H), 3.70-3.58 (m, 2H), 3.56-3.40 (m, 2H), 2.03-1.92 (m, 2H), 1.79-1.64 (m, 3H), 1.58-1.51 (m, 1H). MS (ESI) m/z (M+H)$^+$ 493.2.

210

N-(4-fluorobenzyl)-2-oxo-2-(12-oxo-1,3,4,6,7,8,9,10,11,12-decahydrobenzo[f][1,4]dioxa[9]azacyclotetradecin-10-yl)acetamide (98)

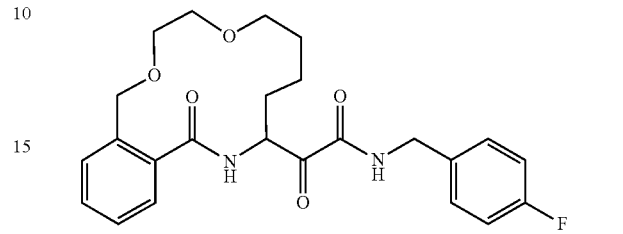

98

Compound 98 (49 mg, yield 17.8%) was obtained as white solid. $^1$H NMR (400 MHz, CDCl$_3$) δ 8.72 (br d, J=4.8 Hz, 1H), 7.82-7.75 (m, 1H), 7.48-7.38 (m, 2H), 7.34-7.28 (m, 1H), 7.24-7.17 (m, 2H), 7.14 (br s, 1H), 6.93-6.83 (m, 2H), 5.07-4.98 (m, 1H), 4.71-4.64 (m, 1H), 4.62-4.56 (m, 1H), 4.43 (d, J=6.3 Hz, 2H), 3.84-3.73 (m, 2H), 3.70-3.63 (m, 1H), 3.62-3.50 (m, 2H), 3.47-3.40 (m, 1H), 2.02-1.88 (m, 2H), 1.76-1.61 (m, 4H). MS (ESI) m/z (M+H)$^+$ 443.2.

N-benzyl-2-oxo-2-(12-oxo-1,3,4,6,7,8,9,10,11,12-decahydrobenzo[f][1,4]dioxa[9]azacyclotetradecin-10-yl)acetamide (97)

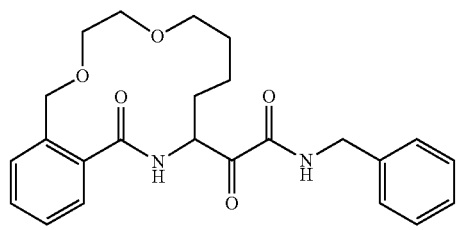

97

Compound 97 (15 mg, yield 5.3%) was obtained as white solid. $^1$H NMR (400 MHz, CDCl$_3$) δ 8.64 (br s, 1H), 7.83-7.74 (m, 1H), 7.46-7.37 (m, 2H), 7.34-7.29 (m, 1H), 7.24 (s, 5H), 7.16 (br s, 1H), 5.12-5.01 (m, 1H), 4.72 (br d, J=9.8 Hz, 1H), 4.62 (br d, J=9.8 Hz, 1H), 4.57-4.38 (m, 2H), 3.82-3.73 (m, 2H), 3.69-3.56 (m, 2H), 3.55-3.42 (m, 2H), 1.98 (br s, 2H), 1.77-1.63 (m, 4H). MS (ESI) m/z (M+H)$^+$ 425.2.

N-(2,4-dimethoxybenzyl)-2-oxo-2-(12-oxo-1,3,4,6,7,8,9,10,11,12-decahydrobenzo[f][1,4]dioxa[9]azacyclotetradecin-10-yl)acetamide (99)

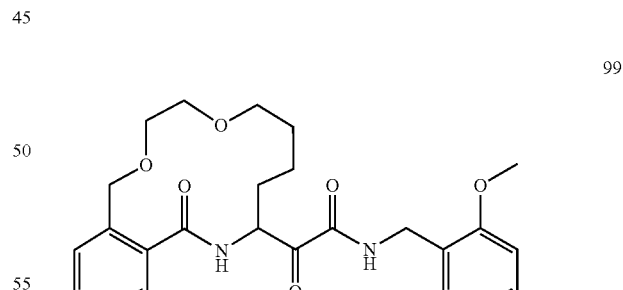

99

Compound 99 (83 mg, yield 28.7%) was obtained as white solid. $^1$H NMR (400 MHz, CDCl$_3$) δ 8.49 (br d, J=5.0 Hz, 1H), 7.85-7.70 (m, 1H), 7.45-7.38 (m, 2H), 7.33-7.28 (m, 1H), 7.14 (d, J=8.0 Hz, 1H), 6.38-6.31 (m, 2H), 5.13-5.06 (m, 1H), 4.73-4.54 (m, 2H), 4.46-4.33 (m, 2H), 3.81-3.72 (m, 8H), 3.65-3.46 (m, 4H), 2.04-1.87 (m, 2H), 1.71-1.60 (m, 4H). MS (ESI) m/z (M+H)$^+$ 485.2.

N-(4-methoxybenzyl)-2-oxo-2-(12-oxo-1,3,4,6,7,8,9,10,11,12-decahydrobenzo[f][1,4]dioxa[9]azacyclotetradecin-10-yl)acetamide (100)

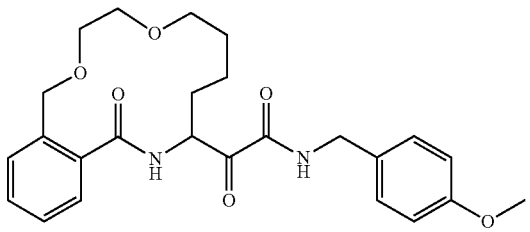

100

Compound 100 (59 mg, yield 33.59%) was obtained as white solid. $^1$H NMR (400 MHz, CDCl$_3$) δ 8.62 (br d, J=5.0 Hz, 1H), 7.91-7.69 (m, 1H), 7.45-7.39 (m, 2H), 7.33-7.29 (m, 1H), 7.17 (d, J=8.8 Hz, 2H), 7.09 (br s, 1H), 6.77 (d, J=8.5 Hz, 2H), 5.12-5.04 (m, 1H), 4.74-4.59 (m, 2H), 4.48-4.33 (m, 2H), 3.82-3.73 (m, 5H), 3.70-3.41 (m, 4H), 2.02-1.91 (m, 2H), 1.72-1.61 (m, 4H). MS (ESI) m/z (M+H)$^+$ 455.2.

2-Oxo-2-(12-oxo-1,3,4,6,7,8,9,10,11,12-decahydrobenzo[f][1,4]dioxa[9]aza-cyclotetradecin-10-yl)-N-(2-(pyridin-3-yl)ethyl)acetamide (101)

101

Compound 101 (110 mg, yield 55.5%) was obtained as white solid. $^1$H NMR (400 MHz, DMSO-d$_6$) δ 8.89-8.72 (m, 1H), 8.58 (br d, J=7.1 Hz, 1H), 8.46-8.36 (m, 2H), 7.62 (br d, J=7.7 Hz, 1H), 7.48-7.38 (m, 4H), 7.27 (dd, J=4.7, 7.6 Hz, 1H), 5.14-5.00 (m, 1H), 4.72 (d, J=9.9 Hz, 1H), 4.52 (d, J=9.9 Hz, 1H), 3.58-3.40 (m, 8H), 2.96-2.68 (m, 2H), 1.78-1.40 (m, 6H). MS (ESI) m/z (M+H)$^+$ 440.3.

N-(2-ethoxybenzyl)-2-oxo-2-(12-oxo-1,3,4,6,7,8,9,10,11,12-decahydrobenzo[f][1,4]dioxa[9]azacyclotetradecin-10-yl)acetamide (102)

102

Compound 102 (140 mg, yield 66.6%) was obtained as white solid. $^1$H NMR (400 MHz, DMSO-d$_6$) δ 8.91 (br t, J=6.3 Hz, 1H), 8.70 (d, J=7.0 Hz, 1H), 7.47-7.38 (m, 4H), 7.18 (br t, J=7.5 Hz, 1H), 7.08 (d, J=7.0 Hz, 1H), 6.94 (d, J=8.0 Hz, 1H), 6.74 (t, J=7.3 Hz, 1H), 5.02 (br t, J=7.3 Hz, 1H), 4.68 (d, J=10.0 Hz, 1H), 4.53 (d, J=10.0 Hz, 1H), 4.38-4.24 (m, 2H), 4.04 (q, J=6.9 Hz, 2H), 3.61-3.38 (m, 6H), 1.85-1.45 (m, 6H), 1.35 (t, J=6.8 Hz, 3H). MS (ESI) m/z (M+H)$^+$ 469.2.

2-Oxo-2-(12-oxo-1,3,4,6,7,8,9,10,11,12-decahydrobenzo[f][1,4]dioxa[9]aza-cyclotetradecin-10-yl)-N-(pyridin-3-ylmethyl)acetamide (103)

103

Compound 103 (50 mg, yield 25.0%) was obtained as white solid. $^1$H NMR (400 MHz, DMSO-d$_6$) δ 9.28 (t, J=6.3 Hz, 1H), 8.71 (d, J=6.6 Hz, 1H), 8.47 (s, 1H), 8.41 (d, J=3.5 Hz, 1H), 7.62 (d, J=7.9 Hz, 1H), 7.47-7.31 (m, 5H), 7.23 (dd, J=4.9, 7.7 Hz, 1H), 5.04-4.90 (m, 1H), 4.65 (d, J=9.9 Hz, 1H), 4.51 (d, J=9.9 Hz, 1H), 4.42-4.26 (m, 2H), 3.66-3.50 (m, 4H), 3.48-3.36 (m, 4H), 1.85-1.75 (m, 1H), 1.73-1.64 (m, 1H), 1.61-1.39 (m, 4H). MS (ESI) m/z (M+H)$^+$ 426.1.

2-Oxo-2-(12-oxo-1,3,4,6,7,8,9,10,11,12-decahydrobenzo[f][1,4]dioxa[9]aza-cyclotetradecin-10-yl)-N-phenethylacetamide (104)

104

Compound 104 (110 mg, yield 55.0%) was obtained as white solid. $^1$H NMR (400 MHz, DMSO-d$_6$) δ 8.76 (t, J=5.7 Hz, 1H), 8.58 (d, J=6.8 Hz, 1H), 7.46-7.36 (m, 4H), 7.29-7.22 (m, 2H), 7.20-7.12 (m, 3H), 5.07 (t, J=7.4 Hz, 1H), 4.71 (d, J=10.1 Hz, 1H), 4.50 (d, J=10.1 Hz, 1H), 3.62-3.32 (m, 10H), 2.80-2.71 (m, 2H), 1.80-1.69 (m, 1H), 1.65-1.52 (m, 2H), 1.50-1.39 (m, 3H). MS (ESI) m/z (M+H)$^+$ 439.2.

N-(3-(4-methylpiperazin-1-yl)propyl)-2-oxo-2-(12-oxo-1,3,4,6,7,8,9,10,11,12-decahydrobenzo[f][1,4]dioxa[9]azacyclotetradecin-10-yl)acetamide (105)

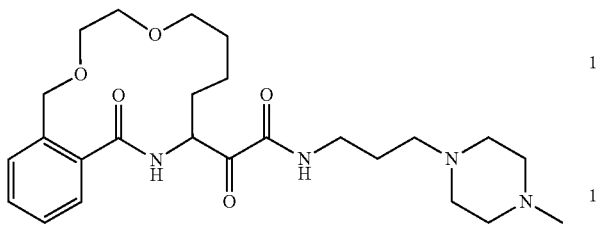

Compound 105 (56.6 mg, yield 16.0%) was obtained as white solid. $^1$H NMR (DMSO-d$_6$, 400 MHz) δ 1.39-1.74 (m, 7H), 1.77-1.90 (m, 1H), 2.13 (s, 3H), 2.16-2.40 (m, 9H), 3.17 (tt, J=12.77, 6.43 Hz, 2H), 3.40-3.51 (m, 4H), 3.52-3.67 (m, 3H), 455 (d, J=9.79 Hz, 1H), 4.71 (d, J=10.04 Hz, 1H), 5.04 (br t, J=7.4 Hz, 1H), 7.31-7.51 (m, 4H), 8.64 (br d, J=6.78 Hz, 1H), 8.73 (br t, J=6.02 Hz, 1H). MS (ESI) m/z (M+H)$^+$ 475.3.

N-(3-fluorobenzyl)-2-oxo-2-(12-oxo-1,3,4,6,7,8,9,10,11,12-decahydrobenzo[f][1,4]dioxa[9]azacyclotetradecin-10-yl)acetamide (106)

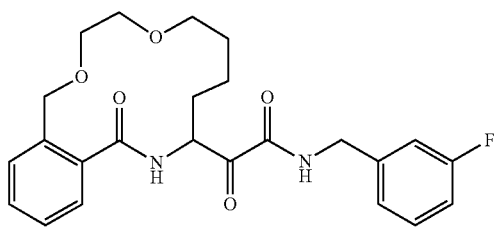

Compound 106 (203 mg, yield 74.2%) was obtained as white solid. $^1$H NMR (400 MHz, DMSO-d$_6$) δ 9.23 (t, J=6.4 Hz, 1H), 8.70 (d, J=6.6 Hz, 1H), 7.45-7.35 (m, 4H), 7.30-7.22 (m, 1H), 7.10-6.98 (m, 3H), 5.00-4.93 (m, 1H), 4.65 (d, J=10.1 Hz, 1H), 4.51 (d, J=9.9 Hz, 1H), 4.40-4.26 (m, 2H), 3.65-3.51 (m, 3H), 3.48-3.42 (m, 1H), 3.41-3.35 (m, 2H), 1.80-1.41 (m, 6H). MS (ESI) m/z (M+H)$^+$ 443.1.

N-(2-chloro-6-fluorobenzyl)-2-oxo-2-(12-oxo-1,3,4,6,7,8,9,10,11,12-decahydrobenzo[f][1,4]dioxa[9]azacyclotetradecin-10-yl)acetamide (107)

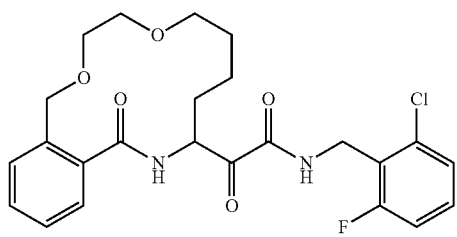

Compound 107 (183 mg, yield 63.7%) was obtained as white solid. $^1$H NMR (400 MHz, DMSO-d$_6$) δ 9.00 (t, J=5.4 Hz, 1H), 8.58 (d, J=7.3 Hz, 1H), 7.44-7.31 (m, 5H), 7.30-7.26 (m, 1H), 7.20-7.15 (m, 1H), 5.06-5.01 (m, 1H), 4.69 (d, J=9.9 Hz, 1H), 4.51-4.44 (m, 3H), 3.59-3.49 (m, 3H), 3.48-3.41 (m, 1H), 3.40-3.33 (m, 2H), 1.82-1.40 (m, 6H). MS (ESI) m/z (M+H)$^+$ 477.1.

N-(5-chloro-2-methylbenzyl)-2-oxo-2-(12-oxo-1,3,4,6,7,8,9,10,11,12-decahydrobenzo[f][1,4]dioxa[9]azacyclotetradecin-10-yl)acetamide (108)

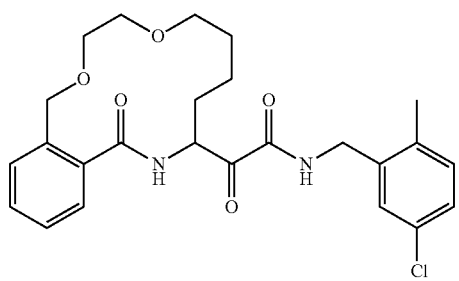

Compound 108 (174 mg, yield 59.2%) was obtained as white solid. $^1$H NMR (400 MHz, DMSO-d$_6$) δ 9.17 (t, J=6.2 Hz, 1H), 8.70 (d, J=6.8 Hz, 1H), 7.44-7.35 (m, 4H), 7.18 (s, 1H), 7.17-7.12 (m, 2H), 4.98-4.93 (m, 1H), 4.65 (d, J=9.9 Hz, 1H), 4.52 (d, J=9.9 Hz, 1H), 4.35-4.21 (m, 2H), 3.62-3.51 (m, 3H), 3.48-3.42 (m, 1H), 3.41-3.34 (m, 2H), 2.23 (s, 3H), 1.84-1.42 (m, 6H). MS (ESI) m/z (M+H)$^+$ 473.1.

N-cyclopentyl-2-oxo-2-(12-oxo-1,3,4,6,7,8,9,10,11,12-decahydrobenzo[f][1,4]dioxa[9]azacyclotetradecin-10-yl)acetamide (109)

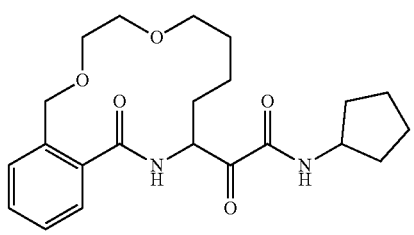

Compound 109 (82.1 mg, yield 45.6%) was obtained as white solid. $^1$H NMR (400 MHz, CDCl$_3$) δ 8.43 (s, 1H), 7.70 (d, J=3.3 Hz, 1H), 7.35 (d, J=3.5 Hz, 2H), 7.26 (d, J=3.5 Hz, 1H), 6.75 (d, J=6.8 Hz, 1H), 5.03 (s, 1H), 4.72 (d, J=9.7 Hz, 1H), 4.58 (d, J=9.7 Hz, 1H), 4.16-4.01 (m, 1H), 3.71 (s, 2H), 3.63-3.51 (m, 2H), 3.42 (d, J=16.8 Hz, 2H), 2.02-1.80 (m, 4H), 1.71-1.56 (m, 7H), 1.37 (dd, J=6.2, 12.6 Hz, 2H), 1.19 (s, 1H). MS (ESI) m/z (M+H)$^+$ 403.2.

215

N-(2-(dimethylamino)ethyl)-2-oxo-2-(12-oxo-1,3,4,6,7,8,9,10,11,12-decahydrobenzo[f][1,4]dioxa[9]azacyclotetradecin-10-yl)acetamide (110)

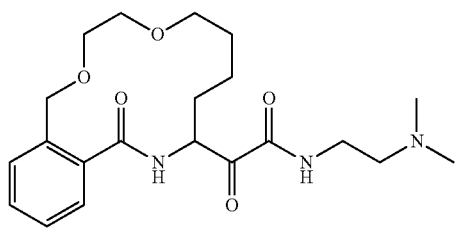

Compound 110 (60.8 mg, yield 32.3%) was obtained as white solid. $^1$H NMR (400 MHz, CDCl$_3$) δ 8.42 (d, J=4.6 Hz, 1H), 7.77-7.65 (m, 1H), 7.39-7.31 (m, 3H), 7.28-7.23 (m, 1H), 5.06 (dt, J=2.6, 5.3 Hz, 1H), 4.74 (d, J=9.5 Hz, 1H), 4.57 (d, J=9.7 Hz, 1H), 3.70 (d, J=3.1 Hz, 2H), 3.64-3.57 (m, 1H), 3.56-3.49 (m, 1H), 3.49-3.37 (m, 2H), 3.31 (q, J=5.7 Hz, 2H), 2.40 (t, J=5.5 Hz, 2H), 2.17 (s, 6H), 2.01-1.91 (m, 1H), 1.83 (s, 5H). MS (ESI) m/z (M+H)$^+$ 406.2.

N-(3,5-dimethylbenzyl)-2-oxo-2-(12-oxo-1,3,4,6,7,8,9,10,11,12-decahydrobenzo[f][1,4]dioxa[9]azacyclotetradecin-10-yl)acetamide (111)

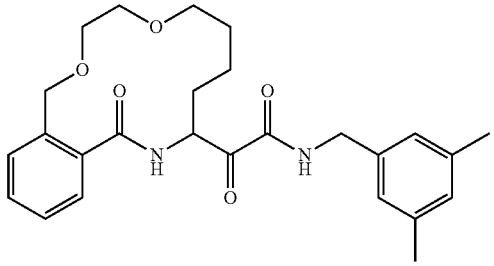

Compound 111 (82.6 mg, yield 61.2%) was obtained as white solid. $^1$H NMR (400 MHz, CDCl$_3$) δ 8.56 (d, J=5.0 Hz, 1H), 7.76-7.69 (m, 1H), 7.39-7.31 (m, 2H), 7.27-7.22 (m, 1H), 7.03 (s, 1H), 6.79 (s, 3H), 5.05-4.97 (m, 1H), 4.69-4.63 (m, 1H), 4.60-4.55 (m, 1H), 4.41-4.25 (m, 2H), 3.76-3.69 (m, 2H), 3.63-3.56 (m, 1H), 3.56-3.49 (m, 1H), 3.49-3.43 (m, 1H), 3.39 (td, J=4.2, 8.3 Hz, 1H), 2.16 (s, 6H), 1.96-1.84 (m, 2H), 1.67-1.57 (m, 4H). MS (ESI) m/z (M+H)$^+$ 453.2.

216

N-(4-butylbenzyl)-2-oxo-2-(12-oxo-1,3,4,6,7,8,9,10,11,12-decahydrobenzo[f][1,4]dioxa[9]azacyclotetradecin-10-yl)acetamide (112)

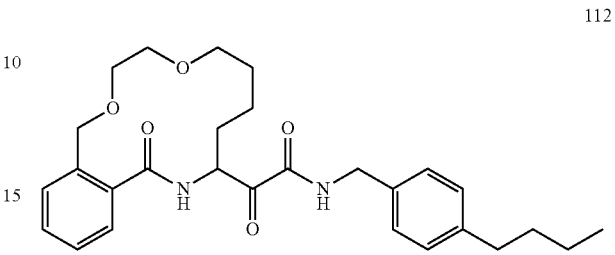

Compound 112 (64.6 mg, yield 22%) was obtained as white solid. $^1$H NMR (CDCl$_3$, 400 MHz) δ 8.63-8.57 (m, 1H), 7.84-7.73 (m, 1H), 7.45-7.39 (m, 2H), 7.33-7.29 (m, 1H), 7.18-7.03 (m, 5H), 5.12-5.06 (m, 1H), 4.75-4.70 (m, 1H), 4.64-4.60 (m, 1H), 4.50-4.36 (m, 2H), 3.81-3.75 (m, 2H), 3.69-3.63 (m, 1H), 3.62-3.56 (m, 1H), 3.56-3.49 (m, 1H), 3.49-3.42 (m, 1H), 2.59-2.52 (m, 2H), 2.05-1.88 (m, 2H), 1.73-1.60 (m, 4H), 1.57-1.50 (m, 2H), 1.38-1.27 (m, 2H), 0.91 (t, J=7.4 Hz, 3H). MS (ESI) m/z (M+H)$^+$ 481.2.

N-(4-(dimethylamino)benzyl)-2-oxo-2-(12-oxo-1,3,4,6,7,8,9,10,11,12-decahydrobenzo[f][1,4]dioxa[9]azacyclotetradecin-10-yl)acetamide (113)

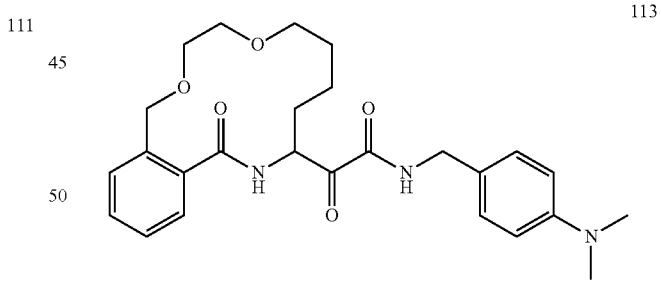

Compound 113 (33.6 mg, yield 15.7%) was obtained as white solid. $^1$H NMR (CDCl$_3$, 400 MHz) δ 8.48 (br d, J=4.9 Hz, 1H), 7.75-7.68 (m, 1H), 7.39-7.32 (m, 2H), 7.28-7.22 (m, 1H), 7.05 (d, J=8.8 Hz, 2H), 6.98 (br s, 1H), 6.55 (d, J=8.6 Hz, 2H), 5.05 (ddd, J=2.9, 5.2, 10.0 Hz, 1H), 4.70-4.64 (m, 1H), 4.60-4.53 (m, 1H), 4.38-4.22 (m, 2H), 3.76-3.67 (m, 2H), 3.63-3.56 (m, 1H), 3.56-3.50 (m, 1H), 3.49-3.43 (m, 1H), 3.40 (br t, J=5.8 Hz, 1H), 2.84 (s, 6H), 1.97-1.81 (m, 2H), 1.63-1.56 (m, 4H). MS (ESI) m/z (M+H)$^+$ 468.2.

N-cyclopropyl-2-oxo-2-(12-oxo-1,3,4,6,7,8,9,10,11,12-decahydrobenzo[f][1,4]dioxa[9]azacyclotetradecin-10-yl)acetamide (114)

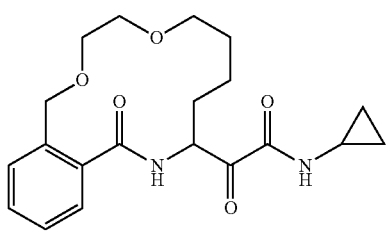

114

Compound 114 (56.1 mg, yield 33.5%) was obtained as white solid. ¹H NMR (400 MHz, CDCl₃) δ 8.61-8.45 (m, 1H), 7.78-7.64 (m, 1H), 7.41-7.23 (m, 3H), 6.89-6.75 (m, 1H), 5.02-4.92 (m, 1H), 4.72-4.56 (m, 2H), 3.80-3.68 (m, 2H), 3.64-3.33 (m, 4H), 2.73-2.63 (m, 1H), 1.98-1.79 (m, 2H), 1.68-1.51 (m, 4H), 0.81-0.67 (m, 2H), 0.57-0.43 (m, 2H). MS (ESI) m/z (M+H)⁺ 375.1.

1-Morpholino-2-(12-oxo-1,3,4,6,7,8,9,10,11,12-decahydrobenzo[f][1,4]dioxa[9]azacyclotetradecin-10-yl)ethane-1,2-dione (115)

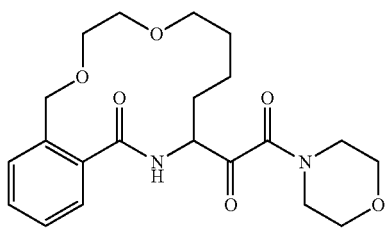

115

Compound 115 (22.9 mg, yield 7.6%) was obtained as white solid. ¹H NMR (DMSO-d₆, 400 MHz) δ 9.01 (br d, J=6.8 Hz, 1H), 7.50-7.38 (m, 4H), 4.67-4.53 (m, 2H), 4.53-4.46 (m, 1H), 3.68-3.38 (m, 14H), 2.01-1.89 (m, 1H), 1.88-1.76 (m, 1H), 1.70-1.55 (m, 1H), 1.50-1.35 (m, 2H). MS (ESI) m/z (M+H)⁺ 405.2.

N-(3-methoxybenzyl)-N-methyl-2-oxo-2-(12-oxo-1,3,4,6,7,8,9,10,11,12-decahydrobenzo[f][1,4]dioxa[9]azacyclotetradecin-10-yl)acetamide (116)

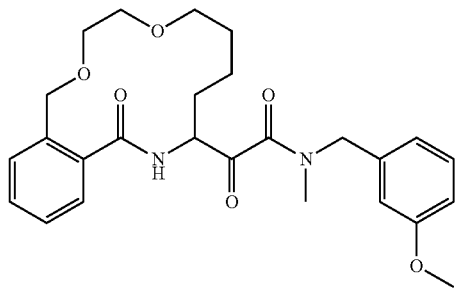

116

Compound 116 (65 mg, yield 46.5%) was obtained as light yellow solid. ¹H NMR (400 MHz, DMSO-d₆): δ 9.03-8.84 (m, 1H), 7.49-7.33 (m, 3H), 7.31-7.25 (m, 1H), 7.13-7.06 (m, 1H), 6.93-6.85 (m, 1H), 6.85-6.79 (m, 1H), 6.77 (d, J=7.5 Hz, 1H), 4.70-4.52 (m, 4H), 4.47-4.33 (m, 1H), 3.71 (s, 1H), 3.68 (s, 2H), 3.65-3.37 (m, 6H), 2.90 (s, 2H), 2.76 (s, 1H), 2.01-1.74 (m, 2H), 1.69-1.36 (m, 4H). MS (ESI) m/z (M+H)⁺ 469.2.

2-Oxo-2-(12-oxo-1,3,4,6,7,8,9,10,11,12-decahydrobenzo[f][1,4]dioxa[9]aza-cyclotetradecin-10-yl)-N-(pyridin-4-ylmethyl)acetamide (117)

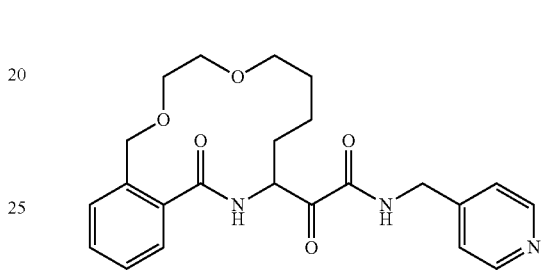

117

Compound 117 (48.2 mg, yield 36.8%) was obtained as white solid. ¹H NMR (DMSO-d₆, 400 MHz) δ 9.31 (t, J=6.3 Hz, 1H), 8.80 (d, J=6.8 Hz, 1H), 8.41-8.36 (m, 2H), 7.52-7.38 (m, 4H), 7.24 (d, J=6.0 Hz, 2H), 5.00-4.91 (m, 1H), 4.66 (d, J=9.9 Hz, 1H), 4.56 (d, J=9.9 Hz, 1H), 4.37 (dq, J=6.2, 15.8 Hz, 2H), 3.68-3.54 (m, 3H), 3.52-3.40 (m, 3H), 1.88-1.69 (m, 2H), 1.66-1.43 (m, 4H). MS (ESI) m/z (M+H)⁺ 426.1.

N-(3-(methylsulfonyl)benzyl)-2-oxo-2-(12-oxo-1,3,4,6,7,8,9,10,11,12-decahydrobenzo[f][1,4]dioxa[9]azacyclotetradecin-10-yl)acetamide (118)

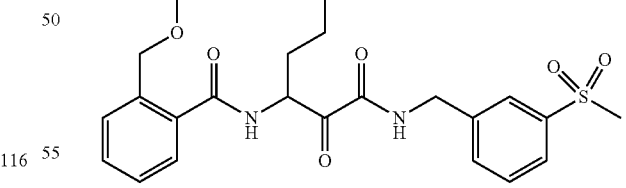

118

Compound 118 (85 mg, yield 37.8%) was obtained as white solid. ¹H NMR (DMSO-d₆, 400 MHz) δ 9.38 (br t, J=6.0 Hz, 1H), 8.74 (br d, J=6.8 Hz, 1H), 7.90-7.76 (m, 2H), 7.67-7.51 (m, 2H), 7.49-7.35 (m, 5H), 5.00 (br d, J=7.3 Hz, 1H), 4.69 (br d, J=9.9 Hz, 1H), 4.55 (br d, J=10.4 Hz, 1H), 4.46 (br t, J=6.2 Hz, 1H), 4.42 (br s, 1H), 3.67-3.39 (m, 7H), 3.17 (s, 3H), 1.90-1.42 (m, 7H). MS (ESI) m/z (M+H)⁺ 503.1.

N-(3,5-dimethoxybenzyl)-2-oxo-2-(12-oxo-1,3,4,6,7,8,9,10,11,12-decahydrobenzo[f][1,4]dioxa[9]azacyclotetradecin-10-yl)acetamide (119)

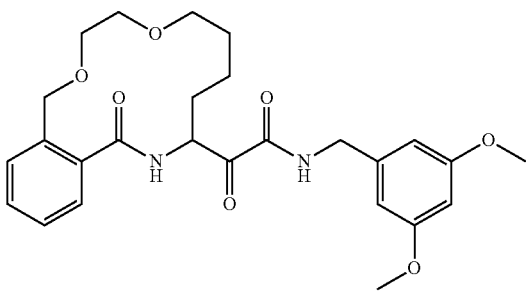

119

Compound 119 (95.0 mg, yield 42.0%) was obtained as white solid. $^1$H NMR (400 MHz, CDCl$_3$) δ: 8.64 (br d, J=5.2 Hz, 1H), 7.76-7.64 (m, 1H), 7.40-7.31 (m, 2H), 7.28-7.22 (m, 1H), 7.13-7.04 (m, 1H), 6.35-6.29 (m, 2H), 6.28-6.23 (m, 1H), 5.02-4.91 (m, 1H), 4.68-4.55 (m, 2H), 4.35 (d, J=5.6 Hz, 2H), 3.78-3.72 (m, 2H), 3.63 (s, 6H), 3.60-3.43 (m, 3H), 3.41-3.32 (m, 1H), 1.95-1.85 (m, 2H), 1.71-1.58 (m, 2H), 1.54-1.44 (m, 2H). MS (ESI) m/z (M+H)$^+$ 485.2.

2-Oxo-2-(12-oxo-1,3,4,6,7,8,9,10,11,12-decahydrobenzo[f][1,4]dioxa[9]aza-cyclotetradecin-10-yl)-N-(3-(trifluoromethoxy)benzyl)acetamide (120)

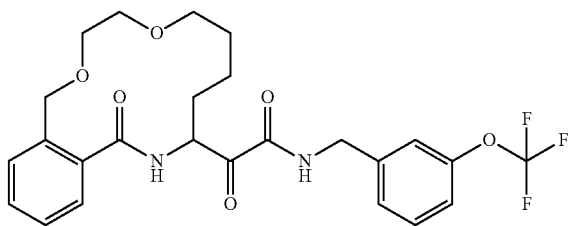

120

Compound 120 (38 mg, yield 15.9%) was obtained as white solid. $^1$H NMR (400 MHz, DMSO-d$_6$): δ 9.28 (t, J=6.4 Hz, 1H), 8.72 (d, J=7.0 Hz, 1H), 7.48-7.32 (m, 5H), 7.27 (d, J=7.8 Hz, 1H), 7.24-7.16 (m, 2H), 5.00-4.92 (m, 1H), 4.65 (d, J=10.0 Hz, 1H), 4.52 (d, J=10.0 Hz, 1H), 4.44-4.29 (m, 2H), 3.65-3.51 (m, 3H), 3.48-3.36 (m, 3H), 1.86-1.36 (m, 6H). MS (ESI) m/z (M+H)$^+$ 509.1.

N-(4-(methylsulfonyl)benzyl)-2-oxo-2-(12-oxo-1,3,4,6,7,8,9,10,11,12-decahydrobenzo[f][1,4]dioxa[9]azacyclotetradecin-10-yl)acetamide (121)

121

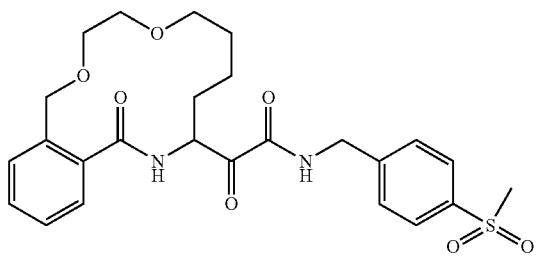

Compound 121 (94 mg, yield 41.82%) was obtained as white solid. $^1$H NMR (400 MHz, DMSO-d$_6$): δ 9.33 (t, J=6.1 Hz, 1H), 8.75 (d, J=6.8 Hz, 1H), 7.77 (d, J=8.3 Hz, 2H), 7.52-7.35 (m, 6H), 4.95 (t, J=7.2 Hz, 1H), 4.64 (d, J=9.8 Hz, 1H), 4.56-4.32 (m, 3H), 3.64-3.51 (m, 3H), 3.49-3.38 (m, 3H), 3.15 (s, 3H), 1.88-1.34 (m, 6H). MS (ESI) m/z (M+H)$^+$ 503.1.

N-(2-(2-(2-methoxyethoxy)ethoxy)ethyl)-2-oxo-2-(12-oxo-1,3,4,6,7,8,9,10,11,12-decahydrobenzo[f][1,4]dioxa[9]azacyclotetradecin-10-yl)acetamide (122)

122

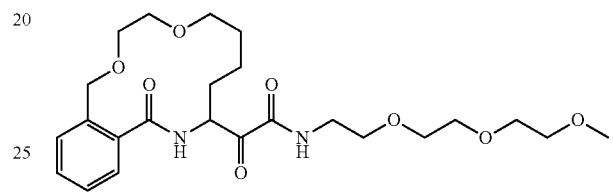

Compound 122 (70.7 mg, yield 22.7%) was obtained as light yellow solid. $^1$H NMR (400 MHz, CDCl$_3$) δ: 8.50 (br d, J=4.8 Hz, 1H), 7.81-7.72 (m, 1H), 7.51-7.28 (m, 4H), 5.17-5.06 (m, 1H), 4.78 (d, J=9.6 Hz, 1H), 4.64 (d, J=9.6 Hz, 1H), 3.82-3.71 (m, 2H), 3.68-3.44 (m, 16H), 3.37 (s, 3H), 2.01-1.56 (m, 5H), 1.55-1.52-1.78 (m, 1H). MS (ESI) m/z (M+H)$^+$ 481.2.

N-(3,4-dimethoxyphenethyl)-2-oxo-2-(12-oxo-1,3,4,6,7,8,9,10,11,12-decahydrobenzo[f][1,4]dioxa[9]azacyclotetradecin-10-yl)acetamide (123)

123

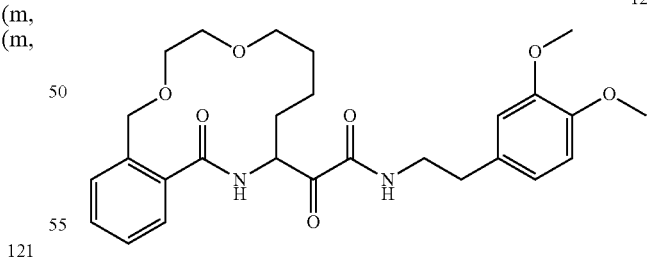

Compound 123 (16 mg, yield 7%) was obtained as white solid. $^1$H NMR (CDCl$_3$, 400 MHz) δ 8.58 (br d, J=4.4 Hz, 1H), 7.81-7.71 (m, 1H), 7.48-7.37 (m, 2H), 7.33 (br d, J=2.6 Hz, 1H), 6.94 (br s, 1H), 6.81-6.77 (m, 1H), 6.75-6.69 (m, 2H), 5.07 (br d, J=4.4 Hz, 1H), 4.76 (d, J=9.7 Hz, 1H), 4.64 (br d, J=9.7 Hz, 1H), 3.90-3.75 (m, 9H), 3.69-3.42 (m, 7H), 2.97-2.87 (m, 1H), 2.83-2.72 (m, 2H), 2.00-1.86 (m, 2H), 1.72-1.65 (m, 1H). MS (ESI) m/z (M+H)$^+$ 499.2.

2-Oxo-2-(12-oxo-1,3,4,6,7,8,9,10,11,12-decahydrobenzo[f][1,4]dioxa[9]azacyclotetradecin-10-yl)-N-(2-(pyridin-3-yl)propan-2-yl)acetamide (124)

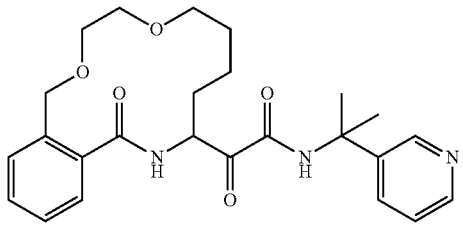

124

Compound 124 (77.3 mg, yield 37.3%) was obtained as white solid. $^1$H NMR (400 MHz, CDCl$_3$) δ 8.89-8.66 (m, 1H), 8.62-8.44 (m, 1H), 8.30-8.22 (m, 1H), 7.85-7.78 (m, 1H), 7.73-7.56 (m, 1H), 7.49-7.40 (m, 2H), 7.32-7.27 (m, 1H), 7.10 (s, 1H), 6.64-6.56 (m, 1H), 4.85-4.76 (m, 1H), 4.46-4.29 (m, 2H), 3.79-3.67 (m, 2H), 3.64-3.58 (m, 1H), 3.57-3.46 (m, 2H), 3.42-3.33 (m, 1H), 2.03-1.81 (m, 3H), 1.73-1.70 (m, 1H), 1.70-1.60 (m, 6H), 1.56-1.41 (m, 2H). MS (ESI) m/z (M+H)$^+$ 454.2.

2-Oxo-2-(12-oxo-1,3,4,6,7,8,9,10,11,12-decahydrobenzo[f][1,4]dioxa[9]aza-cyclotetradecin-10-yl)-N-(1-(pyridin-3-yl)cyclopropyl)acetamide (125)

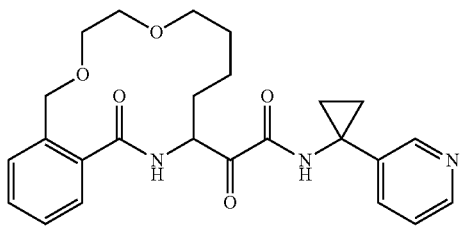

125

Compound 125 (66.3 mg, yield 31.5%) was obtained as white solid. $^1$H NMR (400 MHz, CDCl$_3$) δ 8.90-8.79 (m, 1H), 8.34-8.27 (m, 1H), 8.24-8.16 (m, 1H), 7.79-7.70 (m, 1H), 7.54-7.46 (m, 1H), 7.42-7.21 (m, 4H), 6.77-6.67 (m, 1H), 4.87-4.75 (m, 1H), 4.54-4.42 (m, 2H), 3.78-3.68 (m, 2H), 3.62-3.42 (m, 3H), 3.38-3.27 (m, 1H), 1.92-1.80 (m, 2H), 1.75-1.66 (m, 1H), 1.62-1.56 (m, 1H), 1.53-1.39 (m, 2H), 1.34-1.15 (m, 4H). MS (ESI) m/z (M+H)$^+$ 452.2.

2-Oxo-2-(12-oxo-1,3,4,6,7,8,9,10,11,12-decahydrobenzo[f][1,4]dioxa[9]aza-cyclotetradecin-10-yl)-N—((S)-1-(pyridin-3-yl)ethyl)acetamide (126)

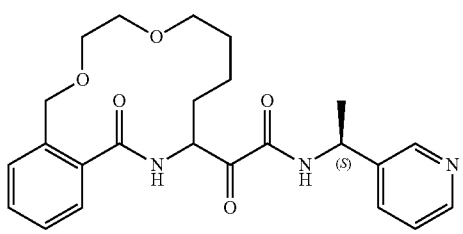

126

Compound 126 (43.3 mg, yield 22.0%) was obtained as white solid. $^1$H NMR (400 MHz, CDCl$_3$) δ 8.81-8.53 (m, 1H), 8.52-8.45 (m, 1H), 8.42-8.19 (m, 1H), 7.75-7.67 (m, 1H), 7.54-7.42 (m, 1H), 7.40-7.33 (m, 2H), 7.27-7.18 (m, 1H), 7.10-6.64 (m, 2H), 5.04-4.81 (m, 2H), 4.63-4.26 (m, 2H), 3.76-3.26 (m, 6H), 1.93-1.80 (m, 2H), 1.74-1.50 (m, 4H), 1.47-1.44 (m, 3H). MS (ESI) m/z (M+H)$^+$ 440.2.

2-Oxo-2-(12-oxo-1,3,4,6,7,8,9,10,11,12-decahydrobenzo[f][1,4]dioxa[9]aza-cyclotetradecin-10-yl)-N—((R)-1-(pyridin-3-yl)ethyl)acetamide (127)

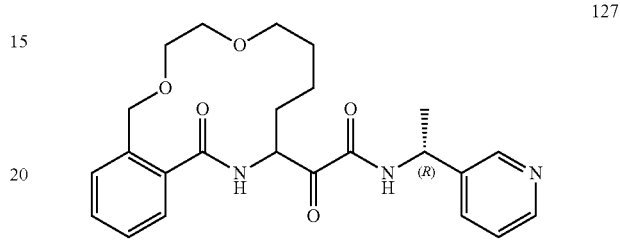

127

Compound 127 (14.7 mg, yield 9.3%) was obtained as light yellow solid. H NMR (400 MHz, CDCl$_3$) δ 8.82-8.53 (m, 1H), 8.52-8.44 (m, 1H), 8.41-8.18 (m, 1H), 7.74-7.68 (m, 1H), 7.55-7.42 (m, 1H), 7.40-7.33 (m, 2H), 7.26-7.17 (m, 1H), 7.09-6.64 (m, 2H), 5.04-4.80 (m, 2H), 4.63-4.26 (m, 2H), 3.76-3.26 (m, 6H), 1.92-1.65 (m, 3H), 1.61-1.38 (m, 6H). MS (ESI) m/z (M+H)$^+$ 440.2.

Example 79

(S)—N-(4-chlorophenethyl)-2-oxo-2-(12-oxo-1,3,4,6,7,8,9,10,11,12-decahydrobenzo[f][1,4]dioxa[9]azacyclotetradecin-10-yl)acetamide (128)

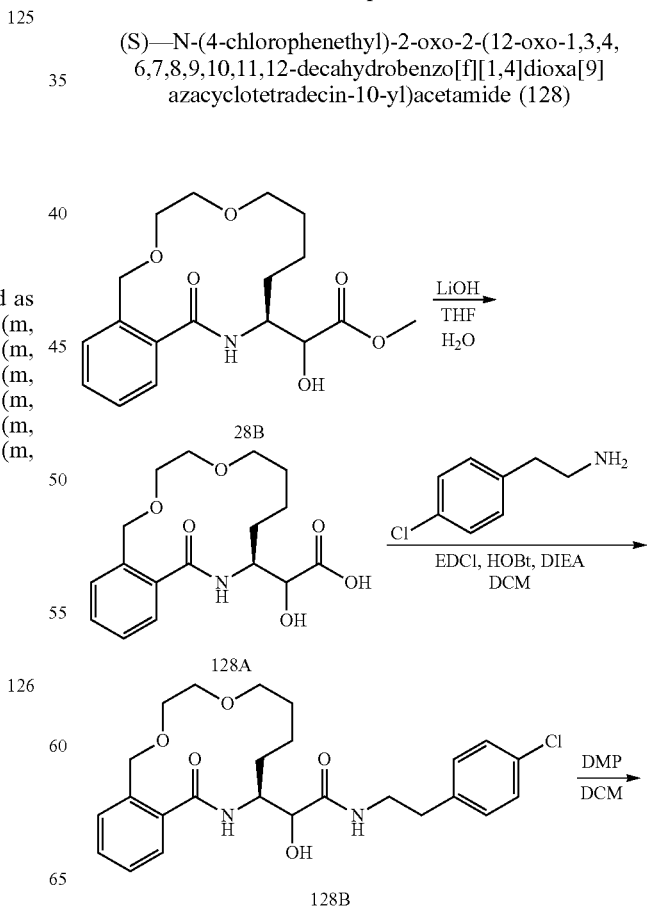

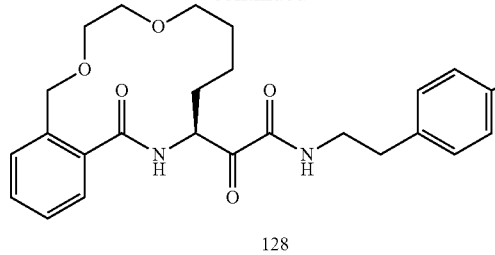

128

Step 1: Synthesis of Compound 128A

To a solution of compound 28B (400 mg, 1.14 mmol) in THF (5 mL) and H₂O (5 mL) was added LiOH.H₂O (240 mg, 5.70 mmol). The mixture was stirred at 25° C. for 2 h. The reaction was diluted with H₂O (10 mL), acidified with 1N HCl to pH~4. The mixture was extracted with EtOAc (10 mL×3). The organics were collected, dried with Na₂SO₄, filtered and concentrated to give compound 128A (380 mg, yield 98.8%) as white solid. MS (ESI) m/z (M+H)⁺ 338.1.

Step 2: Synthesis of Compound 128B

Compound 128B was prepared following the procedure of Example 47 using intermediate 128A and 2-(4-chlorophenyl)ethan-1-amine. Compound 128B was obtained as brown solid (50 mg, yield: 15.8%). MS (ESI) m/z (M+H)⁺ 475.2.

Step 3: Synthesis of Compound 128

Compound 128 was prepared following the procedure of Example 52 using intermediate 128B. Compound 128 was obtained as white solid (15.7 mg, yield: 31.0%). ¹H NMR (400 MHz, CDCl₃) δ 8.52 (br d, J=5.6 Hz, 1H), 7.74-7.69 (m, 1H), 7.39-7.32 (m, 2H), 7.28-7.23 (m, 1H), 7.18-7.13 (m, 2H), 7.07-7.01 (m, 2H), 6.88-6.79 (m, 1H), 5.01-4.93 (m, 1H), 4.68 (d, J=9.6 Hz, 1H), 4.56 (d, J=9.2 Hz, 1H), 3.76-3.67 (m, 2H), 3.62-3.36 (m, 6H), 2.78-2.67 (m, 2H), 1.92-1.79 (m, 2H), 1.64-1.52 (m, 4H). MS (ESI) m/z (M+H)⁺ 473.1.

Example 80

(S)-2-oxo-2-(3-oxo-11-oxa-4-aza-1(2,4)-pyrimidina-2(1,2)-benzena-cycloundecaphane-5-yl)acetamide (129)

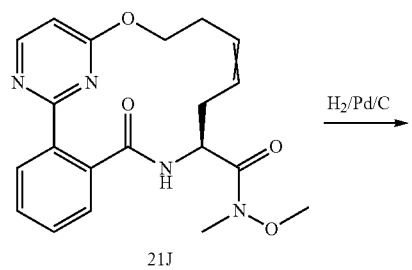

21J

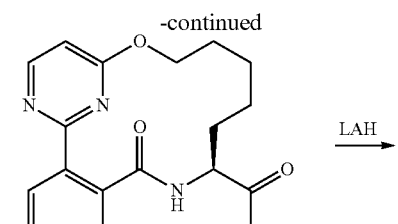

129A

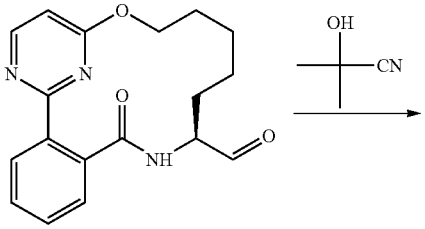

129B

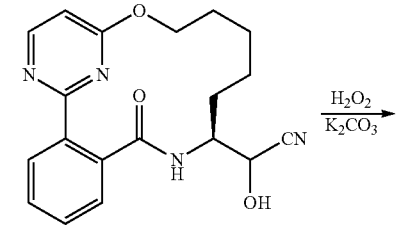

129C

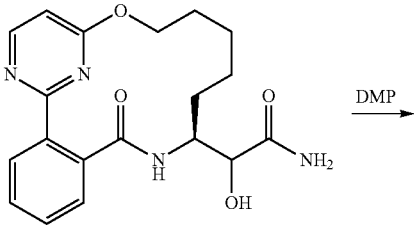

129D

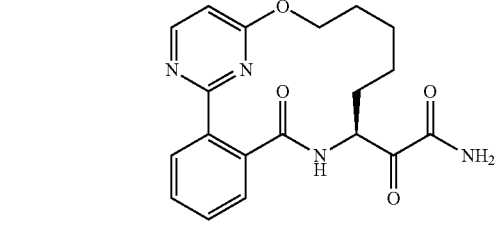

129

Step 1: Synthesis of Compound 129A

A solution of compound 21J (120 mg) and Pd/C (12 mg, 10%) in 20 mL MeOH was hydrogenated at 50 psi for 15 hr. The catalyst was removed, and crude product was purified on silica gel column to afford compound 129A (109 mg, yield 90%).

Step 2: Synthesis of Compound 129B

Compound 129A (109 mg, 1.0 eq.) was dissolved in dry THF (10 ml) and cooled to −78° C. under N₂. LAH (1M, 0.3 mL, 1.1 eq) was added dropwise. The mixture was stirred at −30° C. for 2 hr. Then the reaction was quenched by adding 1N HCl at −10° C., then basified to pH~8 by added saturated NaHCO₃. The mixture was extracted by 3×20 mL acetate. The organic phase was washed with water and brine. The crude mixture was purified on silica-gel column to afford Compound 129B (87 mg, yield 94%).

Step 3: Synthesis of Compound 129C

A solution of compound 129B (87 mg, 1.0 eq), 2-hydroxy-2-methylpropanenitrile (46 mg, 2.0 eq) and TEA (35 mg, 1.0 eq) in dry DCM (8 mL) was stirred at rt. for 2 hrs. The reaction mixture was dried in vacuo, the crude mixture was purified directly on silica gel column to afford 129C (66 mg, yield 70%).

Step 4: Synthesis of Compound 129D

To a solution of compound 129C (66 mg, 1.0 eq) in 4 mL DMSO was added K₂CO₃ (26 mg, 1.0 eq) and 1.5 mL H₂O₂ (50%). The mixture was stirred at 5° C. for 5 hrs. The reaction mixture was diluted with 10 mL water, extracted with 10×20 mL ethyl acetate to afford 129D (30 mg, yield 44%) which was used without purification.

Step 5: Synthesis of Compound 129

To a solution of compound 129D (30 mg, 1.0 eq) in 10 mL dry DCM and 2.5 mL DMSO was added DMP (138 mg, 4.0 eq). The resulting mixture was stirred at rt. for 1 hr, then the mixture was diluted with DCM (10 mL), quenched by adding 10% Na₂S₂O₃/saturated NaHCO₃ (v/v=1/1, 15 mL). The organic layer was separated. The aqueous layer was extracted with ethyl acetate (30 mL×3). The combined organic layer was washed with H₂O (20 mL), brine (20 mL), dried over Na₂SO₄, filtered and concentrated to afford white solid. The solid was triturated in CH₂C₂/Hexane to provide pure product compound 129 (10.4 mg, yield 35%). $^1$H NMR (400 MHz, DMSO-d₆): δ 8.87 (d, 1H), 8.56 (d, 1H), 8.05 (s, 1H), 7.76 (m, 2H), 7.57 (m, 3H), 6.78 (d, 1H), 5.14 (m, 1H), 4.93 (m, 1H), 4.04 (m, 1H), 2.82-2.96 (m, 2H), 1.42-1.73 (m, 6H) ppm. MS (ESI) m/z (M+H)⁺ 369.1.

Example 81

(S)-2-oxo-2-(11-oxo-3-oxa-10-aza-1(2,3)-pyridina-2(1,3)-benzena-cycloundecaphane-9-yl)acetamide (130)

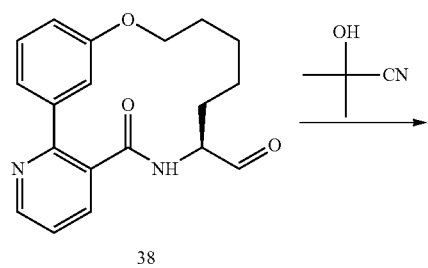

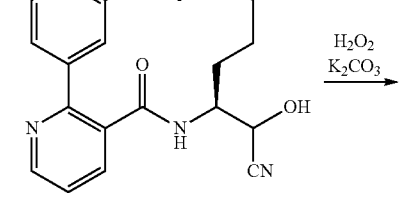

130A

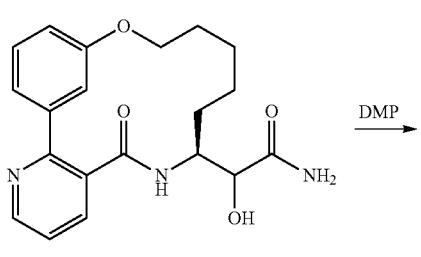

130B

130

Step 1: Synthesis of Compound 130

Compound 130 was prepared following the procedure of Example 80 using compound 38. Compound 130: $^1$H NMR (400 MHz, DMSO-d₆): δ 9.04 (d, 1H), 8.7 (d, 1H), 8.08 (s, 1H), 7.8 (m, 2H), 7.5-7.3 (m, 3H), 7.15 (s, 1H), 6.96 (d, 1H), 5.13 (m, 1H), 4.19 (m, 1H), 4.1 (m, 1H), 1.8-1.3 (m, 8H) ppm. MS (ESI) m/z (M+H)⁺ 368.2.

Example 82

(S)-3-oxo-12-oxa-4-aza-1(2,4)-pyridina-2(1,2)-benzenacyclododecaphane-5-carbaldehyde (131)

and (S)-2-oxo-2-(3-oxo-12-oxa-4-aza-1(2,4)-pyridina-2(1,2)-benzenacyclododecaphane-5-yl)acetamide (132)

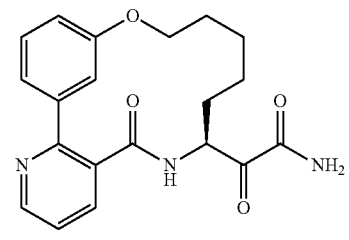

227
-continued

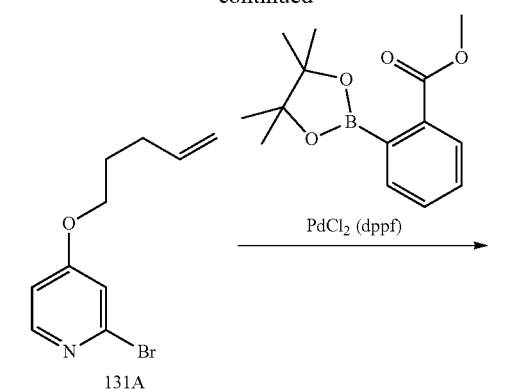
131A

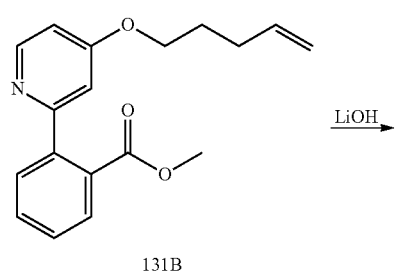
131B

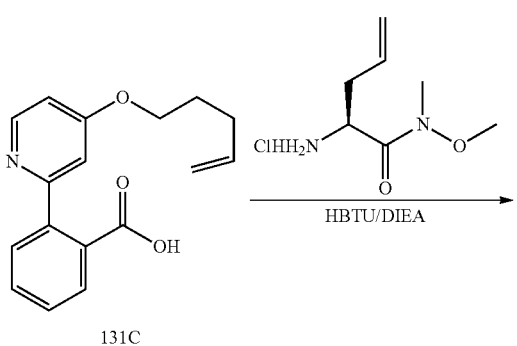
131C

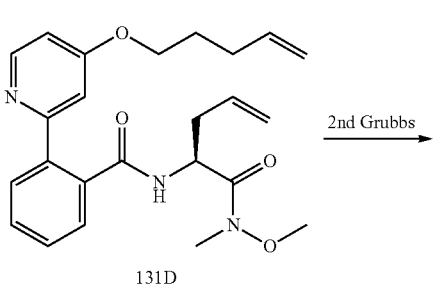
131D

131E

228
-continued

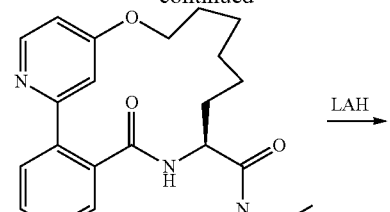
131F

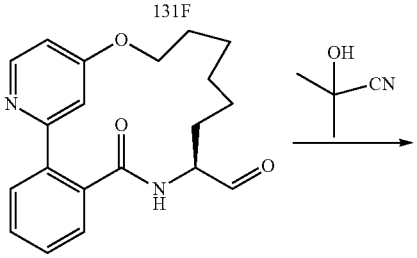
131

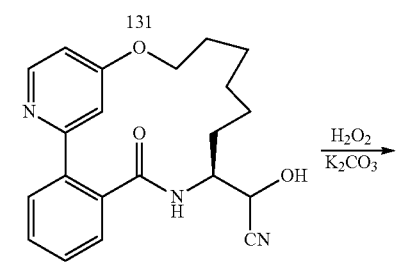
132A

132B

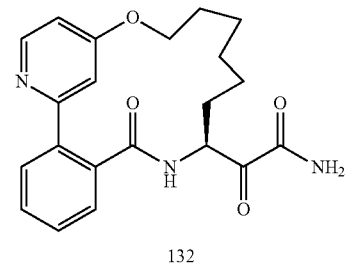
132

Step 1: Synthesis of Compound 131A

To a suspended solution of NaH (0.74 g, 60% in mineral oil, 1 eq) in 40 mL dry THF under $N_2$ was slowly added a solution of pent-4-en-1-ol (1.6 g, 1.0 eq) in 5 mL dry THF. The mixture was stirred at rt. for 1 hr. Then the reaction mixture was cooled to −50° C. A solution of 2,4-dibromopyridine (4.4 g, 1.0 eq) in 15 mL THF was added dropwise. The resulting mixture was stirred at −50° C. for 1 h, and then slowly warmed room temperature overnight. The reaction mixture was quenched with 50 mL saturated $NH_4Cl$ at 0° C., extracted with 2×80 mL ethyl acetate. The crude mixture was purified on ISCO (40 g silica gel column) to provide compound 131A.

Step 2: Synthesis of Compounds 131 and 132

Compounds 131 and 132 were prepared following the procedure of Example 80 using compound 131A. Compound 131: $^1$H NMR (400 MHz, CDCl$_3$): δ 9.5 (s, 1H), 8.43 (d, 1H), 7.65 (m, 2H), 7.55-7.4 (m, 3H), 6.98 (s, 1H), 6.76 (d, 1H), 6.64 (d, 1H), 4.89 (m, 1H), 4.45-4.2 (m, 2H), 1.92 (m, 2H), 1.8-1.3 (m, 10H) ppm. MS (ESI) m/z (M+H)$^+$ 339.4.

Compound 132: MS (ESI) m/z (M+H)$^+$ 382.4.

Example 83

(S)-3-oxo-12-oxa-4-aza-1(2,4)-pyrimidina-2(1,2)-benzenacyclododecaphane-5-carbaldehyde (133)

and (S)-2-oxo-2-(3-oxo-12-oxa-4-aza-1(2,4)-pyrimidina-2(1,2)-benzenacyclododecaphane-5-yl)acetamide (134)

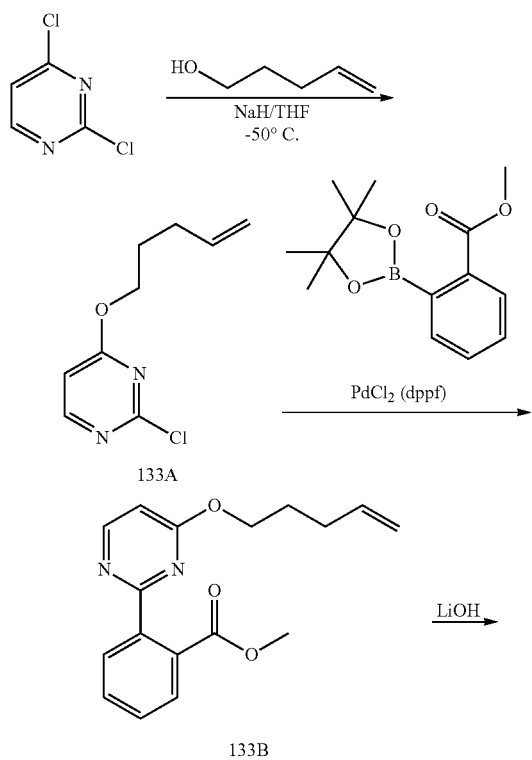

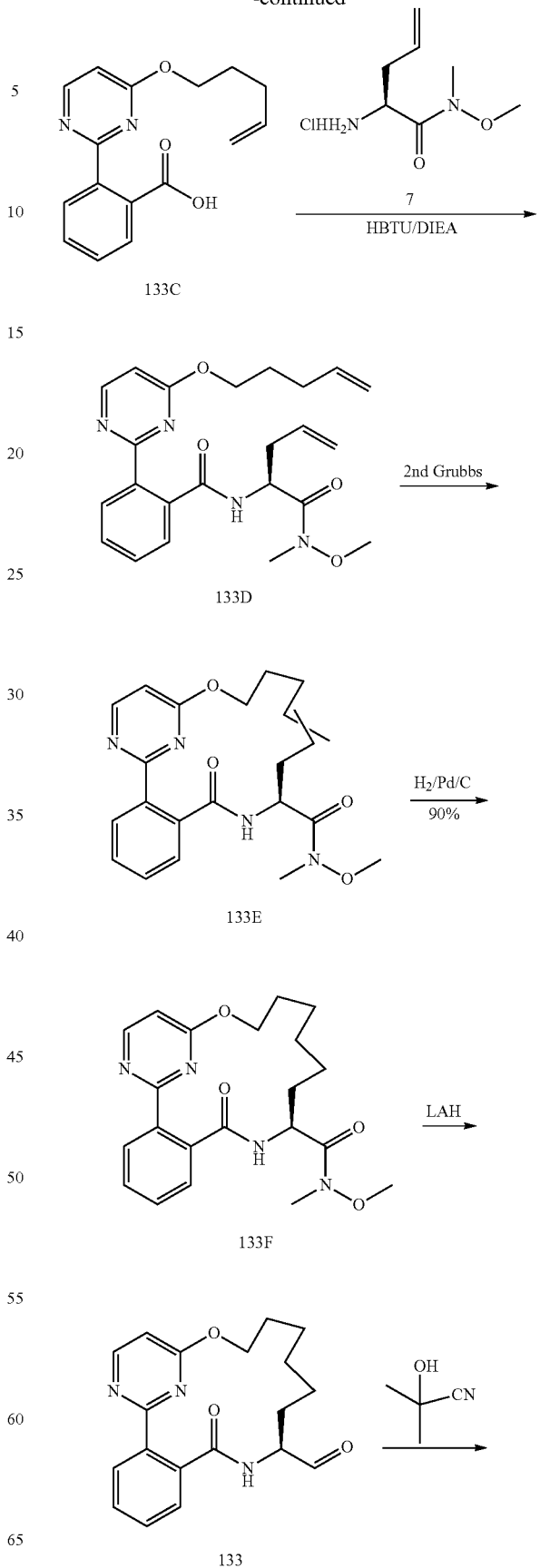

231

-continued

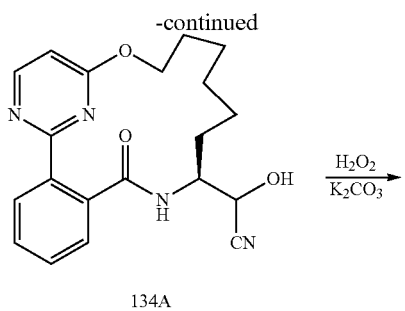

134A

H₂O₂ / K₂CO₃ →

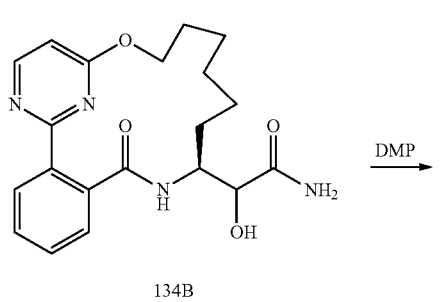

134B

DMP →

134

Step 1: Synthesis of Compounds 133 and 134

Compounds 133 and 134 were prepared following the procedure of Example 80 using 2,4-dichloropyrimidine and compound 133A. Compound 133: ¹H NMR (400 MHz, CDCl₃): δ 9.62 (s, 1H), 8.54 (d, 1H), 7.94 (d, 1H), 7.7 (d, 1H), 7.6-7.5 (m, 2H), 6.64 (d, 1H), 6.31 (d, 1H), 4.81 (m, 1H), 4.52 (m, 1H), 4.36 (m, 1H), 2.04 (m, 2H), 1.8-1.3 (m, 8H) ppm. MS (ESI) m/z (M+H)⁺ 340.3.

Compound 134: ¹H NMR (400 MHz, DMSO-d₆): δ 8.78 (d, 1H), 8.59 (d, 1H), 8.07 (s, 1H), 7.93 (m, 1H), 7.8 (s, 1H), 7.64-7.5 (m, 3H), 6.83 (d, 1H), 5.23 (m, 1H), 4.49 (m, 1H), 4.15 (m, 1H), 1.91 (m, 2H), 1.8-1.3 (m, 8H) ppm MS (ESI) m/z (M+H)⁺ 383.4.

232

Example 84

(S,E)-N-methoxy-N-methyl-3-oxo-11-oxa-4-aza-1(2,4)-pyrimidina-2(1,2)-benzenacycloundecaphan-7-ene-5-carboxamide (135)

and (S,Z)—N-methoxy-N-methyl-3-oxo-11-oxa-4-aza-1(2,4)-pyrimidina-2(1,2)-benzenacycloundecaphan-7-ene-5-carboxamide (136)

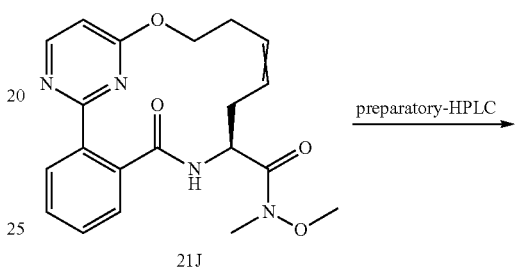

21J preparatory-HPLC →

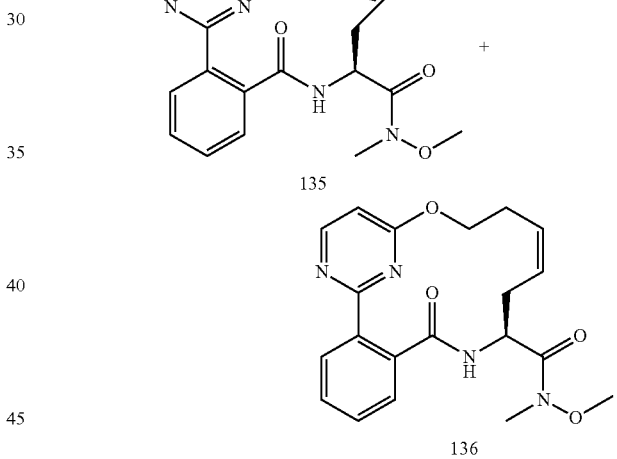

135

+

136

Step 1: Synthesis of Compounds 135 and 136

Compound 21J was purified by preparatory-HPLC (HCl condition) to give compound 135 (150 mg, yield: 47.88%) as a white solid. ¹H NMR (400 MHz, CDCl₃) δ 8.73 (br s, 1H), 7.93 (br s, 1H), 7.75 (br s, 1H), 7.68 (br s, 2H), 7.28 (br d, J=4.4 Hz, 1H), 6.98 (br s, 1H), 5.74 (br s, 1H), 5.59-5.44 (m, 1H), 5.37 (br s, 1H), 5.01 (br s, 1H), 4.72 (br s, 1H), 3.81-3.73 (m, 3H), 3.19 (br s, 3H), 2.56 (br s, 1H), 2.53-2.41 (m, 2H), 2.13 (br s, 1H). MS (ESI) m/z (M+H)+ 383.2.

Compound 136 (70 mg, yield: 22.7%) as a light yellow solid. ¹H NMR (400 MHz, CDCl₃) δ 8.70 (d, J=5.1 Hz, 1H), 8.06 (br s, 1H), 7.70-7.52 (m, 3H), 7.19 (br s, 1H), 6.86 (br d, J=2.2 Hz, 1H), 5.50-5.29 (m, 2H), 5.09-4.91 (m, 2H), 4.37-4.26 (m, 1H), 3.81 (br s, 3H), 3.33-3.23 (m, 3H), 2.83-2.57 (m, 2H), 2.46-2.32 (m, 2H). MS (ESI) m/z (M+H)+ 383.2.

Example 85

(S,E)-2-oxo-2-(3-oxo-11-oxa-4-aza-1(2,4)-pyrimidina-2(1,2)-benzenacycloundecaphan-7-en-5-yl)acetamide (137)

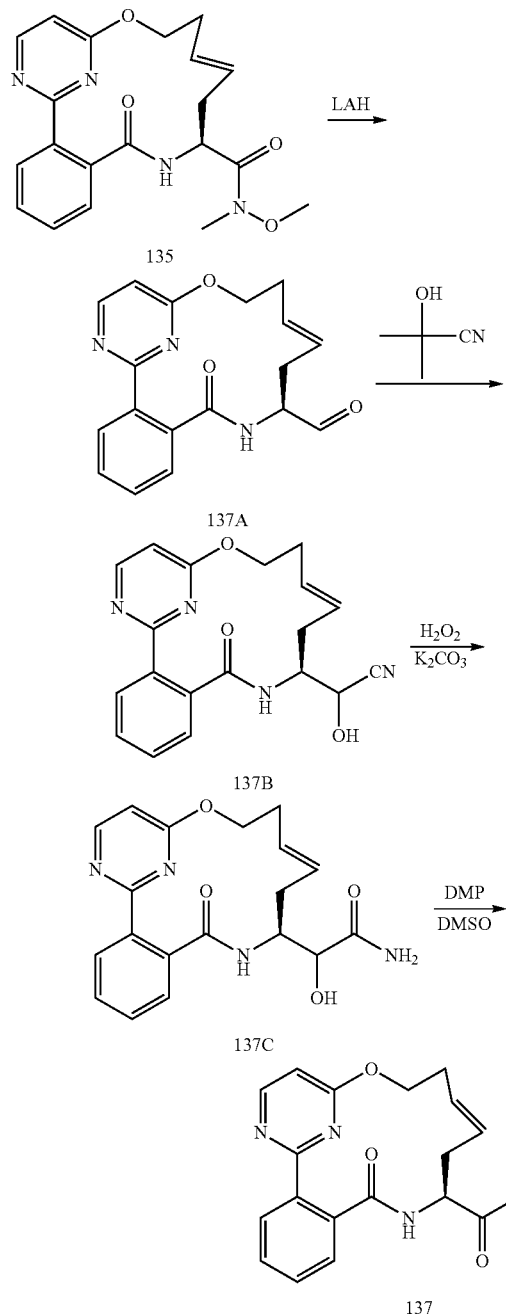

Step 1: Synthesis of Compound 137

Compound 137 was prepared following the procedure of Example 80 using compound 135. Compound 137 (8 mg, yield: 18.76%) was obtained as a light yellow solid. $^1$H NMR (400 MHz, DMSO-$d_6$) δ 8.66-8.54 (m, 2H), 8.05 (br s, 1H), 7.81 (br s, 1H), 7.64-7.53 (m, 4H), 6.83 (d, J=5.5 Hz, 1H), 5.57 (br s, 1H), 5.50 (br s, 1H), 5.28 (br s, 1H), 4.64-4.57 (m, 1H), 4.51 (d, J=4.0 Hz, 1H), 2.46-2.15 (m, 4H). MS (ESI) m/z (M+23) 385.2.

Example 86

(S,Z)-2-oxo-2-(3-oxo-11-oxa-4-aza-1(2,4)-pyrimidina-2(1,2)-benzenacycloundecaphan-7-en-5-yl)acetamide (138)

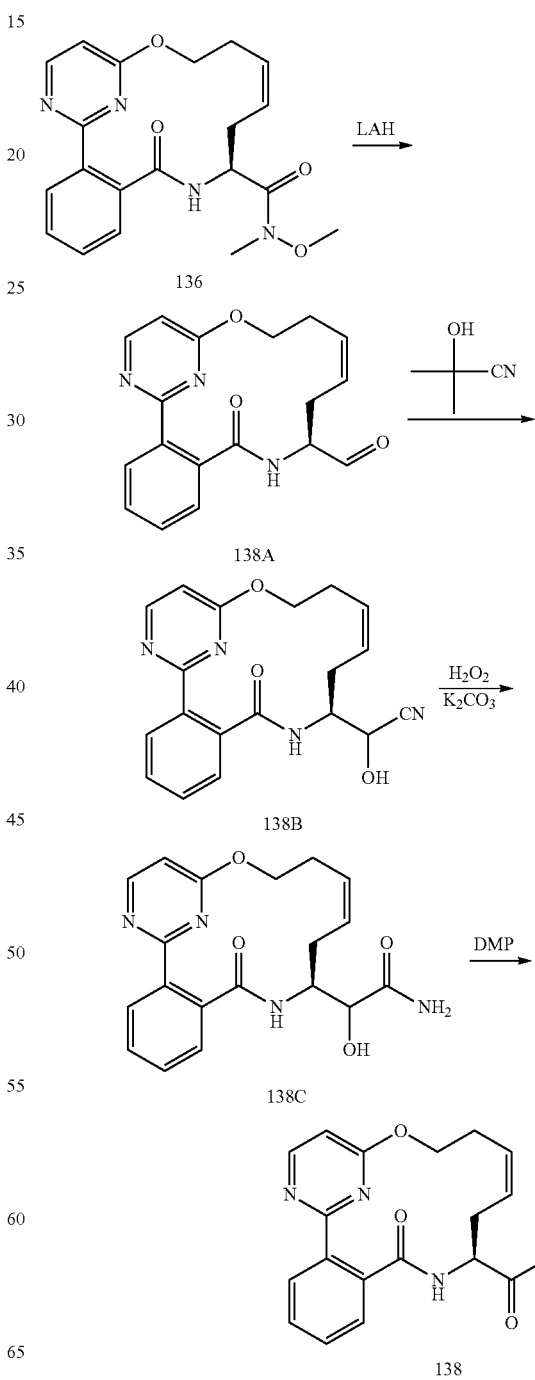

Step 1: Synthesis of Compound 138

Compound 138 was prepared following the procedure of Example 80 using compound 136. Compound 138 (15 mg, yield: 29.86%) was obtained as a white solid. $^1$H NMR (400 MHz, DMSO-$d_6$) δ 8.92 (br d, J=6.6 Hz, 1H), 8.58 (br d, J=5.5 Hz, 1H), 7.85 (br s, 1H), 7.73 (br d, J=6.8 Hz, 1H), 7.68 (br s, 1H), 7.59 (br d, J=6.8 Hz, 1H), 7.52 (br d, J=5.7 Hz, 2H), 6.80 (br d, J=5.5 Hz, 1H), 5.47-5.36 (m, 2H), 4.67 (br s, 1H), 4.54 (br d, J=9.9 Hz, 1H), 4.38 (br d, J=6.6 Hz, 1H), 3.29 (br s, 2H), 2.81-2.71 (m, 1H), 2.31 (br s, 1H). MS (ESI) m/z (M+H)$^+$ 367.1.

Example 87

(S)-3-oxo-11-oxa-4-aza-1(2,4)-pyrimidina-2(1,2)-benzena-cycloundecaphane-5-carbaldehyde (139)

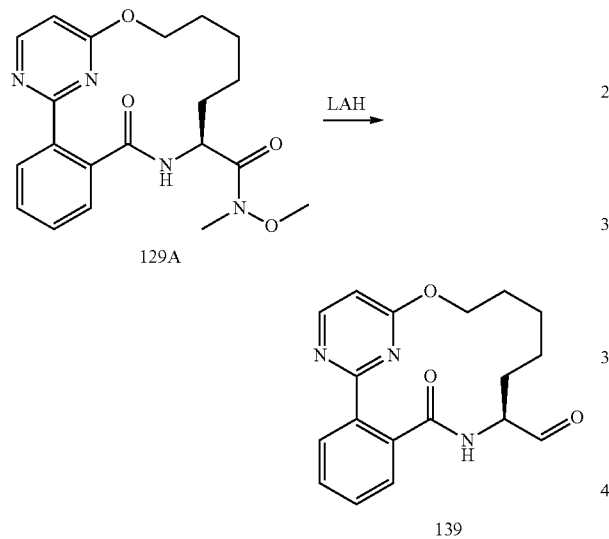

Step 1: Synthesis of Compound 139

To a mixture of LiAlH$_4$ (96 mg, 2.52 mmol) in THF (20 mL) was added compound 129A (807 mg, 2.10 mmol) in THF (20 mL) at −78° C. The mixture was stirred at −30° C. for 2 h. The excess lithium borohydride was quenched by addition of 5 mL ethyl acetate, then 1N HCl to pH~5-6 at 0° C., after that, the mixture was added aqueous saturated NaHCO$_3$ to pH~8~9 at 0° C., then the mixture was extracted with ethyl acetate (10 mL×2). The combined organic layers were dried over Na$_2$SO$_4$, filtered and concentrated under reduced pressure to give a residue. The residue was purified by column chromatography (SiO$_2$, Petroleum ether/Ethyl acetate=1/1 to 1/2). Compound 139 (166.2 mg, yield: 23.89%) was obtained as a white solid. $^1$H NMR (400 MHz, CD$_3$CN) δ 9.61 (s, 1H), 8.54 (d, J=5.7 Hz, 1H), 7.87-7.76 (m, 1H), 7.70-7.66 (m, 1H), 7.61-7.54 (m, 2H), 7.27 (br d, J=6.4 Hz, 1H), 6.69 (d, J=6.0 Hz, 1H), 5.02-4.90 (m, 1H), 4.46-4.40 (m, 1H), 4.23-4.16 (m, 1H), 2.05-1.99 (m, 1H), 1.94-1.88 (m, 1H), 1.79-1.65 (m, 2H), 1.59-1.46 (m, 4H). MS (ESI) m/z (M+H)$^+$ 326.1.

Example 88

(S)-2-oxo-2-(11-oxo-1H-3-oxa-10-aza-1(3,4)-pyrazola-2(1,3)-benzena-cycloundecaphane-9-yl)acetamide (140)

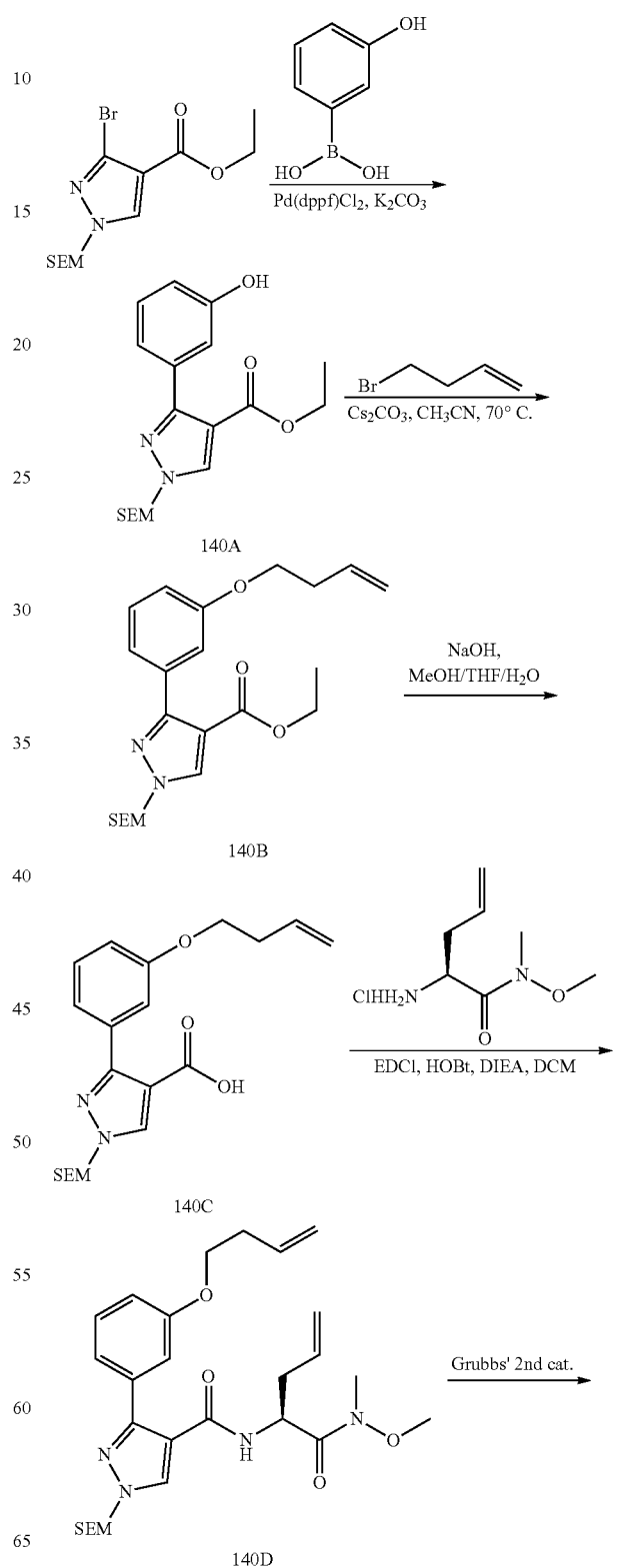

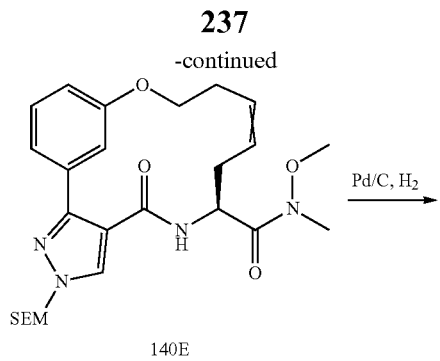

140E

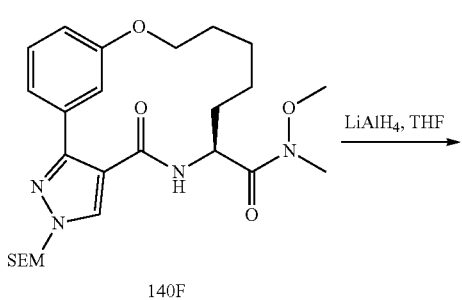

140F

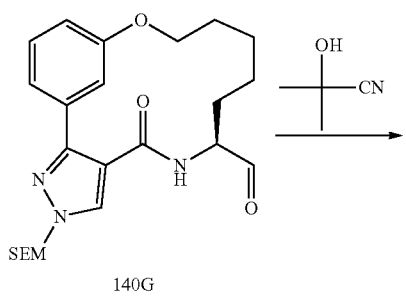

140G

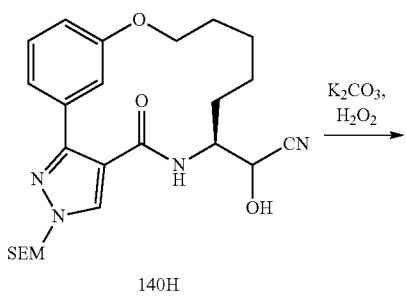

140H

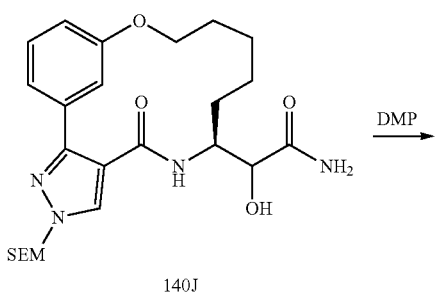

140J

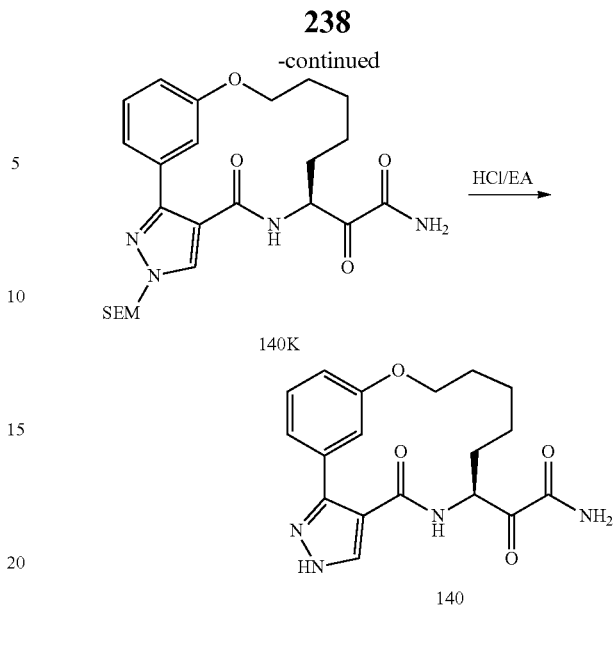

Step 1: Synthesis of Compound 140A

To a solution of ethyl 3-bromo-1-((2-(trimethylsilyl)ethoxy)methyl)-1H-pyrazole-4-carboxylate (15 g, 42.94 mmol) and (3-hydroxyphenyl)boronic acid (7.11 g, 51.53 mmol) in dioxane/H$_2$O (150 mL/30 mL) was added K$_3$PO$_4$ (27.35 g, 128.82 mmol) and Pd(dppf)Cl$_2$ (3.14 g, 4.29 mmol). The mixture was stirred at 70° C. for 6 h. The reaction mixture was concentrated under reduced pressure to remove solvent. The residue was diluted with H$_2$O (200 mL) and extracted with EtOAc (100 mL×2). The combined organic layers were washed with brine (100 mL×2), dried over Na$_2$SO$_4$, filtered and concentrated under reduced pressure to give a residue. The residue was purified by column chromatography (SiO$_2$, Petroleum ether/Ethyl acetate=8/1 to 5:1) to give the compound 140A (9.20 g, yield: 59.1%) was obtained as a yellow oil. $^1$H NMR (400 MHz, CDCl$_3$) δ 8.17 (s, 1H), 7.36-7.24 (m, 3H), 6.93-6.80 (m, 1H), 6.24 (s, 1H), 5.47 (s, 2H), 4.27 (q, J=7.0 Hz, 2H), 3.70-3.62 (m, 2H), 1.33-1.28 (m, 3H), 1.00-0.90 (m, 2H), 0.09-0.05 (m, 9H). MS (ESI) m/z (M+H)$^+$ 363.0.

Step 2: Synthesis of Compound 140B

A mixture of compound 140A (6.4 g, 17.66 mmol), 4-bromobut-1-ene (5.96 g, 44.15 mmol, 4.48 mL), Cs$_2$CO$_3$ (28.7 g, 88.30 mmol) in DMF (100 mL) was degassed and purged with N$_2$ for 3 times, and then the mixture was stirred at 90° C. for 22 h under N$_2$ atmosphere. The reaction mixture was diluted with EtOAc (300 mL) and washed with H$_2$O (200 mL×3). The combined organic layers were washed with brine (200 mL×2), dried over Na$_2$SO$_4$, filtered and concentrated under reduced pressure to give a residue. The residue was purified by column chromatography (SiO$_2$, Petroleum ether/Ethyl acetate=10/1 to 8:1) to give the compound 140B (3.7 g, yield: 50.3%) was obtained as a yellow oil. $^1$H NMR (400 MHz, CDCl$_3$) δ 8.14 (s, 1H), 7.38-7.26 (m, 3H), 6.96-6.89 (m, 1H), 5.98-5.84 (m, 1H), 5.45 (s, 2H), 5.20-5.07 (m, 2H), 4.26 (q, J=7.2 Hz, 2H), 4.06 (t, J=6.7 Hz, 2H), 3.69-3.63 (m, 2H), 2.55 (td, J=1.3, 6.8 Hz, 2H), 1.29 (t, J=7.1 Hz, 3H), 0.95 (dd, J=7.7, 8.8 Hz, 2H), 0.01-0.01 (m, 9H).

Step 3: Synthesis of Compound 140C

To a solution of Compound 140B (4.7 g, 11.28 mmol) in THF/H$_2$O (20 mL/20 mL) was added NaOH (2.26 g, 56.40 mmol). The mixture was stirred at 25° C. for 13 h. The reaction mixture was diluted with H$_2$O (80 mL), then the mixture was concentrated under reduced pressure to remove THF, and extracted with MTBE (50 mL×2). The water layers were neutralized by 1N HCl to pH~3, and extracted with DCM (50 mL×2). The combined organic layers were washed with brine (100 mL), dried over Na$_2$SO$_4$, filtered and concentrated under reduced pressure to give the compound 140C (3.65 g, yield: 83.3%) was obtained as a yellow oil. $^1$H NMR (400 MHz, CDCl$_3$) δ 8.22 (s, 1H), 7.39-7.29 (m, 3H), 6.98-6.92 (m, 1H), 5.97-5.83 (m, 1H), 5.47 (s, 2H), 5.20-5.06 (m, 2H), 4.06 (t, J=6.7 Hz, 2H), 3.70-3.60 (m, 2H), 2.55 (d, J=6.6 Hz, 2H), 1.00-0.87 (m, 2H), 0.04-0.02 (m, 9H).

Step 4: Synthesis of Compound 140K

Compound 140K was prepared following the procedure of Example 83 using compound 140C and (S)-2-amino-N-methoxy-N-methylpent-4-enamide hydrochloride. Compound 140K (91 mg, yield: 60.92%) was obtained as a white solid. $^1$H NMR (400 MHz, CDCl$_3$) δ 8.19-8.11 (m, 2H), 8.04 (br s, 1H), 7.79 (br s, 1H), 7.39-7.24 (m, 2H), 7.06 (br s, 1H), 6.96 (br d, J=7.7 Hz, 1H), 5.45 (s, 2H), 5.14 (br t, J=6.9 Hz, 1H), 4.26-4.16 (m, 1H), 4.16-4.05 (m, 1H), 3.63 (br t, J=8.0 Hz, 2H), 1.85-1.65 (m, 2H), 1.64-1.48 (m, 3H), 1.45-1.28 (m, 3H), 0.88 (br t, J=7.9 Hz, 2H), 0.04-0.06 (m, 9H) MS (ESI) m/z (M+H)$^+$ 487.2.

Step 4: Synthesis of Compound 140

To a solution of compound 140K (42 mg, 86.31 umol) in EtOAc (5 mL) was added HCl/EtOAc (4M, 5 mL). The mixture was stirred at 25° C. for 5 h. The reaction mixture was diluted with MTBE (20 mL), and filtered to give the compound 140 (20 mg, yield: 59.0%, HCl) was obtained as a white solid. $^1$H NMR (400 MHz, DMSO-d$_6$) δ 8.00 (s, 1H), 7.94 (br d, J=7.3 Hz, 1H), 7.83 (s, 1H), 7.76 (br s, 1H), 7.40-7.32 (m, 1H), 7.26 (d, J=7.7 Hz, 1H), 7.06 (s, 1H), 6.95 (br d, J=7.9 Hz, 1H), 5.08 (br t, J=7.5 Hz, 1H), 4.30-4.17 (m, 1H), 4.12-4.06 (m, 1H), 1.82-1.63 (m, 2H), 1.61-1.45 (m, 3H), 1.43-1.23 (m, 3H). MS (ESI) m/z (M+H)+ 357.1.

Example 89

(S)-2-oxo-2-(11-oxo-1$^1$H-3-oxa-10-aza-1(3,4)-pyrazola-2(1,3)-benzena-cycloundecaphane-9-yl)acetamide (141)

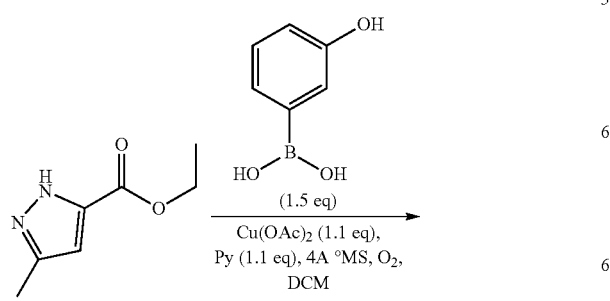

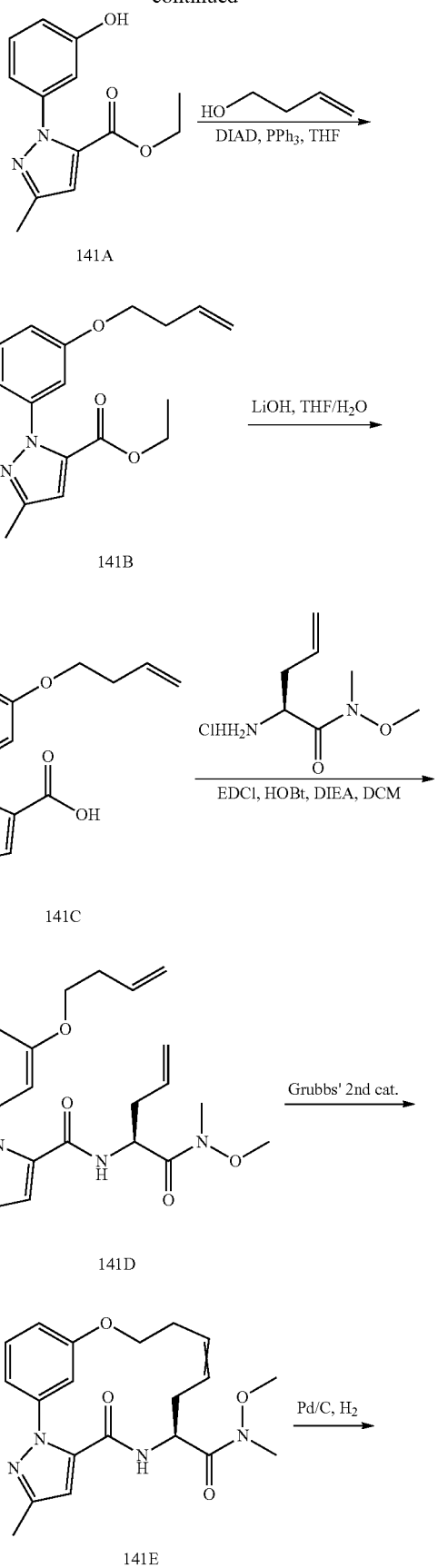

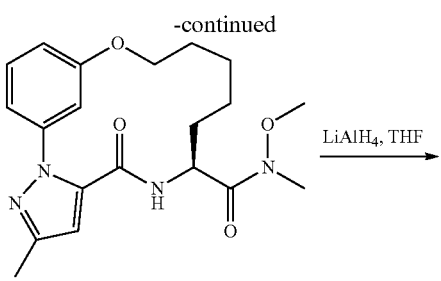

141F

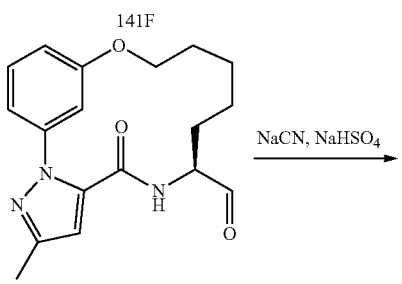

141G

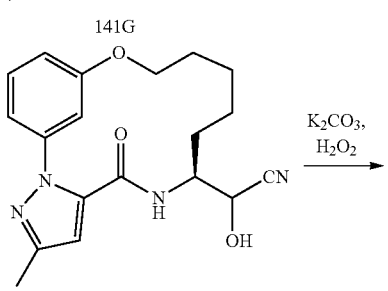

141H

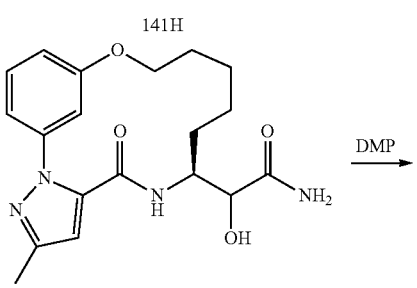

141J

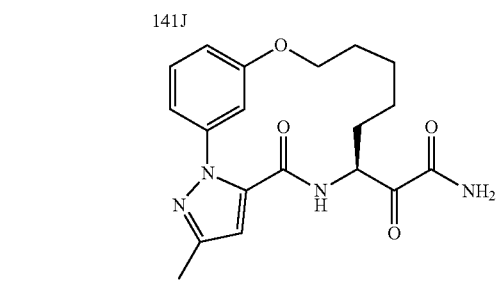

141

Step 1: Synthesis of Compound 141A

To a solution of ethyl 3-methyl-1H-pyrazole-5-carboxylate (20 g, 129.73 mmol), (3-hydroxyphenyl)boronic acid (27 g, 194.59 mmol), 4A ° MS (30 g) and Py (12 mL, 142.70 mmol) in DCM (500 mL) was added Cu(OAc)2 (26 g, 142.70 mmol). After addition, the reaction mixture was stirred at 28° C. for 48 h under $O_2$ (15 psi) atmosphere. 100 mL of DCM was added into the reaction mixture and the mixture was filtered. The filtrate was concentrated in vacuum and the residue was dissolved into 300 mL of EtOAc. The mixture was filtered and the filtrate was concentrated in vacuum. The residue was purified by column chromatography ($SiO_2$, Petroleum ether/Ethyl acetate=5/1 to 4:1 to 3/1) to afford compound 3 (8.0 g, yield 25.04%) as light yellow solid. $^1$H NMR (400 MHz, DMSO-$d_6$) δ 7.21 (t, J=7.9 Hz, 1H), 6.85-6.69 (m, 4H), 4.15 (q, J=7.1 Hz, 2H), 2.23 (s, 3H), 1.16-1.12 (m, 3H). MS (ESI) m/z (M+H)$^+$ 246.9.

Step 2: Synthesis of Compound 141B

To a solution of compound 141A (4.0 g, 16.24 mmol), but-3-en-1-ol (2 mL, 24.36 mmol) and PPh$_3$ (8.5 g, 32.48 mmol) in THF (100 mL) was added DIAD (6 mL, 32.48 mmol, 2.00 eq) under $N_2$ atmosphere. After addition, the reaction mixture was stirred at 25° C. for 14 h. The reaction mixture was concentrated in vacuum. The residue was purified by column chromatography ($SiO_2$, Petroleum ether/Ethyl acetate=20/1 to 10:1) to afford desired compound 141B (3.0 g, yield 55.97%) as colorless oil. $^1$H NMR (400 MHz, CDCl3) δ 7.34-7.27 (m, 1H), 6.98-6.92 (m, 3H), 6.79 (s, 1H), 5.95-5.82 (m, 1H), 5.19-5.06 (m, 2H), 4.22 (q, J=7.1 Hz, 2H), 4.03 (t, J=6.6 Hz, 2H), 2.58-2.50 (m, 2H), 1.23 (t, J=7.2 Hz, 3H). MS (ESI) m/z (M+H)$^+$ 301.4.

Step 3: Synthesis of Compound 141C

To a solution of compound 141B (3.0 g, 9.99 mmol) in THF (80 mL) was added LiOH.H$_2$O (2.5 g, 59.94 mmol) in H$_2$O (80 mL) at 25° C. After addition, the reaction mixture was stirred at 25° C. for 14 h. 50 mL of MTBE was added into the reaction mixture and separated. The aqueous layer was acidified by 1N HCl to pH~4 and extracted with EtOAc (100 mL×2), the combined extracts were washed with brine (40 mL) and dried Na$_2$SO$_4$, then concentrated in vacuum to afford compound 141C (2.3 g, yield 78.63%) as white solid. $^1$H NMR (400 MHz, DMSO-$d_6$) δ 13.23 (br s, 1H), 7.39-7.28 (m, 1H), 7.03-6.91 (m, 3H), 6.81 (s, 1H), 5.96-5.81 (m, 1H), 5.23-5.04 (m, 2H), 4.05 (t, J=6.7 Hz, 2H), 2.49-2.43 (m, 2H), 2.25 (s, 3H). MS (ESI) m/z (M+H)+ 273.3.

Step 4: Synthesis of Compound 141

Compound 141 was prepared following the procedure of Example 83 using compound 141C and (S)-2-amino-N-methoxy-N-methylpent-4-enamide hydrochloride. Compound 141 (20 mg, yield: 24.64%) was obtained as a white solid. $^1$H NMR (400 MHz, DMSO-$d_6$) δ 9.02 (br d, J=6.0 Hz, 1H), 8.09 (br s, 1H), 7.82 (brs, 1H), 7.34 (br d, J=6.6 Hz, 1H), 7.16 (br d, J=6.6 Hz, 1H), 6.86 (br d, J=6.2 Hz, 1H), 6.76 (br s, 1H), 6.43 (br s, 1H), 5.10 (br s, 1H), 4.11 (br d, J=4.2 Hz, 2H), 2.24 (br s, 3H), 1.86 (br s, 1H), 1.69 (br s, 2H), 1.59-1.26 (m, 5H). MS (ESI) m/z (M+H)+ 371.1.

Example 90

(S)-2-(1'-methyl-11-oxo-1$^1$H-3-oxa-10-aza-1(3,4)-pyrazola-2(1,3)-benzenacycloundecaphane-9-yl)-2-oxoacetamide (142)

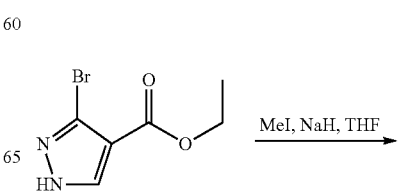

243
-continued
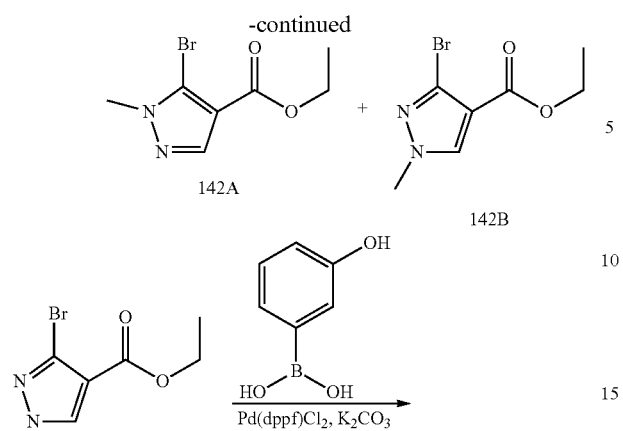
142A
142B
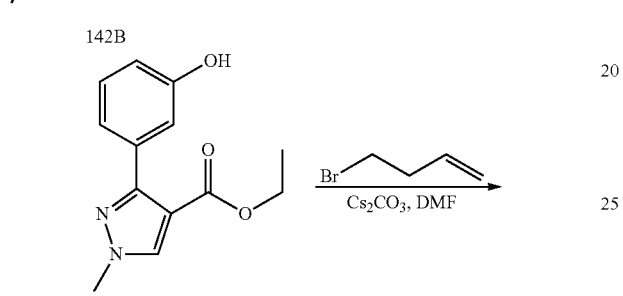
142C
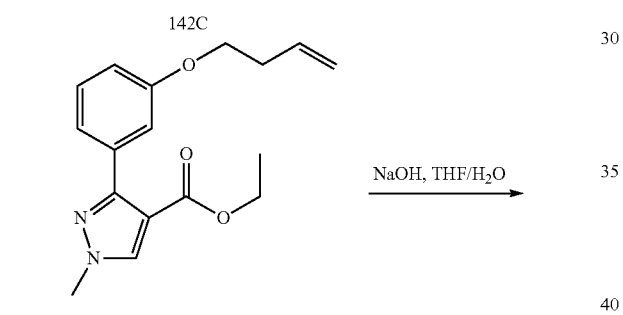
142D
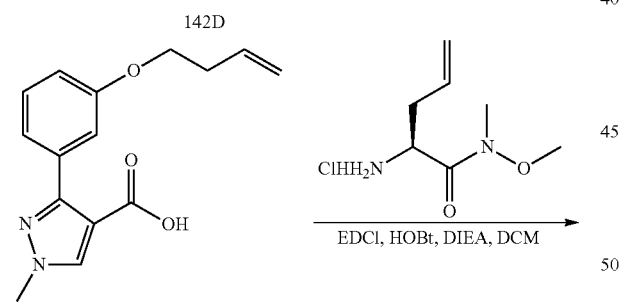
142E
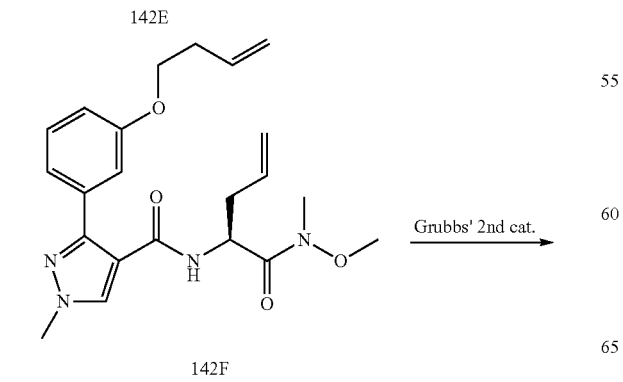
142F
244
-continued
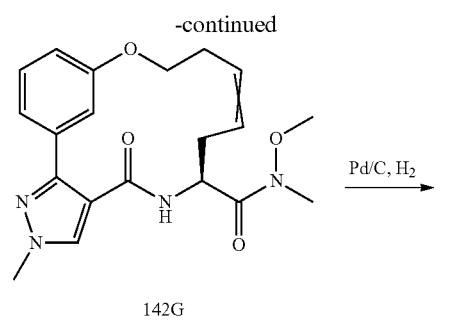
142G
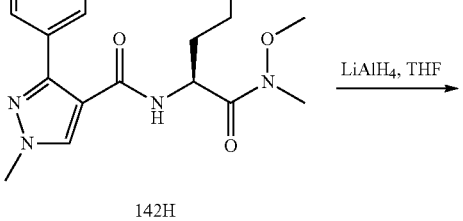
142H
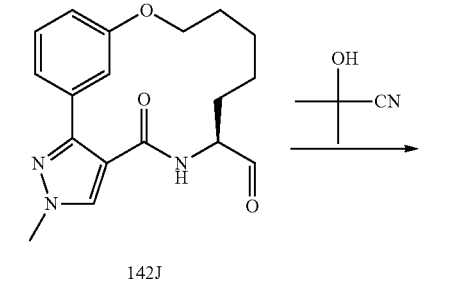
142J
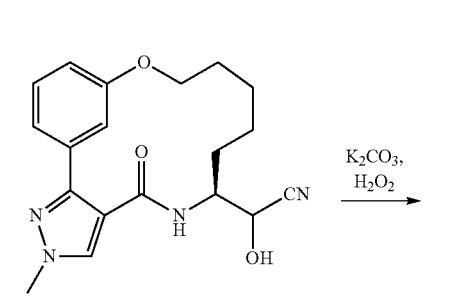
142K
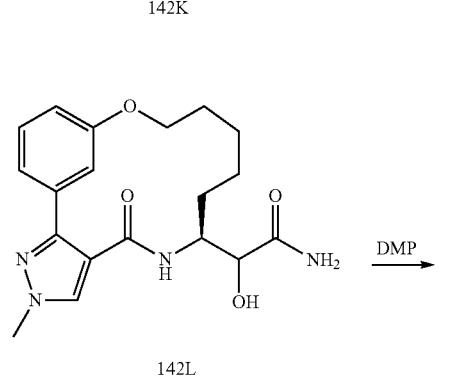
142L

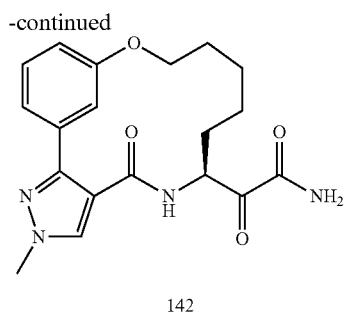

142

Step 1: Synthesis of Compounds 142A and 142B

To a solution of NaH (275 mg, 6.86 mmol, 60% purity) in THF (5 mL) was added dropwise a solution of ethyl 3-bromo-1H-pyrazole-4-carboxylate (1.0 g, 4.57 mmol) in THF (10 mL) at 0° C. After addition, the mixture was stirred at this temperature for 1 h, and then MeI (2.93 g, 20.64 mmol, 1.29 mL) was added dropwise at 0° C. The resulting mixture was stirred at 25° C. for 19 h. The reaction mixture was quenched by addition sat. NH$_4$Cl (5 mL), and then diluted with H$_2$O (10 mL) and extracted with EtOAc (20 mL×2). The combined organic layers were washed with brine (15 mL×2), dried over Na$_2$SO$_4$, filtered and concentrated under reduced pressure to give a residue. The residue was purified by column chromatography (SiO$_2$, Petroleum ether/Ethyl acetate=8/1 to 5:1) to give the Compound 142A (120 mg, yield: 11.27%) was obtained as a yellow oil and Compound 142B (370.00 mg, yield: 34.74%) was obtained as a white solid.

$^1$H NMR (400 MHz, CDCl$_3$) (142A) δ 7.93 (s, 1H), 4.42-4.21 (m, 2H), 3.97-3.82 (m, 3H), 1.36 (t, J=7.2 Hz, 3H)

$^1$H NMR (400 MHz, CDCl$_3$) (142B) δ 7.83 (s, 1H), 4.30 (q, J=7.0 Hz, 2H), 3.94-3.86 (m, 3H), 1.41-1.28 (m, 3H).

Step 2: Synthesis of Compound 142C

To a solution of compound 142B (3.4 g, 14.59 mmol) and (3-hydroxyphenyl)boronic acid (2.41 g, 17.51 mmol) in dioxane/H$_2$O (50 mL/10 mL) was added K$_3$PO$_4$ (9.29 g, 43.77 mmol) and Pd(dppf)Cl$_2$ (1.07 g, 1.46 mmol). The mixture was stirred at 70° C. for 6 h. The reaction mixture was concentrated under reduced pressure to remove solvent. The residue was diluted with H$_2$O (80 mL) and extracted with EtOAc (50 mL×3). The combined organic layers were washed with brine (50 mL×2), dried over Na$_2$SO$_4$, filtered and concentrated under reduced pressure to give a residue. The residue was purified by column chromatography (SiO$_2$, Petroleum ether/Ethyl acetate=10/1 to 7:1) to give the Compound 142C (1.0 g, yield: 27.3%) was obtained as a yellow solid. $^1$H NMR (400 MHz, CDCl$_3$) δ 8.01-7.87 (m, 1H), 7.36-7.32 (m, 1H), 7.30-7.26 (m, 2H), 6.90-6.79 (m, 1H), 5.41-5.30 (m, 1H), 4.24 (q, J=7.1 Hz, 2H), 3.94 (s, 3H), 1.28 (t, J=7.2 Hz, 3H). MS (ESI) m/z (M+H)+ 247.0.

Step 3: Synthesis of Compound 142D

A mixture of compound 142C (3.18 g, 12.91 mmol), 4-bromobut-1-ene (4.36 g, 32.28 mmol, 3.28 mL), Cs$_2$CO$_3$ (21.04 g, 64.55 mmol) in DMF (50 mL) was degassed and purged with N$_2$ for 3 times, and then the mixture was stirred at 90° C. for 23 h under N$_2$ atmosphere. The reaction mixture was diluted with EtOAc (200 mL) and washed with H$_2$O (350 mL×3). The combined organic layers were washed with brine (300 mL×3), dried over Na$_2$SO$_4$, filtered and concentrated under reduced pressure to give a residue. The residue was purified by column chromatography (SiO$_2$, Petroleum ether/Ethyl acetate=5/1 to 2:1) to give the Compound 142D (1.5 g, yield: 38.7%) as a colorless oil. $^1$H NMR (400 MHz, DMSO-d$_6$) δ 8.34 (s, 1H), 7.32-7.22 (m, 3H), 6.96-6.87 (m, 1H), 5.94-5.81 (m, 1H), 5.20-5.02 (m, 2H), 4.18-4.10 (m, 2H), 4.05-3.99 (m, 2H), 3.88 (s, 3H), 1.20 (t, J=7.1 Hz, 3H).

Step 3: Synthesis of Compound 142E

To a solution of compound 142D (2.2 g, 7.32 mmol) in THF/H$_2$O (10 mL/10 mL) was added NaOH (1.46 g, 36.60 mmol). The mixture was stirred at 25° C. for 40 h. The reaction mixture was diluted with H$_2$O (20 mL), then the mixture was concentrated under reduced pressure to remove THF, and extracted with MTBE (15 mL×2). The water layers were neutralized by 1N HCl to pH~3, and extracted with DCM (20 mL×2). The combined organic layers were washed with brine (20 mL), dried over Na$_2$SO$_4$, filtered and concentrated under reduced pressure to give the compound 142E (1.7 g, yield: 85.29%) as a yellow oil. $^1$H NMR (400 MHz, CDCl3) δ 8.01 (s, 1H), 7.40-7.24 (m, 3H), 6.94 (br d, J=8.0 Hz, 1H), 5.98-5.82 (m, 1H), 5.22-5.03 (m, 2H), 4.06 (t, J=6.8 Hz, 2H), 3.96 (s, 3H), 2.62-2.48 (m, 2H).

Step 4: Synthesis of Compound 142

Compound 142 was prepared following the procedure of Example 83 using compound 142E and (S)-2-amino-N-methoxy-N-methylpent-4-enamide hydrochloride. Compound 142 (40 mg, yield: 54.58%) was obtained as a white solid. $^1$H NMR (400 MHz, DMSO-d$_6$) δ 7.99 (br s, 1H), 7.96-7.85 (m, 2H), 7.74 (br s, 1H), 7.34-7.22 (m, 2H), 7.01 (br s, 1H), 6.91 (br d, J=8.2 Hz, 1H), 5.07 (br s, 1H), 4.24-4.14 (m, 1H), 4.06 (br d, J=4.6 Hz, 1H), 3.85 (s, 3H), 1.81-1.61 (m, 2H), 1.60-1.19 (m, 6H) MS (ESI) m/z (M+H)$^+$ 373.1.

Example 91

(S)-2-(1$^3$-methyl-11-oxo-1$^1$H-3-oxa-10-aza-1(1,5)-pyrazola-2(1,3)-benzenacycloundecaphane-9-yl)-2-oxoacetamide (143)

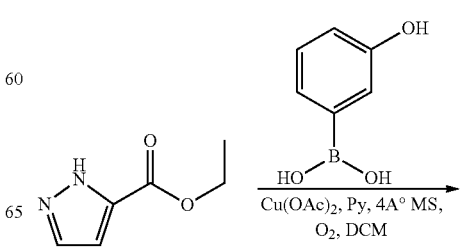

247
-continued
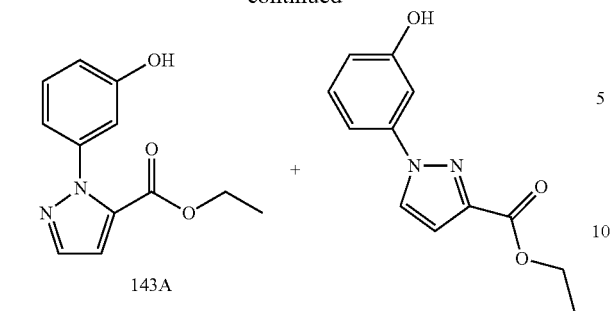
143A
143B
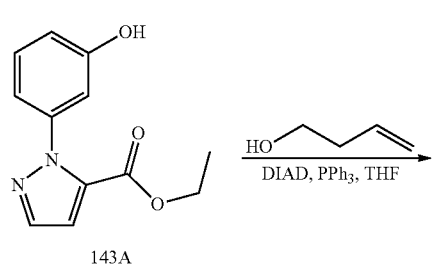
143A
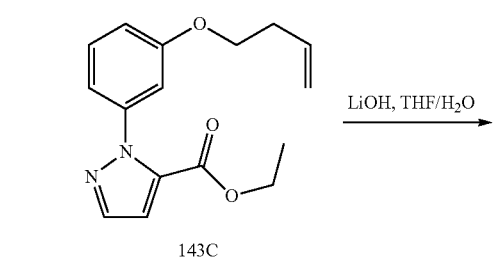
143C
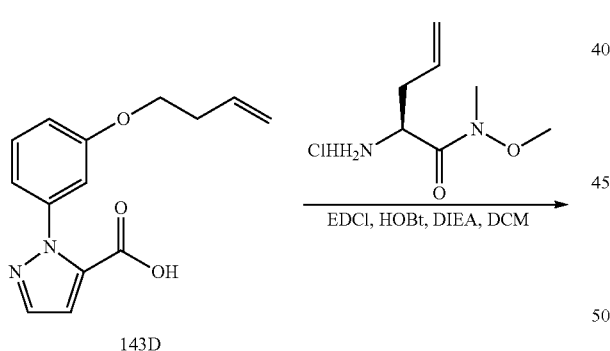
143D
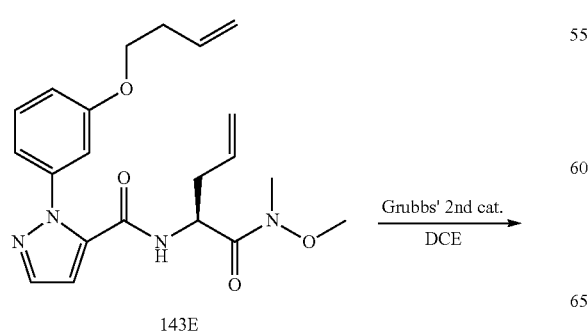
143E
248
-continued
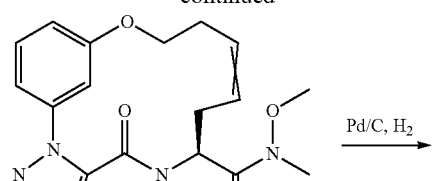
143F
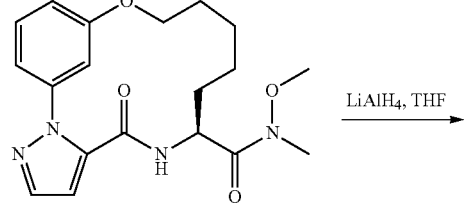
143G
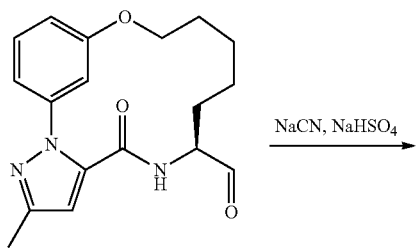
143H
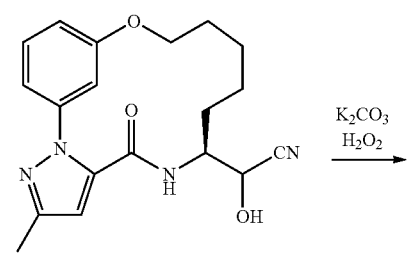
143J
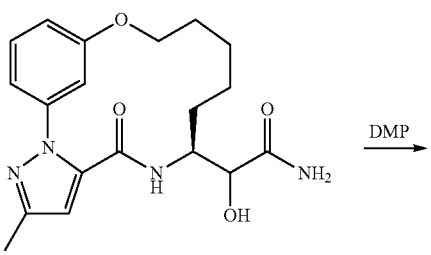
143K
143

Step 1: Synthesis of Compounds 143A and 143B

To a mixture of ethyl 1H-pyrazole-5-carboxylate (20 g, 142.71 mmol), (3-hydroxyphenyl)boronic acid (29.53 g, 214.07 mmol), 4A° MS (30 g) and Py (12.42 g, 156.98 mmol, 12.67 mL) in DCM (200 mL) was added Cu(OAc)$_2$ (28.51 g, 156.98 mmol). The mixture was stirred at 28° C. for 64 h under O$_2$ (15 psi). The reaction mixture was filtered through a pad of Celite. The filtrate was concentrated in vacuo. The residue was purified by column chromatography (SiO$_2$, Petroleum ether/Ethyl acetate=1:0 to 1:10) and the residue was purified by preparatory-HPLC (basic condition) to give compound 143A (2.50 g, 7.24% yield) as colorless oil and compound 143B (5.01 g, 14.97% yield) as white solid. Compound 143A: $^1$H NMR (400 MHz, CHLOROFORM-d) δ 8.23 (br s, 1H), 7.68 (s, 1H), 7.15 (t, J=8.0 Hz, 1H), 7.00 (d, J=2.0 Hz, 1H), 6.86-6.79 (m, 2H), 6.76-6.70 (m, 1H), 4.26-4.07 (m, 2H), 1.21 (q, J=7.1 Hz, 3H). MS (ESI) m/z (M+H)$^+$ 233.1.

Step 2: Synthesis of Compound 143

Compound 143 was prepared following the procedure of Example 83 using compound 143A and but-3-en-1-ol. Compound 143 (25 mg, yield: 41.90%) was obtained as a white solid. $^1$H NMR (400 MHz, DMSO-d$_6$) δ 9.09 (d, J=7.7 Hz, 1H), 8.11 (s, 1H), 7.85 (s, 1H), 7.73 (d, J=1.8 Hz, 1H), 7.43-7.37 (m, 1H), 7.21 (d, J=8.2 Hz, 1H), 6.91 (br d, J=8.2 Hz, 1H), 6.85 (s, 1H), 6.64 (d, J=1.8 Hz, 1H), 5.23-5.05 (m, 1H), 4.22-4.07 (m, 2H), 1.88 (br s, 1H), 1.72 (br s, 2H), 1.59-1.32 (m, 5H). MS (ESI) m/z (M+H)$^+$ 357.1.

Example 92

(S,E)-1$^3$,6-dimethyl-11-oxo-1$^1$H-3-oxa-10-aza-1(1,5)-pyrazola-2(1,3)-benzenacycloundecaphan-6-ene-9-carbaldehyde (144)

and (S,E)-2-(1$^3$,6-dimethyl-11-oxo-1H-3-oxa-10-aza-1(1,5)-pyrazola-2(1,3)-benzenacycloundecaphan-6-en-9-yl)-2-oxoacetamide (145)

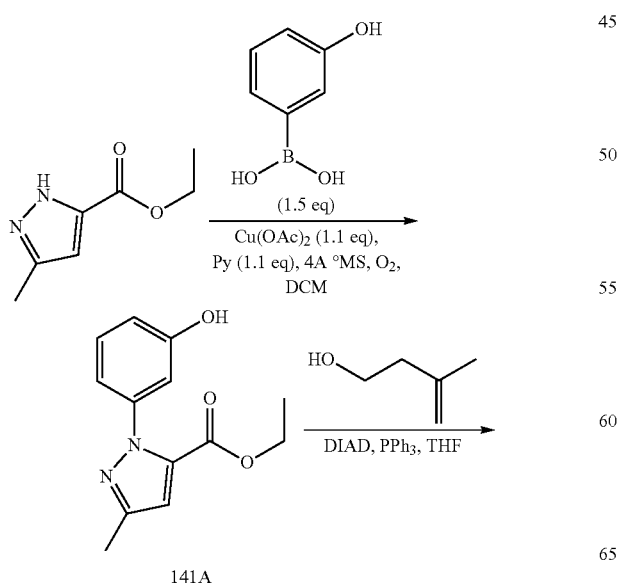

141A

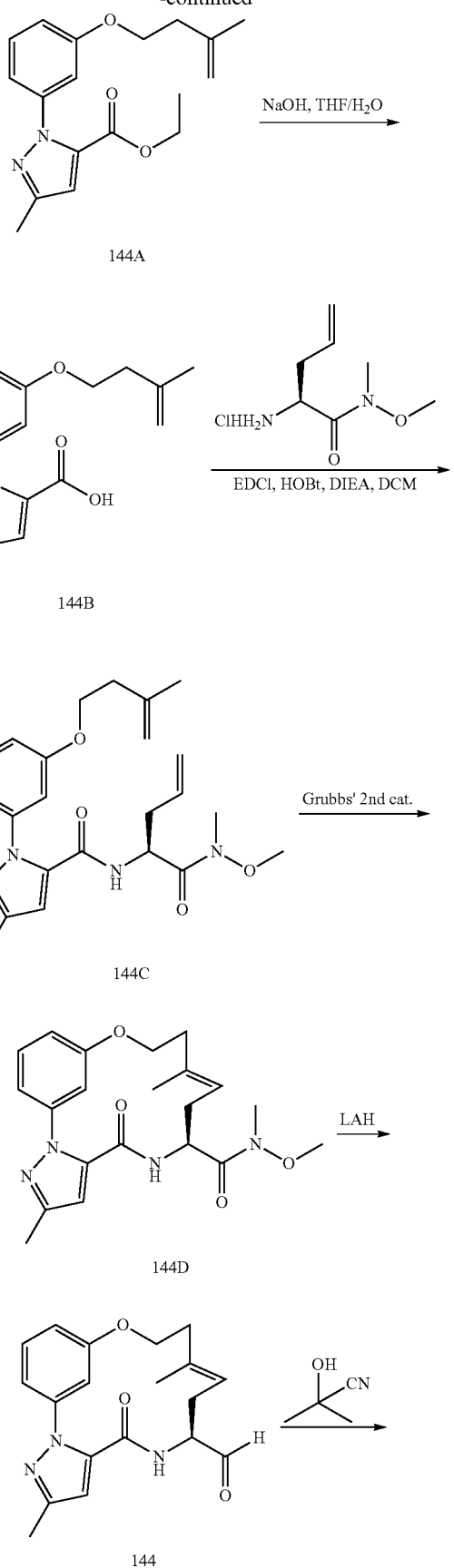

144A

144B

144C

144D

144

251
-continued

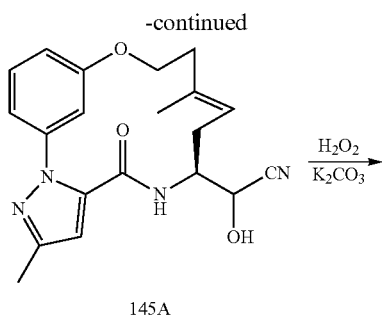
145A

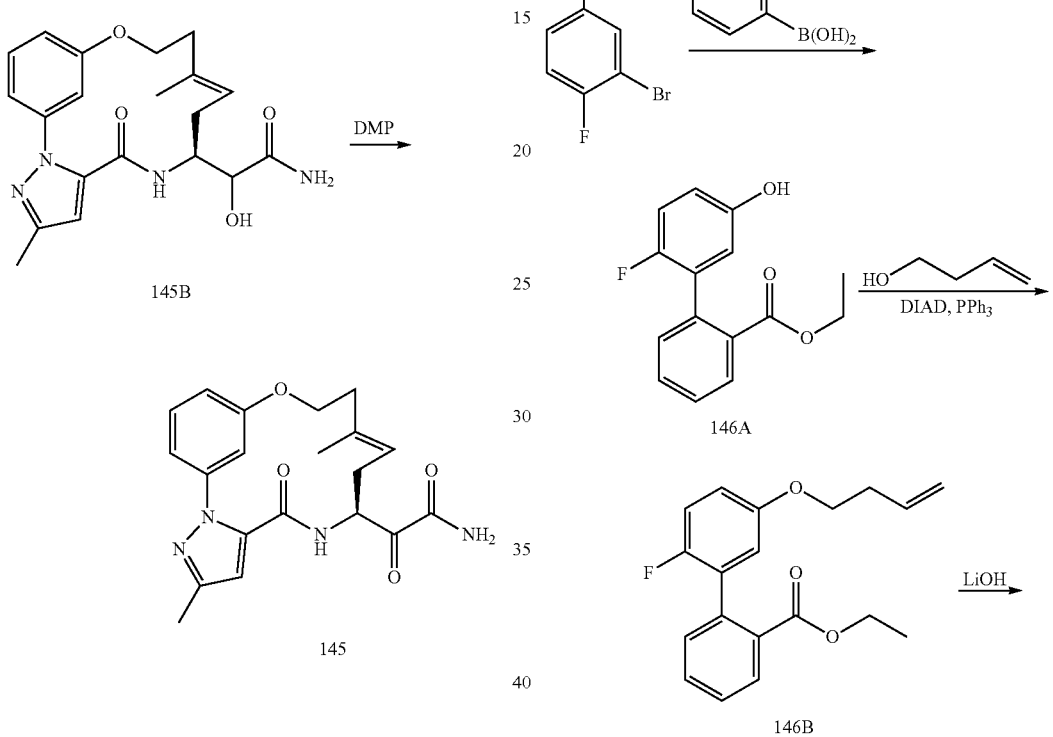

Step 1: Synthesis of Compounds 144 and 145

Compounds 144 and 145 were prepared following the procedure of Example 83 using compound 141A and 3-methylbut-3-en-1-ol. Compound 144 (250 mg, yield: 52.90%) was obtained as a white solid. $^1$H NMR (400 MHz, CDCl$_3$) δ 9.47 (s, 1H), 7.46 (t, J=8.2 Hz, 1H), 7.22 (dd, J=1.1, 7.9 Hz, 1H), 7.01 (dd, J=1.6, 8.4 Hz, 1H), 6.80 (s, 1H), 6.72 (t, J=2.1 Hz, 1H), 5.95 (d, J=5.8 Hz, 1H), 4.71 (t, J=6.7 Hz, 1H), 4.59 (q, J=5.5 Hz, 1H), 4.39-4.30 (m, 2H), 2.99-2.86 (m, 1H), 2.52-2.38 (m, 2H), 2.35 (s, 3H), 2.32-2.25 (m, 1H), 1.68 (s, 3H). MS (ESI) m/z (M+H)$^+$ 340.0. Compound 145 (50 mg, yield: 49.7%) was obtained as a white solid. $^1$H NMR (400 MHz, DMSO-d$_6$) δ 8.41 (br s, 1H), 7.76 (br s, 1H), 7.45-7.35 (m, 1H), 7.28 (br d, J=8.0 Hz, 1H), 7.10-6.99 (m, 1H), 6.75 (br s, 1H), 6.44 (s, 1H), 5.16 (br d, J=8.0 Hz, 1H), 4.96 (t, J=6.7 Hz, 1H), 4.42-4.24 (m, 2H), 2.60 (d, J=11.3 Hz, 1H), 2.44-2.32 (m, 2H), 2.27 (s, 3H), 2.19-2.11 (m, 1H), 1.67 (s, 2H). MS (ESI) m/z (M+H)$^+$ 383.0.

252

Example 93

(S)-2$^6$-fluoro-11-oxo-3-oxa-10-aza-1(1,2),2(1,3)-dibenzenacycloundecaphane-9-carbaldehyde (146)

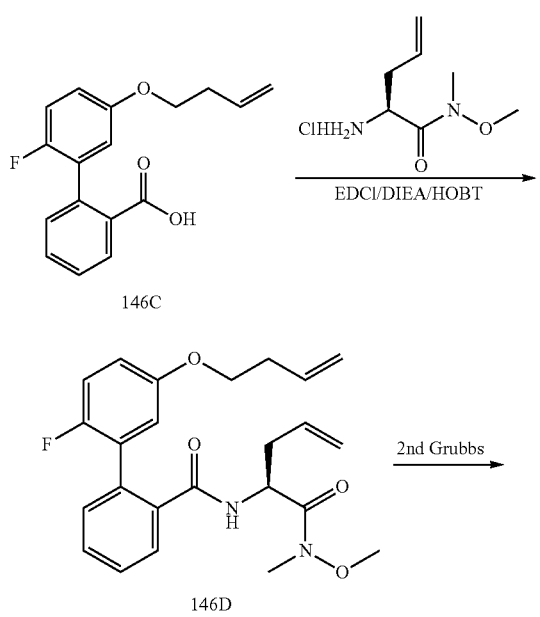

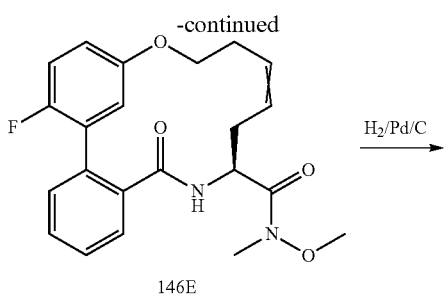

146E

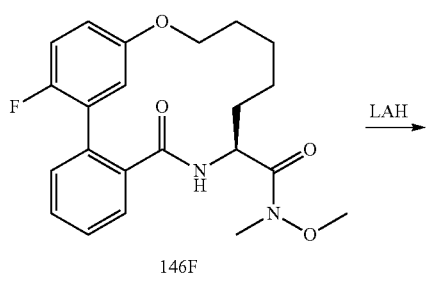

146F

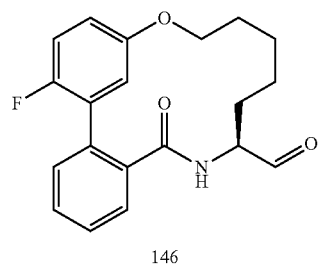

146

Step 1: Synthesis of Compound 146A

To a solution of 3-bromo-4-fluorophenol (3.0 g, 15.71 mmol), (2-(ethoxycarbonyl)phenyl)boronic acid (4.57 g, 23.57 mmol) and K₃PO₄ (6.67 g, 31.42 mmol) in H₂O (30 mL) and dioxane (100 mL) was added Pd(dppf)Cl₂ (575 mg, 785.50 umol) under N₂ atmosphere. After addition, the reaction mixture was stirred at 90° C. for 16 h. The reaction mixture was cooled to room temperature and poured into 50 mL of sat. NH₄Cl, the mixture was extracted with EtOAc (50 mL×2). The combine extracts were washed with water (50 mL) and brine (50 mL), then dried over Na₂SO₄ and concentrated in vacuum. The residue was purified by column chromatography (SiO₂, Petroleum ether/Ethyl acetate=10/1 to 4:1) to afford compound 146A (2.1 g, yield 50.8%) as dark oil. ¹H NMR (400 MHz, DMSO-d6) δ 9.43 (s, 1H), 7.84-7.78 (m, 1H), 7.67-7.59 (m, 1H), 7.55-7.46 (m, 1H), 7.36 (d, J=7.7 Hz, 1H), 7.03-6.93 (m, 1H), 6.77-6.69 (m, 1H), 6.67-6.61 (m, 1H), 4.09-4.02 (m, 2H), 0.99 (t, J=7.2 Hz, 3H).

Step 2: Synthesis of Compounds 146

Compound 146 was prepared following the procedure of Example 88 using compound 146A and but-3-en-1-ol. Compound 146 (350 mg, yield: 80.4%) was obtained as a white solid. ¹H NMR (400 MHz, CHLOROFORM-d) δ 9.46 (s, 1H), 7.62 (br d, J=7.1 Hz, 1H), 7.48-7.32 (m, 3H), 7.09-6.96 (m, 1H), 6.88-6.73 (m, 2H), 6.13 (br d, J=6.2 Hz, 1H), 4.69-4.52 (m, 1H), 4.24-4.08 (m, 2H), 2.07-1.93 (m, 1H), 1.75-1.55 (m, 2H), 1.48-1.38 (m, 1H), 1.33-1.25 (m, 2H), 1.23-1.12 (m, 2H).

Example 94

(S)-2⁶-fluoro-11-oxo-3-oxa-10-aza-1(1,2),2(1,3)-dibenzenacycloundecaphane-9-carbaldehyde (147)

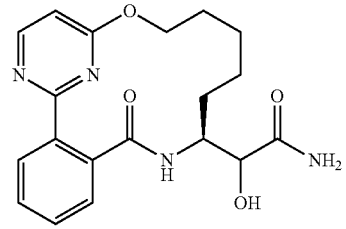

129C

147

Step 1: Synthesis of Compound 147

To a solution of compound 129C (3 g, 8.51 mmol) in DMSO (16 mL) was added K₂CO₃ (2.35 g, 17.03 mmol) and H₂O₂ (9.65 g, 85.13 mmol, 8.18 mL, 30% purity) at 5° C. The mixture was stirred at 5° C. for 2 h. The reaction mixture was quenched by addition sat. Na₂S₂O₃ (20 mL) and NaHCO₃ (20 mL) at 5° C., and then extracted with CHCl₃: i-PrOH=3:1 (30 mL×5) and concentrated under reduced pressure to give a residue. The residue was purified by preparatory-HPLC (TFA condition). Compound 147 (6.5 g, yield: 51.5%) was obtained as a white solid. ¹H NMR (400 MHz, DMSO-d₆) δ 8.55 (d, J=5.7 Hz, 1H), 8.21 (d, J=8.6 Hz, 0.5H), 7.94 (d, J=7.7 Hz, 0.5H), 7.74-7.67 (m, 1H), 7.66-7.61 (m, 0.5H), 7.57 (dd, J=1.8, 6.8 Hz, 0.5H), 7.54-7.44 (m, 2H), 7.33-7.15 (m, 2H), 6.77 (dd, J=1.1, 5.7 Hz, 1H), 5.70 (d, J=6.0 Hz, 0.5H), 5.51 (d, J=6.0 Hz, 0.5H), 5.18-5.01 (m, 1H), 4.19 (br s, 0.5H), 4.08 (br s, 0.5H), 4.01-3.82 (m, 2H), 1.90 (d, J=5.1 Hz, 1H), 1.67 (d, J=11.9 Hz, 0.5H), 1.63-1.20 (m, 6.5H). MS (ESI) m/z (M+H)⁺ 371.0.

Example 95

(S)-2-(2⁶-fluoro-11-oxo-3-oxa-10-aza-1(1,2),2(1,3)-dibenzena-cycloundecaphane-9-yl)-2-oxoacetamide (148)

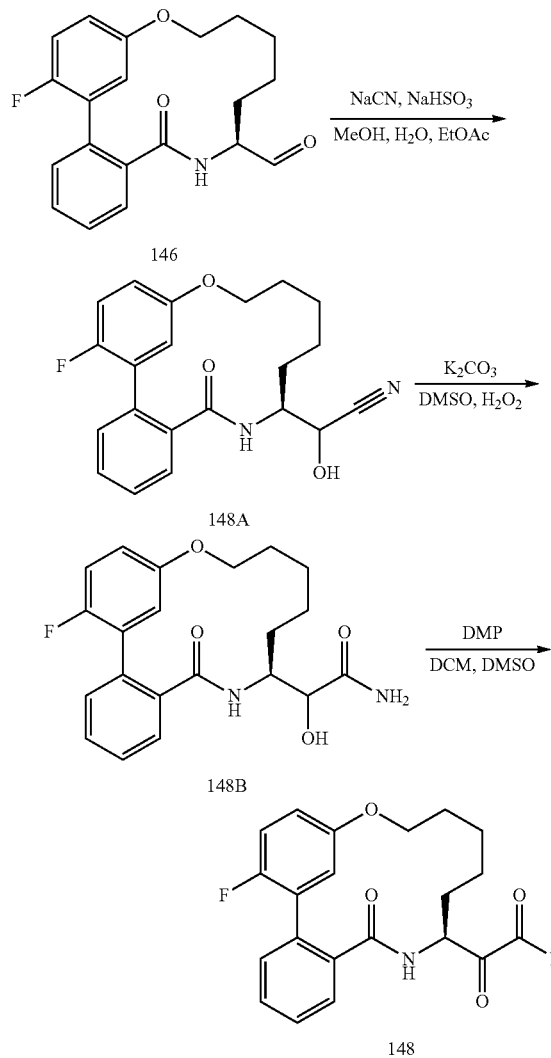

Step 1: Synthesis of Compound 148A

A solution of NaHSO$_3$ (121.7 mg, 1.17 mmol) in 5 mL of H$_2$O was added to a solution of compound 146 (400 mg, 1.2 mmol) in MeOH (15 mL). The mixture was stirred at 20° C. for 5 hours. Then a solution of NaCN (70 mg, 1.4 mmol) in 5 mL of H$_2$O was added, followed by EtOAc (40 mL). The resulting mixture was stirred at 20° C. for 3 h. The organic layer was separated and the aqueous layer was extracted with EA (40 mL×3). The combined organic layer was washed with brine (40 mL×2), dried over Na$_2$SO$_4$, filtered and concentrated to afford compound 148A (380 mg, yield 82.7%) as white solid, which was used directly for the next step without purification. $^1$H NMR (DMSO-d6, 400 MHz): δ 7.82-7.67 (m, 1H), 7.55-7.38 (m, 3H), 7.11 (q, J=9.3 Hz, 1H), 7.03-6.87 (m, 1H), 6.84-6.73 (m, 1H), 6.14-5.80 (m, 1H), 4.99-4.73 (m, 1H), 4.54-4.40 (m, 1H), 4.33-4.15 (m, 2.33H), 4.00 (s, 0.49H), 1.72 (s, 2H), 1.61-1.29 (m, 5.35H), 1.18 (m, 0.57H). MS (ESI) m/z (M+H)$^+$ 369.1.

Step 2: Synthesis of Compound 148B

To a mixture of compound 148A (370 mg, 1.0 mmol) in DMSO (10 mL) was added K$_2$CO$_3$ (277.6 mg, 2.0 mmol) in one portion. Then H$_2$O$_2$ (1 mL, 10.4 mmol, 30% purity) was dropwise added into the mixture, which was stirred at 20° C. for 2 h. Then H$_2$O$_2$ (1 mL, 10.4 mmol, 30% Purity) was added. The reaction mixture was stirred at 20° C. for 1.5 h. H$_2$O$_2$ (0.5 mL, 5.2 mmol, 30% purity) was added into the mixture, which was stirred at 20° C. for 1.5 h. The reaction was quenched by 30 mL of 10% Na$_2$S$_2$O$_3$ solution, and then extracted with EA (30 mL×3). The combined organic layer was washed with brine (30 mL×2), dried over Na$_2$SO$_4$, filtered and concentrated. The residue was triturated with CH$_3$CN:i-propyl ether (1/8, 5 mL). The solid was collected and dried in vacuum to afford compound 148B (240 mg, yield 60.6%) as white solid. $^1$H NMR (DMSO-d$_6$, 400 MHz): δ 8.13-7.74 (m, 1H), 7.61-7.54 (m, 0.48H), 7.53-7.38 (m, 3.67H), 7.33-7.11 (m, 3H), 7.00-6.85 (m, 2H), 5.75-5.45 (m, 1H), 4.29-4.15 (m, 1H), 4.12-3.97 (m, 2H), 3.95-3.79 (m, 1H), 1.74-1.17 (m, 8H) MS (ESI) m/z (M+H)$^+$ 387.1.

Step 3: Synthesis of Compound 148

To a mixture of compound 148B (230 mg, 595.2 umol) in the mixture of DCM (15 mL) and DMSO (1 mL) was added DMP (757.4 mg, 1.8 mmol). The mixture was stirred at 20° C. for 40 min. The reaction was quenched by 15 mL of 10% Na$_2$S$_2$O$_3$ solution and 15 mL of Sat. NaHCO$_3$ solution and stirred for 10 min. After quenching the reaction, the reaction mixture was poured into separatory funnel and separated. The separated aqueous phase was extracted with DCM (30 mL×5). The combined organic phase was washed with brine (40 mL×2), dried over anhydrous Na$_2$SO$_4$, filtered and concentrated in vacuo. The residue was triturated with CH$_3$CN:i-propyl ether (3:2, 4 mL). The solid was collected and dried in vacuum to afford compound 148 (30 mg, yield 12.5%) as offwhite solid. $^1$H NMR (DMSO-d6, 400 MHz): δ 8.86 (br.s., 1H), 8.07 (br.s., 1H), 7.81 (br.s., 1H), 7.49 (br.s., 4H), 7.18 (br.s., 1H), 7.07-6.76 (m, 2H), 5.01 (br.s., 1H), 4.30-3.97 (m, 2H), 1.85-1.25 (m, 8H). MS (ESI) m/z (M+H)$^+$ 385.1.

Example 96

(S)-3-oxo-11-oxa-4-aza-1(2,4)-pyridina-2(1,2)-benzenacycloundecaphane-5-carbaldehyde (149)

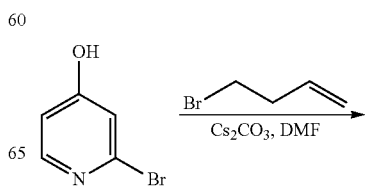

-continued

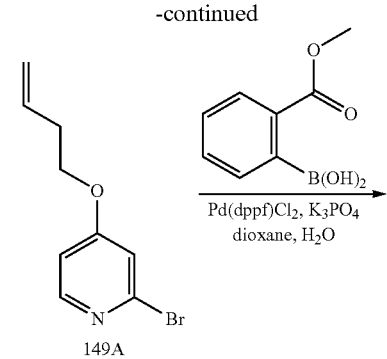
149A

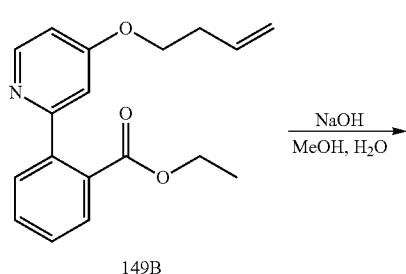
149B

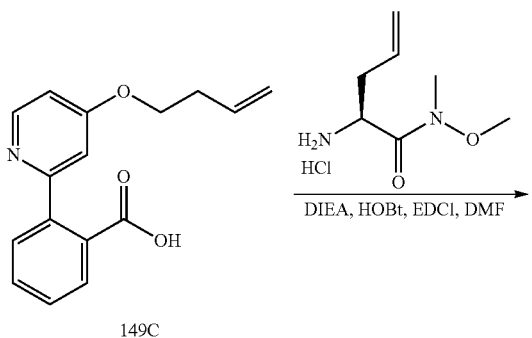
149C

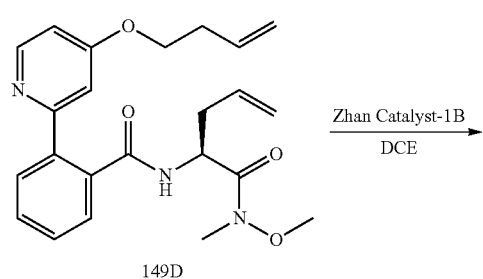
149D

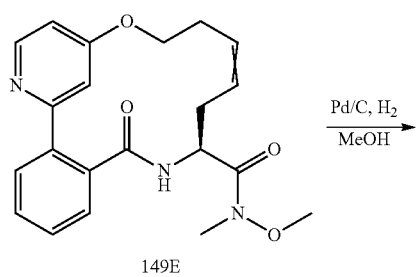
149E

-continued

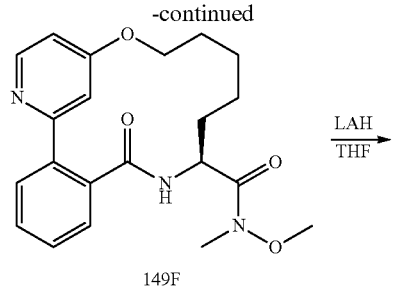
149F

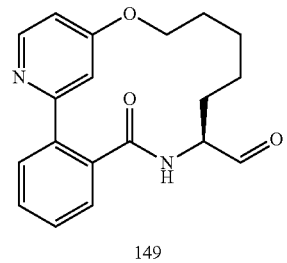
149

Step 1: Synthesis of Compound 149A

To a solution of 2-bromopyridin-4-ol (5.0 g, 28.7 mmol) and 4-bromobut-1-ene (7.2 mL, 71.8 mmol) in DMF (100 mL) was added $Cs_2CO_3$ (46.8 g, 143.7 mmol). The mixture was stirred at 80° C. for 12 h. The mixture was filtered and the residue was washed with EA (15 mL×3). The filter liquor was concentrated under reduced pressure and then $H_2O$ (30 mL) and EA (50 mL) were added to the mixture. The organic layer was separated and the aqueous was extracted with EA (50 mL×2). The combined organic layer was washed with brine (50 mL), dried over anhydrous $Na_2SO_4$, filtered, concentrated under reduced pressure to afford compound 149A (3.55 g, yield 54.1%) as yellow oil, which was used directly in next step. $^1$H NMR (DMSO-$d_6$, 400 MHz): δ 8.09 (d, J=5.7 Hz, 1H), 7.14 (d, J=2.2 Hz, 1H), 6.93 (dd, J=2.2, 5.7 Hz, 1H), 5.78 (tdd, J=6.6, 10.4, 17.1 Hz, 1H), 5.14-4.95 (m, 2H), 4.07 (t, J=6.5 Hz, 2H), 2.42-2.37 (m, 2H).

Step 2: Synthesis of Compound 149B

To a solution of compound 149A (3.6 g, 15.56 mmol) in dioxane (30 mL) and $H_2O$ (3 mL) was added (2-(methoxycarbonyl)phenyl)boronic acid (6.0 g, 31.1 mmol), $K_3PO_4$ (9.9 g, 46.6 mmol), followed by $Pd(dppf)Cl_2$ (1.1 g, 1.5 mmol). The mixture was heated to 80° C. and stirred for 4 h under $N_2$ atmosphere. The reaction mixture was filtered and the residue was washed with EA (10 mL×2). The mixture was concentrated under reduced pressure. $H_2O$ (20 mL) and EA (30 mL) were added to the mixture and the organic layer was separated. The aqueous was extracted with EA (20 mL×2), the combined organic layer was washed with saturated $NaHCO_3$ (30 mL×2), washed with brine (30 mL), dried over anhydrous $Na_2SO_4$, filtered, concentrated under reduced pressure. The crude product was purified by flash column chromatography (PE/EA: 0 to 5/1) to afford compound 149B (3.55 g, yield 76.7%) as yellow oil. $^1$H NMR (DMSO-d6, 400 MHz): δ 8.36 (d, J=5.7 Hz, 1H), 7.70-7.58 (m, 3H), 7.55-7.49 (m, 1H), 7.20 (d, J=2.2 Hz, 1H), 6.95 (dd, J=2.4, 5.7 Hz, 1H), 5.89 (tdd, J=6.6, 10.4, 17.2 Hz, 1H), 5.19 (dd, J=1.8, 17.4 Hz, 1H), 5.10 (dd, J=1.8, 10.4 Hz, 1H), 4.19 (t, J=6.5 Hz, 2H), 4.02 (q, J=7.1 Hz, 2H), 2.56-2.51 (m, 2H), 0.95 (t, J=7.1 Hz, 3H).

Step 3: Synthesis of Compound 149C

To a solution of compound 149B (3.4 g, 11.3 mmol) in MeOH (20 mL) was added a solution of NaOH (4 g, 100.0 mmol) in H$_2$O (10 mL) drop wise. The mixture was stirred at 25° C. for 2 h. The reaction was diluted with H$_2$O (20 mL) and the mixture was concentrated under reduced pressure. The mixture was extracted with MBTE (20 mL) and the aqueous was treated with HCl (1M) until pH~5. The mixture was extracted EA (30 mL×3), the combined organic layer was washed with brine (30 mL), dried over anhydrous Na$_2$SO$_4$, filtered, concentrated under reduced pressure to afford compound 149C (2.5 g, yield 81.6%) as white solid, which was used in next step directly. $^1$H NMR (DMSO-d$_6$, 400 MHz): δ 8.37 (d, J=5.7 Hz, 1H), 7.69-7.64 (m, 1H), 7.63-7.54 (m, 2H), 7.53-7.46 (m, 1H), 7.12 (d, J=2.4 Hz, 1H), 6.93 (dd, J=2.4, 5.7 Hz, 1H), 5.89 (tdd, J=6.6, 10.4, 17.1 Hz, 1H), 5.24-5.08 (m, 2H), 4.17 (t, J=6.6 Hz, 2H), 2.56-2.51 (m, 2H).

Step 4: Synthesis of Compound 149D

To a solution of compound 149C (2.5 g, 9.2 mmol) in DMF (40 mL) was added (S)-2-amino-N-methoxy-N-methylpent-4-enamide hydrochloride (2.4 g, 10.2 mmol HCl), DIEA (6.5 mL, 37.2 mmol), HOBt (376.1 mg, 2.7 mmol). Then EDCI (1.96 g, 10.2 mmol) was added to the mixture and the mixture was stirred at 25° C. for 12 h. The reaction was concentrated under reduced pressure and H$_2$O (20 mL) was added to the mixture. The mixture was extracted with EA (40 mL×3), the combined organic layer was washed with NaHCO$_3$ (40 mL), brine (40 mL), dried over anhydrous Na$_2$SO$_4$, filtered, concentrated under reduced pressure. The crude product was purified by flash column chromatography (PE/EA: 0 to 1/1) to afford compound 149D (3.7 g, yield 97.3%) as yellow oil. $^1$H NMR (DMSO-d$_6$, 400 MHz): δ 8.53 (br d, J=7.9 Hz, 1H), 8.37 (d, J=5.7 Hz, 1H), 7.64 (d, J=7.5 Hz, 1H), 7.55-7.39 (m, 3H), 7.06 (d, J=2.2 Hz, 1H), 6.92 (dd, J=2.4, 5.7 Hz, 1H), 5.89 (tdd, J=6.6, 10.4, 17.2 Hz, 1H), 5.75-5.57 (m, 1H), 5.23-4.95 (m, 4H), 4.82 (br s, 1H), 4.23-4.06 (m, 2H), 3.72 (s, 3H), 3.11 (br s, 3H), 2.53-2.51 (m, 2H), 2.36-2.23 (m, 2H).

Step 5: Synthesis of Compound 149E

To a solution of compound 149D (0.94 g, 2.3 mmol) in DCE (800 mL) was added Zhan Catalyst-1B (282 mg, 384.3 umol). The mixture was heated to 95° C. and stirred for 16 h under N$_2$ atmosphere. The reaction was concentrated under reduced pressure. The crude product was purified by flash column chromatography (PE/EA: 0 to 0/1) to afford compound 149E (0.38 g, yield 43.4%) as black solid. $^1$H NMR (CDCl$_3$, 400 MHz): δ 8.55-8.41 (m, 1H), 7.75-7.35 (m, 4H), 6.97 (d, J=2.4 Hz, 1H), 6.87-6.67 (m, 1H), 6.21 (br d, J=8.6 Hz, 1H), 5.68-5.50 (m, 1H), 5.47-5.23 (m, 2H), 4.49-4.36 (m, 1H), 4.29-4.14 (m, 1H), 3.83-3.69 (m, 3H), 3.25-3.08 (m, 3H), 2.45 (br dd, J=3.9, 7.6 Hz, 3H), 2.00-1.82 (m, 1H).

Step 6: Synthesis of Compound 149E

To a solution of compound 149D (0.18 g, 471.9 umol) in MeOH (30 mL) was added Pd/C (0.1 g, W %=10%, 50% H$_2$O). The suspension was degassed under vacuum and purged with H$_2$ three times. The mixture was stirred at 25° C. for 16 h under H$_2$ (15 Psi) atmosphere. The reaction was filtered and the residue was washed with MeOH (100 mL). The filter liquor was concentrated under reduced pressure to afford compound 149E (0.17 g, yield 93.9%) as black oil, which was used directly in next step. $^1$H NMR (CDCl$_3$, 400 MHz): δ 8.49 (d, J=5.7 Hz, 1H), 7.74 (d, J=7.1 Hz, 1H), 7.58-7.50 (m, 2H), 7.46-7.40 (m, 1H), 7.05 (d, J=2.4 Hz, 1H), 6.80 (dd, J=2.4, 6.0 Hz, 1H), 6.46 (br d, J=8.2 Hz, 1H), 5.08 (br t, J=8.5 Hz, 1H), 4.37-4.26 (m, 2H), 3.76 (s, 3H), 3.18 (s, 3H), 1.92-1.79 (m, 2H), 1.74-1.67 (m, 2H), 1.35-1.19 (m, 4H).

Step 7: Synthesis of Compound 149

To a solution of compound 149E (0.16 g, 417.2 umol) in THF (10 mL) was added dropwise a solution of LiAlH$_4$ (1M in THF, 550 uL, 0.55 mmol) in THF at 0° C. under N$_2$ atmosphere. After addition, the mixture was stirred at 0-5° C. for 1 h. EA (5 mL) was added dropwise into the reaction mixture bellow 10° C. After that HCl (1M, 2 mL) was added slowly, followed by EA (10 mL). The organic layer was separated and the aqueous was extracted with EA (15 mL×2). The combined organic layer was washed with H$_2$O (20 mL), saturated brine (20 mL), dried over anhydrous Na$_2$SO$_4$, filtered, concentrated under reduced pressure. The crude product was purified by flash column chromatography (PE/EA: 2:1 to 100% EA) to afford compound 149 (0.035 g, yield 25.6%) as white solid. $^1$H NMR (CD$_3$CN, 400 MHz): δ 9.60 (s, 1H), 8.44 (d, J=5.8 Hz, 1H), 7.79-7.70 (m, 1H), 7.66-7.49 (m, 3H), 7.28 (br s, 1H), 7.07 (d, J=2.3 Hz, 1H), 6.83 (dd, J=2.4, 5.6 Hz, 1H), 4.48-4.30 (m, 2H), 4.26-4.17 (m, 1H), 1.87-1.79 (m, 1H), 1.76-1.65 (m, 2H), 1.60-1.39 (m, 5H). MS (ESI) m/z (M+H$_2$O+H)$^+$ 343.0.

Biological Data

Example 97

Biochemical Inhibition of Calpains 1, 2, and 9

Calpain 1, 2, and 9 activity and inhibition thereof are assessed by means of a continuous fluorescence assay. The SensoLyte 520 Calpain substrate (Anaspec Inc) is optimized for detecting calpain activity. This substrate contains a novel internally quenched 5-FAM/QXL™ 520 FRET pair. Calpains 1, 2, and 9 cleave the FRET substrate into two separate fragments resulting in an increase of 5-FAM fluorescence that is proportional to calpain activity.

Assays are typically setup in black 384-well plates using automated liquid handling as follows. Calpain assay base buffer typically contains 50 mM Tris, pH~7.5, 100 mM NaCl and 1 mM DTT. Inhibitors are serially diluted in DMSO and used to setup 2× mixtures with calpains in the aforementioned buffer. After incubation at ambient temperature (25C), the reaction is initiated by adding a 2× mix of the fluorescent peptide substrate and CaCl2) (required for in-situ calpain activation) in the same buffer. Reaction progress curve data are typically collected for 10 min using excitation/emission wavelengths of 490 nm/520 nm on SpectraMax i3× or the FLIPR-Tetra plate readers (Molecular Devices Inc). Reaction rates were calculated from progress curve slopes typically over 1-5 min. Dose response curves (rate vs. log inhibitor concentration) were typically fit to a 4-parameter logistic function to extract IC50 values.

Inhibition of Cellular Calpain Activity

Calpain activity in SH-SY5Y cells and inhibition thereof are assessed by means of the Calpain-Glo™ platform (Promega, Inc) which is a homogeneous, luminescence assay that uses the cell-permeable and pro-luminescent calpain substrate Suc-LLVY-aminoluciferin. Upon calpain cleavage followed by cell lysis and quenching the luminescence signal developed is proportional to intra-cellular calpain activity.

Assays are typically setup by seeding SH-SY5Y cells in white 384-well plates at 40 k/per well in RPMI-1640 containing 1% serum followed by 37 C overnight incubation. Next morning, cells are pre-incubated for 1 hr with serially diluted compounds followed by addition of 20 uM each of Suc-LLVY-aminoluciferin substrate and A23187 (ionophore used to induce Ca flux and calpain activity) diluted in Calpain-Glo buffer. After a 4 hr incubation at 37 C (calpain reaction), cells are lysed at 37 C for 1 hr using 0.9% Triton X-100 containing PBS with 100 uM MDL-28170 (excess calpain inhibitor to quench calpain activity). After centrifugation at 300 rpm, the Calpain-Glo™ luciferase detection reagent in Calpain-Glo™ buffer is added followed by 10 min incubation prior to reading luminescence counts using an EnVision plate reader (Perkin Elmer Inc). Dose response curves (luminescence vs. log inhibitor concentration) were typically fit to a 4-parameter logistic function to extract IC50 values.

Calpain Inhibition
A: <3 uM;
B: 3-10 uM;
C: >10 uM;

| No. | Compound | Column A | Column B | Column C |
|---|---|---|---|---|
| 1 | 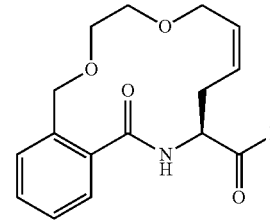 | C | A | A |
| 2 | 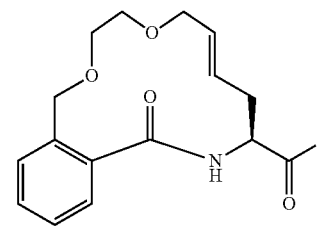 | C | C | B |
| 3 | 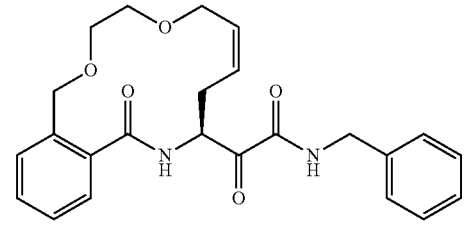 | C | C | A |
| 4 | 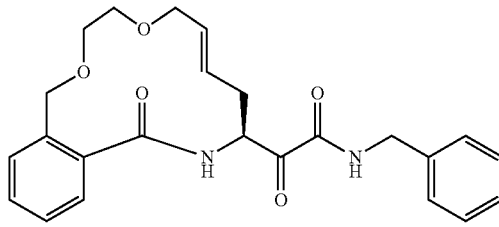 | C | B | A |
| 5 | 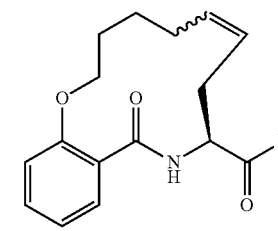 | C | B | A |

-continued

Calpain Inhibition
A: <3 uM;
B: 3-10 uM;
C: >10 uM;

| No. | Compound | Column A | Column B | Column C |
|---|---|---|---|---|
| 6 | | B | A | A |
| 7 | | C | C | B |
| 8 | | B | A | A |
| 9 | | C | A | A |
| 10 | | B | A | A |

-continued

Calpain Inhibition
A: <3 uM;
B: 3-10 uM;
C: >10 uM;

| No. | Compound | Column A | Column B | Column C |
|-----|----------|----------|----------|----------|
| 11 | | B | A | A |
| 12 | | A | A | B |
| 13 | | B | A | B |
| 14 | | B | A | A |
| 15 | | B | A | A |

-continued

| | Calpain Inhibition  
A: <3 uM;  
B: 3-10 uM;  
C: >10 uM; | | | |
|---|---|---|---|---|
| No. | Compound | Column A | Column B | Column C |
| 16 | | B | A | A |
| 17 | | C | C | C |
| 18 | | C | C | B |
| 19 | | C | B | B |
| 20 | | B | A | A |
| 21 | | C | B | B |

-continued

Calpain Inhibition
A: <3 uM;
B: 3-10 uM;
C: >10 uM;

| No. | Compound | Column A | Column B | Column C |
|---|---|---|---|---|
| 22 | | B | B | C |
| 23 | | A | A | A |
| 24 | | C | A | A |
| 25 | | C | C | C |
| 26 | | C | C | B |
| 27 | | C | C | C |

-continued

| | Calpain Inhibition<br>A: <3 uM;<br>B: 3-10 uM;<br>C: >10 uM; | | | |
|---|---|---|---|---|
| No. | Compound | Column A | Column B | Column C |
| 28 | | A | A | A |
| 29 | | A | A | A |
| 30 | | A | A | A |
| 31 | | A | A | A |
| 32 | | A | A | A |

-continued

|  | Calpain Inhibition |  |  |  |
|---|---|---|---|---|
|  | A: <3 uM; |  |  |  |
|  | B: 3-10 uM; |  |  |  |
|  | C: >10 uM; |  |  |  |

| No. | Compound | Column A | Column B | Column C |
|---|---|---|---|---|
| 33 | | C | C | C |
| 34 | | C | C | C |
| 35 | | A | A | A |
| 36 | | A | A | A |
| 37 | | A | A | A |

-continued

| | Calpain Inhibition | | | |
| | A: <3 uM; | | | |
| | B: 3-10 uM; | | | |
| | C: >10 uM; | | | |

| No. | Compound | Column A | Column B | Column C |
|-----|----------|----------|----------|----------|
| 38  | *(macrocyclic structure with phenyl ether, pyridine, amide, and aldehyde)* | A | A | A |
| 39  | *(macrocyclic structure with pyrimidine ether, phenyl, amide, and aldehyde)* | B | A | A |
| 40  | *(macrocyclic structure with pyrimidine ether, phenyl, amide, and aldehyde)* | B | A | A |
| 41  | *(macrocyclic structure with benzyl ether, alkene, amide, and aldehyde)* | C | A | A |
| 42  | *(macrocyclic structure with benzyl ether, amide, and aldehyde)* | C | A | A |
| 43  | *(macrocyclic structure with bis-ether linker, amide, and aldehyde)* | C | A | A |

-continued

Calpain Inhibition
A: <3 uM;
B: 3-10 uM;
C: >10 uM;

| No. | Compound | Column A | Column B | Column C |
|---|---|---|---|---|
| 44 | | A | A | A |
| 45 | | A | A | A |
| 46 | | A | A | A |
| 47 | | A | A | A |

-continued

Calpain Inhibition
A: <3 uM;
B: 3-10 uM;
C: >10 uM;

| No. | Compound | Column A | Column B | Column C |
|---|---|---|---|---|
| 48 | | C | B | A |
| 49 | | C | B | A |
| 50 | | C | B | A |
| 51 | | C | C | B |
| 52 | | C | C | C |
| 53 | | C | C | A |

-continued
Calpain Inhibition
A: <3 uM;
B: 3-10 uM;
C: >10 uM;
| No. | Compound | Column A | Column B | Column C |
|---|---|---|---|---|
| 54 | 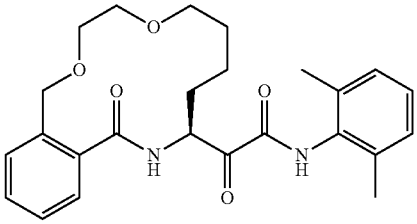 | C | C | C |
| 55 | 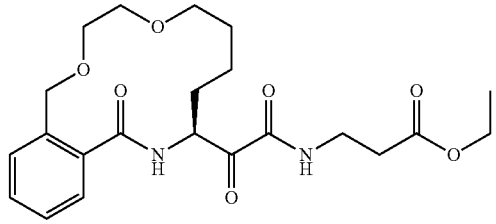 | C | B | B |
| 56 | 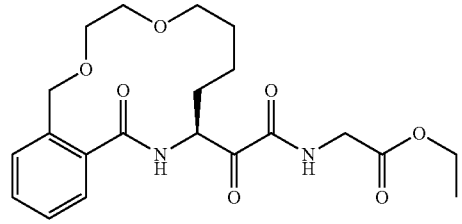 | C | A | A |
| 57 | 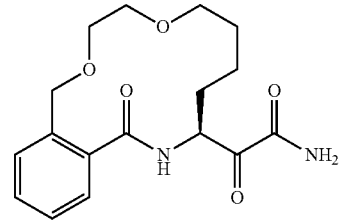 | B | A | A |
| 58 | 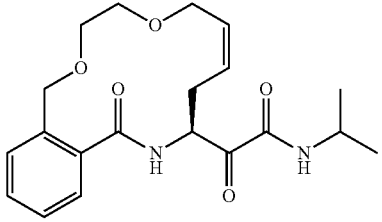 | C | C | C |
| 59 | 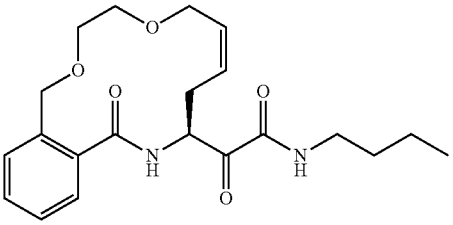 | C | C | A |

-continued

Calpain Inhibition
A: <3 uM;
B: 3-10 uM;
C: >10 uM;

| No. | Compound | Column A | Column B | Column C |
|---|---|---|---|---|
| 60 | | C | C | C |
| 61 | | C | C | C |
| 62 | | C | C | C |
| 63 | | C | C | C |
| 64 | | C | C | A |

-continued

Calpain Inhibition
A: <3 uM;
B: 3-10 uM;
C: >10 uM;

| No. | Compound | Column A | Column B | Column C |
|-----|----------|----------|----------|----------|
| 65  |          | A        | A        | A        |
| 66  |          | A        | A        | A        |
| 67  |          | A        | A        | A        |
| 68  |          | A        | A        | A        |

-continued

Calpain Inhibition
A: <3 uM;
B: 3-10 uM;
C: >10 uM;

| No. | Compound | Column A | Column B | Column C |
|---|---|---|---|---|
| 69 | | B | A | A |
| 70 | | A | A | A |
| 71 | | A | A | A |
| 72 | | A | A | A |

-continued
| | Calpain Inhibition A: <3 uM; B: 3-10 uM; C: >10 uM; | | | |
|---|---|---|---|---|
| No. | Compound | Column A | Column B | Column C |
| 73 | 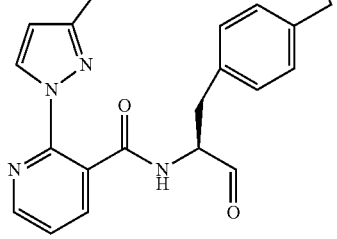 | A | A | A |
| 74 | 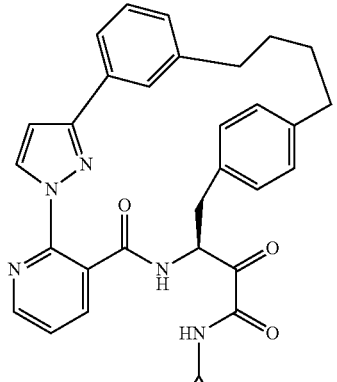 | A | A | A |
| 75 | 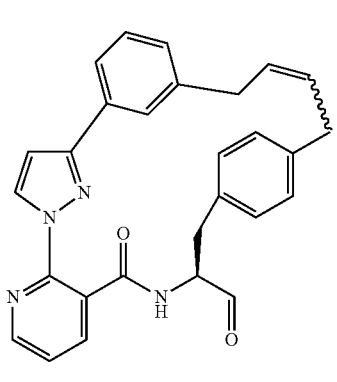 | A | A | A |
| 76 | 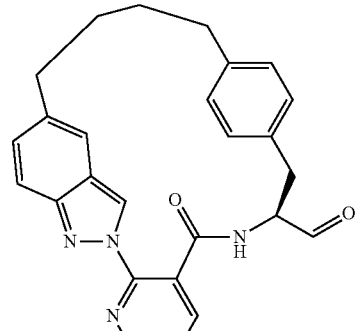 | A | A | A |

-continued
Calpain Inhibition
A: <3 uM;
B: 3-10 uM;
C: >10 uM;
| No. | Compound | Column A | Column B | Column C |
|---|---|---|---|---|
| 77 | 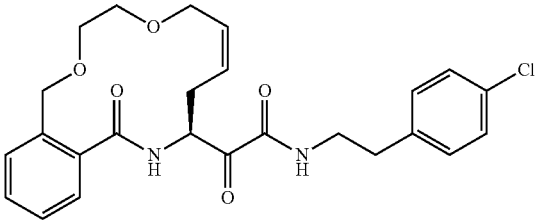 | B | B | A |
| 78 | 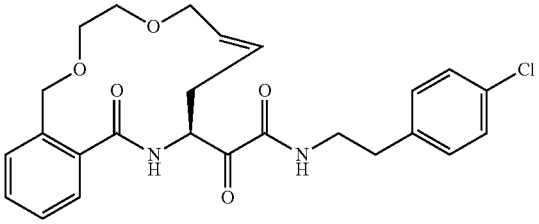 | B | B | A |
| 79 | 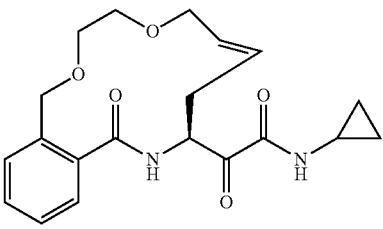 | C | C | B |
| 80 | 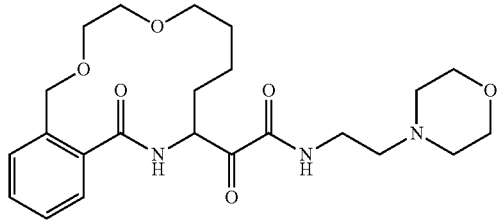 | C | C | C |
| 81 | 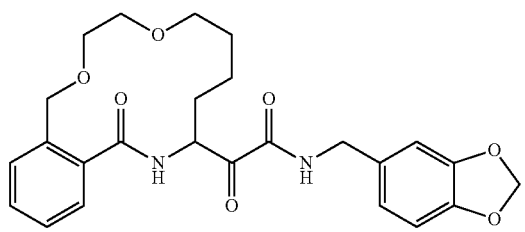 | C | B | A |
| 82 | 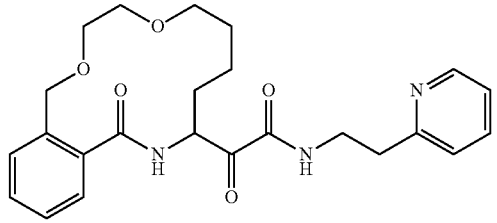 | C | C | B |

-continued

| | Calpain Inhibition<br>A: <3 uM;<br>B: 3-10 uM;<br>C: >10 uM; | | | |
|---|---|---|---|---|
| No. | Compound | Column A | Column B | Column C |
| 83 | | C | B | A |
| 84 | | C | B | A |
| 85 | | C | C | B |
| 86 | | C | C | C |
| 87 | | C | C | A |
| 88 | | C | C | A |

-continued
Calpain Inhibition
A: <3 uM;
B: 3-10 uM;
C: >10 uM;
| No. | Compound | Column A | Column B | Column C |
|---|---|---|---|---|
| 89 | 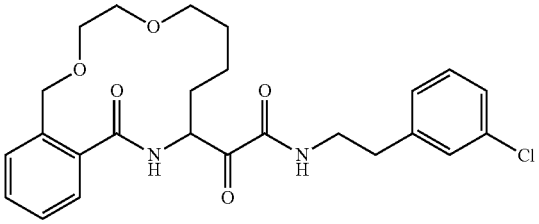 | C | C | A |
| 90 | 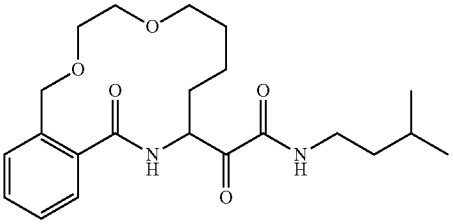 | C | B | A |
| 91 | 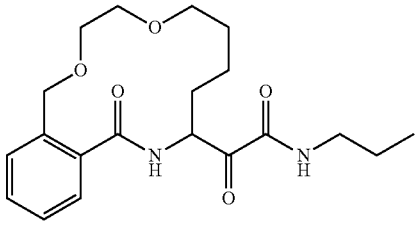 | C | C | C |
| 92 | 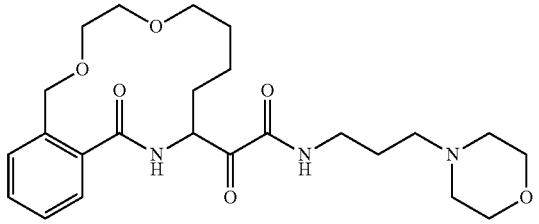 | C | C | B |
| 93 | 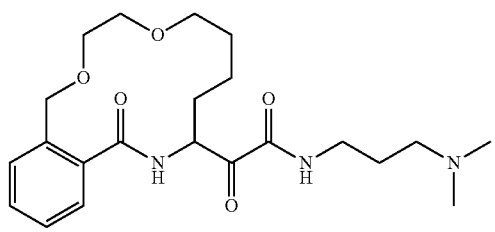 | C | C | C |
| 94 | 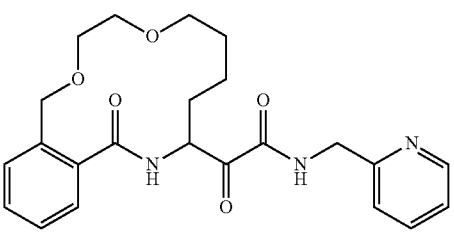 | C | C | A |

-continued

| | Calpain Inhibition<br>A: <3 uM;<br>B: 3-10 uM;<br>C: >10 uM; | | | |
|---|---|---|---|---|
| No. | Compound | Column A | Column B | Column C |
| 95 | | C | C | A |
| 96 | | C | C | B |
| 97 | | C | C | A |
| 98 | | C | A | A |
| 99 | | C | B | B |
| 100 | | C | B | A |

-continued
| | Calpain Inhibition<br>A: <3 uM;<br>B: 3-10 uM;<br>C: >10 uM; | | | |
|---|---|---|---|---|
| No. | Compound | Column A | Column B | Column C |
| 101 | 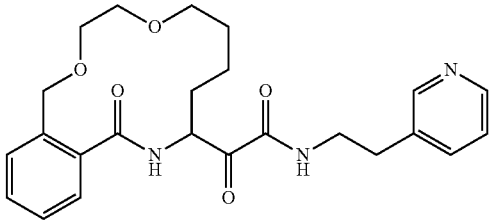 | C | C | B |
| 102 | 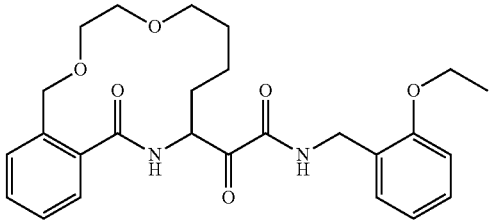 | B | A | A |
| 103 | 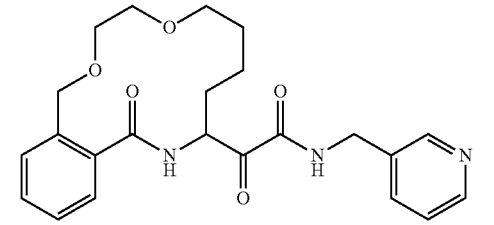 | C | C | A |
| 104 | 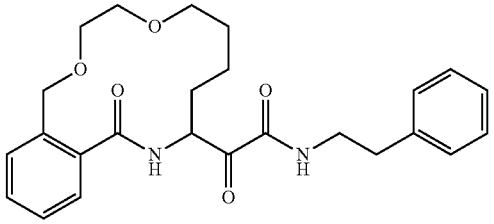 | C | B | A |
| 105 | 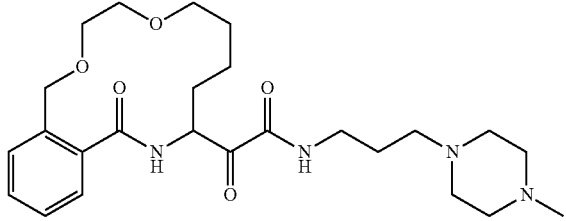 | C | C | A |
| 106 | 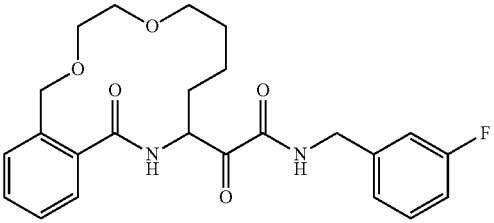 | C | B | A |

-continued

Calpain Inhibition
A: <3 uM;
B: 3-10 uM;
C: >10 uM;

| No. | Compound | Column A | Column B | Column C |
|-----|----------|----------|----------|----------|
| 107 | | C | C | B |
| 108 | | C | B | A |
| 109 | | C | C | V |
| 110 | | C | C | B |
| 111 | | C | B | A |

-continued

| | Calpain Inhibition  A: <3 uM;  B: 3-10 uM;  C: >10 uM; | | | |
|---|---|---|---|---|
| No. | Compound | Column A | Column B | Column C |
| 112 | | C | C | A |
| 113 | | C | C | A |
| 114 | | C | C | C |
| 115 | | C | C | C |
| 116 | | C | C | C |

-continued
| | Calpain Inhibition<br>A: <3 uM;<br>B: 3-10 uM;<br>C: >10 uM; | | | |
|---|---|---|---|---|
| No. | Compound | Column A | Column B | Column C |
| 117 | 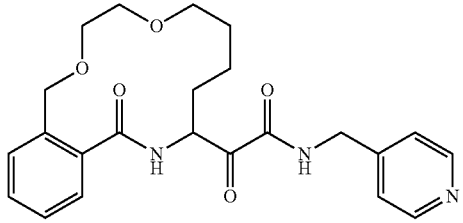 | C | B | A |
| 118 | 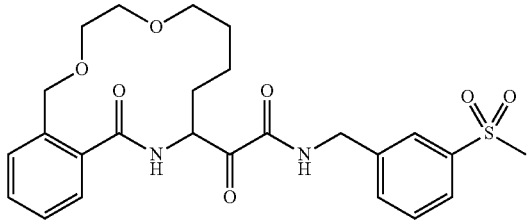 | C | C | A |
| 119 | 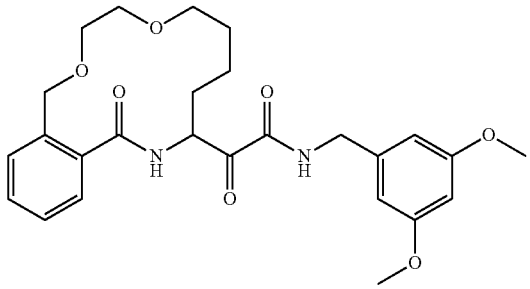 | C | B | A |
| 120 | 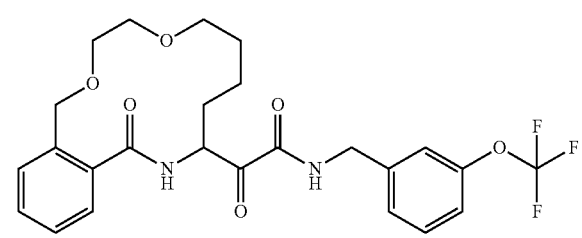 | C | C | A |
| 121 | 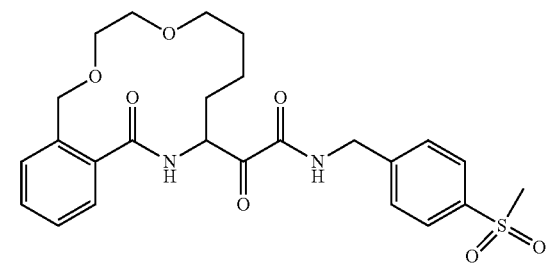 | C | B | A |

-continued
Calpain Inhibition
A: <3 uM;
B: 3-10 uM;
C: >10 uM;
| No. | Compound | Column A | Column B | Column C |
|---|---|---|---|---|
| 122 | 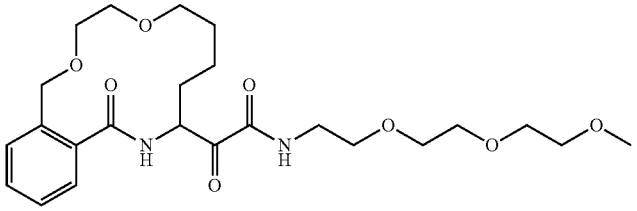 | C | C | C |
| 123 | 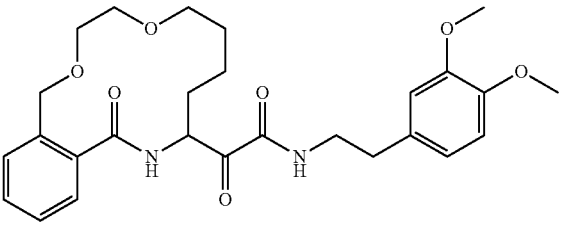 | C | C | B |
| 124 | 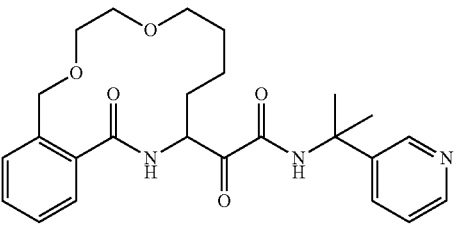 | C | C | C |
| 125 | 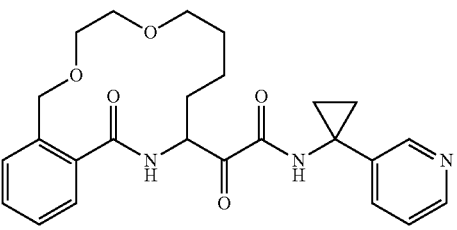 | C | C | C |
| 126 | 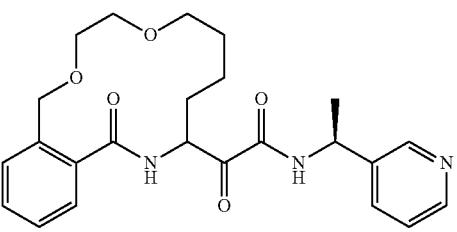 | C | C | C |
| 127 | 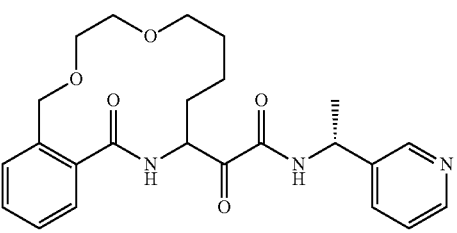 | C | C | C |

-continued

Calpain Inhibition
A: <3 uM;
B: 3-10 uM;
C: >10 uM;

| No. | Compound | Column A | Column B | Column C |
|---|---|---|---|---|
| 128 | | B | A | A |
| 129 | | A | A | A |
| 130 | | A | A | A |
| 131 | | A | A | A |
| 132 | | A | A | A |
| 133 | | A | A | A |

-continued

|  | Calpain Inhibition<br>A: <3 uM;<br>B: 3-10 uM;<br>C: >10 uM; | | | |
|---|---|---|---|---|
| No. | Compound | Column A | Column B | Column C |
| 134 | | A | A | A |
| 135 | | C | C | C |
| 136 | | C | C | C |
| 137 | | A | A | A |
| 138 | | A | A | A |
| 139 | | A | A | A |

-continued

Calpain Inhibition
A: <3 uM;
B: 3-10 uM;
C: >10 uM;

| No. | Compound | Column A | Column B | Column C |
|---|---|---|---|---|
| 140 | | A | A | A |
| 141 | | A | A | A |
| 142 | | C | C | A |
| 143 | | A | A | A |
| 144 | | A | A | A |

-continued

Calpain Inhibition
A: <3 uM;
B: 3-10 uM;
C: >10 uM;

| No. | Compound | Column A | Column B | Column C |
|---|---|---|---|---|
| 145 | | A | A | A |
| 146 | | A | A | A |
| 147 | | C | C | C |
| 148 | | A | A | A |
| 149 | | A | A | A |

Column A: Human Calpain 1/NS1 IC50 (nM)_MEAN
Column B: Human Calpain 2/NS1 IC50 (nM)_MEAN
Column C: Human Calpain 9/NS1 IC50 (nM)_MEAN

Example 98: Animal Models & Studies

Bleomycin-Induced Pulmonary Fibrosis in Mice or Rats

The method for inducing pulmonary fibrosis in mice is described in Current Protocols in Pharmacology: 5.46.1, entitled "Mouse Models of Bleomycin-induced Pulmonary Fibrosis". In order to induce pulmonary fibrosis, 6-8 week old C57Bl/6 mice or Wistar rats are instilled once oropharyngeally with ~1.5 U/kg of bleomycin sulfate (Calbiochem, Billerica, Mass.). Briefly, for oropharyngeal administration of bleomycin, mice or rats are anesthetized with isofluorane and then suspended on its back at a ~60 degree angle on an inclined surface with a rubber band running under the upper incisors. The airway is opened while securing the tongue with one arm of padded forceps and bleomycin is administered into the back of the oral cavity with a syringe. The study is terminated on day 14-28 for oropharyngeally administered bleomycin in mice and rats.

Alternatively, for systemic bleomycin administration by osmotic pumps in mice, the pumps are loaded with bleomycin and implanted subcutaneously under isofluorane anesthesia as described in Lee, Am J Physiol Lung Cell Mol Physiol, 2014. Briefly, mice are systemically administered ~50 U/kg bleomycin (Blenoxane; Teva Pharma, North Wales, Pa.) via osmotic pumps for 7 days. On day 10, the osmotic pumps are removed, and the study is continued until day 35.

All animals are euthanized at the termination of the studies by cervical dislocation for gross necropsy, and blood collected by cardiac puncture. The lungs from each animal are dissected from the animal and weighed. The BAL cells and fluid are collected by lavaging the lung twice with 0.5 ml Hanks Balanced Salt Solution (HBSS; VWR, Radnor, Pa.). After collection of BAL cells and fluid, lungs are dissected and removed from each animal. Whole lungs are inflated with 10% NBF and then fixed in 10% NBF for histology. Severity of fibrosis in the lungs is evaluated using a modified Ashcroft score (Hubner, Biotechniques, 2008).

Carbon Tetrachloride-Induced Liver Fibrosis in Mice or Rats

Carbon tetrachloride-induced liver fibrosis is a widely used and accepted model for evaluating novel antifibrotic therapies. The methods for inducing liver fibrosis by carbon tetrachloride administration is described in Lee, J Clin Invest, 1995 and Tsukamoto, Semin Liver Dis, 1990. Briefly, male C57BL/6 mice are challenged with 1 mg/kg carbon tetrachloride (Sigma Aldrich, diluted 1:7 in corn or olive oil) administered by intraperitoneal injection twice weekly for a period of 4 weeks. Mice are euthanized on day 28. In an alternative implementation, Wistar rats are administered carbon tetrachloride by intraperitoneal injection three times per week for 8-12 weeks. Rats are euthanized at the termination of the experiment, 8-12 after study initiation.

Blood is collected by cardiac puncture and processed into serum for evaluation of liver enzymes (including ALT, AST, ALP, etc) at several timepoints throughout the study and at termination of the study. The liver tissues from all animals are collected and fixed by immersion in 10% neutral buffered formalin, processed, paraffin embedded, sectioned, mounted, and stained with Masson's Trichrome (Tri) or Picrosirius Red (PSR) using standard histological methods for evaluation of fibrosis severity.

Mouse Unilateral Ureteral Obstruction Kidney Fibrosis Model

Female C57BL/6 mice (Harlan, 4-6 weeks of age) will be given free access to food and water and allowed to acclimate for at least 7 days prior to test initiation. After acclimation, mice are anesthetized and undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. All animals are euthanized 4, 8, 14, 21, or 28 days after UUO surgery. Following sacrifice blood is collected via cardiac puncture, the kidneys are harvested and one half of the kidney is frozen at −80 0 C. and the other half is fixed in 10% neutral buffered formalin for histopathological assessment of kidney fibrosis.

Bleomycin Dermal Fibrosis Model

Bleomycin (Calbiochem, Billerica Mass.) is dissolved in phosphate buffered saline (PBS) at 10 ug/ml, and sterilized by filtration. Bleomycin or PBS control (100 µl) is injected subcutaneously into two locations on the shaved back of C57/BL6 or S129 mice (Charles River/Harlan Labs, 20-25 g) once daily for 28 days while under isoflourane anesthesia (5% in 100% 02). After 28 days, mice are euthanized and 6 mm-full thickness punch biopsies are obtained from each injection site. Dermal fibrosis is assessed by standard histopathology and hydroxyproline biochemical assays.

Example 99: Targeting Calpains

Inhibition of EpMT

For assessment of in vitro EMT, NMuMG cells (ATCC) are grown to confluence in 10% serum (Fetal Bovine Serum) growth media (Dubecco's Modified Eagles Medium supplemented with 10 ug/mL insulin) and then are followed by 24 h starvation in 0.5% serum media +/− drug inhibitors. Cells are then treated with recombinant human TGFb1 (R&D Systems 5 ng/mL) +/− drug inhibitors in 0.5% serum media. For time points greater than 24 h, the aforementioned media is refreshed every 24 hours. Cell lysates were analyzed for aSMA protein expression by western blot.

Miettinen et al. (1994). "TGF-beta induced transdifferentiation of mammary epithelial cells to mesenchymal cells: involvement of type I receptors." J Cell Biol 127(6 Pt 2):2021-36.

Lamouille et al. (2014). "Molecular mechanisms of epithelial-mesenchymal transition." Nat Rev Mol Cell Biol 15(3):178-96.

For assessment of in vitro FMT, Normal Human Lung Fibroblasts (NHLF) cells (Lonza) were grown in Fibroblast Growth Media-2 (Lonza CC-3131/with CC-4126 bullet kit) and then were followed by 24 h starvation in serum/growth factor free Fibroblast Basal Media-2 (Lonza CC-3131) +/− drug inhibitors. Cells were then treated with TGFb1 (5 ng/mL) Fibroblast Basal Media +/− drug inhibitors. Cell lysates are analyzed for aSMA protein expression by western blot.

Further details may be found in Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85, which is incorporated herein by reference in its entirety.

Example 100: Human Treatment

The efficacy of treatment with a compound of a preferred embodiment compared with placebo in patients with idiopathic pulmonary fibrosis (IPF) and the safety of treatment with a compound of a preferred embodiment compared with placebo in patients with IPF is assessed. The primary outcome variable is the absolute change in percent predicted forced vital capacity (FVC) from baseline to Week 52. Other possible end-points would include, but are not limited to: mortality, progression free survival, change in rate of FVC decline, change in Sp02, and change in biomarkers (HRCT image analysis; molecular and cellular markers of disease activity). Secondary outcome measures include: composite outcomes of important IPF-related events; progression-free survival; the rate of death from any cause; the rate of death from IPF; categorical assessment of absolute change in percent predicted FVC from baseline to Week 52; change in Shortness-of-Breath from baseline to Week 52; change in percent predicted hemoglobin (Hb)-corrected carbon monoxide diffusing capacity (DLco) of the lungs from baseline to Week 52; change in oxygen saturation during the 6 minute walk test (6MWT) from baseline to Week 52; change in high-resolution computed tomography (HRCT) assessment from baseline to Week 52; change in distance walked in the 6MWT from baseline to Week 52. Patients eligible for this study include, but are not limited to: those patients that satisfy the following inclusion criteria: diagnosis of IPF; 40 to 80 years of age; FVC≥50% predicted value; DLco≥35% predicted value; either FVC or DLco≤90% predicted value; no improvement in past year; a ratio of the forced expiratory volume in 1 second (FEV1) to the FVC of 0.80 or more; able to walk 150 meters in 6 minutes and maintain saturation≥83% while on no more than 6 L/min supplemental oxygen. Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 52 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials. Patients are orally dosed with either placebo or an amount of a compound of a preferred embodiment (1 mg/day-1000 mg/day). The primary outcome variable will be the absolute change in percent predicted FVC from Baseline to Week 52. Patients will receive blinded study treatment from the time of randomization until the last patient randomized has been treated for 52 weeks. Physical and clinical laboratory assessments will be performed at defined intervals during the treatment duration, for example at weeks 2, 4, 8, 13, 26, 39, and 52. Pulmonary function, exercise tolerance, and shortness-of-breath will be assessed at defined intervals during the treatment duration, for example at weeks 13, 26, 39, and 52. A Data Monitoring Committee (DMC) will periodically review safety and efficacy data to ensure patient safety.

Example Trial in SSc

The efficacy of treatment with a compound of a preferred embodiment compared with placebo in patients with systemic sclerosis (SSc) and the safety of treatment with a compound of a preferred embodiment compared with placebo in patients with SSc is assessed. The primary outcome variable is the absolute change in Modified Rodnan Skin Score (mRSS) from baseline to Week 48. Other possible end-points would include, but are not limited to: mortality, percentage of patients with treatment-emergent adverse events (AEs) and serious adverse events (SAEs), composite measurement of disease progression, and change in biomarkers (molecular and cellular markers of disease activity, such as C-reactive protein). Secondary outcome measures include, but are not limited to: Scleroderma Health Assessment Questionnaire (SHAQ) score; the Health Assessment Questionnaire Disability Index (HAQ-DI); Functional Assessment of Chronic Illness Therapy-Fatigue (FACIT) score; severity of pruritus as measured by a standardized scale, such as the 5-D Itch Scale; St. George's Respiratory Questionnaire (SGRQ) score; Tender Joint Count 28 (TCJ28); lung function parameters; standard vital signs (including blood pressure, heart rate, and temperature); electrocardiogram measurements (ECGs); laboratory tests (clinical chemistry, hematology, and urinalysis); pharmacokinetics (PK) measurements. Included in these measurements and in addition, clinical and biomarker samples, such as skin biopsies and blood (or serum and/or plasma), will also be collected prior to initiation of treatment. Additionally, patients eligible for this study include, but are not limited to, those patients that satisfy the following criteria: Patients at least 18 years of age; diagnosis of SSc according to the American College of Rheumatology (ACR) and European League Against Rheumatism (EULAR) Criteria, meeting criteria for active disease and with a total disease duration of less than or equal to 60 months; 10≤mRSS≤35. Patients are excluded from this study if they satisfy any of the following criteria: major surgery within 8 weeks prior to screening; scleroderma limited to area distal to the elbows or knees; rheumatic autoimmune disease other than SSc; use of any investigational, biologic, or immunosuppressive therapies, including intra-articular or parenteral corticosteroids within 4 weeks of screening. Patients are orally dosed with either placebo or an amount of a compound of a preferred embodiment (1 mg/day-1000 mg/day). The primary outcome variable will be the absolute change in mRSS from Baseline to Week 48. Patients will receive blinded study treatment from the time of randomization until the last patient randomized has been treated for 48 weeks. Physical and clinical laboratory assessments will be performed at defined intervals during the treatment duration, such as Weeks 2, 4, 8, 12, 24, 36, and 48. Clinical and biomarker samples will also be collected at Week 48. A Data Monitoring Committee (DMC) will periodically review safety and efficacy data to ensure patient safety.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Although the invention has been described with reference to embodiments and examples, it should be understood that numerous and various modifications can be made without departing from the spirit of the invention. Accordingly, the invention is limited only by the following claims.

REFERENCES CITED

1. U.S. Pat. No. 5,145,684
2. Goll et al. (2003). "The calpain system." Physiol Rev 83(3):731-801.
3. Schad et al. (2002). "A novel human small subunit of calpains." Biochem J 362(Pt 2):383-8.
4. Ravulapalli et al. (2009). "Distinguishing between calpain heterodimerization and homodimerization." FEB S J 276 (4):973-82.
5. Dourdin et al. (2001). "Reduced cell migration and disruption of the actin cytoskeleton in calpain-deficient embryonic fibroblasts." J Biol Chem 276(51):48382-8.
6. Leloup et al. (2006). "Involvement of calpains in growth factor-mediated migration." Int J Biochem Cell Biol 38(12):2049-63.
7. Janossy et al. (2004). "Calpain as a multi-site regulator of cell cycle." Biochem Pharmacol 67(8):1513-21.
8. Santos et al. (2012). "Distinct regulatory functions of calpain 1 and 2 during neural stem cell self-renewal and differentiation." PLoS One 7(3):e33468.
9. Miettinen et al. (1994). "TGF-beta induced transdifferentiation of mammary epithelial cells to mesenchymal cells: involvement of type I receptors." J Cell Biol 127(6 Pt 2):2021-36.
10. Lamouille et al. (2014). "Molecular mechanisms of epithelial-mesenchymal transition." Nat Rev Mol Cell Biol 15(3):178-96.
11. Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85.

What is claimed is:

1. A compound having the structure of the formula I-a or I-b:

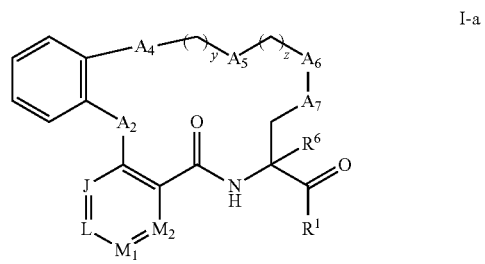

I-a

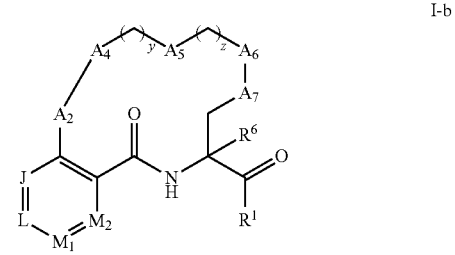

I-b or a pharmaceutically acceptable salt thereof, wherein:
J, L, $M_1$ and $M_2$ are each independently selected from the group consisting of $C(R^4)$ and N;
each $R^4$ is independently selected from the group consisting of —H, $C_{1-4}$ alkyl, $C_{3-7}$ carbocyclyl, halo, hydroxy, and $C_1$-$C_6$ alkoxy;
$A_2$ is selected from the group consisting of optionally substituted 3-10 membered heterocyclyl, optionally substituted $C_{6-10}$ aryl, optionally substituted 5-10 membered heteroaryl, optionally substituted $C_{3-10}$ carbocyclyl, —$CR_2$—, —S—, —O—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;
$A_4$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;
$A_5$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;

$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;

$A_7$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;

y is an integer from 1 to 4;

z is an integer from 0 to 4;

$R^1$ is selected from the group consisting of H, —$CH_2F$, —$CH_2Cl$, —COOH, —C(=O)N(R)OR, —$CONR^2R^3$, —$CH(CH_3)$=$CH_2$, —$CH(CF_3)NR^2R^3$, —C(F)=$CHCH_2CH_3$,

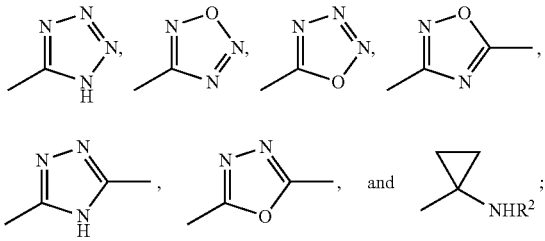

and each R, $R^2$, and $R^3$ are independently selected from H, optionally substituted $C_{1-4}$ alkyl, optionally substituted $C_2$-$C_6$ alkynyl, optionally substituted $C_{1-6}$ alkoxy, optionally substituted 2- to 5-membered polyethylene glycol, optionally substituted $C_{3-7}$ carbocyclyl, optionally substituted 5-10 membered heterocyclyl, optionally substituted $C_{6-10}$ aryl, and optionally substituted 5-10 membered heteroaryl; and $R^6$ is selected from —H and optionally substituted $C_{1-4}$ alkyl.

2. The compound of claim 1, wherein:

$A_4$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH=CH—, and single bond;

$A_5$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH=CH—, and single bond;

$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH=CH—, and single bond;

$A_7$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, —CH=CH—, and single bond;

$R^1$ is selected from the group consisting of H, —$CH_2F$, —$CH_2Cl$, —COOH, —$CONR^2R^3$, —$CH(CH_3)$=$CH_2$, —$CH(CF_3)NR^2R^3$, —C(F)=$CHCH_2CH_3$,

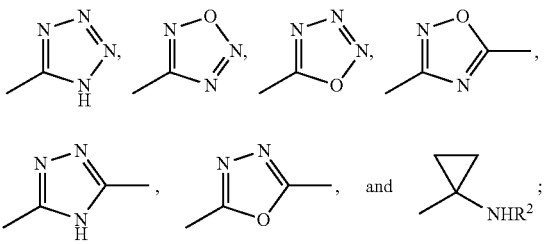

and each R, $R^2$, and $R^3$ are independently selected from —H, optionally substituted $C_{1-4}$ alkyl, optionally substituted $C_{3-7}$ carbocyclyl, optionally substituted 5-10 membered heterocyclyl, optionally substituted $C_{6-10}$ aryl, and optionally substituted 5-10 membered heteroaryl.

3. The compound of claim 1, wherein J, L, $M_1$, and $M_2$ are independently selected from the group consisting of CH and N.

4. A compound having the structure selected from the group consisting of:

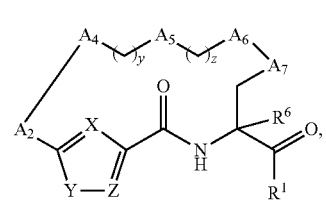

I-g

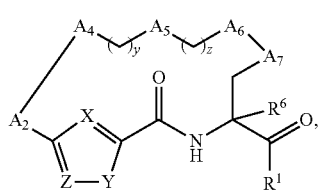

I-g1

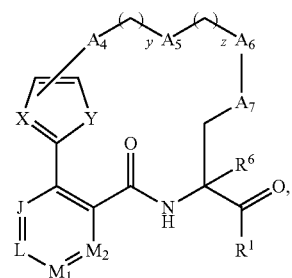

I-h

-continued
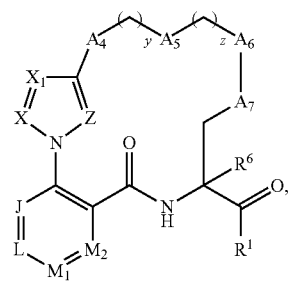
I-j
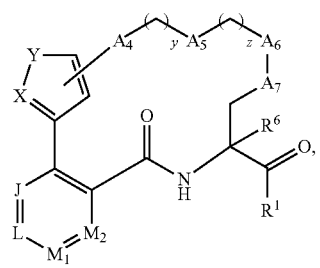
I-k
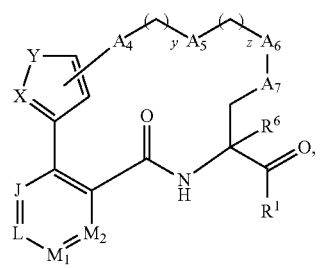
I-k
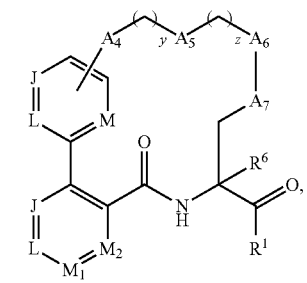
I-l
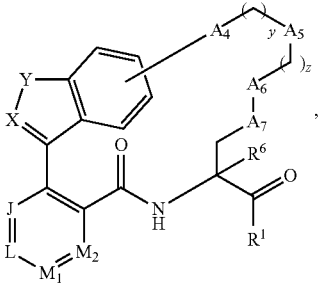
I-m
-continued
I-n
I-o
I-p
I-q
I-r

327

-continued

I-s
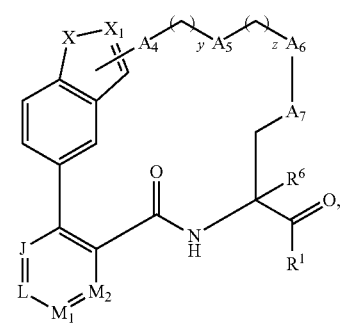

I-t
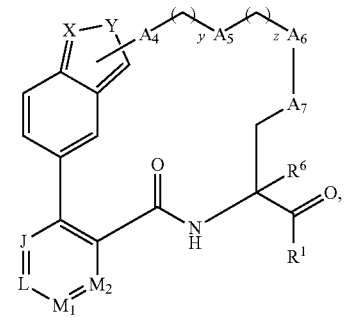

I-u
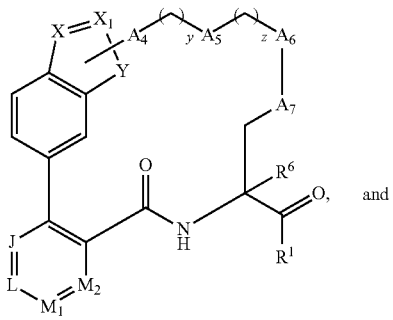

I-v
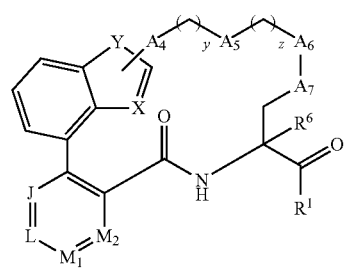

or a pharmaceutically acceptable salt thereof, wherein:
$A_2$ is selected from the group consisting of optionally substituted 3-10 membered heterocyclyl, optionally substituted $C_{6-10}$ aryl, optionally substituted 5-10 membered heteroaryl, and optionally substituted $C_{3-10}$ carbocyclyl, —$CR_2$—, —S—, —O—, —NR—, —CH═CH—, —OC(O)NH—, —NHC(O)NH—, —NHC(O)O—, —NHC(O)—, —NHC(S)NH—, —NHC(S)O—, —NHC(S)—, and single bond;
$A_4$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;

328

$A_5$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;
$A_6$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;
$A_7$ is selected from the group consisting of optionally substituted $C_{6-10}$ aryl, optionally substituted 5-10 membered heteroaryl, optionally substituted 3-10 membered heterocyclyl, optionally substituted $C_{3-10}$ carbocyclyl, —$CR_2$—, —S—, —O—, —NR—, optionally substituted $C_2$-$C_6$ alkenyl, and single bond;
y is an integer from 1 to 4;
z is an integer from 0 to 4;
$R^6$ is independently selected from —H and, optionally substituted $C_{1-4}$ alkyl;
$R^1$ is selected from the group consisting of H, —$CH_2F$, —$CH_2Cl$, —COOH, —C(═O)N(R)OR, —$CONR^2R^3$, —$CH(CH_3)$═$CH_2$, —$CH(CF_3)NR^2R^3$, —C(F)═$CHCH_2CH_3$,

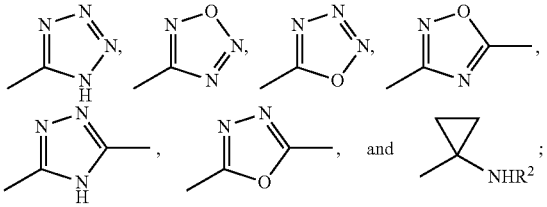

and
each R, $R^2$, and $R^3$ are independently selected from —H, optionally substituted $C_{1-4}$ alkyl, optionally substituted $C_2$-$C_6$ alkynyl, optionally substituted $C_{1-6}$ alkoxy, optionally substituted 2- to 5-membered polyethylene glycol, optionally substituted $C_{3-7}$ carbocyclyl, optionally substituted 5-10 membered heterocyclyl, optionally substituted $C_{6-10}$ aryl, and optionally substituted 5-10 membered heteroaryl;
J, L, M, $M_1$ and $M_2$ are each independently selected from the group consisting of $C(R^4)$ and N;
Y is selected from the group consisting of $NR^5$, O, and S, or Y is a nitrogen atom bonded to the $A_4$ group, wherein the $A_4$ group is —$CH_2$—;
X and Z are each independently selected from the group consisting of $C(R^4)$ and N;
$X_1$ is selected from the group consisting of $C(R^4)$ and N, or $X_1$ is a carbon atom bonded to the $A_4$ group;
each $R^4$ is independently selected from the group consisting of —H, $C_{1-4}$ alkyl, $C_{3-7}$ carbocyclyl, halo, hydroxy, and $C_1$-$C_6$ alkoxy; and
$R^5$ is selected from the group consisting of —H, $C_{1-4}$ alkyl, and $C_{3-7}$ carbocyclyl.
5. The compound of claim 1, wherein $A_2$ is —$CH_2$—.
6. The compound of claim 1, wherein $A_2$ is —O—.
7. The compound of claim 4, wherein J, L, $M_1$, and $M_2$ are independently selected from the group consisting of CH and N.

8. The compound of claim 1, wherein $A_4$ is —O—.

9. The compound of claim 1, wherein $A_4$ is —CH$_2$—.

10. The compound of claim 1, wherein $A_5$ is —O— or single bond.

11. The compound of claim 1, wherein z is 0 or 2.

12. The compound of claim 1, wherein $A_6$ is selected from the group consisting of single bond, —CH$_2$— and —CH=CH—.

13. The compound of claim 1, wherein $A_7$ is selected from the group consisting of —CH=CH—, single bond and phenyl.

14. The compound of claim 1, wherein z is 2 and $A_7$ is

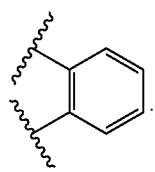

15. The compound of claim 1, wherein $R^1$ is —CONR$_2$R$_3$.

16. The compound of claim 15, wherein $R^2$ is —H and $R^3$ is optionally substituted C$_{1-4}$ alkyl.

17. The compound of claim 16, wherein $R^3$ is C$_{1-4}$ alkyl or benzyl.

18. A compound having the structure selected from the group consisting of:

1

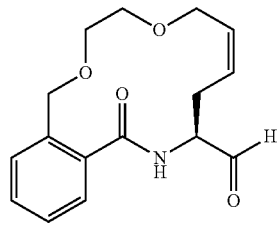

2

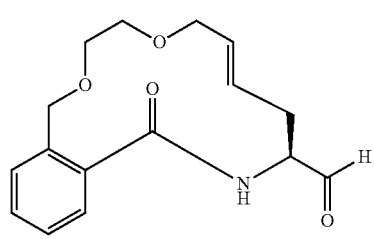

3

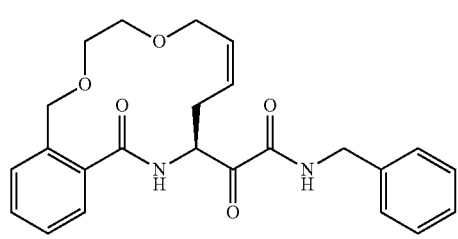

-continued

4

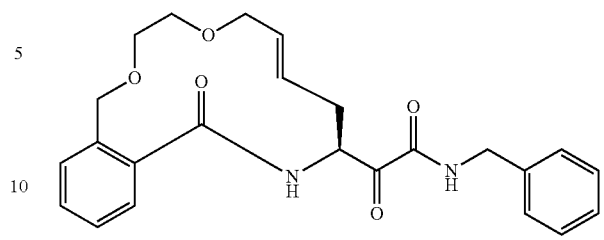

5

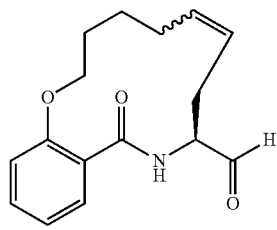

6

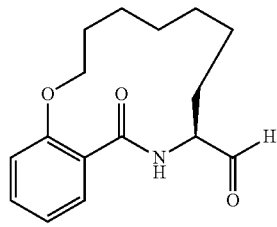

7

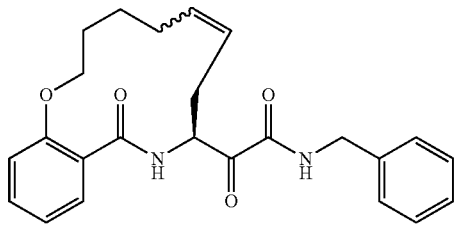

8

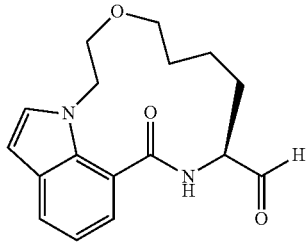

9

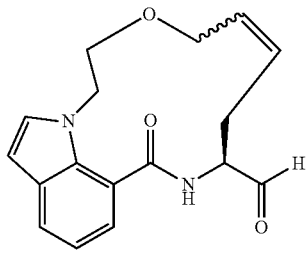

331
-continued
10
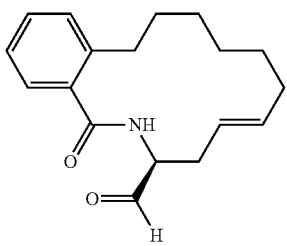
11
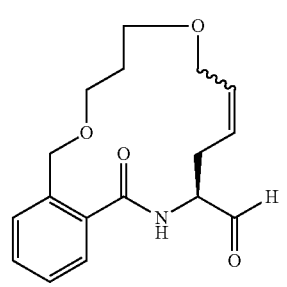
12
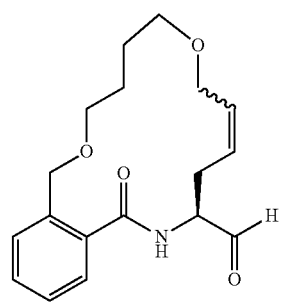
13
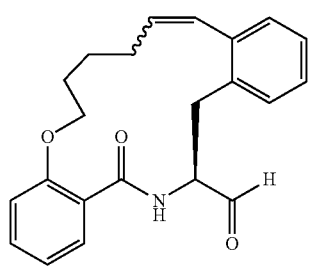
14
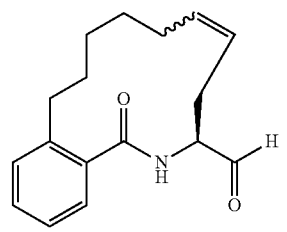
15
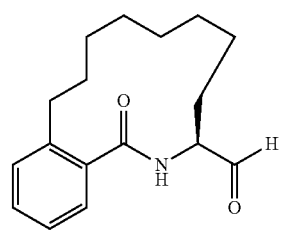
332
-continued
16
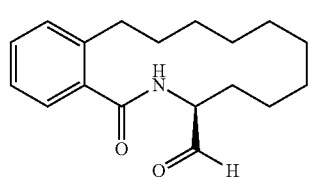
17
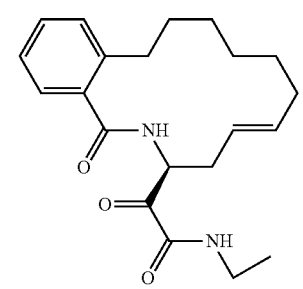
18
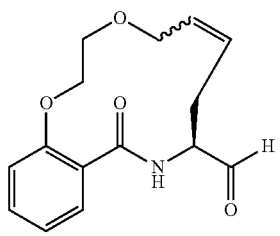
19
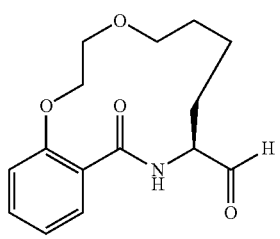
20
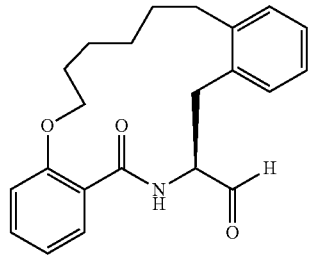
21
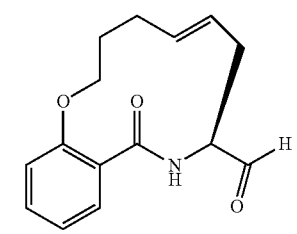

333
-continued
22
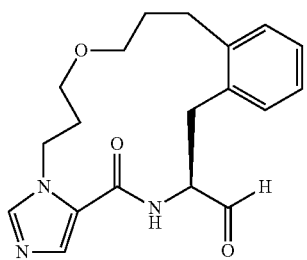
23
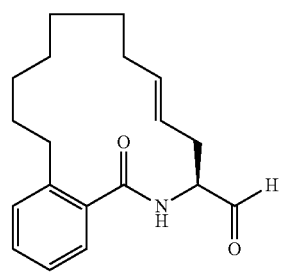
24
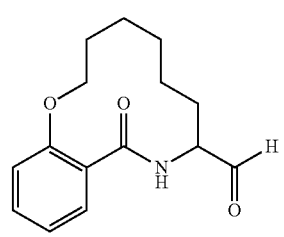
25
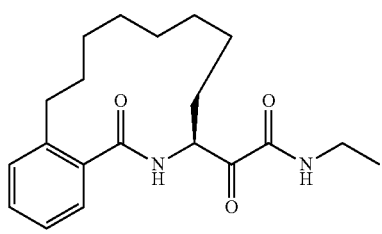
26
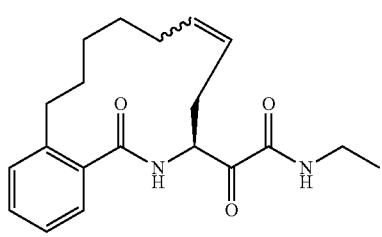
27
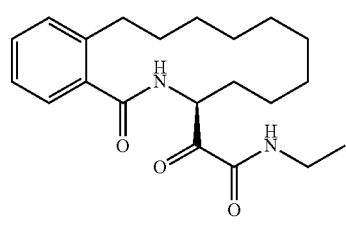
334
-continued
28
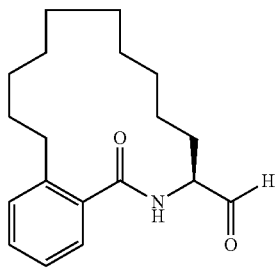
29
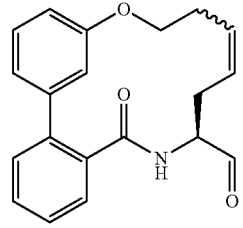
30
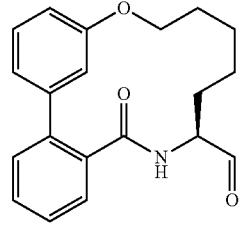
31
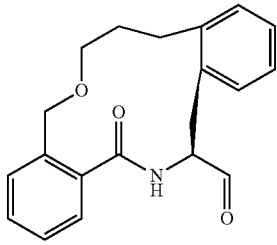
32
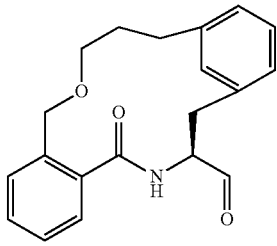
33
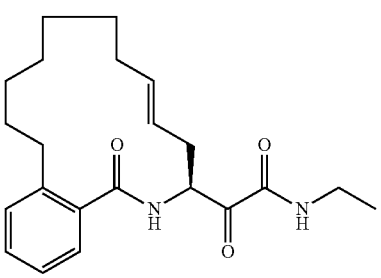

335
-continued
34
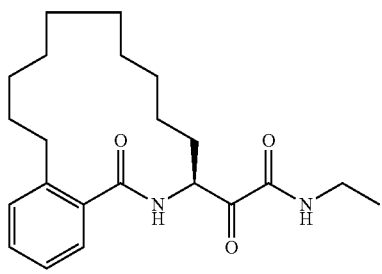
35
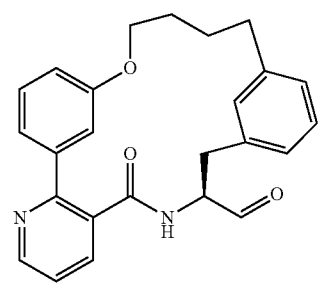
36
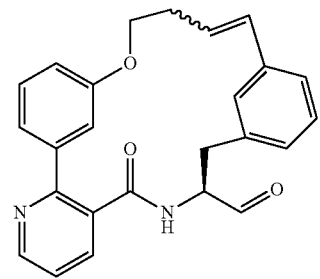
37
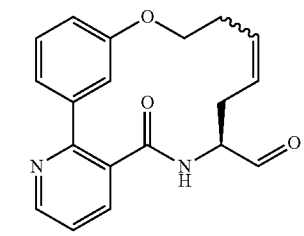
38
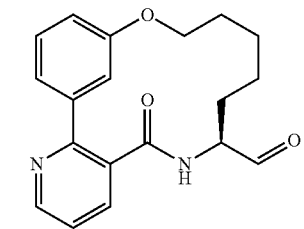
39
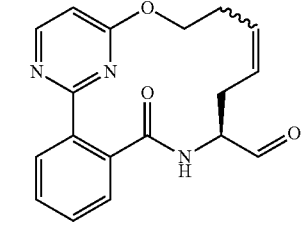
336
-continued
40
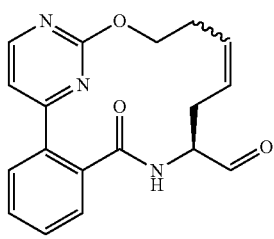
41
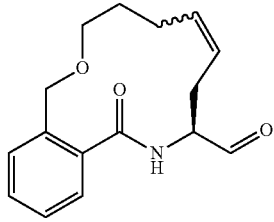
42
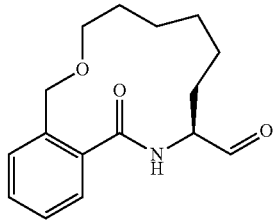
43
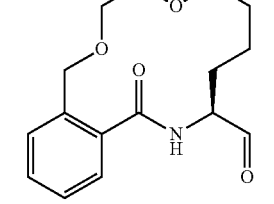
44
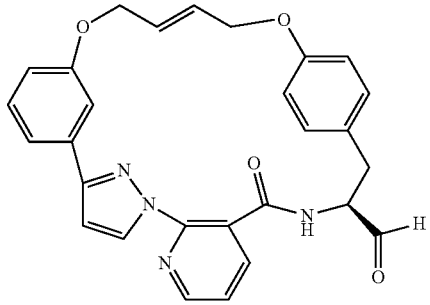
45
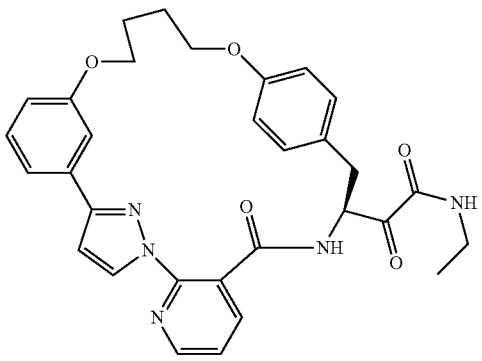

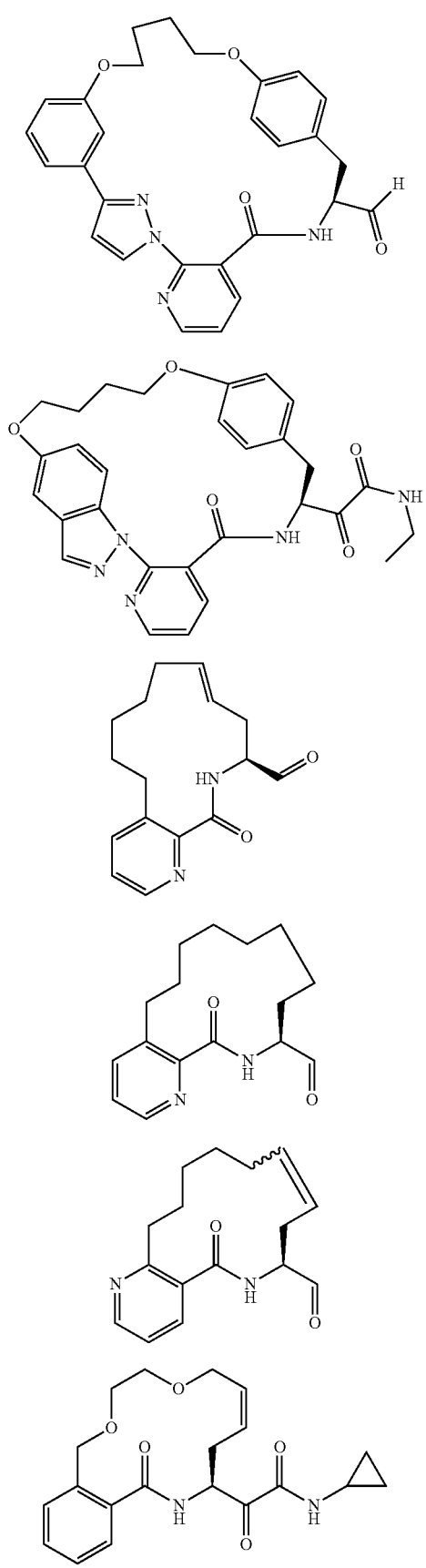
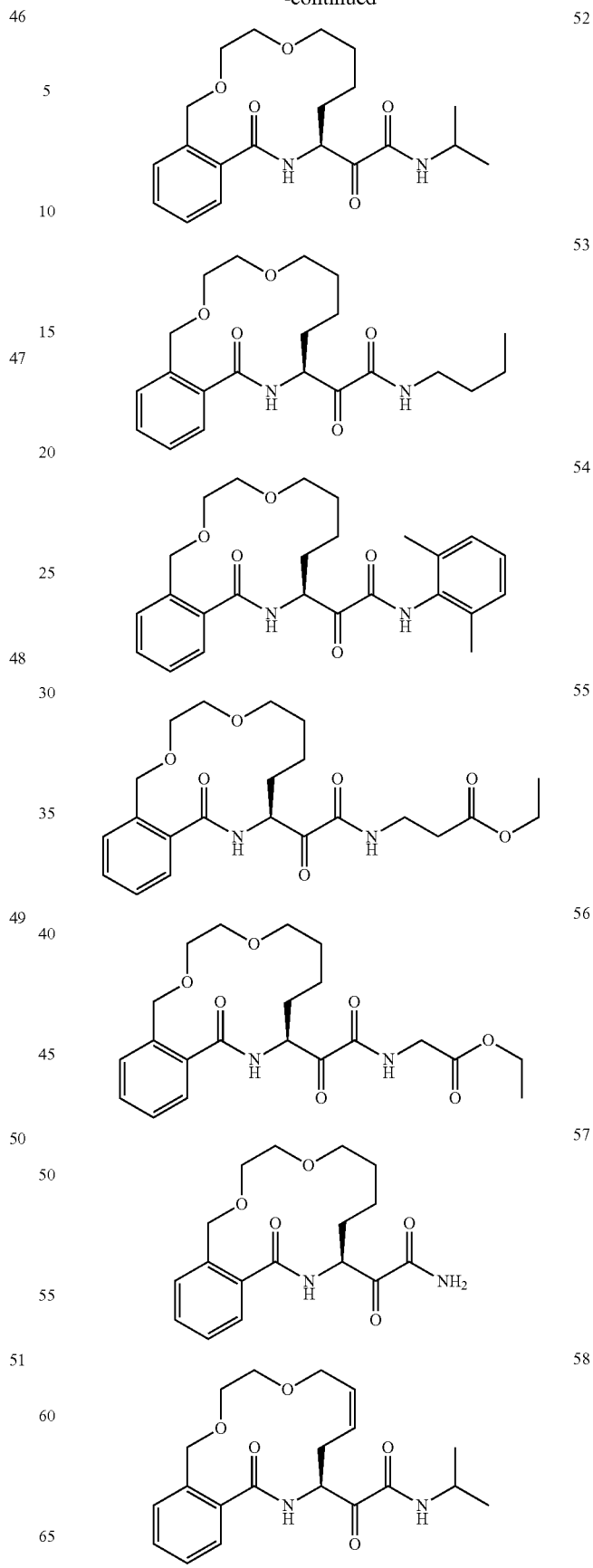

339
-continued
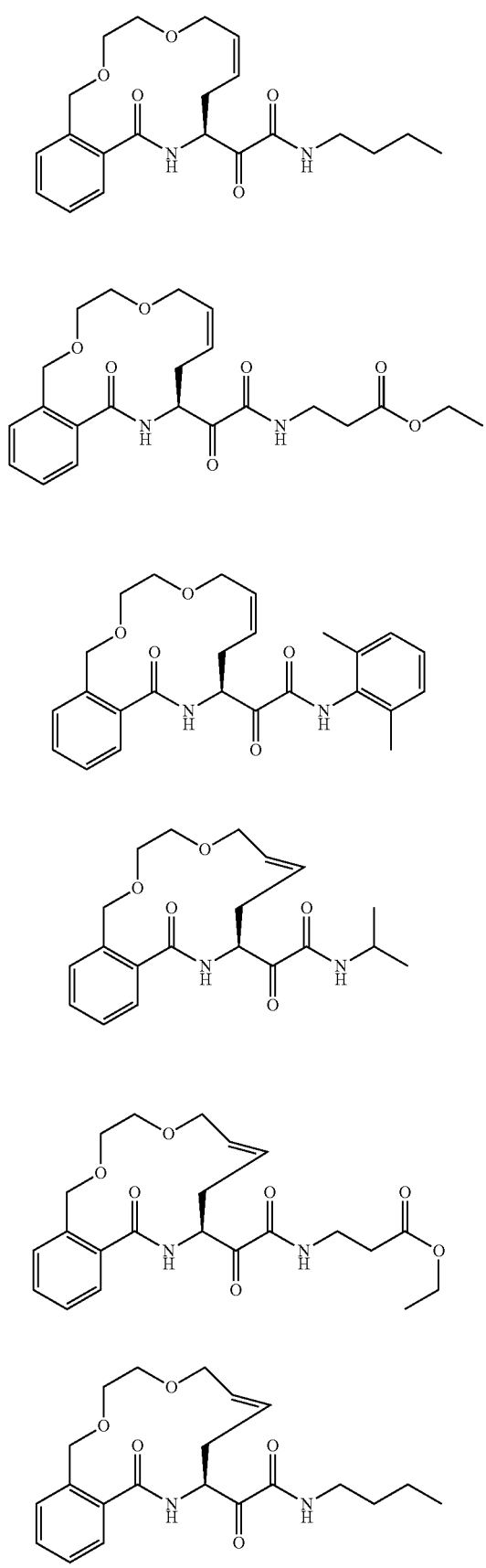
340
-continued
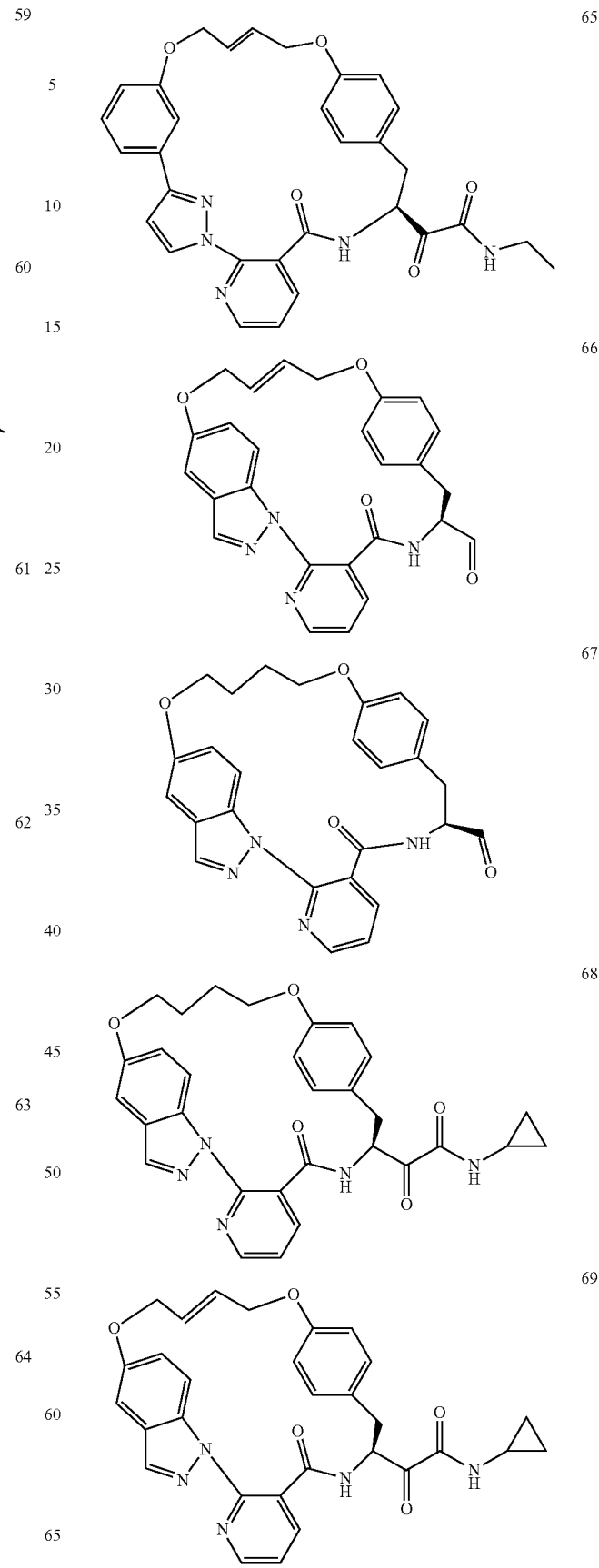

| 341 -continued | 342 -continued |
|---|---|
| 70 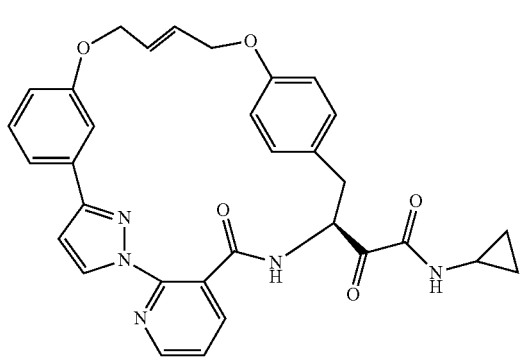 | 74 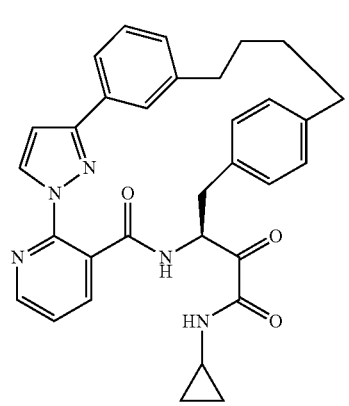 |
| 71 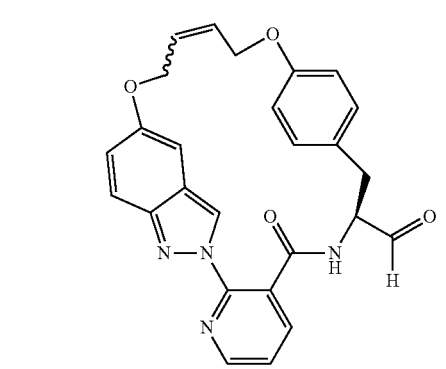 | 75 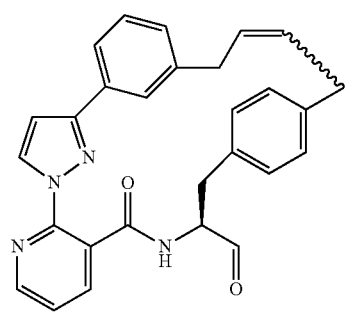 |
| 72 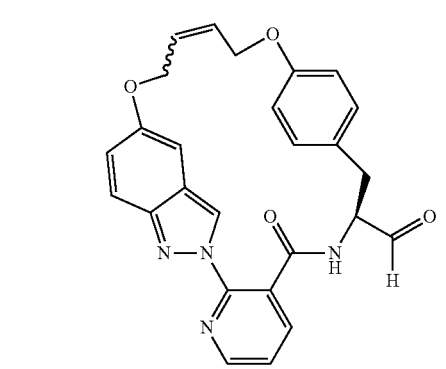 | 76 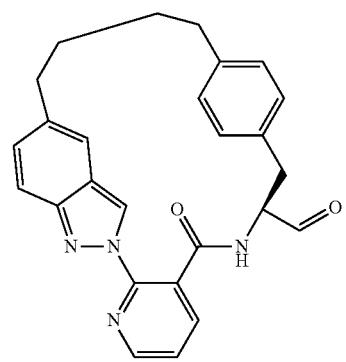 |
| 73 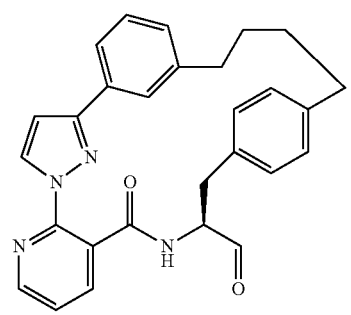 | 77 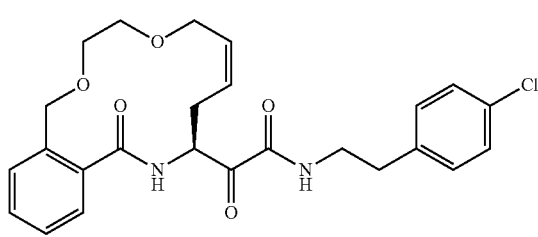 |
|  | 78 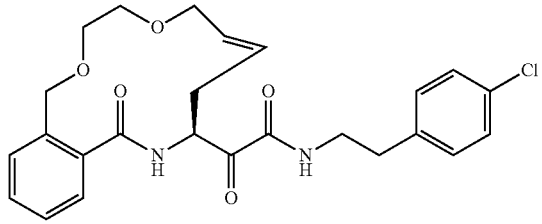 |

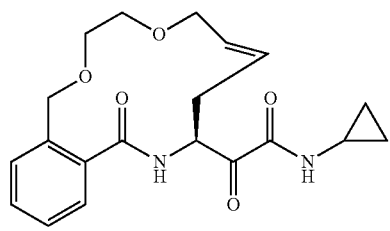
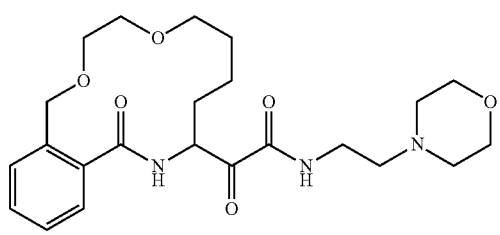
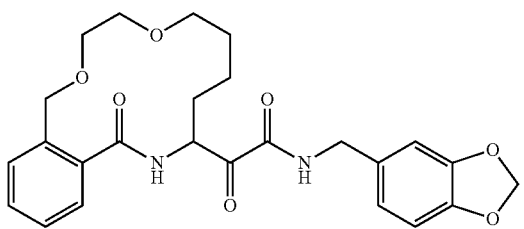
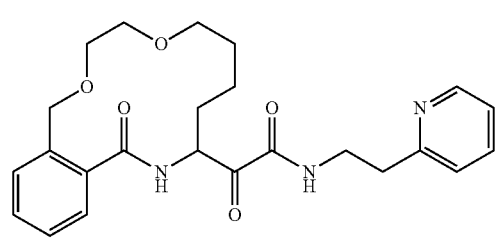
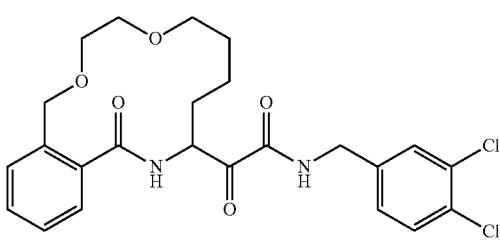
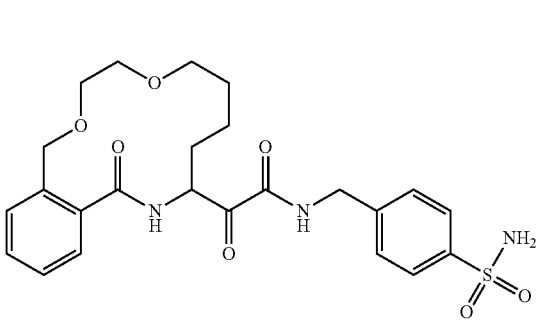
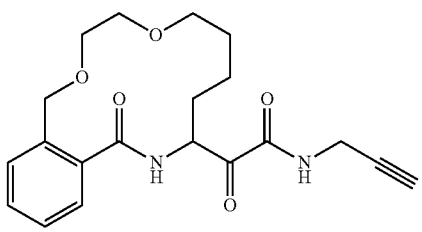
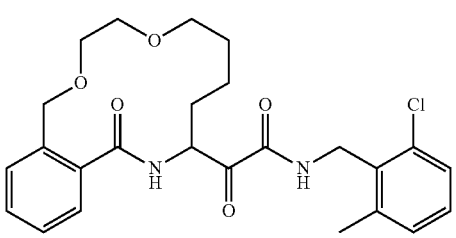
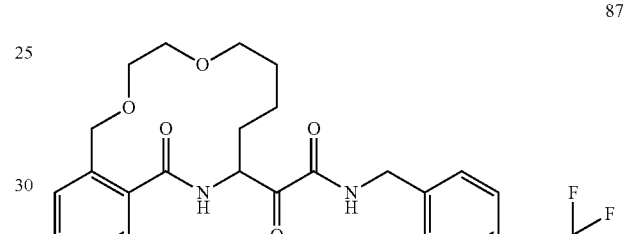
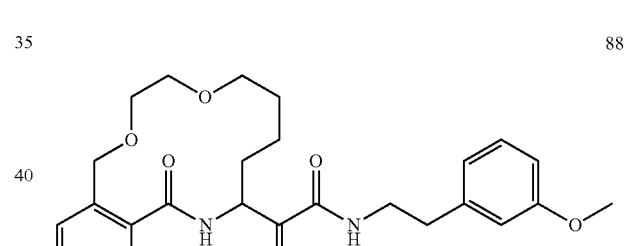
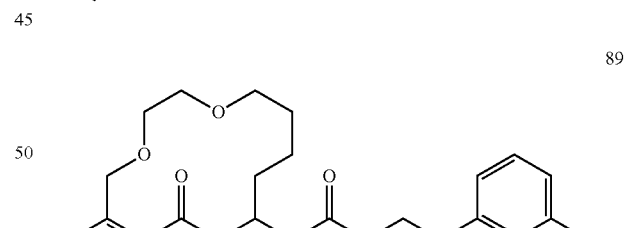
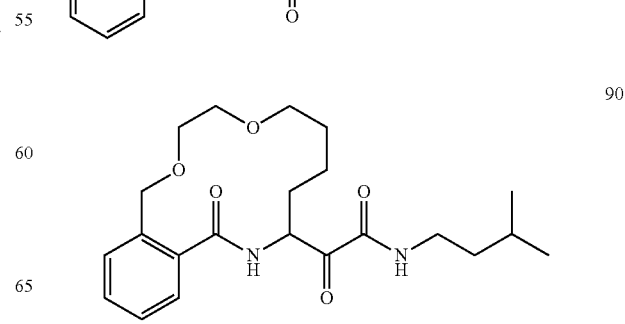

345
91
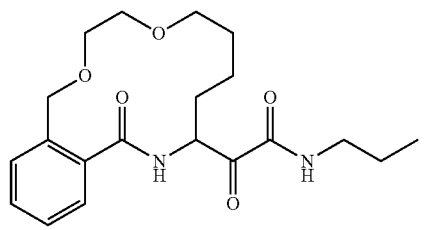
92
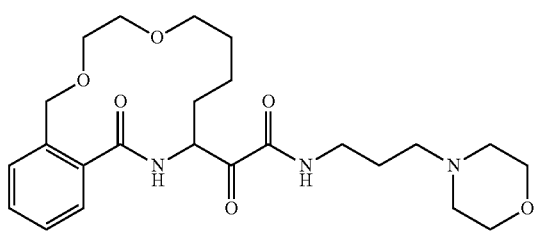
93
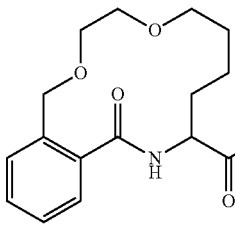
94
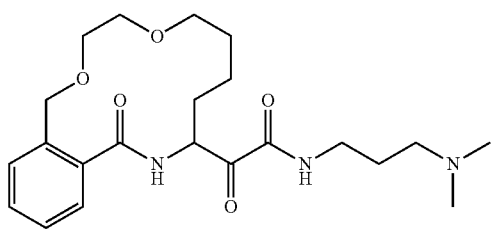
95
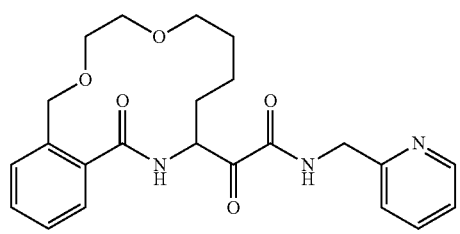
96
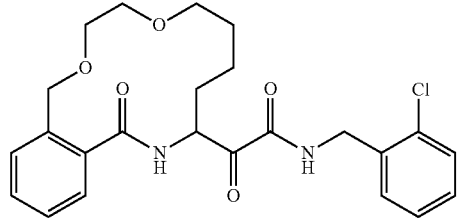
346
97
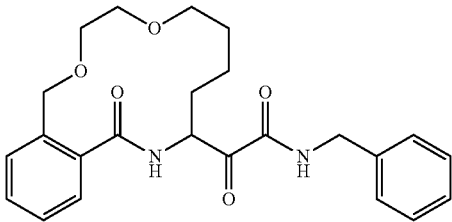
98
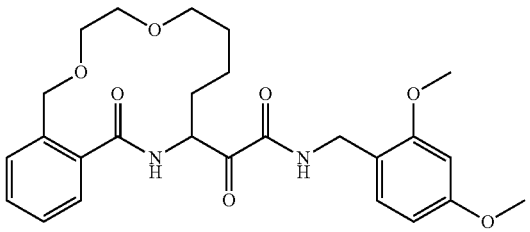
99
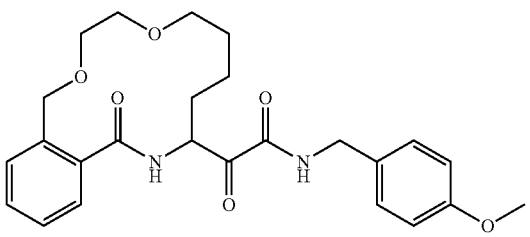
100
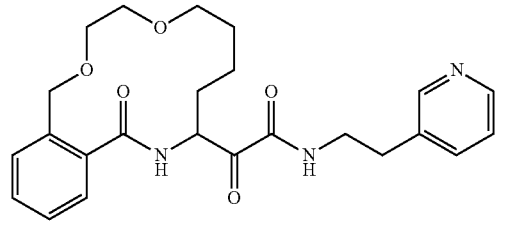
101
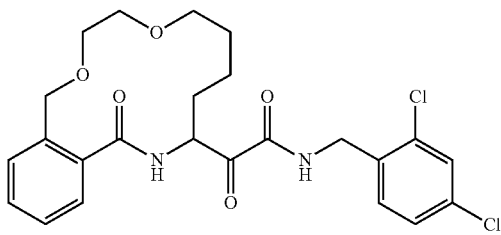
102
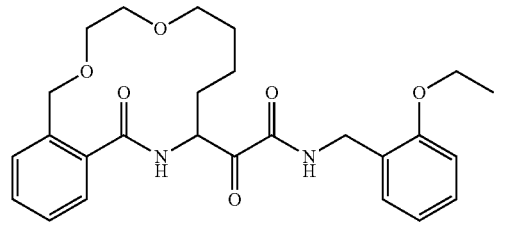

103 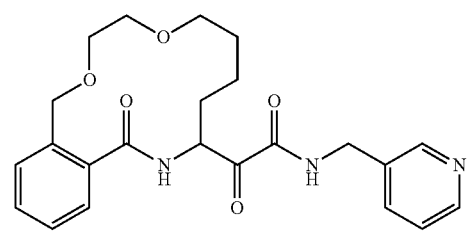
104 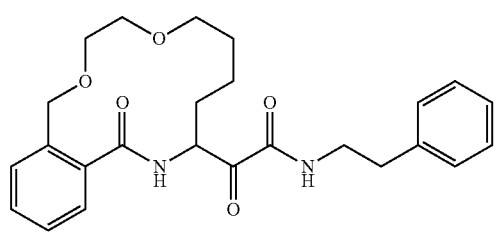
105 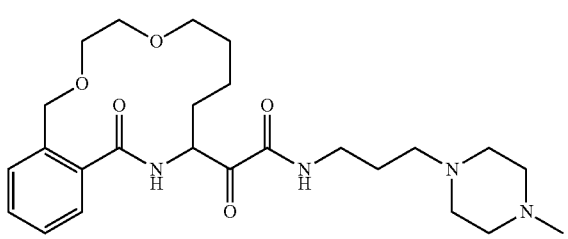
106 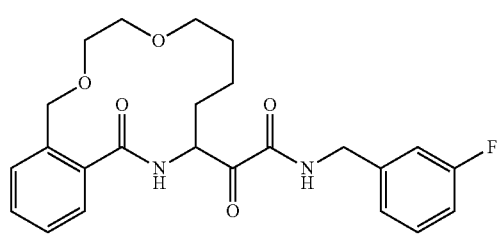
107 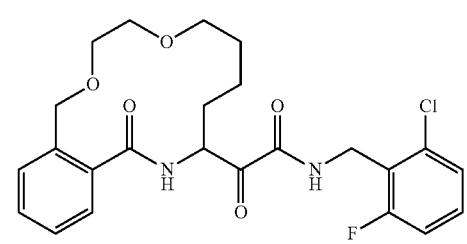
108 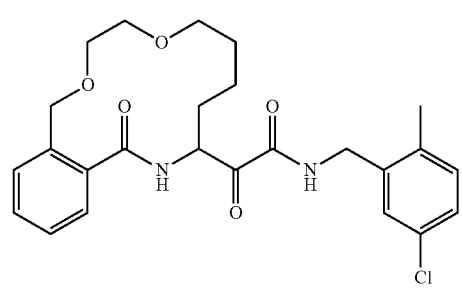
109 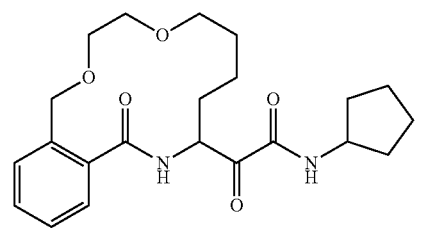
110 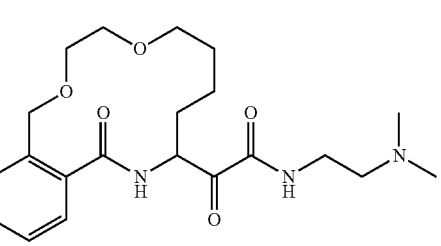
111 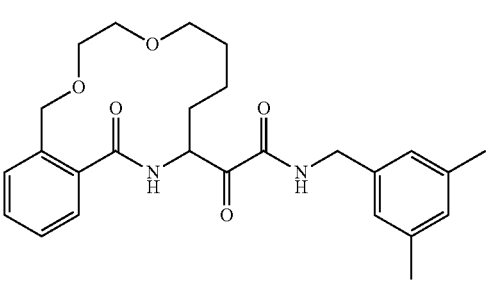
112 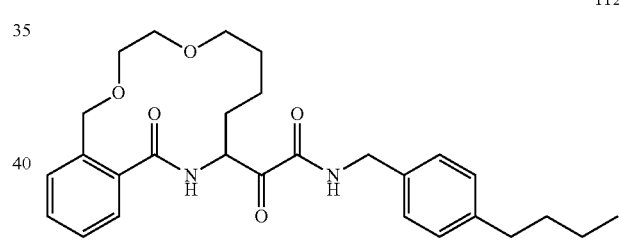
113 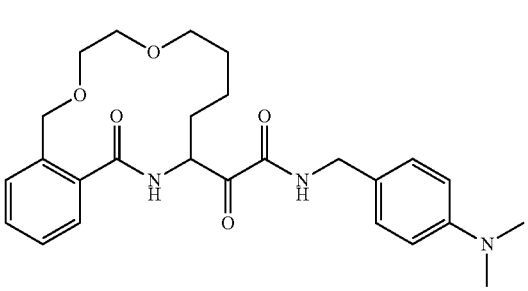
114 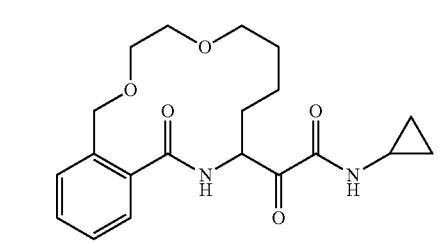

115
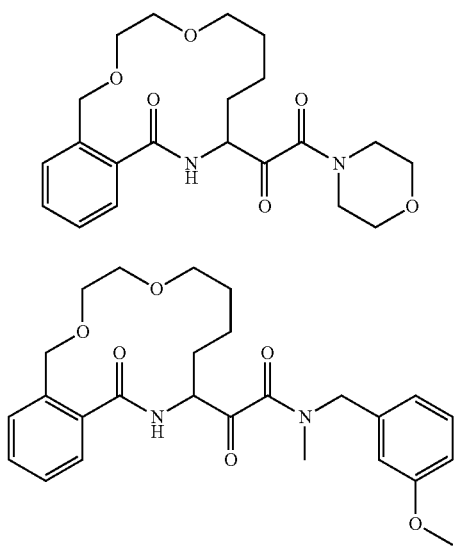
116
117
118
119
120
121
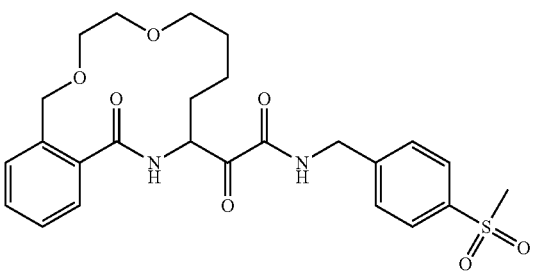
122
123
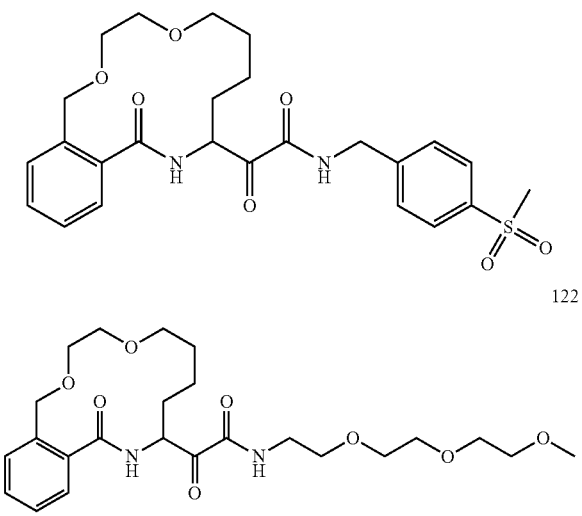
124
125
126

127
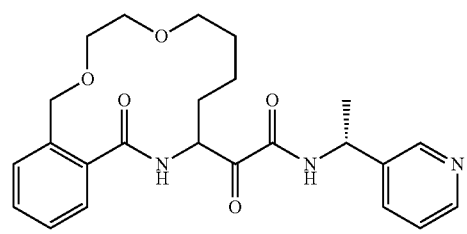
128
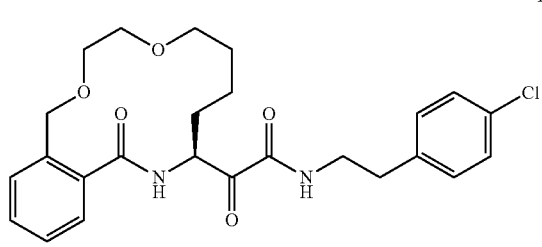
129
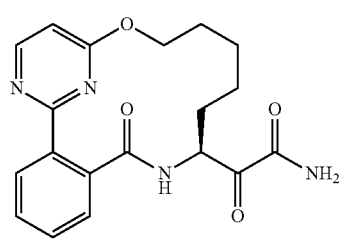
130
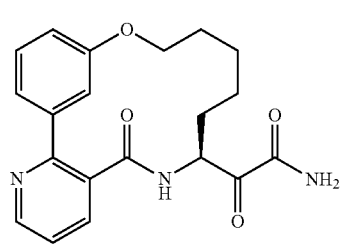
131
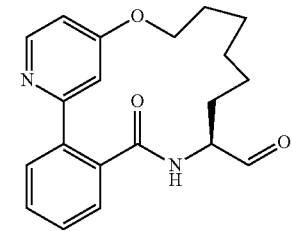
132
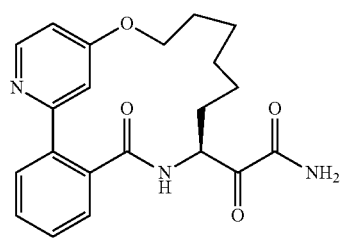
133
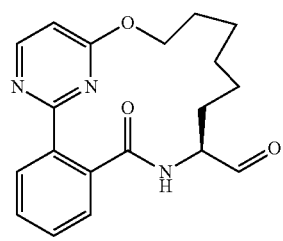
134
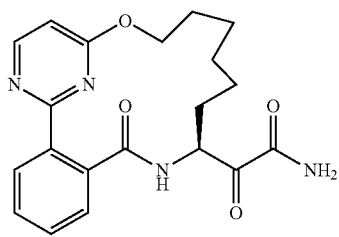
135
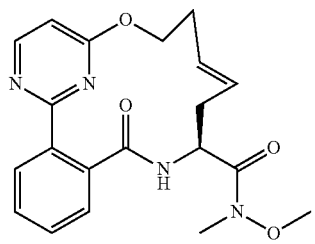
136
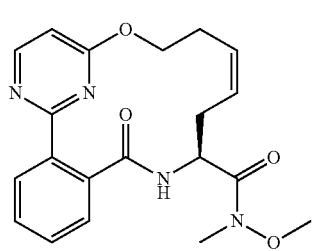
137
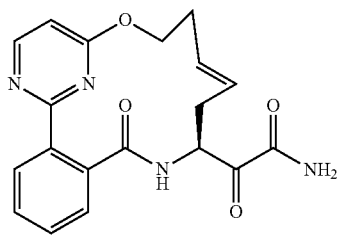
138
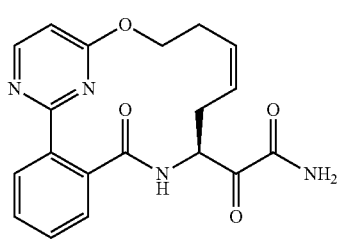

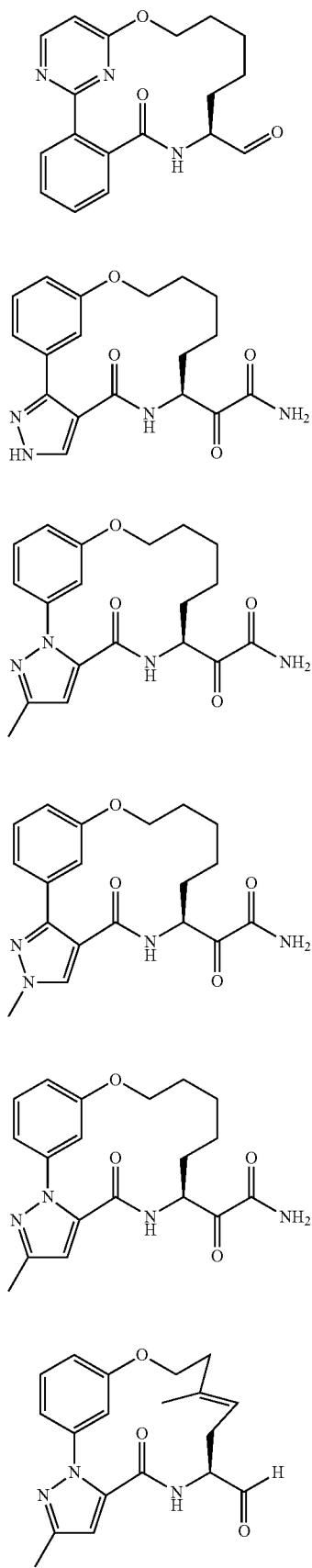
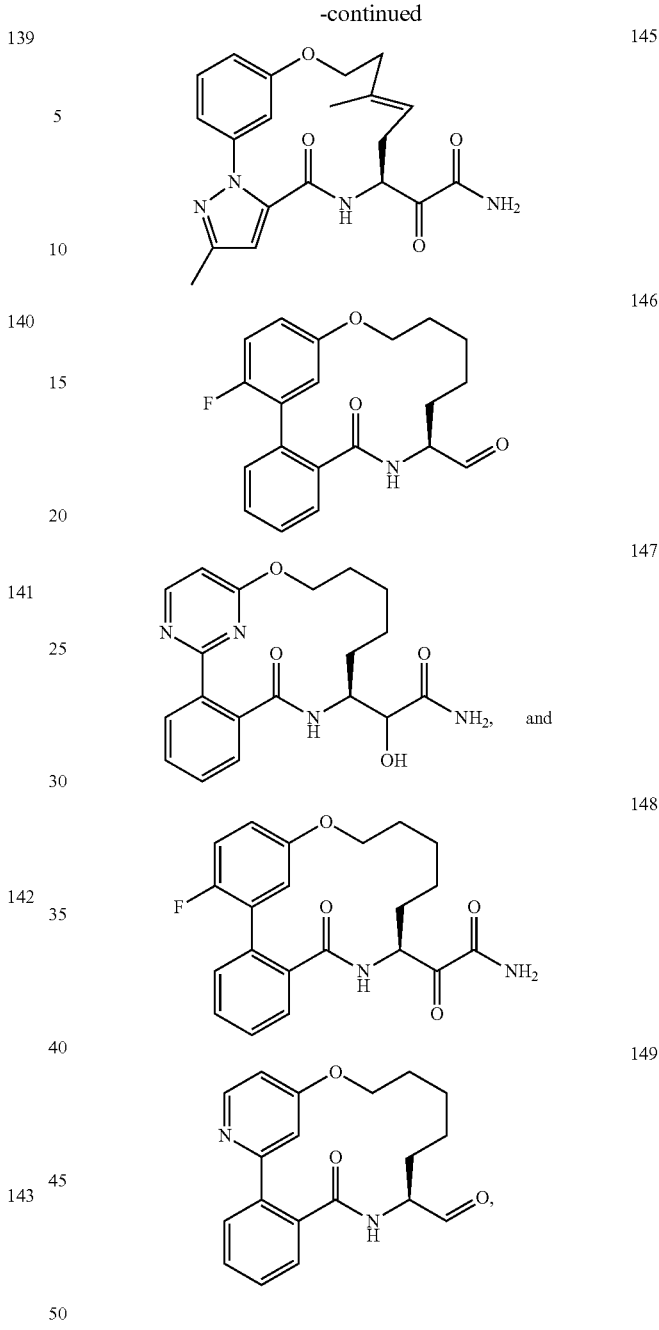

and pharmaceutically acceptable salts thereof.

19. A pharmaceutical composition comprising a therapeutically effective amount of a compound of claim 1 and a pharmaceutically acceptable excipient.

20. A method of treating fibrotic disease or a secondary disease state or condition thereof, comprising administering to a subject in need thereof, a compound according to claim 1.

21. The method of claim 20, wherein the disease is selected from the group consisting of liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis.

22. A method for inhibiting calpain, the method comprising contacting a compound of claim 1 with a CAPN1, CAPN2, and/or CAPN9 enzyme residing inside a subject.

* * * * *